(12) United States Patent
Krueger et al.

(10) Patent No.: US 11,999,699 B2
(45) Date of Patent: Jun. 4, 2024

(54) SUBSTITUTED PYRAZOLE AMIDES

(71) Applicant: GRUENENTHAL GMBH, Aachen (DE)

(72) Inventors: Sebastian Krueger, Aachen (DE); Sebastian Peil, Aachen (DE); Clemens Dialer, Aachen (DE); Marcel Muelbaier, Aachen (DE); Markus Wagener, Aachen (DE); Ingo Konetzki, Aachen (DE); Nikolay Sitnikov, Aachen (DE); Jo Alen, Aachen (DE); Martin Pettersson, Aachen (DE)

(73) Assignee: GRÜNENTHAL GMBH, Aachen (DE)

( * ) Notice: Subject to any disclaimer, the term of this patent is extended or adjusted under 35 U.S.C. 154(b) by 0 days.

(21) Appl. No.: 17/840,712

(22) Filed: Jun. 15, 2022

(65) Prior Publication Data
US 2023/0025025 A1 Jan. 26, 2023

Related U.S. Application Data

(60) Provisional application No. 63/341,107, filed on May 12, 2022, provisional application No. 63/273,417, filed on Oct. 29, 2021, provisional application No. 63/210,607, filed on Jun. 15, 2021.

(30) Foreign Application Priority Data

Jun. 15, 2021 (EP) .................................... 21179636

(51) Int. Cl.
| | | |
|---|---|---|
| *C07D 231/14* | (2006.01) | |
| *C07D 401/12* | (2006.01) | |
| *C07D 403/12* | (2006.01) | |
| *C07D 405/06* | (2006.01) | |
| *C07D 405/14* | (2006.01) | |
| *C07D 413/12* | (2006.01) | |

(52) U.S. Cl.
CPC ......... *C07D 231/14* (2013.01); *C07D 401/12* (2013.01); *C07D 403/12* (2013.01); *C07D 405/06* (2013.01); *C07D 405/14* (2013.01); *C07D 413/12* (2013.01)

(58) Field of Classification Search
None
See application file for complete search history.

(56) References Cited

U.S. PATENT DOCUMENTS

| | | |
|---|---|---|
| 8,519,137 B2 | 8/2013 | Joshi et al. |
| 8,779,197 B2 | 7/2014 | Chen et al. |
| 8,865,771 B2 | 10/2014 | Chen et al. |
| 2021/0198241 A1 | 7/2021 | Durrant |
| 2021/0387966 A1 | 12/2021 | Arasappan et al. |
| 2022/0119363 A1 | 4/2022 | Breslin et al. |

FOREIGN PATENT DOCUMENTS

| | | |
|---|---|---|
| WO | 2009/049180 A2 | 4/2009 |
| WO | 2009/049181 A1 | 4/2009 |
| WO | 2009/049183 A1 | 4/2009 |
| WO | 2020/092187 A1 | 5/2020 |
| WO | 2020/092667 A1 | 5/2020 |
| WO | 2021/113627 A1 | 6/2021 |

OTHER PUBLICATIONS

Database Registry Chemical Abstracts Service, Columbus, Ohio, Accession No. RN 2630996-35-7, Entered STN: Apr. 31, 2021.*
Database Registry Chemical Abstracts Service, Columbus, Ohio, Accession No. RN 2176340-89-7, Entered STN: Feb. 19, 2018.*
Database Registry Chemical Abstracts Service, Columbus, Ohio, Accession No. RN 2242192-85-2, Entered STN: Aug. 31, 2018.*

* cited by examiner

*Primary Examiner* — Samantha L Shterengarts
(74) *Attorney, Agent, or Firm* — Norris McLaughlin, P.A.

(57) ABSTRACT

The present invention relates to compounds according to general formula (I)

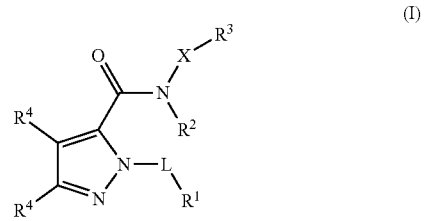

which act as inhibitors of $Na_V1.8$ and can be used in the treatment of pain.

16 Claims, No Drawings

SUBSTITUTED PYRAZOLE AMIDES

This application claims priority of U.S. Provisional Application No. 63/341,107, filed May 12, 2022, U.S. Provisional Application No. 63/273,417, filed Oct. 29, 2021, and U.S. Provisional Application No. 63/210,607, filed Jun. 15, 2021, as well as European Patent Application No. 21179636.2, filed Jun. 15, 2021, the contents of which patent applications are hereby incorporated herein by reference.

The present invention relates to compounds according to general formula (I)

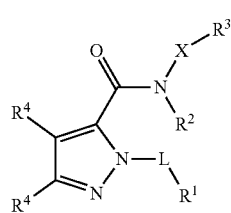

which act as inhibitors of $Na_V1.8$ and can be used in the treatment of pain.

Normal pain sensation (nociception) serves primarily as a survival mechanism, the body's way of self-protection, alerting against (further) tissue damage and disease from noxious stimuli. For instance, acute pain can arise when the external environment (temperature, pressure, chemicals) activates modality specific receptors (nociceptors) and ion channels within the skin. The peripheral terminals of pain-signaling neurons—whose cell bodies are found in the dorsal root ganglia [DRG] and trigeminal ganglia [TG]—convert the external stimuli into electrochemical generator potentials. Specific voltage-gated sodium channels (Nays) integrate and amplify these generator signals until the threshold for an action potential [AP] is reached. Thus, what starts as a noxious stimuli in the periphery eventually leads to action potential firing that travels towards the central nervous system, synapsing first onto neurons in the spinal cord and then towards the brain. Nays also function to support propagation of action potentials to the central terminals within the spinal cord. At the end of its travels along the somatosensory pathway, the action potential signal is interpreted as pain by the brain (Lumpkin and Caterina, Nature (2007), Vol. 445 pp 858-865; and Crawford and Caterina Toxicologic Pathology (2020) 48(1)-174; Goodwin G and McMahon S. B. Nature Reviews Neuroscience (2021) Vol 22 pp 263-274; Bennett D. L. et al. Physiol Rev 99 (2019) Vol 99 pp 1079-1151).

Abnormal persistent neuropathic pain arises as a consequence of a lesion or disease of this somatosensory pathway. In response to nerve injury or inflammation, abnormal changes in ion channel expression can cause hyper-excitability of pain-signaling neurons and their nerves/axons, thus resulting in pathological pain.

The voltage-gated $Na_V1.8$ sodium channel is a therapeutic target for analgesia because of its restricted expression profile (almost exclusive to peripheral sensory tissues), its placement along the pain pathway (free nerve endings, sciatic nerve, and DRG), prominent physiological role in pain signaling (supports upstroke of AP and facilitates repetitive AP firing), and supporting genetic/pharmaco-phenotypic evidence (human/animal studies showing changes in $Na_V1.8$ function cause parallel changes in pain sensitivity).

Regarding its expression profile along the pain pathway, because $Na_V1.8$ was first found predominantly in peripheral sensory neurons of the dorsal root ganglia (DRG) and trigeminal ganglia (TG), it was originally termed SNS (sensory neuron specific) (Akopian A. N. et al Nature (1996) Vol 379 pp 257-261) or PN3 (peripheral nerve 3) (Sangameswaran L. et al J. Biol. Chem. (1996) Vol 271 pp 5953-5956). As well, $Na_V1.8$ is localized at five nerve endings, where pain signaling is initiated in the skin (Persson A. K. et al Mol. Pain. (2010) 6:84) and is diffusely localized along the entire length of non-myelinated axons of sciatic nerve (Rush A. M. et al. Eur. J. Neurosci (2005) Vol 22 pp 39-49).

In contrast, $Na_V1.8$ has minimal expression in nonneuronal tissue, such as heart and skeletal muscle, and in the CNS, including brain and spinal cord (9, 10, 338, 406) (Akopian A. N. op. cit.; Akopian A. N. et al. Nat. Neurosci (1999) Vol 2 pp 541-548; Novakovic S. D. et al. J. Neurosci. (1998) Vol 18, pp 2184-2187; and Sagameswaran L. op. cit.).

Regarding its physiological role, $Na_V1.8$ contributes the majority of the inward current during the rising phase of an all-or-none action potential in nociceptive sensory neurons (Blair N. T. et al. J. Neurosci. (2003) Vol 23 pp 10338-10350 and Renganathan M et al. J. Neurophysiol (2001) Vol 86 pp 629-640)—and also contributes most of the current in subsequent spikes during repetitive firing in DRG neurons (Choi J. S. J. Neurophysiol (2011) Vol 106 pp 3173-3184; and Tan Z. Y. et al. J. Neurosci. (2014) Vol 34 pp 7190-7197).

Regarding genetic and pharmacology studies, gain-of-function mutations in $Na_V1.8$ were found in patients with chronic neuropathic pain such as small fiber neuropathy (Faber C. G. et al. (2012) Arm. Neurol Vol 71 pp 26-39; Han C et al. J. Neurol Neurosurg Psychiatry (2014) Vol 85 pp 499-505; and, Kist A. M. et al. PLoS One (2016) Vol 11 e0161789); Eijkenboom I. et al J. Neurol Neurosurg Psychiatry (2019) 90 (3) pp 342-352); loss-of-function (gene knockout) studies in mice reduced pain sensitivity, notably in nociception (Laird J. M. et al. J. Neurosci (2002) J. Neurosci Vol 22 pp 8352-8356; Jarvis M. F. et al Proc Natl Acad Sci USA (2007) Vol 104 pp 8520-8525; Joshi S. K. et al Pain (2006) Vol 123 pp 75-82) and in neuropathic models (Roza C. et al J Physiol (2003) Vol 550 pp 921-926); $Na_V1.8$-selective small molecule inhibitors reduced pain in rodents, specifically in inflammatory and neuropathic models (Jarvis et al. op. cit.; Kort M. E. et al Bioorg Med Chem Lett (2010) Vol 20 pp 6812-6815; Scanio M. J. et al Bioorg Med Chem (2010) Vol 18 pp 7816-7825; Payne C. E. et al Br J Pharmacol (2015) Vol 172 pp 2654-2670).

Currently, non-selective $Na_V$ channel inhibitors are used to treat epilepsy, cardiac arrhythmia, and chronic pain (Hille, B. J. Gen. Physiol. (1977) Vol. 69 pp. 497-515; Hille. B, Ion Channels of Excitable Membranes (1992) pp. 391-421; Sunderland, Mass., Sinauer Associates, Inc. $3^{rd}$ ed.; Hondeghem L. M. and Katzung B. G. Annu. Rev. Pharmacol. Toxicol. (1984) Vol. 24. Pp. 387-423; Catterall W. A. Trends Pharmacol. Sci. (1987) Vol. 8 pp. 57-65)—however, all of these analgesics have limited efficacy owing to dose-limiting adverse side-effects related to inhibiting $Na_V1.1/Na_V1.2/1.6$ (seizure liability), inhibiting $Na_V1.4$ (muscle weakness/paralysis), inhibiting $Na_V1.5$ (arrhythmia risk).

There is a need to develop a $Na_V1.8$-selective small molecule inhibitor as an effective and safe analgesic.

$Na_V1.8$ inhibitors are also known from WO 2020/092187, WO 2020/092667, WO 2009/049180, WO 2009/049183, WO 2009/049181 and WO 2021/113627.

It was an object of the present invention to provide novel compounds which are inhibitors, preferably selective inhibitors, of $Na_V1.8$, and which preferably have advantages over the compounds of the prior art. The novel compounds should in particular be suitable for use in the treatment of pain.

This object has been achieved by the subject-matter of the patent claims.

It was surprisingly found that the compounds according to the present invention are highly potent and selective inhibitors of the $Na_V1.8$ channel.

The present invention relates to a compound according to general formula (I)

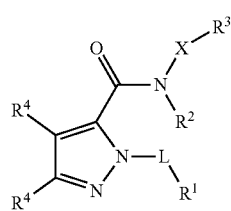

(I)

wherein
L represents $CH_2$, $CH(CH_3)$ or $CH(CH_2CH_3)$;
$R^1$ represents $C_{3-10}$-cycloalkyl, or 4 to 10-membered heterocycloalkyl,
$R^2$ represents H or $C_{1-6}$-alkyl;
X represents phenyl, or 5 to 10-membered heteroaryl;
$R^3$ represents $S(O)_2$—$C_{1-6}$-alkyl, $S(O)_2$—$(C_{3-6}$-cycloalkyl), $S(O)_2$-(4 to 6-membered heterocycloalkyl), $S(O)_2$-phenyl, $S(O)_2$-(5 or 6-membered heteroaryl), $S(O)$—$NH_2$, $S(O)$—$N(H)(C_{1-6}$-alkyl), $S(O)$—$N(C_{1-6}$-alkyl)$_2$, $S(O)_2$—$NH_2$, $S(O)_2$—$N(H)(C_{1-6}$-alkyl), $S(O)_2$—$N(H)(C_{3-6}$-cycloalkyl), $S(O)_2$—$N(C_{1-6}$-alkyl)$_2$, C(O)—$NH_2$, C(O)—$N(H)(C_{1-6}$-alkyl), C(O)—$N(H)(C_{1-6}$-cycloalkyl), C(O)—$N(C_{1-6}$-alkyl)$_2$, C(O)—$N(C_{1-6}$-alkyl)($C_{1-6}$-cycloalkyl), $OCF_3$, $OCF_2H$, CN, OH, O—$C_{3-6}$-cycloalkyl, O-(4 to 6-membered heterocycloalkyl), S(O)—$C_{1-6}$-alkyl, S(O)—($C_{3-6}$-cycloalkyl), S(O)-(4 to 6-membered heterocycloalkyl), S(O)-phenyl, or S(O)-(5 or 6-membered heteroaryl);
$R^4$ and $R^5$ independently from one another represent H, F, Cl, Br, CN, $CHF_2$, $CH_2F$, $CF_3$, $C_{1-6}$-alkyl, $C_{3-10}$-cycloalkyl, $C_{1-6}$-alkylene-$C_{3-10}$-cycloalkyl, 4 to 10-membered heterocycloalkyl, $C_{1-6}$-alkylene-(4 to 10-membered heterocycloalkyl), $NH_2$, $N(H)(C_{1-6}$-alkyl), $N(C_{1-6}$-alkyl)$_2$, O—$C_{1-6}$-alkyl, O—$C_{3-10}$-cycloalkyl, O—$C_{1-6}$-alkylene-$C_{3-10}$-cycloalkyl, O-(4 to 6-membered heterocycloalkyl), or O—$C_{1-6}$-alkylene-(4 to 6-membered heterocycloalkyl);
wherein $C_{1-6}$-alkyl and $C_{1-6}$-alkylene in each case independently from one another is linear or branched,
wherein $C_{1-6}$-alkyl, $C_{1-6}$-alkylene, $C_{3-10}$-cycloalkyl, $C_{3-6}$-cycloalkyl, 4 to 10-membered heterocycloalkyl and 4 to 6-membered heterocycloalkyl in each case independently from one another are unsubstituted or mono- or polysubstituted with F; and/or are unsubstituted or monosubstituted with one substituent selected from the group consisting of Cl, CN, $C_{1-6}$-alkyl, $C_{1-6}$-alkylene-OH, $C_{1-6}$-alkylene-$OCH_3$, $CF_3$, $CF_2H$, $CFH_2$, C(O)—$C_{1-6}$-alkyl, OH, =O, $OCF_3$, $OCF_2H$, $OCFH_2$, O—$C_{1-6}$-alkyl, $C_{1-4}$-alkylene-O—$C_{1-4}$-alkylene-O—$CH_3$, and $C_{0-4}$-alkylene-O—($C_{1-4}$-alkylene-O)$_{1-4}$—$CH_3$;
wherein phenyl, 5 to 10-membered heteroaryl and 5 or 6-membered heteroaryl in each case independently from one another are unsubstituted or mono- or polysubstituted with one or more substituents selected from the group consisting of F, Cl, Br, CN, $C_{1-6}$-alkyl, $C_{3-6}$-cycloalkyl, $CF_3$, $CF_2H$, $CFH_2$, $C_{1-6}$-alkylene-$CF_3$, $C_{1-6}$-alkylene-$CF_2H$, $C_{1-6}$-alkylene-$CFH_2$, $C_{1-6}$-alkylene-OH, $C_{1-6}$-alkylene-$OCH_3$, C(O)—$C_{1-6}$-alkyl, $OCF_3$, $OCF_2H$, $OCFH_2$, and O—$C_{1-6}$-alkyl;
in the form of the free compound or a physiologically acceptable salt thereof.

In a preferred embodiment, the compound according to the present invention is present in form of the free compound. For the purpose of specification, "free compound" preferably means that the compound according to the present invention is not present in form of a salt. Methods to determine whether a chemical substance is present as the free compound or as a salt are known to the skilled artisan such as $^{14}N$ or $^{15}N$ solid state NMR, x-ray diffraction, x-ray powder diffraction, IR, Raman, XPS. $^1H$-NMR recorded in solution may also be used to consider the presence of protonation.

In another preferred embodiment, the compound according to the present invention is present in form of a physiologically acceptable salt. For the purposes of this specification, the term "physiologically acceptable salt" preferably refers to a salt obtained from a compound according to the present invention and a physiologically acceptable acid or base.

According to the present invention, the compound according to the present invention may be present in any possible form including solvates, cocrystals and polymorphs. For the purposes of this specification, the term "solvate" preferably refers to an adduct of (i) a compound according to the present invention and/or a physiologically acceptable salt thereof with (ii) distinct molecular equivalents of one or more solvents.

Further, the compound according to the present invention may be present in form of the racemate, enantiomers, diastereomers, tautomers or any mixtures thereof.

The compounds according to the present invention may have one or more stereocenter. The person skilled in art knows by looking at a chemical structure whether the depicted compound has one or more stereocenters or not. For some compounds according to the present invention that have one or more stereocenters and which chemical structures are disclosed in the examples of the present application, the chemical structure includes bold bonds and/or hashed bonds to indicate the relative structural orientation of those substituents connected by the bold bonds and/or hashed bonds to the superior structure. If the bold bonds and/or hashed bonds are depicted in form of a wedge, the absolute stereochemical configuration of the compound is known and thereby indicated. If the bold bonds and/or hashed bonds are depicted as a straight bond (i.e. no wedge), the absolute stereochemical configuration of the compound has not been determined. In that case, the bold bonds and/or hashed bonds merely serve to indicate that this particular compound is present as one enantiomer or one diastereomer (e.g. cis-diastereomer (i.e. mixture of two cis-enantiomers) or trans-diastereomer (i.e. mixture of two trans-enantiomers)). All compounds according to the present invention that have one or more stereocenters but which chemical structures disclosed in the examples of the present application do not include bold bonds and/or hashed bonds, are present as a mixture of the respective stereoisomers.

The present invention also includes isotopic isomers of a compound of the invention, wherein at least one atom of the compound is replaced by an isotope of the respective atom which is different from the naturally predominantly occurring isotope, as well as any mixtures of isotopic isomers of such a compound. Preferred isotopes are $^2$H (deuterium), $^3$H (tritium), $^{13}$C and $^{14}$C. Isotopic isomers of a compound of the invention can generally be prepared by conventional procedures known to a person skilled in the art.

According to the present invention, the terms "$C_{1-6}$-alkyl" and "$C_{1-4}$-alkyl" preferably mean acyclic and preferably saturated hydrocarbon residues, which can be linear (i.e. unbranched) or branched and which can be unsubstituted or mono- or polysubstituted (e.g. di- or trisubstituted), and which contain 1 to 6 (i.e. 1, 2, 3, 4, 5 or 6) and 1 to 4 (i.e. 1, 2, 3 or 4) carbon atoms, respectively. Preferably, $C_{1-6}$-alkyl and $C_{1-4}$-alkyl are saturated. Preferred $C_{1-6}$-alkyl groups are selected from the group consisting of methyl, ethyl, n-propyl, 2-propyl, n-butyl, isobutyl, sec-butyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; more preferably methyl, ethyl, n-propyl, 2-propyl, n-butyl, isobutyl, sec-butyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl, n-hexyl. Particularly preferred $C_{1-6}$-alkyl groups are selected from $C_{1-4}$-alkyl groups. Preferred $C_{1-4}$-alkyl groups are selected from the group consisting of methyl, ethyl, n-propyl, 2-propyl, n-butyl, isobutyl, sec-butyl and tert-butyl.

Further according to the present invention, the terms "$C_{1-6}$-alkylene" and "$C_{1-4}$-alkylene" relate to linear or branched and preferably saturated aliphatic residues which can be unsubstituted or mono- or polysubstituted (e.g. di- or trisubstituted) and which are preferably selected from the group consisting of $CH_2$, $CH(CH_3)$, $CH_2CH_2$, $CH_2CH(CH_3)$, $CH(CH_3)CH_2$, $CH_2CH_2CH_2$, $CH(CH_3)CH_2CH_2$, $CH_2CH(CH_3)CH_2$, $CH_2CH_2CH(CH_3)$, $CH_2CH_2CH_2CH_2$, $CH(CH_3)CH_2CH_2CH_2$, $CH_2CH(CH_3)CH_2CH_2$, $CH_2CH_2CH(CH_3)CH_2$, $CH_2CH_2CH_2CH(CH_3)$, $CH_2CH_2CH_2CH_2CH_2$, $CH(CH_3)CH_2CH_2CH_2CH_2$, $CH_2CH(CH_3)CH_2CH_2CH_2$, $CH_2CH_2CH(CH_3)CH_2CH_2$, $CH_2CH_2CH_2CH(CH_3)CH_2$, $CH_2CH_2CH_2CH_2CH(CH_3)$, and $CH_2CH_2CH_2CH_2CH_2CH_2$; more preferably $CH_2$, $CH(CH_3)$, $CH_2CH_2$, $CH_2CH(CH_3)$ and $CH(CH_3)CH_2$, most preferably $CH_2$ and $CH(CH_3)$, and in particular $CH_2$. Preferably, $C_{1-6}$-alkylene is selected from $C_{1-4}$-alkylene.

Still further according to the invention, the terms "$C_{3-10}$-cycloalkyl" and "$C_{3-6}$-cycloalkyl" preferably mean monocyclic aliphatic hydrocarbons containing 3, 4, 5, 6, 7, 8, 9 or 10 carbon atoms and 3, 4, 5 or 6 carbon atoms, respectively, wherein the hydrocarbons in each case can be saturated or unsaturated (but not aromatic), unsubstituted or mono- or poly substituted.

Preferably, $C_{3-10}$-cycloalkyl and $C_{3-6}$-cycloalkyl are saturated. The $C_{3-10}$-cycloalkyl and $C_{3-6}$-cycloalkyl can be bound to the respective superordinate general structure via any desired and possible ring member of the cycloalkyl group. The $C_{3-10}$-cycloalkyl and $C_{3-6}$-cycloalkyl are not condensed with further ring systems and are not bridged.

Preferred $C_{3-10}$-cycloalkyl groups are selected from the group consisting of cyclopropyl, cyclobutyl, cyclopentyl, cyclohexyl, cycloheptyl, cyclooctyl, cyclononyl, and cyclodecyl. Preferred $C_{3-10}$-cycloalkyl groups are selected from $C_{3-6}$-cycloalkyl groups.

According to the invention, the terms "4 to 10-membered heterocycloalkyl" and "4 to 6-membered heterocycloalkyl" preferably mean monocyclic, heterocycloaliphatic saturated or unsaturated (but not aromatic) residues having 4 to 10, i.e. 4, 5, 6, 7, 8, 9 or 10 ring members and 4 to 6, i.e. 4, 5 or 6 ring members, respectively, wherein in each case at least one, if appropriate also two or three carbon atoms are replaced by a heteroatom or a heteroatom group each selected independently of one another from the group consisting of O, S, S(=O), S(=O)$_2$, N, NH and N($C_{3-4}$-alkyl) such as N($CH_3$), wherein the carbon atoms of the ring can be unsubstituted or mono- or polysubstituted. Preferably, the 4 to 10-membered heterocycloalkyl and the 4 to 6-membered heterocycloalkyl contain only one heteroatom or heteroatom group within the ring.

Preferably, 4 to 10-membered heterocycloalkyl and 4 to 6-membered heterocycloalkyl are saturated. The 4 to 10-membered heterocycloalkyl and 4 to 6-membered heterocycloalkyl are not condensed with further ring systems and are not bridged.

The 4 to 10-membered heterocycloalkyl and the 4 to 6-membered heterocycloalkyl group can be bound to the superordinate general structure via any desired and possible ring member of the heterocycloaliphatic residue if not indicated otherwise. In a preferred embodiment, 4 to 10-membered heterocycloalkyl and 4 to 6-membered heterocycloalkyl are bound to the superordinate general structure via a carbon atom.

Preferred 4 to 10-membered heterocycloalkyl groups are selected from the group consisting of oxetanyl, tetrahydrofuranyl, tetrahydropyranyl, morpholinyl, thiomorpholinyl, tetrahydrothiopyranyl, tetrahydrothiopyranyl 1,1-dioxide, oxepanyl, piperidinyl, piperidinonyl, azetidinyl, pyrrolidinyl, pyrrolidinonyl, 4-methylpiperazinyl, morpholinonyl, dioxanyl, piperazinyl, tetrahydropyrrolyl, azepanyl, dioxepanyl, oxazepanyl, diazepanyl, thiazolidinyl, tetrahydrothiophenyl, tetrahydropyridinyl, dithiolanyl, dihydropyrrolyl, dioxolanyl, dihydropyridinyl, dihydrofuranyl, dihydroisoxazolyl, dihydrooxazolyl, imidazolidinyl, isoxazolidinyl, oxazolidinyl, piperazinyl, N-methylpyridinonyl, pyrazolidinyl, pyranyl; dihydroquinolinyl, dihydroisoquinolinyl, dihydroindolinyl, dihydroisoindolyl, tetrahydroquinolinyl, tetrahydroisoquinolinyl and tetrahydroindolinyl; more preferably oxetanyl, tetrahydrofuranyl, tetrahydropyranyl, morpholinyl, thiomorpholinyl, tetrahydrothiopyranyl, tetrahydrothiopyranyl 1,1-dioxide, oxepanyl, piperidinyl, piperidinonyl, azetidinyl, pyrrolidinyl, pyrrolidinonyl, 4-methylpiperazinyl, morpholinonyl, dioxanyl, piperazinyl, and tetrahydropyrrolyl.

Preferred 4 to 6-membered heterocycloalkyl groups are selected from the group consisting of oxetanyl, tetrahydrofuranyl, tetrahydropyranyl, morpholinyl, thiomorpholinyl, tetrahydrothiopyranyl, tetrahydrothiopyranyl 1,1-dioxide, piperidinyl, piperidinonyl, azetidinyl, pyrrolidinyl, pyrrolidinonyl, 4-methylpiperazinyl, morpholinonyl, dioxanyl, piperazinyl, tetrahydropyrrolyl, thiazolidinyl, tetrahydrothiophenyl, tetrahydropyridinyl, dithiolanyl, dihydropyrrolyl, dioxolanyl, dihydropyridinyl, dihydrofuranyl, dihydroisoxazolyl, dihydrooxazolyl, imidazolidinyl, isoxazolidinyl, oxazolidinyl, N-methylpyridinonyl, pyrazolidinyl, and pyranyl; more preferably oxetanyl, tetrahydrofuranyl, tetrahydropyranyl, morpholinyl, thiomorpholinyl, tetrahydrothiopyranyl, tetrahydrothiopyranyl 1,1-dioxide, piperidinyl, piperidinonyl, azetidinyl, pyrrolidinyl, pyrrolidinonyl, 4-methylpiperazinyl, morpholinonyl, dioxanyl, piperazinyl, and tetrahydropyrrolyl.

According to the invention, the term "5- to 10-membered heteroaryl" and "5- or 6-membered heteroaryl", respectively, preferably means a 5 to 10-membered or 5- or 6-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or poly substituted, if not indicated otherwise. In the case of substitution on the heteroaryl, the substituents can be the same or different and be in any desired and possible position of the heteroaryl. The binding to the superordinate general structure can be carried out via any desired and possible ring member of the heteroaryl residue if not indicated otherwise. Preferably, the 5- to 10-membered heteroaryl and 5- or 6-membered heteroaryl is bound to the superordinate general structure via a carbon atom of the heterocycle. The heteroaryl can also be condensed with a further ring system, e.g. saturated or (partially) unsaturated (hetero)cyclic, aromatic or heteroaromatic ring systems, which can in turn be unsubstituted or mono- or polysubstituted, if not indicated otherwise.

Preferably, the 5- to 10-membered heteroaryl is selected from the group consisting of pyridyl (i.e. 2-pyridyl, 3-pyridyl, 4-pyridyl), pyrazolyl, pyrrolo[2,3-b]pyridyl, pyridonyl (pyridinonyl), thienyl (thiophenyl), thiazolyl, 2,3-dihydrobenzo[d]isothiazolyl 1,1-dioxide, isoindolinonyl, pyrimidinyl, pyrazinyl, pyridazinyl, isoxazolyl, triazolyl, oxazolyl, oxadiazolyl, indazolyl, pyrazolopyridyl, pyrrolyl, imidazolyl, isothiazolyl, furanyl, thiadiazolyl, N-methylpyridinonyl, benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, imidazothiazolyl, indolizinyl, indolyl, isoquinolinyl, naphthyridinyl, phenazinyl, phenothiazinyl, phthalazinyl, purinyl, phenazinyl, tetrazolyl and triazinyl; more preferably pyridyl, pyrazolyl, pyrrolo[2,3-b]pyridyl, pyridonyl, thienyl, thiazolyl, 2,3-dihydrobenzo[d]isothiazolyl 1,1-dioxide, isoindolinonyl, pyrimidinyl, pyrazinyl, pyridazinyl, isoxazolyl, triazolyl, oxazolyl, oxadiazolyl, indazolyl, pyrazolopyridyl, pyrrolyl, imidazolyl, isothiazolyl, furanyl, and thiadiazolyl. Particularly preferably, 5 to 10-membered heteroaryl is selected from 5- or 6-membered heteroaryl.

Preferably, the 5- or 6-membered heteroaryl is selected from the group consisting of pyridyl, pyrazolyl, pyridonyl, thienyl, thiazolyl, pyrimidinyl, pyrazinyl, pyridazinyl, isoxazolyl, triazolyl, oxazolyl, oxadiazolyl, pyrrolyl, imidazolyl, isothiazolyl, furanyl, thiadiazolyl, N-methylpyridinonyl, tetrazolyl and triazinyl; more preferably pyridyl, pyrazolyl, pyridonyl, thienyl, thiazolyl, pyrimidinyl, pyrazinyl, pyridazinyl, isoxazolyl, triazolyl, oxazolyl, oxadiazolyl, pyrrolyl, imidazolyl, isothiazolyl, furanyl, and thiadiazolyl.

As pyridones and 2-hydroxypyridine are tautomers, for the purpose of the specification the definition of pyridines that may optionally be substituted with OH covers pyridones.

In connection with the terms "$C_{1-6}$-alkyl", "$C_{1-4}$-alkyl", "$C_{1-6}$-alkylene", "$C_{1-4}$-alkylene", "$C_{3-10}$-cycloalkyl", "$C_{1-6}$-cycloalkyl", "4 to 10-membered heterocycloalkyl" and "4 to 6-membered heterocycloalkyl", the term "substituted" refers in the sense of the present invention, with respect to the corresponding residues or groups, to the single substitution (monosubstitution) or multiple substitution (polysubstitution), e.g. disubstitution, trisubstitution or tetrasubstitution; more preferably to monosubstitution, disubstitution or trisubstitution; of one or more hydrogen atoms each independently of one another by at least one substituent. In case of a multiple substitution, i.e. in case of polysubstituted residues, such as di- or trisubstituted residues, these residues may be polysubstituted either on different or on the same atoms, for example trisubstituted on the same carbon atom, as in the case of $CF_3$, $CH_2CF_3$ or disubstituted as in the case of 1,1-difluorocyclohexyl, or at various points, as in the case of 1-chloro-3-fluorocyclohexyl. The multiple substitution can be carried out using the same or using different substituents.

If a residue occurs multiply within a molecule, then this residue can have respectively different meanings for various substituents: if, for example, both $R^4$ and $R^5$ denote $C_{1-6}$-alkyl, then $C_{1-6}$-alkyl can e.g. represent methyl for $R^4$ and can represent 2-propyl for $R^5$.

According to the present invention, $C_{1-6}$-alkyl, $C_{1-4}$-alkyl, $C_{1-6}$-alkylene, $C_{1-4}$-alkylene, $C_{3-10}$-cycloalkyl, $C_{3-6}$-cycloalkyl, 4 to 10-membered heterocycloalkyl and 4 to 6-membered heterocycloalkyl, in each case independently from one another are unsubstituted or mono- or polysubstituted, more preferably unsubstituted or mono-, di-, tri-, tetra- or pentasubstituted, with F; and/or are unsubstituted or monosubstituted with one substituent selected from the group consisting of Cl, CN, $C_{1-6}$-alkyl, $C_{1-6}$-alkylene-OH, $C_{1-6}$-alkylene-$OCH_3$, $CF_3$, $CF_2H$, $CFH_2$, $C(O)—C_{1-6}$-alkyl, OH, $=O$, $OCF_3$, $OCF_2H$, $OCFH_2$, $O—C_{1-6}$-alkyl, $C_{1-4}$-alkylene-O—$C_{1-4}$-alkylene-O—$CH_3$, and $C_{0-4}$-alkylene-O—$(C_{1-4}$-alkylene-O$)_{1-4}$—$CH_3$; preferably $CH_3$, $CF_3$, $CF_2H$, $CFH_2$, and $OCH_3$; more preferably $CF_3$, $CF_2H$, and $CFH_2$; and most preferably $CF_3$.

Preferably, $C_{1-6}$-alkylene groups are unsubstituted.

According to the present invention, phenyl, 5 to 10-membered heteroaryl and 5 or 6-membered heteroaryl in each case independently from one another are unsubstituted or mono- or poly substituted, more preferably unsubstituted or mono- or disubstituted, with one or more substituents selected from the group consisting of F, Cl, Br, CN, $C_{1-6}$-alkyl, $C_{3-6}$-cycloalkyl, $CF_3$, $CF_2H$, $CFH_2$, $C_{1-6}$-alkylene-$CF_3$, $C_{1-6}$-alkylene-$CF_2H$, $C_{1-6}$-alkylene-$CFH_2$, $C_{1-6}$-alkylene-OH, $C_{1-6}$-alkylene-$OCH_3$, $C(O)—C_{1-6}$-alkyl, $OCF_3$, $OCF_2H$, $OCFH_2$, and $O—C_{1-6}$-alkyl; preferably F, $CH_3$, $CF_3$, $CF_2H$, $CFH_2$, and $OCH_3$; more preferably F, $CF_3$, $CF_2H$, and $CFH_2$; and most preferably F.

According to the present invention, L represents $CH_2$, $CH(CH_3)$ or $CH(CH_2CH_3)$. In a preferred embodiment, L represents $CH_2$, or $CH(CH_3)$; more preferably $CH_2$.

According to the present invention, $R^1$ represents $C_{3-10}$-cycloalkyl, or 4 to 10-membered heterocycloalkyl. Preferably, $R^1$ represents $C_{3-2}$-cycloalkyl or 5 or 6-membered heterocycloalkyl; more preferably $C_{3-6}$-cycloalkyl or 5 or 6-membered heterocycloalkyl.

Preferably, $R^1$ is selected from the group consisting of cyclopropyl, cyclobutyl, cyclopentyl, difluorocyclopentyl, cyclohexyl, difluorocyclohexyl, cycloheptyl, cycloheptyl, cyclooctyl, cyclononyl, cyclodecyl, oxetanyl, tetrahydrofuranyl, tetrahydropyranyl, morpholinyl, thiomorpholinyl, tetrahydrothiopyranyl, tetrahydrothiopyranyl 1,1-dioxide, oxepanyl, piperidinyl, piperidinonyl, azetidinyl, pyrrolidinyl, pyrrolidinonyl, 4-methylpiperazinyl, morpholinonyl, dioxanyl, piperazinyl, tetrahydropyrrolyl, azepanyl, dioxepanyl, oxazepanyl, diazepanyl, thiazolidinyl, tetrahydrothiophenyl, tetrahydropyridinyl, dithiolanyl, dihydropyrrolyl, dioxolanyl, dihydropyridinyl, dihydrofuranyl, dihydroisoxazolyl, dihydrooxazolyl, imidazolidinyl, isoxazolidinyl, oxazolidinyl, piperazinyl, N-methylpyridinonyl, pyrazolidinyl, pyranyl; dihydroquinolinyl, dihydroisoquinolinyl, dihydroindolinyl, dihydroisoindolyl, tetrahydroquinolinyl, tetrahydroisoquinolinyl and tetrahydroindolinyl.

In a preferred embodiment, $R^1$ represents $C_{3-10}$-cycloalkyl selected from the group consisting of cyclopropyl, cyclobutyl, cyclopentyl, cyclohexyl, cycloheptyl, and cyclooctyl;
wherein the $C_{3-10}$-cycloalkyl is unsubstituted or mono- or polysubstituted with F; and/or is unsubstituted or monosubstituted with one substituent selected from the group consisting of Cl, CN, $CH_3$, $CF_3$, $CHF_2$, $CH_2F$, OH, $OCH_3$, $OCF_3$, $OCF_2H$, $OCFH_2$, and $CH_2$—O—$CH_2CH_2$—O—$CH_3$, more preferably the $C_{3-10}$-cycloalkyl is unsubstituted or mono- or poly substituted with F; and/or is unsubstituted or monosubstituted with one substituent selected from the group consisting of $CH_3$, $CF_3$, $CHF_2$, and $CH_2F$, and most preferably the $C_{3-10}$-cycloalkyl is unsubstituted or mono- or polysubstituted with F, and/or unsubstituted or monosubstituted with $CH_3$;

or 4 to 10-membered heterocycloalkyl selected from the group consisting of oxetanyl, tetrahydrofuranyl, tetrahydropyranyl, morpholinyl, thiomorpholinyl, tetrahydrothiopyranyl, tetrahydrothiopyranyl 1,1-dioxide, oxepanyl, piperidinyl, piperidinonyl, azetidinyl, pyrrolidinyl, pyrrolidinonyl, 4-methylpiperazinyl, morpholinonyl, dioxanyl, piperazinyl, and tetrahydropyrrolyl;
wherein the 4 to 10-membered heterocycloalkyl is unsubstituted or mono- or polysubstituted with F; and/or is unsubstituted or monosubstituted with one substituent selected from the group consisting of Cl, CN, $CH_3$, $CF_3$, $CHF_2$, $CH_2F$, OH, $OCH_3$, $OCF_3$, $OCF_2H$, and $OCFH_2$, more preferably the 4 to 10-membered heterocycloalkyl is unsubstituted or mono- or polysubstituted with F; and/or is unsubstituted or monosubstituted with one substituent selected from the group consisting of $CH_3$, $CF_3$, $CHF_2$, and $CH_2F$, and most preferably the 4 to 10-membered heterocycloalkyl is unsubstituted or mono- or polysubstituted with F, and/or unsubstituted or monosubstituted with $CH_3$.

In another preferred embodiment, $R^1$ represents $C_{3-7}$-cycloalkyl selected from the group consisting of cyclopropyl, cyclobutyl, cyclopentyl, cyclohexyl, and cycloheptyl;
wherein the $C_{3-7}$-cycloalkyl is unsubstituted or mono- or polysubstituted with F; and/or is unsubstituted or monosubstituted with one substituent selected from the group consisting of Cl, CN, $CH_3$, $CF_3$, $CHF_2$, $CH_2F$, OH, $OCH_3$, $OCF_3$, $OCF_2H$, and $OCFH_2$; or 5 or 6-membered heterocycloalkyl selected from the group consisting of tetrahydrofuranyl, tetrahydropyranyl, morpholinyl, thiomorpholinyl, tetrahydrothiopyranyl, tetrahydrothiopyranyl 1,1-dioxide, piperidinyl, piperidinonyl, pyrrolidinyl, pyrrolidinonyl, 4-methylpiperazinyl, morpholinonyl, dioxanyl, piperazinyl, and tetrahydropyrrolyl;
wherein the 5 or 6-membered heterocycloalkyl is unsubstituted or mono- or polysubstituted with F; and/or is unsubstituted or monosubstituted with one substituent selected from the group consisting of Cl, CN, $CH_3$, $CF_3$, $CHF_2$, $CH_2F$, OH, $OCH_3$, $OCF_3$, $OCF_2H$, and $OCFH_2$.

In a more preferred embodiment, $R^1$ represents cyclopropyl, cyclobutyl, cyclopentyl, cyclohexyl, cycloheptyl, tetrahydrofuranyl, or tetrahydropyranyl;
wherein said cyclopropyl, cyclobutyl, cyclopentyl, cyclohexyl, cycloheptyl, tetrahydrofuranyl, or tetrahydropyranyl is unsubstituted or mono- or polysubstituted with F; and/or is unsubstituted or monosubstituted with $CH_3$ or $CF_3$; more preferably the cyclopropyl, cyclobutyl, cyclopentyl, cyclohexyl, cycloheptyl, tetrahydrofuranyl, or tetrahydropyranyl is disubstituted with F, and is unsubstituted or monosubstituted with $CH_3$.

According to the present invention, $R^2$ represents H or $C_{1-6}$-alkyl. Preferably, $R^2$ represents H, $CH_3$, or $CH_2CH_3$. In a particularly preferred embodiment, $R^2$ represents H.

According to the present invention, X represents phenyl, or 5 to 10-membered heteroaryl.

Preferably, X represents phenyl, fluorophenyl, pyridyl, pyrazolyl, pyrrolo[2,3-b]pyridyl, pyridonyl, thienyl, thiazolyl, 2,3-dihydrobenzo[d]isothiazolyl 1,1-dioxide, isoindolinonyl, pyrimidinyl, pyrazinyl, pyridazinyl, isoxazolyl, triazolyl, oxazolyl, oxadiazolyl, indazolyl, pyrazolopyridyl, pyrrolyl, imidazolyl, isothiazolyl, furanyl, thiadiazolyl, N-methylpyridinonyl, benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, imidazothiazolyl, indolizinyl, indolyl, isoquinolinyl, naphthyridinyl, phenazinyl, phenothiazinyl, phthalazinyl, purinyl, phenazinyl, tetrazolyl or triazinyl.

In another preferred embodiment, X represents phenyl, wherein phenyl is unsubstituted or mono- or polysubstituted, preferably unsubstituted or monosubstituted, with one or more substituents selected from the group consisting of F, Cl, Br, CN, $CH_3$, $CF_3$, $CHF_2$, $CH_2F$, OH, $OCH_3$, $OCF_3$, $OCF_2H$, and $OCFH_2$; preferably F, $CH_3$, and $CF_3$; more preferably F;

or 5 to 10-membered heteroaryl selected from the group consisting of pyridyl, pyrazolyl, pyrrolo[2,3-b]pyridyl, pyridonyl, thienyl, thiazolyl, 2,3-dihydrobenzo[d]isothiazolyl 1,1-dioxide, isoindolinonyl, pyrimidinyl, pyrazinyl, pyridazinyl, isoxazolyl, triazolyl, oxazolyl, oxadiazolyl, indazolyl, pyrazolopyridyl, pyrrolyl, imidazolyl, isothiazolyl, furanyl, and thiadiazolyl;
wherein said 5 to 10-membered heteroaryl is unsubstituted or mono- or polysubstituted, preferably unsubstituted or monosubstituted, with one or more substituents selected from the group consisting of F, Cl, Br, CN, $CH_3$, $CF_3$, $CHF_2$, $CH_2F$, OH, $OCH_3$, $OCF_3$, $OCF_2H$, and $OCFH_2$; preferably F, $CH_3$, and $CF_3$; more preferably F.

In a preferred embodiment, X represents phenyl, pyridyl, pyrazolyl, or pyrrolo[2,3-b]pyridyl; wherein said phenyl, pyridyl, pyrazolyl, or pyrrolo[2,3-b]pyridyl is unsubstituted or mono- or polysubstituted, preferably unsubstituted or monosubstituted, with F.

In a particularly preferred embodiment, X represents

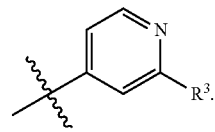

According to the present invention, $R^3$ represents $S(O)_2$—$C_{1-6}$-alkyl, $S(O)_2$—$(C_{3-6}$-cycloalkyl), $S(O)_2$-(4 to 6-membered heterocycloalkyl), $S(O)_2$-phenyl, $S(O)_2$-(5 or 6-membered heteroaryl), $S(O)$—$NH_2$, $S(O)$—$N(H)(C_{1-6}$-alkyl), $S(O)$—$N(C_{1-6}$-alkyl)$_2$, $S(O)_2$—$NH_2$, $S(O)_2$—$N(H)(C_{1-6}$-alkyl), $S(O)_2$—$N(H)(C_{3-6}$-cycloalkyl), $S(O)_2$—$N(C_{1-6}$-alkyl)$_2$, $C(O)$—$NH_2$, $C(O)$—$N(H)(C_{1-6}$-alkyl), $C(O)$—$N(H)(C_{3-6}$-cycloalkyl), $C(O)$—$N(C_{1-6}$-alkyl)$_2$, C(O)—N(C$_{1-6}$-alkyl)(C$_{3-6}$-cycloalkyl), OCF$_3$, OCF$_2$H, CN, OH, O—C$_{3-6}$-cycloalkyl, O-(4 to 6-membered heterocycloalkyl), S(O)—C$_{1-6}$-alkyl, S(O)—(C$_{3-6}$-cycloalkyl), S(O)-(4 to 6-membered heterocycloalkyl), S(O)-phenyl, or S(O)-(5 or 6-membered heteroaryl); preferably S(O)$_2$—C$_{1-6}$-alkyl, S(O)$_2$—(C$_{3-6}$-cycloalkyl), S(O)$_2$-(4 to 6-membered heterocycloalkyl), S(O)$_2$-phenyl, S(O)$_2$-(5 or 6-membered heteroaryl), S(O)$_2$—NH$_2$, S(O)—NH$_2$, S(O)—N(H)(C$_{1-6}$-alkyl), S(O)—N(C$_{1-6}$-alkyl)$_2$, C(O)—NH$_2$, C(O)—N(H)(C$_{1-6}$-alkyl), C(O)—N(H)(C$_{3-6}$-cycloalkyl), C(O)—N(C$_{1-6}$-alkyl)$_2$, C(O)—N(C$_{1-6}$-alkyl)(C$_{1-6}$-cycloalkyl), OCF$_3$, OCF$_2$H, CN, OH, O—C$_{3-6}$-cycloalkyl, O-(4 to 6-membered heterocycloalkyl), S(O)—C$_{1-6}$-alkyl, S(O)—(C$_{3-6}$-cycloalkyl), S(O)-(4 to 6-membered heterocycloalkyl), S(O)-phenyl, or S(O)-(5 or 6-membered heteroaryl); more preferably S(O)$_2$—C$_{1-6}$-alkyl, S(O)$_2$—(C$_{3-6}$-cycloalkyl), S(O)$_2$-(4 to 6-membered heterocycloalkyl), S(O)$_2$-phenyl, S(O)$_2$-(5 or 6-membered heteroaryl), S(O)$_2$—NH$_2$, C(O)—NH$_2$, C(O)—N(H)(C$_{1-6}$-alkyl), C(O)—N(H)(C$_{3-6}$-cycloalkyl), C(O)—N(C$_{1-6}$-alkyl)$_2$, C(O)—N(C$_{1-6}$-alkyl)(C$_{3-6}$-cycloalkyl), OH, S(O)—C$_{1-6}$-alkyl, S(O)—(C$_{3-6}$-cycloalkyl), S(O)-(4 to 6-membered heterocycloalkyl), S(O)-phenyl, or S(O)-(5 or 6-membered heteroaryl); and most preferably S(O)$_2$—C$_{1-6}$-alkyl, C(O)—NH$_2$, OH, S(O)—C$_{1-6}$-alkyl, or S(O)$_2$—NH$_2$; and in particular S(O)$_2$—C$_{1-6}$-alkyl, C(O)—NH$_2$, OH, or S(O)—C$_{1-6}$-alkyl.

In another preferred embodiment, R$^3$ represents S(O)$_2$—C$_{1-6}$-alkyl, S(O)$_2$—(C$_{3-6}$-cycloalkyl), S(O)$_2$-(4 to 6-membered heterocycloalkyl), S(O)$_2$-phenyl, S(O)$_2$-(5 or 6-membered heteroaryl), S(O)—NH$_2$, S(O)—N(H)(C$_{1-6}$-alkyl), S(O)—N(C$_{1-6}$-alkyl)$_2$, C(O)—NH$_2$, C(O)—N(H)(C$_{1-6}$-alkyl), C(O)—N(H)(C$_{3-6}$-cycloalkyl), C(O)—N(C$_{1-6}$-alkyl)$_2$, C(O)—N(C$_{1-6}$-alkyl)(C$_{3-6}$-cycloalkyl), OCF$_3$, OCF$_2$H, CN, OH, O—C$_{3-6}$-cycloalkyl, O-(4 to 6-membered heterocycloalkyl), S(O)—C$_{1-6}$-alkyl, S(O)—(C$_{3-6}$-cycloalkyl), S(O)-(4 to 6-membered heterocycloalkyl), S(O)-phenyl, or S(O)-(5 or 6-membered heteroaryl).

Preferably, R$^3$ represents S(O)$_2$—CH$_3$, S(O)$_2$-(cyclopropyl), S(O)$_2$-(oxetanyl), S(O)$_2$-phenyl, S(O)$_2$-(pyridyl), S(O)—NH$_2$, S(O)—N(H)(CH$_3$), S(O)—N(CH$_3$)$_2$, S(O)$_2$—NH$_2$, S(O)$_2$—N(H)(CH$_3$), S(O)$_2$—N(H)(cyclopropyl), S(O)$_2$—N(CH$_3$)$_2$, C(O)—NH$_2$, C(O)—N(H)(CH$_3$), C(O)—N(H)(cyclopropyl), C(O)—N(CH$_3$)$_2$, C(O)—N(CH$_3$)(cyclopropyl), OCF$_3$, OCF$_2$H, CN, OH, O-cyclopropyl, O-(oxetanyl), S(O)—CH$_3$, S(O)-(cyclopropyl), S(O)-(oxetanyl), S(O)-phenyl, or S(O)-(pyridyl); more preferably S(O)$_2$—CH$_3$, S(O)$_2$-(cyclopropyl), S(O)$_2$-(oxetanyl), S(O)$_2$-phenyl, S(O)$_2$-(pyridyl), S(O)$_2$—NH$_2$, S(O)—NH$_2$, S(O)—N(H)(CH$_3$), S(O)—N(CH$_3$)$_2$, C(O)—NH$_2$, C(O)—N(H)(CH$_3$), C(O)—N(H)(cyclopropyl), C(O)—N(CH$_3$)$_2$, C(O)—N(CH$_3$)(cyclopropyl), OCF$_3$, OCF$_2$H, CN, OH, O-cyclopropyl, 0-(oxetanyl), S(O)—CH$_3$, S(O)-(cyclopropyl), S(O)-(oxetanyl), S(O)-phenyl, or S(O)-(pyridyl).

In another preferred embodiment, R$^3$ represents S(O)$_2$—C$_{1-6}$-alkyl, S(O)$_2$—NH$_2$, C(O)NH$_2$, OH or S(O)—C$_{1-6}$-alkyl; more preferably S(O)$_2$—C$_{1-6}$-alkyl, C(O)NH$_2$, OH or S(O)—C$_{1-6}$-alkyl. In a particularly preferred embodiment, R$^3$ represents S(O)$_2$—CH$_3$, S(O)$_2$—NH$_2$, C(O)NH$_2$, OH, or S(O)—CH$_3$; more preferably S(O)$_2$—CH$_3$, C(O)NH$_2$, or OH.

In a particularly preferred embodiment, X represents

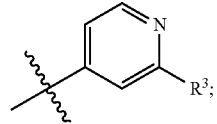

wherein R$^3$ represents S(O)$_2$—CH$_3$ or C(O)NH$_2$.

According to the present invention, R$^4$ and R$^5$ independently from one another represent H, F, Cl, Br, CN, CHF$_2$, CH$_2$F, CF$_3$, C$_{1-6}$-alkyl, C$_{3-10}$-cycloalkyl, C$_{1-6}$-alkylene-C$_{3-10}$-cycloalkyl, 4 to 10-membered heterocycloalkyl, C$_{1-6}$-alkylene-(4 to 10-membered heterocycloalkyl), NH$_2$, N(H)(C$_{1-6}$-alkyl), N(C$_{1-6}$-alkyl)$_2$, O—C$_{1-6}$-alkyl, O—C$_{3-10}$-cycloalkyl, O—C$_{1-6}$-alkylene-C$_{3-10}$-cycloalkyl, O-(4 to 10-membered heterocycloalkyl), or O—C$_{1-6}$-alkylene-(4 to 10-membered heterocycloalkyl). Preferably, R$^4$ and R$^5$ independently from one another represent H, F, Cl, Br, CN, CHF$_2$, CH$_2$F, CF$_3$, C$_{1-6}$-alkyl, C$_{1-6}$-alkylene-C$_{3-10}$-cycloalkyl, C$_{1-6}$-alkylene-(4 to 10-membered heterocycloalkyl), NH$_2$, N(H)(C$_{1-6}$-alkyl), N(C$_{1-6}$-alkyl)$_2$, O—C$_{1-6}$-alkyl, O—C$_{3-10}$-cycloalkyl, O—C$_{1-6}$-alkylene-C$_{3-10}$-cycloalkyl, O-(4 to 10-membered heterocycloalkyl), or O—C$_{1-6}$-alkylene-(4 to 10-membered heterocycloalkyl).

Preferably, at least one of R$^4$ and R$^5$ does not represent H. In another preferred embodiment, R$^4$ and R$^5$ do not represent H.

Preferably, R$^4$ and R$^5$ independently from one another represent H, F, Cl, CN, CHF$_2$, CH$_2$F, CF$_3$, CH$_2$CHF$_2$, CH$_2$CH$_2$F, CH$_2$CF$_3$, CF$_2$CH$_3$, CHFCH$_3$, CF$_2$CF$_3$, CHFCF$_3$, CH(CHF$_2$)(CH$_3$), CH(CH$_2$F)(CH$_3$), CH(CF$_3$)(CH$_3$), CH$_3$, CH$_2$CH$_3$, CH(CH$_3$)$_2$, cyclopropyl, CH$_2$-cyclopropyl, CF$_2$-cyclopropyl, cyclobutyl, CH$_2$-cyclobutyl, CF$_2$-cyclobutyl, oxetanyl, CH$_2$-oxetanyl, CF$_2$-oxetanyl, tetrahydrofuranyl, CH$_2$-tetrahydrofuranyl, CF$_2$-tetrahydrofuranyl, NH$_2$, N(H)(CH$_3$), N(CH$_3$)$_2$, O—CHF$_2$, O—CH$_2$F, O—CF$_3$, O—CH$_2$CHF$_2$, O—CH$_2$CH$_2$F, O—CH$_2$CF$_3$, O—CF$_2$CH$_3$, O—CHFCH$_3$, O—CF$_2$CF$_3$, O—CHFCF$_3$, O—CH$_3$, O—CH$_2$CH$_3$, O—CH(CH$_3$)$_2$, O-cyclopropyl, O—CH$_2$-cyclopropyl, O-cyclobutyl, O—CH$_2$-cyclobutyl, O-oxetanyl, O—CH$_2$-oxetanyl, 0-tetrahydrofuranyl, or O—CH$_2$-tetrahydrofuranyl; more preferably H, F, Cl, CN, CHF$_2$, CH$_2$F, CF$_3$, CH$_2$CHF$_2$, CH$_2$CH$_2$F, CH$_2$CF$_3$, CF$_2$CH$_3$, CHFCH$_3$, CF$_2$CF$_3$, CHFCF$_3$, CH(CHF$_2$)(CH$_3$), CH(CH$_2$F)(CH$_3$), CH(CF$_3$)(CH$_3$), CH$_3$, CH$_2$CH$_3$, CH(CH$_3$)$_2$, CH$_2$-cyclopropyl, CF$_2$-cyclopropyl, CH$_2$-cyclobutyl, CF$_2$-cyclobutyl, CH$_2$-oxetanyl, CF$_2$-oxetanyl, CH$_2$-tetrahydrofuranyl, CF$_2$-tetrahydrofuranyl, NH$_2$, N(H)(CH$_3$), N(CH$_3$)$_2$, O—CHF$_2$, O—CH$_2$F, O—CF$_3$, O—CH$_2$CHF$_2$, O—CH$_2$CH$_2$F, O—CH$_2$CF$_3$, O—CF$_2$CH$_3$, O—CHFCH$_3$, O—CF$_2$CF$_3$, O—CHFCF$_3$, O—CH$_3$, O—CH$_2$CH$_3$, O—CH(CH$_3$)$_2$, O-cyclopropyl, O—CH$_2$-cyclopropyl, O-cyclobutyl, O—CH$_2$-cyclobutyl, O-oxetanyl, O—CH$_2$-oxetanyl, O-tetrahydrofuranyl, or O—CH$_2$-tetrahydrofuranyl.

Preferably, R$^4$ and R$^5$ independently from one another represent H, F, Cl, CN, CHF$_2$, CH$_2$F, CF$_3$, CH$_2$CHF$_2$, CH$_2$CH$_2$F, CH$_2$CF$_3$, CF$_2$CH$_3$, CHFCH$_3$, CF$_2$CF$_3$, CHFCF$_3$, CH(CHF$_2$)(CH$_3$), CH(CH$_2$F)(CH$_3$), CH(CF$_3$)(CH$_3$), CH$_3$, CH$_2$CH$_3$, CH(CH$_3$)$_2$, cyclopropyl, CH$_2$-cyclopropyl, CF$_2$-cyclopropyl, O—CHF$_2$, O—CH$_2$F, O—CF$_3$, O—CH$_2$CHF$_2$, O—CH$_2$CH$_2$F, O—CH$_2$CF$_3$, O—CF$_2$CH$_3$, O—CHFCH$_3$, O—CF$_2$CF$_3$, O—CHFCF$_3$, O—CH$_3$, O—CH$_2$CH$_3$, O—CH(CH$_3$)$_2$, O-cyclopropyl, or O—CH$_2$-cyclopropyl. More preferably, R$^4$ and R$^5$ independently from one another represent H, F, Cl, CN, CHF$_2$, CH$_2$F, CF$_3$, CH$_2$CHF$_2$, CH$_2$CH$_2$F, CH$_2$CF$_3$, CF$_2$CH$_3$, CHFCH$_3$, $CF_2CF_3$, $CHFCF_3$, $CH(CHF_2)(CH_3)$, $CH(CH_2F)(CH_3)$, $CH(CF_3)(CH_3)$, $CH_3$, $CH_2CH_3$, $CH(CH_3)_2$, $CH_2$-cyclopropyl, $CF_2$-cyclopropyl, O—$CHF_2$, O—$CH_2F$, O—$CF_3$, O—$CH_2CHF_2$, O—$CH_2CH_2F$, O—$CH_2CF_3$, O—$CF_2CH_3$, O—$CHFCH_3$, O—$CF_2CF_3$, O—$CHFCF_3$, O—$CH_3$, O—$CH_2CH_3$, O—$CH(CH_3)_2$, O-cyclopropyl, or O—$CH_2$-cyclopropyl.

In another preferred embodiment, $R^4$ represents H, F, Cl, CN, $CHF_2$, $CH_2F$, $CF_3$, $CH_2CHF_2$, $CH_2CH_2F$, $CH_2CF_3$, $CF_2CH_3$, $CHFCH_3$, $CF_2CF_3$, $CHFCF_3$, $CH(CHF_2)(CH_3)$, $CH(CH_2F)(CH_3)$, $CH(CF_3)(CH_3)$, $CH_3$, $CH_2CH_3$, $CH(CH_3)_2$, cyclopropyl, $CH_2$-cyclopropyl, $CF_2$-cyclopropyl, O—$CHF_2$, O—$CH_2F$, O—$CF_3$, O—$CH_2CHF_2$, O—$CH_2CH_2F$, O—$CH_2CF_3$, O—$CF_2CH_3$, O—$CHFCH_3$, O—$CF_2CF_3$, O—$CHFCF_3$, O—$CH_3$, O—$CH_2CH_3$, O—$CH(CH_3)_2$, O- cyclopropyl, or O—$CH_2$-cyclopropyl; more preferably F, Cl, CN, $CHF_2$, $CH_2F$, $CF_3$, $CH_2CHF_2$, $CH_2CH_2F$, $CH_2CF_3$, $CF_2CH_3$, $CHFCH_3$, $CF_2CF_3$, $CHFCF_3$, $CH(CHF_2)(CH_3)$, $CH(CH_2F)(CH_3)$, $CH(CF_3)(CH_3)$, $CH_3$, $CH_2CH_3$, $CH(CH_3)_2$, $CH_2$-cyclopropyl, $CF_2$-cyclopropyl, O—$CHF_2$, O—$CH_2F$, O—$CF_3$, O—$CH_2CHF_2$, O—$CH_2CH_2F$, O—$CH_2CF_3$, O—$CF_2CH_3$, O—$CHFCH_3$, O—$CF_2CF_3$, O—$CHFCF_3$, O—$CH_3$, O—$CH_2CH_3$, O—$CH(CH_3)_2$, O-cyclopropyl, or O—$CH_2$-cyclopropyl; still more preferably Cl, $CHF_2$, $CF_3$, $CH_2CF_3$, $CH_2CF_3$, $CF_2CF_3$, $CH(CHF_2)(CH_3)$, $CH(CF_3)(CH_3)$, $CH_3$, $CH_2CH_3$, $CH(CH_3)_2$, $CH_2$-cyclopropyl, $CF_2$-cyclopropyl, O—$CHF_2$, O—$CF_3$, O—$CF_2CH_3$, O—$CH_3$, O—$CH_2CH_3$, O—$CH(CH_3)_2$, or O—$CH_2$-cyclopropyl.

In still another preferred embodiment, $R^5$ represents H, F, Cl, CN, $CHF_2$, $CH_2F$, $CF_3$, $CH_2CHF_2$, $CH_2CH_2F$, $CH_2CF_3$, $CF_2CH_3$, $CHFCH_3$, $CF_2CF_3$, $CHFCF_3$, $CH(CHF_2)(CH_3)$, $CH(CH_2F)(CH_3)$, $CH(CF_3)(CH_3)$, $CH_3$, $CH_2CH_3$, $CH(CH_3)_2$, cyclopropyl, $CH_2$-cyclopropyl, $CF_2$-cyclopropyl, O—$CHF_2$, O—$CH_2F$, O—$CF_3$, O—$CH_2CHF_2$, O—$CH_2CH_2F$, O—$CH_2CF_3$, O—$CF_2CH_3$, O—$CHFCH_3$, O—$CF_2CF_3$, O—$CHFCF_3$, O—$CH_3$, O—$CH_2CH_3$, O—$CH(CH_3)_2$, O- cyclopropyl, or O—$CH_2$-cyclopropyl; more preferably F, Cl, CN, $CHF_2$, $CH_2F$, $CF_3$, $CH_2CHF_2$, $CH_2CH_2F$, $CH_2CF_3$, $CF_2CH_3$, $CHFCH_3$, $CF_2CF_3$, $CHFCF_3$, $CH(CHF_2)(CH_3)$, $CH(CH_2F)(CH_3)$, $CH(CF_3)(CH_3)$, $CH_3$, $CH_2CH_3$, $CH(CH_3)_2$, $CH_2$-cyclopropyl, $CF_2$-cyclopropyl, O—$CHF_2$, O—$CH_2F$, O—$CF_3$, O—$CH_2CHF_2$, O—$CH_2CH_2F$, O—$CH_2CF_3$, O—$CF_2CH_3$, O—$CHFCH_3$, O—$CF_2CF_3$, O—$CHFCF_3$, O—$CH_3$, O—$CH_2CH_3$, O—$CH(CH_3)_2$, O-cyclopropyl, or O—$CH_2$-cyclopropyl; still more preferably Cl, $CHF_2$, $CF_3$, $CH_3$, or $CH(CH_3)_2$.

In another preferred embodiment, $R^3$ represents $S(O)_2$—$C_{1-6}$-alkyl, $S(O)_2$—($C_{3-6}$-cycloalkyl), $S(O)_2$-(4 to 6-membered heterocycloalkyl), $S(O)_2$-phenyl, $S(O)_2$-(5 or 6-membered heteroaryl), $S(O)$—$NH_2$, $S(O)$—$N(H)(C_{1-6}$-alkyl), $S(O)$—$N(C_{1-6}$-alkyl)$_2$, $C(O)$—$NH_2$, $C(O)$—$N(H)(C_{1-6}$-alkyl), $C(O)$—$N(H)(C_{3-6}$-cycloalkyl), $C(O)$—$N(C_{1-6}$-alkyl)$_2$, $C(O)$—$N(C_{1-6}$-alkyl)($C_{3-6}$-cycloalkyl), $OCF_3$, $OCF_2H$, CN, OH, O—$C_{3-6}$-cycloalkyl, O-(4 to 6-membered heterocycloalkyl), $S(O)$—$C_{1-6}$-alkyl, $S(O)$—($C_{1-6}$-cycloalkyl), $S(O)$-(4 to 6-membered heterocycloalkyl), $S(O)$-phenyl, or $S(O)$-(5 or 6-membered heteroaryl); and/or $R^4$ and $R^5$ independently from one another represent H, F, Cl, Br, CN, $CHF_2$, $CH_2F$, $CF_3$, $C_{1-6}$-alkyl, $C_{1-6}$-alkylene-$C_{3-10}$-cycloalkyl, $C_{1-6}$-alkylene-(4 to 10-membered heterocycloalkyl), $NH_2$, $N(H)(C_{1-6}$-alkyl), $N(C_{1-6}$-alkyl)$_2$, O—$C_{1-6}$-alkyl, O—$C_{3-10}$-cycloalkyl, O—$C_{1-6}$-alkylene-$C_{3-10}$-cycloalkyl, O-(4 to 10-membered heterocycloalkyl), or O—$C_{1-6}$-alkylene-(4 to 10-membered heterocycloalkyl).

In a particularly preferred embodiment, $R^1$ represents cyclopropyl, cyclobutyl, cyclopentyl, cyclohexyl, cycloheptyl, tetrahydrofuranyl, or tetrahydropyranyl;

wherein said cyclopropyl, cyclobutyl, cyclopentyl, cyclohexyl, cycloheptyl, tetrahydrofuranyl, or tetrahydropyranyl is unsubstituted or mono- or polysubstituted with F, and/or unsubstituted or monosubstituted with $CH_3$ or $CF_3$; and/or $R^2$ represents H; and/or L represents $CH_2$ or $CH(CH_3)$; and/or X represents phenyl, pyridyl, pyrazolyl, or pyrrolo[2,3-b]pyridyl; wherein said phenyl, pyridyl, pyrazolyl, or pyrrolo[2,3-b]pyridyl is unsubstituted or mono- or polysubstituted, preferably unsubstituted or monosubstituted, with F; and/or $R^3$ represents $S(O)_2$—$CH_3$, $C(O)NH_2$, or OH; and/or $R^4$ and $R^5$ independently from one another represent H, F, Cl, CN, $CHF_2$, $CH_2F$, $CF_3$, $CH_2CHF_2$, $CH_2CH_2F$, $CH_2CF_3$, $CF_2CH_3$, $CHFCH_3$, $CF_2CF_3$, $CHFCF_3$, $CH(CHF_2)(CH_3)$, $CH(CH_2F)(CH_3)$, $CH(CF_3)(CH_3)$, $CH_3$, $CH_2CH_3$, $CH(CH_3)_2$, cyclopropyl, $CH_2$-cyclopropyl, $CF_2$-cyclopropyl, O—$CHF_2$, O—$CH_2F$, O—$CF_3$, $CH_2CHF_2$, O—$CH_2CH_2F$, O—$CH_2CF_3$, O—$CF_2CH_3$, O—$CHFCH_3$, O—$CF_2CF_3$, O—$CHFCF_3$, O—$CH_3$, O—$CH_2CH_3$, O—$CH(CH_3)_2$, O-cyclopropyl, or O—$CH_2$-cyclopropyl; wherein at least one of $R^4$ and $R^5$ does not represent H.

In a particularly preferred embodiment, $R^1$ represents cyclopropyl, cyclobutyl, cyclopentyl, cyclohexyl, cycloheptyl, tetrahydrofuranyl, or tetrahydropyranyl;

wherein said cyclopropyl, cyclobutyl, cyclopentyl, cyclohexyl, cycloheptyl, tetrahydrofuranyl, or tetrahydropyranyl is unsubstituted or mono- or polysubstituted with F, and/or unsubstituted or monosubstituted with $CH_3$, $OCH_3$, or $CF_3$; and/or $R^2$ represents H; and/or L represents $CH_2$ or $CH(CH_3)$; and/or X represents phenyl, pyridyl, pyrazolyl, or pyrrolo[2,3-b]pyridyl; wherein said phenyl, pyridyl, pyrazolyl, or pyrrolo[2,3-b]pyridyl is unsubstituted or mono- or polysubstituted, preferably unsubstituted or monosubstituted, with F; and/or $R^3$ represents $S(O)_2$—$CH_3$, $S(O)_2$—$NH_2$, $C(O)NH_2$, OH, $S(O)$—$NH_2$, or $S(O)$—$CH_3$; and/or $R^4$ represents $CHF_2$, $CH_2F$, $CF_3$, $CH_2CHF_2$, $CH_2CH_2F$, $CH_2CF_3$, $CF_2CH_3$, $CHFCH_3$, $CF_2CF_3$, $CHFCF_3$, $CH(CHF_2)(CH_3)$, $CH(CH_2F)(CH_3)$, $CH(CF_3)(CH_3)$, $CH_3$, $CH_2CH_3$, cyclopropyl, $CF_2$-cyclopropyl, $CHF_2$, O—$CH_2F$, O—$CF_3$, O—$CH_2CHF_2$, O—$CH_2CH_2F$, O—$CH_2CF_3$, O—$CF_2CH_3$, O—$CHFCH_3$, O—$CF_2CF_3$, or O—$CHFCF_3$; and/or $R^5$ represents H, F, Cl, CN, $CHF_2$, $CH_2F$, $CF_3$, $CH_3$, $CH_2CH_3$, $CH(CH_3)_2$, cyclopropyl, or $CH_2$-cyclopropyl.

In a particularly preferred embodiment, $R^1$ represents cyclopropyl, cyclobutyl, cyclopentyl, cyclohexyl, or cycloheptyl;

wherein said cyclopropyl, cyclobutyl, cyclopentyl, cyclohexyl, or cycloheptyl is unsubstituted or mono- or polysubstituted with F, and/or unsubstituted or monosubstituted with $CH_3$, $OCH_3$ or $CF_3$;

$R^2$ represents H;

L represents $CH_2$ or $CH(CH_3)$;

X represents

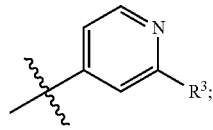

R³ represents S(O)₂—CH₃, S(O)₂—NH₂, C(O)NH₂, OH, S(O)—NH₂, or S(O)—CH₃; and/or
R⁴ represents CHF₂, CH₂F, CF₃, CH₂CHF₂, CH₂CH₂F, CH₂CF₃, CF₂CH₃, CHFCH₃, CF₂CF₃, CHFCF₃, CH(CHF₂)(CH₃), CH(CH₂F)(CH₃), CH(CF₃)(CH₃), CH₂CH₃, cyclopropyl, or CF₂-cyclopropyl; and/or
R⁵ represents F, Cl, CN, CHF₂, CH₂F, CF₃, CH₃, CH₂CH₃, CH(CH₃)₂, cyclopropyl, or CH₂-cyclopropyl.

In a particularly preferred embodiment,
R¹ represents cyclopropyl, cyclobutyl, or cyclopentyl;
wherein said cyclopropyl, cyclobutyl, or cyclopentyl is monosubstituted with CF₃, OCH₃, and/or CH₃; and/or disubstituted with F;
R² represents H;
L represents CH₂ or CH(CH₃), preferably CH₂;
X represents

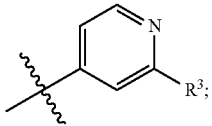

R³ represents S(O)₂—CH₃, S(O)₂—NH₂, C(O)NH₂, S(O)—NH₂, or S(O)—CH₃; and/or
R⁴ represents CHF₂, CH₂CHF₂, CF₂CH₃, CHFCH₃, CH(CHF₂)(CH₃), CH₂CH₃, cyclopropyl, or CF₂-cyclopropyl, preferably CF₂CH₃; and/or
R⁵ represents F, Cl, CHF₂, CF₃, CH₃, CH₂CH₃, CH(CH₃)₂, cyclopropyl, or CH₂-cyclopropyl, preferably Cl CH₃, CHF₂, or CF₃.

In a particularly preferred embodiment, the compound according to the present invention is selected from the group consisting of

| | |
|---|---|
| SC-01 | 2-(cyclohexylmethyl)-N-(3-methylsulfonylphenyl)-5-(trifluoromethyl)pyrazole-3-carboxamide |
| SC-02 | 2-[(4,4-difluorocyclohexyl)methyl]-N-(3-methylsulfonylphenyl)-5-(trifluoromethyl)pyrazole-3-carboxamide |
| SC-03 | 2-(cyclopentylmethyl)-N-(3-methylsulfonylphenyl)-5-(trifluoromethyl)pyrazole-3-carboxamide |
| SC-04 | N-(3-methylsulfonylphenyl)-2-(oxan-4-ylmethyl)-5-(trifluoromethyl)pyrazole-3-carboxamide |
| SC-05 | 2-[(4,4-difluorocyclohexyl)methyl]-N-(3-methylsulfonylphenyl)-4-(trifluoromethyl)pyrazole-3-carboxamide |
| SC-06 | 2-(cyclohexylmethyl)-4,5-dimethyl-N-(3-methylsulfonylphenyl)pyrazole-3-carboxamide |
| SC-07 | 1-(cyclohexylmethyl)-3,4-dimethyl-N-(2-oxo-1,2-dihydropyridin-4-yl)-1H-pyrazole-5-carboxamide |
| SC-08 | 2-(cyclohexylmethyl)-4-fluoro-N-(3-methylsulfonylphenyl)pyrazole-3-carboxamide |
| SC-09 | 1-(cyclohexylmethyl)-3-(difluoromethyl)-N-(3-(methylsulfonyl)phenyl)-1H-pyrazole-5-carboxamide |
| SC-10 | 4-cyano-2-(cyclohexylmethyl)-N-(3-methylsulfonylphenyl)pyrazole-3-carboxamide |
| SC-11 | 2-(cyclohexylmethyl)-5-methyl-N-(3-methylsulfonylphenyl)pyrazole-3-carboxamide |
| SC-12 | 2-(cyclohexylmethyl)-5-cyclopropyl-N-(3-methylsulfonylphenyl)pyrazole-3-carboxamide |
| SC-13 | 2-[(4,4-difluorocyclohexyl)methyl]-N-(4-fluoro-3-methylsulfonylphenyl)-4-(trifluoromethyl)pyrazole-3-carboxamide |
| SC-14 | 2-[(4,4-difluorocyclohexyl)methyl]-N-(2-methylsulfonylpyridin-4-yl)-4-(trifluoromethyl)pyrazole-3-carboxamide |
| SC-15 | 2-[(4,4-difluorocyclohexyl)methyl]-N-(5-methylsulfonylpyridin-3-yl)-4-(trifluoromethyl)pyrazole-3-carboxamide |
| SC-16 | 2-[(4,4-difluorocyclohexyl)methyl]-N-(2-fluoro-3-methylsulfonylphenyl)-4-(trifluoromethyl)pyrazole-3-carboxamide |
| SC-17 | 2-(cyclohexylmethyl)-5-methoxy-N-(3-methylsulfonylphenyl)pyrazole-3-carboxamide |
| SC-18 | 2-(cyclohexylmethyl)-N-(3-methylsulfonylphenyl)-4-propan-2-ylpyrazole-3-carboxamide |
| SC-19 | 2-(cyclohexylmethyl)-4-cyclopropyl-N-(3-methylsulfonylphenyl)pyrazole-3-carboxamide |
| SC-21 | N-(4-carbamoyl-3-fluorophenyl)-1-[(4,4-difluorocyclohexyl)methyl]-4-(trifluoromethyl)-1H-pyrazole-5-carboxamide |
| SC-22 | 2-[(4,4-difluorocyclohexyl)methyl]-N-(2-fluoro-5-methylsulfonylphenyl)-4-(trifluoromethyl)pyrazole-3-carboxamide |
| SC-23 | 2-[(3,3-difluorocyclohexyl)methyl]-N-(3-methylsulfonylphenyl)-4-(trifluoromethyl)pyrazole-3-carboxamide |
| SC-24 | 2-(cyclobutylmethyl)-N-(3-methylsulfonylphenyl)-4-(trifluoromethyl)pyrazole-3-carboxamide |
| SC-25 | 2-(cyclopentylmethyl)-N-(3-methylsulfonylphenyl)-4-(trifluoromethyl)pyrazole-3-carboxamide |
| SC-26 | 2-(cyclohexylmethyl)-N-(3-methylsulfonylphenyl)-4-(trifluoromethyl)pyrazole-3-carboxamide |
| SC-27 | 2-(cycloheptylmethyl)-N-(3-methylsulfonylphenyl)-4-(trifluoromethyl)pyrazole-3-carboxamide |
| SC-28 | N-(3-methylsulfonylphenyl)-2-(oxan-4-ylmethyl)-4-(trifluoromethyl)pyrazole-3-carboxamide |
| SC-29 | 2-(1-cyclohexylethyl)-N-(3-methylsulfonylphenyl)-4-(trifluoromethyl)pyrazole-3-carboxamide |
| SC-30 | 1-(cyclohexylmethyl)-N-(2-oxo-1,2-dihydropyridin-4-yl)-4-(trifluoromethyl)-1H-pyrazole-5-carboxamide |
| SC-31 | 2-(cycloheptylmethyl)-N-(2-hydroxypyridin-4-yl)-4-(trifluoromethyl)pyrazole-3-carboxamide |
| SC-32 | 2-(1-cyclohexylethyl)-N-(2-hydroxypyridin-4-yl)-4-(trifluoromethyl)pyrazole-3-carboxamide |
| SC-33 | 2-(cyclohexylmethyl)-N-(3-sulfamoylphenyl)-4-(trifluoromethyl)pyrazole-3-carboxamide |
| SC-35 | N-(3-carbamoyl-4-fluorophenyl)-1-(cyclohexylmethyl)-4-(trifluoromethyl)-1H-pyrazole-5-carboxamide |
| SC-36 | 2-(cyclohexylmethyl)-N-(1-methylsulfonylpyrazol-4-yl)-4-(trifluoromethyl)pyrazole-3-carboxamide |

-continued

| | |
|---|---|
| SC-37 | 2-(cyclohexylmethyl)-4-methyl-N-(3-methylsulfonylphenyl)pyrazole-3-carboxamide |
| SC-38 | 5-cyano-2-(cyclohexylmethyl)-N-(3-methylsulfonylphenyl)pyrazole-3-carboxamide |
| SC-39 | N-(3-carbamoyl-4-fluorophenyl)-2-[(4,4-difluorocyclohexyl)methyl]-4-(trifluoromethyl)pyrazole-3-carboxamide |
| SC-41 | N-(3-carbamoylphenyl)-2-[(4,4-difluorocyclohexyl)methyl]-4-(trifluoromethyl)pyrazole-3-carboxamide |
| SC-42 | 2-[(4,4-difluorocyclohexyl)methyl]-N-(3-fluoro-5-methylsulfonylphenyl)-4-(trifluoromethyl)pyrazole-3-carboxamide |
| SC-43 | 2-[(4,4-difluorocyclohexyl)methyl]-N-(3-sulfamoylphenyl)-4-(trifluoromethyl)pyrazole-3-carboxamide |
| SC-44 | 2-[(4,4-difluorocyclohexyl)methyl]-4,5-dimethyl-N-(3-methylsulfonylphenyl)pyrazole-3-carboxamide |
| SC-45 | 3,4-dimethyl-N-(3-sulfamoylphenyl)-1-((tetrahydro-2H-pyran-4-yl)methyl)-1H-pyrazole-5-carboxamide |
| SC-46 | 2-(cyclohexylmethyl)-5-methyl-N-(3-methylsulfonylphenyl)-4-(trifluoromethyl)pyrazole-3-carboxamide |
| SC-47 | N-(3-carbamoyl-4-fluorophenyl)-2-[(4,4-difluorocyclohexyl)methyl]-5-methyl-4-(trifluoromethyl)pyrazole-3-carboxamide |
| SC-48 | 2-[(4,4-difluorocyclohexyl)methyl]-N-(4-fluoro-3-sulfamoylphenyl)-4,5-dimethylpyrazole-3-carboxamide |
| SC-49 | 2-[(4,4-difluorocyclohexyl)methyl]-N-(4-fluoro-3-sulfamoylphenyl)-4-(trifluoromethyl)pyrazole-3-carboxamide |
| SC-50 | 4-[[2-[(4,4-difluorocyclohexyl)methyl]-4-(trifluoromethyl)pyrazole-3-carbonyl]amino]pyridine-2-carboxamide |
| SC-51 | 2-[(4,4-difluorocyclohexyl)methyl]-4,5-dimethyl-N-(3-sulfamoylphenyl)pyrazole-3-carboxamide |
| SC-52 | N-(3-(methylsulfonyl)phenyl)-1-((tetrahydro-2H-pyran-3-yl)methyl)-4-(trifluoromethyl)-1H-pyrazole-5-carboxamide |
| SC-53 | 2-(cyclohexylmethyl)-N-(1-methylsulfonylpyrrolo[2,3-b]pyridin-3-yl)-4-(trifluoromethyl)pyrazole-3-carboxamide |
| SC-54 | 5-methyl-N-(3-methylsulfonylphenyl)-2-(oxan-3-ylmethyl)-4-(trifluoromethyl)pyrazole-3-carboxamide |
| SC-55 | 5-methyl-N-(3-methylsulfonylphenyl)-2-(oxan-2-ylmethyl)-4-(trifluoromethyl)pyrazole-3-carboxamide |
| SC-56 | 5-methyl-N-(3-methylsulfonylphenyl)-2-(oxolan-2-ylmethyl)-4-(trifluoromethyl)pyrazole-3-carboxamide |
| SC-57 | 2-[(4,4-difluorocyclohexyl)methyl]-5-methyl-N-(3-sulfamoylphenyl)-4-(trifluoromethyl)pyrazole-3-carboxamide |
| SC-60 | 2-[(3,3-difluorocyclopentyl)methyl]-N-(3-sulfamoylphenyl)-4-(trifluoromethyl)pyrazole-3-carboxamide |
| SC-61 | N-(3-carbamoylphenyl)-2-[(4,4-difluorocyclohexyl)methyl]-5-methyl-4-(trifluoromethyl)pyrazole-3-carboxamide |
| SC-62 | 2-[(4,4-difluorocyclohexyl)methyl]-5-methyl-N-(3-methylsulfonylphenyl)-4-(trifluoromethyl)pyrazole-3-carboxamide |
| SC-63 | 3-methyl-N-(3-(methylsulfonyl)phenyl)-1-((tetrahydrofuran-3-yl)methyl)-4-(trifluoromethyl)-1H-pyrazole-5-carboxamide |
| SC-64 | 2-(cyclohexylmethyl)-N-(2-hydroxypyridin-4-yl)-5-methyl-4-(trifluoromethyl)pyrazole-3-carboxamide |
| SC-65 | N-(3-carbamoyl-4-fluorophenyl)-2-[(4,4-difluorocyclohexyl)methyl]-4,5-dimethylpyrazole-3-carboxamide |
| SC-66 | N-(2-hydroxypyridin-4-yl)-5-methyl-2-(oxan-4-ylmethyl)-4-(trifluoromethyl)pyrazole-3-carboxamide |
| SC-67 | N-(2-hydroxypyridin-4-yl)-3-methyl-1-((tetrahydro-2H-pyran-3-yl)methyl)-4-(trifluoromethyl)-1H-pyrazole-5-carboxamide |
| SC-68 | N-(2-hydroxypyridin-4-yl)-3-methyl-1-((tetrahydro-2H-pyran-2-yl)methyl)-4-(trifluoromethyl)-1H-pyrazole-5-carboxamide |
| SC-69 | 2-[(4,4-difluorocyclohexyl)methyl]-N-(2-sulfamoylpyridin-4-yl)-4-(trifluoromethyl)pyrazole-3-carboxamide |
| SC-73 | N-(3-carbamoyl-4-fluorophenyl)-2-[(3,3-difluorocyclopentyl)methyl]-4-(trifluoromethyl)pyrazole-3-carboxamide |
| SC-77 | 4-[[2-[(4,4-difluorocyclohexyl)methyl]-4,5-dimethylpyrazole-3-carbonyl]amino]pyridine-2-carboxamide |
| SC-78 | (1-((3,3-difluorocyclopentyl)methyl)-N-(3-sulfamoylphenyl)-4-(trifluoromethyl)-1H-pyrazole-5-carboxamide |
| SC-80 | 1-((3,3-difluorocyclopentyl)methyl)-N-(2-sulfamoyipyridin-4-yl)-4-(trifluoromethyl)-1H-pyrazole-5-carboxamide |
| SC-82 | 1-((3,3-difluorocyclopentyl)methyl)-N-(2-(methylsulfonyl)pyridin-4-yl)-4-(trifluoromethyl)-1H-pyrazole-5-carboxamide |
| SC-84 | 4-(1-((4,4-difluorocyclohexyl)methyl)-3-methyl-4-(trifluoromethyl)-1H-pyrazole-5-carboxamido)picolinamide |
| SC-85 | 1-((4,4-difluorocyclohexyl)methyl)-3-methyl-N-(2-(methylsulfonyl)pyridin-4-yl)-4-(trifluoromethyl)-1H-pyrazole-5-carboxamide |
| SC-86 | 4-(1-((4,4-difluorocyclohexyl)methyl)-4-(difluoromethyl)-3-methyl-1H-pyrazole-5-carboxamido)picolinamide |
| SC-87 | 1-((4,4-difluorocyclohexyl)methyl)-4-(difluoromethyl)-3-methyl-N-(2-(methylsulfonyl)pyridin-4-yl)-1H-pyrazole-5-carboxamide |

| | -continued |
|---|---|
| SC-88 | N-(3-carbamoyl-4-fluorophenyl)-1-((4,4-difluorocyclohexyl)methyl)-4-(difluoromethyl)-3-methyl-1H-pyrazole-5-carboxamide |
| SC-89 | 1-((4,4-difluorocyclohexyl)methyl)-4-(difluoromethyl)-3-methyl-N-(3-sulfamoylphenyl)-1H-pyrazole-5-carboxamide |
| SC-90 | 4-(3-chloro-1-((4,4-difluorocyclohexyl)methyl)-4-(trifluoromethyl)-1H-pyrazole-5-carboxamido)picolinamide |
| SC-91 | 3-chloro-1-((4,4-difluorocyclohexyl)methyl)-N-(2-(methylsulfonyl)pyridin-4-yl)-4-(trifluoromethyl)-1H-pyrazole-5-carboxamide |
| SC-92 | N-(3-carbamoyl-4-fluorophenyl)-3-chloro-1-((4,4-difluorocyclohexyl)methyl)-4-(trifluoromethyl)-1H-pyrazole-5-carboxamide |
| SC-93 | 3-chloro-1-((4,4-difluorocyclohexyl)methyl)-N-(3-sulfamoylphenyl)-4-(trifluoromethyl)-1H-pyrazole-5-carboxamide |
| SC-94 | 4-(1-((4,4-difluorocyclohexyl)methyl)-4-methyl-3-(trifluoromethyl)-1H-pyrazole-5-carboxamido)picolinamide |
| SC-95 | 1-((4,4-difluorocyclohexyl)methyl)-4-methyl-N-(2-(methylsulfonyl)pyridin-4-yl)-3-(trifluoromethyl)-1H-pyrazole-5-carboxamide |
| SC-96 | N-(3-carbamoyl-4-fluorophenyl)-1-((4,4-difluorocyclohexyl)methyl)-4-methyl-3-(trifluoromethyl)-1H-pyrazole-5-carboxamide |
| SC-97 | 1-((4,4-difluorocyclohexyl)methyl)-4-methyl-N-(3-sulfamoylphenyl)-3-(trifluoromethyl)-1H-pyrazole-5-carboxamide |
| SC-98 | 4-(1-((4,4-difluorocyclohexyl)methyl)-3-(difluoromethyl)-4-methyl-1H-pyrazole-5-carboxamido)picolinamide |
| SC-99 | 1-((4,4-difluorocyclohexyl)methyl)-3-(difluoromethyl)-4-methyl-N-(2-(methylsulfonyl)pyridin-4-yl)-1H-pyrazole-5-carboxamide |
| SC-100 | N-(3-carbamoyl-4-fluorophenyl)-1-((4,4-difluorocyclohexyl)methyl)-3-(difluoromethyl)-4-methyl-1H-pyrazole-5-carboxamide |
| SC-101 | 1-((4,4-difluorocyclohexyl)methyl)-3-(difluoromethyl)-4-methyl-N-(3-sulfamoylphenyl)-1H-pyrazole-5-carboxamide |
| SC-102 | 4-(4-chloro-1-((4,4-difluorocyclohexyl)methyl)-3-(trifluoromethyl)-1H-pyrazole-5-carboxamido)picolinamide |
| SC-103 | 4-chloro-1-((4,4-difluorocyclohexyl)methyl)-N-(2-(methylsulfonyl)pyridin-4-yl)-3-(trifluoromethyl)-1H-pyrazole-5-carboxamide |
| SC-104 | N-(3-carbamoyl-4-fluorophenyl)-4-chloro-1-((4,4-difluorocyclohexyl)methyl)-3-(trifluoromethyl)-1H-pyrazole-5-carboxamide |
| SC-105 | 4-chloro-1-((4,4-difluorocyclohexyl)methyl)-N-(3-sulfamoylphenyl)-3-(trifluoromethyl)-1H-pyrazole-5-carboxamide |
| SC-106 | 1-((3,3-difluorocyclopentyl)methyl)-3-methyl-N-(3-sulfamoylphenyl)-4-(trifluoromethyl)-1H-pyrazole-5-carboxamide |
| SC-108 | 1-((3,3-difluorocyclopentyl)methyl)-3-methyl-N-(2-(methylsulfonyl)pyridin-4-yl)-4-(trifluoromethyl)-1H-pyrazole-5-carboxamide |
| SC-110 | 4-(1-((3,3-difluorocyclopentyl)methyl)-3-methyl-4-(trifluoromethyl)-1H-pyrazole-5-carboxamido)picolinamide |
| SC-112 | N-(3-carbamoyl-4-fluorophenyl)-1-((3,3-difluorocyclopentyl)methyl)-3-methyl-4-(trifluoromethyl)-1H-pyrazole-5-carboxamide |
| SC-114 | 1-((3,3-difluorocyclopentyl)methyl)-4-methyl-N-(3-sulfamoylphenyl)-3-(trifluoromethyl)-1H-pyrazole-5-carboxamide |
| SC-116 | 1-((3,3-difluorocyclopentyl)methyl)-4-methyl-N-(2-(methylsulfonyl)pyridin-4-yl)-3-(trifluoromethyl)-1H-pyrazole-5-carboxamide |
| SC-118 | 4-(1-((3,3-difluorocyclopentyl)methyl)-4-methyl-3-(trifluoromethyl)-1H-pyrazole-5-carboxamido)picolinamide |
| SC-120 | N-(3-carbamoyl-4-fluorophenyl)-1-((3,3-difluorocyclopentyl)methyl)-4-methyl-3-(trifluoromethyl)-1H-pyrazole-5-carboxamide |
| SC-122 | 4-(3-methyl-1-((3,3,4,4-tetrafluorocyclopentyl)methyl)-4-(trifluoromethyl)-1H-pyrazole-5-carboxamido)picolinamide |
| SC-123 | 3-methyl-N-(2-(methylsulfonyl)pyridin-4-yl)-1-((3,3,4,4-tetrafluorocyclopentyl)methyl)-4-(trifluoromethyl)-1H-pyrazole-5-carboxamide |
| SC-124 | 4-(1-((4,4-difluorocyclohexyl)methyl)-3-(difluoromethyl)-4-(trifluoromethyl)-1H-pyrazole-5-carboxamido)picolinamide |
| SC-125 | 1-((4,4-difluorocyclohexyl)methyl)-3-(difluoromethyl)-N-(2-(methylsulfonyl)pyridin-4-yl)-4-(trifluoromethyl)-1H-pyrazole-5-carboxamide |
| SC-126 | N-(3-carbamoyl-4-fluorophenyl)-1-((4,4-difluorocyclohexyl)methyl)-3-(difluoromethyl)-4-(trifluoromethyl)-1H-pyrazole-5-carboxamide |
| SC-127 | 1-((4,4-difluorocyclohexyl)methyl)-3-(difluoromethyl)-N-(3-sulfamoylphenyl)-4-(trifluoromethyl)-1H-pyrazole-5-carboxamide |
| SC-128 | 4-(3-cyclopropyl-1-((4,4-difluorocyclohexyl)methyl)-4-(trifluoromethyl)-1H-pyrazole-5-carboxamido)picolinamide |
| SC-129 | 4-(3-cyclopropyl-1-((3,3-difluorocyclopentyl)methyl)-4-(trifluoromethyl)-1H-pyrazole-5-carboxamido)picolinamide |
| SC-131 | 4-(3-cyclopropyl-1-((tetrahydro-2H-pyran-4-yl)methyl)-4-(trifluoromethyl)-1H-pyrazole-5-carboxamido)picolinamide |
| SC-132 | 3-cyclopropyl-N-(2-(methylsulfonyl)pyridin-4-yl)-1-((tetrahydro-2H-pyran-4-yl)methyl)-4-(trifluoromethyl)-1H-pyrazole-5-carboxamide |
| SC-133 | 4-(3-cyclopropyl-1-((tetrahydro-2H-pyran-4-yl)methyl)-4-(trifluoromethoxy)-1H-pyrazole-5-carboxamido)picolinamide |
| SC-134 | 4-(3-methoxy-1-((tetrahydro-2H-pyran-4-yl)methyl)-4-(trifluoromethyl)-1H-pyrazole-5-carboxamido)picolinamide |
| SC-135 | 4-(3-cyclopropyl-1-((2-methyltetrahydro-2H-pyran-4-yl)methyl)-4-(trifluoromethyl)-1H-pyrazole-5-carboxamido)picolinamide |

-continued

| | |
|---|---|
| SC-138 | 4-(3-cyclopropyl-1-((5-methyltetrahydrofuran-3-yl)methyl)-4-(trifluoromethyl)-1H-pyrazole-5-carboxamido)picolinamide |
| SC-139 | 4-(3-cyclopropyl-1-((5-methyltetrahydrofuran-2-yl)methyl)-4-(trifluoromethyl)-1H-pyrazole-5-carboxamido)picolinamide |
| SC-140 | N-(3-carbamoyl-4-fluorophenyl)-3-cyclopropyl-1-((tetrahydro-2H-pyran-2-yl)methyl)-4-(trifluoromethyl)-1H-pyrazole-5-carboxamide |
| SC-141 | N-(3-carbamoyl-4-fluorophenyl)-1-((3,3-difluorocyclobutyl)methyl)-3-(difluoromethyl)-4-(trifluoromethyl)-1H-pyrazole-5-carboxamide |
| SC-143 | 4-(3-cyclopropyl-1-((6-methyltetrahydro-2H-pyran-2-yl)methyl)-4-(trifluoromethyl)-1H-pyrazole-5-carboxamido)picolinamide |
| SC-144 | 4-(3-cyclopropyl-1-((3,3-difluorocyclobutyl)methyl)-4-(trifluoromethyl)-1H-pyrazole-5-carboxamido)picolinamide |
| SC-145 | 4-(3-cyclopropyl-1-((tetrahydro-2H-pyran-3-yl)methyl)-4-(trifluoromethyl)-1H-pyrazole-5-carboxamido)picolinamide |
| SC-147 | 4-(3-cyclopropyl-4-(trifluoromethyl)-1-((2-(trifluoromethyl)tetrahydrofuran-3-yl)methyl)-1H-pyrazole-5-carboxamido)picolinamide |
| SC-148 | 4-(3-cyclopropyl-4-(trifluoromethyl)-1-((5-(trifluoromethyl)tetrahydrofuran-3-yl)methyl)-1H-pyrazole-5-carboxamido)picolinamide |
| SC-149 | 4-(4-chloro-1-((3,3-difluorocyclopentyl)methyl)-3-(1,1-difluoroethyl)-1H-pyrazole-5-carboxamido)picolinamide |
| SC-150 | 3-cyclopropyl-N-(2-(methylsulfonyl)pyridin-4-yl)-4-(trifluoromethyl)-1-((2-(trifluoromethyl)tetrahydrofuran-3-yl)methyl)-1H-pyrazole-5-carboxamide |
| SC-151 | 3-cyclopropyl-1-((3,3-difluorocyclobutyl)methyl)-N-(2-(methylsulfonyl)pyridin-4-yl)-4-(trifluoromethyl)-1H-pyrazole-5-carboxamide |
| SC-153 | 3-cyclopropyl-4-(difluoromethyl)-N-(2-(methylsulfonyl)pyridin-4-yl)-1-((tetrahydro-2H-pyran-4-yl)methyl)-1H-pyrazole-5-carboxamide |
| SC-154 | 4-(3-cyclopropyl-1-((2,2-difluorocyclobutyl)methyl)-4-(trifluoromethyl)-1H-pyrazole-5-carboxamido)picolinamide |
| SC-155 | 4-(1-((3,3-difluorocyclopentyl)methyl)-3-isopropoxy-4-(trifluoromethyl)-1H-pyrazole-5-carboxamido)picolinamide |
| SC-156 | 4-(1-((3,3-difluorocyclopentyl)methyl)-3-ethoxy-4-(trifluoromethyl)-1H-pyrazole-5-carboxamido)picolinamide |
| SC-157 | 4-(3-(cyclopropylmethoxy)-1-((3,3-difluorocyclopentyl)methyl)-4-(trifluoromethyl)-1H-pyrazole-5-carboxamido)picolinamide |
| SC-158 | 4-(1-((3,3-difluorocyclopentyl)methyl)-3-(difluoromethoxy)-4-(trifluoromethyl)-1H-pyrazole-5-carboxamido)picolinamide |
| SC-159 | 4-(1-(cyclobutylmethyl)-3-cyclopropyl-4-(trifluoromethyl)-1H-pyrazole-5-carboxamido)picolinamide |
| SC-160 | 4-(4-chloro-1-((3,3-difluorocyclopentyl)methyl)-3-(trifluoromethyl)-1H-pyrazole-5-carboxamido)picolinamide |
| SC-161 | 4-(1-((3,3-difluorocyclobutyl)methyl)-3-(1,1-difluoroethyl)-4-methyl-1H-pyrazole-5-carboxamido)picolinamide |
| SC-163 | 4-(1-((4,4-difluorocyclohexyl)methyl)-3-(difluoromethyl)-4-methyl-1H-pyrazole-5-carboxamido)picolinamide |
| SC-165 | 1-((3,3-difluorocyclopentyl)methyl)-3-(1,1-difluoroethyl)-4-methyl-N-(2-(methylsulfonyl)pyridin-4-yl)-1H-pyrazole-5-carboxamide |
| SC-166 | 3-(1,1-difluoroethyl)-4-methyl-N-(2-(methylsulfonyl)pyridin-4-yl)-1-((3,3,4,4-tetrafluorocyclopentyl)methyl)-1H-pyrazole-5-carboxamide |
| SC-167 | 4-(1-((3,3-difluorocyclopentyl)methyl)-3-(1,1-difluoroethyl)-4-methyl-1H-pyrazole-5-carboxamido)picolinamide |
| SC-168 | 4-(3-(1,1-difluoroethyl)-4-methyl-1-((3,3,4,4-tetrafluorocyclopentyl)methyl)-1H-pyrazole-5-carboxamido)picolinamide |
| SC-169 | 1-((3,3-difluorocyclobutyl)methyl)-3-isopropyl-N-(2-(methylsulfonyl)pyridin-4-yl)-4-(trifluoromethyl)-1H-pyrazole-5-carboxamide |
| SC-170 | 4-(1-((3,3-difluorocyclobutyl)methyl)-3-isopropyl-4-(trifluoromethyl)-1H-pyrazole-5-carboxamido)picolinamide |
| SC-171 | 1-((3,3-difluorocyclobutyl)methyl)-3-ethyl-N-(2-(methylsulfonyl)pyridin-4-yl)-4-(trifluoromethyl)-1H-pyrazole-5-carboxamide |
| SC-172 | 4-(1-((3,3-difluorocyclobutyl)methyl)-3-ethyl-4-(trifluoromethyl)-1H-pyrazole-5-carboxamido)picolinamide |
| SC-173 | 1-((3,3-difluorocyclobutyl)methyl)-N-(2-(methylsulfonyl)pyridin-4-yl)-4-(trifluoromethyl)-3-(1,1,1-trifluoropropan-2-yl)-1H-pyrazole-5-carboxamide |
| SC-174 | 4-(1-((3,3-difluorocyclobutyl)methyl)-4-(trifluoromethyl)-3-(1,1,1-trifluoropropan-2-yl)-1H-pyrazole-5-carboxamido)picolinamide |
| SC-175 | 1-((3,3-difluorocyclobutyl)methyl)-3-(1,1-difluoropropan-2-yl)-N-(2-(methylsulfonyl)pyridin-4-yl)-4-(trifluoromethyl)-1H-pyrazole-5-carboxamide |
| SC-176 | 4-(1-((3,3-difluorocyclobutyl)methyl)-3-(1,1-difluoropropan-2-yl)-4-(trifluoromethyl)-1H-pyrazole-5-carboxamido)picolinamide |
| SC-177 | 4-(4-chloro-1-((3,3-difluorocyclobutyl)methyl)-3-(1,1-difluoroethyl)-1H-pyrazole-5-carboxamido)picolinamide |
| SC-178 | 4-chloro-1-((3,3-difluorocyclopentyl)methyl)-3-(1,1-difluoroethyl)-N-(2-(methylsulfonyl)pyridin-4-yl)-1H-pyrazole-5-carboxamide |
| SC-179 | 1-((3,3-difluorocyclobutyl)methyl)-3-(1,1-difluoroethyl)-N-(2-(methylsulfonyl)pyridin-4-yl)-4-(trifluoromethyl)-1H-pyrazole-5-carboxamide |
| SC-180 | 4-(1-((3,3-difluorocyclobutyl)methyl)-3-(1,1-difluoroethyl)-4-(trifluoromethyl)-1H-pyrazole-5-carboxamido)picolinamide |

| | -continued |
|---|---|
| SC-181 | 1-((3,3-difluorocyclopentyl)methyl)-3-(1,1-difluoroethyl)-N-(2-(methylsulfonyl)pyridin-4-yl)-4-(trifluoromethyl)-1H-pyrazole-5-carboxamide |
| SC-182 | 4-(1-((3,3-difluorocyclopentyl)methyl)-3-(1,1-difluoroethyl)-4-(trifluoromethyl)-1H-pyrazole-5-carboxamido)picolinamide |
| SC-183 | 1-((3,3-difluorocyclobutyl)methyl)-4-methyl-N-(2-(methylsulfonyl)pyridin-4-yl)-3-(perfluoroethyl)-1H-pyrazole-5-carboxamide |
| SC-184 | 4-(1-((3,3-difluorocyclobutyl)methyl)-4-methyl-3-(perfluoroethyl)-1H-pyrazole-5-carboxamido)picolinamide |
| SC-185 | 1-((3,3-difluorocyclopentyl)methyl)-4-methyl-N-(2-(methylsulfonyl)pyridin-4-yl)-3-(perfluoroethyl)-1H-pyrazole-5-carboxamide |
| SC-186 | 4-(1-((3,3-difluorocyclopentyl)methyl)-4-methyl-3-(perfluoroethyl)-1H-pyrazole-5-carboxamido)picolinamide |
| SC-187 | 1-((3,3-difluorocyclobutyl)methyl)-4-methyl-N-(2-(methylsulfonyl)pyridin-4-yl)-3-(1,1,1-trifluoropropan-2-yl)-1H-pyrazole-5-carboxamide |
| SC-188 | 4-(1-((3,3-difluorocyclobutyl)methyl)-4-methyl-3-(1,1,1-trifluoropropan-2-yl)-1H-pyrazole-5-carboxamido)picolinamide |
| SC-189 | 1-((3,3-difluorocyclopentyl)methyl)-4-methyl-N-(2-(methylsulfonyl)pyridin-4-yl)-3-(1,1,1-trifluoropropan-2-yl)-1H-pyrazole-5-carboxamide |
| SC-190 | 4-(1-((3,3-difluorocyclopentyl)methyl)-4-methyl-3-(1,1,1-trifluoropropan-2-yl)-1H-pyrazole-5-carboxamido)picolinamide |
| SC-191 | 1-((3,3-difluorocyclobutyl)methyl)-3-(1,l-difluoropropan-2-yl)-4-methyl-N-(2-(methylsulfonyl)pyridin-4-yl)-1H-pyrazole-5-carboxamide |
| SC-192 | 4-(1-((3,3-difluorocyclobutyl)methyl)-3-(1,1-difluoropropan-2-yl)-4-methyl-1H-pyrazole-5-carboxamido)picolinamide |
| SC-193 | 1-((3,3-difluorocyclopentyl)methyl)-3-(1,1-difluoropropan-2-yl)-4-methyl-N-(2-(methylsulfonyl)pyridin-4-yl)-1H-pyrazole-5-carboxamide |
| SC-194 | 4-(1-((3,3-difluorocyclopentyl)methyl)-3-(1,1-difluoropropan-2-yl)-4-methyl-1H-pyrazole-5-carboxamido)picolinamide |
| SC-195 | 1-((3,3-difluorocyclopentyl)methyl)-3-(difluoromethoxy)-N-(2-(methylsulfonyl)pyridin-4-yl)-4-(trifluoromethyl)-1H-pyrazole-5-carboxamide |
| SC-196 | 4-(1-((3,3-difluorocyclopentyl)methyl)-3-(difluoromethoxy)-4-methyl-1H-pyrazole-5-carboxamido)picolinamide |
| SC-197 | 1-((3,3-difluorocyclopentyl)methyl)-3-(difluoromethoxy)-4-methyl-N-(2-(methylsulfonyl)pyridin-4-yl)-1H-pyrazole-5-carboxamide |
| SC-198 | 4-(1-((3,3-difluorocyclopentyl)methyl)-4-methyl-3-(trifluoromethoxy)-lH-pyrazole-5-carboxamido)picolinamide |
| SC-199 | 1-((3,3-difluorocyclopentyl)methyl)-4-methyl-N-(2-(methylsulfonyl)pyridin-4-yl)-3-(trifluoromethoxy)-1H-pyrazole-5-carboxamide |
| SC-200 | 4-(1-((3,3-difluorocyclopentyl)methyl)-3-(1,1-difluoroethoxy)-4-methyl-1H-pyrazole-5-carboxamido)picolinamide |
| SC-201 | 1-((3,3-difluorocyclopentyl)methyl)-3-(1,1-difluoroethoxy)-4-methyl-N-(2-(methylsulfonyl)pyridin-4-yl)-1H-pyrazole-5-carboxamide |
| SC-202 | 3-(cyclopropyldifluoromethyl)-1-((3,3-difluorocyclobutyl)methyl)-4-methyl-N-(2-(methylsulfonyl)pyridin-4-yl)-1H-pyrazole-5-carboxamide |
| SC-203 | 4-(3-(cyclopropyldifluoromethyl)-1-((3,3-difluorocyclobutyl)methyl)-4-methyl-1H-pyrazole-5-carboxamido)picolinamide |
| SC-204 | 4-(3-(1,1-difluoroethyl)-4-methyl-1-((2-(trifluoromethyl)cyclopropyl)methyl)-1H-pyrazole-5-carboxamido)picolinamide |
| SC-205 | 3-(1,1-difluoroethyl)-4-methyl-N-(2-(methylsulfonyl)pyridin-4-yl)-1-((2-(trifluoromethyl)cyclopropyl)methyl)-1H-pyrazole-5-carboxamide |
| SC-206 | 4-(3-(1,1-difluoroethyl)-1-((2-(difluoromethyl)cyclopropyl)methyl)-4-methyl-lH-pyrazole-5-carboxamido)picolinamide |
| SC-207 | 3-(1,1-difluoroethyl)-1-((2-(difluoromethyl)cyclopropyl)methyl)-4-methyl-N-(2-(methylsulfonyl)pyridin-4-yl)-1H-pyrazole-5-carboxamide |
| SC-208 | 4-(1-((3,3-difluoro-1-methyleyclobutyl)methyl)-3-(1,l-difluoroethyl)-4-methyl-1H-pyrazole-5-carboxamido)picolinamide |
| SC-209 | 1-((3,3-difluoro-1-methyleyclobutyl)methyl)-3-(1,1-difluoroethyl)-4-methyl-N-(2-sulfamoylpyridin-4-yl)-1H-pyrazole-5-carboxamide |
| SC-210 | 1-((3,3-difluoro-1-methyleyclobutyl)methyl)-3-(1,1-difluoroethyl)-4-methyl-N-(2-(methylsulfonyl)pyridin-4-yl)-1H-pyrazole-5-carboxamide |
| SC-211 | 1-((3,3-difluorocyclopentyl)methyl)-3-(1,1-difluoroethyl)-4-methyl-N-(2-sulfamoylpyridin-4-yl)-1H-pyrazole-5-carboxamide |
| SC-212 | 1-((3,3-difluoro-1-methyleyclopentyl)methyl)-3-(1,l-difluoroethyl)-4-methyl-N-(2-sulfamoylpyridin-4-yl)-1H-pyrazole-5-carboxamide |
| SC-213 | 1-((3,3-difluoro-1-methyleyclopentyl)methyl)-3-(1,l-difluoroethyl)-4-methyl-N-(2-(methylsulfonyl)pyridin-4-yl)-1H-pyrazole-5-carboxamide |
| SC-214 | 4-(1-((3,3-difluoro-1-methyleyclopentyl)methyl)-3-(1,1-difluoroethyl)-4-methyl-1H-pyrazole-5-carboxamido)picolinamide |
| SC-215 | 1-((3,3-difluorocyclobutyl)methyl)-3-(1,1-difluoroethyl)-4-methyl-N-(2-sulfamoylpyridin-4-yl)-lH-pyrazole-5-carboxamide |
| SC-216 | 4-(3-cyclopropyl-1-((3,3-difluorocyclopentyl)methyl)-4-(difluoromethyl)-1H-pyrazole-5-carboxamido)picolinamide |
| SC-217 | 4-(1-((4,4-difluoro-2-(trifluoromethyl)cyclopentyl)methyl)-3-(1,1-difluoroethyl)-4-methyl-1H-pyrazole-5-carboxamido)picolinamide |
| SC-218 | 4-(1-((3,3-difluorocyclopentyl)methyl)-3-ethyl-4-(trifluoromethyl)-1H-pyrazole-5-carboxamido)picolinamide |

| | |
|---|---|
| SC-219 | 4-(3-cyclopropyl-1-((3-(trifluoromethoxy)cyclobutyl)methyl)-4-(trifluoromethyl)-1H-pyrazole-5-carboxamido)picolinamide |
| SC-220 | 1-((3,3-difluoro-1-(trifluoromethyl)cyclobutyl)methyl)-3-(1,1-difluoroethyl)-4-methyl-N-(2-(methylsulfonyl)pyridin-4-yl)-1H-pyrazole-5-carboxamide |
| SC-221 | 4-(3-cyclopropyl-1-((3-(difluoromethyl)cyclobutyl)methyl)-4-(trifluoromethyl)-1H-pyrazole-5-carboxamido)picolinamide |
| SC-222 | 1-(1-(3,3-difluorocyclobutyl)ethyl)-3-(1,1-difluoroethyl)-4-methyl-N-(2-(methylsulfonyl)pyridin-4-yl)-1H-pyrazole-5-carboxamide |
| SC-223 | 4-(3-(1,1-difluoroethyl)-1-((2-((2-methoxyethoxy)methyl)cyclohexyl)methyl)-4-methyl-1H-pyrazole-5-ca±oxamido)picolinamide |
| SC-224 | 1-((3,4-difluorocyclopentyl)methyl)-3-(1,1-difluoroethyl)-4-methyl-N-(2-(methylsulfonyl)pyridin-4-yl)-1H-pyrazole-5-carboxamide |
| SC-225 | 1-((3,3-difluorocyclopentyl)methyl)-3-methoxy-N-(2-(methylsulfonyl)pyridin-4-yl)-4-(trifluoromethyl)-1H-pyrazole-5-carboxamide |
| SC-226 | 1-(cyclohexylmethyl)-N-(3-(methylsulfonyl)phenyl)-1H-pyrazole-5-carboxamide |
| SC-229 | 1-(cyclohexylmethyl)-4-(difluoromethyl)-N-(3-(methylsulfonyl)phenyl)-1H-pyrazole-5-carboxamide |
| SC-230 | 3-cyclopropyl-1-((4,4-difluorocyclohexyl)methyl)-N-(3-sulfamoylphenyl)-4-(trifluoromethyl)-lH-pyrazole-5-carboxamide |
| SC-231 | N-(2-cyanopyridin-4-yl)-1-((4,4-difluorocyclohexyl)methyl)-3,4-dimethyl-1H-pyrazole-5-carboxamide |
| SC-232 | 1-((1-methylcyclohexyl)methyl)-N-(3-(methylsulfonyl)phenyl)-4-(trifluoromethyl)-1H-pyrazole-5-carboxamide |
| SC-233 | 1-((1-fluorocyclohexyl)methyl)-N-(3-(methylsulfonyl)phenyl)-4-(trifluoromethyl)-1H-pyrazole-5-carboxamide |
| SC-234 | 3-methyl-N-(3-(methylsulfonyl)phenyl)-1-(oxetan-3-ylmethyl)-4-(trifluoromethyl)-1H-pyrazole-5-carboxamide |
| SC-235 | 1-((2,2-difluorocyclopentyl)methyl)-N-(3-sulfamoylphenyl)-4-(trifluoromethyl)-1H-pyrazole-5-carboxamide |
| SC-236 | 4-chloro-1-((4,4-difluorocyclohexyl)methyl)-3-methyl-N-(3-sulfamoylphenyl)-1H-pyrazole-5-carboxamide |
| SC-237 | 3-methyl-N-(3-(methylsulfonyl)phenyl)-1-(oxetan-2-yimethyl)-4-(trifluoromethyl)-1H-pyrazole-5-carboxamide |
| SC-238 | 1-(cyclohexyimethyl)-N-(4-fluoro-3-sulfamoylphenyl)-3-methyl-4-(trifluoromethyl)-1H-pyrazole-5-carboxamide |
| SC-239 | 4-(3-chloro-1-((4,4-difluorocyclohexyl)methyl)-4-methyl-1H-pyrazole-5-carboxamido)picolinamide |
| SC-241 | 1-((4,4-difluorocyclohexyl)methyl)-3-methyl-N-(5-(methyisulfonyl)pyridin-3-yl)-4-(trifluoromethyl)-1H-pyrazole-5-carboxamide |
| SC-242 | 1-((4,4-difluorocyclohexyl)methyl)-4-methyl-N-(5-sulfamoylpyridin-3-yl)-3-(trifluoromethyl)-1H-pyrazole-5-carboxamide |
| SC-243 | 1-((4,4-difluorocyclohexyl)methyl)-4-methyl-N-(6-sulfamoylpyridin-2-yl)-3-(trifluoromethyl)-1H-pyrazole-5-carboxamide |
| SC-244 | 1-(cyclohexyimethyl)-3-methyl-N-(3-sulfamoylphenyl)-4-(trifluoromethyl)-1H-pyrazole-5-carboxamide |
| SC-246 | 3-cyclopropyl-1-((4,4-difluorocyclohexyl)methyl)-N-(2-sulfamoylpyridin-4-yl)-4-(trifluoromethyl)-1H-pyrazole-5-carboxamide |
| SC-247 | 5-(1-((3,3-difluorocyclopentyl)methyl)-3-methyl-4-(trifluoromethyl)-1H-pyrazole-5-carboxamido)nicotinamide |
| SC-248 | 4-(1-((3,3-difluorocyclopentyl)methyl)-3-methyl-4-(trifluoromethyl)-1H-pyrazole-5-carboxamido)pyrimidine-2-carboxamide |
| SC-249 | 4-(1-((4,4-difluorocyclohexyl)methyl)-3-methyl-4-(trifluoromethyl)-1H-pyrazole-5-carboxamido)-5-methyipicolinamide |
| SC-250 | 3-cyclopropyl-1-((4,4-difluorocyclohexyl)methyl)-N-(2-(methylsulfonyl)pyridin-4-yl)-4-(trifluoromethyl)-1H-pyrazole-5-carboxamide |
| SC-251 | 5-(1-((4,4-difluorocyclohexyl)methyl)-3-methyl-4-(trifluoromethyl)-1H-pyrazole-5-carboxamido)-2-methylnicotinamide |
| SC-252 | 1-((4,4-difluorocyclohexyl)methyl)-3-methyl-N-(2-methylpyridin-4-yl)-4-(trifluoromethyl)-1H-pyrazole-5-carboxamide |
| SC-253 | 6-(1-((4,4-difluorocyclohexyl)methyl)-3-methyl-4-(trifluoromethyl)-1H-pyrazole-5-carboxamido)picolinamide |
| SC-254 | 1-((3,3-difluorocyclopentyl)methyl)-4-methyl-N-(2-sulfamoyipyridin-4-yl)-3-(trifluoromethyl)-1H-pyrazole-5-carboxamide |
| SC-255 | 1-((1-hydroxycyclohexyl)methyl)-N-(3-(methylsulfonyl)phenyl)-4-(trifluoromethyl)-1H-pyrazole-5-carboxamide |
| SC-256 | 2-(1-((4,4-difluorocyclohexyl)methyl)-3-methyl-4-(trifluoromethyl)-1H-pyrazole-5-carboxamido)oxazole-5-carboxamide |
| SC-257 | 5-(1-((4,4-difluorocyclohexyl)methyl)-3-methyl-4-(trifluoromethyl)-1H-pyrazole-5-carboxamido)picolinamide |
| SC-258 | 4-(3-cyclopropyl-1-((tetrahydro-2H-pyran-2-yl)methyl)-4-(trifluoromethyl)-1H-pyrazole-5-carboxamido)picolinamide |
| SC-259 | 3-cyclopropyl-N-(2-(methylsulfonyl)pyridin-4-yl)-1-((tetrahydro-2H-pyran-2-yl)methyl)-4-(trifluoromethyl)-1H-pyrazole-5-carboxamide |
| SC-260 | 4-(1-((4,4-difluorocyclohexyl)methyl)-3-methyl-4-(trifluoromethyl)-1H-pyrazole-5-carboxamido)-N-methyipicolinamide |
| SC-261 | 4-(4-chloro-3-cyclopropyl-1-((tetrahydro-2H-pyran-4-yl)methyl)-1H-pyrazole-5-carboxamido)picolinamide |
| SC-262 | 1-((3,3-difluorocyclopentyl)methyl)-3-(difluoromethyl)-N-(3-sulfamoyiphenyl)-4-(trifluoromethyl)-1H-pyrazole-5-carboxamide |

-continued

| | |
|---|---|
| SC-263 | 3-cyclopropyl-N-(2-(methylsulfonyl)pyridin-4-yl)-1-((tetrahydrofuran-2-yl)methyl)-4-(trifluoromethyl)-1H-pyrazole-5-carboxamide |
| SC-264 | 3-cyclopropyl-N-(3-sulfamoylphenyl)-1-((tetrahydro-2H-pyran-2-yl)methyl)-4-(trifluoromethyl)-1H-pyrazole-5-carboxamide |
| SC-265 | 1-((3,3-difluorocyclopentyl)methyl)-3-methoxy-N-(3-sulfamoylphenyl)-4-(trifluoromethyl)-1H-pyrazole-5-carboxamide |
| SC-266 | 4-(3-cyclopropyl-1-(cyclopropylmethyl)-4-(trifluoromethyl)-1H-pyrazole-5-carboxamido)picolinamide |
| SC-267 | 4-(1-((4,4-difluorocyclohexyl)methyl)-3-methyl-4-(trifluoromethyl)-1H-pyrazole-5-carboxamido)-6-methylpicolinamide |
| SC-268 | 2-(1-((4,4-difluorocyclohexyl)methyl)-3-methyl-4-(trifluoromethyl)-1H-pyrazole-5-carboxamido)-5-fluoroisonicotinamide |
| SC-269 | 4-(1-((3,3-difluorocyclopentyl)methyl)-4-methoxy-3-(trifluoromethyl)-1H-pyrazole-5-carboxamido)picolinamide |
| SC-271 | 4-(1-((3,3-difluorocyclopentyl)methyl)-3-(1,1-difluoroethyl)-4-methoxy-1H-pyrazole-5-carboxamido)picolinamide |
| SC-273 | 4-(1-((3,3-difluorocyclopentyl)methyl)-3-methoxy-4-(trifluoromethyl)-1H-pyrazole-5-carboxamido)picolinamide |
| SC-274 | N-(3-carbamoyl-4-fluorophenyl)-3-cyclopropyl-1-((3,3-difluorocyclobutyl)methyl)-4-(trifluoromethyl)-1H-pyrazole-5-carboxamide |
| SC-275 | 3-cyclopropyl-1-((3,3-difluorocyclopentyl)methyl)-4-(difluoromethyl)-N-(2-(methylsulfonyl)pyridin-4-yl)-1H-pyrazole-5-carboxamide |
| SC-276 | 3-cyclopropyl-1-((3,3-difluorocyclobutyl)methyl)-N-(3-sulfamoylphenyl)-4-(trifluoromethyl)-1H-pyrazole-5-carboxamide |
| SC-277 | 3-cyclopropyl-1-((3,3-difluorocyclopentyl)methyl)-N-(2-(methylsulfonyl)pyridin-4-yl)-4-(trifluoromethyl)-1H-pyrazole-5-carboxamide |
| SC-278 | 4-(1-((2,2-difluorocyclobutyl)methyl)-4-methyl-3-(perfluoroethyl)-1H-pyrazole-5-carboxamido)picolinamide |
| SC-279 | 4-(3-cyclopropyl-1-((2,2-difluorocyclopropyl)methyl)-4-(trifluoromethyl)-1H-pyrazole-5-carboxamido)picolinamide |
| SC-280 | 1-((4,4-difluorocyclohexyl)methyl)-3-methyl-N-(6-(methylsulfonyl)pyridazin-4-yl)-4-(trifluoromethyl)-1H-pyrazole-5-carboxamide |
| SC-281 | 4-(3-cyclopropyl-1-((3-methoxycyclobutyl)methyl)-4-(trifluoromethyl)-1H-pyrazole-5-carboxamido)picolinamide |
| SC-282 | 3-cyclopropyl-1-((3,3-difluorocyclobutyl)methyl)-N-(2-sulfamoylpyridin-4-yl)-4-(trifluoromethyl)-1H-pyrazole-5-carboxamide |
| SC-283 | 4-(3-(3,3-difluorocyclobutoxy)-1-((3,3-difluorocyclopentyl)methyl)-4-(trifluoromethyl)-1H-pyrazole-5-ca±oxamido)picolinamide |
| SC-284 | 4-(3-cyclopropyl-4-(trifluoromethyl)-1-((5-(trifluoromethyl)tetrahydrofuran-2-yl)methyl)-1H-pyrazole-5-ca±oxamido)picolinamide |
| SC-286 | 3-cyclopropyl-N-(2-(methylsulfonyl)pyridin-4-yl)-1-((5-methyltetrahydrofuran-2-yl)methyl)-4-(trifluoromethyl)-1H-pyrazole-5-carboxamide |
| SC-289 | 4-(1-((4,4-difluorocyclohexyl)methyl)-3-methyl-4-(trifluoromethyl)-1H-pyrazole-5-carboxamido)-3-fluoropicolinamide |
| SC-290 | 3-cyclopropyl-1-((3-(difluoromethoxy)cyclobutyl)methyl)-N-(2-(methylsulfonyl)pyridin-4-yl)-4-(trifluoromethyl)-1H-pyrazole-5-carboxamide |
| SC-291 | 4-(3-cyclopropyl-1-((2,2,3,3-tetrafluorocyclobutyl)methyl)-4-(trifluoromethyl)-1H-pyrazole-5-carboxamido)picolinamide |
| SC-293 | 1-((3,3-difluorocyclopentyl)methyl)-3-(difluoromethoxy)-N-(2-(methylsulfonyl)pyridin-4-yl)-4-(trifluoromethyl)-1H-pyrazole-5-carboxamide |
| SC-294 | 4-(1-((4,4-difluorocyclohexyl)methyl)-3-methyl-4-(trifluoromethyl)-1H-pyrazole-5-carboxamido)-3-methyipicolinamide |
| SC-295 | 1-((3,3-difluorocyclobutyl)methyl)-3-(1,1-difluoroethyl)-4-methyl-N-(3-sulfamoylphenyl)-1H-pyrazole-5-carboxamide |
| SC-296 | 1-((3,3-difluorocyclopentyl)methyl)-3-(1,1-difluoroethyl)-4-methyl-N-(3-sulfamoylpheny))-1H-pyrazole-5-carboxamide |
| SC-297 | 1-((3,3-difluorocyclopentyl)methyl)-3-ethyl-N-(2-(methylsulfonyl)pyridin-4-yl)-4-(trifluoromethyl)-1H-pyrazole-5-carboxamide |
| SC-298 | 4-(3-cyclopropyl-1-((3,3-difluorocyclopentyl)methyl)-4-(2,2,2-trifluoroethoxy)-1H-pyrazole-5-carboxamido)picolinamide |
| SC-299 | 4-(1-((3,3-difluoro-1-(trifluoromethyl)cyclobutyl)methyl)-3-(1,1-difluoroethyl)-4-methyl-1H-pyrazole-5-ca±oxamido)picolinamide |
| SC-301 | 4-(3-(1,1-difluoroethyl)-1-((3-fluorocyclobutyl)methyl)-4-methyl-1H-pyrazole-5-carboxamido)picolinamide |
| SC-302 | 1-((3,3-difluorocyclobutyl)methyl)-3-ethyl-4-methyl-N-(2-(methylsulfonyl)pyridin-4-yl)-1H-pyrazole-5-carboxamide |
| SC-303 | 1-((3,3-difluorocyclobutyl)methyl)-3-(1,1-difluoroethyl)-N-(2-(methylsulfinyl)pyridin-4-yl)-4-(trifluoromethyl)-1H-pyrazole-5-carboxamide |
| SC-304 | 1-((3,3-difluorocyclopentyl)methyl)-3-methyl-N-(3-sulfamoyiphenyl)-4-(trifluoromethoxy)-1H-pyrazole-5-carboxamide |
| SC-305 | 3-cyclopropyl-N-(2-(methylsulfonyl)pyridin-4-yl)-1-((tetrahydro-2H-pyran-4-yl)methyl)-4-(2,2,2-trifluoroethyl)-1H-pyrazole-5-carboxamide |
| SC-308 | 3-(1,1-difluoroethyl)-1-((1-methoxycyclopropyl)methyl)-4-methyl-N-(2-sulfamoylpyridin-4-yl)-1H-pyrazole-5-carboxamide |
| SC-309 | 4-(1-((3,3-difluorocyclobutyl)methyl)-3-(1,1-difluoroethoxy)-4-methyl-1H-pyrazole-5-carboxamido)picolinamide |
| SC-310 | 3-(1,1-difluoroethyl)-1-((1-fluorocyclopropyl)methyl)-4-methyl-N-(2-sulfamoylpyridin-4-yl)-1H-pyrazole-5-carboxamide |

| | |
|---|---|
| SC-311 | 4-(3-(1,1-difluoroethyl)-1-((1-(difluoromethyl)-3,3-difluorocyclobutyl)methyl)-4-methyl-1H-pyrazole-5-carboxamido)picolinamide |
| SC-312 | 3-(1,1-difluoroethyl)-4-methyl-1-((2-methyltetrahydro-2H-pyran-2-yl)methyl)-N-(2-sulfamoylpyridin-4-yl)-1H-pyrazole-5-carboxamide |
| SC-313 | 3-(1,1-difluoroethyl)-4-methyl-1-((1-methylcyclopropyl)methyl)-N-(2-sulfamoylpyridin-4-yl)-lH-pyrazole-5-carboxamide |
| SC-314 | 3-(1,1-difluoroethyl)-4-methyl-1-((2-methylcyclopropyl)methyl)-N-(2-sulfamoylpyridin-4-yl)-lH-pyrazole-5-carboxamide |
| SC-315 | 4-(3-(1,1-difluoroethyl)-4-methyl-1-((2-(trifluoromethyl)cyclobutyl)methyl)-1H-pyrazole-5-carboxamido)picolinamide |
| SC-316 | 3-(1,1-difluoroethyl)-1-((1-(difluoromethyl)-3,3-difluorocyclobutyl)methyl)-4-methyl-N-(2-sulfamoylpyridin-4-yl)-1H-pyrazole-5-carboxamide |
| SC-317 | 3-(1,1-difluoroethyl)-4-methyl-1-((2-methyloxetan-2-yl)methyl)-N-(2-sulfamoylpyridin-4-yl)-lH-pyrazole-5-carboxamide |
| SC-318 | 4-(1-((3,3-difluorocyclobutyl)methyl)-4-methyl-3-(trifluoromethoxy)-lH-pyrazole-5-carboxamido)picolinamide |
| SC-319 | 3-(1,1-difluoroethyl)-4-methyl-1-((2-methyltetrahydrofuran-2-yl)methyl)-N-(2-sulfamoylpyridin-4-yl)-1H-pyrazole-5-carboxamide |
| SC-320 | 1-((4,4-difluorocyclohexyl)methyl)-4-methyl-N-(2-sulfamoylpyridin-4-yl)-3-(trifluoromethyl)-lH-pyrazole-5-carboxamide |
| SC-321 | 5-(1-((4,4-difluorocyclohexyl)methyl)-3-methyl-4-(trifluoromethyl)-1H-pyrazole-5-carboxamido)pyridazine-3-carboxamide |
| SC-322 | 3-cyclopropyl-4-(difluoromethoxy)-N-(2-(methylsulfonyl)pyridin-4-yl)-1-((tetrahydro-2H-pyran-4-yl)methyl)-1H-pyrazole-5-carboxamide |
| SC-323 | 1-((3,3-difluorocyclobutyl)methyl)-3-(difluoromethoxy)-4-methyl-N-(2-(methylsulfonyl)pyridin-4-yl)-1H-pyrazole-5-carboxamide |
| SC-324 | 4-(1-((3,3-difluorocyclobutyl)methyl)-3-(difluoromethyl)-4-(trifluoromethyl)-1H-pyrazole-5-carboxamido)picolinamide |
| SC-325 | 4-(1-((3,3-difluorocyclopentyl)methyl)-3-(difluoromethyl)-4-(trifluoromethyl)-1H-pyrazole-5-carboxamido)picolinamide | in the form of the free compound or a physiologically acceptable salt thereof.

In a preferred embodiment, the compound according to the present invention is an inhibitor of $Na_V1.8$. In the sense of the present invention, the term "inhibitor of $Na_V1.8$" preferably means that the respective compound exhibits in a patch clamp assay an IC50 value on $Na_V1.8$ of at most 10 µM ($10·10^{-6}$ mol/L); more preferably at most 1 µM; still more preferably at most 500 nM ($10^{-9}$ mol/L); even more preferably at most 100 nM; and most preferably at most 10 nM.

A preferred assay for testing compounds for their potency and method for determining an IC50 on $Na_V1.8$ is described in the experimental part down below.

In a preferred embodiment, the compound according to the present invention is a selective inhibitor of $Na_V1.8$. In the sense of the present invention, the term "selective inhibitor of $Na_V1.8$" preferably means that the respective compound preferably does not exhibit any inhibitory activity on $Na_V1.1$, $Na_V1.2$, $Na_V1.4$, $Na_V1.5$ and $Na_V1.6$. The skilled artisan knows suitable ways to determine whether a compound exhibits inhibitory effects on any of $Na_V1.1$, $Na_V1.2$, $Na_V1.4$, $Na_V1.5$ and $Na_V1.6$.

The present invention therefore relates to a compound according to the present invention for use in the inhibition of $Na_V1.8$.

Therefore, another aspect of the present invention relates to a compound according to the present invention for use in the treatment of pain. Still another aspect of the present invention relates to a method of treatment of pain; comprising the administration of a therapeutically effective amount of a compound according to the present invention to a subject in need thereof, preferably a human.

A further aspect of the invention relates to a compound according to the present invention as medicament.

Another aspect of the present invention relates to a pharmaceutical dosage form comprising a compound according to the present invention. Preferably, the pharmaceutical dosage form comprises a compound according to the present invention and one or more pharmaceutical excipients such as physiologically acceptable carriers, additives and/or auxiliary substances; and optionally one or more further pharmacologically active ingredient. Examples of suitable physiologically acceptable carriers, additives and/or auxiliary substances are fillers, solvents, diluents, colorings and/or binders. These substances are known to the person skilled in the art (see H. P. Fiedler, Lexikon der Hilfsstoffe fur Pharmazie, Kosmetik and angrenzende Gebiete, Editio Cantor Aulendoff).

The pharmaceutical dosage form according to the present invention is preferably for systemic, topical or local administration, preferably for oral administration. Therefore, the pharmaceutical dosage form can be in form of a liquid, semisolid or solid, e.g. in the form of injection solutions, drops, juices, syrups, sprays, suspensions, tablets, patches, films, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and can also be administered as such.

The pharmaceutical dosage form according to the present invention is preferably prepared with the aid of conventional means, devices, methods and processes known in the art. The amount of the compound according to the present invention to be administered to the patient may vary and is e.g. dependent on the patients weight or age and also on the type of administration, the indication and the severity of the disorder. Preferably 0.001 to 100 mg/kg, more preferably 0.05 to 75 mg/kg, most preferably 0.05 to 50 mg of a compound according to the present invention are administered per kg of the patients body weight.

Therefore, another aspect of the present invention relates to the pharmaceutical dosage form according to the present invention for use in the treatment of pain. Still another aspect of the present invention relates to a method of treatment of pain; comprising the administration of a pharmaceutical dosage form according to the present invention to a subject in need thereof, preferably a human.

EXAMPLES

Experimental Protocols

The following abbreviations are used in the descriptions of the experimental protocols: ABPR=automatic back pressure regulator; ACN=acetonitrile; aq.=aqueous; Boc=tert-butyloxycarbonyl; DAST=diethylaminosulfur trifluoride; dba=dibenzylideneacetone, mCPBA=m-chloroperoxybenzoic acid; DCE=dichloroethane, DCM=dichloromethane; DIAD=diisopropylazodicarboxylate; DIPEA=N,N-diisopropylethylamine; DMF=N,N-dimethylformamide; DMP=Dess-Martin periodinane, DMSO=dimethylsulfoxide; dppf=1,1'-bis(diphenylphosphino)ferrocene; EDCHCl=1-ethyl-3-(3-dimethylaminopropyl)carbodiimide hydrochloride; EtOAc or EA=ethyl acetate; EtOH=ethanol; HATU=1-[bis(dimethylamino)methylene]-1H-1,2,3-triazolo[4,5-b]pyridinium 3-oxide hexafluorophosphate; h=hour; HPLC=high-performance liquid chromatography; Int=intermediate; KHMDS=potassium bis(trimethylsilyl)amide, KOtBu=potassium tert-butoxide, LAH=lithium aluminium hydride, LCMS=liquid chromatography-mass spectrometry; LiHMDS=Lithium bis(trimethylsilyl)amide, mCPBA=meta-chloroperoxybenzoic acid, MeCN=acetonitrile; MeOH=methanol; min=minute; Ms=methanesulfonyl; MTBE=methyl tert-butyl ether; Mukaiyama's regant=2-chloro-1-methyl-pyridiniumiodide, MW=molecular weight; NCS=N-chlorosuccinimide, NIS=N-iodosuccinimide, NMIVI=N-methylmorpholine, NMR=nuclear magnetic resonance; prep.=preparative; PTSA=p-toluenesulfonylchloride; RP=reversed phase; RT=room temperature; $R_t$=retention time; sat.=saturated; SEM=2-(trimethylsilyl)ethoxymethyl, SFC=supercritical fluid chromatography; TBAF=tetra-n-butylammonium fluoride, TEA=triethylamine; Tf=trifluoromethylsulfonyl; TFA=trifluoro acetic acid; TLC=thin-layer chromatography; THF=tetrahydrofurane; TMS=trimethylsilyl, TMSCl=trimethylsilylchloride; Togni's reagent=1-trifluoromethyl-1,2-benziodoxol-3(1H)-one, TPP=triphenyl phosphine; Ts=p-toluenesulfonyl; pTSA=p-toluenesulfonic acid; Xantphos=4,5-Bis(diphenylphosphino)-9,9-dimethylxanthene.

General Synthesis Schemes

As illustrated in Scheme 1, compounds of the invention can be prepared by N-alkylation of alkyl 1H-pyrazole-5-carboxylates of the general formula (A) with appropriately functionalized alkylation reagents of the general formula (B) (where Y is leaving group, such as Br, Cl, OTs, OMs, OTf) under basic conditions to afford compounds of general formula (C). Alternatively, intermediates of the general formula (C) can be prepared using a Mitsunobu reaction between alkyl 1H-pyrazole-5-carboxylates of type (A) and alcohols of the general formula (B) (where Y is OH) (Chem. Rev. 2009, 109, 6, 2551-2651). Intermediates of the general formula (C) can be further converted into heteroarylcarboxamides of the general formula (E) upon nucleophilic addition of (hetero)arylamines of the general formula (D) in the presence of a strong anionic base, preferably LiHMDS or KHMDS (Chem. Com. 2014, 50, 15094-15097, Tet. Lett. 1999, 40, 6177-6180).

Scheme 1: L, X, $R^1$, $R^2$, $R^3$, $R^4$, $R^5$ are as defined in claim 1.

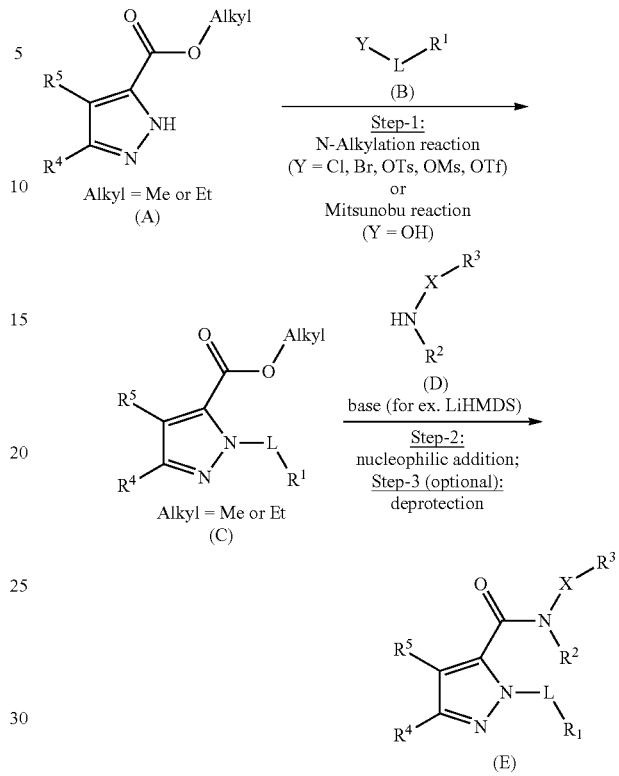

Alternatively and as illustrated in Scheme 2, intermediates of the general formula (C) can be hydrolized to carboxylic acids of the general formula (F) and converted to compounds of the general formula (E) using amide coupling with (hetero)arylamines of the general formula (D) in the presence of a carboxylic acid activating reagent, preferably EDCHCl, HATU, POCl$_3$ or SOCl$_2$, and a base, preferably pyridine or DIPEA (March's Advanced Organic Chemistry, 2007, 6th Edition, page 1427-1474) to provide compounds of the general formula (E).

Scheme 2: L, X, $R^1$, $R^2$, $R^3$, $R^4$, $R^5$ are as defined in claim 1.

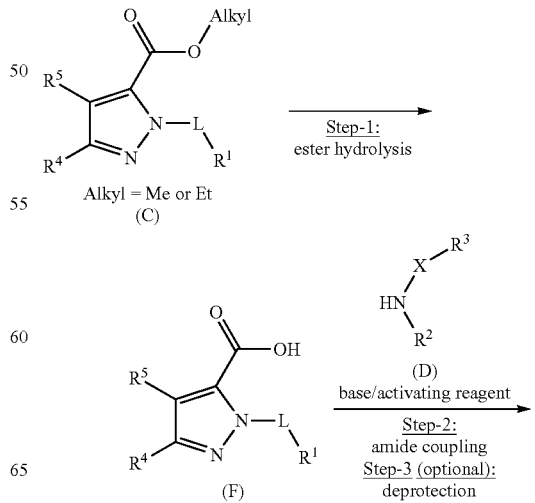

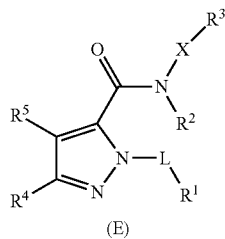

Alternatively and as illustrated in Scheme 3, carboxylic acids of the general formula (F) can be converted into carboxamides of the general formula (H) upon amide coupling with amines of the general formula (G) under coupling conditions well precedented in the literature (March's Advanced Organic Chemistry, 2007, 6th Edition, page 1427-1474). Intermediates of the general formula (H) can be further used in metal-catalyzed C—N coupling reactions with the corresponding aryl halides or heteroaryl halides of the general formula (I), preferably with corresponding aryl bromides, aryl iodides, heteroaryl bromides or heteroaryl iodides, to provide compounds of the general formula (E). Metal catalyzed C—N coupling reactions are generally known in the art (*Current Organic Synthesis*, 2011, 8, 53). Favorable C—N coupling reactions are palladium and copper catalyzed cross-coupling reactions (*Chem. Rev.* 2016, 116, 12564; *Chem. Soc. Rev.* 2014, 43, 3525; *Chem. Sci.* 2010, 1, 13).

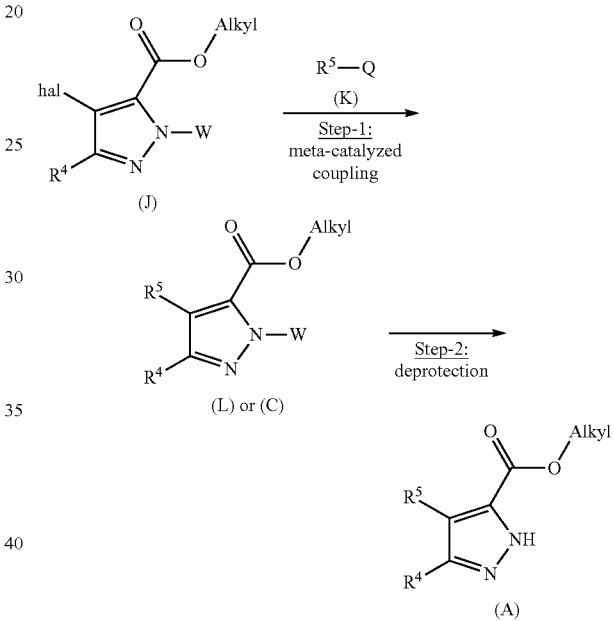

Alternatively and as illustrated in Scheme 4, halogenated pyrazoles of the general formula (J) can be converted into pyrazoles of the general formula (L) when —W is a protecting group or (C) if W is -L-R¹ under metal-catalyzed coupling conditions well precedented in the literature (*Chem. Rev.* 1995, 95, 2457-2483, *Chem. Soc. Rev.* 2014, 43, 412-443, *J. Am. Chem. Soc.* 2001, 123, 10770-10771, *J. Am. Chem. Soc.* 1997, 119, 10539-10540, *Chem. Rev.* 2011, 111, 4475-4521, *Org. Lett.* 2002, 4, 973-976.). Preferred are Suzuki couplings with Q being boronic acids or boronic esters under palladium catalysis (preferably using Pd(PPh₃)₄ and PdCl₂(dPPf) as catalysts), ether formation under copper catalysis (preferably using CuI) using R⁵-Q with R5=alkoxy and Q=sodium, copper-catalyzed trifluoromethylation (*Beilstein J. Org. Chem.* 2018, 14, 155-181) or palladium-catalyzed nitrile addition. Pyrazoles of the general formula (J) can be obtained from halogenation of pyrazoles (using preferably NIS or NCS) and subsequent attachment of W as outlined in scheme 1. Alternatively, the same chemistry can be used with a nitrile instead of an alkyl ester (e.g. IntB-115).

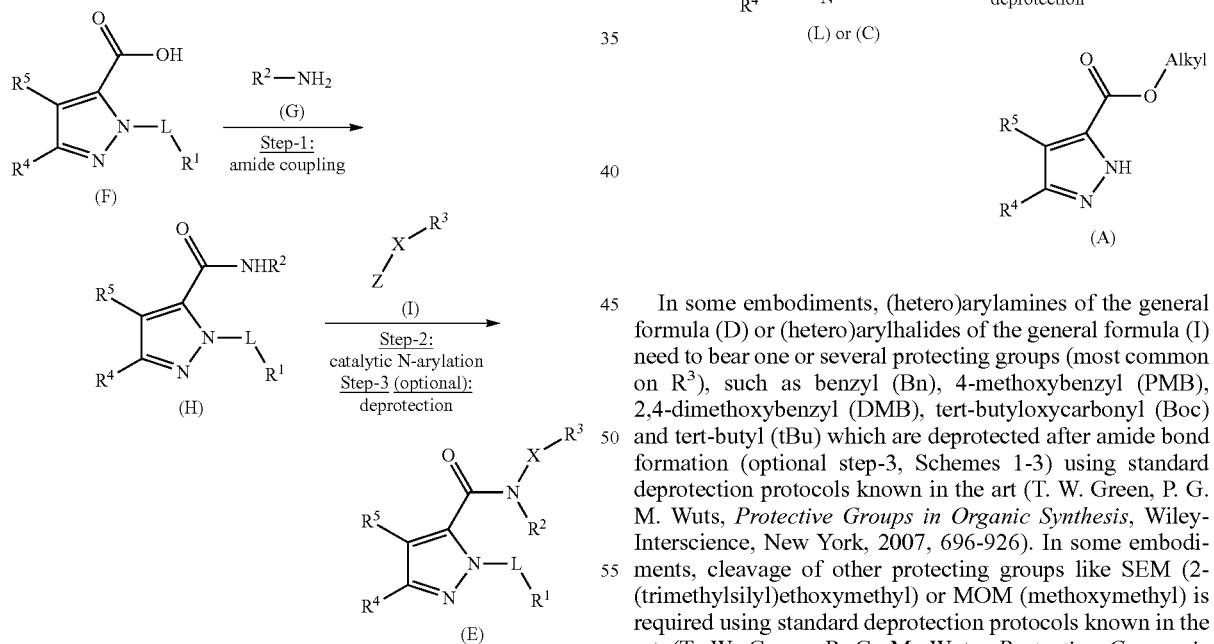

In some embodiments, (hetero)arylamines of the general formula (D) or (hetero)arylhalides of the general formula (I) need to bear one or several protecting groups (most common on R³), such as benzyl (Bn), 4-methoxybenzyl (PMB), 2,4-dimethoxybenzyl (DMB), tert-butyloxycarbonyl (Boc) and tert-butyl (tBu) which are deprotected after amide bond formation (optional step-3, Schemes 1-3) using standard deprotection protocols known in the art (T. W. Green, P. G. M. Wuts, *Protective Groups in Organic Synthesis*, Wiley-Interscience, New York, 2007, 696-926). In some embodiments, cleavage of other protecting groups like SEM (2-(trimethylsilyl)ethoxymethyl) or MOM (methoxymethyl) is required using standard deprotection protocols known in the art (T. W. Green, P. G. M. Wuts, *Protective Groups in Organic Synthesis*, Wiley-Interscience, New York, 2007, 696-926).

Alkyl 1H-pyrazole-5-carboxylates of the general formula (A), alkylation reagents of the general formula (B), (hetero)arylamines of the general formula (D) and (hetero)arylhalides of the general formula (I) can be either commercially available or prepared as described in the present invention or synthesized according to the standard procedures known to the person skilled in the art.

In some embodiments, carboxamides of the general formula E need to be converted into target compounds using further protocols known to the person skilled in the art, for example oxidation (similar to the procedure described for SC-35 step-2), amidation (similar to the procedure described for SC-21 steps 2,3) or sulfonylation.

Preparation of Synthetic Intermediates

Synthesis of 1-(cyclohexylmethyl)-3-(trifluoromethyl)-1H-pyrazole-5-carboxylic acid (Int-B1)

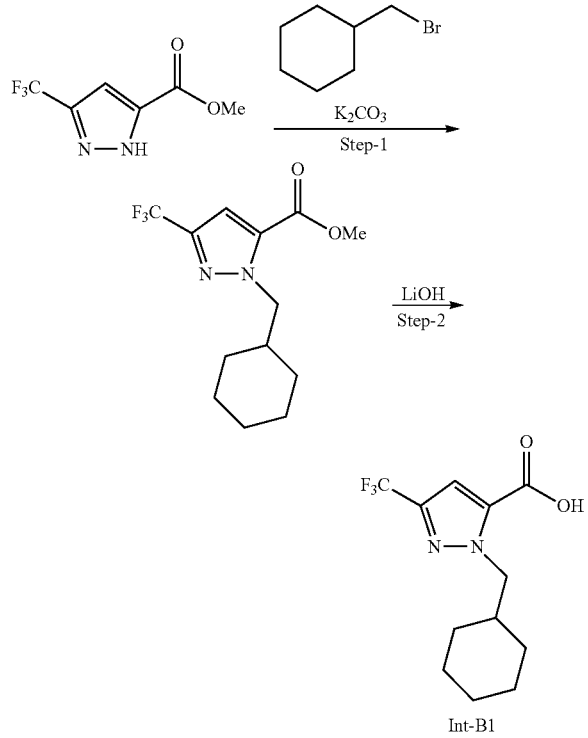

Int-B1

Step-1: To a solution of methyl 3-(trifluoromethyl)-1H-pyrazole-5-carboxylate (500 mg, 2.57 mmol, 1.00 eq.) in DMF (5 mL) was added $K_2CO_3$ (1100 mg, 7.71 mmol, 3.00 eq.) at ambient temperature and the reaction mixture was stirred for 15 min. (Bromomethyl)cyclohexane (0.5 mL, 3.85 mmol, 1.50 eq.) was added and the resulting mixture was stirred at ambient temperature for 16 h, then poured into ice-water (20 mL) and extracted with EtOAc (100 mL). The organic layer was washed with brine (50 mL), dried over anhydrous $Na_2SO_4$ and concentrated under reduced pressure to get the crude product which was purified by flash column chromatography (silica gel; 40% EtOAc/hexanes) to afford methyl 1-(cyclohexylmethyl)-3-(trifluoromethyl)-1H-pyrazole-5-carboxylate (400 mg, 1.37 mmol, 54%).

Step-2: To a solution of methyl 1-(cyclohexylmethyl)-3-(trifluoromethyl)-1H-pyrazole-5-carboxylate (350 mg, 1.20 mmol, 1.00 eq.) in THF/$H_2O$ (5 mL, 4:1) was added LiOH monohydrate (152 mg, 3.61 mmol, 3.00 eq.) at 0° C. The reaction mixture was stirred at ambient temperature for 16 h, concentrated under reduced pressure, diluted with water (10 mL), acidified with sat. aq. $NaHSO_4$ up to pH=4 and extracted with EtOAc (50 mL). The organic layers were dried over anhydrous $Na_2SO_4$ and concentrated under reduced pressure to get 1-(cyclohexylmethyl)-3-(trifluoromethyl)-1H-pyrazole-5-carboxylic acid (Int-B1) (320 mg, 1.15 mmol, 96%). LCMS: m/z [M−H]⁻=275.2 (calc.=275.1).

Synthesis of 1-(cyclohexylmethyl)-3,4-dimethyl-1H-pyrazole-5-carboxylic acid (Int-B6)

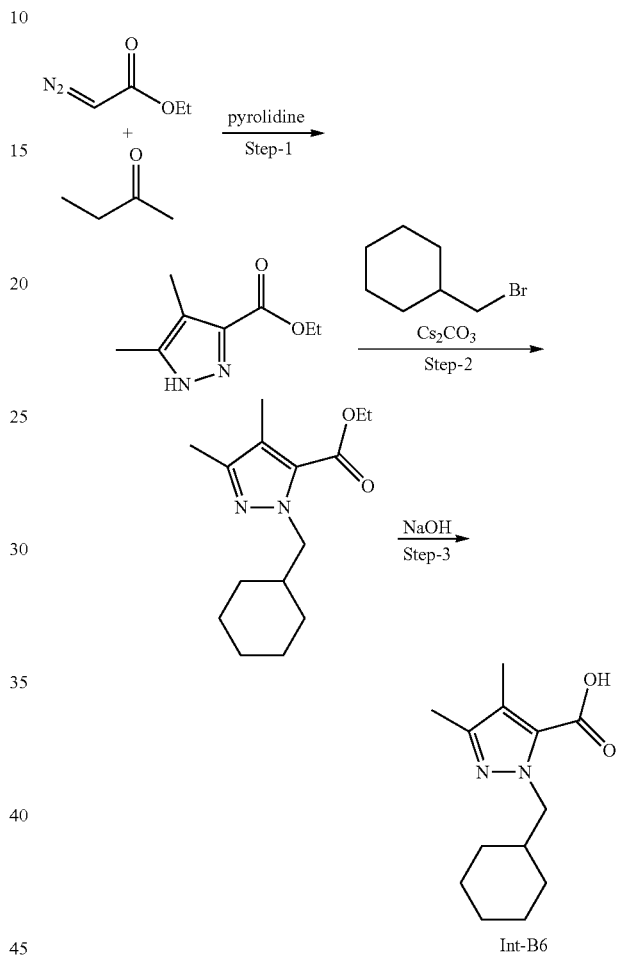

Int-B6

Step-1: To a solution of ethyl 2-diazoacetate (6.0 g, 52.58 mmol, 1.00 eq.) in DMSO (60 mL) were added butan-2-one (7.0 mL, 105.17 mmol, 2.00 eq.) and pyrrolidine (0.45 mL, 5.25 mmol, 0.10 eq.) at RT and the reaction mixture was stirred at ambient temperature for 16 h. After complete conversion of the starting material (monitored by TLC), the reaction mixture was quenched with ice and extracted with EtOAc (3×100 mL). The combined organic layers were washed with brine, dried over anhydrous $Na_2SO_4$ and concentrated under reduced pressure to give the crude product which was purified by flash column chromatography (silica gel; 30-40% EtOAc/hexanes) to furnish ethyl 4,5-dimethyl-1H-pyrazole-3-carboxylate. Yield: 34% (3.0 g, 17.84 mmol).

Step-2: To a solution of ethyl 4,5-dimethyl-1H-pyrazole-3-carboxylate (0.80 g, 4.76 mmol, 1.00 eq.) in DMF (10 mL) were added $Cs_2CO_3$ (3.10 g, 9.52 mmol) and (bromomethyl)cyclohexane (2.52 g, 14.28 mmol) at ambient temperature. The reaction mixture was stirred at 70° C. for 2 h, quenched with ice-water and extracted with EtOAc (3×50 mL). The combined organic layers were washed with brine, dried over anhydrous $Na_2SO_4$ and concentrated under reduced pressure to give the crude product which was purified by flash column chromatography (silica gel; 30-40% EtOAc/hexanes) to furnish ethyl 1-(cyclohexylmethyl)-3,4-dimethyl-1H-pyrazole-5-carboxylate. Yield: 48% (0.60 g, 2.27 mmol).

Step-3: To a solution of ethyl 1-(cyclohexylmethyl)-3,4-dimethyl-1H-pyrazole-5-carboxylate (0.35 g, 1.32 mmol, 1.00 eq.) in ethanol (7.5 mL) was added 2M aq. NaOH (1.32 mL, 2.64 mmol) at 0° C. and the reaction mixture was stirred at ambient temperature for 16 h. The reaction mixture was concentrated under reduced pressure, diluted with water, acidified with sat. aq. $NaHSO_4$ to pH~4 and extracted with EtOAc (3×30 mL). The combined organic layers were dried over anhydrous $Na_2SO_4$ and concentrated under reduced pressure to afford 1-(cyclohexylmethyl)-3,4-dimethyl-1H-pyrazole-5-carboxylic acid (Int-B6). Yield: 80% (0.25 g, 1.05 mmol). LCMS: m/z $[M+H]^+$=237.4 (calc.=237.2).

Synthesis of 4-cyano-1-(cyclohexylmethyl)-1H-pyrazole-5-carboxylic acid (Int-B7)

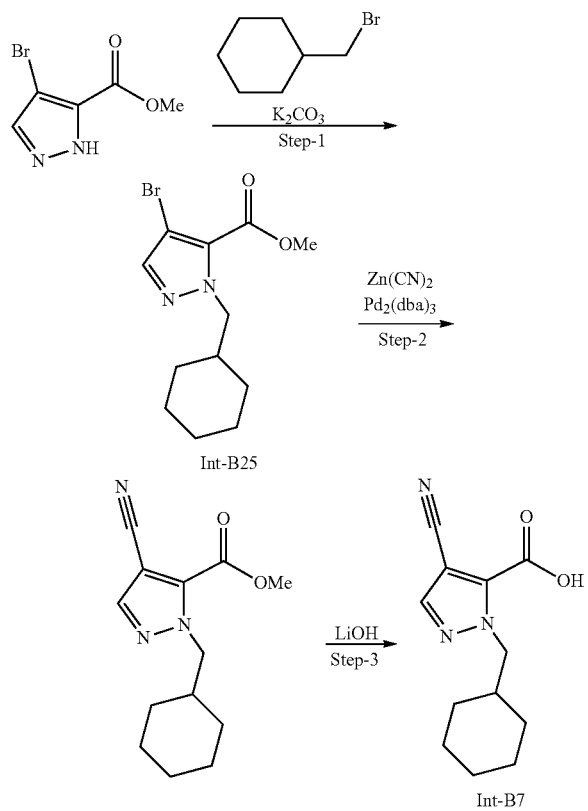

Step-1: To a stirred solution of methyl 4-bromo-1H-pyrazole-5-carboxylate (2.00 g, 0.09 mmol, 1.00 eq.) in DMF (20 mL) was added (bromomethyl)cyclohexane (1.64 mL, 0.11 mmol) followed by $K_2CO_3$ (2.69 g, 0.19 mmol). The reaction mixture was stirred at 80° C. for 16 h, then diluted with ice-cold water (50 mL) and extracted with EtOAc (2×50 mL). The combined organic layers were washed with brine (50 mL), dried over anhydrous $Na_2SO_4$ and concentrated under reduced pressure. The crude product was purified by flash column chromatography on silica gel (100-200 mesh) eluting with 8% EtOAc in petroleum ether to afford methyl 4-bromo-1-(cyclohexylmethyl)-1H-pyrazole-5-carboxylate (Int-B25). Yield: 1.5 g (51%).

Step-2: To a stirred solution of methyl 4-bromo-1-(cyclohexylmethyl)-1H-pyrazole-5-carboxylate (600 mg, 0.02 mmol, 1.00 eq.) in DMF (5 mL) were added $Zn(CN)_2$ (469 mg, 0.04 mmol) and Zn dust (260 mg, 0.04 mmol). The resulting mixture was purged with argon for 5 min followed by the addition of $Pd_2(dppf)Cl_2 \cdot DCM$ (274 mg, 0.003 mmol) and 1,1'-bis(diphenylphosphino)ferrocene (554 mg, 0.01 mmol). The reaction mixture was stirred at 130° C. in a microwave reactor for 2 h, then filtered through a celite pad, the filter cake was washed with EtOAc (30 mL), the combined filtrate diluted with ice-cold water (30 mL) and finally extracted with EtOAc (2×40 mL). The combined organic layers were dried over $Na_2SO_4$ and concentrated under reduced pressure. The resulting residue was purified by flash column chromatography on silica gel (100-200 mesh) eluting with 12% of EtOAc in petroleum ether to afford methyl 4-cyano-1-(cyclohexylmethyl)-1H-pyrazole-5-carboxylate. Yield: (260 mg, 52%).

Step-3: To a stirred solution of methyl 4-cyano-1-(cyclohexylmethyl)-1H-pyrazole-5-carboxylate (260 mg, 0.01 mmol) in $THF/MeOH/H_2O$ (1:1:1) (20 mL) was added LiOH monohydrate (131 mg, 0.03 mmol) at 0° C. The reaction mixture was stirred at ambient temperature for 12 h, then diluted with $H_2O$ (20 mL), acidified with 2N aq. HCl (10 mL) (pH=2), and extracted with diethyl ether (30 mL). The aqueous layer was extracted with EtOAc (2×30 mL). The combined organic layers were dried over anhydrous $Na_2SO_4$ and concentrated under reduced pressure to afford 4-cyano-1-(cyclohexylmethyl)-1H-pyrazole-5-carboxylic acid (Int-B7). Yield: 220 mg (94%). LCMS: m/z $[M+H]^+$=234.1 (calc.=234.1).

Synthesis of 1-(cyclohexylmethyl)-3-methyl-1H-pyrazole-5-carboxylic acid (Int-B8)

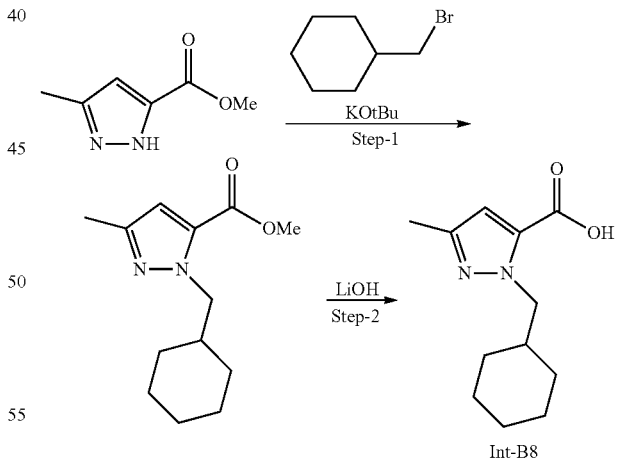

Step-1: To a solution of methyl 3-methyl-1H-pyrazole-5-carboxylate (1.00 g, 7.14 mmol, 1.00 eq.) in DMSO (10 mL) at 10° C. were added KOtBu (1.6 g, 14.28 mmol) and (bromomethyl)cyclohexane (1.6 g, 10.71 mmol). The resulting reaction mixture was stirred at ambient temperature for 16 h, then diluted with water (20 mL) and extracted with EtOAc (2×50 mL). The combined organic layers were washed with brine (20 mL) and concentrated under reduced pressure to afford a crude product which upon purification by flash column chromatography on silica gel (100-200 mesh) using 5-20% of EtOAc in petroleum ether afforded 350 mg of methyl 1-(cyclohexylmethyl)-3-methyl-1H-pyrazole-5-carboxylate.

Step-2: To a solution of methyl 1-(cyclohexylmethyl)-3-methyl-1H-pyrazole-5-carboxylate (350 mg, 1.48 mmol, 1.00 eq.) in MeOH/THF/H$_2$O (1:1:1, 10 mL) was added LiOH monohydrate (390 mg, 2 eq.) at 10° C. The resulting reaction mixture was stirred at ambient temperature for 3 h, then concentrated under reduced pressure, diluted with water (10 mL), acidified with sat. aq. KHSO$_4$ solution (pH=2) and extracted with EtOAc (3×20 mL). The combined organic layers were dried over Na$_2$SO$_4$ and concentrated under reduced pressure to afford 220 mg of 1-(cyclohexylmethyl)-3-methyl-1H-pyrazole-5-carboxylic acid (Int-B8). LCMS: m/z [M+H]$^+$=223.1 (calc.=223.1).

Synthesis of 1-(cyclobutylmethyl)-4-(trifluoromethyl)-1H-pyrazole-5-carboxylic acid (Int-B12)

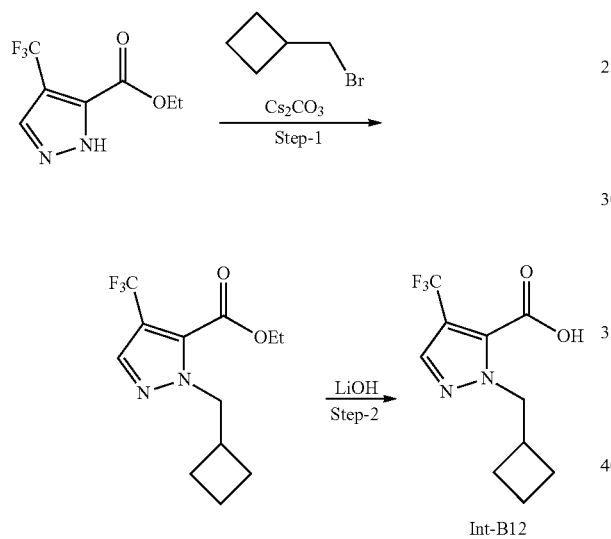

Int-B12

Step-1: To a solution of methyl 3-(trifluoromethyl)-1H-pyrazole-5-carboxylate (1.01 g, 4.80 mmol, 1.00 eq.) in DMF (20 mL) was added Cs$_2$CO$_3$ (4.68 g, 14.41 mmol, 3.00 eq.) at ambient temperature under an argon atmosphere. The resulting reaction mixture was stirred for 15 min and then (bromomethyl)cyclobutane (0.49 mL, 4.367 mmol, 1.10 eq.) was added at RT. The reaction mixture was stirred at ambient temperature for 18 h, then diluted with water (80 mL), extracted with EtOAc (2×70 mL) and washed with brine (50 mL). The combined organic layers were dried over anhydrous Na$_2$SO$_4$ and concentrated under reduced pressure. The crude product was purified by flash column chromatography on silica gel (100-200 mesh) using 0-40% EtOAc/hexanes as an eluent to afford ethyl 1-(cyclobutylmethyl)-4-(trifluoromethyl)-1H-pyrazole-5-carboxylate (450 mg, 33%).

Step-2: To a solution of ethyl 1-(cyclobutylmethyl)-4-(trifluoromethyl)-1H-pyrazole-5-carboxylate (300 mg, 1.085 mmol, 1.00 eq.) in THF/water (9 mL, 2:1) was added LiOH monohydrate (91.1 mg, 2.172 mmol, 2.00 eq.) at 0° C. The reaction mixture was warmed up to ambient temperature and stirred for 18 h. The reaction mixture was cooled to 0° C., acidified with 1N aq. HCl up to pH~3 and extracted with EtOAc (2×40 mL). The combined organic layers were dried over anhydrous Na$_2$SO$_4$ and concentrated under reduced pressure to afford 1-(cyclobutylmethyl)-4-(trifluoromethyl)-1H-pyrazole-5-carboxylic acid (Int-B12) (210 mg, 77%). LCMS: m/z [M+H]$^+$=249.1 (calc.=249.1).

Synthesis of 1-((4,4-difluorocyclohexyl)methyl)-3,4-dimethyl-1H-pyrazole-5-carboxylic acid (Int-B22)

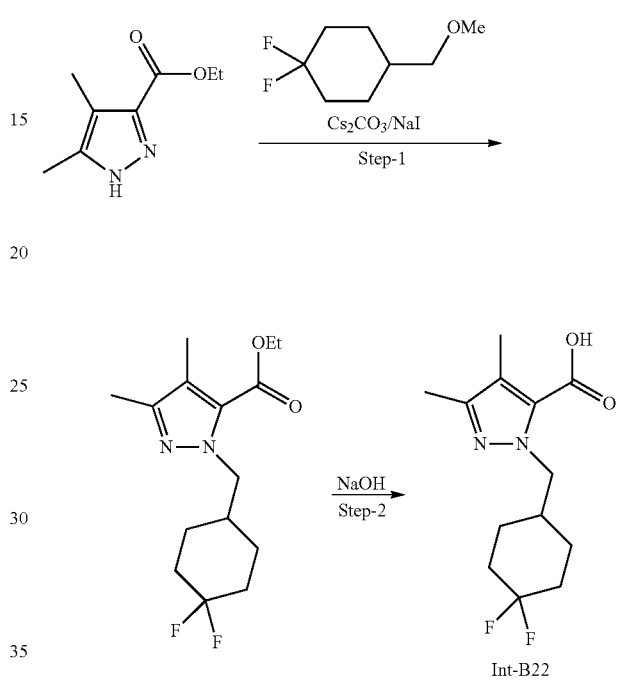

Int-B22

Step-1: To a solution of ethyl 4,5-dimethyl-1H-pyrazole-3-carboxylate (746 mg, 4.44 mmol, 1.00 eq.) in DMF (20 mL) were added Cs$_2$CO$_3$ (2.9 g, 8.88 mmol, 2.00 eq.) and (4,4-difluorocyclohexyl)methyl methanesulfonate (6.66 mmol, 1.50 eq.) at ambient temperature and the reaction mixture was heated to 100° C. for 16 h. The reaction mixture was filtered through celite and the filter cake was washed with EtOAc (50 mL). The combined filtrate was concentrated under reduced pressure to give the crude product which was purified by flash column chromatography (silica gel; 40-50% EtOAc/hexanes) to yield ethyl 1-((4,4-difluorocyclohexyl)methyl)-3,4-dimethyl-1H-pyrazole-5-carboxylate. Yield: 37% (1.66 mmol).

Step-2: To a solution of ethyl 1-((4,4-difluorocyclohexyl)methyl)-3,4-dimethyl-1H-pyrazole-5-carboxylate (700 mg, 2.34 mmol, 1.0 eq.) in MeOH (5 mL) was added 2M aq. NaOH (2.34 mL, 4.67 mmol) at 0° C. and the reaction mixture was stirred at ambient temperature for 16 h. The reaction mixture was concentrated under reduced pressure. The resulting residue was diluted with water (30 mL), acidified with sat. aq. NaHSO$_4$ to pH=4 and extracted with EtOAc (3×50 mL). The combined organic layers were dried over anhydrous Na$_2$SO$_4$ and concentrated under reduced pressure to yield crude 1-((4,4-difluorocyclohexyl)methyl)-3,4-dimethyl-1H-pyrazole-5-carboxylic acid (Int-B22) (630 mg, 99%) which was used in the next steps without additional purification. LCMS: m/z [M-H]$^-$=271.2 (calc.=271.1).

Synthesis of 1-(cyclohexylmethyl)-4-isopropyl-1H-pyrazole-5-carboxylic acid (Int-B26)

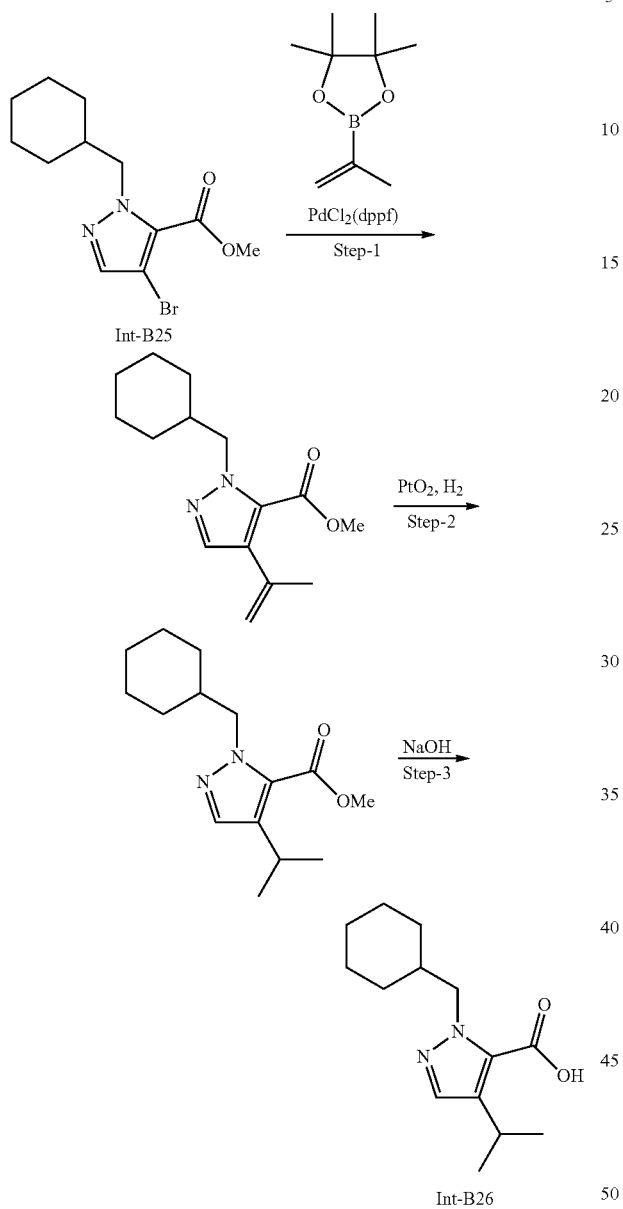

Step-1: A solution of methyl 4-bromo-1-(cyclohexylmethyl)-1H-pyrazole-5-carboxylate (Int-B25) (0.35 g, 1.16 mmol, 1.00 eq.) in dry DMF (12 mL) was degassed with argon for 15 min followed by the addition of $Na_2CO_3$ (0.25 g, 2.3 mmol), $PdCl_2$(dppf)DCM (47 mg, 0.06 mmol) and 4,4,5,5-tetramethyl-2-(prop-1-en-2-yl)-1,3,2-dioxaborolane (0.39 mL, 2.09 mmol) at ambient temperature and the reaction mixture was then heated in a sealed tube to 90-100° C. for 16 h. The reaction mixture was cooled to ambient temperature, ice-water was added and the resulting mixture was extracted with EtOAc (3×100 mL). The combined organic layers were washed with cold brine, dried over anhydrous $Na_2SO_4$ and concentrated under reduced pressure to give the crude product which was purified by flash column chromatography (silica gel; 0-20% EtOAc/hexanes) to yield methyl 1-(cyclohexylmethyl)-4-(prop-1-en-2-yl)-1H-pyrazole-5-carboxylate. Yield: 65% (0.20 g, 0.76 mmol).

Step-2: A solution of methyl 1-(cyclohexylmethyl)-4-(prop-1-en-2-yl)-1H-pyrazole-5-carboxylate (0.20 g, 0.76 mmol, 1.00 eq.) in MeOH/THF (2:1) was degassed with nitrogen for 15 min followed by the addition of $PtO_2$ (0.10 g) at ambient temperature. The reaction mixture was stirred at ambient temperature under hydrogen balloon pressure for 15 min. The resulting mixture was filtered through a celite pad and the filtrate was concentrated under reduced pressure to give the crude product which was purified by flash column chromatography on silica gel (100-200 mesh) eluting with 0-20% EtOAc in hexanes to yield methyl 1-(cyclohexylmethyl)-4-isopropyl-1H-pyrazole-5-carboxylate. Yield: 85% (0.17 g, 0.64 mmol).

Step-3: To a solution of methyl 1-(cyclohexylmethyl)-4-isopropyl-1H-pyrazole-5-carboxylate (0.17 g, 0.64 mmol, 1.00 eq.) in THF/MeOH/$H_2O$ (2:2:1) was added NaOH (0.10 g, 2.58 mmol) at ambient temperature and the reaction mixture was stirred at ambient temperature for 16 h. The reaction mixture was concentrated under reduced pressure and acidified with sat. aq. $KHSO_4$ (precipitation observed). The resulting suspension was filtered through a sintered funnel, the filter cake was washed with water and dried under reduced pressure (removal of residual water as azeotropic mixture with toluene) to yield 1-(cyclohexylmethyl)-4-isopropyl-1H-pyrazole-5-carboxylic acid (Int-B26). Yield: 93% (0.15 g, 0.60 mmol). LCMS: m/z $[M+H]^+$=251.2 (calc.=251.2).

Synthesis of 1-(cyclohexylmethyl)-4-cyclopropyl-1H-pyrazole-5-carboxylic acid (Int-B27)

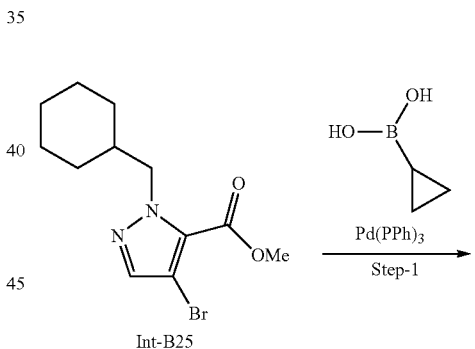

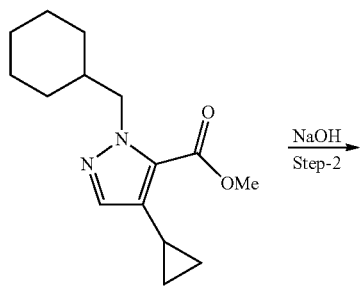

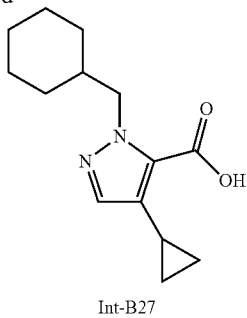

Int-B27

Step-1: To a solution of methyl 4-bromo-1-(cyclohexylmethyl)-1H-pyrazole-5-carboxylate (Int-B25) (0.05 g, 0.166 mmol, 1.00 eq.) in toluene (2.0 mL) and H₂O (0.2 mL) was added K₃PO₄ (0.141 g, 0.664 mmol) and cyclopropylboronic acid (0.03 g, 0.249 mmol) at ambient temperature. After degassing the reaction for 15 min using argon, Pd(PPh₃)₄ (0.019 g, 0.016 mmol) was added at ambient temperature. The reaction mixture was then heated to 110° C. for 16 h. After completion of the reaction, the reaction mixture was filtered through a sintered glass filter, the filter cake was washed with EtOAc (10 mL) and the combined filtrate was concentrated under reduced pressure. The resulting crude residue was purified by flash column chromatography (silica gel, 0 to 70% acetone in hexanes) to afford methyl 1-(cyclohexylmethyl)-4-cyclopropyl-1H-pyrazole-5-carboxylate. Yield: 69% (0.03 g, 0.114 mmol).

Step-2: To a solution of methyl 1-(cyclohexylmethyl)-4-cyclopropyl-1H-pyrazole-5-carboxylate (0.37 g, 1.41 mmol, 1.00 eq.) in methanol/THF/H₂O (1:1:0.5) (15.0 mL), NaOH (0.226 g, 5.64 mmol) was added at 0° C. and the reaction mixture was stirred at ambient temperature for 2 h. The reaction mixture was concentrated under reduced pressure. The resulting residue was diluted with water, acidified with sat. aq. NaHSO₄ and extracted with EtOAc (3×30 mL). The combined organic layers were dried over anhydrous Na₂SO₄ and concentrated under reduced pressure to furnish 1-(cyclohexylmethyl)-4-cyclopropyl-1H-pyrazole-5-carboxylic acid (Int-B27). Yield: 77% (0.27 g, 1.088 mmol). LCMS: m/z [M+H]⁺=249.2 (calc.=249.2).

The following intermediates were prepared by analogy to the procedures described above using appropriate reactants and adjusted purification protocols:

| Intermediate structure/code | Procedure | Analytics |
|---|---|---|
| Int-B2 | in analogy to the synthesis of Int-B1 using methyl 3-(trifluoromethyl)-1H-pyrazole-5-carboxylate and (4,4-difluorocyclohexyl)methyl 4-methylbenzenesulfonate in the first step | LCMS: m/z [M − H]⁻ = 311.38, (calc. = 311.08). |
| Int-B3 | in analogy to the synthesis of Int-B1 using methyl 3-(trifluoromethyl)-1H-pyrazole-5-carboxylate and (bromomethyl)cyclopentane in the first step | ¹H NMR (400 MHz, DMSO-d6): δ (ppm) = 13.90 (br s, 1H), 7.26 (s, 1H), 4.51 (d, 2H), 2.50 - 2.35 (m, 1H9, 1.58 - 1.52 (m, 6H), 1.25 - 1.15 (m, 2H). |
| Int-B4 | in analogy to the synthesis of Int-B1 using methyl 3-(trifluoromethyl)-1H-pyrazole-5-carboxylate and 4-(bromomethyl)tetrahydro-2H-pyrane in the first step | LCMS: m/z [M − H]⁻ = 277.0, (calc. = 277.1). |

-continued

| Intermediate structure/code | Procedure | Analytics |
|---|---|---|
| 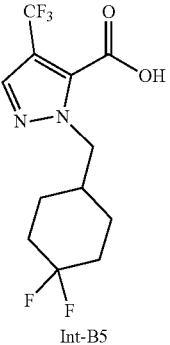 [SMILES: O=C(O)c1c(C(F)(F)F)cnn1CC1CCC(F)(F)CC1]<br>Int-B5 | in analogy to the synthesis of Int-B1 using ethyl 4-(trifluoromethyl)-1H-pyrazole-5-carboxylate and (4,4-difluorocyclohexyl)methyl 4-methylbenzenesulfonate in the first step | LCMS: m/z $[M + H]^+$ = 313.31 (calc. = 313.10). |
| 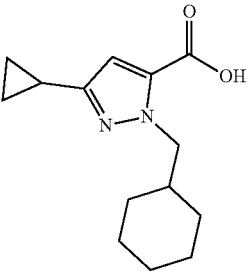<br>Int-B9 | in analogy to the synthesis of Int-B8 using methyl 3-cyclopropyl-1H-pyrazole-5-carboxylate and (bromomethyl)cyclohexane in the first step | LCMS: m/z $[M + H]^+$ = 249.2 (calc. = 249.2). |
| 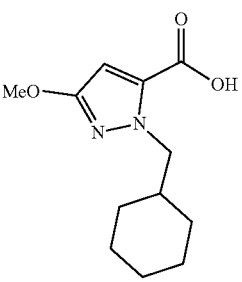<br>Int-B10 | in analogy to the synthesis of Int-B1 using methyl 3-methoxy-1H-pyrazole-5-carboxylate and (bromomethyl)cyclohexane in the first step | LCMS: m/z $[M + H]^+$ = 239.1 (calc. = 239.1). |
| 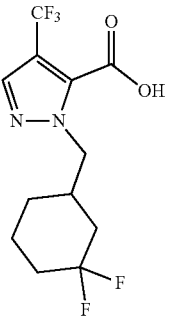<br>Int-B11 | in analogy to the synthesis of Int-B1 using ethyl 4-(trifluoromethyl)-1H-pyrazole-5-carboxylate and 3-(bromomethyl)-1,1-difluorocyclohexane in the first step | LCMS: m/z $[M + H]^+$ = 313.12 (calc. = 313.10). |

-continued

| Intermediate structure/code | Procedure | Analytics |
|---|---|---|
| 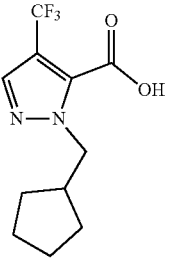<br>Int-B13 | in analogy to the synthesis of Int-B12 using ethyl 4-(trifluoromethyl)-1H-pyrazole-5-carboxylate and (bromomethyl)cyclopentane in the first step | LCMS: m/z [M + H]$^+$ = 263.1 (calc. = 263.1). |
| 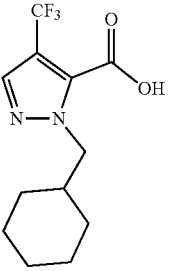<br>Int-B14 | in analogy to the synthesis of Int-B12 using ethyl 4-(trifluoromethyl)-1H-pyrazole-5-carboxylate and (bromomethyl)cyclohexane in the first step | LCMS: m/z [M + H]$^+$ = 277.1 (calc. = 277.1). |
| 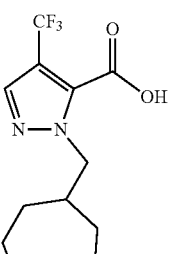<br>Int-B15 | in analogy to the synthesis of Int-B12 using ethyl 4-(trifluoromethyl)-1H-pyrazole-5-carboxylate and (bromomethyl)cycloheptane in the first step | LCMS: m/z [M + H]$^+$ = 291.1 (calc. = 291.1). |
| 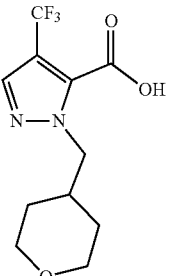<br>Int-B16 | in analogy to the synthesis of Int-B1 using ethyl 4-(trifluoromethyl)-1H-pyrazole-5-carboxylate and 4-(bromomethyl)tetrahydro-2H-pyrane in the first step | LCMS: m/z [M + H]$^+$ = 279.1 (calc. = 279.1). |
| 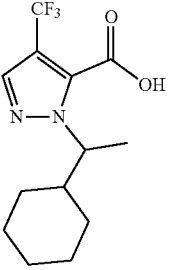<br>Int-B17 | in analogy to the synthesis of Int-B1 using ethyl 1-(1-cyclohexylethyl)-4-(trifluoromethyl)-1H-pyrazole-5-carboxylate and 1-cyclohexylethyl methanesulfonate in the first step | LCMS: m/z [M + H]$^+$ = 291.2 (calc. = 291.1). |

| Intermediate structure/code | Procedure | Analytics |
|---|---|---|
| 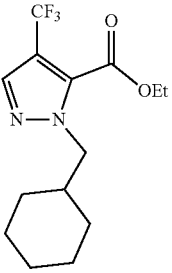<br>Int-B18 | in analogy to step-1 of the synthesis of Int-B12 using ethyl 4-(trifluoromethyl)-1H-pyrazole-5-carboxylate and (bromomethyl)cyclohexane | LCMS: m/z $[M + H]^+$ = 305.2 (calc. = 305.2). |
| 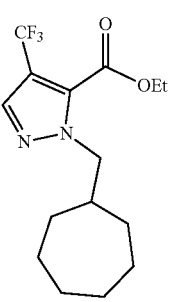<br>Int-B19 | in analogy to step-1 of of the synthesis of Int-B12 using ethyl 4-(trifluoromethyl)-1H-pyrazole-5-carboxylate and (bromomethyl)cycloheptane | LCMS: m/z $[M + H]^+$ = 319.2 (calc. = 319.2). |
| 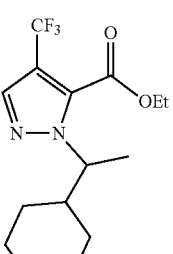<br>Int-B20 | in analogy to step 1 of of the synthesis of Int-B1 using ethyl 1-(1-cyclohexylethyl)-4-(trifluoromethyl)-1H-pyrazole-5-carboxylate and 1-cyclohexylethyl methanesulfonate | LCMS: m/z $[M + H]^+$ = 319.4 (calc. = 319.2). |
| 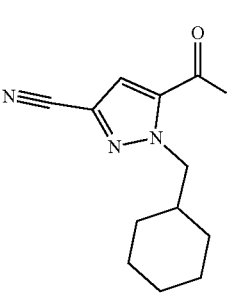<br>Int-B21 | in analogy to the synthesis of Int-B7 using methyl 3-bromo-1H-pyrazole-5-carboxylate and (bromomethyl)cyclohexane in the first step | LCMS: m/z $[M + H]^+$ = 234.3 (calc. = 234.1). |

-continued

| Intermediate structure/code | Procedure | Analytics |
|---|---|---|
| 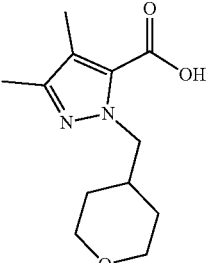<br>Int-B23 | in analogy to the synthesis of Int-B1 using ethyl 4,5-dimethyl-1H-pyrazole-3-carboxylate and 4-(bromomethyl)tetrahydro-2H-pyrane in the first step | LCMS: m/z [M + H]$^+$ = 239.2 (calc. = 239.1). |
| 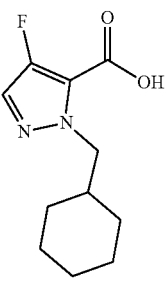<br>Int-B24 | in analogy to the synthesis of Int-B12 using methyl 4-fluoro-1H-pyrazole-5-carboxylate and (bromomethyl)cyclohexane in the first step | LCMS: m/z [M + H]$^+$ = 227.05 (calc. = 227.12). |
| 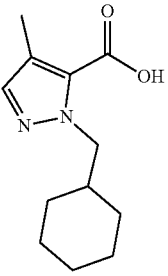<br>Int-B28 | in analogy to the synthesis of Int-B12 using methyl 4-methyl-1H-pyrazole-5-carboxylate and (bromomethyl)cyclohexane in the first step | LCMS: m/z [M + H]$^+$ = 223.19 (calc. = 223.15). |
| 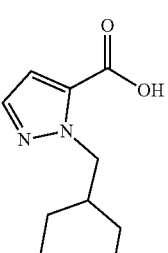<br>Int-B66 | in analogy to the synthesis of Int-B1 using methyl 1H-pyrazole-5-carboxylate and (bromomethyl)cyclohexane | LCMS: m/z [M + H]$^+$ = 209.27 (calc. = 209.13). |
| 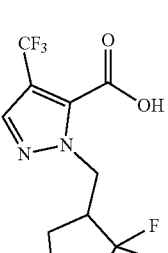<br>Int-B67 | in analogy to the synthesis of Int-B1 using ethyl 1-(1-cyclohexylethyl)-4-(trifluoromethyl)-1H-pyrazole-5-carboxylate and 2-(bromomethyl)-1,1-difluorocyclopentane | LCMS: m/z [M + H]$^+$ = 299.23 (calc. = 299.08). |

| Intermediate structure/code | Procedure | Analytics |
|---|---|---|
| Int-B68 | in analogy to the synthesis of Int-B1 using ethyl 3-cyclopropyl-4-(trifluoromethyl)-1H-pyrazole-5-carboxylate and (bromomethyl)cyclopropane | LCMS: m/z [M + H]$^+$ = 275.10 (calc. = 275.10). |

Synthesis of 3-cyclopropyl-1-((tetrahydro-2H-pyran-3-yl)methyl)-4-(trifluoromethyl)-1H-pyrazole-5-carboxylic acid (Int-B29)

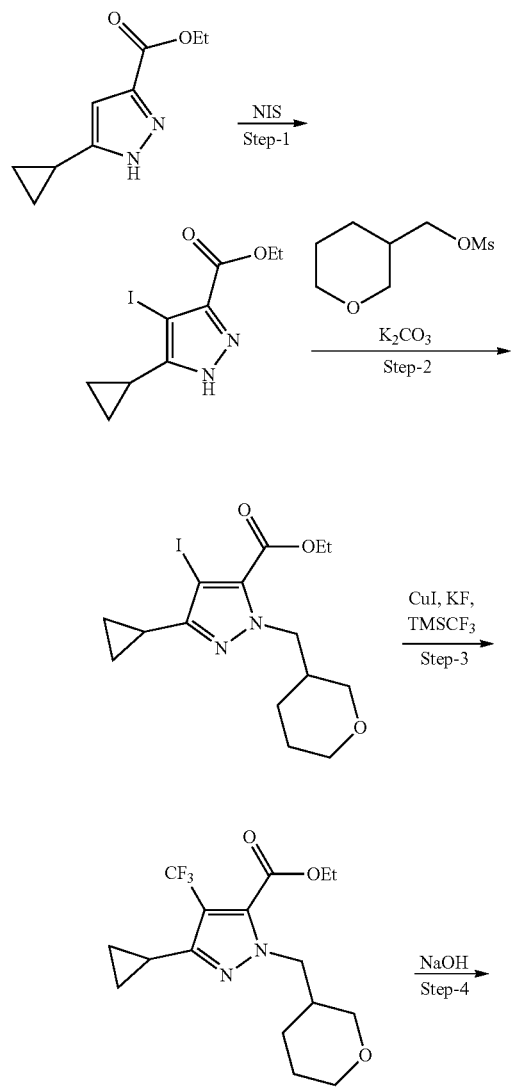

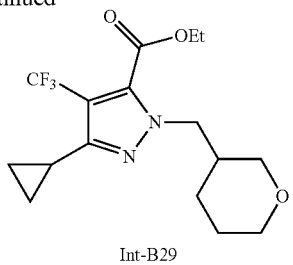

Int-B29

Step 1: NIS (2.74 g, 12.22 mmol, 1.1 eq.) was added to a solution of ethyl 5-cyclopropyl-1H-pyrazole-3-carboxylate (2.0 g, 11.11 mmol, 1.0 eq.) and TFA (379.9 mg, 3.33 mmol, 0.3 eq.) in ACN (20 mL) and the resulting reaction mixture was stirred for 16 h at ambient temperature. The reaction mixture was concentrated under reduced pressure to give a residue, which was diluted with ethyl acetate (100 mL). The organic layer was washed with water (2×50 mL), dried over anhyd. Na$_2$SO$_4$ and concentrated under reduced pressure to give ethyl 3-cyclopropyl-4-iodo-1H-pyrazole-5-carboxylate. Yield: 58% (2.5 g).

Step 2: A solution of ethyl 3-cyclopropyl-4-iodo-1H-pyrazole-5-carboxylate (0.400 g, 1.307 mmol, 1.0 eq.), (tetrahydro-2H-pyran-3-yl)methyl methanesulfonate (0.304 g, 1.568 mmol, 1.2 eq.) and K$_2$CO$_3$ (0.270 g, 1.960 mmol, 1.5 eq.) in acetonitrile (10 mL) was heated to 70° C. for 16 h. The reaction mixture was allowed to cool to ambient temperature and was filtered through a celite pad. The filterate was concentrated under reduced pressure and the residue obtained was diluted with ethyl acetate (50 mL). The organic layer was washed with water (2×50 mL), dried over anhyd. Na$_2$SO$_4$ and concentrated under reduced pressure to obtain a residue, which was purified by column chromatography using 5% ethyl acetate in Pet-ether as an eluent to afford ethyl 3-cyclopropyl-4-iodo-1-((tetrahydro-2H-pyran-3-yl)methyl)-1H-pyrazole-5-carboxy late (300 mg, crude).

Step 3: CuI (211.6 mg, 1.113 mmol, 1.5 eq.) was added to a solution of ethyl 3-cyclopropyl-4-iodo-1-((tetrahydro-2H-pyran-3-yl)methyl)-1H-pyrazole-5-carboxylate (0.300 g, 0.742 mmol, 1.0 eq.) and KF (51.6 mg, 0.891 mmol, 1.2 eq.) in DMF (8 mL). The reaction mixture was purged with argon for 15 minutes, followed by the addition of TMSCF$_3$ (0.527 g, 3.712 mmol, 5.0 eq.). The reaction mixture was then heated to 80° C. for 16 h. The reaction mixture was allowed to cool to ambient temperature, quenched with water (5 mL) and filtered through a celite pad. The filterate was concentrated under reduced pressure, and the obtained residue was diluted with ethyl acetate (50 mL). The organic layer was washed with water (3×50 mL), dried over anhyd. Na₂SO₄ and concentrated under reduced pressure to obtain a reside, which was purified by column chromatography using 20% ethyl acetate in pet-ether as an eluent to afford ethyl 3-cyclopropyl-1-((tetrahydro-2H-pyran-3-yl)methyl)-4-(trifluoromethyl)-1H-pyrazole-5-carboxylate (300 mg, crude).

Step 4: To a solution ethyl 3-cyclopropyl-1-((tetrahydro-2H-pyran-3-yl)methyl)-4-(trifluoromethyl)-1H-pyrazole-5-carboxylate (0.300 mg, 0.867 mmol, 1.0 eq.) in EtOH:THF (1:1, 4 mL) was added 2N NaOH (6 mL). The resulting suspension was stirred at ambient temperature for 16 h. The reaction mixture was diluted with water (15 mL), acidified to pH~2 with 1N aq. HCl solution and extracted with 10% methanol in dichloromethane (2×30 mL). The combined organic layers were dried over anhyd. Na₂SO₄ and concentrated under reduced pressure to afford 3-cyclopropyl-14 (tetrahydro-2H-pyran-3-yl)methyl)-4-(trifluoromethyl)-1H-pyrazole-5-carboxylic acid (Int-B29) (200 mg, crude). LCMS: m/z [M+H]⁺=319.1 (calc.=319.1).

The following intermediates were prepared by analogy to the procedures described above using appropriate reactants and adjusted purification protocols:

| Intermediate structure/code | Procedure | Analytics |
|---|---|---|
| Int-B58 | in analogy to the synthesis of Int-B29 using (3,3-difluorocyclobutyl)methyl methanesulfonate in step 2 | LCMS: m/z [M + H]⁺ = 327.0 (calc. = 327.1). |
| Int-B (ethyl, CF₃, difluorocyclobutyl) | in analogy to the synthesis of Int-B29 using (3,3-difluorocyclobutyl)methyl methanesulfonate in step 2 | LCMS: m/z [M + H]⁺ = 313.2 (calc. = 313.1). |
| Int-B70 | in analogy to the synthesis of Int-B29, but using Step 4 in the synthesis of Int-B32 for pyrazole alkylation using (3,3-difluorocyclobutyl)methanol and the following modified conditions in step 3: methyl boronic acid, PdCl₂(dppf), K₂CO₃, H₂O/dioxane 100° C., 16 h | LCMS: m/z [M − H]⁻ = 257.3 (calc. = 257.1). |
| Int-B71 | in analogy to the synthesis of Int-B29, using (3,3-difluorocyclobutyl)methyl methanesulfonate in step 2 | LCMS: m/z [M + H]⁺ = 327.0 (calc. = 327.1). |

| Intermediate structure/code | Procedure | Analytics |
|---|---|---|
| 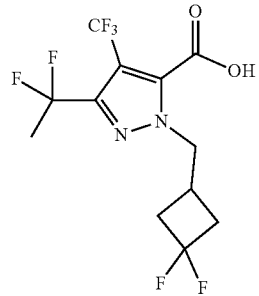<br>Int-B72 | in analogy to the synthesis of Int-B29, but using 3-(bromomethyl)-1,1-difluorocyclobutane in step 2 | LCMS: m/z [M + H]$^+$ = 349.2 (calc. = 349.1). |
| 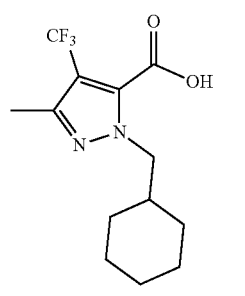<br>Int-B121 | in analogy to the synthesis of Int-B29, using (bromomethyl)cyclohexane in step 2 | $^1$H NMR (400 MHz, DMSO-d6): δ (ppm) = 14.32 (bs, 1H), 4.20 (d, 2H), 4.06 – 3.98 (m , 1H), 2.28 (s, 3H), 1.70 – 1.52 (m, 4H), 1.51 – 1.40 (m, 3H), 1.20 – 1.05 (m, 3H). |

Synthesis of 3-cyclopropyl-4-(trifluoromethyl)-1-((2-(trifluoromethyl)tetrahydrofuran-3-yl)methyl)-1H-pyrazole-5-carboxylic acid (Int-B30)

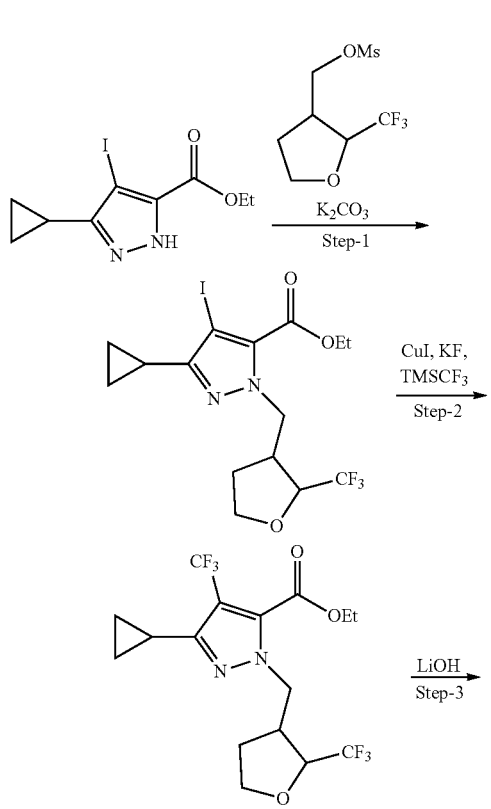

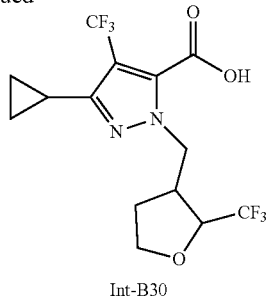

Int-B30

Step 1: To a stirred solution of ethyl 3-cyclopropyl-4-iodo-1H-pyrazole-5-carboxylate (1.5 g, 4.902 mmol, 1.0 eq.) in acetonitrile (50 mL) were added K$_2$CO$_3$ (2.0 g, 14.706 mmol, 3.0 eq.) and (2-(trifluoromethyl)tetrahydrofuran-3-yl)methyl methanesulfonate (1.8 g, 7.353 mmol, 1.5 eq.) at ambient temperature. The reaction mixture was heated to 90° C. for 16 h. The reaction mixture was filtered, and the filter cake was washed with ethyl acetate (30 mL). The filtrate was concentrated under reduced pressure to get the crude product, which was purified using column chromatography (silica gel 100-200 mesh, 10% ethyl acetate in Pet ether as an eluent) to afford ethyl 3-cyclopropyl-4-iodo-1-((2-(trifluoromethyl)tetrahydrofuran-3-yl)methyl)-1H-pyrazole-5-carboxylate (0.85 g, crude).

Step 2: To a stirred solution of ethyl 3-cyclopropyl-4-iodo-1-((2-(trifluoromethyl)tetrahydrofuran-3-yl)methyl)-1H-pyrazole-5-carboxylate (400 mg, 0.873 mmol, 1.0 eq.) in DMF (10 mL) were added CuI (248.8 mg, 1.309 mmol, 1.5 eq.) and KF (60.8 mg, 1.047 mmol, 1.2 eq.) at ambient temperature. The reaction mixture was degassed with argon for 10 minutes, followed by the addition of TMSCF$_3$ (650.6 mg, 4.366 mmol, 5.0 eq) at ambient temperature. The resulting reaction mixture was heated to 100° C. for 48 h. The reaction was carried out in in two different batches of the same size, which were combined for workup. After cooling to ambient temperature, the combined reaction mixtures were diluted with water (50 mL) and extracted with diethylether (2×50 mL). The combined organic layers were dried over anhydrous Na₂SO₄ and concentrated under reduced pressure to afford ethyl 3-cyclopropyl-4-(trifluoromethyl)-1-((2-(trifluoromethyl)tetrahydrofuran-3-yl)methyl)-1H-pyrazole-5-carboxylate (800 mg, crude).

Step 3: To a stirred solution of ethyl 3-cyclopropyl-4-(trifluoromethyl)-1-((2-(trifluoromethyl)tetrahydrofuran-3-yl)methyl)-1H-pyrazole-5-carboxylate (400 mg, 1.0 mmol, 1.0 eq.) in THF:MeOH:H₂O (1:1:0.5, 25 mL) was added a solution of LiOH·H₂O (210 mg, 5.0 mmol, 5.0 eq.) at ambient temperature. The reaction mixture was stirred for 16 h at ambient temperature. The reaction mixture was concentrated under reduced pressure to obtain a residue, which was diluted with water (10 mL), acidified to pH~2 with 1N aq. HCl solution and extracted with 5% MeOH in dichloromethane (2×50 mL). The combined organic layers were dried over anhydrous Na₂SO₄ and concentrated under reduced pressure to afford 3-cyclopropyl-4-(trifluoromethyl)-1-((2-(trifluoromethyl)tetrahydrofuran-3-yl)methyl)-1H-pyrazole-5-carboxylic acid (Int-B30) (400 mg, crude). LCMS m/z [M+H]⁺=373.2 (calc.=373.1)

Step 4: To a stirred solution of 2-(trifluoromethyl)furan-3-carboxylic acid (2.0 g, 11.111 mmol, 1.0 eq.) in acetic acid (20 mL) was added Pd/C (10%, w/w, 2.0 g) under an argon atmosphere at ambient temperature. The resulting reaction mixture was stirred at ambient temperature for 48 h under hydrogen pressure (using a hydrogen balloon). The reaction mixture was filtered through a celite bed and the celite bed was washed with EtOAc (50 mL). The filtrate was concentrated under reduced pressure to afford 2-(trifluoromethyl)tetrahydrofuran-3-carboxylic acid (2.0 g, crude).

Step 5: To a stirred solution of 2-(trifluoromethyl)tetrahydrofuran-3-carboxylic acid (2.0 g, 10.869 mmol, 1.0 eq.) in THF (30 mL) was added LAH in THF (1 M, 16.3 mL, 16.304 mmol, 1.5 eq.) at 0° C. The reaction mixture was warmed to ambient temperature and was stirred for 3 h. The reaction mixture was quenched with saturated Na₂SO₄ solution (10 mL) and stirred for 30 minutes. The reaction mixture was filtered through a celite bed which was washed with ethyl acetate (2×30 mL). The filtrate was concentrated under reduced pressure to afford (2-(trifluoromethyl)tetrahydrofuran-3-yl)methanol (2.0 g, crude).

Step 6: To a stirred solution of (2-(trifluoromethyl)tetrahydrofuran-3-yl)methanol (2.0 g, 11.764 mmol, 1.0 eq.) in dichloromethane (50 mL) were added triethylamine (4.8 mL, 35.292 mmol, 3.0 eq.) and MsCl (1.35 mL, 17.647 mmol, 1.5 eq.) at 0° C. The reaction mixture was stirred for 3 h at ambient temperature. The reaction mixture was quenched with water (50 mL) and extracted with dichloromethane (2×50 mL). The combined organic layers were washed with water (50 mL) and brine (50 mL), dried over anhydrous Na₂SO₄ and concentrated under reduced pressure to afford (2-(trifluoromethyl)tetrahydrofuran-3-yl)methyl methanesulfonate (2.2 g, crude). The compound was used in the next step without further purification. LCMS m/z [M+H]⁺=372.9 (calc.=373.1)

The following intermediates were prepared by analogy to the procedures described above using appropriate reactants and adjusted purification protocols:

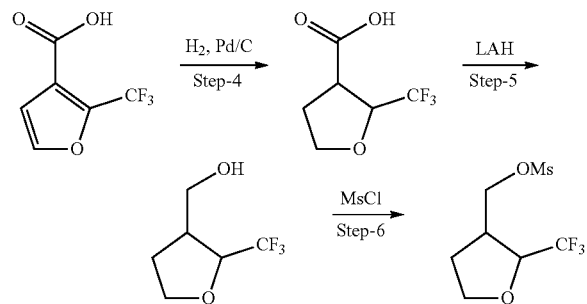

| Intermediate structure/code | Procedure | Analytics |
|---|---|---|
|  | in analogy to the synthesis of Int-B30 | LCMS: m/z [M + H]⁺ = 327.2 (calc. = 327.1). |

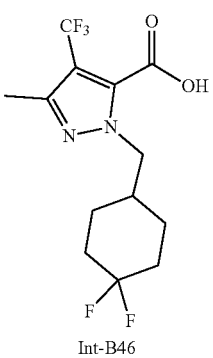 [SMILES: Cc1nn(CC2CCC(F)(F)CC2)c(C(=O)O)c1C(F)(F)F]

Int-B46

-continued

| Intermediate structure/code | Procedure | Analytics |
|---|---|---|
| 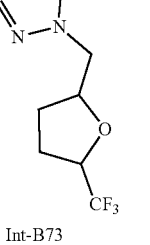<br>Int-B73 | in analogy to the synthesis of Int-B30 | LCMS: m/z [M + H]⁺ = 373.2 (calc. = 373.1). |
| 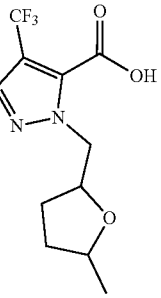<br>Int-B74 | in analogy to the synthesis of Int-B30 | LCMS: m/z [M + H]⁺ = 319.2 (calc. = 319.1). |
| 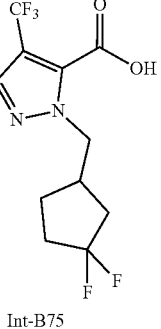<br>Int-B75 | in analogy to the synthesis of Int-B30 | LCMS: m/z [M + H]⁺ = 339.2 (calc. = 339.1). |
| 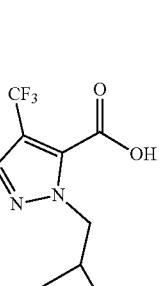<br>Int-B122 | in analogy to the synthesis of Int-B30, but using Step 4 in the synthesis of Int-B32 for pyrazole alkylation | LCMS: m/z [M + H]⁺ = 355.2 (calc. = 355.1). |

Synthesis of 3-cyclopropyl-4-(trifluoromethyl)-1-((5-(trifluoromethyl)tetrahydrofuran-3-yl)methyl)-1H-pyrazole-5-carboxylic acid (IntB-31)

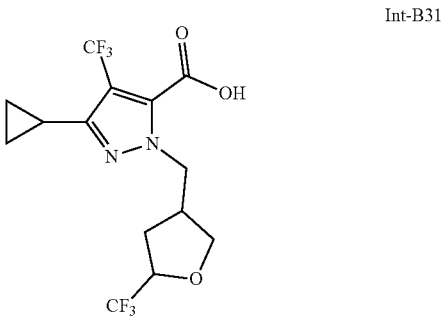 [SMILES: O=C(O)c1c(C(F)(F)F)c(C2CC2)nn1CC1COC(C(F)(F)F)C1]

IntB-31 was prepared in analogy to the first three steps of the synthesis for Int-30. LCMS m/z [M+H]$^+$=372.9 (calc.=373.1)

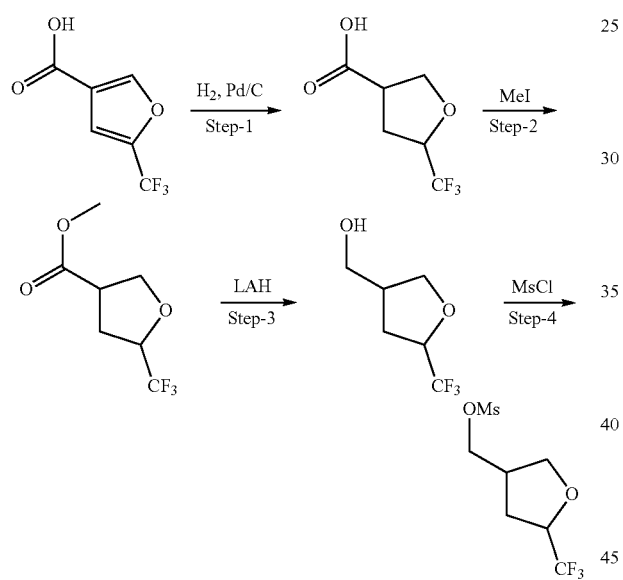

Step 1: To a stirred solution of 5-(trifluoromethyl)furan-3-carboxylic acid (2.5 g, 13.88 mmol, 1.0 eq.) in acetic acid (20 mL) was added Pd/C (10% w/w, 2.0 g) under an argon atmosphere at ambient temperature. The resulting reaction mixture was stirred for 16 h at ambient temperature under hydrogen pressure (using a hydrogen balloon). The reaction mixture was filtered through a celite bed and the celite bed was washed with EtOAc (50 mL). The filtrate was concentrated under reduced pressure to afford 5-(trifluoromethyl)tetrahydrofuran-3-carboxylic acid (2.5 g, crude).

Step 2: To a stirred solution of 5-(trifluoromethyl)tetrahydrofuran-3-carboxylic acid (2.5 g, 13.58 mmol, 1.0 eq.) in acetonitrile (50 mL) were added K$_2$CO$_3$ (2.81 g, 20.37 mmol, 1.5 eq.) and methyl iodide (2.9 g, 20.37 mmol, 1.5 eq.) at 0° C. The reaction mixture was allowed to warm to ambient temperature and was then stirred for 16 h. The reaction mixture was filtered and the filter cake was washed with ethyl acetate (30 mL). The filtrate was concentrated under reduced pressure to afford methyl 5-(trifluoromethyl)tetrahydrofuran-3-carboxylate (2.5 g, crude).

Step 3: To a stirred solution of methyl 5-(trifluoromethyl)tetrahydrofuran-3-carboxylate (2.5 g, 12.62 mmol, 1.0 eq.) in THF (30 mL) was added LAH in THF (1 M, 18.92 mL, 18.93 mmol, 1.5 eq.) at 0° C. The reaction mixture was warmed to ambient temperature and was stirred for 3 h. The reaction mixture was quenched with saturated Na$_2$SO$_4$ solution (10 mL) and the resulting mixture was stirred for 30 minutes. The mixture was filtered through a celite bed which was washed with ethyl acetate (2×30 mL). The filtrate was concentrated under reduced pressure to afford (5-(trifluoromethyl)tetrahydrofuran-3-yl)methanol (1.5 g, crude).

Step 4: To a stirred solution of (5-(trifluoromethyl)tetrahydrofuran-3-yl)methanol (1.5 g, 8.81 mmol, 1.0 eq.) in dichloromethane (50 mL) were added triethylamine (1.34 g, 13.22 mmol, 1.5 eq.) and MsCl (1.51 g, 13.22 mmol, 1.5 eq.) at 0° C. The reaction mixture was stirred for 3 h at ambient temperature. The reaction mixture was quenched with water (50 mL) and was extracted with dichloromethane (2×50 mL). The combined organic layers were washed with water (50 mL) and brine (50 mL), dried over anhydrous Na$_2$SO$_4$ and concentrated under reduced pressure to afford (5-(trifluoromethyl)tetrahydrofuran-3-yl)methyl methanesulfonate (2.1 g, crude). The compound was used in the next step without further purification.

Synthesis of 3-cyclopropyl-1-((3,3-difluorocyclobutyl)methyl)-4-(trifluoromethyl)-1H-pyrazole-5-carboxylic acid (Int-B32)

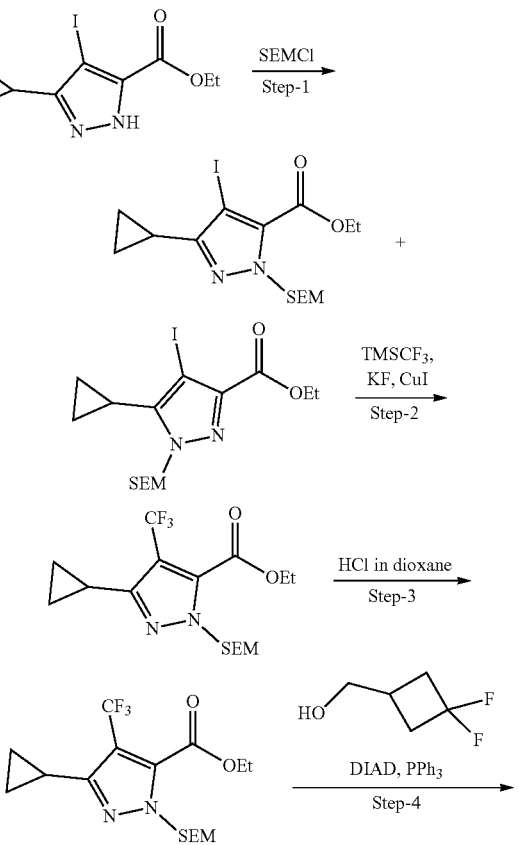

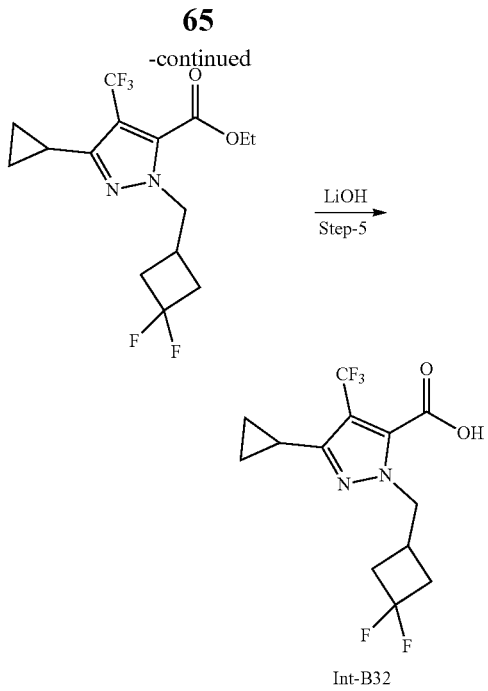

Int-B32

Step-1: To a solution of ethyl 3-cyclopropyl-4-iodo-1H-pyrazole-5-carboxylate (20.0 g, 65.57 mmol, 1.0 eq.) in DCM (200 mL) was added DIPEA (34.37 mL, 535.58 mmol, 3.0 eq.) at 0° C. and the mixture was stirred for 30 min. A solution of SEM-Cl (15.61 mL, 131.14 mmol, 1.2 eq.) in DCM (100 mL) was then added dropwise at 0° C. The reaction mixture was then allowed to stir for 16 h at ambient temperature. The reaction mixture was quenched with ice water and extracted with DCM (2×250 mL). The organic layer was washed with brine (250 mL) and dried over sodium sulfate. The solvent was evaporated under reduced pressured to get the crude product which was purified by column chromatography (silica gel 100-200 mesh, 5% EA in hexane as eluent) to afford ethyl 3-cyclopropyl-4-iodo-1-((2-(trimethylsilyl)ethoxy)methyl)-1H-pyrazole-5-carboxy late and ethyl 5-cyclopropyl-4-iodo-1-((2-(trimethylsilyl)ethoxy)methyl)-1H-pyrazole-3-carboxy late. Yield: 90% for both regioisomers combined (22.0 g, 51.49 mmol).

Step-2: To a solution of ethyl 3-cyclopropyl-4-iodo-1-((2-(trimethylsilyl)ethoxy)methyl)-1H-pyrazole-5-carboxylate (10.0 g, 22.96 mmol, 1.0 eq.) in DMF (60 mL) were added KF (4.0 g, 69.76 mmol, 3.0 eq.) and TMSCF$_3$ (23.8 mL, 160.54 mmol, 7.0 eq.) followed by CuI (8.72 g, 45.94 mmol, 2.0 eq.) at ambient temperature. The reaction mixture was heated to 90° C. in a sealed tube for 10 h. The reaction mixture was cooled to ambient temperature and was then diluted with cold water (300 mL). The reaction mixture was filtered through a celite bed which was washed with ethyl acetate (800 mL). The filtrate was washed with water (3×100 mL) and brine (200 mL) and dried over Na$_2$SO$_4$. The combined organic layer was concentrated under reduced pressure to obtain the crude product which was purified by combiflash column chromatography (silica gel, 2-5% EA in hexane as eluent) to yield ethyl 3-cyclopropyl-4-(trifluoromethyl)-14 (2-(trimethylsilyl)ethoxy)methyl)-1H-pyrazole-5-carboxy late. Yield: 78% (7.8 g, 11.23 mmol).

Step-3: To a solution of ethyl 3-cyclopropyl-4-(trifluoromethyl)-1-((2-(trimethylsilyl)ethoxy)methyl)-1H-pyrazole-5-carboxylate (4.7 g, 12.43 mmol, 1.0 eq.) in EtOH (35 mL) was added 4M HCl in dioxane at 0° C. The reaction mixture was then allowed to warm to ambient temperature and was stirred for 2.5 h. The reaction mixture was concentrated under reduced pressure, the obtained residue was diluted with ethyl acetate (800 mL), washed subsequently with sat. NaHCO$_3$ solution (200 mL), water (2×100 mL), brine (250 mL) and was then dried over sodium sulfate. The solvent was evaporated under reduced pressure to obtain the crude product which was purified by combiflash column chromatography (silica gel, 6% EA in hexane as eluent) to yield ethyl 3-cyclopropyl-4-(trifluoromethyl)-1H-pyrazole-5-carboxylate. Yield: 58% (1.8 g, 7.25 mmol).

Step-4: To a mixture of ethyl 3-cyclopropyl-4-(trifluoromethyl)-1H-pyrazole-5-carboxylate (1.0 g, 4.03 mmol, 1.0 eq.), (3,3-difluorocyclobutyl)methanol (736 mg, 6.04 mmol, 2.0 eq.) and triphenylphosphine (2.1 g, 8.0 mmol, 2.0 eq.) in THF (10 mL) was added DIAD (1.5 mL, 8.06 mmol, 2.0 eq.) dropwise at 0° C. The reaction mixture was then allowed to warm to ambient temperature and was stirred for 16 h. The reaction mixture was quenched with water and extracted with EtOAc (3×50 mL). The organic layers were washed with cold brine and dried over Na$_2$SO$_4$, concentrated under reduced pressure to obtain the crude product which was purified by combiflash column chromatography (silica gel, 10% EA/hexane) to afford ethyl 3-cyclopropyl-1-((3,3-difluorocyclobutyl)methyl)-4-(trifluoromethyl)-1H-pyrazole-5-carboxylate. Yield: 49% (700 mg, 1.98 mmol).

Step-5: To a solution of ethyl 3-cyclopropyl-1-((3,3-difluorocyclobutyl)methyl)-4-(trifluoromethyl)-1H-pyrazole-5-carboxylate (750 mg, 2.13 mmol, 1.0 eq.) in THF:H$_2$O (4:1, 12.5 mL) was added LiOH·H$_2$O (268 mg, 6.39 mmol, 3.0 eq.) and the reaction mixture was stirred at ambient temperature for 16 h. The reaction mixture was acidified with sat. NaH SO$_4$ solution and extracted with DCM (3×20 mL). The organic layer was dried over Na$_2$SO$_4$ and concentrated under reduced pressure to obtain crude 3-cyclopropyl-1-((3,3-difluorocyclobutyl)methyl)-4-(trifluoromethyl)-1H-pyrazole-5-carboxylic acid (Int-B32) which was used in next step without further purification. Yield: 70% (485 mg, 1.49 mmol). LCMS: m/z [M−H]$^−$=323.1 (calc.=323.1).

The following intermediates were prepared by analogy to the procedures described above using appropriate reactants and adjusted purification protocols:

| Intermediate structure/code | Procedure | Analytics |
|---|---|---|
| Int-B33 | in analogy to the synthesis of Int-B32 using (2,2-difluorocyclobutyl)methanol instead of (3,3-difluorocyclobutyl)methanol | LCMS m/z [M − H]$^−$ = 323.2 (calc. = 323.1). |

| Intermediate structure/code | Procedure | Analytics |
|---|---|---|
| 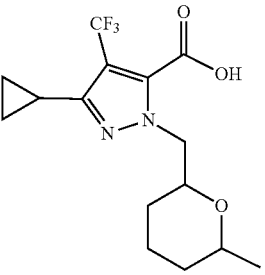<br>IntB-34 | in analogy to the synthesis of Int-B32 using (6-methyloxan-2-yl)methanol instead of (3,3-difluorocyclobutyl)methanol | LCMS: m/z [M + H]$^+$ = 333.3 (calc. = 333.3) |
| 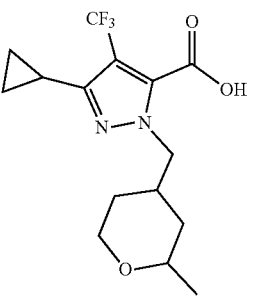<br>Int-B35 | in analogy to the synthesis of Int-B32 using (2-methyltetrahydro-2H-pyran-4-yl)methanol instead of (3,3-difluorocyclobutyl)methanol | LCMS: m/z [M + H]$^+$ = 333.2 (calc. = 333.3) |
| 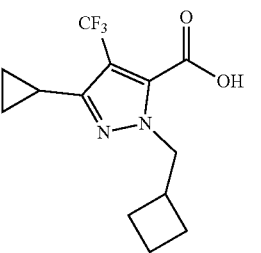<br>Int-B37 | in analogy to the synthesis of Int-B32 using cyclobutylmethanol instead of (3,3-difluorocyclobutyl)methanol | LCMS: m/z [M + H]$^+$ = 289.2 (calc. = 289.1). |
| 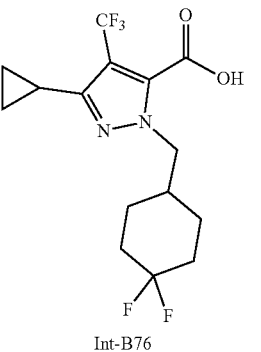 [SMILES: O=C(O)c1c(C(F)(F)F)c(C2CC2)nn1CC1CCC(F)(F)CC1]<br>Int-B76 | in analogy to the synthesis of Int-B32 using (4,4-difluorocyclohexyl)methanol instead of (3,3-difluorocyclobutyl)methanol | LCMS: m/z [M + H]$^+$ = 353.2 (calc. = 353.1) |

-continued

| Intermediate structure/code | Procedure | Analytics |
|---|---|---|
| 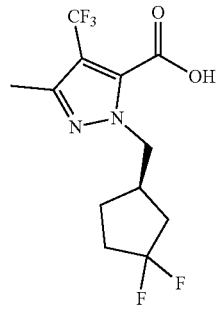<br>Int-B77R | in analogy to the synthesis of Int-B32 (step 4 and step 5) using [(1R)-3,3-difluorocyclopentyl] methanol instead of (3,3-difluorocyclobutyl)methanol | LCMS: m/z [M + H]⁺ = 313.2 (calc. = 313.1) |
| 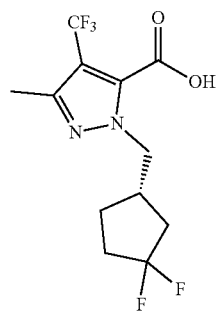<br>Int-B77S | in analogy to the synthesis of Int-B32 (step 4 and step 5) using [(1S)-3,3-difluorocyclopentyl] methanol instead of (3,3-difluorocyclobutyl)methanol | LCMS: m/z [M + H]⁺ = 313.4 (calc. = 313.1) |

Synthesis of 3-cyclopropyl-1-((tetrahydro-2H-pyran-2-yl)methyl)-4-(trifluoromethyl)-1H-pyrazole-5-carboxylic acid (Int-B38)

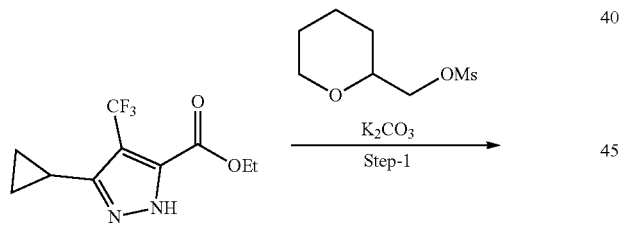

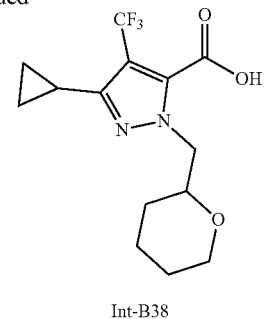

Int-B38

Step-1: To a solution of ethyl 3-cyclopropyl-4-(trifluoromethyl)-1H-pyrazole-5-carboxylate (2.5 g, 10.08 mmol, 1.0 eq.) in DMF (25 mL), $K_2CO_3$ (3.5 g, 25.20 mmol, 2.5 eq.) and oxan-2-ylmethyl methanesulfonate (2.35 g, 12.09 mmol, 1.2 eq.) were added at ambient temperature. The reaction mixture was heated to 80° C. for 16 h. After completion of the reaction, the reaction mixture was diluted with ice and extracted with EtOAc (3×80 mL). The combined organic layers were washed with brine, dried over $Na_2SO_4$, filtered and evaporated under reduced pressure to obtain the crude product which was purified through combiflash column chromatography (silica gel; 0-40% EtOAc/hexane as eluent) to afford ethyl 3-cyclopropyl-1-(oxan-2-ylmethyl)-4-(trifluoromethyl)-1H-pyrazole-5-carboxylate. Yield: 60% (2.1 g, 6.06 mmol).

Step-2: To a stirred solution of ethyl 3-cyclopropyl-1-(oxan-2-ylmethyl)-4-(trifluoromethyl)-1H-pyrazole-5-carboxylate (2.1 g, 6.06 mmol, 1.0 eq.) in a mixture of THF (20 mL), EtOH (20 mL) and $H_2O$ (10 mL) was added LiOH·H₂O (0.51 g, 12.13 mmol, 2.0 eq.) at ambient temperature. The reaction mixture was stirred at ambient temperature for 16 h. The reaction mixture was then concentrated under reduced pressure and diluted with ice water. The aqueous layer was acidified with saturated KHSO₄ solution to pH 2. The solid was filtered off and coevaporated with toluene to yield 3-cyclopropyl-1-(oxan-2-ylmethyl)-4-(trifluoromethyl)-1H-pyrazole-5-carboxylic acid (Int-B38). Yield: 88% (1.7 g, 5.34 mmol). LCMS m/z [M+H]⁺=319.0 (calc. 319.3).

Synthesis of 3-cyclopropyl-4-(difluoromethyl)-1-((tetrahydro-2H-pyran-4-yl)methyl)-1H-pyrazole-5-carboxylic acid (Int-B40)

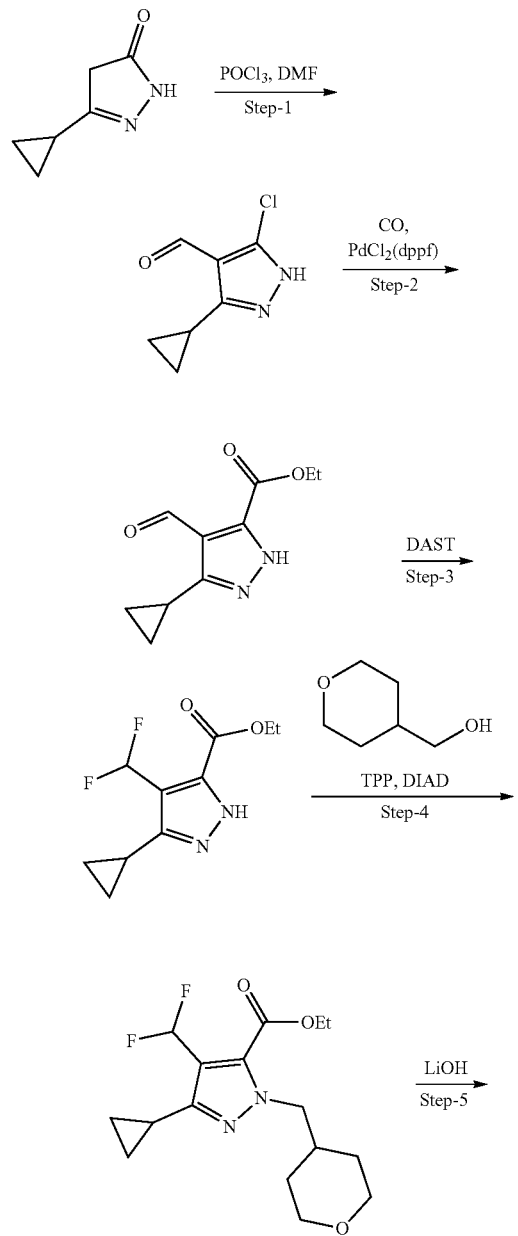

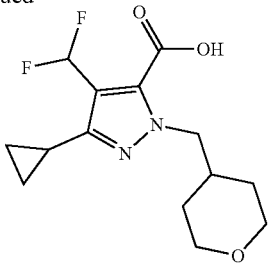

Int-B40

Step-1: POCl₃ (33.8 mL, 362 mmol, 5.0 eq.) was added dropwise to DMF (11.2 mL, 145 mmol, 2 eq.) at 0° C. over 15 minutes. The resulting reaction mixture was stirred at 0° C. for 30 min followed by the addition of 5-cyclopropyl-2,4-dihydro-3H-pyrazol-3-one (9.0 g, 72.58 mmol, 1.0 eq.) at 0° C. The reaction mixture was heated to 100° C. for 2 h. The reaction mixture was cooled to ambient temperature and saturated NaHCO₃ solution and crushed ice were added. The mixture was extracted with EtOAc (3×100 mL), the combined organic layers were washed with brine, dried over Na₂SO₄ and concentrated to get the crude product which was purified by combiflash column chromatography (silica gel; 0-100% EtOAc/hexane as eluent) to yield 5-chloro-3-cyclopropyl-1H-pyrazole-4-carbaldehyde. Yield: 20% (2.6 g, 15.24 mmol).

Step-2: A solution of 5-chloro-3-cyclopropyl-1H-pyrazole-4-carbaldehyde (2.0 g, 11.76 mmol, 1.0 eq.) in ethanol (80 mL) was degassed with argon for 10 min followed by the addition of NaOAc (2.89 g, 35.29 mmol, 3.0 eq.) and PdCl₂ (410 (0.86 g, 1.17 mmol, 0.1 equiv.) at ambient temperature. The reaction mixture was heated to 120° C. under 17.23 bar pressure of CO gas for 16 h. The reaction mixture was then cooled to ambient temperature, filtered through a celite bed and the filtrate was concentrated to get the crude product which was purified by combiflash column chromatography (silica gel, 0-60% EtOAc in hexane as eluent) to yield ethyl 3-cyclopropyl-4-formyl-1H-pyrazole-5-carboxylate. Yield: 40% (1.0 g, 4.80 mmol).

Step-3: To ethyl 3-cyclopropyl-4-formyl-1H-pyrazole-5-carboxylate (0.3 g, 1.44 mmol, 1.0 eq.) was added dropwise DAST (3 mL) at 0° C. and the reaction mixture was then stirred at ambient temperature for 16 h. The reaction mixture was diluted with ethyl acetate and was then quenched by the addition of cold saturated NaHCO₃ solution and extracted with EtOAc (3×100 mL). The combined organic layers were dried over Na₂SO₄ and concentrated to get the crude product which was purified by combiflash column chromatography (silica gel; 0-40% EtOAc/hexane as eluent) to yield ethyl 3-cyclopropyl-4-(difluoromethyl)-1H-pyrazole-5-carboxylate. Yield: 40% (0.125 g, 4.80 mmol).

Step 4 and step 5 were carried out in analogy to the synthesis of Int-B32, steps 4 and 5 to yield 3-cyclopropyl-4-(difluoromethyl)-1-((tetrahydro-2H-pyran-4-yl)methyl)-1H-pyrazole-5-carboxylic acid (Int-B40): Yield: 78% (0.10 g, 0.332 mmol). LCMS: m/z [M+H]⁺=301.3 (calc.=301.3).

The following intermediates were prepared by analogy to the procedures described above using appropriate reactants and adjusted purification protocols:

| Intermediate structure/code | Procedure | Analytics |
|---|---|---|
| Int-B64 | in analogy to the synthesis of Int-B40 using (3,3-difluorocyclopentyl)methanol instead of (tetrahydro-2H-pyran-4-yl)methanol | LCMS: m/z [M + H]+ = 321.3 (calc. = 321.1) |

Synthesis of 1-((3,3-difluorocyclopentyl)methyl)-3-methoxy-4-(trifluoromethyl)-1H-pyrazole-5-carboxylic acid (Int-B41)

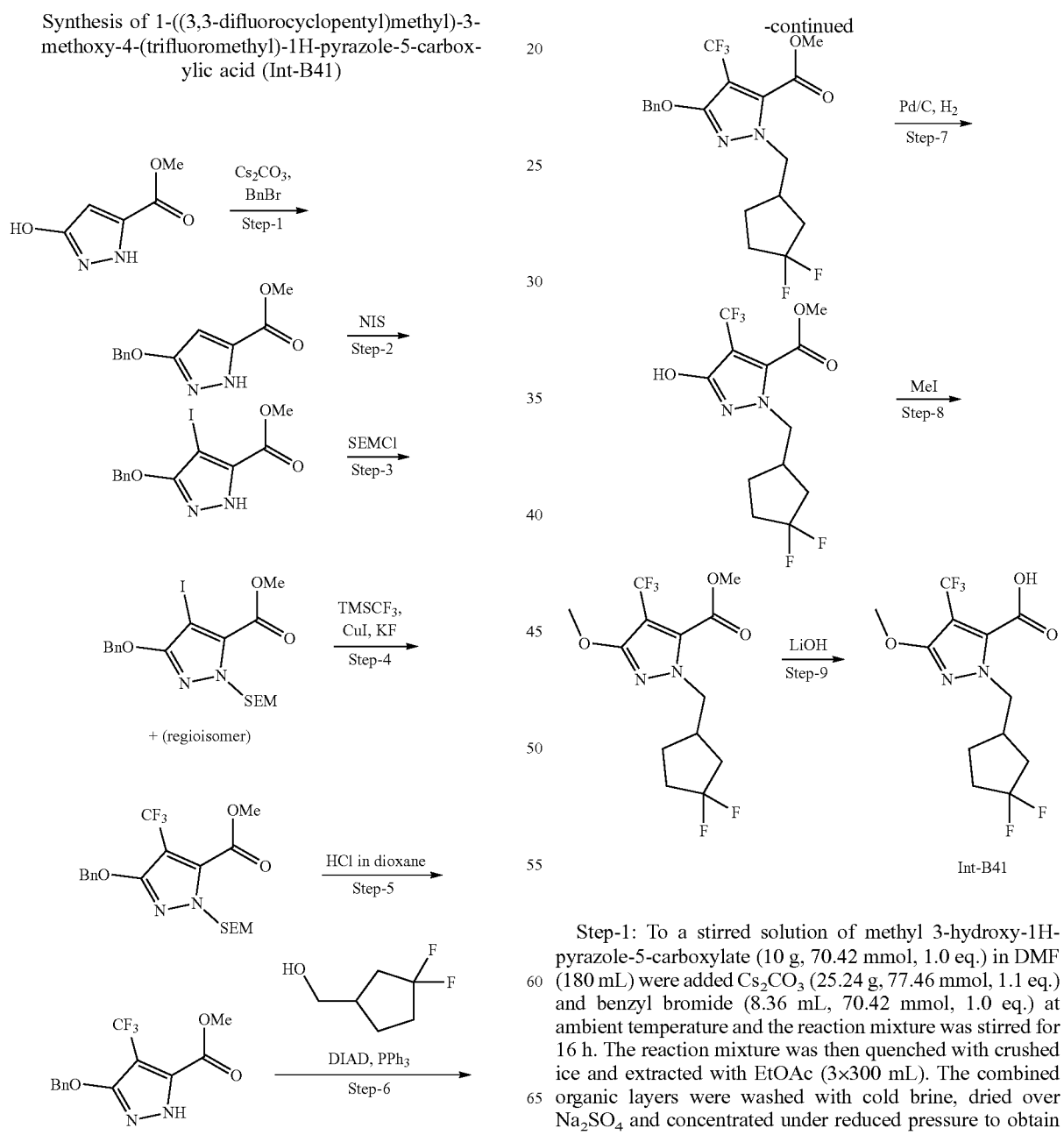

Step-1: To a stirred solution of methyl 3-hydroxy-1H-pyrazole-5-carboxylate (10 g, 70.42 mmol, 1.0 eq.) in DMF (180 mL) were added $Cs_2CO_3$ (25.24 g, 77.46 mmol, 1.1 eq.) and benzyl bromide (8.36 mL, 70.42 mmol, 1.0 eq.) at ambient temperature and the reaction mixture was stirred for 16 h. The reaction mixture was then quenched with crushed ice and extracted with EtOAc (3×300 mL). The combined organic layers were washed with cold brine, dried over $Na_2SO_4$ and concentrated under reduced pressure to obtain the crude product which was purified by combiflash column chromatography (silica gel, 0-20% EtOAc in hexane as eluent) to yield methyl 3-(benzyloxy)-1H-pyrazole-5-carboxylate. Yield: 73% (12 g, 51.67 mmol).

Step-2: To a stirred solution of methyl 3-(benzyloxy)-1H-pyrazole-5-carboxylate (2.5 g, 10.77 mmol, 1.0 eq.) in DCM (50 mL) was added NIS (2.9 g, 12.92 mmol, 1.2 eq.) at ambient temperature and the reaction was stirred for 1 h. The reaction mixture was quenched with crushed ice and was extracted with DCM (3×100 mL). The combined organic layers were washed with cold brine and sat. $Na_2S_2O_3$ solution, dried over $Na_2SO_4$ and concentrated under reduced pressure to get the crude product which was purified by combiflash column chromatography (silica gel, 0-20% EtOAc in hexane as eluent) to yield methyl 3-(benzyloxy)-4-iodo-1H-pyrazole-5-carboxylate. Yield: 73% (2.8 g, 7.82 mmol).

Step-3: To a stirred solution of methyl 3-(benzyloxy)-4-iodo-1H-pyrazole-5-carboxylate (2.7 g, 7.54 mmol, 1.0 eq.) in DCM (35 mL) was added DIPEA (3.75 mL, 22.62 mmol, 3.0 eq.) at 0° C. and the mixture was stirred at that temperature for 0.5 h. SEM-Cl (1.6 mL, 9.05 mmol, 1.2 eq.) was added to the reaction mixture at 0° C. The reaction mixture was then warned to ambient temperature and was stirred for 1 h. The reaction mixture was then quenched with crushed ice and was extracted with DCM (3×100 mL). The combined organic layers were washed with cold brine and dried over $Na_2SO_4$ and concentrated under reduced pressure to get the crude compound which was purified by combiflash column chromatography (silica gel, 0-15% EtOAc in hexane as eluent) to yield methyl 3-(benzyloxy)-4-iodo-1-{[2-(trimethylsilyl)ethoxy]methyl}-1H-pyrazole-5-carboxy late. Yield: 81% (3 g, 8.13 mmol).

Step-4: To a stirred solution of methyl 3-(benzyloxy)-4-iodo-1-{[2-(trimethylsilyl)ethoxy]methyl}-1H-pyrazole-5-carboxylate (5 g, 10.24 mmol, 1.0 eq.) in DMF (70 mL) were added CuI (3.9 g, 20.48 mmol, 2.0 eq.), dry KF (1.78 g, 30.74 mmol, 3.0 eq.) and $TMSCF_3$ (10.6 mL, 71.72 mmol, 7 eq.) at ambient temperature. The reaction mixture was then heated in a sealed tube to 90° C. for 16 h. The reaction mixture was then quenched with crushed ice and was extracted with EtOAc (3×150 mL). The combined organic layers were washed with cold brine, dried over $Na_2SO_4$ and concentrated under reduced pressure to get the crude product which was purified by combiflash column chromatography (silica gel, 0-15% EtOAc in hexane as eluent) to yield methyl 3-(benzyloxy)-4-(trifluoromethyl)-1-{[2-(trimethylsilyl)ethoxy]methyl}-1H-pyrazole-5-carboxy late. Yield: 79% (3.5 g, 8.13 mmol).

Step-5: To a stirred solution of methyl 3-(benzyloxy)-4-(trifluoromethyl)-1-{[2-(trimethylsilyl)ethoxy]methyl}-1H-pyrazole-5-carboxylate (6.7 g, 15.58 mmol, 1.0 eq.) in MeOH (30 mL) was added 4(M) dioxane-HCl (48 mL) at 0° C. The reaction mixture was stirred at ambient temperature for 2 h. The reaction mixture was then concentrated under reduced pressure and was quenched with sat. $NaHCO_3$ solution at 0° C. to maintain pH-8. The aqueous part was extracted with EtOAc (3×200 mL). The combined organic layers were washed with brine, dried over $Na_2SO_4$ and were concentrated under reduced pressure to get the crude product which was purified by combiflash column chromatography (silica gel, 0-50% EtOAc in hexane as eluent) to yield methyl 3-(benzyloxy)-4-(trifluoromethyl)-1H-pyrazole-5-carboxylate. Yield: 68% (3.2 g, 10.67 mmol).

Step-6: To a solution of methyl 3-(benzyloxy)-4-(trifluoromethyl)-1H-pyrazole-5-carboxylate (1.0 g, 3.3 mmol, 1.0 eq.) and (3,3-difluorocyclopentyl)methanol (0.68 g, 4.99 mmol, 1.5 eq.) in THF (30 mL) was added $PPh_3$ (1.3 g, 4.99 mmol, 1.5 eq.) at 0° C. After 5 minutes, DIAD (1.0 mL, 4.99 mmol, 1.5 eq.) was added to the reaction mixture at 0° C. and the reaction was stirred at ambient temperature for 16 h. The reaction mixture was concentrated under reduced pressure to get the crude product which was purified by combiflash column chromatography (silica gel; 0-20% EtOAc in hexane as eluent) to yield methyl 3-(benzyloxy)-1-((3,3-difluorocyclopentyl)methyl)-4-(trifluoromethyl)-1H-pyrazole-5-carboxylate. Yield: 72% (1.0 g, 2.39 mmol).

Step-7: A solution of methyl 3-(benzyloxy)-1-((3,3-difluorocyclopentyl)methyl)-4-(trifluoromethyl)-1H-pyrazole-5-carboxylate (1.0 g, 2.39 mmol, 1.0 eq.) in MeOH (30 mL) was degassed with $N_2$ for 15 minutes followed by the addition of Pd—C (10% wet) (0.5 g) at ambient temperature. The reaction mixture was stirred at ambient temperature under 1.4 bar of pressure using a $H_2$-balloon for 16 h. The reaction mixture was filtered through celite and the filtrate was concentrated under reduced pressure to get the crude product which was purified by combiflash column chromatography (silica gel, 0-50% EtOAc in hexane as eluent) to yield methyl 1-((3,3-difluorocyclopentyl)methyl)-3-hydroxy-4-(trifluoromethyl)-1H-pyrazole-5-carboxylate. Yield: 92% (0.72 g, 2.19 mmol).

Step-8: To a solution of methyl 1-((3,3-difluorocyclopentyl)methyl)-3-hydroxy-4-(trifluoromethyl)-1H-pyrazole-5-carboxylate (1.0 g, 3.04 mmol, 1.0 eq.) in DMF (20 mL) were added $K_2CO_3$ (0.50 g, 3.6 mmol, 1.2 eq.) and MeI (0.72 mL, 12.16 mmol, 4.0 eq.) at ambient temperature and the reaction mixture was stirred for 3 h. The reaction mixture was diluted with ice water and extracted with EtOAc (3×30 mL). The combined organic layers were washed with brine and dried over $Na_2SO_4$ and concentrated under reduced pressure to get the crude product which was purified by combiflash column chromatography (silica gel, 0-10% EtOAc in hexane as eluent) to yield methyl 1-((3,3-difluorocyclopentyl)methyl)-3-methoxy-4-(trifluoromethyl)-1H-pyrazole-5-carboxy late. Yield: 72% (0.75 g, 2.19 mmol).

Step-9: To a solution of methyl 1-((3,3-difluorocyclopentyl)methyl)-3-methoxy-4-(trifluoromethyl)-1H-pyrazole-5-carboxylate (0.20 g, 0.61 mmol, 1.0 eq.) in a mixture of THF-MeOH—$H_2O$ (2:1:1) (8 mL) was added LiOH·$H_2O$ (0.077 g, 1.83 mmol, 3.0 eq.) at ambient temperature and the reaction was stirred for 16 h. The reaction mixture was concentrated under reduced pressure and was acidified with saturated $KHSO_4$ solution to maintain pH-2. The resulting solid was filtered off and coevaporated with toluene to yield 1-((3,3-difluorocyclopentyl)methyl)-3-methoxy-4-(trifluoromethyl)-1H-pyrazole-5-carboxylic acid (Int-B41). Yield: 90% (0.18 g, 0.54 mmol). LCMS: m/z $[M+H]^+$=329.2 (calc.=329.1).

The following intermediates were prepared by analogy to the procedures described above using appropriate reactants and adjusted purification protocols:

| Intermediate structure/code | Procedure | Analytics |
|---|---|---|
| 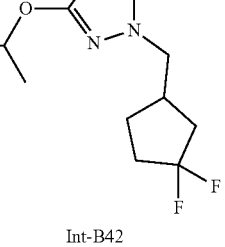<br>Int-B42 | in analogy to the synthesis of Int-B41 using 2-iodopropane instead of methyl iodide in step 8. | LCMS: m/z [M + H]⁺ = 357.2 (calc. = 357.3). |
| 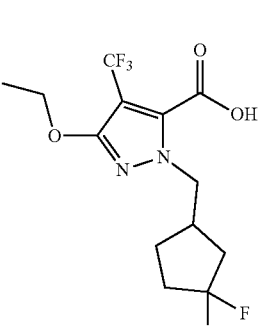<br>Int-B43 | in analogy to the synthesis of Int-B41 using ethyl iodide instead of methyl iodide in step 8. | LCMS: m/z [M + H]⁺ = 343.3 (calc. = 343.3). |
| 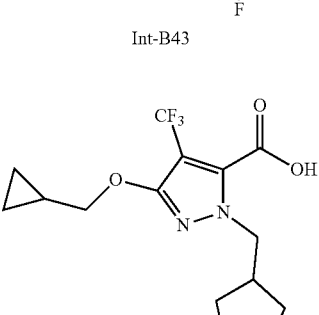<br>Int-B44 | in analogy to the synthesis of Int-B41 using (iodomethyl)-cyclopropane instead of methyl iodide in step 8. | LCMS: m/z [M + H]⁺ = 369.1 (calc. = 369.3). |
| 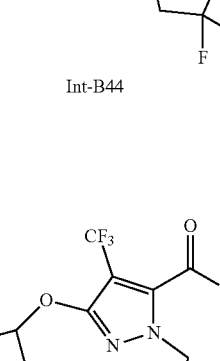<br>Int-B78 | in analogy to the synthesis of Int-B41 using 3,3-difluorocyclobutyl methanesulfonate instead of methyl iodide in step 8. | LCMS: m/z [M − H]⁻ = 403.0 (calc. = 403.1). |

| Intermediate structure/code | Procedure | Analytics |
|---|---|---|
| 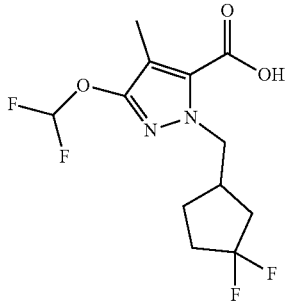<br>Int-B79 | in analogy to the synthesis of Int-B41 using the following modified conditions in step 4: methyl boronic acid, PdCl$_2$(dppf), Cs$_2$CO$_3$, H$_2$O/dioxane 100° C., 16 h and difluoro(iodo)methane instead of methyl iodide in step 8. | LCMS: m/z [M + H]$^+$ = 311.0 (calc. = 311.1). |
| 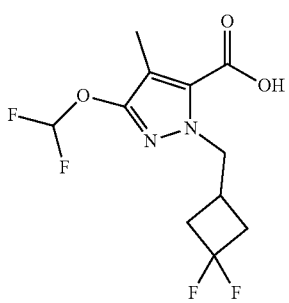<br>Int-B80 | in analogy to the synthesis of Int-B41 using the following modified conditions in step 4: methyl boronic acid, PdCl$_2$(dppf), Cs$_2$CO$_3$, HO/dioxane 100° C., 16 h and (3,3-difluorocyclobutyl)methanol in step-6 and sodium 2-chloro-2,2-difluoroacetate instead of methyl iodide in step 8. | LCMS: m/z [M + H]$^+$ = 297.3 (calc. = 297.1). |

Synthesis of (R)-1-((3,3-difluorocyclopentyl)methyl)-3-(difluoromethoxy)-4-(trifluoromethyl)-1H-pyrazole-5-carboxylic acid (Int-B45a)

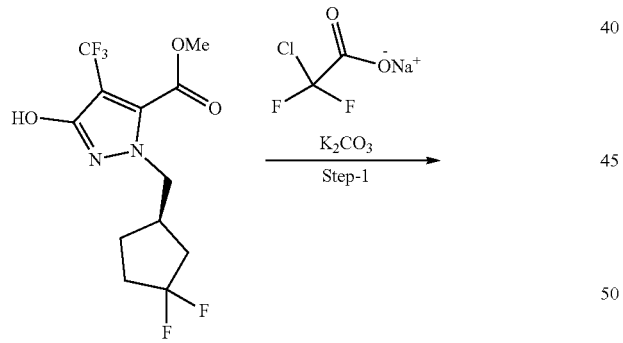

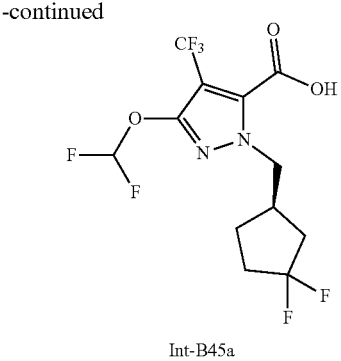

Int-B45a

Methyl (R)-1-((3,3-difluorocyclopentyl)methyl)-3-hydroxy-4-(trifluoromethyl)-1H-pyrazole-5-carboxy late was prepared in analogy to the synthesis of methyl 1-((3,3-difluorocyclopentyl)methyl)-3-hydroxy-4-(trifluoromethyl)-1H-pyrazole-5-carboxylate using the corresponding chiral alcohol.

Step-1: To a solution of methyl (R)-1-((3,3-difluorocyclopentyl)methyl)-3-hydroxy-4-(trifluoromethyl)-1H-pyrazole-5-carboxylate (0.37 g, 1.13 mmol, 1.0 eq.) in acetonitrile (15 mL) were added K$_2$CO$_3$ (0.39 g, 2.83 mmol, 2.5 eq.) and sodium 2-chloro-2,2-difluoroacetate (0.22 g, 1.47 mmol, 1.3 eq.) at ambient temperature. The reaction mixture was then was heated to 80° C. for 7 h. The reaction mixture was then cooled to ambient temperature, filtered through a sintered funnel and the filtrate was concentrated to get the crude product which was purified by combiflash column chromatography (silica gel, 0-20% EtOAc in hexane as eluent) to yield methyl (R)-1-((3,3-difluorocyclopentyl)methyl)-3-(difluoromethoxy)-4-(trifluoromethyl)-1H-pyrazole-5-carboxy late. Yield: 72% (0.31 g, 0.82 mmol).

Step-2: To a solution of methyl (R)-1-((3,3-difluorocyclopentyl)methyl)-3-(difluoromethoxy)-4-(trifluoromethyl)-1H-pyrazole-5-carboxylate (0.31 g, 0.82 mmol, 1.0 eq.) in a mixture of THF-MeOH—H$_2$O (2:1:1) (10 mL) was added LiOH·H$_2$O (0.14 g, 3.28 mmol, 4.0 eq.) at ambient temperature and the mixture was stirred for 16 h. The reaction mixture was concentrated under reduced pressure, and diluted with ice water. The aqeuous part was acidified with saturated NaHSO$_4$ solution to pH-2 and was extracted with EtOAc (3×50 mL). The combined combined organic layers were dried over anhydrous Na$_2$SO$_4$ and concentrated to yield (R)-1-((3,3-difluorocyclopentyl)methyl)-3-(difluoromethoxy)-4-(trifluoromethyl)-1H-pyrazole-5-carboxylic acid (Int-B45a). Yield: 97% (0.29 g, 0.79 mmol). LCMS: m/z [M−H]$^-$=363.0 (calc.=363.1).

The following intermediates were prepared by analogy to the procedures described above using appropriate reactants and adjusted purification protocols:

| Intermediate structure/code | Procedure | Analytics |
|---|---|---|
| Int-B45b | in analogy to the synthesis of Int-B45a using the other, corresponding enatiomeric alcohol as the starting material. | LCMS: m/z [M − H]$^-$ = 363.0 (calc. = 363.1). |

Synthesis of 3-(1,1-difluoroethyl)-4-methyl-1-(((trans)-2-(trifluoromethyl)cyclobutyl)methyl)-1H-pyrazole-5-carboxylic acid (Int-B81)

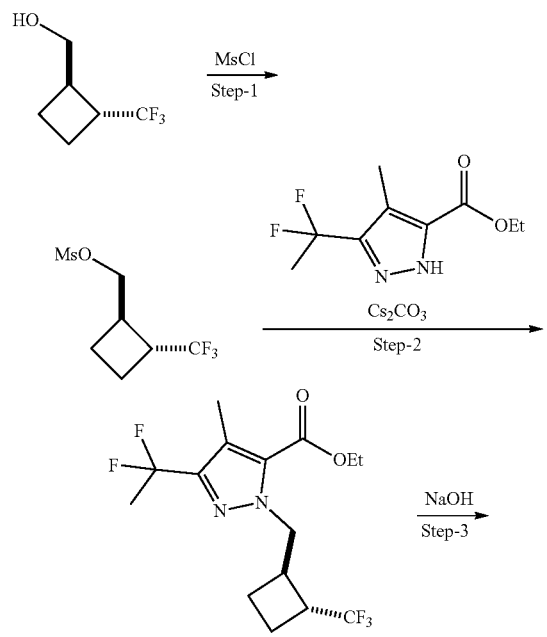

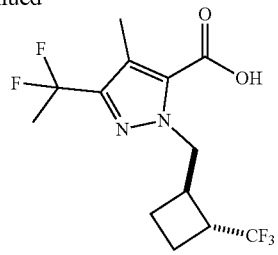

Int-B81

Step-1: To a solution of trans 2-(trifluoromethyl)cyclopropylmethanol (1.4 g, 9.15 mmol, 1.2 eq.) in DCM (25 mL) was added TEA (3.9 mL, 27.45 mmol, 3.0 eq.) followed by methane sulfonyl chloride (1.1 mL, 13.73 mmol, 1.5 eq.) at 0° C. and the reaction mixture was stirred at ambient temperature for 1 h. The reaction mixture was then quenched with water (100 mL) and extracted with DCM (3×50 mL). The combined organic layers were washed with cold brine (100 mL) and dried over Na$_2$SO$_4$ and the solvent was evaporated under reduced pressure to get crude trans 2-(trifluoromethyl)cyclopropylmethyl methanesulfonate which was used to next step without purification. Yield: 2.0 g (crude material)

Step-2: To a solution of ethyl 3-(1,1-difluoroethyl)-4-methyl-1H-pyrazole-5-carboxylate (2.0 g, 9.15 mmol, 1.0 eq.) and crude trans 2-(trifluoromethyl)cyclopropylmethyl methanesulfonate (2.0 g) in DMF (25 mL) was added Cs$_2$CO$_3$ (6.0 g, 18.30 mmol, 2.0 eq.) at ambient temperature and the reaction mixture was then heated to 70° C. for 4 h. The reaction mixture was diluted with cold water (150 mL) and extracted with EA (2×100 mL). The combined organic layers were washed with cold brine (100 mL) and dried over sodium sulfate. The solvent was evaporated under reduced pressure to get the crude product which was purified by combiflash column chromatography (silica gel, 0-5% EA in hexane as eluent) to yield trans ethyl-3-(1,1-difluoroethyl)-4-methyl-1-{[-2-(trifluoromethyl)cyclobutyl]methyl}-1H-pyrazole-5-carboxylate. Yield: 64% (2.1 g, 5.91 mmol).

Step-3: To a solution of trans ethyl-3-(1,1-difluoroethyl)-4-methyl-1-{[-2-(trifluoromethyl)cyclobutyl]methyl}-1H-pyrazole-5-carboxylate (1.5 g, 4.22 mmol, 1.0 eq.) in MeOH (25 mL) was added 2N NaOH (5 mL) at ambient temperature and the mixture was then stirred at 70° C. for 1 h. The reaction mixture was concentrated under reduced pressure, diluted with water (100 mL) and washed with diethyl ether (2×25 mL). The aqueous layer was acidified with sat. NaHSO₄ solution up to pH-5-6 and extracted with EA (2×100 mL). The combined organic layers was dried over Na₂SO₄ and concentrated under reduced pressure to yield trans 3-(1,1-difluoroethyl)-4-methyl-1-((-2-(trifluoromethyl)cyclobutyl)methyl)-1H-pyrazole-5-carboxylic acid. Yield: 94% (1.3 g, 3.98 mmol). LCMS: m/z [M+H]⁺=327.3 (calc.=327.1).

The following intermediates were prepared by analogy to the procedures described above using appropriate reactants and adjusted purification protocols:

| Intermediate structure/code | Procedure | Analytics |
|---|---|---|
| 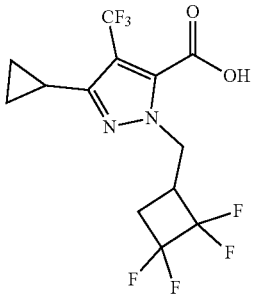 Int-B82 | in analogy to the synthesis of Int-B81, using the corresponding mesylates. | LCMS m/z [M + H]⁺ = 361.4 (calc. 361.1). |
| 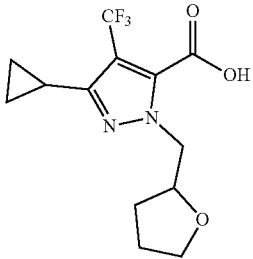 Int-B83 | in analogy to the synthesis of Int-B81, using the corresponding mesylates. | LCMS: m/z [M + H]⁺ = 305.1 (calc. = 305.1). |
| 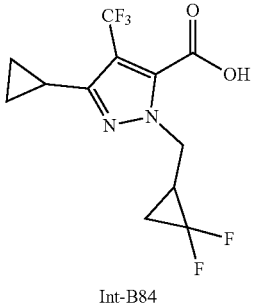 [SMILES: O=C(O)c1c(C(F)(F)F)c(C2CC2)nn1CC1CC1(F)F] Int-B84 | in analogy to the synthesis of Int-B81, using the corresponding mesylates. | LCMS: m/z [M + H]⁺ = 311.2 (calc. = 311.1). |
| 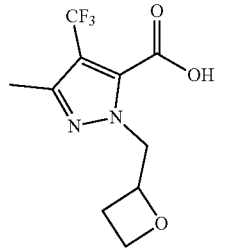 Int-B85 | in analogy to the synthesis of Int-B81, using the corresponding mesylates. | LCMS: m/z [M + H]⁺ = 264.4 (calc. = 264.1). |

| Intermediate structure/code | Procedure | Analytics |
|---|---|---|
| Int-B117 (structure) | in analogy to the synthesis of Int-B81, using the corresponding mesylates. | LCMS: m/z [M + H]⁺ = 313.2 (calc. = 313.1). |
| Int-B118 (structure) | in analogy to the synthesis of Int-B81, using the corresponding mesylates. | LCMS: m/z [M + H]⁺ = 277.2 (calc. = 277.1). |
| Int-B119 (structure) | in analogy to the synthesis of Int-B81, using the corresponding mesylates. | LCMS: m/z [M + H]⁺ = 295.2 (calc. = 295.1). |
| Int-B120 (structure) | in analogy to the synthesis of Int-B81, using the corresponding mesylates. | LCMS: m/z [M + H]⁺ = 295.2 (calc. = 295.1). |

87

Synthesis of 1-((3,3-difluorocyclobutyl)methyl)-3-(difluoromethyl)-4-(trifluoromethyl)-1H-pyrazole-5-carboxylic acid (Int-B47)

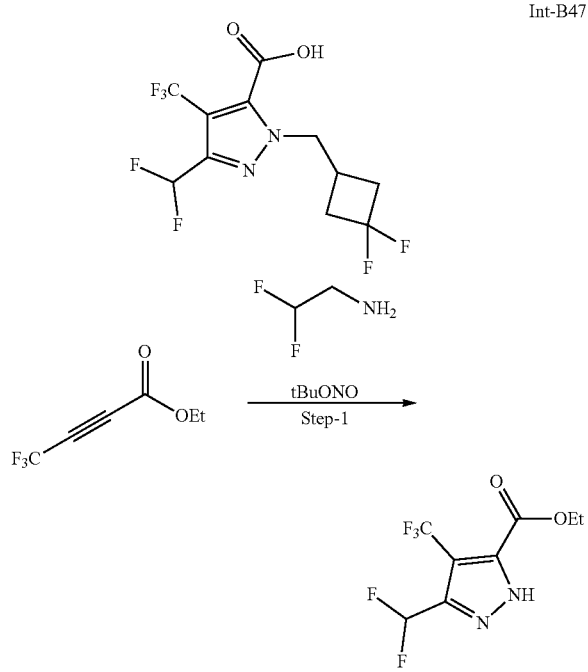

88

Step-1: To a solution of 2,2-difluoroethan-1-amine (4.8 g, 60.2 mmol, 2.0 eq.) in chloroform were added tert-butyl nitrite (1.80 mL, 75.25 mmol, 2.5 eq.) and acetic acid (0.14 mL, 12 mmol, 0.4 eq.) at ambient temperature. The reaction mixture was heated to 60° C. for 15 minutes, was then cooled to ambient temperature followed by the addition of ethyl 4,4,4-trifluorobut-2-ynoate (5.0 g, 30.1 mmol, 1 eq.). The resulting solution was stirred at ambient temperature for 16 h. The reaction mixture was concentrated under reduced pressure and was then diluted with ice water and extracted with ethyl acetate (3×50 mL). The combined organic layers were washed with brine, dried over $Na_2SO_4$ and concentrated under reduced pressure to get the crude compound which was purified by combiflash column chromatography (silica; 0-30% ethyl acetate/hexane as eluent) to yield ethyl 3-(difluoromethyl)-4-(trifluoromethyl)-1H-pyrazole-5-carboxylate. Yield: 25% (2.0 g, 7.75 mmol). LCMS: m/z $[M-H]^-$=256.6 (calc.=257.0).

Ethyl 3-(difluoromethyl)-4-(trifluoromethyl)-1H-pyrazole-5-carboxylate was converted to 1-((3,3-difluorocyclobutyl)methyl)-3-(difluoromethyl)-4-(trifluoromethyl)-1H-pyrazole-5-carboxylic acid (Int-B47) in analogy to the synthesis described for Int-B32, steps 4 and 5. LCMS: m/z $[M+H]^+$=335.1 (calc.=335.2).

The following intermediates were prepared by analogy to the procedure described above:

| Intermediate structure/code | Procedure | Analytics |
|---|---|---|
| ![Int-B52 structure]<br>Int-B52 | in analogy to the synthesis of Int-B47 for the pyrazole formation using ethyl but-2-ynoate instead of ethyl 4,4,4-trifluorobut-2-ynoate. Alkylation/saponification was carried out in analogy to to the synthesis of Int-B51, step 2 and step 3 | LCMS: m/z $[M + H]^+$ = 357.2 (calc. = 357.3). |
| ![Int-B86 structure]<br>Int-B86 | in analogy to the synthesis of Int-B47. Alkylation/saponification was carried out in analogy to the synthesis of Int-B51, step 2 and step 3 | LCMS: m/z $[M + H]^+$ = 349.1 (calc.= 349.1). |

Synthesis of 1-((3,3-difluorocyclopentyl)methyl)-4-methyl-3-(trifluoromethyl)-1H-pyrazole-5-carboxylic acid (Int-B48)

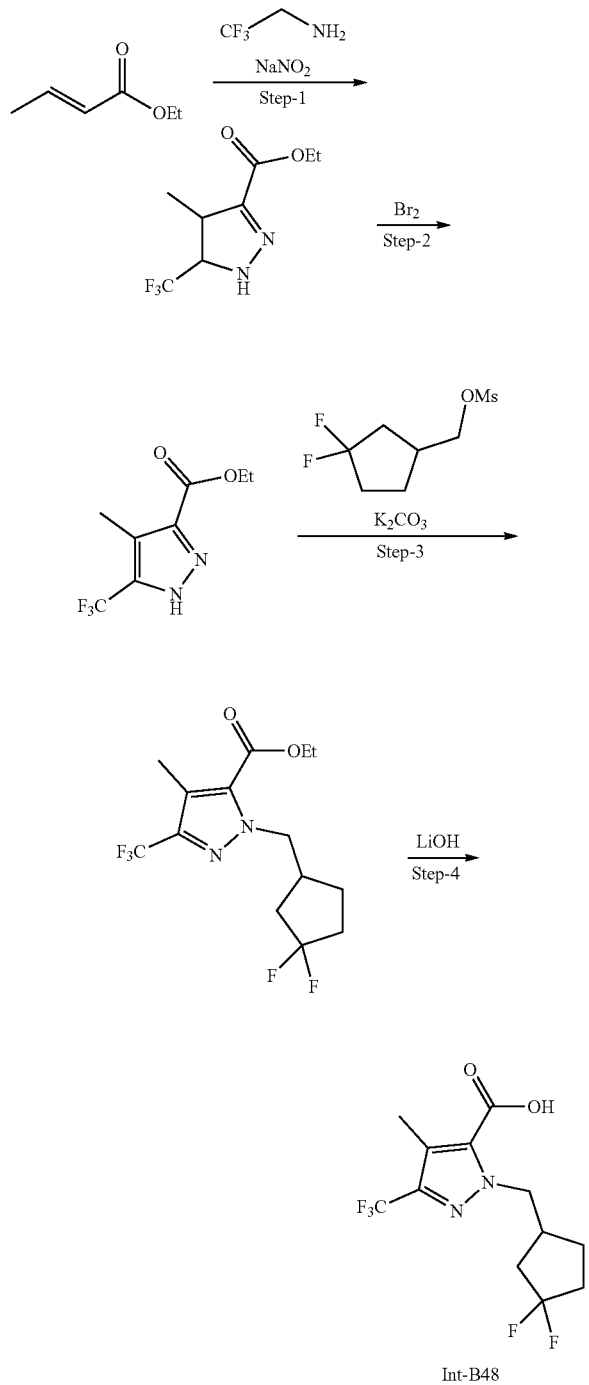

Step 1: A solution of NaNO₂ (90.6 g, 1314 mmol, 3.0 eq.) in water (500 mL) was slowly added to a stirred solution of ethyl but-2-enoate (50 g, 438 mmol, 1.0 eq.) and 2,2,2-trifluoroethanamine hydrochloride (178 g, 1314 mmol, 3.0 eq.) in DCM (1000 mL) at 0° C. The resulting reaction mixture was stirred at ambient temperature for 16 h. The reaction mixture was diluted with water (500 mL) and the two layers were separated. The organic layer was washed with water (500 mL), brine (500 mL), dried over anhydrous Na₂SO₄ and concentrated under reduced pressure to afford ethyl 4-methyl-5-(trifluoromethyl)-4,5-dihydro-1H-pyrazole-3-carboxylate (45 g, crude).

Step 2: To a stirred solution of ethyl 4-methyl-5-(trifluoromethyl)-4,5-dihydro-1H-pyrazole-3-carboxylate (50 g, 223 mmol, 1.0 eq.) in diethyl ether (500 mL) was added bromine (13.7 mL, 267 mmol, 1.2 eq.) at 0° C. and the resulting reaction mixture was stirred at ambient temperature for 16 h. The reaction mixture was quenched with water (500 mL) at 0° C. and the resulting mixture was extracted with diethyl ether (3×500 mL). The combined organic layers were washed with water (1000 mL), brine (1000 mL), dried over anhyd. Na₂SO₄ and concentrated under reduced pressure to get the crude product which was purified by column chromatography (100-200 mesh silica gel, 10% EtOAc in pet-ether as an eluent) to afford ethyl 4-methyl-5-(trifluoromethyl)-1H-pyrazole-3-carboxylate. Yield: 33% over 2 steps (40 g).

Step 3: K₂CO₃ (18.6 g, 135.1 mmol, 2.0 eq.) was added to a stirred solution of ethyl 4-methyl-5-(trifluoromethyl)-1H-pyrazole-3-carboxylate (15.0 g, 67.5 mmol, 1.0 eq.) and (3,3-difluorocyclopentyl)methyl methanesulfonate (21.6 g, 101.3 mmol, 1.5 eq.) in MeCN (400 mL) at ambient temperature. The resulting reaction mixture was heated to 80° C. for 16 h. The reaction mixture was allowed to cool to ambient temperature and was filtered through a pad of celite. The filtrate was concentrated under reduced pressure to get the crude product, which was purified by column chromatography (100-200 mesh silica gel, 2% EtOAc in pet-ether as an eluent) to afford ethyl 1-((3,3-difluorocyclopentyl)methyl)-4-methyl-3-(trifluoromethyl)-1H-pyrazole-5-carboxylate. Yield: 52% (12 g).

Step 4: To a stirred solution of ethyl 1-((3,3-difluorocyclopentyl)methyl)-4-methyl-3-(trifluoromethyl)-1H-pyrazole-5-carboxylate (20 g, 58.8 mmol, 1.0 eq.) in THF/H₂O/MeOH (1:1:1, 450 mL) was added LiOH·H₂O (9.87 g, 235 mmol, 4.0 eq.) at ambient temperature and the reaction mixture was stirred for 4 h. The reaction mixture was concentrated under reduced pressure to obtain a residue, which was diluted with water (500 mL), acidified with 1N aq. HCl solution and the precipitated solid was filtered and dried under vacuum to afford 1-((3,3-difluorocyclopentyl)methyl)-4-methyl-3-(trifluoromethyl)-1H-pyrazole-5-carboxylic acid (Int-B48). Yield: 81% (15 g). LCMS: m/z [M+H]⁺=313.1 (calc.=313.1).

The following intermediates were prepared by analogy to the procedures described above using appropriate reactants and adjusted purification protocols:

| Intermediate structure/code | Procedure | Analytics |
|---|---|---|
| 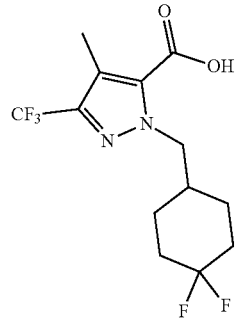<br>Int-B87 | in analogy to the synthesis of Int-B48 using the corresponding alcohol as the starting material. | LCMS: m/z [M + H]$^+$ = 327.3 (calc. = 327.1). |

Synthesis of 4-chloro-1-((3,3-difluorocyclopentyl)methyl)-3-(1,1-difluoroethyl)-1H-pyrazole-5-carboxylic acid (Int-B49)

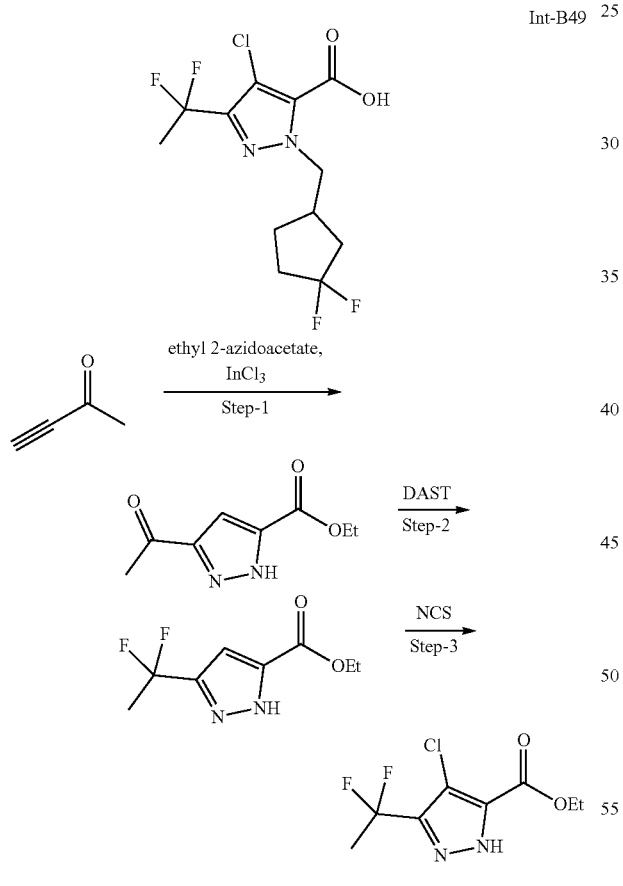

Step 1: To a stirred solution of InCl$_3$ (2.59 g, 11.7 mmol, 0.2 eq.) in water (200 mL) were added but-3-yn-2-one (4.0 g, 58.8 mmol, 1.0 eq.) and ethyl 2-azidoacetate (9.1 g, 70.5 mmol, 1.2 eq.) at ambient temperature and the resulting reaction mixture was stirred for 4 h. The precipitated solid was filtered off, washed with water (200 mL) and dried under vacuum for 8 h to afford ethyl 3-acetyl-1H-pyrazole-5-carboxylate. Yield: 61% (6.5 g).

Step 2: To a stirred solution of ethyl 3-acetyl-1H-pyrazole-5-carboxylate (6.0 g, 32.9 mmol, 1.0 eq.) in DCM (100 mL) was added DAST (17.1 mL, 131.8 mmol, 4.0 eq.) slowly at 0° C. and the resulting reaction mixture was then stirred at ambient temperature for 16 h. The reaction mixture was slowly poured into ice cold water (200 mL) and extracted with DCM (3×150 mL). The combined organic layers were washed with saturated NaHCO$_3$ solution (300 mL), water (300 mL) and brine (300 mL), dried over anhydrous Na$_2$SO$_4$ and concentrated under reduced pressure to afford ethyl 3-(1,1-difluoroethyl)-1H-pyrazole-5-carboxylate. Yield: 60% (4.0 g).

Step 3: In a sealed tube NCS (1.30 g, 9.80 mmol, 2.0 eq.) was added to a stirred solution of ethyl 3-(1,1-difluoroethyl)-1H-pyrazole-5-carboxylate (1.0 g, 4.90 mmol, 1.0 eq.) in DMF (10 mL) at ambient temperature and the resulting reaction mixture was heated to 80° C. for 16 h. The reaction mixture was cooled to ambient temperature, poured into water (25 mL) and extracted with EtOAc (3×25 mL). The combined organic layers were washed with water (50 mL) and brine (50 mL), dried over anhydrous Na$_2$SO$_4$ and concentrated under reduced pressure to get the crude product, which was purified by column chromatography (100-200 mesh silica gel, 30% EtOAc in pet-ether as an eluent) to afford ethyl 4-chloro-3-(1,1-difluoroethyl)-1H-pyrazole-5-carboxylate. Yield: 52% (600 mg).

Ethyl 4-chloro-3-(1,1-difluoroethyl)-1H-pyrazole-5-carboxylate was converted to 4-chloro-1-((3,3-difluorocyclopentyl)methyl)-3-(1,1-difluoroethyl)-1H-pyrazole-5-carboxylic acid (Int-B49) in analogy to the synthesis of Int-B48. LCMS: m/z [M−H]$^-$=327.0 (calc.=327.1).

Synthesis of 1-((3,3-difluorocyclopentyl)methyl)-3-(1,1-difluoroethyl)-4-methyl-1H-pyrazole-5-carboxylic acid (Int-B55)

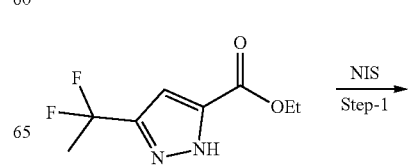

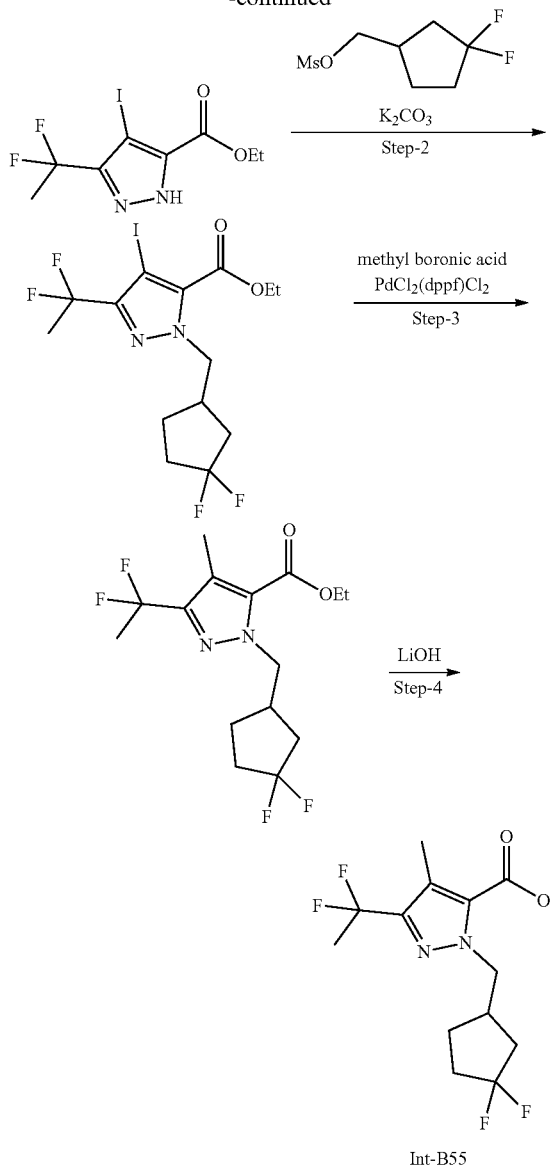

Int-B55

Step 1: To a stirred solution of ethyl 3-(1,1-difluoroethyl)-1H-pyrazole-5-carboxylate (5.0 g, 24.49 mmol, 1.15 eq.) in DMF (40 mL) was added N-iodosuccinimide (4.8 g, 21.34 mmol, 1.00 eq.) at ambient temperature. The reaction mixture was then heated to 80° C. for 12 h. The reaction mixture was quenched with ice cool water (125 mL) and extracted with EtOAc (2×100 mL). The combined organic layers were washed with brine (4×50 mL), dried over anhydrous Na$_2$SO$_4$ and concentrated under reduced pressure to afford ethyl 3-(1,1-difluoroethyl)-4-iodo-1H-pyrazole-5-carboxylate (5.0 g, 15.15 mmol, 62%).

Step-2: K$_2$CO$_3$ (1.25 g, 9.04 mmol, 3.0 eq.) was added to a stirred solution of ethyl 3-(1,1-difluoroethyl)-4-iodo-1H-pyrazole-5-carboxylate (1.0 g, 3.03 mmol, 1.0 eq.) and (3,3-difluorocyclopentyl)methyl methanesulfonate (700 mg, 3.27 mmol, 1.1 eq.) in MeCN (10 mL) at ambient temperature. The resulting reaction mixture was heated to 80° C. for 16 h. The reaction mixture was allowed to cool to ambient temperature, filtered through a celite pad and the solvent was concentrated under reduced pressure to get the crude product, which was purified by column chromatography (silica gel 100-200 mesh, 2% EtOAc in pet-ether as an eluent) to afford ethyl 1-((3,3-difluorocyclopentyl)methyl)-3-(1,1-difluoroethyl)-4-iodo-1H-pyrazole-5-carb oxy late (680 mg, 1.52 mmol, 50%).

Step-3: In a sealed tube a solution of ethyl 1-((3,3-difluorocyclopentyl)methyl)-3-(1,1-difluoroethyl)-4-iodo-1H-pyrazole-5-carboxylate (800 mg, 1.78 mmol, 1.0 eq.), methylboronic acid (749 mg, 12.51 mmol, 7.0 eq.) and K$_2$CO$_3$ (739 mg, 5.35 mmol, 3.0 eq.) in DMF (10 mL) was degassed with argon for 15 min. To the reaction mixture was added [1,1'-bis(diphenylphosphino)ferrocene]dichloropalladium(II) complex with dichloromethane (Pd(dppf) Cl$_2$CH$_2$Cl$_2$, 291 mg, 0.35 mmol, 0.2 eq.) at ambient temperature. The resulting solution was heated to 100° C. for 16 h. The reaction mixture was cooled to ambient temperature, diluted with water (10 mL) and extracted with EtOAc (3×10 mL). The combined organic layers were washed with water (20 mL) and then brine (20 mL), dried over anhydrous Na$_2$SO$_4$ and concentrated under reduced pressure to afford ethyl 1-((3,3-difluorocyclopentyl)methyl)-3-(1,1-difluoroethyl)-4-methyl-1H-pyrazole-5-carboxylate (350 mg, crude).

Step-4: To a solution of ethyl 1-((3,3-difluorocyclopentyl)methyl)-3-(1,1-difluoroethyl)-4-methyl-1H-pyrazole-5-carboxy late (350 mg, max. 1.04 mmol, 1.0 eq.) in MeOH:THF (1:2, 6 mL) was added a solution of LiOH·H$_2$O (213 mg, 5.08 mmol, 4.9 eq.) in water (2 mL). The resulting suspension was stirred at ambient temperature for 2 h. The reaction mixture was diluted with water (10 mL), acidified to pH~2 with 1N aq. HCl solution and extracted with ethyl acetate (2×20 mL). The combined organic layers were dried over anhydrous Na$_2$SO$_4$ and concentrated under reduced pressure to afford 1-((3,3-difluorocyclopentyl)methyl)-3-(1,1-difluoroethyl)-4-methyl-1H-pyrazole-5-carboxylic acid (350 mg, crude). LCMS: m/z [M+H]$^+$=309.2 (calc.=309.1).

Preparation of (3,3-difluorocyclopentyl)methyl methanesulfonate:

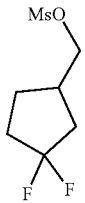

To a stirred solution of (3,3-difluorocyclopentyl)methanol (750 mg, 5.51 mmol) in dichloromethane (15 mL) were added Et$_3$N (2.39 mL, 17.14 mmol, 3.1 eq.) and MsCl (1.57 g, 13.71 mmol, 2.5 eq.) at 0° C. The reaction mixture was then warmed to ambient temperature and was stirred for 2 h. The reaction mixture was quenched with water (20 mL) and extracted with dichloromethane (2×20 mL). The combined organic layers were washed with water (25 mL) and then brine (25 mL), dried over anhydrous Na$_2$SO$_4$ and concentrated under reduced pressure to afford (3,3-difluorocyclopentyl)methyl methanesulfonate (500 mg, crude).

The following intermediates were prepared by analogy to the procedures described above using appropriate reactants and adjusted purification protocols:

| Intermediate structure/code | Procedure | Analytics |
|---|---|---|
| 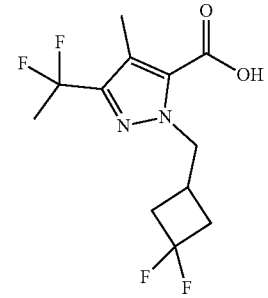<br>IntB-50 | in analogy to the synthesis of Int-B55 using (3,3-difluorocyclobutyl)methyl methanesulfonate instead of (3,3-difluorocyclopentyl)-methyl methanesulfonate | LCMS: m/z [M + H]$^+$ = 295.2 (calc. = 295.11). |
| 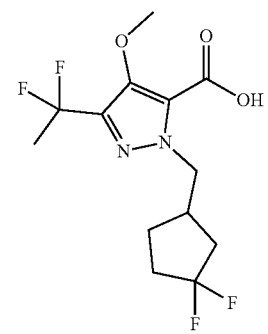<br>IntB-88 | in analogy to the synthesis of Int-B55 using the following modified conditions in step 3: CuI, NaOMe, MeOH, 120° C., 16 h. | LCMS: m/z [M + H]$^+$ = 325.0 (calc. = 325.1). |

Synthesis of 4-chloro-1-((3,3-difluorocyclopentyl)methyl)-3-(trifluoromethyl)-1H-pyrazole-5-carboxylic acid (Int-B51)

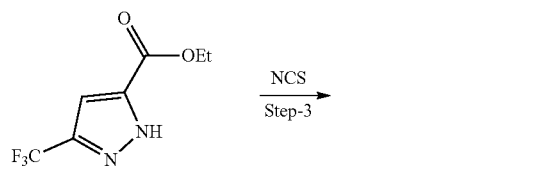

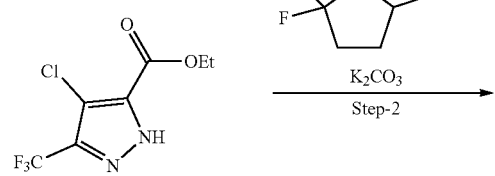

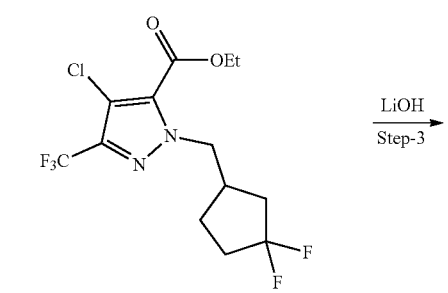

-continued

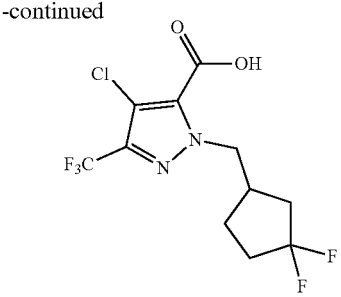

Int-B51

Step-1: NCS (959.1 mg, 7.211 mmol, 1.5 eq.) was added to a stirred solution of ethyl 3-(trifluoromethyl)-1H-pyrazole-5-carboxylate (1.0 g, 4.807 mmoles, 1.0 eq.) in DMF (10 mL) at ambient temperature. The reaction mixture was then heated to 100° C. and stirred for 16 h. The reaction mixture was quenched with ice cold water (50 mL), stirred for 15 minutes and extracted with ethyl acetate (2×50 mL). The combined organic layers were dried over anhydrous Na$_2$SO$_4$ and concentrated under reduced pressure to get the crude compound, which was purified by prep-HPLC to get ethyl 4-chloro-3-(trifluoromethyl)-1H-pyrazole-5-carboxylate. Yield: 43% (500 mg).

Step-2: To a stirred solution of ethyl 4-chloro-3-(trifluoromethyl)-1H-pyrazole-5-carboxylate (600 mg, 2.489 mmol, 1.0 eq.), (3,3-difluorocyclopentyl)methyl methanesulfonate (586 mg, 2.738 mmol, 1.1 eq.) in MeCN (10 mL) was added K$_2$CO$_3$ (1.02 g, 7.438 mmol, 3.0 eq.) at ambient temperature and the resulting reaction mixture was heated to 80° C. for 16 h. The reaction mixture was allowed to cool to ambient temperature and was filtered through a pad of celite.

The filtrate was concentrated under reduced pressure to get the crude product which was purified by (100-200 mesh) silica gel column chromatography using 4% ethyl acetate in pet ether as an eluent to afford ethyl 4-chloro-1-((3,3-difluorocyclopentyl)methyl)-3-(trifluoromethyl)-1H-pyrazole-5-carboxylate. Yield: 39% (420 mg).

Step-3: To a stirred solution of ethyl 4-chloro-1-((3,3-difluorocyclopentyl)methyl)-3-(trifluoromethyl)-1H-pyrazole-5-carboxylate (350 mg, 0.972 mmol, 1.0 eq.) in methanol:THF:water (1:1:1, 6 mL) was added LiOH·H₂O (199 mg, 4.861 mmol, 5.0 eq.) at ambient temperature. The reaction mixture was stirred at ambient temperature for 2 h and the reaction progress was monitored by TLC. The reaction mixture was concentrated under reduced pressure to obtain a residue which was diluted with water (10 mL), acidified to pH~4 with 1N aq. HCl solution and extracted with EtOAc (3×10 mL). The combined organic layers were washed with water (20 mL) and brine (20 mL), dried over anhydrous Na₂SO₄ and concentrated under reduced pressure to afford 4-chloro-1-((tetrahydro-2H-pyran-2-yl)methyl)-3-(trifluoromethyl)-1H-pyrazole-5-carboxylic acid (Int-B51, 350 mg, crude product). LCMS: m/z [M−H]⁻=331.1 (calc.=331.0).

Synthesis of 1-((3,3-difluoro-1-methylcyclobutyl)methyl)-3-(1,1-difluoroethyl)-4-methyl-1H-pyrazole-5-carboxylic acid (Int-B54)

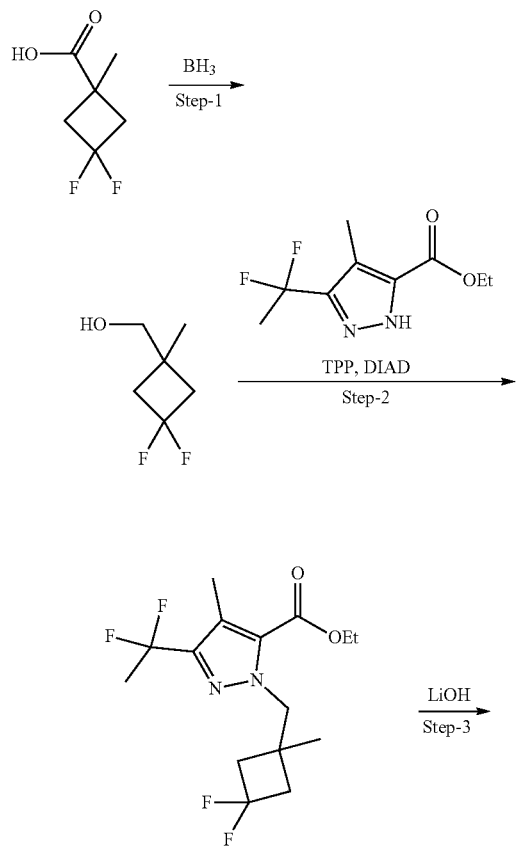

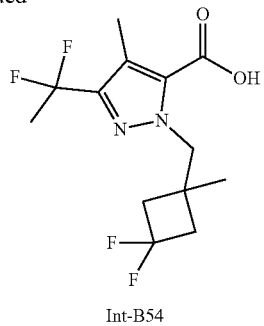

Int-B54

Step-1: To a stirred solution of 3,3-difluoro-1-methylcyclobutane-1-carboxylic acid (1.0 g, 6.67 mmol, 1.0 eq.) in THF (20 mL) was added borane in THF (1M, 6.7 mL, 6.67 mmol, 1.0 eq.) at 0° C. The reaction mixture was allowed to warm to ambient temperature and was stirred for 3 h. The reaction mixture was quenched with sat. solution of Na₂CO₃ (25 mL) and extracted with ethyl acetate (2×50 mL). The combined organic layers were washed with water (25 mL) and then brine (25 mL), dried over anhydrous Na₂SO₄ and concentrated under reduced pressure to afford (3,3-difluoro-1-methylcyclobutyl)methanol (1.0 g, crude) which was used in the next step without further purification.

Step-2: To a stirred solution of TPP (3.00 g, 11.46 mmol, 2.5 eq.) in tetrahydrofuran (20 mL) was added DIAD (2.31 g, 11.46 mmol, 2.5 eq.) at 0° C. and the reaction mixture was then stirred for 30 minutes at 0° C., followed by the addition of ethyl 3-(1,1-difluoroethyl)-4-methyl-1H-pyrazole-5-carboxylate (1.00 g, 4.58 mmol, 1.0 eq.) at 0° C. The reaction mixture was stirred at ambient temperature for 10 minutes, followed by the addition of crude (3,3-difluoro-1-methylcyclobutyl)methanol (0.94 g, max. 6.90 mmol, 1.5 eq.) at 0° C. The reaction mixture was then warmed to ambient temperature and was stirred for 16 h. The reaction mixture was quenched with water (30 mL) and extracted with ethyl acetate (50 mL). The combined organic layers were washed with water (20 mL) and then brine (20 mL), dried over anhydrous Na₂SO₄ and concentrated under reduced pressure to get the crude product which was purified by column chromatography (silica gel 100-200 mesh, 5% ethyl acetate in pet ether as an eluent) to afford ethyl 1-((3,3-difluoro-1-methylcyclobutyl)methyl)-3-(1,1-difluoroethyl)-4-methyl-1H-pyrazole-5-carboxy late (0.70 g, 2.08 mmol, 45%).

Step-3: To a stirred solution of ethyl 1-((3,3-difluoro-1-methylcyclobutyl)methyl)-3-(1,1-difluoroethyl)-4-methyl-1H-pyrazole-5-carboxylate (700 mg, 2.08 mmol, 1.0 eq.) in THF:MeOH:H₂O (1:1:0.5, 20 mL) was added LiOH·H₂O (262 mg, 6.24 mmol, 3.0 eq.) at ambient temperature. The reaction mixture was then stirred at ambient temperature for 2 h. The reaction mixture was concentrated, diluted with water (20 mL), acidified to pH~2 with 1N HCl solution and extracted with 5% MeOH in dichloromethane (2×50 mL). The combined organic layers were dried over anhydrous Na₂SO₄ and concentrated under reduced pressure to afford 1-((3,3-difluoro-1-methylcyclobutyl)methyl)-3-(1,1-difluoroethyl)-4-methyl-1H-pyrazole-5-carboxylic acid (Int-B54, 700 mg, crude). LCMS: m/z [M+H]⁺=309.2 (calc.=309.1).

Preparation of ethyl 3-(1,1-difluoroethyl)-4-methyl-1H-pyrazole-5-carboxylate

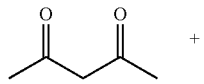

brine (2×200 mL), dried over anhydrous Na₂SO₄ and concentrated under reduced pressure to get the crude product, which was purified by column chromatography (silica gel 100-200 mesh, 10% ethyl acetate in pet ether as an eluent) to afford ethyl 3-(1,1-difluoroethyl)-4-methyl-1H-pyrazole-5-carboxylate (33 g, 151 mmol, 59%).

The following intermediates were prepared by analogy to the procedures described above using appropriate reactants and adjusted purification protocols:

| Intermediate structure/code | Procedure | Analytics |
|---|---|---|
| 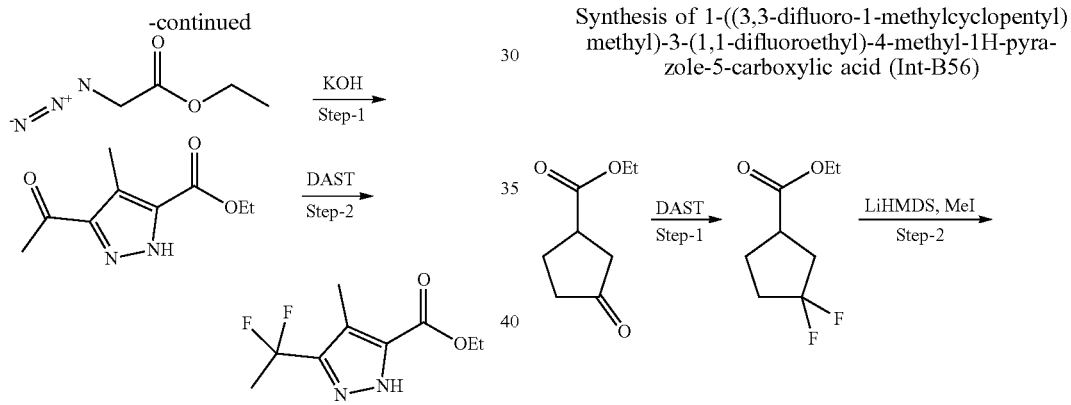 Int-B59 | in analogy to the synthesis of Int-B54 (3,3-difluoro-1-(trifluoromethyl)-cyclobutyl)methanol instead of (3,3-difluoro-1-methylcyclobutyl)-methanol | LCMS: m/z [M + H]⁺ = 363.1 (calc. = 363.1). |

-continued

Step-1: To a stirred solution of KOH (17 g, 303 mmol, 1.01 eq.) in ethanol (500 mL) was added pentane-2,4-dione (30 g, 300 mmol, 1.00 eq.) followed by ethyl diazoacetate (39 g, 302 mmol, 1.01 eq.) at 80° C. The resulting reaction mixture was stirred at 80° C. for 1 h. The reaction mixture was concentrated under reduced pressure, diluted with water and the pH was adjusted to ~2 using 3N HCl solution at 15-20° C. The precipitated solid was filtered off, washed with water (1000 mL) and dried under reduced pressure to afford ethyl 3-acetyl-4-methyl-1H-pyrazole-5-carboxylate (17 g, 86 mmol, 29%).

Step-2: To a stirred solution of ethyl 3-acetyl-4-methyl-1H-pyrazole-5-carboxylate (50 g, 255 mmol, 1.0 eq.) in dichloromethane (500 mL) was added DAST (68.4 mL, 518 mmol, 2.0 eq.) at 0° C. The reaction mixture was stirred for 16 h at ambient temperature. The reaction mixture was quenched with 50% aq. NaHCO₃ solution (200 mL) and extracted with dichloromethane (2×100 mL). The combined organic layers were washed with water (2×200 mL) and then Synthesis of 1-((3,3-difluoro-1-methylcyclopentyl)methyl)-3-(1,1-difluoroethyl)-4-methyl-1H-pyrazole-5-carboxylic acid (Int-B56)

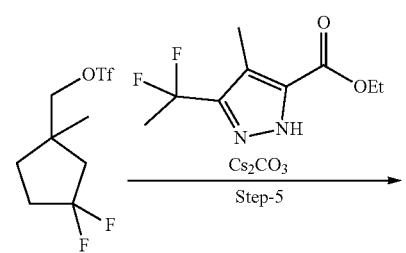

-continued

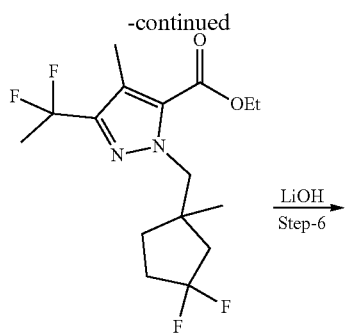

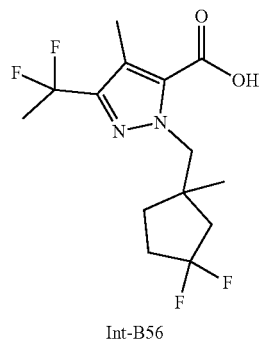

Int-B56

Step-1: To a stirred solution of ethyl 3-oxocyclopentane-1-carboxylate (7.0 g, 44.87 mmol, 1.0 eq.) in dichloromethane (175 mL) was added DAST (28.9 g, 179.48 mmol, 4.0 eq.) at 0° C. under an argon atmosphere. The resulting reaction mixture was stirred at ambient temperature for 24 h. The reaction mixture was quenched with sat. NaHCO₃ solution (200 mL) and extracted with dichloromethane (2×200 mL). The combined organic layers were washed with water (200 mL) and then brine (200 mL), dried over anhydrous Na₂SO₄ and concentrated under reduced pressure to afford ethyl 3,3-difluorocyclopentane-1-carboxylate (8.0 g, crude). The crude product was directly used in the next step without further purification.

Step-2: To a stirred solution of ethyl 3,3-difluorocyclopentane-1-carboxylate (4.0 g, 22.47 mmol, 1.0 eq.) in THF (70 mL) was added LiHMDS in THF (1M, 29.2 mL, 29.21 mmol, 1.3 eq.) at −5° C. and the mixture was then stirred at 0° C. under an argon atmosphere for 30 minutes. To the reaction mixture was added a solution of methyl iodide (4.78 g, 33.70 mmol, 1.5 eq.) in THF (10 mL), the mixture was then warmed to ambient temperature and was stirred for 12 h. The reaction mixture was then slowly quenched with saturated aq. NH₄Cl solution (100 mL) and extracted with ethyl acetate (2×100 mL). The combined organic layers were washed with water (100 mL) and then brine (100 mL), dried over anhydrous Na₂SO₄ and concentrated under reduced pressure to afford ethyl 3,3-difluoro-1-methylcyclopentane-1-carboxylate (3.5 g, crude). The crude product was directly used in the next step without further purification.

Step-3: To a stirred solution of ethyl 3,3-difluoro-1-methylcyclopentane-1-carboxylate (3.5 g, 18.21 mmol, 1.0 eq.) in THF (87.5 mL) was added LAH in THF (1M, 27.3 mL, 27.31 mmol, 1.5 eq.) at 0° C. under an argon atmosphere. The reaction mixture was then stirred at 0° C. for 2 h. The reaction mixture was slowly poured into crushed ice (200 g), the pH was adjusted with 1N aq. HCl solution to ~6 and the resulting mixture was extracted with ethyl acetate (2×100 mL). The combined organic layers were washed with water (100 mL) and then brine (100 mL), dried over anhydrous Na₂SO₄ and concentrated under reduced pressure to give the crude product, which was purified by column chromatography (silica gel 100-200 mesh, 15% ethyl acetate in pet ether as an eluent) to afford (3,3-difluoro-1-methylcyclopentyl)methanol (1.8 g, 11.97 mmol, 53% over 3 steps).

Step-4: To a stirred solution of (3,3-difluoro-1-methylcyclopentyl)methanol (1.3 g, 8.67 mmol, 1.0 eq.) in dichloromethane (32.5 mL) was added pyridine (1.37 g, 17.33 mmol, 2.0 eq.) followed by the addition of trifluoromethanesulfonic anhydride (3.17 g, 11.27 mmol, 1.3 eq.) at 0° C. under an argon atmosphere. The resulting reaction mixture was stirred at 0° C. for 2 h. The reaction mixture was then quenched with water (50 mL) and extracted with dichloromethane (2×40 mL). The combined organic layers were washed with water (30 mL) and brine (30 mL), dried over anhydrous Na₂SO₄ and concentrated under reduced pressure to afford (3,3-difluoro-1-methylcyclopentyl)methyl trifluoromethanesulfonate (2.5 g, crude). The crude product was directly used in the next step without further purification.

Step-5: To a stirred solution of ethyl 3-(1,1-difluoroethyl)-4-methyl-1H-pyrazole-5-carboxylate (1.6 g, 7.34 mmol, 1.0 eq.) and (3,3-difluoro-1-methylcyclopentyl)methyl trifluoromethanesulfonate (2.48 g, 8.81 mmol, 1.2 eq.) in DMF (32 mL) was added Cs₂CO₃ (4.78 g, 14.68 mmol, 2.0 eq.) at ambient temperature under an argon atmosphere. The resulting reaction mixture was stirred at 85° C. for 6 h. The reaction mixture was quenched with water (75 mL) and extracted with ethyl acetate (2×70 mL). The combined organic layers were washed with water (40 mL) and then brine (40 mL), dried over anhydrous Na₂SO₄ and concentrated under reduced pressure to give the crude product, which was purified by column chromatography (silica gel 100-200 mesh, 5% ethyl acetate in petrol ether as an eluent) to afford ethyl 1-((3,3-difluoro-1-methylcyclopentyl)methyl)-3-(1,1-difluoroethyl)-4-methyl-1H-pyrazole-5-carboxylate (2.3 g, 6.57 mmol 90%).

Step-6: To a stirred solution of ethyl 1-((3,3-difluoro-1-methylcyclopentyl)methyl)-3-(1,1-difluoroethyl)-4-methyl-1H-pyrazole-5-carboxylate (2.2 g, 6.28 mmol, 1.0 eq.) in THF:MeOH (2:1, 44 mL) was added a solution of LiOH·H₂O (528 mg, 12.57 mmol, 2.0 eq.) in water (1.1 mL) at 0° C. The reaction mixture was stirred at ambient temperature for 3 h. The mixture was concentrated under reduced pressure, diluted with water (70 mL) and extracted with diethyl ether (2×30 mL). The aqueous layer was acidified to pH~5 with 1N aq. HCl solution and extracted with ethyl acetate (2×40 mL). The combined ethyl acetate layers were washed with water (30 mL) and then brine (30 mL), dried over anhydrous Na₂SO₄ and concentrated under reduced pressure to afford 1-((3,3-difluoro-1-methylcyclopentyl)methyl)-3-(1,1-difluoroethyl)-4-methyl-1H-pyrazole-5-carboxylic acid (Int-B56, 1.9 g, crude). The crude product was directly used in the next step without further purification. LCMS: m/z [M+H]⁺=323.2 (calc.=323.1).

Synthesis of ethyl 1-(((trans)-4,4-difluoro-2-(trifluoromethyl)cyclopentyl)methyl)-3-(1,1-difluoroethyl)-4-methyl-1H-pyrazole-5-carboxylate (Int-B57)

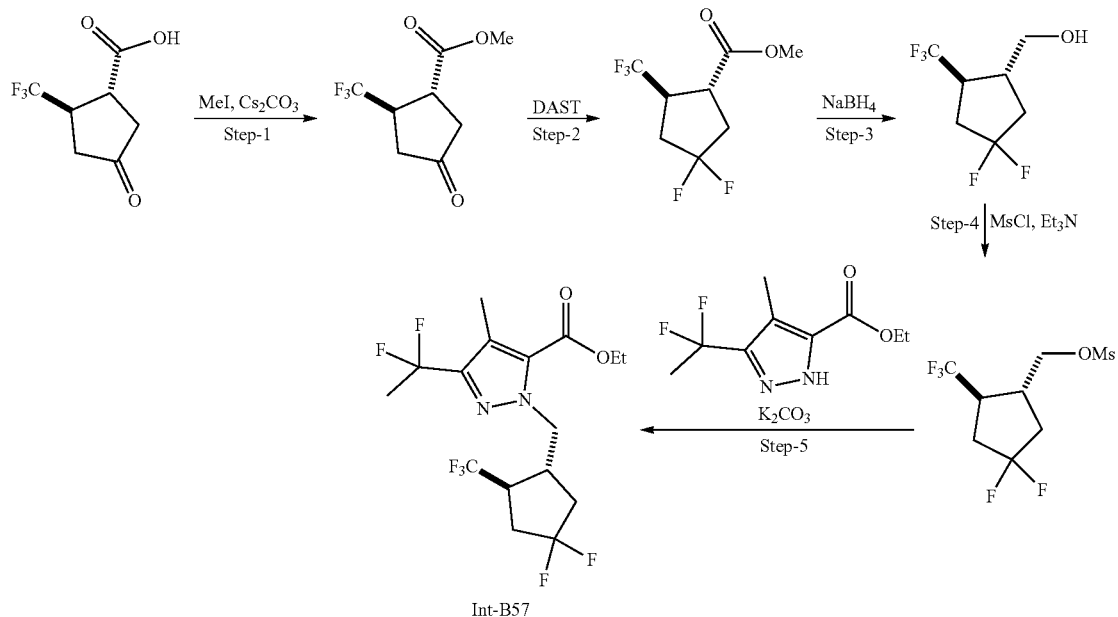

Step-1: To a stirred solution of (trans)-4-oxo-2-(trifluoromethyl)cyclopentane-1-carboxylic acid (1.5 g, 7.65 mmol, 1.0 eq.) in acetonitrile (20 mL) were added $Cs_2CO_3$ (4.97 g, 15.30 mmol, 2.0 eq.) and methyl iodide (1.62 g, 11.40 mmol, 1.5 eq.) at ambient temperature and the reaction mixture was stirred for 6 h. The reaction mixture was filtered through a celite bed, and the filtrate was concentrated under reduced pressure to afford methyl (trans)-4-oxo-2-(trifluoromethyl)cyclopentane-1-carboxylate (1.2 g, crude).

Step-2: DAST (3.67 g, 22.85 mmol, 4.0 eq.) was slowly added to a stirred solution of methyl (trans)-4-oxo-2-(trifluoromethyl)cyclopentane-1-carboxylate (1.2 g, 5.71 mmol, 1.0 eq.) in dichloromethane (25 mL) at 0° C. The reaction mixture was then stirred at ambient temperature for 48 h. The reaction mixture was diluted with dichloromethane (15 mL), washed with water (30 mL), saturated $NaHCO_3$ solution (30 mL) and brine (30 mL), dried over anhydrous $Na_2SO_4$ and concentrated under reduced pressure to afford methyl (trans)-4,4-difluoro-2-(trifluoromethyl)cyclopentane-1-carboxylate (1.0 g, crude).

Step-3: $NaBH_4$ (655 mg, 17.2 mmol, 4.0 eq.) was added to a stirred solution of methyl (trans)-4,4-difluoro-2-(trifluoromethyl)cyclopentane-1-carboxylate (1.0 g, 4.31 mmol, 1.0 eq.) in methanol (15 mL) at 0° C. and the reaction mixture was then stirred at ambient temperature for 2 h. The reaction mixture was quenched with ice cold water (25 mL) and extracted with EtOAc (2×25 mL). The combined organic layers were washed with water (30 mL) and brine (30 mL), dried over anhydrous $Na_2SO_4$ and concentrated under reduced pressure to afford ((trans)-4,4-difluoro-2-(trifluoromethyl)cyclopentyl)methanol (800 mg, crude).

Step-4: To a stirred solution of ((trans)-4,4-difluoro-2-(trifluoromethyl)cyclopentyl)methanol (800 mg, 3.92 mmol, 1.0 eq.) in dichloromethane (15 mL) were added triethylamine (1.13 mL, 7.84 mmol, 2.0 eq.) and MsCl (0.45 mL, 5.88 mmol, 1.58 eq.) at 0° C. and the reaction mixture was then stirred at ambient temperature for 1 h. The reaction mixture was quenched with water (20 mL) and extracted with dichloromethane (2×15 mL). The combined organic layers were washed with water (25 mL) and brine (25 mL), dried over anhydrous $Na_2SO_4$ and concentrated under reduced pressure to afford ((trans)-4,4-difluoro-2-(trifluoromethyl)cyclopentyl)methyl methanesulfonate (1.0 g, crude).

Step-5: To a stirred solution of ethyl 3-(1,1-difluoroethyl)-4-methyl-1H-pyrazole-5-carboxylate (1.0 g, 4.58 mmol, 1.3 eq.) and ((trans)-4,4-difluoro-2-(trifluoromethyl)cyclopentyl)methyl methanesulfonate (1.0 g, 3.66 mmol, 1.0 eq.) in acetonitrile (20 mL) was added $K_2CO_3$ (1.26 g, 9.17 mmol) at ambient temperature. The reaction mixture was then heated to 80° C. for 16 hours. The reaction mixture was filtered and the filtrate was concentrated under reduced pressure to get the crude product which was purified by column chromatography (silica gel 100-200 mesh, 2% ethyl acetate in pet ether as an eluent) to afford ethyl 1-(((trans)-4,4-difluoro-2-(trifluoromethyl)cyclopentyl)methyl)-3-(1,1-difluoroethyl)-4-methyl-1H-pyrazole-5-carboxylate (Int-B57, 450 mg, crude). LCMS: m/z $[M+H]^+$=405.2 (calc.=405.1).

Synthesis of 3-cyclopropyl-1-((3-(difluoromethyl)cyclobutyl)methyl)-4-(trifluoromethyl)-1H-pyrazole-5-carboxylic acid (Int-B60)

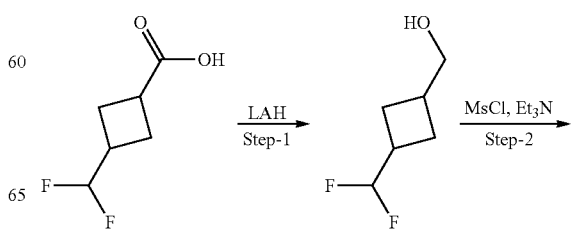

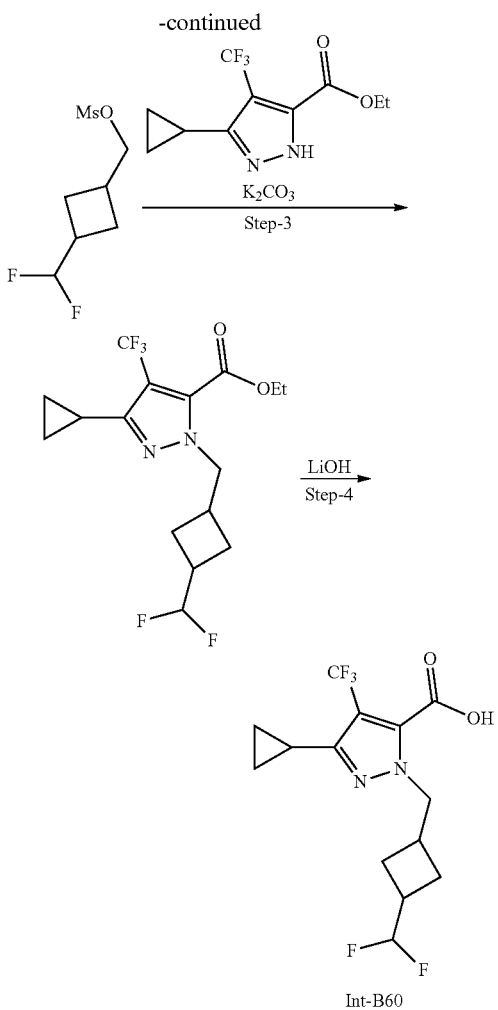

Int-B60 mmol, 1.0 eq.) in acetonitrile (30 mL) were added $K_2CO_3$ (626 mg, 4.53 mmol, 1.5 eq.) and (3-(difluoromethyl)cyclobutyl)methyl methanesulfonate (971 mg, 4.53 mmol, 1.53 eq.) at ambient temperature. The reaction mixture was then heated to 90° C. for 16 h. The reaction mixture was filtered, and the filter bed was washed with ethyl acetate (30 mL). The filtrate was concentrated under reduced pressure to get the crude product which was purified by column chromatography (silica gel 100-200 mesh, 10% ethyl acetate in pet ether as an eluent) to afford ethyl 3-cyclopropyl-1-((3-(difluoromethyl)cyclobutyl)methyl)-4-(trifluoromethyl)-1H-pyrazole-5-carboxy late (550 mg, 13% over 3 steps).

Step-4: To a stirred solution of ethyl 3-cyclopropyl-1-((3-(difluoromethyl)cyclobutyl)methyl)-4-(trifluoromethyl)-1H-pyrazole-5-carboxylate (50 mg, 0.14 mmol, 1.0 eq.) in $THF:H_2O$ (1:1, 5 mL) was added a solution of $LiOH·H_2O$ (23 mg, 0.55 mmol, 4.0 eq.) in 2.5 mL of water at ambient temperature and the reaction mixture was then stirred at ambient temperature for 16 h. For workup, this reaction was combined with another experiment using the same reaction conditions, starting with 500 mg of ethyl 3-cyclopropyl-1-((3-(difluoromethyl)cyclobutyl)methyl)-4-(trifluoromethyl)-1H-pyrazole-5-carboxylate. The combined reaction mixtures were concentrated under reduced pressure, diluted with water (10 mL), acidified to pH~2 with 1N aq. HCl solution and extracted with 5% MeOH in dichloromethane (2×50 mL). The combined organic layers were dried over anhydrous $Na_2SO_4$ and concentrated under reduced pressure to afford 3-cyclopropyl-1-((3-(difluoromethyl)cyclobutyl)methyl)-4-(trifluoromethyl)-1H-pyrazole-5-carboxylic acid (Int-B60, 500 mg, crude). LCMS: m/z $[M+H]^+$=339.2 (calc.=339.1).

Synthesis of 1-(1-(3,3-difluorocyclobutyl)ethyl)-3-(1,1-difluoroethyl)-4-methyl-1H-pyrazole-5-carboxylic acid (Int-B61)

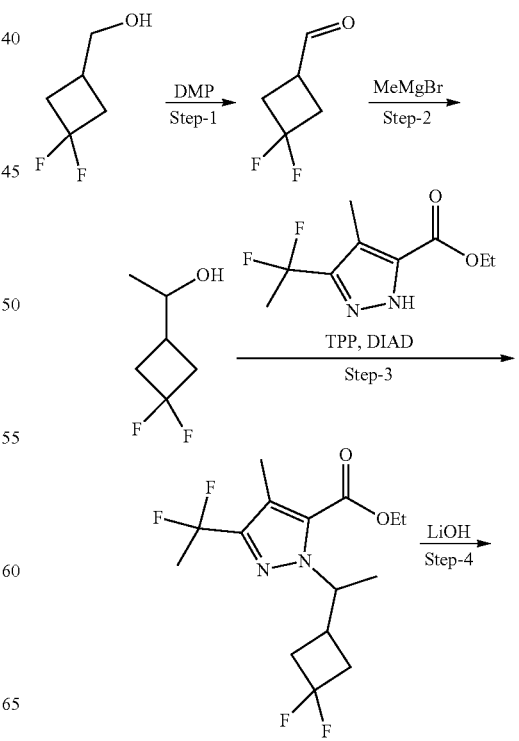

Step-1: To a stirred solution of 3-(difluoromethyl)cyclobutane-1-carboxylic acid (500 mg, 3.33 mmol, 1.0 eq.) in THF (10 mL) was added LAH in THF (1 M, 6.66 mL, 6.66 mmol, 2.0 eq.) at 0° C. The reaction mixture was warmed to ambient temperature and was stirred for 16 h. For workup, this reaction was combined with another experiment using the same reaction conditions, starting with 1.2 g of 3-(difluoromethyl)cyclobutane-1-carboxylic acid. The reaction mixture was quenched with saturated aq. $Na_2SO_4$ solution (10 mL) and stirred for 30 minutes. The reaction mixture was filtered through a celite bed, and the celite bed was washed with ethyl acetate (2×30 mL). The filtrate was concentrated under reduced pressure to afford (3-(difluoromethyl)cyclobutyl)methanol (1 g, crude).

Step-2: To a stirred solution of (3-(difluoromethyl)cyclobutyl)methanol (1.0 g, 7.34 mmol, 1.0 eq.) in dichloromethane (50 mL) were added triethylamine (1.12 g, 11.02 mmol, 1.5 eq.) and MsCl (1.27 g, 11.02 mmol, 1.5 eq.) at 0° C. The reaction mixture was then stirred at ambient temperature for 3 h. The reaction mixture was quenched with water (50 mL) and extracted with dichloromethane (2×50 mL). The combined organic layers were washed with water (50 mL) and brine (50 mL), dried over anhydrous $Na_2SO_4$ and concentrated under reduced pressure to afford (3-(difluoromethyl)cyclobutyl)methyl methanesulfonate (1.3 g, crude).

Step-3: To a stirred solution of ethyl 3-cyclopropyl-4-(trifluoromethyl)-1H-pyrazole-5-carboxylate (750 mg, 3.02

-continued

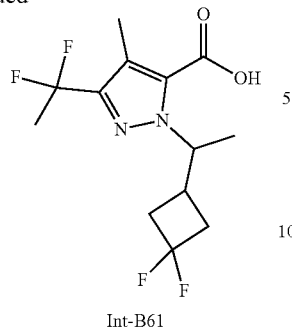

Int-B61

Step-1: To a stirred solution of (3,3-difluorocyclobutyl) methanol (1.0 g, 8.196 mmol, 1.0 eq.) in dichloromethane (15 mL) was added Dess-Martin periodinane (5.2 g, 12.29 mmol, 1.5 eq.) portionwise at 0° C. The resulting reaction mixture was allowed to warm to ambient temperature and then stirred for 16 h. The reaction mixture was quenched with sat. sodium thiosulfate solution (50 mL) and extracted with dichloromethane (2×100 mL). The combined organic layers were washed with water (50 mL) and brine (50 mL), dried over anhydrous Na$_2$SO$_4$ and concentrated under reduced pressure to afford 3,3-difluorocyclobutane-1-carbaldehyde (1.0 g, crude).

Step-2: To a stirred solution of 3,3-difluorocyclobutane-1-carbaldehyde (1.0 g, 8.340 mmol, 1.0 eq.) in THF (15 mL) was added MeMgBr in THF (1.5M, 8.34 mL, 12.50 mmol, 1.5 eq.) dropwise at 0° C. The resulting reaction mixture was then warmed to ambient temperature and was stirred for 5 h. The reaction mixture was quenched with sat. ammonium chloride solution (50 mL) and extracted with dichloromethane (2×100 mL). The combined organic layers were washed with water (50 mL) and brine (50 mL), dried over anhydrous Na$_2$SO$_4$ and concentrated under reduced pressure to afford 1-(3,3-difluorocyclobutyl)ethan-1-ol (1.0 g, crude).

Step 3: To a stirred solution of TPP (3.90 g, 14.90 mmol, 2.5 eq.) in tetrahydrofuran (20 mL) was added DIAD (3.01 g, 14.90 mmol, 2.5 eq.) at 0° C. The mixture was stirred for 30 min at 0° C., followed by the addition of ethyl 3-(1,1-difluoroethyl)-4-methyl-1H-pyrazole-5-carboxylate (1.3 g, 5.96 mmol, 1.0 eq.). The mixture was then stirred for 10 minutes, before the addition of 1-(3,3-difluorocyclobutyl) ethan-1-ol (0.973 g, 7.16 mmol, 1.2 eq.). The reaction mixture was then allowed to warm to ambient temperature and was stirred for 16 h. The reaction mixture was quenched with water (50 mL) and extracted with ethyl acetate (2×50 mL). The combined organic layers were washed with water (20 mL) and brine (20 mL), dried over anhydrous Na$_2$SO$_4$ and concentrated under reduced pressure to get the crude compound, which was purified by column chromatography (silica gel 100-200 mesh, 10% ethyl acetate in pet ether as an eluent) to afford ethyl 1-(1-(3,3-difluorocyclobutyl) ethyl)-3-(1,1-difluoroethyl)-4-methyl-1H-pyrazole-5-carboxylate (1.0 g, 36% over 3 steps).

Step-4: To a stirred solution of ethyl 1-(1-(3,3-difluorocyclobutyl)ethyl)-3-(1,1-difluoroethyl)-4-methyl-1H-pyrazole-5-carboxylate (500 mg, 2.976 mmol, 1.0 eq.) in THF: MeOH:H$_2$O (1:1:0.5, 20 mL) was added LiOH·H$_2$O (375 mg, 8.928 mmol, 3.0 eq.) at ambient temperature. The reaction mixture was then stirred for 2 h. The reaction mixture was then concentrated under reduced pressure, diluted with water (10 mL), acidified to pH~2 with 1N HCl and extracted with 5% MeOH in dichloromethane (2×25 mL). The combined organic layers were dried over anhydrous Na$_2$SO$_4$ and concentrated under reduced pressure to afford 1-(1-(3,3-difluorocyclobutyl)ethyl)-3-(1,1-difluoroethyl)-4-methyl-1H-pyrazole-5-carboxylic acid (Int-B61, 700 mg, crude). LCMS: m/z [M+H]$^+$=309.3 (calc.=309.1).

Synthesis of 3-(1,1-difluoroethyl)-1-(((cis)-2-((2-methoxyethoxy)methyl)cyclohexyl)methyl)-4-methyl-1H-pyrazole-5-carboxylic acid (Int-B62)

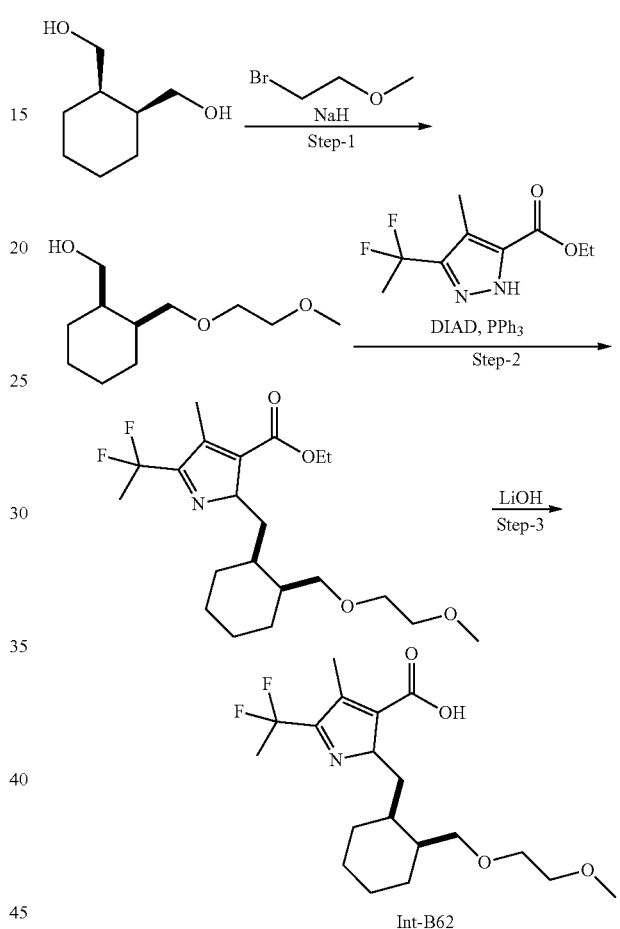

Int-B62

Step-1: To a stirred suspension of NaH (0.488 g, 20.0 mmol, 2.0 eq.) in THF (10 mL) was added ((1R,2S)-cyclohexane-1,2-diyl)dimethanol (1.6 g, 11.1 mmol, 1.1 eq.) dropwise at 0° C. and the reaction mixture was stirred for 30 min. Then, 1-bromo-2-methoxyethane (1.38 g, 10.0 mmol, 1.0 eq.) was added and the reaction was allowed to warm to ambient temperature and was stirred for 24 h. The reaction mixture was quenched with ice-cold water (30 mL) and extracted with EtOAc (3×30 mL). The combined organic layers were washed with brine (15 mL), dried over anhydrous Na$_2$SO$_4$, filtered and concentrated under reduced pressure to get the crude product which was purified by column chromatography (silica gel 230-400 mesh, 25% ethyl acetate in pet ether as an eluent) to afford ((cis)-2-((2-methoxyethoxy)methyl)cyclohexyl)methanol (550 mg).

Step-2: To a stirred solution of triphenylphosphine (1.5 g, 5.733 mmol, 2.5 eq.) in THF (5.0 mL) at 0° C. was added DIAD (1.158 g, 5.733 mmol, 2.5 eq.) dropwise over 15 minutes and the resulting mixture was stirred for 20 minutes. Then, ethyl 3-(1,1)-difluoroethyl)-4-methyl-1H-pyrazole-5- carboxylate (500 mg, 2.294 mmol, 1.0 eq.) and (((cis)-2-((2-methoxyethoxy)methyl)cyclohexyl)methanol (550 mg, 2.752 mmol, 1.2 eq.) were added. The reaction mixture was allowed to warm to ambient temperature and was then stirred for 12 h. The reaction mixture was quenched with water (20 mL) and extracted with EtOAc (3×20 mL). The combined organic layers were washed with brine (15 mL), dried over Na₂SO₄, filtered and concentrated under reduced pressure to get the crude product which was purified by column chromatography (silica gel 230-400 mesh, 20% ethyl acetate in pet ether as an eluent) to afford ethyl 3-(1,1-difluoroethyl)-1-(((cis)-2-((2-methoxy ethoxy)methyl)cyclohexyl)methyl)-4-methyl-1H-pyrazole-5-carboxylate (400 mg).

Step-3: To a stirred solution of ethyl 3-(1,1-difluoroethyl)-1-(((cis)-2-((2-methoxyethoxy)methyl)cyclohexyl)methyl)-4-methyl-1H-pyrazole-5-carboxylate (400 mg, 0.995 mmol, 1.0 eq.) in THF:H₂O (45.0 mL) was added LiOH·H₂O (63 mg, 1.493 mmol, 1.5 eq.) at ambient temperature and the reaction mixture was stirred for 16 h. The reaction mixture was then quenched with 1N aq. HCl solution (5.0 mL) causing a white precipitate which was filtered off and dried under vacuum to afford 3-(1,1-difluoroethyl)-1-(((cis)-2-((2-methoxyethoxy)methyl)cyclohexyl)methyl)-4-methyl-1H-pyrazole-5-carboxylic acid (Int-B62, 400 mg). LCMS: m/z [M+H]⁺=375.3 (calc.=375.2).

The following intermediates were prepared by analogy to the procedures described above using appropriate reactants and adjusted purification protocols:

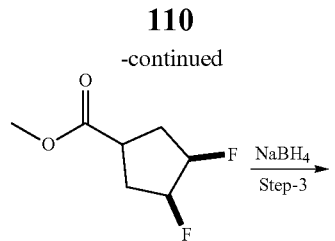

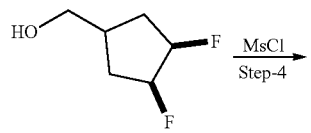

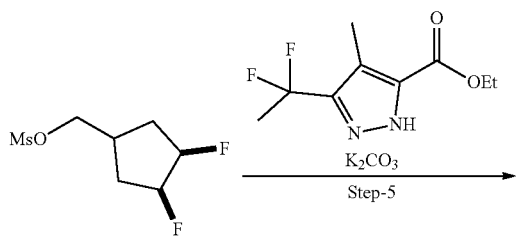

| Intermediate structure/code | Procedure | Analytics |
|---|---|---|
| Int-B89 (CF₃/methyl pyrazole ester with oxetanylmethyl) | in analogy to the synthesis of Int-B62 (step 2 only) | ¹H NMR (400 MHz, DMSO-d6): δ (ppm) = 4.65-4.61 (m, 4H), 4.41-4.33 (m, 4H), 3.49-3.42 (m, 1H), 2.28 (s, 3H), 1.32-1.26 (m, 3H). |

Synthesis of 1-(((cis)-3,4-difluorocyclopentyl)methyl)-3-(1,1-difluoroethyl)-4-methyl-1H-pyrazole-5-carboxylic acid (Int-B63)

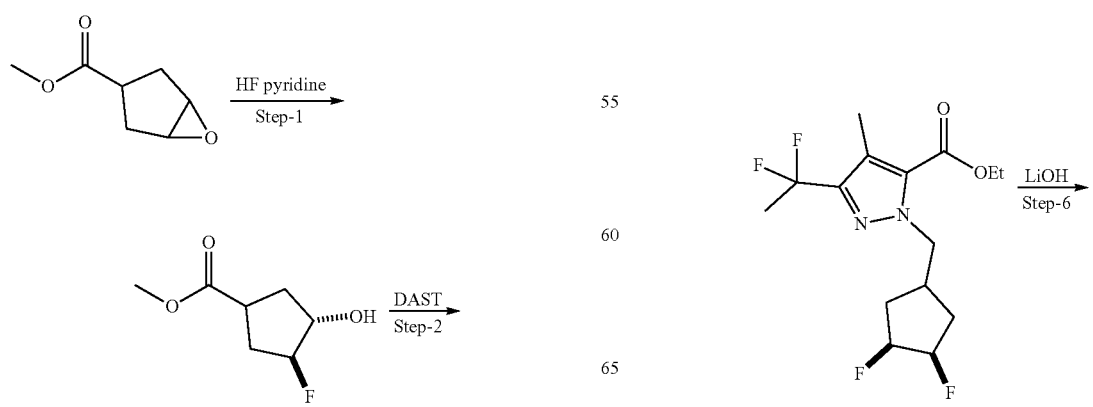

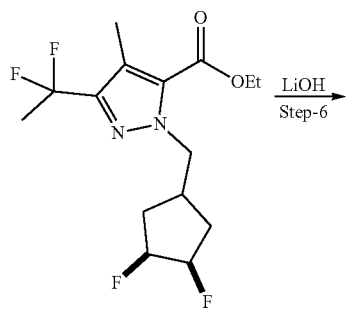

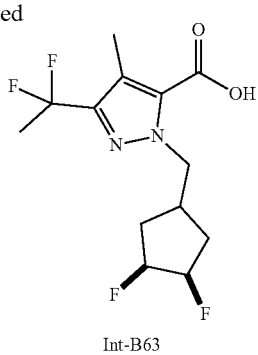

Int-B63

Step-1: To a solution of methyl 6-oxabicyclo[3.1.0]hexane-3-carboxylate (2.0 g, 14.08 mmol, 1.0 equiv) in DCM (50 mL) was added HF·pyridine (3.4 mL, 47.8 mmol, 3.4 eq.) dropwise over 10 min at 0° C. The reaction mixture was then warmed to ambient temperature and was stirred for 4 h. The reaction mixture was then cooled to 0° C. and was quenched with sat. NaHCO$_3$ solution (100 mL). The organic layer was washed with aqueous 2M HCl (100 mL), water (100 mL) and brine (100 mL), dried over sodium sulfate and evaporated under reduced pressure to get the crude material which was purified by combiflash column chromatography (silica gel, 5-25% EA in hexane as eluent) to yield methyl (trans)-3-fluoro-4-hydroxycyclopentane-1-carboxylate. Yield: 52%.

Step-2: To a solution of methyl (trans)-3-fluoro-4-hydroxycyclopentane-1-carboxylate (1.2 g, 7.4 mmol, 1.0 eq.) in DCM (50 mL) was added DAST (2.4 mL, 18.51 mmol, 2.5 eq.) at 0° C. The reaction mixture was then allowed to warm to ambient temperature and was stirred for 8 h. The reaction mixture was then concentrated under reduced pressure and diluted with DCM (200 mL). The organic layer was washed sequentially with sat. NaHCO$_3$ solution (200 mL), water (2×100 mL), brine (100 mL) and was then dried over sodium sulfate. The solvent was evaporated under reduced pressure to get the crude product which was purified by combiflash column chromatography (silica gel, 0-20% EA in hexane as eluent) to yield methyl (cis)-3,4-difluorocyclopentane-1-carboxylate. Yield: 49% (600 mg, 3.65 mmol).

Step-3: To a solution of methyl (cis)-3,4-difluorocyclopentane-1-carboxylate (500 mg, 3.04 mmol, 1.0 eq.) in THF (50 mL) was added NaBH$_4$ (283 mg, 7.6 mmol, 2.5 eq.) at ambient temperature and the reaction mixture was heated to 55° C. for 15 min followed by the addition of MeOH (5 mL) dropwise at the same temperature. The mixture was kept at that temperature for 1 h. The reaction mixture was then concentrated under reduced pressure, diluted with ethyl acetate (200 mL), washed sequentially with sat. NH$_4$Cl solution (100 mL), water (2×50 mL), brine (50 mL) and dried over sodium sulfate. The solvent was evaporated under reduced pressure to get the crude product which was purified by combiflash column chromatography (silica gel, 30-50% EA in hexane as eluent) to yield cis-(3,4-difluorocyclopentyl)methanol. Yield: 72% (300 mg, 2.21 mmol).

Step-4: To a solution of ca-(3,4-difluorocyclopentyl)methanol (350 mg, 2.5 mmol, 1.0 eq.) in DCM (20 mL) were added TEA (0.896 mL, 6.434 mmol, 3.0 eq.) and methanesulfonyl chloride (0.607 mL, 7.7 mmol, 1.5 eq.) at 0° C. The reaction mixture was then warmed to ambient temperature and was stirred for 1 h. The reaction mixture was quenched with water (50 mL) and extracted with DCM (2×100 mL). The combined organic layers were washed with cold brine (100 mL) and dried over Na$_2$SO$_4$. The solvent was evaporated under reduced pressure to get crude cis (3,4-difluorocyclopentyl)methyl methanesulfonate which was used in the next step without purification. Yield: 450 mg (crude).

Step-5: To a solution of ethyl 3-(1,1-difluoroethyl)-4-methyl-1H-pyrazole-5-carboxylate (400 mg, 1.83 mmol, 1.0 eq.) and crude cis-(3,4-difluorocyclopentyl)methyl methanesulfonate (392 mg, 1.83 mmol, 1.0 eq.) in DMF (10 mL) was added K$_2$CO$_3$ (507 g, 3.67 mmol, 2.0 eq.) at ambient temperature and the resulting reaction mixture was stirred at 80° C. for 12 h. The reaction mixture was then quenched with cold water (50 mL) and extracted with ethyl acetate (3×50 mL). The combined organic layers were washed with cold brine (50 mL) and dried over sodium sulfate. The solvent was evaporated under reduced pressure to get the crude material which was purified by combiflash column chromatography (silica gel, 0-14% ethyl acetate in hexane as eluent) to yield cis ethyl 1-((-3,4-difluorocyclopentyl)methyl)-3-(1,1-difluoroethyl)-4-methyl-1H-pyrazole-5-carboxylate. Yield: 32% (200 mg, 0.59 mmol).

Step-6: To a solution of ethyl 1-(((cis)-3,4-difluorocyclopentyl)methyl)-3-(1,1-difluoroethyl)-4-methyl-1H-pyrazole-5-carboxylate (200 mg, 0.59 mmol, 1.0 eq.) in THF: H$_2$O (25 mL, 4:1) was added LiOH H$_2$O (68 mg, 2.9 mmol, 5.0 eq.) at 0° C. The reaction mixture was allowed to warm to ambient temperature and was stirred for 16 h. The reaction mixture was concentrated, diluted with water (100 mL) and washed with diethyl ether (2×25 mL). The aqueous layer was acidified with sat. NaHSO$_4$ solution up to pH-5-6 and extracted with ethyl acetate (2×100 mL). The combined organic layers were dried over anhydrous Na$_2$SO$_4$ and concentrated under reduced pressure to get 1-(((cis)-3,4-difluorocyclopentyl)methyl)-3-(1,1-difluoroethyl)-4-methyl-1H-pyrazole-5-carboxylic acid (Int-B63). Yield: 86% (160 mg, 0.51 mmol). LCMS: m/z [M–H]$^-$=307.1 (calc.=307.1).

Synthesis of 3-cyclopropyl-1-((3-(trifluoromethoxy)cyclobutyl)methyl)-4-(trifluoromethyl)-1H-pyrazole-5-carboxylic acid (Int-B65)

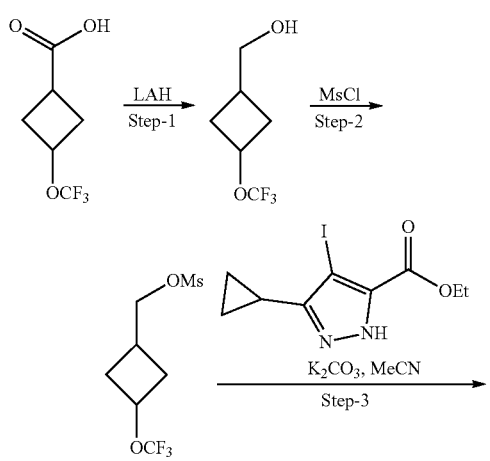

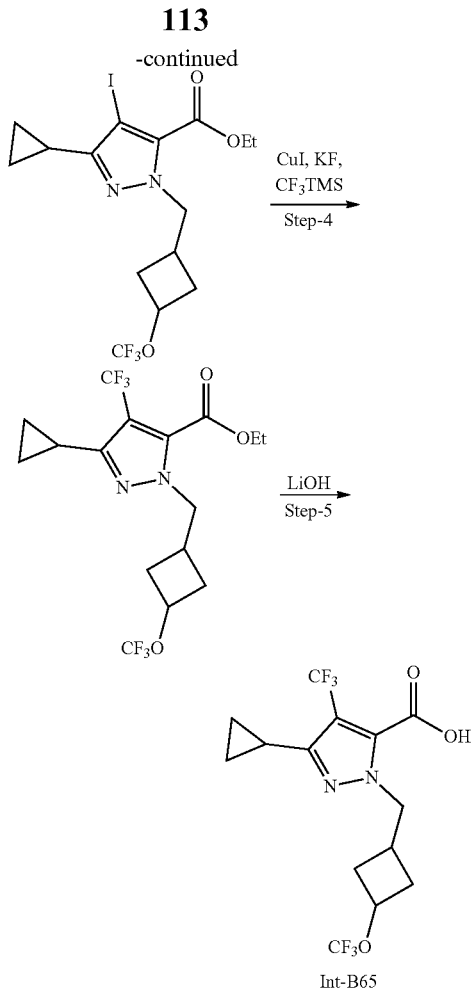

Step-1: To a stirred solution of 3-(trifluoromethoxy)cyclobutanecarboxylic acid (1.2 g, 6.52 mmol, 1.0 eq.) in THF (24 mL) was added LAH in THF (1 M, 13.0 mL, 13.04 mmol, 2.0 eq.) at 0° C. under an argon atmosphere. The reaction mixture was stirred at 0° C. for 2 h. The reaction mixture was quenched with cold water (50 mL) followed by the addition of 1N aq. HCl solution (to pH~6) and extracted with ethyl acetate (2×50 mL). The combined organic layers were washed with water (50 mL), dried over anhydrous Na$_2$SO$_4$ and concentrated under reduced pressure to afford (3-(trifluoromethoxy)cyclobutyl)methanol (1.1 g, crude).

Step-2: To a stirred solution of (3-(trifluoromethoxy)cyclobutyl)methanol (1.1 g, 6.47 mmol, 1.0 eq.) in dichloromethane (22 mL) were added triethylamine (2.3 mL, 16.17 mmol, 2.7 eq.) followed by MsCl (1.1 g, 9.70 mmol, 1.5 eq.) dropwise at 0° C. under an argon atmosphere. The reaction mixture was stirred at 0° C. for 2 h. The reaction mixture was quenched with cold water (60 mL) and extracted with dichloromethane (2×50 mL). The combined organic layers were washed with water (50 mL) and then brine (50 mL), dried over anhydrous Na$_2$SO$_4$ and concentrated under reduced pressure to afford (3-(trifluoromethoxy)cyclobutyl)methyl methanesulfonate (1.6 g, crude).

Step-3: To a stirred solution of ethyl 3-cyclopropyl-4-iodo-1H-pyrazole-5-carboxylate (1.5 g, 4.90 mmol, 1.0 eq.) and (3-(trifluoromethoxy)cyclobutyl)methyl methanesulfonate (1.58 g, 6.37 mmol, 1.3 eq.) in acetonitrile (45 mL) was added K$_2$CO$_3$ (1.35 g, 9.80 mmol, 2.0 eq.) at ambient temperature. The resulting reaction mixture was heated to 80° C. under an argon atmosphere for 16 h. The reaction mixture was quenched with cold water (75 mL) and extracted with ethyl acetate (2×50 mL). The combined organic layers were washed with water (50 mL) and then brine (50 mL), dried over anhydrous Na$_2$SO$_4$ and concentrated under reduced pressure to give the crude product, which was purified by column chromatography (silica gel 100-200 mesh, 10% ethyl acetate in pet ether as an eluent) to afford ethyl 3-cyclopropyl-4-iodo-1-((3-(trifluoromethoxy)cyclobutyl)methyl)-1H-pyrazole-5-carboxylate (1.7 g, 75%).

Step-4: To a stirred solution of ethyl 3-cyclopropyl-4-iodo-1-((3-(trifluoromethoxy)cyclobutyl)methyl)-1H-pyrazole-5-carboxylate (1.7 g, 3.71 mmol, 1.0 eq.) in DMF (34 mL) were added CuI (1.05 g, 5.56 mmol, 1.5 eq.) and KF (258.3 mg, 4.45 mmol, 1.2 eq.) at ambient temperature in a sealed tube. The reaction mixture was then purged with argon for 10 minutes before the addition of TMSCF$_3$ (2.63 g, 18.55 mmol, 5.0 eq.) at ambient temperature. The resulting reaction mixture was heated to 80° C. for 36 h. The reaction mixture was diluted with water (100 mL) and ethyl acetate (100 mL) and was stirred vigorously for 5 minutes. The insoluble materials were filtered off and the remaining filter cake was washed with ethylacetate (20 mL). The combined organic layers were separated and washed with brine (80 mL), dried over anhydrous Na$_2$SO$_4$ and concentrated under reduced pressure to give the crude product, which was purified by column chromatography (silica gel 100-200 mesh, 7% ethyl acetate in pet ether as an eluent) to afford ethyl 3-cyclopropyl-1-((3-(trifluoromethoxy)cyclobutyl)methyl)-4-(trifluoromethyl)-1H-pyrazole-5-carboxylate (1.4 g, 94%).

Step-5: To a stirred solution of ethyl 3-cyclopropyl-1-((3-(trifluoromethoxy)cyclobutyl)methyl)-4-(trifluoromethyl)-1H-pyrazole-5-carboxylate (1.4 g, 3.50 mmol, 1.0 eq.) in THF:MeOH:H$_2$O (1:1:0.5, 28 mL) was added a solution of LiOH·H$_2$O in water (7 mL) (294 mg, 7.00 mmol, 2.0 eq.) at 0° C. The reaction mixture was allowed to warm to ambient temperature and was stirred for 3 h. The volatiles were removed under reduced pressure to obtain a residue, which was diluted with water (70 mL) and extracted with diethyl ether (2×50 mL). The aqueous layer was acidified to pH~4 with 1N aq. HCl solution and extracted with ethyl acetate (2×75 mL). The combined organic layers were washed with water (75 mL) and then brine (75 mL), dried over anhydrous Na$_2$SO$_4$ and concentrated under reduced pressure to give the crude compound, which was triturated with n-pentane (2×15 mL) and dried under high vacuum to afford 3-cyclopropyl-1-((3-(trifluoromethoxy)cyclobutyl)methyl)-4-(trifluoromethyl)-1H-pyrazole-5-carboxylic acid (Int-B65, 950 mg, 73%). LC-MS: m/z [M+H]$^+$=373.2 (calc.=373.1).

The following intermediates were prepared by analogy to the procedures described above using appropriate reactants and adjusted purification protocols:

| Intermediate structure/code | Procedure | Analytics |
|---|---|---|
| 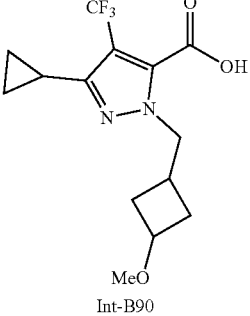<br>Int-B90 | in analogy to the synthesis of Int-B65 (step 3 to step 5) using (3-methoxycyclobutyl)methyl methanesulfonate as the alkylating agent | LCMS: m/z [M + H]$^+$ = 319.2 (calc. = 319.1). |

Synthesis of 1-((3,3-difluorocyclobutyl)methyl)-3-(1,1-difluoroethyl)-4-(trifluoromethyl)-1H-pyrazole-5-carboxylic acid (Int-B91)

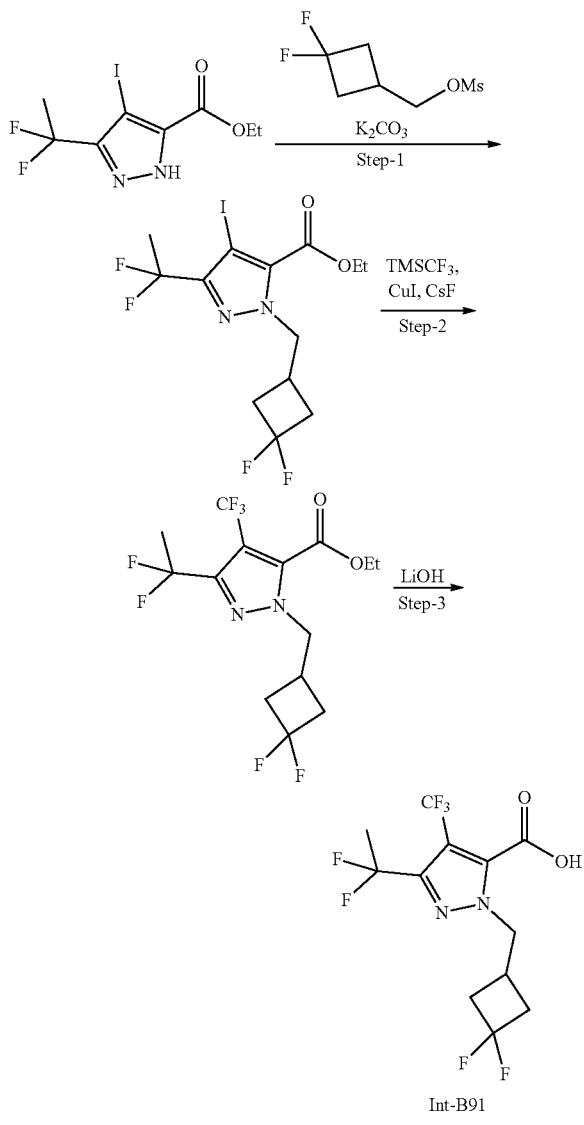

Step-1: To a stirred solution of ethyl 3-(1,1-difluoroethyl)-4-iodo-1H-pyrazole-5-carboxylate (1.0 g, 3.03 mmol, 1.0 eq.) in acetonitrile (30 mL) were added $K_2CO_3$ (0.838 g, 6.07 mmol, 2.0 eq.) and (3,3-difluorocyclobutyl)methyl methanesulfonate (0.729 g, 364 mmol, 1.2 eq.) at ambient temperature. The reaction mixture was heated to 80° C. for 16 h. The reaction mixture was then cooled to ambient temperature, diluted with cold water and extracted with EtOAc (3×50 mL). The combined organic layers were washed with brine and dried over anhydrous $Na_2SO_4$. The organic layer was concentrated under reduced pressure to get the crude product which was purified by combiflash column chromatography (Silica gel, 0-20% ethyl acetate in hexane as eluent) to yield ethyl 1-[(3,3-difluorocyclobutyl)methyl]-3-(1,1-difluoroethyl)-4-iodo-1H-pyrazole-5-carboxy late. Yield: 60% (0.8 g, 1.84 mmol).

Step-2: To a solution of ethyl 1-[(3,3-difluorocyclobutyl)methyl]-3-(1,1-difluoroethyl)-4-iodo-1H-pyrazole-5-carboxy late (0.5 g, 1.15 mmol, 1.0 eq.) in DMF (8 mL), KF (0.2 g, 3.45 mmol, 3.0 eq.) and CuI (0.43 g, 2.30 mmol, 2.0 eq.) were added at ambient temperature. TMSCF$_3$ (1.2 mL, 8.06 mmol, 7.0 eq.) was added dropwise at 0° C. The reaction mixture was heated to 110° C. in a sealed tube for 16 h. The reaction mixture was cooled to ambient temperature and diluted with cold-water (30 mL). The reaction mixture was filtered through a celite pad and the celite pad was washed with EtOAc (300 mL). The filtrate was washed with water (1×50 mL), brine (30 mL) and dried over anhydrous $Na_2SO_4$. The organic layer was concentrated under reduced pressure to get the crude product which was purified by combiflash column chromatography (silica gel, 0-20% EtOAc in hexane as eluent) to yield ethyl 1-[(3,3-difluorocyclobutyl)methyl]-3-(1,1-difluoroethyl)-4-(trifluoromethyl)-1H-pyrazole-5-carboxylate. Yield: 46% (0.20 g, 0.531 mmol).

Step-3: To a stirred solution of ethyl 1-[(3,3-difluorocyclobutyl)methyl]-3-(1,1-difluoroethyl)-4-(trifluoromethyl)-1H-pyrazole-5-carboxylate (0.35 g, 0.93 mmol, 1.0 eq.) in a mixture of THF (8 mL) and $H_2O$ (2 mL) was added LiOH·$H_2O$ (0.058 g, 1.39 mmol, 1.5 eq.) at 0° C. and the mixture was stirred at ambient temperature for 16 h. The reaction mixture was concentrated under reduced pressure and diluted with water. The aqueous part was acidified with saturated KHSO$_4$ solution to pH=2 at 0° C. The aqueous part was extracted with ethyl acetate (3×30 mL). The combined organic layers were washed with brine and dried over anhydrous $Na_2SO_4$. The organic layer was concentrated under reduced pressure to yield 1-[(3,3-difluorocyclobutyl)methyl]-3-(1,1-difluoroethyl)-4-(trifluoromethyl)-1H-pyrazole-5-carboxylic acid (Int-B91). Yield: 92% (0.30 g, 0.861 mmol). LC-MS: m/z [M+H]$^+$=349.3 (calc.=349.1).

Synthesis of 1-((1-methylcyclohexyl)methyl)-4-(trifluoromethyl)-1H-pyrazole-5-carboxylic acid (Int-B92)

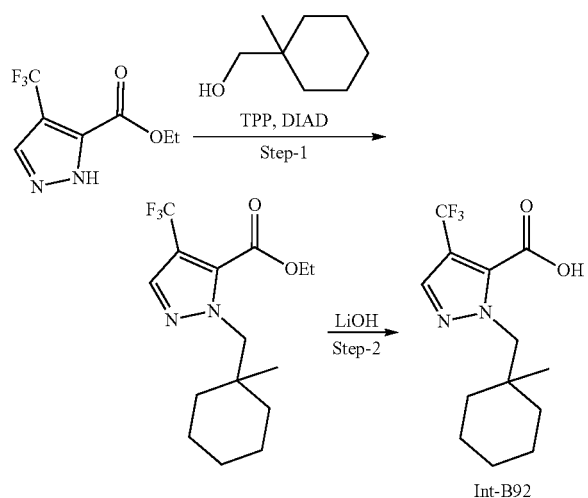

Int-B92

Step-1: DIAD (0.97 mL, 4.8 mmol, 2.0 eq.) was added to a stirred solution of ethyl 4-(trifluoromethyl)-1H-pyrazole-5-carboxylate (0.5 g, 2.40 mmol, 1.0 eq.), (1-methylcyclohexyl)methanol (0.37 g, 2.88 mmol, 1.2 eq.) and PPh$_3$ (1.2 g, 4.8 mmol, 2.0 eq.) in THF (20 mL) at 0° C. The reaction mixture was then heated to 70° C. for 16 h. The reaction mixture was concentrated under reduced pressure and the resulting residue was purified by column chromatography (silica gel, 0-15% ethyl acetate in hexane as eluent) to yield ethyl 1-[(1-methylcyclohexyl)methyl]-4-(trifluoromethyl)-1H-pyrazole-5-carboxy late. Yield: 50% (0.38 g, 13.23 mmol).

Step-2: To a solution of methyl ethyl 1-[(1-methylcyclohexyl)methyl]-4-(trifluoromethyl)-1H-pyrazole-5-carboxylate (0.38 g, 1.19 mmol, 1 eq.) in THF (8 mL), MeOH (4 mL) and water (2 mL) was added LiOH·H$_2$O (0.15 g, 3.57 mmol, 3 eq.) at 0° C. and the mixture was stirred at ambient temperature for 4 h. The reaction mixture was then concentrated under reduced pressure, diluted with water (25 mL) and washed with ethyl acetate (25 mL). The aqueous layer was acidified with saturated NaHSO$_4$ solution to pH-2 and extracted with ethyl acetate (50 mL×3). The combined organic layers were dried over sodium sulfate and concentrated under reduced pressure to get 1-[(1-methylcyclohexyl)methyl]-4-(trifluoromethyl)-1H-pyrazole-5-carboxylic acid (Int-B92). Yield: 90% (0.31 g, 1.07 mmol). LCMS: m/z [M+H]$^+$=291.2 (calc.=291.1).

The following intermediates were prepared by analogy to the procedures described above using appropriate reactants and adjusted purification protocols:

| Intermediate structure/code | Procedure | Analytics |
| --- | --- | --- |
| Int-B93 | in analogy to the synthesis of Int-B92 using (1-fluorocyclohexyl)methanol instead of (1-methylcyclohexyl)methanol | $^1$H NMR (400 MHz, DMSO-d6): δ (ppm) = 14.40-14.31 (bs, 1H), 8.02 (s, 1H), 4.80-4.74 (d, 2H), 1.51-1.10 (m, 10H). |
| Int-B94 | in analogy to the synthesis of Int-B92 using (1-(methoxymethoxy)cyclohexyl)methanol instead of (1-methylcyclohexyl)methanol | LCMS: m/z [M + H]$^+$ = 337.2 (calc. = 337.1). |

-continued

| Intermediate structure/code | Procedure | Analytics |
|---|---|---|
| 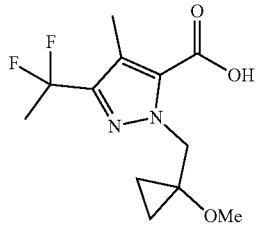<br>Int-B95 | in analogy to the synthesis of Int-B92 using (1-methoxycyclopropyl)methanol instead of (1-methylcyclohexyl)methanol and ethyl 3-(1,1-difluoroethyl)-4-methyl-1H-pyrazole-5-carboxylate instead of ethyl 4-(trifluoromethyl)-1H-pyrazole-5-carboxylate | LCMS: m/z [M + H]$^+$ = 275.1 (calc. = 275.1). |
| 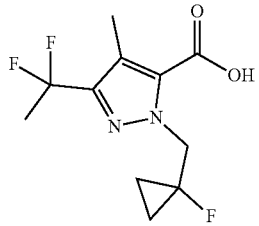<br>Int-B96 | in analogy to the synthesis of Int-B92 using (1-fluorocyclopropyl)methanol instead of (1-methylcyclohexyl)methanol and ethyl 3-(1,1-difluoroethyl)-4-methyl-1H-pyrazole-5-carboxylate instead of ethyl 4-(trifluoromethyl)-1H-pyrazole-5-carboxylate | LCMS: m/z [M + H]$^+$ = 263.1 (MW calc. = 263.1). |
| 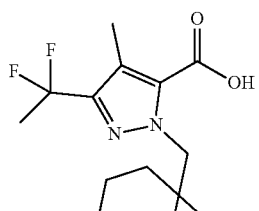<br>Int-B97 | in analogy to the synthesis of Int-B92 using (2-methyltetrahydro-2H-pyran-2-yl)methanol instead of (1-methylcyclohexyl)methanol and ethyl 3-(1,1-difluoroethyl)-4-methyl-1H-pyrazole-5-carboxylate instead of ethyl 4-(trifluoromethyl)-1H-pyrazole-5-carboxylate | LCMS: m/z [M + H]$^+$ = 303.2 (MW calc. = 303.2) |
| 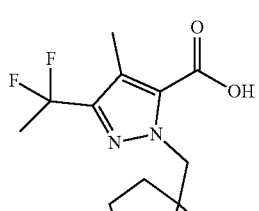<br>Int-B98 | in analogy to the synthesis of Int-B92 using (2-methyltetrahydrofuran-2-yl)methanol instead of (1-methylcyclohexyl)methanol and ethyl 3-(1,1-difluoroethyl)-4-methyl-1H-pyrazole-5-carboxylate instead of ethyl 4-(trifluoromethyl)-1H-pyrazole-5-carboxylate | LCMS: m/z [M + H]$^+$ = 289.2 (calc. = 289.1) |
| 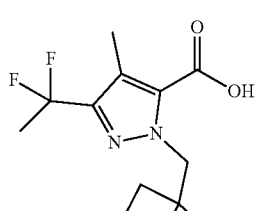<br>Int-B99 | in analogy to the synthesis of Int-B92 using (2-methyloxetan-2-yl)methanol instead of (1-methylcyclohexyl)methanol and ethyl 3-(1,1-difluoroethyl)-4-methyl-1H-pyrazole-5-carboxylate instead of ethyl 4-(trifluoromethyl)-1H-pyrazole-5-carboxylate | LCMS: m/z [M + H]$^+$ = 275.1 (calc. = 275.1) |

-continued

| Intermediate structure/code | Procedure | Analytics |
|---|---|---|
| 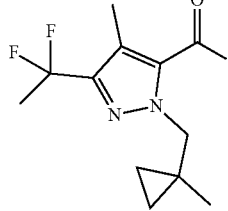<br>Int-B100 | in analogy to the synthesis of Int-B92 using (1-methylcyclopropyl)methanol instead of (1-methylcyclohexyl)methanol and ethyl 3-(1,1-difluoroethyl)-4-methyl-1H-pyrazole-5-carboxylate instead of ethyl 4-(trifluoromethyl)-1H-pyrazole-5-carboxylate | LCMS: m/z [M + H]$^+$ = 259.2 (calc. = 259.1). |
| 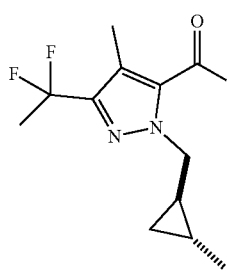<br>Int-B101 | in analogy to the synthesis of Int-B92 using ((trans)-2-methylcyclopropyl)methanol instead of (1-methylcyclohexyl)methanol and ethyl 3-(1,1-difluoroethyl)-4-methyl-1H-pyrazole-5-carboxylate instead of ethyl 4-(trifluoromethyl)-1H-pyrazole-5-carboxylate | LCMS: m/z [M + H]$^+$ = 259.1 (calc. = 259.1). |

Synthesis of ethyl 3-(1,1-difluoroethyl)-1-((1-(difluoromethyl)-3,3-dimethoxycyclobutyl)methyl)-4-methyl-1H-pyrazole-5-carboxylate (Int-B102)

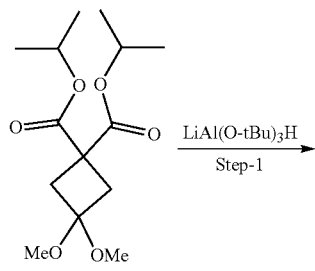

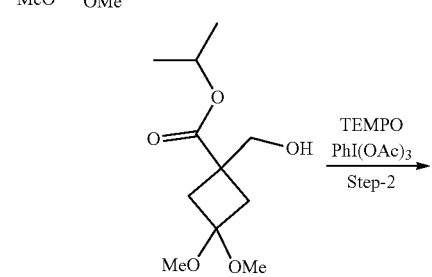

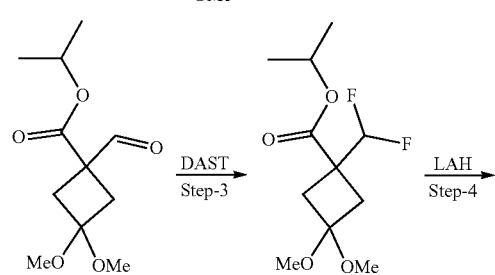

-continued

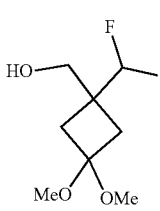

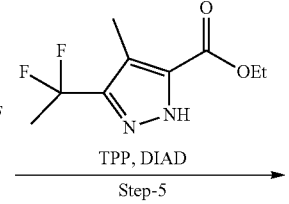

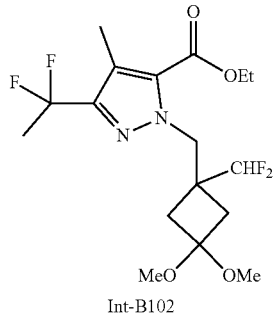

Int-B102

Step-1: LiAl(O-tBu)$_3$H (1M in THF, 69.4 mL, 69.4 mmol, 2.0 eq.) was added to a stirred solution of diisopropyl 3,3-dimethoxycyclobutane-1,1-dicarboxylate (10 g, 34.7 mmol, 1.0 eq.) in THF (50 mL) at −78° C. under an argon atmosphere. The resulting reaction mixture was stirred at ambient temperature for 16 h and was then heated to 50° C. for 2 h. The reaction mixture was quenched with sat. NH$_4$Cl solution (20 mL), diluted with EtOAc (100 mL) and filtered through a celite bed. The filtrate was dried over anhydrous Na$_2$SO$_4$ and concentrated under reduced pressure to obtain the crude product, which was purified by column chromatography (silica gel 100-200 mesh, 30% EtOAc in pet-ether as an eluent) to afford isopropyl 1-(hydroxymethyl)-3,3-dimethoxycyclobutane-1-carboxylate (6.0 g, 75%).

Step-2: To a stirred solution of isopropyl 1-(hydroxymethyl)-3,3-dimethoxycyclobutane-1-carboxylate (8 g, 34.4 mmol, 1.0 eq.) in dichloromethane (150 mL) were added PhI(OAc)$_2$ (13.3 g, 41.3 mmol, 1.2 eq.) and TEMPO (537 mg, 3.44 mmol) at ambient temperature and the mixture was stirred for 16 h. The reaction mixture was diluted with dichloromethane (150 mL), washed with water (300 mL) and then brine (300 mL), dried over anhydrous Na$_2$SO$_4$ and concentrated under reduced pressure to the give crude product which was purified by column chromatography (silica gel 100-200 mesh, 20% EtOAc in pet-ether as an eluent) to afford isopropyl 1-formyl-3,3-dimethoxycyclobutane-1-carboxylate (7.0 g, 88%).

Step-3: To a stirred solution of isopropyl 1-formyl-3,3-dimethoxycyclobutane-1-carboxylate (7.0 g, 30.40 mmol, 1.0 eq.) in dichloromethane (100 mL) was added DAST (10.79 g, 66.95 mmol, 2.2 eq.) at 0° C. under an argon atmosphere. The resulting reaction mixture was stirred at ambient temperature for 16 h. The reaction mixture was diluted with dichloromethane (100 mL) and washed subsequently with water (150 mL), NaHCO$_3$ solution (150 mL) and brine (150 mL). The organic layers were then dried over anhydrous Na$_2$SO$_4$ and concentrated under reduced pressure to afford isopropyl 1-(difluoromethyl)-3,3-dimethoxycyclobutane-1-carboxylate (6 g, crude).

Step-4: LAH in THF (1M, 9.52 mL, 9.52 mmol, 1.2 eq.) was added to a stirred solution of isopropyl 1-(difluoromethyl)-3,3-dimethoxycyclobutane-1-carboxylate (2.0 g, 7.93 mmol, 1.0 eq.) in THF (20 mL) at 0° C. under an argon atmosphere and the resulting mixture was stirred for 1 h. The reaction mixture was slowly quenched with saturated sodium sulfate solution (5 mL), diluted with diethyl ether (25 mL) and filtered through a celite bed.

The filtrate was dried over anhydrous Na$_2$SO$_4$ and concentrated under reduced pressure to afford (1-(difluoromethyl)-3,3-dimethoxycyclobutyl)methanol (1.2 g, crude).

Step-5: To a stirred solution of triphenylphosphene (4.50 g, 17.20 mmol, 2.5 eq.) in THF (50 mL) was added DIAD (3.47 g, 17.20 mmol, 2.5 eq.) at 0° C. and the mixture was stirred for 30 min at 0° C. To the mixture were then added ethyl 3-(1,1-difluoroethyl)-4-methyl-1H-pyrazole-5-carboxylate (1.5 g, 6.88 mmol, 1.0 eq.) and (1-(difluoromethyl)-3,3-dimethoxycyclobutyl)methanol (1.48 g, 7.56 mmol, 1.1 eq.) and the resulting reaction mixture was stirred at ambient temperature for 4 h. The reaction mixture was quenched with water (50 mL) and extracted with ethyl acetate (3×50 mL). The combined organic layers were washed with water (100 mL) and then brine (100 mL), dried over anhydrous Na$_2$SO$_4$ and concentrated under reduced pressure to get the crude product which was purified by column chromatography over silica gel (100-200 mesh) using 5% Ethyl acetate in Pet ether as an eluent to afford ethyl 3-(1,1-difluoroethyl)-1-((1-(difluoromethyl)-3,3-dimethoxy cyclobutyl)methyl)-4-methyl-1H-pyrazole-5-carboxylate (Int-B102, 1.4 g, 52%). NMR (400 MHz, DMSO-d6): δ (ppm)=5.94 (t, 1H), 4.81 (s, 2H), 4.42-4.35 (m, 2H), 3.08 (s, 6H), 2.38 (s, 3H), 2.32-2.25 (m, 2H), 2.21-2.17 (m, 2H), 2.02 (t, 3H), 1.39 (t, 3H).

Synthesis of 1-((3,3-difluorocyclopentyl)methyl)-3-methyl-4-(trifluoromethoxy)-1H-pyrazole-5-carboxylic acid (Int-B103)

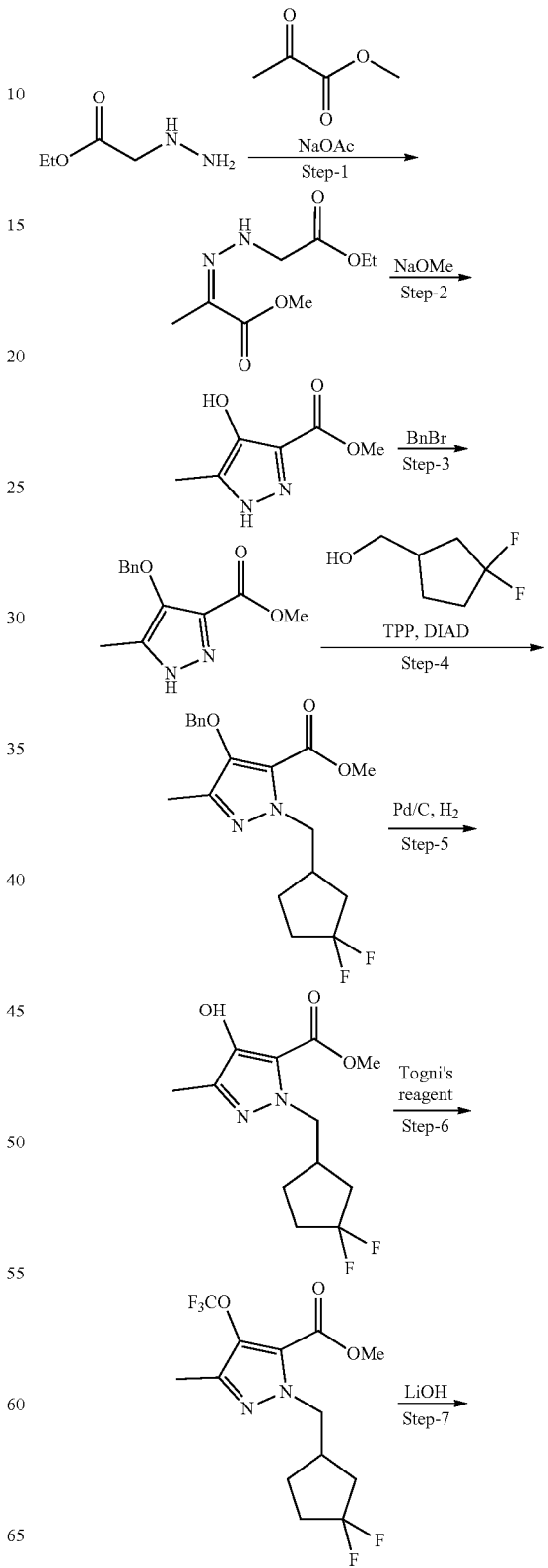

-continued

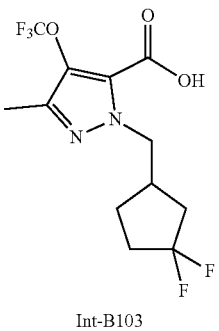 [SMILES: Cc1nn(CC2CCC(F)(F)C2)c(C(=O)O)c1OC(F)(F)F]

Int-B103

Step-1: To a solution of methyl 2-oxopropanoate (6.0 g, 58.77 mmol, 1.0 eq.) in a mixture of MeOH—H$_2$O (3:1) (80 mL) were added NaOAc (4.8 g, 58.77 mmol, 1.0 eq.) and ethyl aminoglycinate hydrochloride (9.0 g, 58.77 mmol, 1.0 eq.) at ambient temperature. The reaction mixture was stirred at ambient temperature for 24 h and was then concentrated under reduced pressure to get a residue which was diluted with water and extracted with DCM (3×100 mL). The combined organic layers were dried over anhyd. Na$_2$SO$_4$ and concentrated to yield a mixture of methyl (Z)-2-(2-(2-ethoxy-2-oxoethyl)hydrazono)propanoate and methyl (E)-3-(2-(2-ethoxy-2-oxoethyl)hydrazono)-2-oxobutanoate which was used for the next step without purification. Yield: Quantitative (12.0 g, crude).

Step-2: Sodium (1.47 g, 64.28 mmol, 2.6 eq.) was added portionwise to MeOH (100 mL). After complete addition a mixture of methyl (Z)-2-(2-(2-ethoxy-2-oxoethyl)hydrazono)propanoate and methyl (E)-3-(2-(2-ethoxy-2-oxoethyl)hydrazono)-2-oxobutanoate (5.0 g, 24.72 mmol, 1.0 eq.) was added. The resulting reaction mixture was heated to 70° C. for 3 h. The reaction mixture was then cooled to ambient temperature and concentrated under reduced pressure to obtain a residue which was diluted with water and neutralized with 2N HCl. The mixture was extracted with EtOAc (3×100 mL), the combined organic layers were dried over anhyd. Na$_2$SO$_4$ and concentrated to yield methyl 4-hydroxy-5-methyl-1H-pyrazole-3-carboxylate. Yield: 58% (2.0 g, 12.8 mmol).

Step-3: To a stirred solution of methyl 4-hydroxy-5-methyl-1H-pyrazole-3-carboxylate (2.0 g, 12.8 mmol, 1.0 eq.) in DMF (30 mL) were added Cs$_2$CO$_3$ (4.17 g, 12.8 mmol, 1.0 eq.) and benzyl bromide (1.3 mL, 10.88 mmol, 0.85 eq.) at 0° C. The reaction mixture was then stirred at ambient temperature for 16 h. The reaction mixture was diluted with ice water and extracted with EtOAc (3×100 mL). The combined organic layers were washed with cold brine, dried over anhyd. Na$_2$SO$_4$ and concentrated under reduced pressure to get the crude material which was purified by combiflash column chromatography (silica gel, 0-20% EtOAc in hexane as eluent) to yield methyl 4-(benzyloxy)-3-methyl-1H-pyrazole-5-carboxylate. Yield: 60% (1.9 g, 7.7 mmol).

Step-4: To a solution of methyl 4-(benzyloxy)-3-methyl-1H-pyrazole-5-carboxylate (1.0 g, 4.06 mmol, 1.0 eq.) in dry THF (40 mL) were added triphenyl phosphine (3.2 g, 12.19 mmol, 3.0 eq.) and (3,3-difluorocyclopentyl)methanol (1.64 g, 12.19 mmol, 1.15 eq.) at ambient temperature, followed by the dropwise addition of DIAD (2.4 mL, 12.19 mmol, 3 eq.) after cooling to 0° C. The reaction mixture was then stirred at ambient temperature for 16 h. The reaction mixture was concentrated under reduced pressure to get the crude material which was purified by column chromatography (silica; 0-30% ethyl acetate in hexane as eluent) to yield methyl 4-(benzyloxy)-1-((3,3-difluorocyclopentyl)methyl)-3-methyl-1H-pyrazole-5-carboxylate. Yield: 81% (1.2 g, 3.3 mmol).

Step-5: A solution of methyl 4-(benzyloxy)-1-((3,3-difluorocyclopentyl)methyl)-3-methyl-1H-pyrazole-5-carboxylate (0.66 g, 3.3 mmol, 1.0 eq.) in MeOH (40 mL) was degassed with N$_2$ for 15 minutes followed by the addition of Pd/C (10% wet, 0.33 g) at ambient temperature. The reaction mixture was then stirred at ambient temperature under 1.4 bar pressure of hydrogen (using a H$_2$-balloon) for 2 h. The reaction mixture was filtered through celite and the filtrate was concentrated under reduced pressure to get the crude material which was purified by combiflash column chromatography (silica gel, 0-50% EtOAc in hexane as eluent) to yield methyl 1-((3,3-difluorocyclopentyl)methyl)-4-hydroxy-3-methyl-1H-pyrazole-5-carboxylate. Yield: 84% (0.90 g, 3.28 mmol).

Step-6: To a solution of methyl 1,3-difluorocyclopentyl)methyl)-4-hydroxy-3-methyl-1H-pyrazole-5-carboxy late (0.60 g, 2.20 mmol, 1.0 eq.) in dry DMF (10 mL) was added 1-trifluoromethyl-1,2-benziodoxol-3(1H)-one (0.76 g, 2.42 mmol, 1.1 eq.) at ambient temperature and the reaction mixture was heated to 90° C. for 10 h. The reaction mixture was cooled to ambient temperature, followed by the addition of ice water and extraction with EtOAc (3×100 mL). The combined organic layers were washed with cold brine, dried over anhyd. Na$_2$SO$_4$ and concentrated under reduced pressure to get the crude material which was purified by combiflash column chromatography (silica gel, 0-20% EtOAc in hexane as eluent) to yield methyl 1-((3,3-difluorocyclopentyl)methyl)-3-methyl-4-(trifluoromethoxy)-1H-pyrazole-5-carboxylate. Yield: 12% (0.090 g, 0.26 mmol).

Step-7: To a solution of methyl 1-((3,3-difluorocyclopentyl)methyl)-3-methyl-4-(trifluoromethoxy)-1H-pyrazole-5-carboxylate (0.09 g, 0.28 mmol, 1.0 eq.) in a mixture of THF-MeOH—H$_2$O (3:1:1) (5 mL) was added LiOH H$_2$O (0.02 g, 0.56 mmol, 2.0 eq.) at 0° C. and the reaction mixture was then stirred at ambient temperature for 3 h. The reaction mixture was concentrated under reduced pressure, acidified with saturated NaHSO$_4$ solution to maintain pH-2 and the residue was extracted with 10% THF-EtOAc (3×50 mL). The combined organic layers were dried over anhyd. Na$_2$SO$_4$ and concentrated to yield 1-((3,3-difluorocyclopentyl)methyl)-3-methyl-4-(trifluoromethoxy)-1H-pyrazole-5-carboxylic acid (Int-B103). Yield: 77% (0.07 g, 0.21 mmol). LC-MS: m/z [M−H]$^−$=327.1 (calc. 327.1).

Synthesis of 3-cyclopropyl-4-(difluoromethoxy)-1-((tetrahydro-2H-pyran-4-yl)methyl)-1H-pyrazole-5-carboxylic acid (Int-B104)

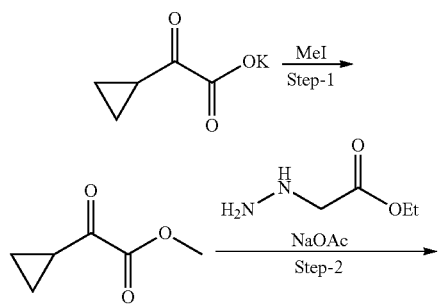

-continued

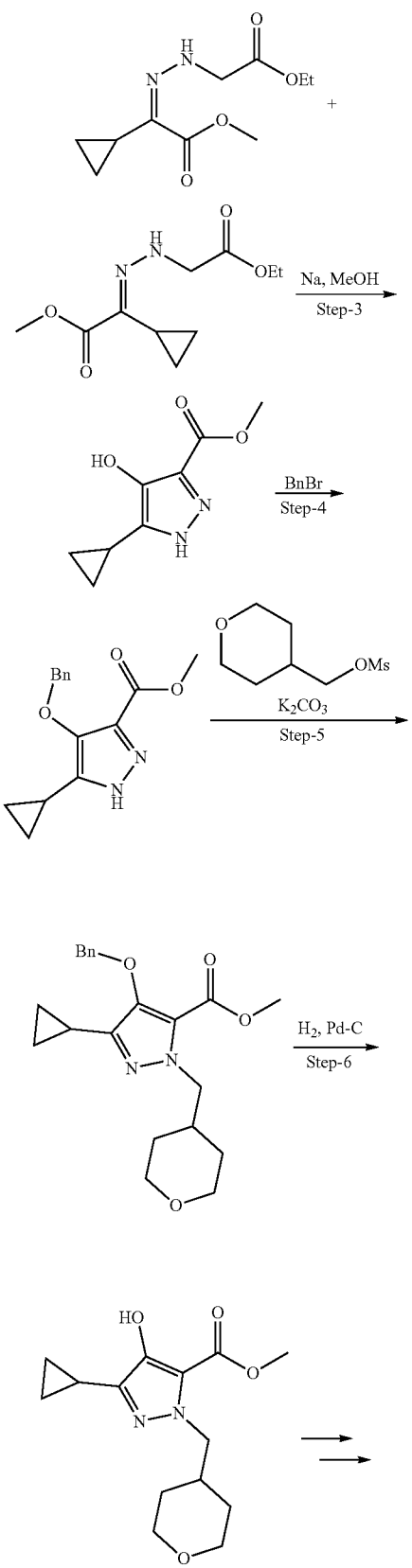

Int-B104

Step-1: To a solution of potassium 2-cyclopropyl-2-oxoacetate (2.0 g, 13.14 mmol, 1.0 eq.) in acetone (13 mL) was added methyl iodide (1.1 mL, 17 mmol, 1.3 eq.) at ambient temperature and the reaction mixture was heated in a sealed tube to 80° C. for 18 h. The reaction mixture was then cooled to ambient temperature, filtered through celite and the filtrate was concentrated at low temperature (~35° C.) under reduced pressure to yield methyl 2-cyclopropyl-2-oxoacetate which was used for the next step without purification. Yield: 80% (1.4 g, 10.67 mmol).

Step-2: To a solution of methyl 2-cyclopropyl-2-oxoacetate (3.9 g, 30.45 mmol, 1.0 eq.) in a mixture of MeOH:$H_2O$ (3:1) (52 mL) were added NaOAc (2.5 g, 30.45 mmol, 1.0 eq.) and ethyl aminoglycinate hydrochloride (4.7 g, 7.81 mmol, 1.0 eq.) at ambient temperature and the mixture was stirred for 24 h. The reaction mixture was concentrated under reduced pressure to get a residue which was diluted with water and extracted with DCM (3×100 mL). The combined organic layers were dried over anhydrous $Na_2SO_4$ and concentrated under reduced pressure to yield a mixture of methyl (Z)-2-cyclopropyl-2-(2-(2-ethoxy-2-oxoethyl)hydrazono)acetate and methyl (E)-2-cyclopropyl-2-(2-(2-ethoxy-2-oxoethyl)hydrazono)acetate. Yield: Quantitative (5.2 g, crude).

Step-3: Sodium (0.84 g, 36.5 mmol, 2.6 eq.) was added portionwise to MeOH (50 mL). After complete dissolution of the sodium metal, a mixture of methyl (Z)-2-cyclopropyl-2-(2-(2-ethoxy-2-oxoethyl)hydrazono)acetate and methyl (E)-2-cyclopropyl-2-(2-(2-ethoxy-2-oxoethyl)hydrazono) acetate (3.2 g, 14.03 mmol, 1.0 eq.) was added. The resulting reaction mixture was heated to 70° C. for 3 h. The reaction mixture was cooled to ambient temperature, concentrated under reduced pressure to get a residue which was diluted with water and neutralized with 2N HCl. The mixture was extracted with EtOAc (3×100 mL). The combined organic layers were dried over anhydrous $Na_2SO_4$ and concentrated under reduced pressure to yield methyl 5-cyclopropyl-4-hydroxy-1H-pyrazole-3-carboxylate. Yield: 58% (1.5 g, 8.24 mmol).

Step-4: To a stirred solution of methyl 5-cyclopropyl-4-hydroxy-1H-pyrazole-3-carboxylate (2.8 g, 15.38 mmol, 1.0 eq.) in DMF (50 mL) were added $Cs_2CO_3$ (5.0 g, 15.38 mmol, 1.0 eq.) and benzyl bromide (1.5 mL, 13.0 mmol, 0.85 eq.) at 0° C. The reaction mixture was then stirred at ambient temperature for 16 h. The reaction mixture was diluted with ice water and extracted with EtOAc (3×100 mL). The combined organic layers were washed with cold brine, dried over anhydrous $Na_2SO_4$ and concentrated under reduced pressure to get the crude product which was purified by combiflash column chromatography (silica gel, 0-20%

EtOAc in hexane as eluent) to yield methyl 4-(benzyloxy)-5-cyclopropyl-1H-pyrazole-3-carboxylate. Yield: 62% (2.6 g, 9.55 mmol).

Step-5: To a solution of methyl 4-(benzyloxy)-5-cyclopropyl-1H-pyrazole-3-carboxylate (0.85 g, 3.12 mmol, 1.0 eq.) in dry DMF (10 mL) were added $K_2CO_3$ (1.0 g, 7.8 mmol, 2.5 eq.) and (tetrahydro-2H-pyran-4-yl)methyl methanesulfonate (0.70 g, 3.59 mmol, 1.15 eq.) at ambient temperature. The reaction mixture was heated to 80° C. for 16 h. The reaction mixture was cooled to ambient temperature, diluted with ice water and extracted with EtOAc (3×100 mL). The combined organic layers were washed with cold brine, dried over anhydrous $Na_2SO_4$ and concentrated under reduced pressure to get the crude material which was purified by combiflash column chromatography (silica gel, 0-30% EtOAc in hexane as eluent) to yield methyl 4-(benzyloxy)-3-cyclopropyl-1-((tetrahydro-2H-pyran-4-yl)methyl)-1H-pyrazole-5-carboxylate. Yield: 35% (0.40 g, 1.08 mmol).

Step-6: A solution of methyl 4-(benzyloxy)-3-cyclopropyl-1-((tetrahydro-2H-pyran-4-yl)methyl)-1H-pyrazole-5-carboxylate (0.40 g, 1.08 mmol, 1.0 eq.) in MeOH (15 mL) was degassed with $N_2$ for 15 min followed by the addition of 10% Pd/C (50% wet, 0.20 g) at ambient temperature. The reaction mixture was then stirred at ambient temperature under 1.4 bar pressure of hydrogen (using a $H_2$-balloon) for 2 h. The reaction mixture was filtered through celite and the filtrate was concentrated under reduced pressure to yield methyl 3-cyclopropyl-4-hydroxy-1-((tetrahydro-2H-pyran-4-yl)methyl)-1H-pyrazole-5-carboxylate. Yield: 92% (0.28 g, 1.0 mmol).

Methyl 3-cyclopropyl-1-((3,3-difluorocyclopentyl)methyl)-4-hydroxy-1H-pyrazole-5-carboxy late was converted to 3-cyclopropyl-4-(difluoromethoxy)-1-((tetrahydro-2H-pyran-4-yl)methyl)-1H-pyrazole-5-carboxylic acid (Int-B104) in analogy to the synthesis described for Int-B45a, steps 1 and 2. LCMS: m/z [M+H]$^+$=317.4 (calc.=317.1).

The following intermediates were prepared by analogy to the procedures described above using appropriate reactants and adjusted purification protocols:

Synthesis of 4-chloro-1-((4,4-difluorocyclohexyl)methyl)-3-methyl-1H-pyrazole-5-carboxylic acid
(Int-B106)

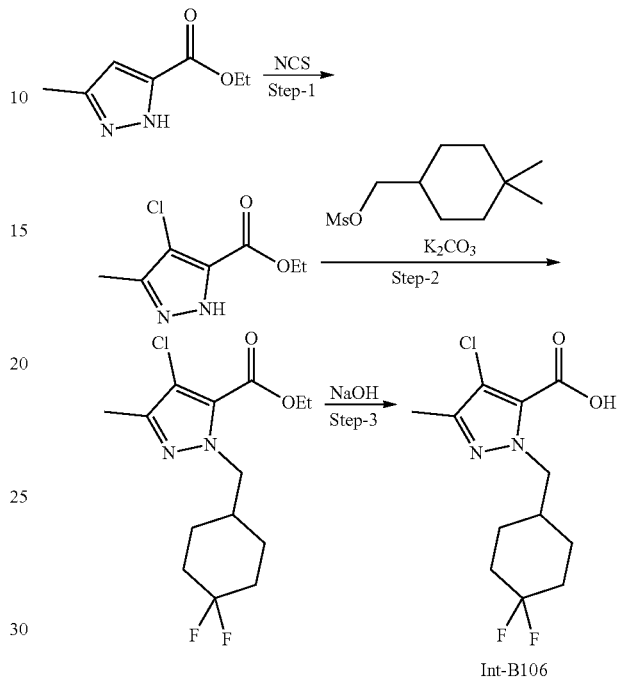

Int-B106

Step-1: NCS (1.13 g, 8.571 mmol, 1.1 eq.) was added to a stirred solution of ethyl 3-methyl-1H-pyrazole-5-carboxylate (1.0 g, 7.142 mmol, 1.0 eq.) in DMF (15 mL) at ambient temperature and the reaction mixture was stirred for 16 h. The reaction mixture was quenched with ice cold water (100 mL) and the mixture was stirred for 15 minutes. The precipitated solid was collected by filtration and dried under reduced pressure to afford ethyl 4-chloro-3-methyl-1H-pyrazole-5-carboxylate. Yield: 83% (2.0 g).

Step-2: To a stirred solution of crude ethyl 4-chloro-3-methyl-1H-pyrazole-5-carboxylate (1.0 g, 5.319 mmol, 1.0 eq.) and $K_2CO_3$ (1.46 g, 10.638 mmol, 2.0 eq.) in acetoni-

| Intermediate structure/code | Procedure | Analytics |
|---|---|---|
| ![Int-B105 structure] Int-B105 | in analogy to the synthesis of Int-B104 using 3,3-difluorocyclopentyl)methyl methanesulfonate instead of (tetrahydro-2H-pyran-4-yl)methyl methanesulfonate and 2,2,2-trifluoroethyl methanesulfonate instead of sodium 2-chloro-2,2-difluoroacetate | LCMS: m/z [M + H]$^+$ = 369.1 (calc. = 369.1) | trile (20 mL) was added (4,4-difluorocyclohexyl)methyl methanesulfonate (1.8 g, 7.978 mmol, 1.5 eq.) at ambient temperature. The reaction mixture was heated to 80° C. for 16 h. The reaction mixture was filtered and the filtrate was concentrated under reduced pressure to afford the crude product which was purified by column chromatography using silica gel (100-200 mesh) and 5% ethyl acetate in pet-ether as an eluent to furnish ethyl 4-chloro-1-((4,4-difluorocyclohexyl)methyl)-3-methyl-1H-pyrazole-5-carboxylate. Yield: 35% (600 mg).

Step-3: 2N NaOH (4 mL) was added to a stirred solution of ethyl 4-chloro-1-((4,4-difluorocyclohexyl)methyl)-3-methyl-1H-pyrazole-5-carboxylate (300 mg, 0.937 mmol 1.0 eq.) in EtOH (5 mL) and the resulting mixture was stirred at ambient temperature for 16 h. The reaction mixture was concentrated under reduced pressure to get the crude residue which was diluted with water (5 mL), acidified to pH~4 with 1N aq. HCl solution and extracted with 5% methanol in DCM (3×30 mL). The combined organic layers were dried over anhydrous $Na_2SO_4$ and concentrated under reduced pressure to get 4-chloro-1-((4,4-difluorocyclohexyl)methyl)-3-methyl-1H-pyrazole-5-carboxylic acid (Int-B106). Yield: 92% (250 mg). LCMS: m/z $[M+H]^+$=293.0 (calc. 293.1).

The following intermediates were prepared by analogy to the procedures described above using appropriate reactants and adjusted purification protocols:

Synthesis of 3-cyclopropyl-1-((tetrahydro-2H-pyran-4-yl)methyl)-4-(2,2,2-trifluoroethyl)-1H-pyrazole-5-carboxylic acid (Int-B109)

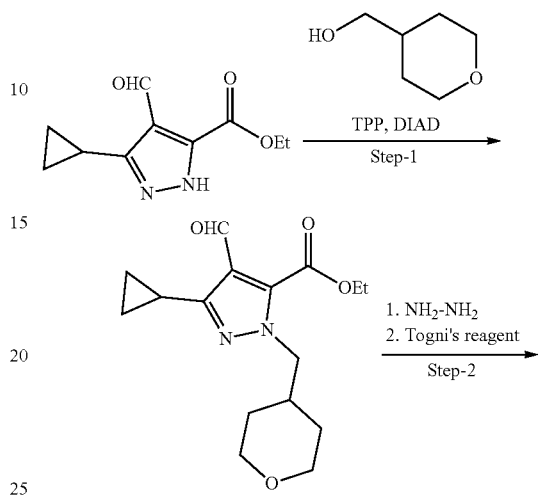

| Intermediate structure/code | Procedure | Analytics |
|---|---|---|
| 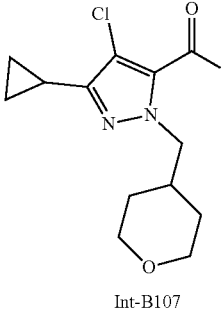<br>Int-B107 | in analogy to the synthesis of Int-B106 using ethyl 3-cyclopropyl-1H-pyrazole-5-carboxylate instead of ethyl 3-methyl-1H-pyrazole-5-carboxylate as the starting material and (tetrahydro-2H-pyran-4-yl)methyl methanesulfonate in step 2 instead of (4,4-difluorocyclohexyl)methyl methanesulfonate | LCMS: m/z $[M + H]^+$ = 285.3 (calc. 285.1) |
| 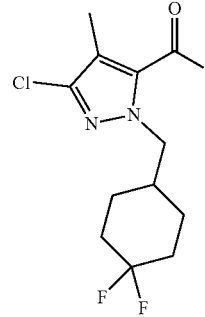<br>Int-B108 | in analogy to the synthesis of Int-B106 using ethyl 4-methyl-1H-pyrazole-5-carboxylate instead of ethyl 3-methyl-1H-pyrazole-5-carboxylate as the starting material | LCMS: m/z $[M + H]^+$ = 293.2 (calc. 293.1) |

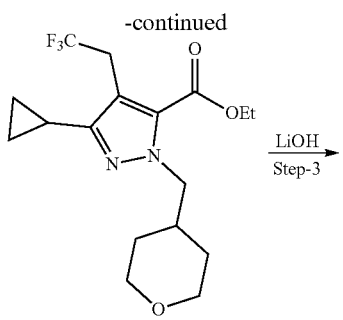

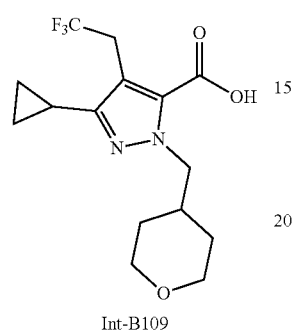

Int-B109

Step-1: To a stirred solution of ethyl 3-cyclopropyl-4-formyl-1H-pyrazole-5-carboxylate (1.0 g, 4.81 mmol, 1.0 eq.) in THF (40 mL) were added (oxan-4-yl)methanol (0.613 g, 5.29 mmol, 1.1 eq.), PPh₃ (2.5 g, 9.61 mmol, 2.0 eq.) and DIAD (2.0 mL, 9.61 mmol, 2.0 eq.) at 0° C. and the reaction mixture was then heated to 90° C. for 16 h. The reaction mixture was then concentrated under reduced pressure to get the crude material which was purified by combi flash column chromatography (silica gel, 0-30% ethyl acetate in hexane as eluent) to yield ethyl 3-cyclopropyl-4-formyl-1-[(oxan-4-yl)methyl]-1H-pyrazole-5-carboxylate. Yield: 50% (0.73 g, 2.38 mmol).

Step-2: To a stirred solution of ethyl 3-cyclopropyl-4-formyl-1-[(oxan-4-yl)methyl]-1H-pyrazole-5-carboxylate (0.5 g, 1.63 mmol, 1.0 eq.) in THF (15 mL) was added hydrazine solution (1.0 M in THF) (1.96 mL, 1.95 mmol, 1.2 eq.) at ambient temperature and the mixture was allowed to stir for 2 h. The reaction mixture was concentrated under reduced pressure to get the crude material, which was dissolved in acetonitrile (15 mL) and H₂O (15 mL). CsF (0.071 g, 0.468 mmol, 0.3 mmol), KOH (0.193 g, 3.43 mmol, 2.2 eq.) and 1-trifluoromethyl-1,2-benziodoxol-3(1H)-one (0.592 g, 1.2 mmol, 1.2 eq.) were added to that solution and the mixture was stirred for 20 min at ambient temperature. The reaction mixture was diluted with water, the aqueous part was extracted with ethyl acetate (3×100 mL). The combined organic layers were washed with brine, dried over Na₂SO₄ and concentrated under reduced pressure to get the crude material which was purified by combiflash column chromatography (silica; 0-20% ethyl acetate in hexane as eluent) to yield ethyl 3-cyclopropyl-1-[(oxan-4-yl)methyl]-4-(2,2,2-trifluoroethyl)-1H-pyrazole-5-carboxylate. Yield: 34% (0.20 g, 0.55 mmol).

Step-3: To a stirred solution of ethyl 3-cyclopropyl-1-[(oxan-4-yl)methyl]-4-(2,2,2-trifluoroethyl)-1H-pyrazole-5-carboxy late (0.14 g, 0.388 mmol, 1.0 eq.) in THF (6 mL), MeOH (1.5 mL) and H₂O (3 mL), LiOH H₂O (0.033 g, 0.777 mmol, 2.0 eq.) was added at 0° C. and the reaction mixture was then stirred at ambient temperature for 2 h. The reaction mixture was concentrated under reduced pressure to get a solid residue which was diluted with water and washed with MTBE (20 mL). The aqueous part was acidified with NaHSO₄ to pH-2 and extracted with ethyl acetate (3×50 mL). The combined organic layers were washed with brine, dried over Na₂SO₄ and concentrated under reduced pressure to yield 3-cyclopropyl-1-[(oxan-4-yl)methyl]-4-(2,2,2-trifluoroethyl)-1H-pyrazole-5-carboxylic acid (Int-B109). Yield: 93% (0.12 g, 0.361 mmol). NMR (400 MHz, DMSO-d6): δ (ppm)=11.75 (s, 1H), 4.30-4.27 (m, 2H), 3.83-3.75 (m, 4H), 3.23-3.17 (m, 2H), 1.98-1.87 (m, 2H), 1.35-1.13 (m, 4H), 0.88-0.85 (m, 2H), 0.78-0.68 (m, 2H).

Synthesis of ethyl 1-((3,3-difluorocyclobutyl)methyl)-3-(1,1-difluoropropan-2-yl)-4-methyl-1H-pyrazole-5-carboxylate (Int-B110)

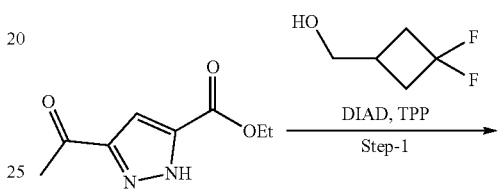

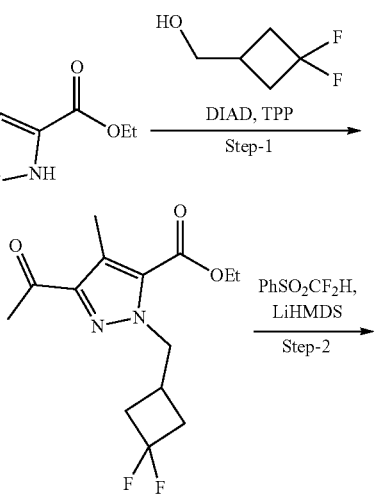

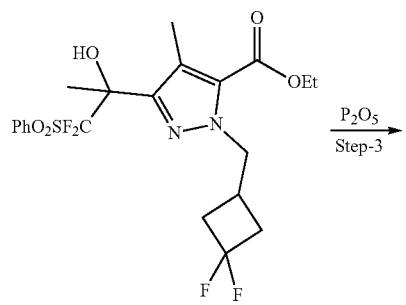

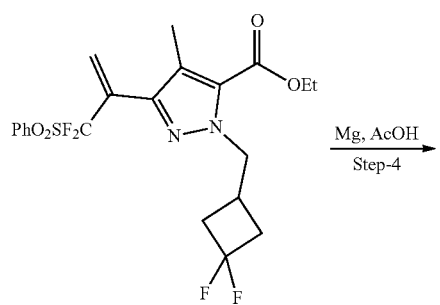

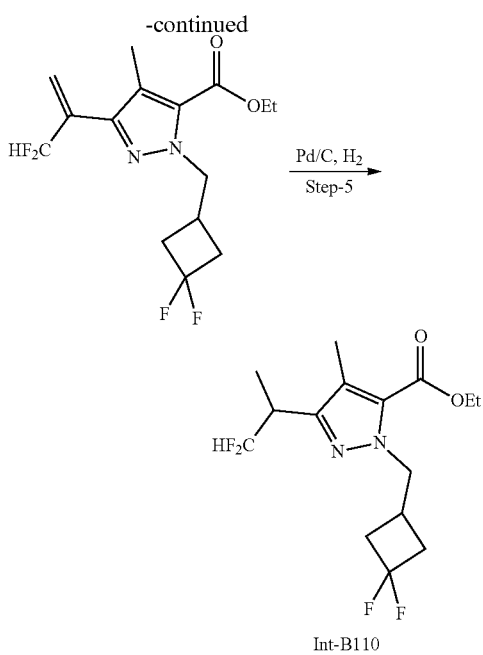

Int-B110

Step-1: To a suspension of triphenyl phosphine (12.6 g, 62.5 mmol, 2.5 eq.) and DIAD (16.3 g, 62.5 mmol 2.5 eq.) in THF (100 mL) was added (3,3-difluorocyclobutyl)methanol (3.73 g, 30.5 mmol, 1.2 eq.) dropwise at 0° C. After 5 min, ethyl 3-acetyl-4-methyl-1H-pyrazole-5-carboxylate (5.0 g, 25.0 mmol, 1.0 eq.) was added. The reaction mixture was stirred for 16 h at ambient temperature under an argon atmosphere. The reaction mixture was diluted with water (500 mL) and extracted with ethyl acetate (2×250 mL). The combined organic layers were washed with cold water (100 mL) and then brine (100 mL), dried over anhydrous $Na_2SO_4$ and concentrated under reduced pressure to get the crude product which was purified by column chromatography (silicagel 100-200 mesh, 2% EtOAC in Pet ether as an eluent) to get ethyl 3-acetyl-1-((3,3-difluorocyclobutyl)methyl)-4-methyl-1H-pyrazole-5-carboxylate (6.1 g, 79%).

Step-2: To a stirred solution of ethyl 3-acetyl-1-((3,3-difluorocyclobutyl)methyl)-4-methyl-1H-pyrazole-5-carboxylate (5.8 g, 19.3 mmol, 1.0 eq.) and $PhSO_2CF_2H$ (6.67 g, 34.7 mmol, 1.8 eq.) in THF (100 mL) were added HMPA (6.22 mL, 34.7 mmol, 1.8 eq.) and LiHMDS in THF (1M, 38.6 mL, 38.6 mmol, 2.0 eq.) at −78° C. under a nitrogen atmosphere. The reaction mixture was stirred for 3 h at −78° C. The reaction mixture was quenched with sat $NH_4Cl$ solution (100 mL) and extracted with ethyl acetate (2×100 mL). The combined organic layers were washed with cold water (100 mL) and then brine (100 mL), dried over anhydrous $Na_2SO_4$ and concentrated under reduced pressure to obtain a residue, which was purified by column chromatography (silicagel 100-200 mesh, 10% EtOAC in Pet ether as an eluent) to get ethyl 3-(1,1-difluoro-2-hydroxy-1-(phenylsulfonyl)propan-2-yl)-1-((3,3-difluorocyclobutyl)methyl)-4-methyl-1H-pyrazole-5-carboxy late (4.2 g, 44%).

Step-3: To a stirred solution of ethyl 3-(1,1-difluoro-2-hydroxy-1-(phenylsulfonyl)propan-2-yl)-1-((3,3-difluorocyclobutyl)methyl)-4-methyl-1H-pyrazole-5-carboxylate (4.0 g, 8.130 mmol, 1.0 eq.) in toluene (100 mL) was added $P_2O_5$ (23.0 g, 162.60 mmol. 20.0 eq.) at ambient temperature. The reaction mixture was then heated to 100° C. for 16 h. The reaction mixture was cooled to ambient temperature, diluted with water (250 mL), and extracted with ethyl acetate (2×150 mL). The combined organic layers were washed with water (100 mL) and then brine (100 mL), dried over anhydrous $Na_2SO_4$ and concentrated under reduced pressure to get the crude product which was purified by column chromatography (silicagel 60-120 mesh, 8-10% EtOAC in Pet ether as an eluent) to get ethyl 3-(3,3-difluoro-3-(phenylsulfonyl)prop-1-en-2-yl)-1-((3,3-difluorocyclobutyl)methyl)-4-methy-1H-pyrazole-5-carboxylate (1.3 g, 33%).

Step-4: To a stirred solution of ethyl 3-(3,3-difluoro-3-(phenylsulfonyl)prop-1-en-2-yl)-1-((3,3-difluorocyclobutyl)methyl)-4-methyl-1H-pyrazole-5-carboxylate (1.0 g, 2.109 mmol, 1.0 eq.) in DMF (20 mL) were added a buffer solution of AcOH—NaOAc (1:1, 20 mL) and activated Mg turnings (1.02 g, 42.1 mmol, 20.0 eq.) portionwise at ambient temperature under a nitrogen atmosphere. The reaction mixture was then stirred at ambient temperature for 16 h. The reaction mixture was quenched with ice cold water (100 mL) and extracted with ethyl acetate (2×70 mL). The combined organic layers were washed with water (50 mL) and then brine (50 mL), dried over anhydrous $Na_2SO_4$ and concentrated under reduced pressure to afford ethyl 1-((3,3-difluorocyclobutyl)methyl)-3-(3,3-difluoroprop-1-en-2-yl)-4-methyl-1H-pyrazole-5-carboxylate (750 mg; crude).

Step-5: To a stirred solution of ethyl 1-((3,3-difluorocyclobutyl)methyl)-3-(3,3-difluoroprop-1-en-2-yl)-4-methyl-1H-pyrazole-5-carboxylate (700 mg, 0.0029 mmol, 1.0 eq.) in MeOH (10 mL) was added 10% Pd/C (w/w, 300 mg) at ambient temperature. The reaction mixture was then stirred under $H_2$ gas (balloon pressure) for 16 h at ambient temperature. The reaction mixture was filtered through a celite bed and the celite bed was washed with methanol (50 mL). The filtrate was concentrated under reduced pressure to afford ethyl 1-((3,3-difluorocyclobutyl)methyl)-3-(1,1-difluoropropan-2-yl)-4-methyl-1H-pyrazole-5-carboxylate (Int-B110, 560 mg, 79%). LCMS: m/z $[M+H]^+$=337.2 (calc. 337.2).

Synthesis of 1-((3,3-difluorocyclobutyl)methyl)-3-(1,1-difluoroethoxy)-4-methyl-1H-pyrazole-5-carboxylic acid (Int-B111)

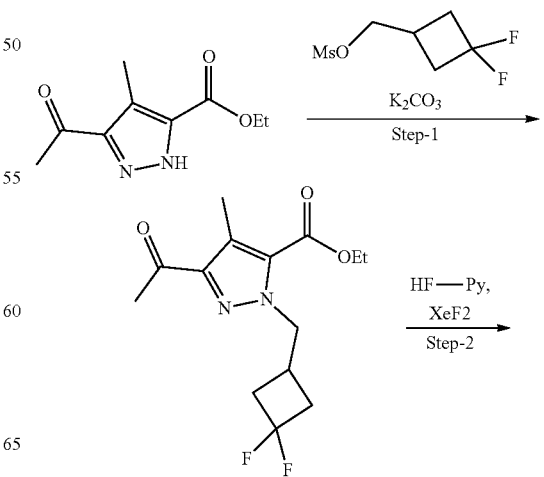

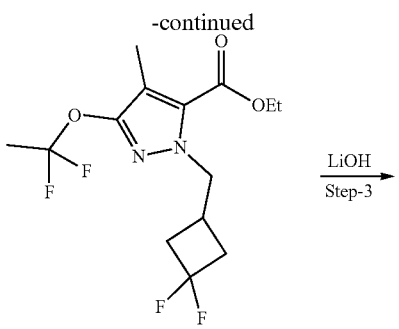

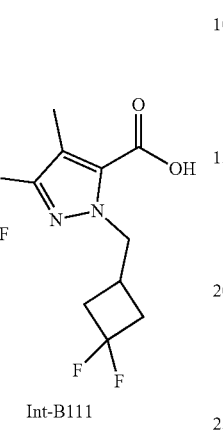

Int-B111

Step-1: To a stirred solution of ethyl 3-acetyl-4-methyl-1H-pyrazole-5-carboxylate (0.1.2 g, 6.12 mmol, 1.0 eq.) in acetonitrile (60 mL) were added K₂CO₃ (1.6 g, 12.24 mmol, 2.0 eq.) and (3,3-difluorocyclobutyl)methyl methanesulfonate (1.83 g, 9.18 mmol, 1.5 eq.) at ambient temperature. The reaction mixture was then heated to 80° C. for 16 h. The reaction mixture was then cooled to ambient temperature and was diluted with cold water. The aqueous layer was extracted with EtOAc (3×60 mL), the combined organic layers were washed with brine and dried over Na₂SO₄. The combined organic layers were concentrated under reduced pressure to get the crude material which was purified by combiflash column chromatography (Silica gel, 0-20% ethyl acetate in hexane as eluent) to yield ethyl 3-acetyl-1-[(3,3-difluorocyclobutyl)methyl]-4-methyl-1H-pyrazole-5-carboxylate. Yield: 81%(1.5 g, 4.99 mmol).

Step-2: To a solution of ethyl 3-acetyl-1-[(3,3-difluorocyclobutyl)methyl]-4-methyl-1H-pyrazole-5-carboxylate (0.6 g, 2.0 mmol, 1.0 eq.) in DCM (20 mL) in a tarsons bottle were added XeF₂ (0.845 g, 5.0 mmol, 2.5 eq.) and HF-pyridine (4.0 mL, 70% in pyridine) at ambient temperature. The reaction mixtures was the stirred at ambient temperature for 16 h. The reaction mixture was diluted with DCM and quenched by addition of cold sat. NaHCO₃ solution. The aqueous layer was extracted with DCM (3×50 mL). The combined organic layers were dried over anhy. Na₂SO₄ and concentrated under reduced pressure to get the crude material which was purified by combiflash column chromatography (silica gel; 0-20% EtOAc/hexane as eluent) to afford ethyl 1-[(3,3-difluorocyclobutyl)methyl]-3-(1,1-difluoroethoxy)-4-methyl-1H-pyrazole-5-carboxylate. Yield: 48% (0.33 g, 0.975 mmol).

Step-3: To a stirred solution of ethyl 1-[(3,3-difluorocyclobutyl)methyl]-3-(1,1-difluoroethoxy)-4-methyl-1H-pyrazole-5-carboxylate (0.15 g, 0.443 mmol, 1.0 eq.) in a mixture of THF (6 mL) and H₂O (2 mL) was added LiOH·H₂O (0.027 g, 0.665 mmol, 1.5 eq.) at 0° C. and the resulting mixture was stirred at ambient temperature for 16 h. The reaction mixture was concentrated under reduced pressure and diluted with water. The aqueous part was acidified with saturated KHSO₄ solution to pH 2 at 0° C. and extracted with ethyl acetate (3×30 mL). The combined organic layers were washed with brine and dried over Na₂SO₄ and concentrated under reduced pressure to yield 1-[(3,3-difluorocyclobutyl)methyl]-3-(1,1-difluoroethoxy)-4-methyl-1H-pyrazole-5-carboxylic acid (Int-B111). Yield: 80% (0.11 g, 0.354 mmol). LCMS: m/z [M+H]⁺=311.2 (calc. 311.1).

Synthesis of 1-((3,3-difluorocyclobutyl)methyl)-4-methyl-3-(trifluoromethoxy)-1H-pyrazole-5-carboxylic acid (Int-B112)

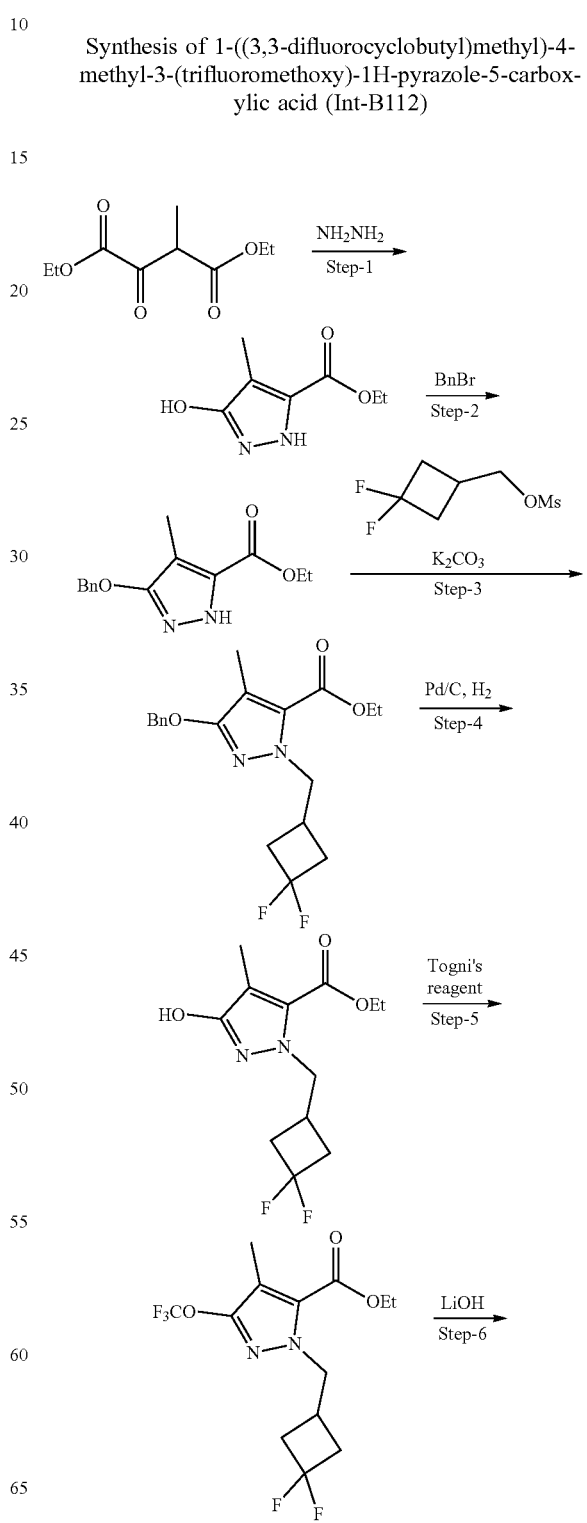

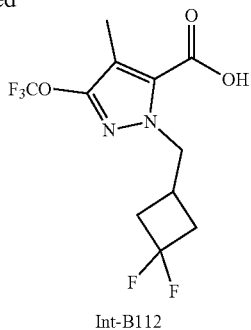

Int-B112

Step-1: To a stirred solution of 1,4-diethyl 2-methyl-3-oxobutanedioate (10.0 g, 49.45 mmol, 1.0 eq.) in ethanol (40 mL) and acetic acid (2.0 mL) was added hydrazine (1 M in THF, 44.5 mL, 44.5 mmol, 0.9 eq.) at ambient temperature. The resulting solution was heated to 80° C. for 16 h. The reaction mixture was then concentrated under reduced pressure to obtain a residue which was triturated with ether (30 mL). The resulting solid was filtered off and dried under vacuum to obtain ethyl 3-hydroxy-4-methyl-1H-pyrazole-5-carboxylate. Yield: 54% (4.5 g, 26.44 mmol).

Step-2: To a stirred solution of ethyl 3-hydroxy-4-methyl-1H-pyrazole-5-carboxylate (0.25 g, 1.469 mmol, 1.0 eq.) in DMF (5.0 mL) were added Cs$_2$CO$_3$ (0.503 g, 1.542 mmol, 1.05 eq.) and benzyl bromide (0.16 mL, 1.322 mmol, 0.9 eq.) at 0° C. The reaction mixture was then stirred at ambient temperature for 16 h. The reaction mixture was diluted with ice water and extracted with EtOAc (3×20 mL). The combined organic layers were washed with cold brine, dried over Na$_2$SO$_4$ and concentrated under reduced pressure to get the crude material which was purified by combiflash column chromatography (silica gel, 0-20% EtOAc in hexane as eluent) to yield ethyl 3-(benzyloxy)-4-methyl-1H-pyrazole-5-carboxylate. Yield: 71% (0.27 g, 1.04 mmol).

Step-3: To a solution of (3,3-difluorocyclobutyl)methanol (1.0 g, 8.19 mmol, 1.0 eq.) in DCM (40 mL), were added TEA (3.4 mL, 24.57 mmol, 3.0 eq.) and methanesulfonyl chloride (0.76 mL, 9.83 mmol, 1.2 eq.) at 0° C. The reaction mixture was then stirred at ambient temperature for 2 h. Ammonium chloride solution was then added to the mixture, which was extracted with DCM (3×50 mL). The combined organic layers were washed with brine, dried over anhyd. Na$_2$SO$_4$ and concentrated under reduced pressure to obtain the crude product which was dissolved in DMF (40 mL). Ethyl 3-(benzyloxy)-4-methyl-1H-pyrazole-5-carboxylate (1.5 g, 5.733 mmol, 0.7 eq.) and K$_2$CO$_3$ (1.7 g, 12.285 mmol, 1.5 eq.) were added to the mixture at ambient temperature and the mixture was heated to 90° C. for 16 h. The reaction mixture was cooled to ambient temperature, diluted with cold water and extracted with EtOAc (3×50 mL). The combined organic layers were washed with brine, dried over anhyd. Na$_2$SO$_4$ and concentrated under reduced pressure to get the crude material which was purified by combiflash column chromatography (silica gel; 0-30% EtOAc in hexane as eluent) to yield ethyl 3-(benzyloxy)-1-[(3,3-difluorocyclobutyl)methyl]-4-methyl-1H-pyrazole-5-carboxylate. Yield: 62%(1.3 g, 3.57 mmol)

Step-4: A solution of ethyl 3-(benzyloxy)-1-[(3,3-difluorocyclobutyl)methyl]-4-methyl-1H-pyrazole-5-carboxylate (1.3 g, 3.57 mmol, 1.0 eq.) in MeOH (50 mL) was degassed with N$_2$ for 5 min followed by the addition of 10% Pd/C (50% wet, 0.6 g) at ambient temperature. The reaction mixture was then stirred at ambient temperature under H$_2$-balloon pressure for 4 h. The reaction mixture was filtered through celite and the filtrate was concentrated under reduced pressure. The residue was purified by combiflash column chromatography (silica gel; 0-40% EtOAc in hexane as eluent) to yield ethyl 1-[(3,3-difluorocyclobutyl)methyl]-3-hydroxy-4-methyl-1H-pyrazole-5-carboxylate. Yield: 87% (0.85 g, 3.1 mmol).

Step-5: To a solution of 1-(trifluoromethyl)-3H-1λ$^3$,2-benziodaoxol-3-one (0.98 g, 3.1 mmol, 1.0 eq.) in DMF (15.0 mL) was added ethyl 1-[(3,3-difluorocyclobutyl)methyl]-3-hydroxy-4-methyl-1H-pyrazole-5-carboxy late (0.85 g, 3.1 mmol, 1.0 eq.) and the mixture was heated to 90° C. for 16 h. The reaction mixture was diluted with ice water and extracted with EtOAc (3×20 mL). The combined organic layers were washed with cold brine, dried over Na$_2$SO$_4$ and concentrated under reduced pressure. The obtained residue was purified by combiflash column chromatography (silica gel; 0-15% EtOAc in hexane as eluent.) to afford ethyl 1-[(3,3-difluorocyclobutyl)methyl]-4-methyl-3-(trifluoromethoxy)-1H-pyrazole-5-carboxylate. Yield: 14% (0.15 g, 0.438 mmol).

Step-6: To a solution of ethyl 1-[(3,3-difluorocyclobutyl)methyl]-4-methyl-3-(trifluoromethoxy)-1H-pyrazole-5-carboxylate (0.15 g, 0.438 mmol, 1.0 eq.) in a mixture of THF:H$_2$O:MeOH (4:2:1, 14 mL) was added LiOH H$_2$O (0.055 g, 1.314 mmol, 3.0 eq.) at 0° C. The reaction mixture was then stirred at ambient temperature for 2 h. The reaction mixture was concentrated under reduced pressure, diluted with water and acidified with saturated NaHSO$_4$ solution to pH-4. The aqueous layer was extracted with ethyl acetate (3×30 mL). The combined organic layers were washed with brine, dried over Na$_2$SO$_4$ and concentrated under reduced pressure to yield 1-[(3,3-difluorocyclobutyl)methyl]-4-methyl-3-(trifluoromethoxy)-1H-pyrazole-5-carboxylic acid (Int-B112). Yield: 87% (0.12 g, 0.382 mmol). LCMS: m/z [M+H]$^+$=315.2 (calc. 315.1).

Synthesis of 1-((3,3-difluorocyclopentyl)methyl)-4-methoxy-3-(trifluoromethyl)-1H-pyrazole-5-carboxylic acid (Int-B113)

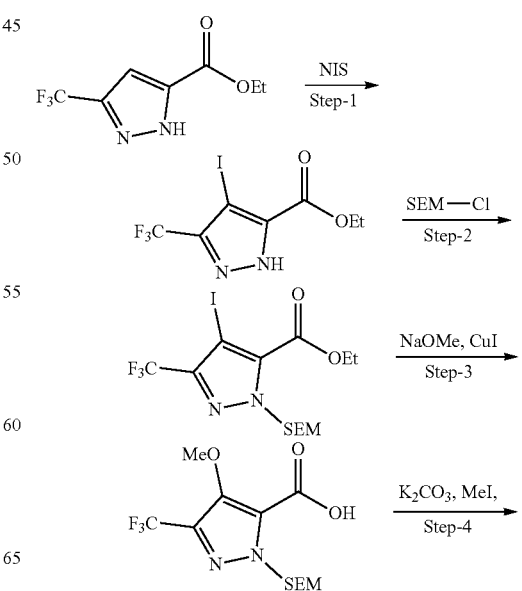

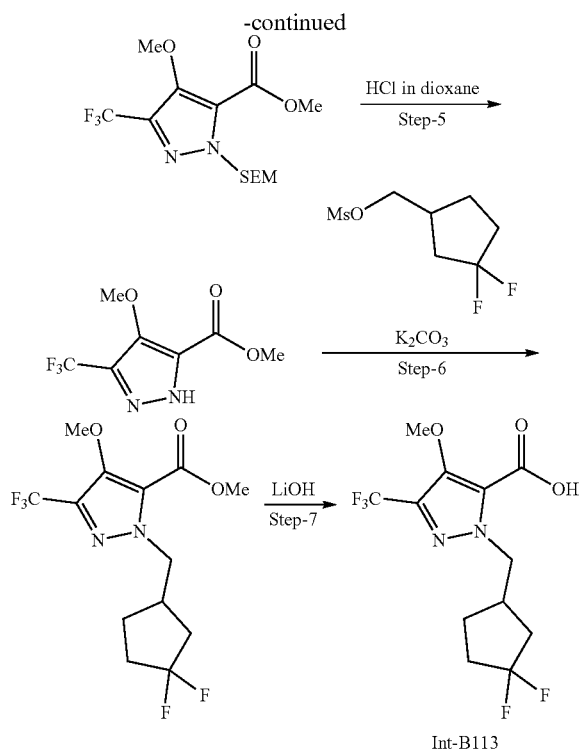

Int-B113

Step-1: To a stirred solution of ethyl 3-(trifluoromethyl)-1H-pyrazole-5-carboxylate (1.0 g, 4.80 mmol, 1.0 eq.) in DMF (10 mL) was added NIS (2.16 g, 9.60 mmol, 2.0 equiv) at ambient temperature. The reaction mixture was then heated to 70° C. for 16 h. The reaction mixture was diluted with ice water and the resulting mixture was extracted with ethyl acetate (3×100 mL). The combined organic layers were washed with brine, dried over Na$_2$SO$_4$ and concentrated under reduced pressure to get the crude material which was purified by column chromatography (Silica gel, 0-20% ethyl acetate in hexane as eluent) to yield ethyl 4-iodo-3-(trifluoromethyl)-1H-pyrazole-5-carboxylate. Yield: quantitative (1.8 g, 5.38 mmol).

Step-2: To a stirred solution of ethyl 4-iodo-3-(trifluoromethyl)-1H-pyrazole-5-carboxylate (1.3 g, 3.89 mmol, 1.0 eq.) in DCM (40 mL) were added DIPEA (1.9 mL, 11.67 mmol, 3 eq.) and SEM-Cl (0.8 mL, 4.66 mmol, 1.2 eq.) dropwise at 0° C. The reaction mixture was then stirred at ambient temperature for 2 h. The reaction mixture was diluted with ice water and extracted with DCM (3×100 mL). The combined organic layers were dried over anhyd. Na$_2$SO$_4$ and concentrated under reduced pressure to get the crude material which was purified by combiflash column chromatography (silica gel; 0-30% EtOAc in hexane as eluent) to yield ethyl 4-iodo-3-(trifluoromethyl)-1-{[2-(trimethylsilyl)ethoxy]methyl}-1H-pyrazole-5-carboxylate. Yield: 55% (1 g, 2.15 mmol).

Step-3: To a stirred solution of sodium (15 mg, 0.65 mmol, 3.0 eq.) in MeOH (5 mL) were added ethyl 4-iodo-3-(trifluoromethyl)-1-{[2-(trimethylsilyl)ethoxy]methyl}-1H-pyrazole-5-carboxylate (0.1 g, 0.22 mmol, 1.0 eq.) and CuI (13 mg, 0.07 mmol, 0.3 equiv) at ambient temperature. The resulting mixture was heated to 80° C. for 16 h. The reaction mixture was filtered through celite and the filtrate was concentrated under reduced pressure to get crude 4-methoxy-3-(trifluoromethyl)-1-{[2-(trimethylsilyl)ethoxy]methyl}-1H-pyrazole-5-carboxylic acid. This crude material was directly used for next step without further purification. Yield: quantitative (0.15 g, crude).

Step-4: To a stirred solution of 4-methoxy-3-(trifluoromethyl)-1-{[2-(trimethylsilyl) ethoxy]methyl}-1H-pyrazole-5-carboxylic acid (0.15 g, 0.44 mmol, 1.0 eq.) in DMF (2 mL) were added K$_2$CO$_3$ (0.18 g, 1.32 mmol, 3 eq.) and MeI (0.05 mL, 0.88 mmol, 2.0 eq.) at 0° C. The reaction mixture was then stirred at ambient temperature for 2 h. The reaction mixture was diluted with ice water and the resulting mixture was extracted with ethyl acetate (3×40 mL). The combined organic layers were dried over anhyd. Na$_2$SO$_4$ and concentrated under reduced pressure to get the crude material which was purified by combiflash column chromatography (silica gel; 0-30% EtOAc in hexane as eluent) to yield methyl 4-methoxy-3-(trifluoromethyl)-1-{[2-(trimethylsilyl)ethoxy]methyl}-1H-pyrazole-5-carboxylate. Yield (over two step): 77% (0.06 g, 0.17 mmol).

Step-5: To a stirred solution of methyl 4-methoxy-3-(trifluoromethyl)-1-{[2-(trimethylsilyl)ethoxy]methyl}-1H-pyrazole-5-carboxylate (0.18 g, 0.51 mmol, 1.0 eq.) in MeOH (10 mL) was added 4 (M) dioxane-HCl (10 mL) at ambient temperature. The reaction mixture was then stirred at ambient temperature for 3 h. The reaction mixture was then concentrated under reduced pressure and diluted with ice water. The resulting mixture was neutralized with sat. NaHCO$_3$ solution and extracted with ethyl acetate (3×50 mL). The combined organic layers were washed with brine, dried over Na$_2$SO$_4$ and concentrated under reduced pressure to get the crude material which was purified by column chromatography (silica gel, 0-40% ethyl acetate in hexane as eluent) to yield ethyl methyl 4-methoxy-3-(trifluoromethyl)-1H-pyrazole-5-carboxylate. Yield: 87% (0.1 g, 0.45 mmol)

Step-6: To a stirred solution of ethyl methyl 4-methoxy-3-(trifluoromethyl)-1H-pyrazole-5-carboxylate (0.09 g, 0.40 mmol, 1.0 eq.) in DMF (3 mL) were added (3,3-difluorocyclopentyl)methyl methanesulfonate (0.10 g, 0.48 mmol, 1.2 eq.) and Cs$_2$CO$_3$ (0.16 g, 1.2 mmol, 3.0 eq.) at ambient temperature. The resulting mixture was heated to 90° C. for 2 h. The reaction mixture was diluted with ice water (30 mL) and extracted with ethyl acetate (3×50 mL). The combined organic layers were washed with brine (50 mL), dried over Na$_2$SO$_4$ and concentrated under reduced pressure to get the crude product which was purified by combiflash column chromatography (silica gel; 0-30% ethyl acetate in hexane as eluent) to obtain methyl 1-[(3,3-difluorocyclopentyl)methyl]-4-methoxy-3-(trifluoromethyl)-1H-pyrazole-5-carboxylate. Yield: 55% (75 mg, 0.22 mmol).

Step-7: To a stirred solution of methyl 1-[(3,3-difluorocyclopentyl)methyl]-4-methoxy-3-(trifluoromethyl)-1H-pyrazole-5-carboxylate (0.20 g, 0.58 mmol, 1.0 eq.) in THF (4 mL), water (2 mL) and MeOH (2 mL) was added LiOH·H$_2$O (0.1 g, 2.34 mmol, 4.0 eq.) portionwise at 0° C. The resulting reaction mixture was then stirred for 16 h at ambient temperature. The reaction mixture was concentrated under reduced pressure to obtain a solid residue which was diluted with water and washed with ethyl acetate (20 mL). The aqueous layer was acidified with KHSO$_4$ solution under ice cooling and the resulting mixture was extracted with ethyl acetate (3×100 mL). The combined organic layers were washed with brine, dried over Na$_2$SO$_4$ and concentrated under reduced pressure to yield 1-[(3,3-difluorocyclopentyl)methyl]-4-methoxy-3-(trifluoromethyl)-1H-pyrazole-5-carboxylic acid (Int-B113). Yield: 92% (0.17 g, 0.53 mmol). LCMS m/z [M−H]$^−$=327.1 (calc. 327.1)

Synthesis of 1-((2,2-difluorocyclobutyl)methyl)-4-methyl-3-(perfluoroethyl)-1H-pyrazole-5-carboxylic acid (Int-B114)

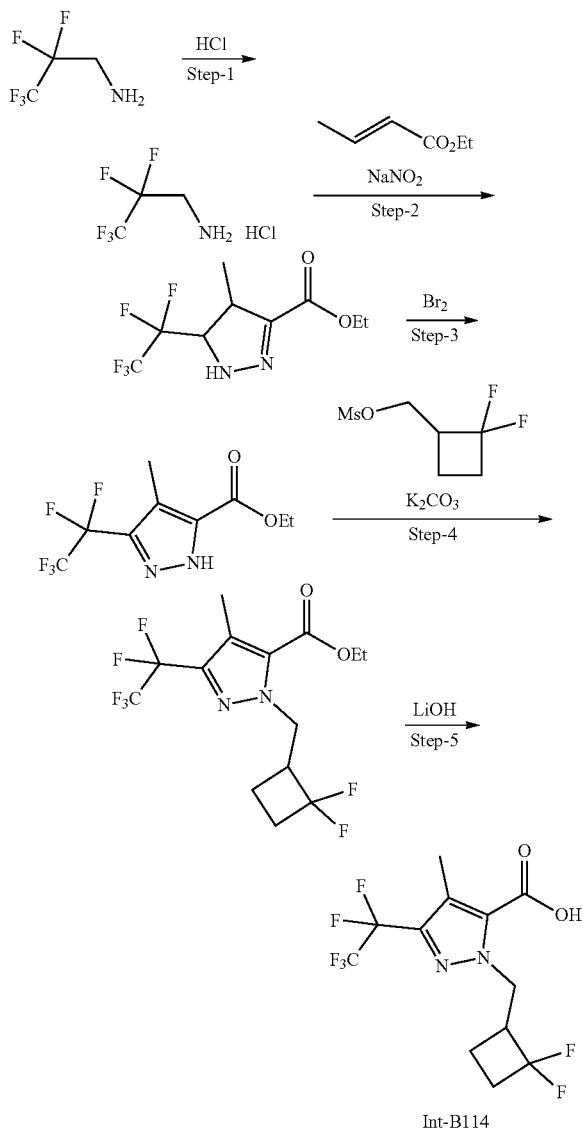

Int-B114

Step-1: To a stirred solution of 2,2,3,3,3-pentafluoropropan-1-amine (5 g, 33.55 mmol) in 1,4-dioxane (10 mL) was added 4M HCl in 1,4-dioxane (50 mL, 10 Vol) under an argon atmosphere at ambient temperature. The resulting reaction mixture was then stirred for 2 h at ambient temperature. The experiment was conducted in the same fashion on twice the scale in parallel. The workup was conducted for both experiments in a combined fashion. The solvent was concentrated under reduced pressure to afford 2,2,3,3,3-pentafluoropropan-1-amine hydrochloride (18 g, crude product).

Step-2: To a stirred solution of 2,2,3,3,3-pentafluoropropan-1-amine hydrochloride (9 g, 50.0 mmol, 1.0 eq.) in dichloromethane and water (7:3, 100 mL) were added NaNO₃ (8.3 g, 97.01 mmol, 1.9 eq.) and ethyl (E)-but-2-enoate (5.6 g, 50.0 mmol 1.0 eq.) at 0° C. The reaction mixture was then warmed to ambient temperature and was stirred for 96 h. The experiment was conducted in the same fashion on the same scale in parallel. The workup was conducted for both experiments in a combined fashion. The reaction mixtures were quenched with water (50 mL) and extracted with dichloromethane (2×50 mL). The combined organic layers were washed with water (50 mL) and then brine (50 mL), dried over Na₂SO₄ and concentrated under reduced pressure to afford ethyl 4-methyl-5-(perfluoroethyl)-4,5-dihydro-1H-pyrazole-3-carboxylate (2 g, crude).

Step 3: To a stirred solution of ethyl 4-methyl-5-(perfluoroethyl)-4,5-dihydro-1H-pyrazole-3-carboxylate (2.0 g, 7.29 mmol, 1.0 eq.) in diethylether (20 mL) was added bromine (1.4 g, 8.75 mmol, 1.2 eq.) at 0° C. The reaction mixture was warmed to ambient temperature and was stirred for 16 h. The reaction mixture was quenched with water (50 mL) and extracted with dichloromethane (2×50 mL). The combined organic layers were washed with water (50 mL) and then brine (50 mL), dried over Na₂SO₄ and concentrated under reduced pressure to afford ethyl 4-methyl-3-(perfluoroethyl)-1H-pyrazole-5-carboxylate (1.6 g, 6% over 3 steps).

Step 4: To a stirred solution of ethyl 4-methyl-3-(perfluoroethyl)-1H-pyrazole-5-carboxylate (71 mg, 0.26 mmol, 1.0 eq.) in acetonitrile (5 mL) were added K₂CO₃ (54 mg, 0.39 mmol, 1.5 eq.) and (2,2-difluorocyclobutyl)methyl methanesulfonate (55 mg, 0.26 mmol, 1.0 eq.) at ambient temperature. The reaction mixture was heated to 90° C. for 16 h. The reaction mixture was then warmed to ambient temperature and was stirred for 96 h. The experiment was conducted in the same fashion using 500 mg of ethyl 4-methyl-3-(perfluoroethyl)-1H-pyrazole-5-carboxylate as starting material in parallel. The workup was conducted for both experiments in a combined fashion. The reaction mixture was filtered, the filter was washed with ethyl acetate (30 mL) and the filtrate was concentrated under reduced pressure to afford ethyl 1-((2,2-difluorocyclobutyl)methyl)-4-methyl-3-(perfluoroethyl)-1H-pyrazole-5-carboxylate (500 mg, crude).

Step 5: To a stirred solution of ethyl 1-((3,3-difluorocyclobutyl)methyl)-4-methyl-3-(perfluoroethyl)-1H-pyrazole-5-carboxylate (100 mg, 0.27 mmol, 1.0 eq.) in THF:H₂O (1:1:) (10 mL) was added LiOH H₂O (111 mg, 2.7 mmol, 10.0 eq.) at ambient temperature. The reaction mixture was then stirred for 16 h. The experiment was conducted in the same fashion using 400 mg of ethyl 1-((3,3-difluorocyclobutyl)methyl)-4-methyl-3-(perfluoroethyl)-1H-pyrazole-5-carboxylate as starting material in parallel. The workup was conducted for both experiments in a combined fashion. The combined reaction mixtures were concentrated under reduced pressure, diluted with water (10 mL), acidified to pH~2 with 1N HCl and extracted with 5% MeOH in dichloromethane (2×50 mL). The combined organic layers were dried over Na₂SO₄ and concentrated under reduced pressure to afford 1-((2,2-difluorocyclobutyl)methyl)-4-methyl-3-(perfluoroethyl)-1H-pyrazole-5-carboxylic acid (Int-B114, 500 mg, crude). LCMS m/z [M+H]⁺=349.2 (calc. 349.1).

Synthesis of 1-((3,3-difluorocyclobutyl)methyl)-4-methyl-3-(1,1,1-trifluoropropan-2-yl)-1H-pyrazole-5-carboxamide (Int-B115)

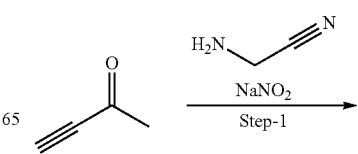

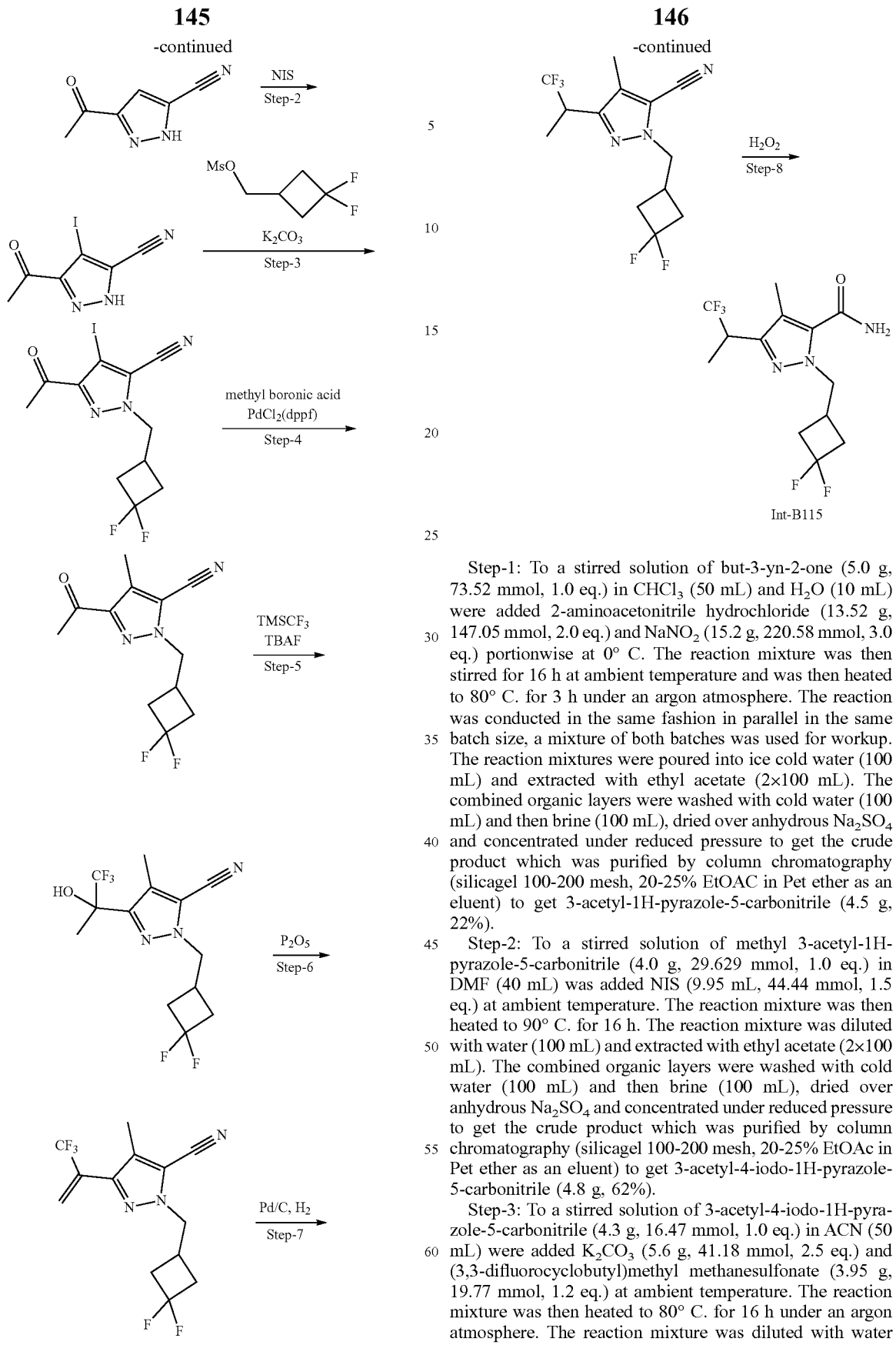

Step-1: To a stirred solution of but-3-yn-2-one (5.0 g, 73.52 mmol, 1.0 eq.) in CHCl$_3$ (50 mL) and H$_2$O (10 mL) were added 2-aminoacetonitrile hydrochloride (13.52 g, 147.05 mmol, 2.0 eq.) and NaNO$_2$ (15.2 g, 220.58 mmol, 3.0 eq.) portionwise at 0° C. The reaction mixture was then stirred for 16 h at ambient temperature and was then heated to 80° C. for 3 h under an argon atmosphere. The reaction was conducted in the same fashion in parallel in the same batch size, a mixture of both batches was used for workup. The reaction mixtures were poured into ice cold water (100 mL) and extracted with ethyl acetate (2×100 mL). The combined organic layers were washed with cold water (100 mL) and then brine (100 mL), dried over anhydrous Na$_2$SO$_4$ and concentrated under reduced pressure to get the crude product which was purified by column chromatography (silicagel 100-200 mesh, 20-25% EtOAC in Pet ether as an eluent) to get 3-acetyl-1H-pyrazole-5-carbonitrile (4.5 g, 22%).

Step-2: To a stirred solution of methyl 3-acetyl-1H-pyrazole-5-carbonitrile (4.0 g, 29.629 mmol, 1.0 eq.) in DMF (40 mL) was added NIS (9.95 mL, 44.44 mmol, 1.5 eq.) at ambient temperature. The reaction mixture was then heated to 90° C. for 16 h. The reaction mixture was diluted with water (100 mL) and extracted with ethyl acetate (2×100 mL). The combined organic layers were washed with cold water (100 mL) and then brine (100 mL), dried over anhydrous Na$_2$SO$_4$ and concentrated under reduced pressure to get the crude product which was purified by column chromatography (silicagel 100-200 mesh, 20-25% EtOAc in Pet ether as an eluent) to get 3-acetyl-4-iodo-1H-pyrazole-5-carbonitrile (4.8 g, 62%).

Step-3: To a stirred solution of 3-acetyl-4-iodo-1H-pyrazole-5-carbonitrile (4.3 g, 16.47 mmol, 1.0 eq.) in ACN (50 mL) were added K$_2$CO$_3$ (5.6 g, 41.18 mmol, 2.5 eq.) and (3,3-difluorocyclobutyl)methyl methanesulfonate (3.95 g, 19.77 mmol, 1.2 eq.) at ambient temperature. The reaction mixture was then heated to 80° C. for 16 h under an argon atmosphere. The reaction mixture was diluted with water (100 mL) and extracted with ethyl acetate (2×100 mL). The combined organic layers were washed with cold water (50 mL) and then brine (50 mL), dried over anhydrous Na$_2$SO$_4$ and concentrated under reduced pressure to get the crude product which was purified by column chromatography (silicagel 100-200 mesh, 20-25% EtOAC in Pet ether as an eluent) to get methyl 2-((3,3-difluorocyclobutyl)methyl)-7-methyl-2H-indazole-3-carboxylate (3.0 g, 50%).

Step-4: To a stirred solution of methyl 2-((3,3-difluorocyclobutyl)methyl)-7-methyl-2H-indazole-3-carboxylate (3.0 g, 8.219 mmol, 1.0 eq.) in DMF (30 mL) in a sealed tube were added methyl boronic acid (3.45 g, 57.534 mmol, 7.0 eq.) and K₂CO₃ (3.4 g, 24.65 mmol, 3.0 eq.) at ambient temperature. The reaction mixture was degassed with argon for 10 min before the addition of Pd(dppf)Cl₂CH₂Cl₂ (1.34 g, 1.643 mmol, 0.2 eq.) at ambient temperature and was then again degassed with argon for another 5 min. The reaction mixture was then heated to 100° C. for 16 h. The reaction mixture was cooled to ambient temperature, filtered though a celite bed and the celite bed was washed with ethyl acetate (50 mL). The filtrate was diluted with water (50 mL) and extracted with ethyl acetate (2×100 mL). The combined organic layers were washed with water (50 mL) and then brine (50 mL), dried over anhydrous Na₂SO₄ and concentrated under reduced pressure to get the crude product which was purified by column chromatography (silicagel 100-200 mesh, 10-12% EtOAC in Pet ether as an eluent) to get 3-acetyl-1-((3,3-difluorocyclobutyl)methyl)-4-methyl-1H-pyrazole-5-carbonitrile (1.1 g, 50%).

Step-5: To a solution of 3-acetyl-1-((3,3-difluorocyclobutyl)methyl)-4-methyl-1H-pyrazole-5-carbonitrile (1.6 g, 6.324 mmol, 1.0 eq.) in THF (20 mL) were added TMFCF₃ (1.92 mL, 12.64 mmol, 2.0 eq.) and TBAF in THF (1M, 63 µL 0.063 mmol, 0.01 eq.) at −78° C. The resulting reaction mixture was stirred for 0.5 h at −78° C. The reaction mixture was then allowed to warm to ambient temperature and was stirred for 2 h. Then TBAF in THF (1M, 12.6 mL, 12.64 mmol) was added at ambient temperature and the reaction was stirred for 2 h. The reaction mixture was diluted with water (50 mL) and extracted with ethyl acetate (2×50 mL). The combined organic layers were washed with water (50 mL) and then brine (50 mL), dried over anhydrous Na₂SO₄ and concentrated under reduced pressure to get the crude product which was purified by column chromatography (silicagel 100-200 mesh, 12-14% EtOAC in Pet ether as an eluent) to get 1-((3,3-difluorocyclobutyl)methyl)-4-methyl-3-(1,1,1-trifluoro-2-hydroxypropan-2-yl)-1H-pyrazole-5-carbonitrile (2.0 g, 90%).

Step-6: To a stirred solution of 1-((3,3-difluorocyclobutyl)methyl)-4-methyl-3-(1,1,1-trifluoro-2-hydroxypropan-2-yl)-1H-pyrazole-5-carbonitrile (2.0 g, 6.191 mmol, 1.0 eq.) in toluene (50 mL) was added P₂O₅ (17.5 g, 123.82 mmol, 20.0 eq.) at ambient temperature. The reaction mixture was then stirred at 100° C. for 16 h. The reaction mixture was cooled to ambient temperature, diluted with water (50 mL) and extracted with ethyl acetate (2×50 mL). The combined organic layers were washed with water (50 mL) and then brine (50 mL), dried over anhydrous Na₂SO₄ and concentrated under reduced pressure to get the crude product which was purified by column chromatography (silicagel 100-200 mesh, 7-8% EtOAc in Pet ether as an eluent) to get 1-((3,3-difluorocyclobutyl)methyl)-4-methyl-3-(3,3,3-trifluoroprop-1-en-2-yl)-1H-pyrazole-5-carbonitrile (1.0 g, 55%).

Step-7: To a stirred solution of 1-((3,3-difluorocyclobutyl)methyl)-4-methyl-3-(3,3,3-trifluoroprop-1-en-2-yl)-1H-pyrazole-5-carbonitrile (500 mg, 1.639 mmol, 1.0 eq.) in MeOH (10 mL) was added 10% Pd/C (50 mg) at ambient temperature. The reaction mixture was then stirred under H₂ gas balloon pressure for 30 min at ambient temperature. The reaction mixture was filtered through a celite bed, the celite bed was washed with MeOH (50 mL). The filtrate was concentrated under reduced pressure to afford 1-((3,3-difluorocyclobutyl)methyl)-4-methyl-3-(1,1,1-trifluoropropan-2-yl)-1H-pyrazole-5-carbonitrile (400 mg; 79%).

Step-8: To a stirred solution of 1-((3,3-difluorocyclobutyl)methyl)-4-methyl-3-(3,3,3-trifluoroprop-1-en-2-yl)-1H-pyrazole-5-carbonitrile (400 mg, 1.302 mmol, 1.0 eq.) in DMSO (10 mL) were added K₂CO₃ (359 mg, 2.605 mmol, 2.0 eq.) and 30% H₂O₂ (2 mL) at 0° C. The reaction mixture was then stirred at ambient temperature for 1 h. The reaction mixture was then poured into ice cold water (30 mL) and the mixture was stirred for 30 min. The formed precipitates were filtered off and dried under reduced pressure to afford 1-((3,3-difluorocyclobutyl)methyl)-4-methyl-3-(1,1,1-trifluoropropan-2-yl)-1H-pyrazole-5-carboxamide (Int-B115, 400 mg; 94%). LCMS: m/z [M+H]⁺=326.2 (calc. 326.1).

Selected Examples of the Invention

Synthesis of 1-(cyclohexylmethyl)-N-(3-(methylsulfonyl)phenyl)-3-(trifluoromethyl)-1H-pyrazole-5-carboxamide (SC-01)

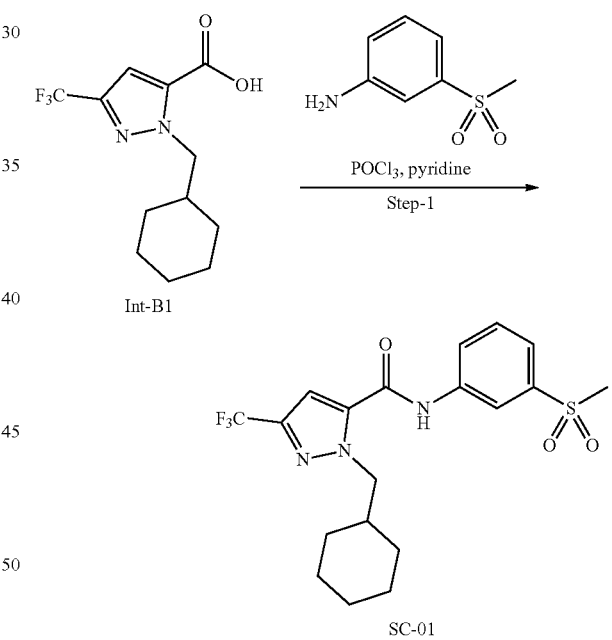

Step-1: To a mixture of 1-(cyclohexylmethyl)-3-(trifluoromethyl)-1H-pyrazole-5-carboxylic acid (Int-B1) (320 mg, 1.15 mmol, 1.00 eq.) and 3-(methylsulfonyl)aniline (237 mg, 1.38 mmol, 1.20 eq.) in pyridine (5 mL) was added POCl₃ (0.22 mL, 2.31 mmol, 2.00 eq.) dropwise at 0° C. The reaction mixture was stirred at ambient temperature for 3 h, then poured into ice-water and extracted with EtOAc (2×25 mL). The combined organic layers were washed with water (25 mL), sat. aq. NaHCO₃ (25 mL) and brine (25 mL), dried over anhydrous Na₂SO₄ and concentrated under reduced pressure to give the crude product which was purified by flash column chromatography (silica gel; 2-20% EtOAc/Hexane) to yield 1-(cyclohexylmethyl)-N-(3-(methylsulfonyl)phenyl)-3-(trifluoromethyl)-1H-pyrazole-5-carboxamide (SC-01, 180 mg, 0.41 mmol, 36%). $^1$H NMR (400 MHz, DMSO-d6): δ (ppm)=10.75 (s, 1H), 8.33 (s, 1H), 8.05 (d, 1H), 7.72-7.65 (m, 2H), 7.57 (s, 1H), 4.47-4.45 (m, 2H), 3.23 (s, 1H), 1.89-1.84 (m, 1H), 1.65-1.59 (m, 3H), 1.50-1.47 (m, 2H), 1.23-1.10 (m, 3H), 0.97-0.95 (m, 2H). LCMS: m/z [M+H]$^+$=430.3 (calc.=430.1).

Synthesis of 1-(cyclohexylmethyl)-3,4-dimethyl-N-(2-oxo-1,2-dihydropyridin-4-yl)-1H-pyrazole-5-carboxamide (SC-07)

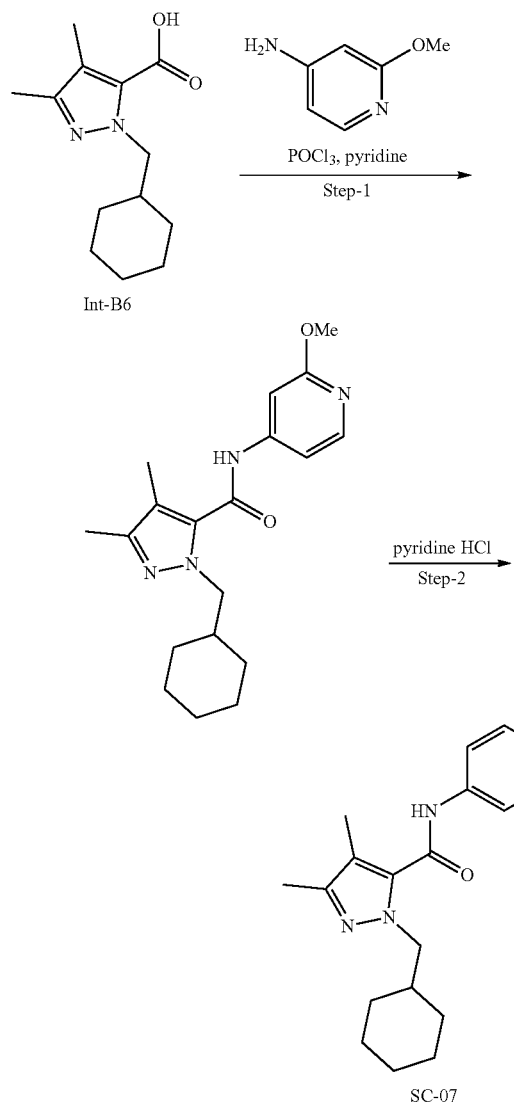

Step-1: To a solution of 1-(cyclohexylmethyl)-3,4-dimethyl-1H-pyrazole-5-carboxylic acid (Int-B6) (0.3 g, 1.27 mmol, 1.00 eq.) and 2-methoxypyridin-4-amine (0.24 g, 1.9 mmol) in pyridine (7.5 mL) was added dropwise POCl$_3$ (0.2 mL, 1.90 mmol) at 0° C. under a nitrogen atmosphere and the reaction mixture was stirred at ambient temperature for 16 h. Then ice-water was added and the reaction mixture was concentrated under reduced pressure. The resulting crude mixture was diluted with water and extracted with EtOAc (3×30 mL). The combined organic layers were washed with brine, dried over anhydrous Na$_2$SO$_4$ and concentrated under reduced pressure to give the crude product which was purified by flash column chromatography (silica gel; 20-40% EtOAc/hexanes) to get 1-(cyclohexylmethyl)-N-(2-methoxypyridin-4-yl)-3,4-dimethyl-1H-pyrazole-5-carboxamide. Yield: 29% (0.09 g, 0.371 mmol).

Step-2: To a solution of 1-(cyclohexylmethyl)-N-(2-methoxypyridin-4-yl)-3,4-dimethyl-1H-pyrazole-5-carboxamide (0.07 g, 0.20 mmol, 1.00 eq.) in DMF (5 mL) was added pyridine hydrochloride (0.115 g, 1.023 mmol) at ambient temperature and the reaction mixture was stirred in a sealed tube at 100° C. for 16 h. The reaction mixture was concentrated under reduced pressure to give the crude product which was purified by flash column chromatography (silica gel; 0-10% MeOH/DCM) to afford 1-(cyclohexylmethyl)-3,4-dimethyl-N-(2-oxo-1,2-dihydropyridin-4-yl)-1H-pyrazole-5-carboxamide (SC-07). Yield: 30% (0.02 g, 0.060 mmol). NMR (400 MHz, DMSO-d6): δ (ppm)=11.26 (s, 1H), 10.32 (s, 1H), 7.31 (d, 1H), 6.75 (s, 1H), 6.43 (d, 1H), 3.98 (d, 2H), 2.11-2.03 (m, 6H), 1.68-1.45 (m, 6H), 1.11 (br s, 3H), 0.89-0.86 (m, 2H).). LCMS: m/z [M+H]$^+$=329.3 (calc.=329.2).

Synthesis of 1-(cyclohexylmethyl)-3-(difluoromethyl)-N-(3-(methylsulfonyl)phenyl)-1H-pyrazole-5-carboxamide (SC-09)

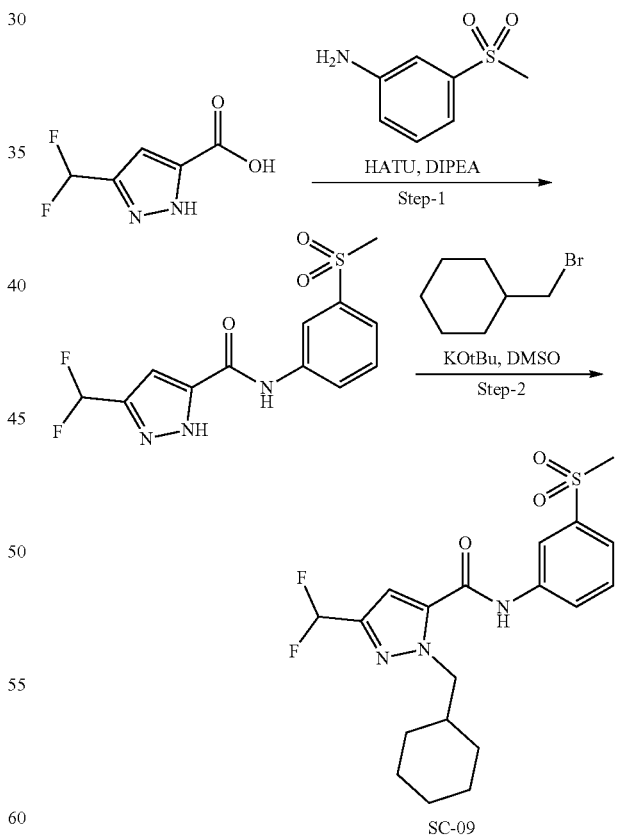

Step-1: To a solution of 3-(difluoromethyl)-1H-pyrazole-5-carboxylic acid (800 mg, 4.90 mmol, 1.00 eq.) in DMF (10 mL) were added 3-(methylsulfonyl)aniline (845 mg, 4.90 mmol, 1.00 eq.), HATU (3.72 g, 9.8 mmol) and DIPEA (2.6 mL, 14.7 mmol) at 0° C. under a nitrogen atmosphere. The resulting suspension was stirred at ambient temperature for 16 h. The reaction mixture was diluted with water (200 mL) and extracted with EtOAc (2×200 mL). The combined organic layers were washed with brine (200 mL), dried over anhydrous Na$_2$SO$_4$ and concentrated under reduced pressure. The resulting residue was purified by flash column chromatography (100-200 silica mesh) using 0-60% EtOAc in petroleum ether as eluent to afford 3-(difluoromethyl)-N-(3-(methylsulfonyl)phenyl)-1H-pyrazole-5-carboxamide. Yield: 1000 mg (66%).

Step-2: To a solution of 3-(difluoromethyl)-N-(3-(methylsulfonyl)phenyl)-1H-pyrazole-5-carboxamide (500 mg, 1.9 mmol, 1.00 eq.) in DMSO (10 mL) at 10° C. was added KOtBu (426.3 mg, 3.8 mmol) and (bromomethyl)cyclohexane (337.14 mg, 1.9 mmol). The resulting reaction mixture was stirred at ambient temperature for 16 h. The reaction mixture was diluted with water (100 mL) and extracted with EtOAc (2×20 mL). The combined organic layers were washed with brine (200 mL) and concentrated under reduced pressure to afford the crude product which was purified by flash column chromatography on silica gel (100-200 mesh) using 20% of EtOAc in petroleum ether to afford 1-(cyclohexylmethyl)-3-(difluoromethyl)-N-(3-(methylsulfonyl)phenyl)-1H-pyrazole-5-carboxamide (SC-09). Yield: 90 mg (13%). $^1$H NMR (400 MHz, DMSO-d6): δ (ppm)=10.70 (s, 1H), 8.35 (s, 1H), 8.07 (d, J=2.0 Hz, 1H), 7.71-7.64 (m, 2H), 7.38 (s, 1H), 7.10 (t, 1H), 4.42 (d, 2H), 3.23 (s, 3H), 1.86-1.84 (m, 1H), 1.64-1.58 (m, 3H), 1.50.1.46 (m, 2H), 1.16-1.12 (m, 3H), 1.02-0.96 (m, 2H). LCMS: m/z [M+H]$^+$=412.1 (calc.=412.2).

Synthesis of 4-cyano-1-(cyclohexylmethyl)-N-(3-(methylsulfonyl)phenyl)-1H-pyrazole-5-carboxamide (SC-10)

Step-1: To a solution of 4-cyano-1-(cyclohexylmethyl)-1H-pyrazole-5-carboxylic acid (Int-B7) (220 mg, 0.009 mmol, 1.00 eq.) and 3-(methylsulfonyl)aniline (161 mg, 0.009 mmol, 1.00 eq.) in DMF (20 mL) were added DIPEA (0.5 mL, 0.028 mmol) and HATU (717 mg, 0.018 mmol). The reaction mixture was stirred at ambient temperature for 16 h. The reaction mixture was diluted with ice-cold water (20 mL). Precipitation occurred, the resulting solid was filtered off, washed with water (30 mL) and purified by flash column chromatography on silica gel (100-200 mesh) eluting with 35% EtOAc in petroleum ether to afford desired product which was triturated with diethyl ether to afford 4-cyano-1-(cyclohexylmethyl)-N-(3-(methylsulfonyl)phenyl)-1H-pyrazole-5-carboxamide (SC-10). Yield: 99.6 mg (27%). $^1$H NMR (400 MHz, DMSO-d6): δ (ppm)=11.40 (s, 1H), 8.33 (s, 1H), 8.25 (s, 1H), 7.93 (d, 1H), 7.77-7.68 (m, 2H), 4.22 (d, 2H), 3.25 (s, 3H), 1.86-1.80 (m, 1H), 1.64-1.46 (m, 5H), 1.16-0.89 (m, 5H). LCMS: m/z [M-H]$^-$=385.1 (calc.=385.1).

Synthesis of N-(4-carbamoyl-3-fluorophenyl)-1-[(4,4-difluorocyclohexyl)methyl]-4-(trifluoromethyl)-1H-pyrazole-5-carboxamide (SC-21)

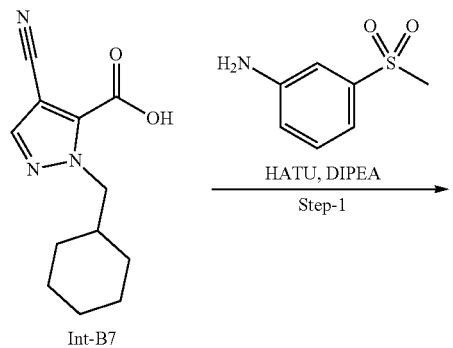

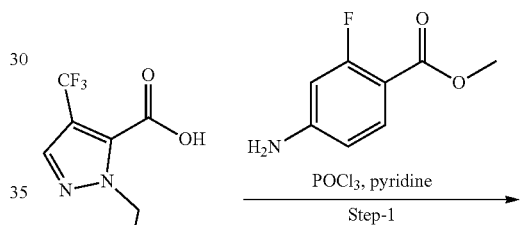

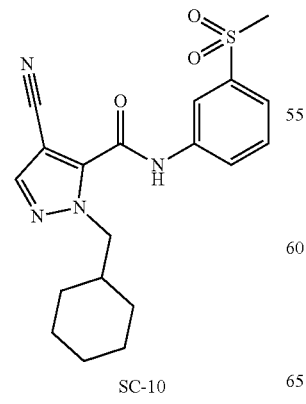

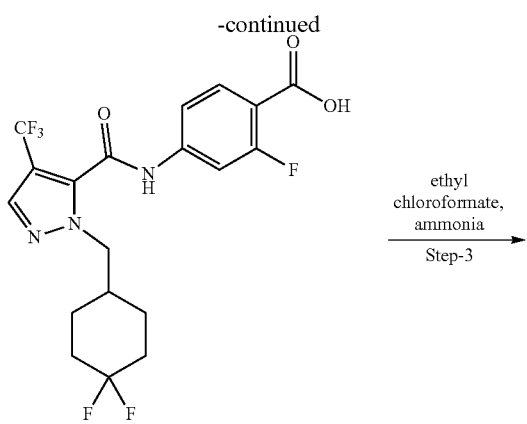

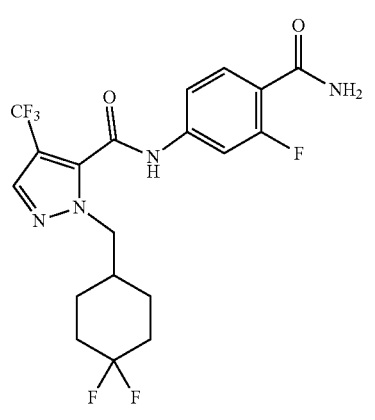

SC-21

Step-1: To a solution of 1-((4,4-difluorocyclohexyl)methyl)-4-(trifluoromethyl)-1H-pyrazole-5-carboxylic acid (Int-B5) (0.15 g, 0.48 mmol, 1.00 eq.) and methyl 4-amino-2-fluorobenzoate (0.10 g, 0.576 mmol) in pyridine (6 mL) was added POCl₃ (0.18 mL, 1.92 mmol) dropwise at −10° C. The reaction mixture was stirred at ambient temperature for 3 h, then quenched with ice-cold water and extracted with EtOAc. The combined organic layers were washed with brine, dried over Na₂SO₄ and concentrated under reduced pressure. The resulting crude product was purified by flash column chromatography on silica gel (100-200 mesh) eluting with 0-50% EtOAc in hexanes to obtain methyl 4-[[chloro({1-[(4,4-difluorocyclohexyl)methyl]-4-(trifluoromethyl)-1H-pyrazol-5-yl})methylene]amino]-2-fluorobenzoate. Yield (crude): 52% (0.120 g, 0.249 mmol).

Step-2: A mixture of methyl 4-[[chloro({1-[(4,4-difluorocyclohexyl)methyl]-4-(trifluoromethyl)-1H-pyrazol-5-yl})methylene]amino]-2-fluorobenzoate (0.12 g, 0.249 mmol) in THF (3.0 mL) and 1M aq. NaOH (3.0 mL) was stirred at 80° C. for 7 h. The reaction mixture was cooled to ambient temperature, acidified using sat. aq. NaHSO₄ (pH-3) and extracted with EtOAc. The combined organic layers were washed with brine, dried over anhydrous Na₂SO₄ and concentrated under reduced pressure to obtain 4-{1-[(4,4-difluorocyclohexyl)methyl]-4-(trifluoromethyl)-1H-pyrazole-5-amido}-2-fluorobenzoic acid. Yield: 85% (0.095 g, 0.211 mmol).

Step-3: Ethyl chloroformate (0.03 mL, 0.317 mmol) was added dropwise to a solution of 4-{1-[(4,4-difluoro cyclohexyl)methyl]-4-(trifluoromethyl)-1H-pyrazole-5-amido}-2-fluorobenzoic acid (0.095 g, 0.211 mmol, 1.00 eq.) and triethyl amine (0.09 mL, 0.633 mmol) in THF (3.0 mL) at 0° C. and the mixture was stirred at the same temperature for 2 h. Aq. ammonia (28%, 2 mL) was added and the reaction mixture was stirred for 3 h. The reaction mixture was diluted with EtOAc, washed with brine, dried over Na₂SO₄ and concentrated under reduced pressure. The resulting residue was purified by flash column chromatography on silica gel (100-200 mesh) eluting with 0-70% EtOAc in hexanes to obtain N-(4-carbamoyl-3-fluorophenyl)-1-[(4,4-difluorocyclohexyl)methyl]-4-(trifluoromethyl)-1H-pyrazole-5-carboxamide (SC-21). Yield: 48% (0.045 g, 0.1 mmol). NMR (400 MHz, DMSO-d6): δ (ppm)=11.32 (s, 1H), 8.08 (s, 1H), 7.32 (t, 1H), 7.67-7.58 (m, 3H), 7.44 (d, 1H), 4.14 (d, 2H), 2.05-1.95 (m, 3H), 1.83-1.68 (m, 2H), 1.62-1.58 (m, 2H), 1.27-1.18 (m, 2H). LCMS: m/z [M+H]⁺=449.3 (calc.=449.1).

Synthesis of 1-[(4,4-difluorocyclohexyl)methyl]-N-(2-fluoro-5-methanesulfonylphenyl)-4-(trifluoromethyl)-1H-pyrazole-5-carboxamide (SC-22)

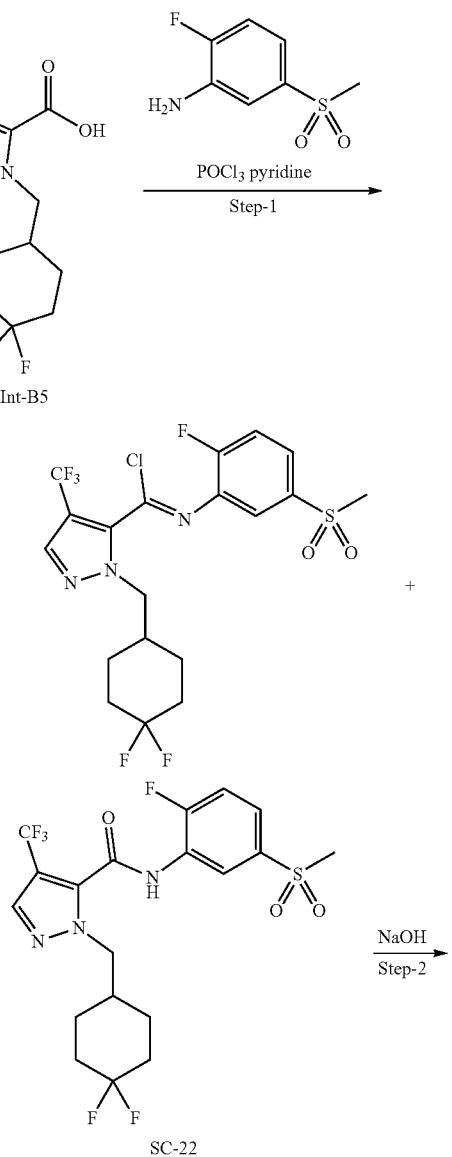

SC-22

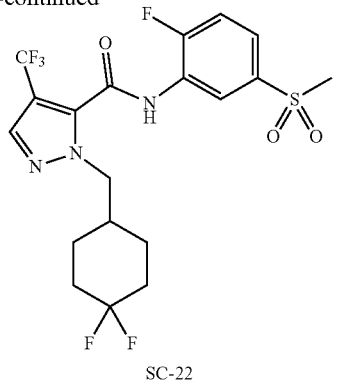

SC-22

Step-1: To a solution of 1-((4,4-difluorocyclohexyl)methyl)-4-(trifluoromethyl)-1H-pyrazole-5-carboxylic acid (Int-B5) (0.1 g, 0.32 mmol, 1.00 eq.) and 2-fluoro-5-methanesulfonylaniline (0.073 g, 0.384 mmol) in pyridine (5.0 mL) was added POCl$_3$ (0.12 mL, 1.28 mmol) dropwise at −10° C. The reaction mixture was stirred at ambient temperature for 3 h, was then quenched with ice-cold water and the aqueous part was extracted with EtOAc (3×30 mL). The combined organic layers were washed with brine, dried over Na$_2$SO$_4$ and concentrated under reduced pressure. The resulting crude residue was purified by flash column chromatography (0-50% EtOAc in hexanes) to obtain 1-[(4,4-difluorocyclohexyl)methyl]-N-(2-fluoro-5-methanesulfonylphenyl)-4-(trifluoromethyl)-1H-pyrazole-5-carbonimidoyl chloride (0.04 g) and 1-[(4,4-difluorocyclohexyl)methyl]-N-(2-fluoro-5-methanesulfonylphenyl)-4-(trifluoromethyl)-1H-pyrazole-5-carboxamide (SC-22, 0.01 g).

Step-2: A mixture of 1-[(4,4-difluorocyclohexyl)methyl]-N-(2-fluoro-5-methanesulfonylphenyl)-4-(trifluoromethyl)-1H-pyrazole-5-carbonimidoyl chloride (0.04 g, 1.00 eq.), THF (1.0 mL) and 1M aq. NaOH (0.5 mL) was stirred at ambient temperature for 7 h. The reaction mixture was diluted with water and extracted with EtOAc (3×30 mL). The combined organic layers were washed with brine, dried over Na$_2$SO$_4$ and the resulting crude was mixed with SC-22 of step-1 (0.01 g) and purified initially by flash column chromatography (silica gel, 50% EtOAc in hexanes) and then by preparative TLC (50% EtOAc in hexanes) to obtain 1-[(4,4-difluorocyclohexyl)methyl]-N-(2-fluoro-5-methanesulfonylphenyl)-4-(trifluoromethyl)-1H-pyrazole-5-carboxamide (SC-22). Yield: 19% after 2 steps (0.03 g, 0.062 mmol). $^1$H NMR (400 MHz, DMSO-d6): δ (ppm)=11.18 (s, 1H), 8.41 (d, 1H), 8.05 (s, 1H), 7.87 (bs, 1H), 7.65 (t, 1H), 4.18 (d, 2H), 3.27 (s, 3H), 2.09-1.91 (m, 3H), 1.81-1.68 (m, 2H), 1.65-1.59 (m, 2H), 1.29-1.21 (m, 2H). LCMS: m/z [M+H]$^+$=484.2 (calc.=484.1).

Synthesis of 1-(cyclohexylmethyl)-N-(2-oxo-1,2-dihydropyridin-4-yl)-4-(trifluoromethyl)-1H-pyrazole-5-carboxamide (SC-30)

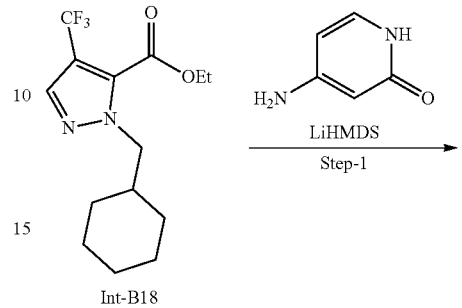

Int-B18

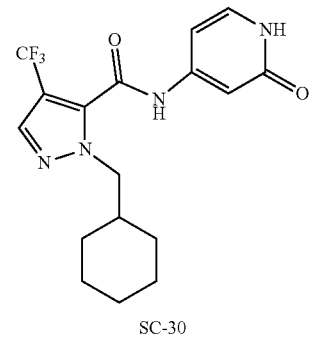

SC-30

Step-1: To a stirred solution of 4-aminopyridin-2(1H)-one (97.7 mg, 0.887 mmol, 1.8 eq.) in THF (6 mL) was added LiHMDS (1M in THF, 0.88 mL, 0.887 mmol, 1.8 eq.) at 0° C. under an argon atmosphere. The reaction mixture was stirred for 10 min and then ethyl 1-(cyclohexylmethyl)-4-(trifluoromethyl)-1H-pyrazole-5-carboxylate (Int-B18) (150 mg, 0.492 mmol, 1.0 eq.) was added dropwise at the same temperature. The reaction mixture was warmed to ambient temperature and stirred for 18 h. The reaction mixture was cooled to 0° C., diluted with ice-cold water (10 mL), acidified with 1N aq. HCl up to pH=3 and extracted with EtOAc (3×20 mL). The combined organic layers were dried over anhydrous Na$_2$SO$_4$ and concentrated under reduced pressure. The crude product was purified by flash column chromatography on silica gel (100-200 mesh) using 0-15% MeOH in DCM as an eluent to afford 1-(cyclohexylmethyl)-N-(2-oxo-1,2-dihydropyridin-4-yl)-4-(trifluoromethyl)-1H-pyrazole-5-carboxamide (SC-30) (80 mg; 44%). $^1$H NMR (400 MHz, DMSO-d6): δ (ppm)=11.40 (s, 1H), 11.02 (s, 1H), 8.04 (s, 1H), 7.36 (d, 1H), 6.72 (d, J=1.6 Hz, 1H), 6.36 (dd, 1H), 4.02 (d, 2H), 1.84-1.77 (m, 1H), 1.64-1.48 (m, 5H), 1.19-1.09 (m, 3H), 0.97-0.88 (m, 2H). LCMS: m/z [M+H]$^+$=369.2 (calc.=369.2).

Synthesis of N-(3-carbamoyl-4-fluorophenyl)-1-(cyclohexylmethyl)-4-(trifluoromethyl)-1H-pyrazole-5-carboxamide (SC-35)

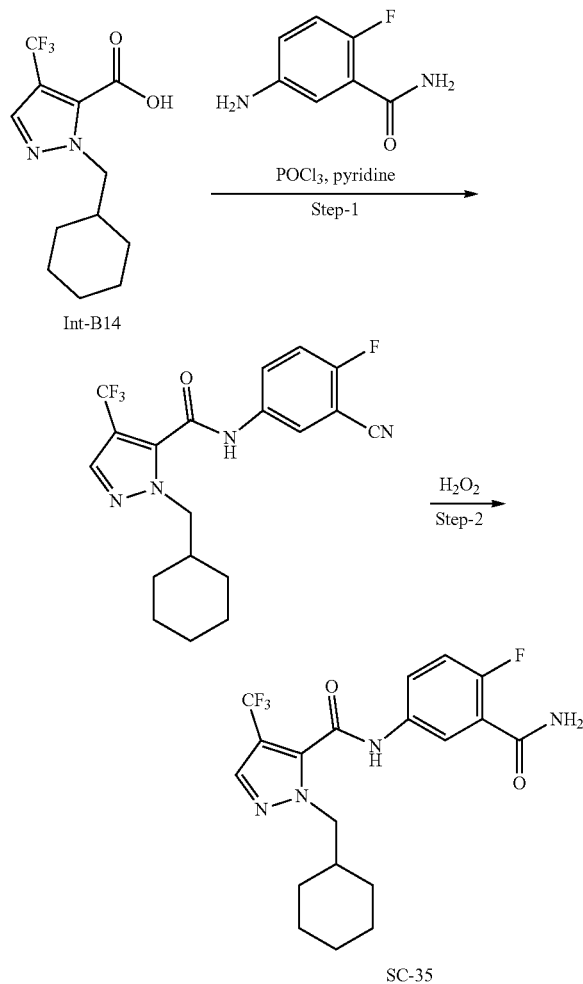

Int-B14

SC-35

Step-1: To a solution of 1-(cyclohexylmethyl)-4-(trifluoromethyl)-1H-pyrazole-5-carboxylic acid (Int-B14) (200 mg, 0.726 mmol, 1.00 eq.) in pyridine (4 mL) was added POCl$_3$ (0.136 mL, 1.452 mmol, 2 eq.) dropwise at 0° C. under an argon atmosphere. The reaction mixture was stirred for 10 min and subsequently 5-amino-2-fluorobenzamide (169.6 mg, 1.089 mmol, 1.5 eq.) was added at the same temperature. The reaction mixture was allowed to warm up to ambient temperature and was stirred for 3 h. The reaction mixture was cooled to 0° C., diluted with ice-cold water (15 mL), acidified with 1N aq. HCl up to pH=3 and extracted with EtOAc (2×40 mL). The combined organic layers were dried over anhydrous Na$_2$SO$_4$ and concentrated under reduced pressure to afford crude N-(3-cyano-4-fluorophenyl)-1-(cyclohexylmethyl)-4-(trifluoromethyl)-1H-pyrazole-5-carboxamide (165 mg).

Step-2: To a solution of crude N-(3-cyano-4-fluorophenyl)-1-(cyclohexylmethyl)-4-(trifluoromethyl)-1H-pyrazole-5-carboxamide (160 mg, 0.406 mmol, 1.00 eq.) in DMSO (4 mL) was added K$_2$CO$_3$ (84.04 mg, 0.609 mmol, 1.50 eq.) at 0° C. under argon atmosphere. The resulting reaction mixture was stirred for 10 min and then 30% H$_2$O$_2$ in water (0.65 mL) was added dropwise at the same temperature. The reaction mixture was allowed to warm up to ambient temperature and stirred for 4 h. The reaction mixture was diluted with water (25 mL) and extracted with EtOAc (2×30 mL). The combined organic layers were dried over anhydrous Na$_2$SO$_4$ and concentrated under reduced pressure to afford N-(3-carbamoyl-4-fluorophenyl)-1-(cyclohexylmethyl)-4-(trifluoromethyl)-1H-pyrazole-5-carboxamide (SC-35) (46 mg, 15% over two steps). $^1$H NMR (400 MHz, DMSO-d6): δ (ppm)=11.08 (s, 1H), 8.02 (s, 1H), 7.95 (dd, 1H), 7.76-7.72 (m, 3H), 7.32 (t, 1H), 4.04 (d, 2H), 1.87-1.81 (m, 1H), 1.64-1.49 (m, 5H), 1.24-1.08 (m, 3H), 0.97-0.89 (m, 2H). LCMS: m/z [M−H]$^-$=411.1 (calc.=411.1).

Synthesis of 3,4-dimethyl-N-(3-sulfamoylphenyl)-1-((tetrahydro-2H-pyran-4-yl)methyl)-1H-pyrazole-5-carboxamide (SC-45)

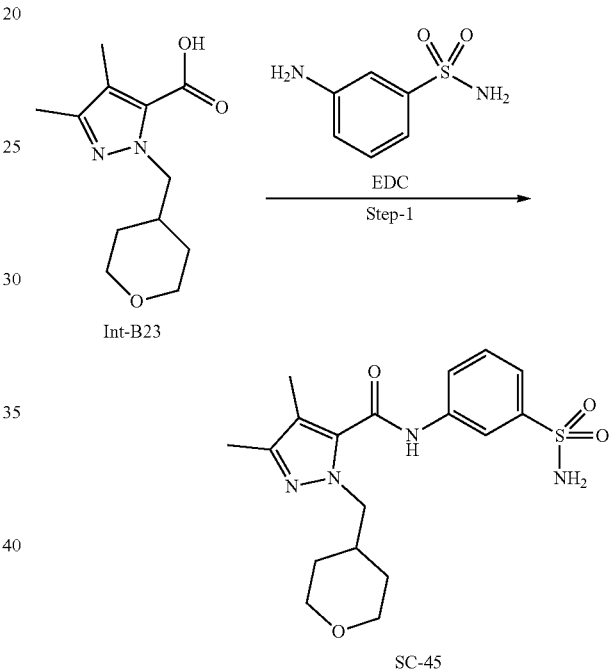

Int-B23

SC-45

Step-1: To a solution of 3,4-dimethyl-1-((tetrahydro-2H-pyran-4-yl)methyl)-1H-pyrazole-5-carboxylic acid (Int-B23) (180 mg, 0.75 mmol, 1.00 eq.) in pyridine (5 mL) were added 3-aminobenzene-1-sulfonamide (195 mg, 1.13 mmol, 1.50 eq.) and EDCHCl (218 mg, 1.13 mmol, 1.50 eq.) at 0° C. The reaction mixture was stirred at ambient temperature for 16 h. The reaction mixture was diluted with water (50 mL) and extracted with 10 vol % MeOH in DCM (3×100 mL). The organic layers were dried over anhydrous Na$_2$SO$_4$ and concentrated under reduced pressure to give the crude product which was purified by flash column chromatography (silica gel; 50-60% EtOAc in hexanes) to yield 3,4-dimethyl-N-(3-sulfamoylphenyl)-1-((tetrahydro-2H-pyran-4-yl)methyl)-1H-pyrazole-5-carboxamide (SC-45). Yield: 58% (172 mg, 0.212 mmol). $^1$H NMR (400 MHz, DMSO-d6): δ (ppm)=10.54 (s, 1H), 8.31 (s, 1H), 7.78 (d, 1H), 7.58-7.52 (m, 2H), 7.39 (s, 1H), 4.06 (d, 2H), 3.80-3.77 (m, 1H), 3.23-3.18 (m, 2H), 2.12 (s, 3H), 2.07 (m, 3H), 2.01-1.96 (m, 1H), 1.40-1.36 (m, 2H), 1.23-1.13 (m, 2H). LCMS: m/z [M+H]$^+$=393.2 (calc.=393.2).

The following examples were synthesized in analogy to the procedures described above using appropriate reactants and adjusted purification protocols:

| Ex. No. | Structure | Procedure | Reactants | Analytical data |
|---|---|---|---|---|
| SC-02 | 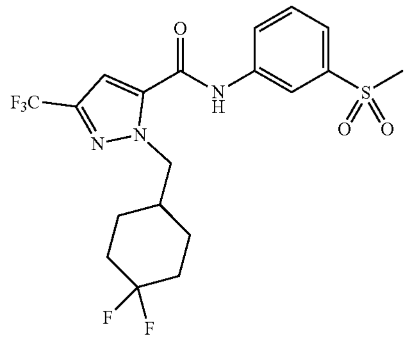 [SMILES: CS(=O)(=O)c1cccc(NC(=O)c2cc(C(F)(F)F)nn2CC2CCC(F)(F)CC2)c1] | in analogy to SC-01 | Int-B2, 3-(methylsulfonyl)aniline | ¹H NMR (400 MHz, DMSO-d6): δ (ppm) = 10.75 (bs, 1H), 8.33 (s, 1H), 8.07-8.05 (m, 1H), 7.73-7.65 (m, 2H), 7.60 (s, 1H), 4.55 (d, 1H), 3.23 (s, 3H), 2.07-1.98 (m, 3H), 1.85-1.70 (m, 2H), 1.60-1.58 (m, 2H), 1.32-1.17 (m, 2H). LCMS: m/z [M + H]⁺ = 466 (calc. = 466). |
| SC-03 | 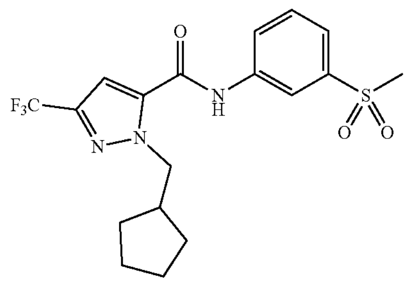 [SMILES: CS(=O)(=O)c1cccc(NC(=O)c2cc(C(F)(F)F)nn2CC2CCCC2)c1] | in analogy to SC-01 | Int-B3, 3-(methylsulfonyl)aniline | ¹H NMR (400 MHz, DMSO-d6): δ (ppm) = 10.76 (s, 1H), 8.34 (s, 1H), 8.05 (d, 1H), 7.72-7.65 (m, 2H), 7.56 (s, 1H), 4.54 (d, 2H), 3.22 (s, 3H), 2.45-2.38 (m, 1H), 1.59-1.48 (m, 6H), 1.28-1.25 (m, 2H). LCMS: m/z [M + H]⁺ = 416.4 (calc. = 416.1). |
| SC-04 | 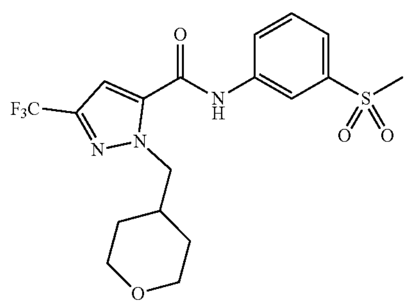 [SMILES: CS(=O)(=O)c1cccc(NC(=O)c2cc(C(F)(F)F)nn2CC2CCOCC2)c1] | in analogy to SC-01 | Int-B4, 3-(methylsulfonyl)aniline | ¹H NMR (400 MHz, DMSO-d6): δ (ppm) = 10.75 (s, 1H), 8.34 (s, 1H), 8.06 (d, 1H), 7.73-7.65 (m, 2H), 7.60 (s, 1H), 4.52 (d, 2H), 3.83-3.79 (m, 2H), 3.29-3.21 (m, 5H), 2.17-2.11 (m, 1H), 1.39-1.37 (m, 2H), 1.33-1.23 (m, 2H). LCMS: m/z [M + H]⁺ = 432.4 (calc. = 432.1). |
| SC-05 | 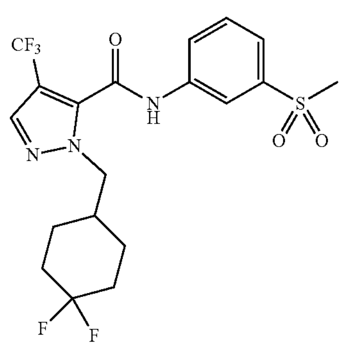 [SMILES: CS(=O)(=O)c1cccc(NC(=O)c2c(C(F)(F)F)cnn2CC2CCC(F)(F)CC2)c1] | in analogy to SC-01 | Int-B5, 3-(methylsulfonyl)aniline | ¹H NMR (400 MHz, DMSO-d6): δ (ppm) = 11.34 (s, 1H), 8.30 (s, 1H), 8.07 (s, 1H), 7.91 (d, 1H), 7.75 (d, 1H), 7.71-7.67 (m, 1H), 4.15 (d, 1H), 3.24 (s, 3H), 2.07-1.97 (m, 3H), 1.83-1.68 (m, 2H), 1.63-1.59 (m, 2H), 1.28-1.20 (m, 2H). LCMS: m/z [M + H]⁺ = 466.4 (calc. = 466.1). |

| Ex. No. | Structure | Procedure | Reactants | Analytical data |
|---|---|---|---|---|
| SC-06 | 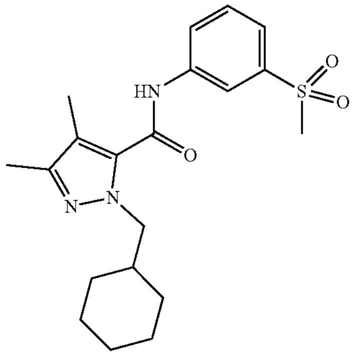 [SMILES: Cc1nn(CC2CCCCC2)c(C(=O)Nc2cccc(S(C)(=O)=O)c2)c1C] | in analogy to SC-01 | Int-B6, 3-(methyl-sulfonyl)aniline | $^1$H NMR (400 MHz, DMSO-d6): δ (ppm) = 10.60 (s, 1H), 8.37 (s, 1H), 7.94-7.92 (m, 1H), 7.69-7.62 (m, 2H), 4.02 (d, 2H), 3.22 (s, 3H), 2.12-2.07 (m, 6H), 1.75-1.69 (m, 1H), 1.62-1.56 (m, 3H), 1.48 (d, 2H), 1.13-1.06 (m, 3H), 0.93-0.90 (m, 2H). LCMS: m/z [M + H]$^+$ = 390.3 (calc. = 390.2). |
| SC-08 | 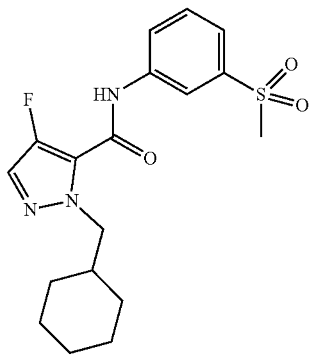 [SMILES: CS(=O)(=O)c1cccc(NC(=O)c2c(F)cnn2CC2CCCCC2)c1] | in analogy to SC-01 | Int-B24, 3-(methyl-sulfonyl)aniline | $^1$H NMR (400 MHz, DMSO-d6): δ (ppm) = 10.74 (bs, 1H), 8.33 (s, 1H), 7.96 (d, 1H), 7.70-7.63 (m, 3H), 4.19 (d, 2H), 3.22 (s, 3H), 1.77 (bs, 1H), 1.62-1.57 (m, 3H), 1.47 (d, 2H), 1.12-1.10 (m, 3H), 0.97-0.91 (m, 2H). LCMS: m/z [M + H]$^+$ = 380.3 (calc. = 380.2). |
| SC-11 | 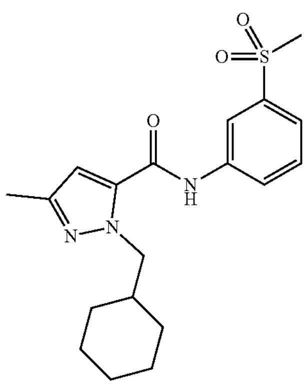 | in analogy to SC-10 | Int-B8, 3-(methyl-sulfonyl)aniline | $^1$H NMR (400 MHz, DMSO-d6): δ (ppm) = 10.47 (s, 1H), 8.35 (d, 1H), 8.05-8.02 (m, 1H), 7.68-7.61 (m, 2H), 6.86 (s, 1H), 4.30 (d, 2H), 3.21 (s, 3H), 2.22 (s, 3H), 1.82-1.76 (m, 1H), 1.63-1.46 (m, 5H), 1.13-1.11 (m, 3H), 0.99-0.93 (m, 2H). LCMS: m/z [M + H]$^+$ = 376.1 (calc. = 376.2). |
| SC-12 | 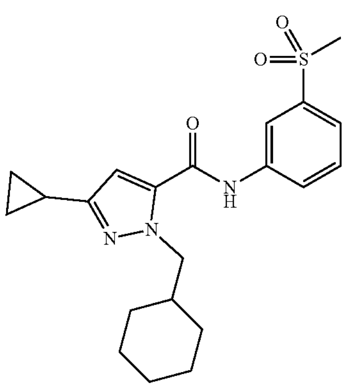 [SMILES: CS(=O)(=O)c1cccc(NC(=O)c2cc(C3CC3)nn2CC2CCCCC2)c1] | in analogy to SC-10 | Int-B9, 3-(methyl-sulfonyl)aniline | $^1$H NMR (400 MHz, DMSO-d6) δ (ppm) = 10.44 (s, 1H), 8.33 (d, 1H), 8.06-8.03 (m, 2H), 7.68-7.61 (m, 2H), 6.75 (s, 1H), 4.28 (d, 2H), 3.21 (s, 3H), 1.94-1.89 (m, 1H), 1.80-1.76 (m, 1H), 1.64-1.62 (m, 3H), 1.48-1.45 (m, 2H), 1.19-1.15 (m, 3H), 0.98-0.89 (m, 4H), 0.89-0.67 (m, 2H). LCMS: m/z [M + H]$^+$ = 402.1 (calc. = 402.2). |

| Ex. No. | Structure | Procedure | Reactants | Analytical data |
|---|---|---|---|---|
| SC-13 | 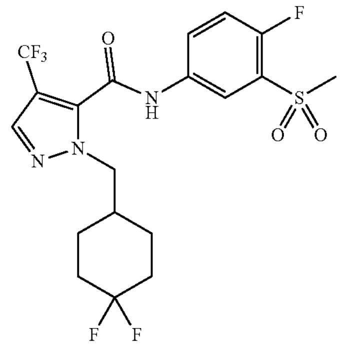 [SMILES: CS(=O)(=O)c1cc(NC(=O)c2c(C(F)(F)F)cnn2CC2CCC(F)(F)CC2)ccc1F] | in analogy to SC-01 | Int-B5, 4-fluoro-3-methane-sulfonyl-aniline | $^1$H NMR (400 MHz, DMSO-d6): δ (ppm) = 11.35 (s, 1H), 8.29 (s, 1H), 8.08 (s, 1H), 7.98 (s, 1H), 7.58 (t, 1H), 4.14 (d, 2H), 3.31 (t, 3H), 1.98 (m, 3H), 1.80-1.71 (m, 2H), 1.61-1.58 (m, 2H), 1.24-1.22 (m, 2H). LCMS: m/z [M + H]$^+$ = 484.2 (calc. = 484.1). |
| SC-14 | 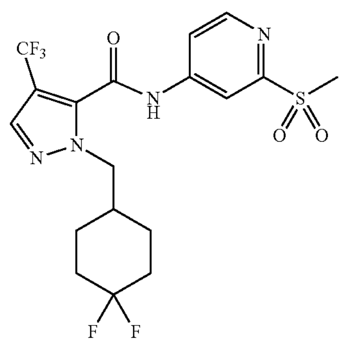 [SMILES: CS(=O)(=O)c1cc(NC(=O)c2c(C(F)(F)F)cnn2CC2CCC(F)(F)CC2)ccn1] | in analogy to SC-01 | Int-B5, 2-methane-sulfonyl-pyridin-4-amine | $^1$H NMR (400 MHz, DMSO-d6): δ (ppm) = 11.78 (s, 1H), 8.73 (d, 2H), 8.38 (s, 1H), 8.11 (s, 1H), 7.86 (s, 1H), 4.16 (d, 2H), 3.47-3.21 (m, 3H), 1.98-1.97 (m, 3H), 1.85-1.68 (m, 2H), 1.60-1.57 (m, 2H), 1.28-1.22 (m, 2H). LCMS: m/z [M + H]$^+$ = 467.2 (calc. = 467.1). |
| SC-15 | 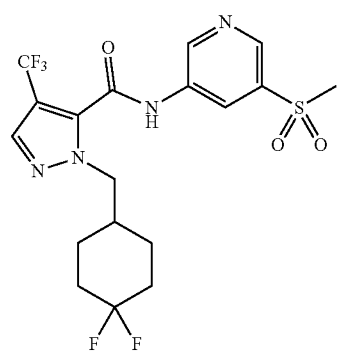 [SMILES: CS(=O)(=O)c1cncc(NC(=O)c2c(C(F)(F)F)cnn2CC2CCC(F)(F)CC2)c1] | in analogy to SC-01 | Int-B5, 5-(methyl-sulfonyl)pyridin-3-amine | $^1$H NMR (400 MHz, DMSO-d6): δ (ppm) = 11.62 (s, 1H), 9.02 (s, 1H), 8.92 (s, 1H), 8.68 (s, 1H), 8.11 (s, 1H), 4.17 (d, 2H), 3.38-3.20 (m, 3H), 2.07-1.99 (m, 3H), 1.80-1.69 (m, 2H), 1.61-1.58 (m, 2H), 1.26-1.23 (m, 2H). LCMS: m/z [M + H]$^+$ = 467.2 (calc. = 467.1). |
| SC-16 | 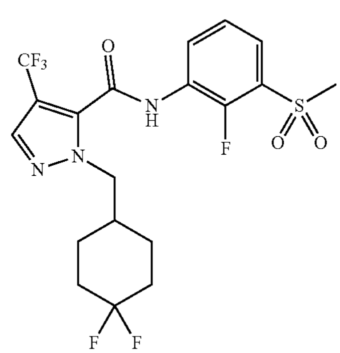 [SMILES: CS(=O)(=O)c1cccc(NC(=O)c2c(C(F)(F)F)cnn2CC2CCC(F)(F)CC2)c1F] | in analogy to SC-01 | Int-B5, 2-fluoro-3-methane-sulfonyl-aniline | $^1$H NMR (400 MHz, DMSO-d6): δ (ppm) = 11.18 (bs, 1H), 8.11 (t, 1H), 8.02 (s, 1H), 7.70 (bs, 1H), 7.48 (t, 1H), 4.20 (d, 2H), 3.42-3.28 (m, 3H), 2.07-1.98 (m, 3H), 1.83-1.75 (m, 2H), 1.69-1.61 (m, 2H), 1.30-1.21 (m, 2H). LCMS: m/z [M + H]$^+$ = 484.2 (calc. = 484.1). |

-continued

| Ex. No. | Structure | Procedure | Reactants | Analytical data |
|---|---|---|---|---|
| SC-17 | 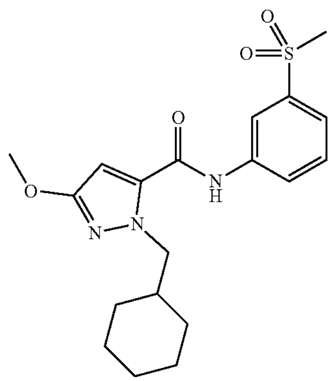 | in analogy to SC-10 | Int-B10, 3-(methyl-sulfonyl) aniline | $^1$H NMR (400 MHz, DMSO-d6): δ (ppm) = 10.47 (s, 1H), 8.32 (d, 1H), 8.06-8.03 (m, 1H), 7.69-7.62 (m, 2H), 6.52 (s, 1H), 4.23 (d, 2H), 3.81 (s, 3H), 3.22 (s, 3H), 1.85-1.75 (m, 1H), 1.64-1.58 (m, 3H), 1.48 (d, 2H), 1.16-0.93 (m, 5H). LCMS: m/z [M + H]$^+$ = 392.1 (calc. = 392.2). |
| SC-18 | 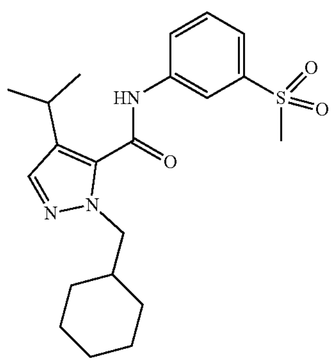 [SMILES: CC(C)c1cnn(CC2CCCCC2)c1C(=O)Nc1cccc(S(C)(=O)=O)c1] | in analogy to SC-01 | Int-B26, 3-(methyl-sulfonyl) aniline | $^1$H NMR (400 MHz, DMSO-d6): δ (ppm) = 10.83 (s, 1H), 8.36 (s, 1H), 7.95 (d, 1H), 7.71-7.64 (m, 2H), 7.43 (s, 1H), 4.05 (d, 2H), 3.23 (s, 3H), 3.09-3.06 (m, 1H), 1.76-1.72 (m, 1H), 1.62-1.45 (m, 5H), 1.17-1.09 (m, 8H), 0.93-0.87 (m, 2H). LCMS: m/z [M + H]$^+$ = 404.3 (calc. = 404.2). |
| SC-19 | 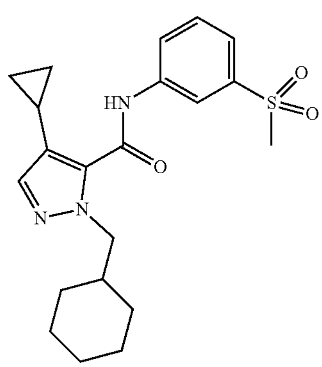 [SMILES: CS(=O)(=O)c1cccc(NC(=O)c2c(C3CC3)cnn2CC2CCCCC2)c1] | in analogy to SC-01 | Int-B27, 3-(methyl-sulfonyl) aniline | $^1$H NMR (400 MHz, DMSO-d6): δ (ppm) = 10740 (s, 1H), 8.39 (s, 1H), 7.95 (d, 1H), 7.70-7.63 (m, 2H), 7.25 (s, 1H), 4.08 (d, 2H), 3.23 (s, 3H), 1.91 (m, 1H), 1.73 (m, 1H), 1.61-1.56 (m, 3H), 1.47 (d, 2H), 1.11-1.09 (m, 3H), 0.91-0.83 (m, 4H), 0.55 (bs, 2H). LCMS: m/z [M + H]$^+$ = 402.2 (calc. = 402.2). |
| SC-23 | 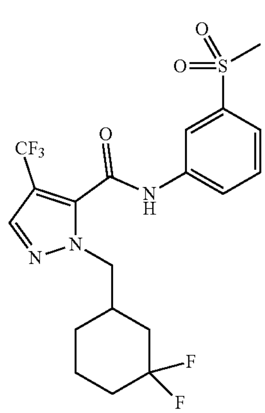 [SMILES: CS(=O)(=O)c1cccc(NC(=O)c2c(C(F)(F)F)cnn2CC2CCCC(F)(F)C2)c1] | in analogy to SC-01 | Int-B11, 3-(methyl-sulfonyl) aniline | $^1$H NMR (400 MHz, DMSO-d6): δ (ppm) = 11.36 (s, 1H), 8.31 (s, 1H), 8.09 (s, 1H), 7.90 (d, 1H), 7.77-7.67 (m, 2H), 4.17 (d, 2H), 3.24 (s, 3H), 2.17 (bs, 1H), 1.93 (bs, 2H), 1.72-1.50 (m, 4H), 1.36-1.33 (m, 1H), 1.10-1.02 (m, 1H). LCMS: m/z [M − H]$^-$ = 464.3 (calc. = 464.1). |

-continued

| Ex. No. | Structure | Procedure | Reactants | Analytical data |
|---|---|---|---|---|
| SC-24 | 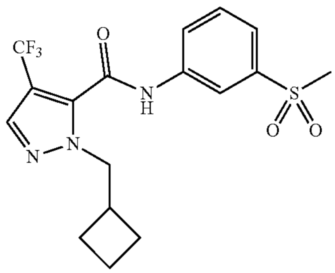 [SMILES: CS(=O)(=O)c1cccc(NC(=O)c2c(C(F)(F)F)cnn2CC2CCC2)c1] | in analogy to SC-01 | Int-B12, 3-(methyl-sulfonyl)aniline | $^1$H NMR (400 MHz, DMSO-d6): δ (ppm) = 11.36 (s, 1H), 8.33 (s, 1H), 8.03 (s, 1H), 7.91 (d, 1H), 7.75 (t, 1H), 7.69 (t, 1H), 4.25 (d, 2H), 3.24 (s, 3H), 2.80-2.70 (m, 1H), 1.94-1.91 (m, 2H), 1.81-1.76 (m, 4H). LCMS: m/z [M − H]$^-$ = 400.0 (calc. = 400.1). |
| SC-25 | 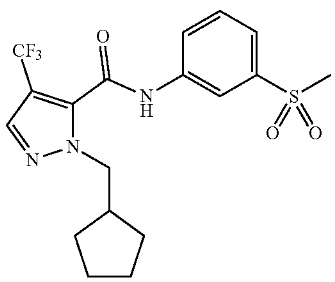 [SMILES: CS(=O)(=O)c1cccc(NC(=O)c2c(C(F)(F)F)cnn2CC2CCCC2)c1] | in analogy to SC-01 | Int-B13, 3-(methyl-sulfonyl)aniline | $^1$H NMR (400 MHz, DMSO-d6): δ (ppm) = 11.35 (s, 1H), 8.31 (s, 1H), 8.04 (s, 1H), 7.91 (d, 1H), 7.75 (d, 1H), 7.69 (t, 1H), 4.14 (d, 2H), 3.24 (s, 3H), 2.42-2.35 (m, 1H), 1.64-1.46 (m, 6H), 1.28-1.21 (m, 2H). LCMS: m/z [M − H]$^-$ = 414.3 (calc. = 414.1). |
| SC-26 | 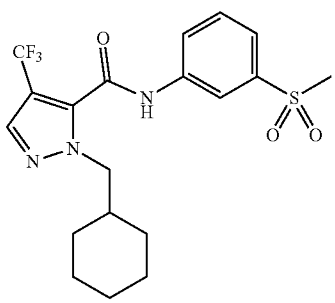 [SMILES: CS(=O)(=O)c1cccc(NC(=O)c2c(C(F)(F)F)cnn2CC2CCCCC2)c1] | in analogy to SC-01 | Int-B14, 3-(methyl-sulfonyl)aniline | $^1$H NMR (400 MHz, DMSO-d6): δ (ppm) = 11.33 (s, 1H), 8.31 (s, 1H), 8.04 (s, 1H), 7.91 (d, 1H), 7.75 (d, 1H), 7.69 (t, 1H), 4.06 (d, 2H), 3.24 (s, 3H), 1.87-1.83 (m, 1H), 1.65-1.49 (m, 5H), 1.17-1.11 (m, 3H), 0.95-0.92 (m, 2H). LCMS: m/z [M − H]$^-$ = 428.0 (calc. = 428.1). |
| SC-27 | 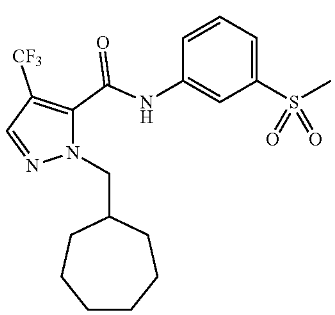 [SMILES: CS(=O)(=O)c1cccc(NC(=O)c2c(C(F)(F)F)cnn2CC2CCCCCC2)c1] | in analogy to SC-01 | Int-B15, 3-(methyl-sulfonyl)aniline | $^1$H NMR (400 MHz, DMSO-d6): δ (ppm) = 11.35 (s, 1H), 8.30 (s, 1H), 8.05 (s, 1H), 7.91 (d, 1H), 7.75 (d, 1H) 7.69 (t, 1H), 4.04 (d, 2H), 3.25 (s, 3H), 2.09-2.07 (m, 1H), 1.59-1.31 (m, 11H), 1.19-1.14 (m, 4H). LCMS: m/z [M − H]$^-$ = 442.1 (calc. = 442.1). |
| SC-28 | 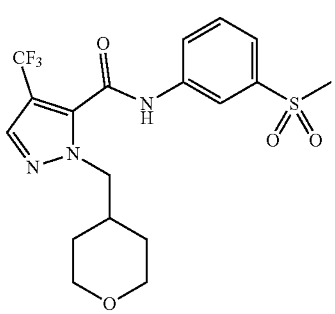 [SMILES: CS(=O)(=O)c1cccc(NC(=O)c2c(C(F)(F)F)cnn2CC2CCOCC2)c1] | in analogy to SC-01 | Int-B16, 3-(methyl-sulfonyl)aniline | $^1$H NMR (400 MHz, DMSO-d6): δ (ppm) = 11.34 (s, 1H), 8.30 (s, 1H), 8.04 (s, 1H), 7.89 (d, 1H), 7.72-7.67 (m, 2H), 4.15 (d, 2H), 3.80 (dd, 2H), 3.25-3.18 (m, 5H), 2.14-2.07 (m, 1H), 1.40 (d, 2H), 1.28-1.18 (m, 2H). LCMS: m/z [M − H]$^-$ = 430.0 (calc. = 430.1). |

| Ex. No. | Structure | Procedure | Reactants | Analytical data |
|---|---|---|---|---|
| SC-29 | (structure) | in analogy to SC-01 | Int-B17, 3-(methyl-sulfonyl)aniline | ¹H NMR (400 MHz, DMSO-d6): δ (ppm) = 11.31 (s, 1H), 8.33 (s, 1H), 8.06 (s, 1H), 7.91 (d, 1H), 7.77-7.67 (m, 2H), 4.10-4.06 (m, 1H), 3.25 (s, 3H), 1.80-1.78 (m, 2H), 171-1.67 (m, 1H), 1.62-1.52 (m, 2H), 1.46 (d, 3H), 1.25-1.18 (m, 1H), 1.12-1.02 (m, 3H), 0.90-0.82 (m, 2H). LCMS: m/z [M − H]⁻ = 442.1 (calc. = 442.1). |
| SC-31 | (structure) | in analogy to SC-30 | Int-B19, 4-amino-pyridin-2(1H)-one | ¹H NMR (400 MHz, DMSO-d6): δ (ppm) = 11.39 (s, 1H), 11.02 (s, 1H), 8.02 (s, 1H), 7.35 (d, 1H), 6.70 (s, 1H), 6.34 (dd, 1H), 3.99 (d, 2H), 2.04-2.02 (m, 1H), 1.57-1.37 (m, 8H), 1.34-1.18 (m, 2H), 1.093-1.087 (m, 2H). LCMS: m/z [M + H]⁺ = 383.2 (calc. = 383.2). |
| SC-32 | (structure) | in analogy to SC-30 | Int-B20, 4-amino-pyridin-2(1H)-one | ¹H NMR (400 MHz, DMSO-d6): δ (ppm) = 11.40 (s, 1H), 11.00 (s, 1H), 8.05 (s, 1H), 7.35 (d, 1H), 6.74 (s, 1H), 6.36 (d, 1H), 4.03-4.00 (m, 1H), 1.81-1.65 (m, 3H), 1.65-1.52 (m, 2H), 1.48-1.42 (m, 3H), 1.25-1.11 (m, 1H), 1.12-1.00 (m, 3H), 0.99-0.75 (m, 2H). LCMS: m/z [M + H]⁺ = 383.4 (calc. = 383.2). |
| SC-33 | (structure) | in analogy to SC-01 | Int-B14, 3-amino-benzene-sulfonamide | ¹H NMR (400 MHz, DMSO-d6): δ (ppm) = 11.24 (s, 1H), 8.26 (s, 1H), 8.03 (s, 1H), 7.76 (d, 1H), 7.62-7.59 (m, 2H), 7.44 (s, 2H), 4.05 (d, 2H), 1.88-1.82 (m, 1H), 1.65-1.50 (m, 5H), 1.16-1.08 (m, 3H), 0.98-0.89 (m, 2H). LCMS: m/z [M − H]⁻ = 429.1 (calc. = 429.1). |
| SC-36 | (structure) | in analogy to SC-01 | Int-B14, 1-(methyl-sulfonyl)-1H-pyrazol-4-amine | ¹H NMR (400 MHz, DMSO-d6): δ (ppm) = 11.41 (s, 1H), 8.46 (s, 1H), 8.04 (s, 1H), 8.02 (s, 1H), 4.02 (d, 2H), 3.59 (s, 3H), 1.85-1.79 (m, 1H), 1.64-1.58 (m, 3H), 1.46 (d, 2H), 1.19-1.07 (m, 3H), 0.95-0.86 (m, 2H). LCMS: m/z [M − H]⁻ = 418.0 (calc. = 418.1). |

| Ex. No. | Structure | Procedure | Reactants | Analytical data |
|---|---|---|---|---|
| SC-37 | 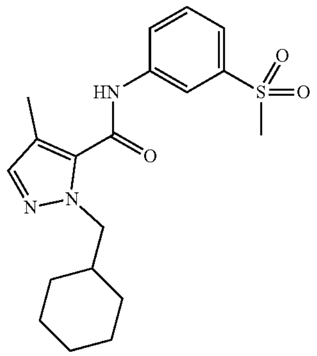 [SMILES: Cc1cnn(CC2CCCCC2)c1C(=O)Nc1cccc(S(C)(=O)=O)c1] | in analogy to SC-01 | Int-B28, 3-(methyl-sulfonyl)aniline | ¹H NMR (400 MHz, DMSO-d6): δ (ppm) = 10.61 (s, 1H), 8.37 (s, 1H), 7.95 (d, 1H), 7.37 (s, 1H), 4.11 (d, 2H), 3.22 (s, 3H), 2.17 (s, 3H), 1.77-1.71 (m, 1H), 1.61-1.56 (m, 3H), 1.49-1.46 (m, 2H), 1.17-1.09 (m, 3H), 0.95-0.86 (m, 2H). LCMS: m/z [M + H]⁺ = 376.4 (calc. = 376.2). |
| SC-38 | 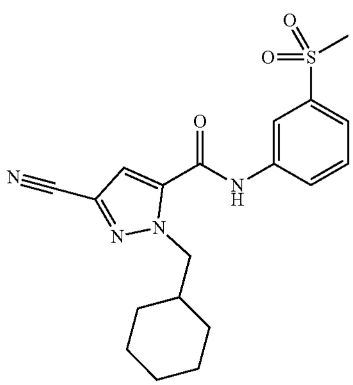 [SMILES: CS(=O)(=O)c1cccc(NC(=O)c2cc(C#N)nn2CC2CCCCC2)c1] | in analogy to SC-10 | Int-B21, 3-(methyl-sulfonyl)aniline | ¹H NMR (400 MHz, DMSO-d6): δ (ppm) = 10.83 (br s, 1H), 8.29 (s, 1H), 7.95 (s, 1H), 7.61-7.58 (m, 3H), 4.51 (d, 2H), 3.20 (s, 3H), 1.88-1.86 (m, 1H), 1.64-1.46 (m, 5H), 1.17-1.02 (m, 5H). LCMS: m/z [M − H]⁻ = 385.1 (calc. = 385.1). |
| SC-39 | 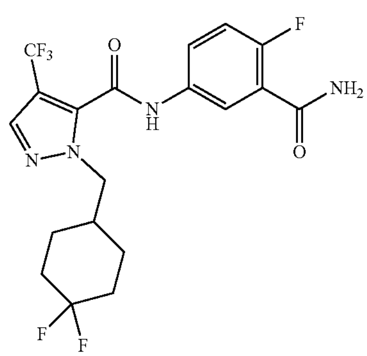 [SMILES: NC(=O)c1cc(NC(=O)c2c(C(F)(F)F)cnn2CC2CCC(F)(F)CC2)ccc1F] | in analogy to SC-21 | Int-B5, methyl 5-amino-2-fluoro-benzoate | ¹H NMR (400 MHz, DMSO-d6): δ (ppm) = 11.09 (s, 1H), 8.05 (s, 1H), 7.97-7.95 (s, 1H), 7.76-7.71 (m, 3H), 7.32 (t, 1H), 4.13 (d, 2H), 1.83-1.75 (m, 3H), 1.71-1.59 (m, 4H), 1.27-1,18 (m, 2H). LCMS: m/z [M + H]⁺ = 449.2 (calc. = 449.1). |
| SC-41 | 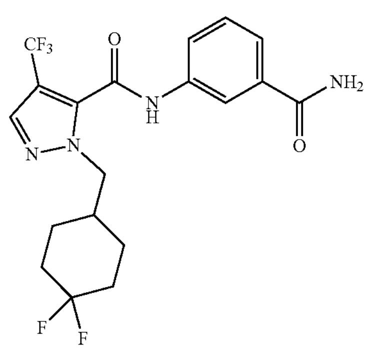 [SMILES: NC(=O)c1cccc(NC(=O)c2c(C(F)(F)F)cnn2CC2CCC(F)(F)CC2)c1] | in analogy to SC-10 | Int-B5, 3-aminobenz-amide | ¹H NMR (400 MHz, DMSO-d6): δ (ppm) = 11.06 (s, 1H), 8.14 (s, 1H), 8.05 (s, 1H), 8.0 (s, 1H), 7.76 (d, 1H), 7.66 (d, 1H), 7.48-7.41 (m, 2H), 4.14 (d, 2H), 2.08, 1.96 (m, 3H), 1.83-1.60 (m, 4H), 1.27-1.19 (m, 2H). LCMS: m/z [M + H]⁺ = 431.2 (calc. = 431.2). |

-continued

| Ex. No. | Structure | Procedure | Reactants | Analytical data |
|---|---|---|---|---|
| SC-42 | 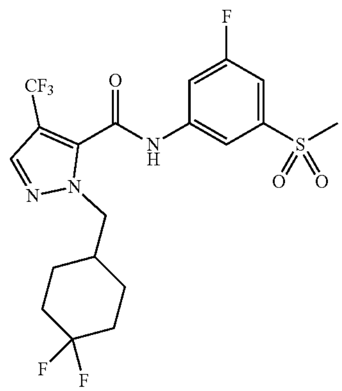 [SMILES: CS(=O)(=O)c1cc(F)cc(NC(=O)c2c(C(F)(F)F)cnn2CC2CCC(F)(F)CC2)c1] | in analogy to SC-01 | Int-B5, 3-fluoro-5-methane-sulfonyl-aniline | ¹H NMR (400 MHz, DMSO-d6): δ (ppm) = 11.54 (bs, 1H), 8.09 (s, 1H), 8.05 (s, 1H), 7.85 (d, 1H), 7.65 (d, 1H), 4.16 (d, J = 6.52 Hz, 2H), 3.31 (s, 3H, masked with H2O peak), 2.09-1.91 (m, 3H), 1.85-1.69 (m, 2H), 1.61-1.52 (m, 2H), 1.25-1.22 (m, 2H). LCMS: m/z [M + H]⁺ = 484.2 (calc. = 484.1). |
| SC-43 | 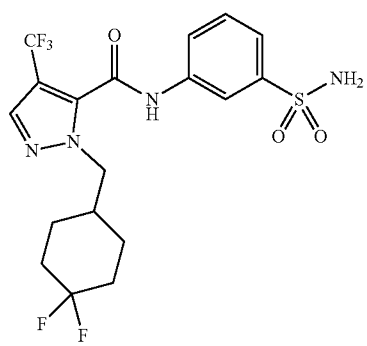 [SMILES: NS(=O)(=O)c1cccc(NC(=O)c2c(C(F)(F)F)cnn2CC2CCC(F)(F)CC2)c1] | in analogy to SC-01 | Int-B5, 3-amino-benzene-1-sulfonamide | ¹H NMR (400 MHz, DMSO-d6): δ (ppm) = 11.25 (s, 1H), 8.26 (s, 1H), 8.07 (s, 1H), 7.77 (d, 1H), 7.64-7.57 (m, 2H), 7.44 (s, 2H), 4.14 (d, 2H), 1.99-1.97 (m, 3H), 1.89-1.69 (m, 2H), 1.68-1.53 (m, 2H), 1.25-1.22 (m, 2H). LCMS: m/z [M + H]⁺ = 467.3 (calc. = 467.1). |
| SC-44 | 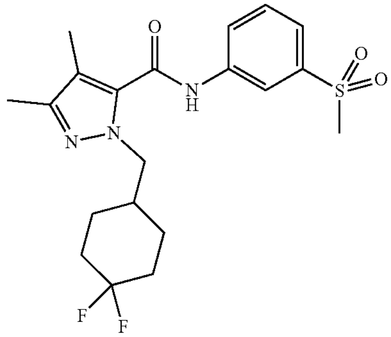 [SMILES: Cc1nn(CC2CCC(F)(F)CC2)c(C(=O)Nc2cccc(S(C)(=O)=O)c2)c1C] | in analogy to SC-01 | Int-B22, 3-(methyl-sulfonyl)aniline | ¹H NMR (400 MHz, DMSO-d6), δ (ppm) = 10.63 (s, 1H), 8.37 (s, 1H), 7.92 (d, 1H), 7.69-7.62 (m, 2H), 4.08 (d, 2H), 3.22 (s, 3H), 2.13 (s, 3H), 2.08 (s, 3H), 1.94 (bs, 3H), 1.81-1.57 (m, 4H), 1.23-1.15 (m, 2H). LCMS: m/z [M + H]⁺ = 426.5 (calc. = 426.2). |
| SC-153 | 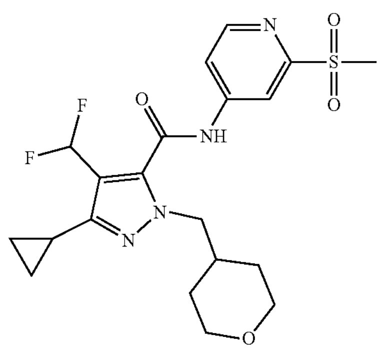 [SMILES: CS(=O)(=O)c1cc(NC(=O)c2c(C(F)F)c(C3CC3)nn2CC2CCOCC2)ccn1] | in analogy to SC-01 | Int-B40, 2-methane-sulfonyl-pyridin-4-amine | ¹H NMR (400 MHz, DMSO-d6): δ (ppm) = 11.56 (s, 1H), 8.72 (d, 1H), 8.39 (s, 1H), 7.87 (d, 1H), 7.28-7.01 (m, 1H), 4.03 (d, 2H), 3.79 (d, 2H), 3.29 (s, 3H), 3.23-3.12 (m, 2H), 2.02-2.01 (m, 2H), 1.36-1.33 (m, 2H), 1.18-1.16 (m, 2H), 0.94-0.93 (m, 2H), 0.82-0.75 (m, 2H). UPLC-MS: m/z [M + H]⁺ = 455.3 (calc. = 455.2). |

| Ex. No. | Structure | Procedure | Reactants | Analytical data |
|---|---|---|---|---|
| SC-196 | 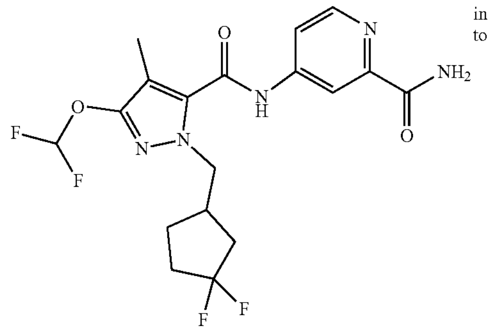 | in analogy to SC-21 | Int-B79, methyl 4-amino-picolinate | ¹H NMR (400 MHz, DMSO-d6): δ (ppm) = 8.56 (d, 1H), 8.36 (d, 1H), 8.10 (s, 1H), 7.85-7.83 (m, 1H), 7.66 (s, 1H), 7.27 (t, 1H), 4.22-4.14 (m, 2H), 2.66-2.55 (m, 1H), 2.13-1.77 (m, 8H), 1.75-1.53 (m, 1H). LCMS: m/z [M + H]⁺ = 430.3 (calc. = 430.2). |
| SC-224 | 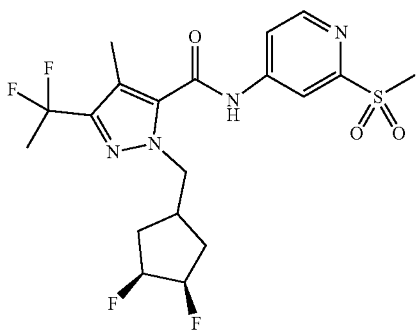 [SMILES: Cc1c(C(C)(F)F)nn(CC2C[C@@H](F)[C@@H](F)C2)c1C(=O)Nc1ccnc(S(C)(=O)=O)c1] | in analogy to SC-01 | Int-B63, 2-methane-sulfonyl-pyridin-4-amine | ¹H NMR (400 MHz, DMSO-d6): δ (ppm) = 11.32 (s, 1H), 8.71 (d, 1H), 8.43 (d, 1H), 7.91 (dd, 1H), 5.06-4.98 (m, 1H), 4.94-4.86 (m, 1H), 4.26 (d, 2H), 3.29 (s, 3H), 2.25 (s, 3H), 2.04 (t, 4H), 1.77-1.56 (m, 4H). LCMS: m/z [M + H]⁺ = 463.2 (calc. = 463.1). |
| SC-226 | 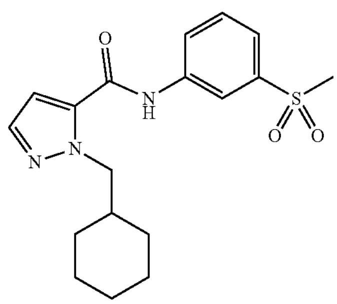 [SMILES: CS(=O)(=O)c1cccc(NC(=O)c2ccnn2CC2CCCCC2)c1] | in analogy to SC-01 | Int-B66, 3-(methyl-sulfonyl) aniline | ¹H NMR (400 MHz, DMSO-d6): δ (ppm) = 10.54 (s, 1H), 8.35 (s, 1H), 8.07 (d, 1H), 7.69-7.63 (m, 2H), 7.58 (d, 1H), 7.10 (s, 1H), 4.40 (d, 2H), 3.22 (s, 3H), 1.86-1.80 (m, 1H), 1.63-1.45 (m, 5 H), 1.03-0.95 (m, 5 H). LCMS: m/z [M + H]⁺ = 362.2 (calc. 362.2). |
| SC-231 | 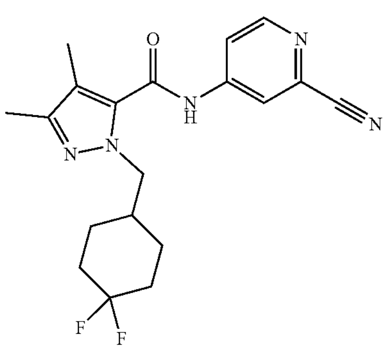 [SMILES: Cc1nn(CC2CCC(F)(F)CC2)c(C(=O)Nc2ccnc(C#N)c2)c1C] | in analogy to SC-01 | Int-B22, 4-amino-picolino-nitrile | ¹H NMR (400 MHz, DMSO-d6), δ (ppm) = 10.97 (s, 1H), 8.65 (d, 1H), 8.20 (d, 1H), 7.92-7.90 (m, 1H), 4.09 (d, 2H), 2.14 (s, 3H), 2.07 (s, 3H), 1.94 (bs, 3H), 1.81-1.69 (m, 2H), 1.58-1.55 (m, 2H), 1.23-1.17 (m, 2H). LCMS: m/z [M + H]⁺ = 374.2 (calc. = 374.2). |

| Ex. No. | Structure | Procedure | Reactants | Analytical data |
|---|---|---|---|---|
| SC-232 | 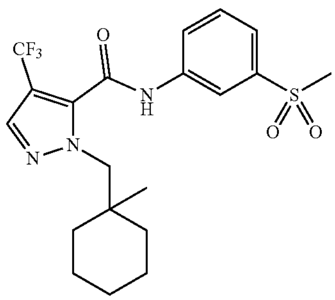 [SMILES: CC1(Cn2ncc(C(F)(F)F)c2C(=O)Nc2cccc(S(C)(=O)=O)c2)CCCCC1] | in analogy to SC-01 | Int-B92, 3-(methyl-sulfonyl)aniline | ¹H NMR (400 MHz, DMSO-d6): δ (ppm) = 11.29 (s, 1H), 8.27 (s, 1H), 8.05 (s, 1H), 7.92-7.90 (m, 1H), 7.76-7.74 (m, 1H), 7.71-7.67 (m, 1H), 4.12 (s, 2H), 3.24 (s, 3H), 1.43-1.23 (m, 10H), 0.83 (s, 3H). LCMS: m/z [M + H]⁺ = 444.3 (calc. 444.2). |
| SC-233 | 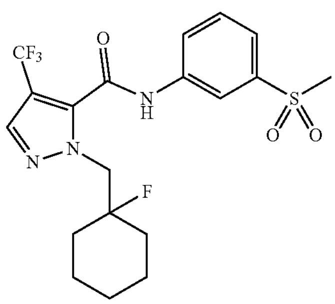 [SMILES: CS(=O)(=O)c1cccc(NC(=O)c2c(C(F)(F)F)cnn2CC2(F)CCCCC2)c1] | in analogy to SC-01 | Int-B93, 3-(methyl-sulfonyl)aniline | ¹H NMR (400 MHz, DMSO-d6): δ (ppm) = 11.24 (brs, 1H), 8.30 (s, 1H), 8.09 (s, 1H), 7.91-7.89 (m, 1H), 7.74-7.73 (m, 1H), 7.69-7.65 (m, 1H), 4.56-4.50 (m, 2H), 3.24 (s, 3H), 1.54-1.40 (m, 9H), 1.26-1.23 (m, 1H). LCMS: m/z [M + H]⁺ = 448.2 (calc. 448.1). |
| SC-234 | 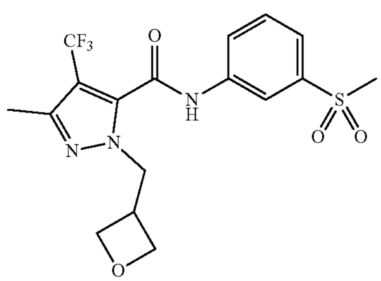 | in analogy to SC-30 | Int-B89 | ¹H NMR (400 MHz, DMSO-d6): δ (ppm) = 11.4 (s, 1H), 8.33 (s, 1H), 7.9-7.88 (d, 1H), 7.76-7.66 (m, 2H), 4.64-4.6 (m, 2H), 4.42-4.39 (m, 4H), 3.45-3.41 (m, 1H), 3.24 (s, 3H), 2.29 (s, 3H). LCMS: m/z [M − H]⁻ = 418.2 (calc. = 418.1). |
| SC-236 | 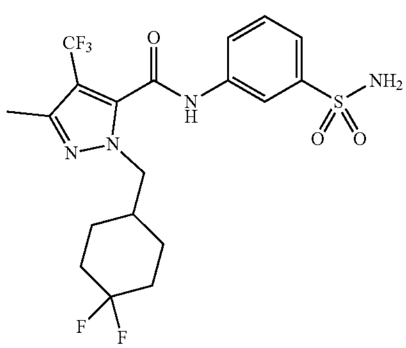 | in analogy to SC-45 | Int-B106, 3-amino-benzene-1-sulfonamide | ¹H NMR (400 MHz, DMSO-d6): δ (ppm) = 10.84 (bs, 1H), 8.29 (s, 1H), 7.82-7.77 (m, 1H), 7.63-7.35 (m, 4H), 4.14 (d, 2H), 2.20 (s, 3H), 2.03-1.90 (m, 3H), 1.85-1.55 (m, 4H), 1.28-1.15 (m, 2H). LCMS: m/z [M + H]⁺ = 447.0 (calc. = 447.1). |
| SC-237 | 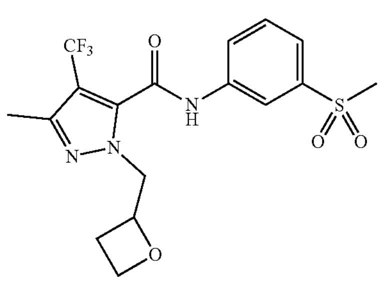 | in analogy to SC-10 | Int-B85 | ¹H NMR (400 MHz, DMSO-d6): δ (ppm) = 11.25 (bs, 1H), 8.30 (s, 1H), 7.89-7.87 (d, 1H), 7.74-7.72 (m, 1H), 7.66 (t, 1H), 5.00-4.97 (m, 1H), 4.47-4.38 (m, 3H), 4.31-4.25 (m, 1H), 3.23 (s, 3H), 2.67-2.63 (m, 1H), 2.41-2.37 (m, 1H), 2.30 (s, 3H). LCMS: m/z [M + H]⁺ = 418.1 (calc. 418.1). |

-continued

| Ex. No. | Structure | Procedure | Reactants | Analytical data |
|---|---|---|---|---|
| SC-241 | 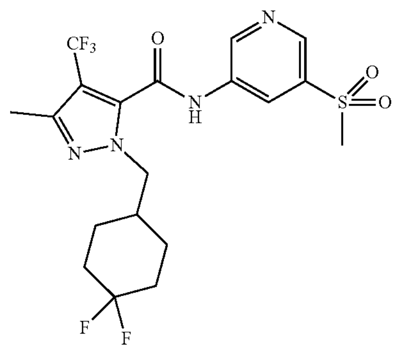 [SMILES: Cc1nn(CC2CCC(F)(F)CC2)c(C(=O)Nc2cncc(S(C)(=O)=O)c2)c1C(F)(F)F] | in analogy to SC-22 | Int-B46, 5-methane-sulfonyl-pyridin-3-amine | $^1$H NMR (400 MHz, DMSO-d6): δ (ppm) = 11.61 (s, 1H), 9.01 (s, 1H), 8.91-8.90 (d, 1H), 8.67 (s, 1H), 4.06-4.04 (d, 2H), 3.37 (s, 3H), 2.32 (s, 3H), 2.09-1.99 (m, 3H), 1.89-1.69 (m, 2H), 1.63-1.59 (m, 2H), 1.28-1.14 (m, 2H). LCMS: m/z [M + H]$^+$ = 481.3 (calc. = 481.1). |
| SC-247R | 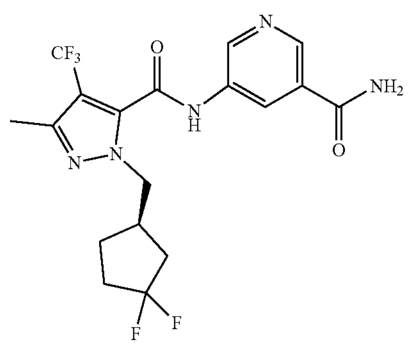 [SMILES: Cc1nn(C[C@@H]2CCC(F)(F)C2)c(C(=O)Nc2cncc(C(N)=O)c2)c1C(F)(F)F] | in analogy to SC-21 | Int-B77R, methyl 5-amino-pyridine-3-carboxylate | $^1$H NMR (400 MHz, DMSO-d6): δ (ppm) = 11.36 (s, 1H), 8.87-8.83 (m, 2H), 8.52 (m, 1H), 8.23 (s, 1H), 7.67 (s, 1H), 4.15 (d, 2H), 2.67-2.63 (m, 1H), 2.31 (s, 3H), 2.18-1.78 (m, 5H), 1.56-1.50 (m, 1H). LCMS: m/z [M + H]$^+$ = 432.3 (calc. = 432.2). |
| SC-247S | 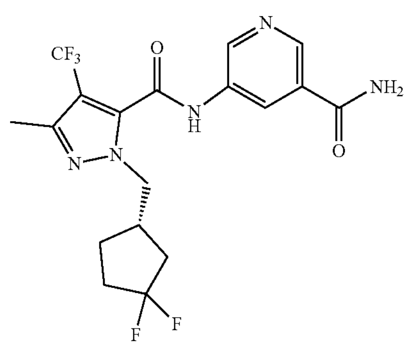 [SMILES: Cc1nn(C[C@H]2CCC(F)(F)C2)c(C(=O)Nc2cncc(C(N)=O)c2)c1C(F)(F)F] | in analogy to SC-21 | Int-B77S, methyl 5-amino-pyridine-3-carboxylate | $^1$H NMR (400 MHz, DMSO-d6): δ (ppm) = 11.34 (s, 1H), 8.88-8.84 (m, 2H), 8.52-8.51 (m, 1H), 8.21 (s, 1H), 7.65 (s, 1H), 4.15-4.13 (m, 2H), 2.67-2.63 (m, 1H), 2.18 (s, 3H), 2.16-1.79 (m, 5H), 1.56-1.51 (m, 1H). LCMS: m/z [M + H]$^+$ = 432.3 (calc. = 432.2). |
| SC-248R | 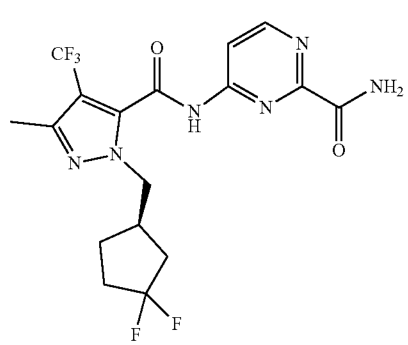 [SMILES: Cc1nn(C[C@@H]2CCC(F)(F)C2)c(C(=O)Nc2ccnc(C(N)=O)n2)c1C(F)(F)F] | in analogy to SC-21 | Int-B77R, methyl 4-amino-2-carboxy-late | $^1$H NMR (400 MHz, DMSO-d6): δ (ppm) = 12.39 (s, 1H), 8.89 (d, 1H), 8.22 (m, 1H), 8.08 (m, 1H), 7.80 (m, 1H), 4.12 (d, 2H), 2.67-2.49 (m, 1H), 2.32 (s, 3H), 2.16-1.78 (m, 5H), 1.54-1.51 (m, 1H). LCMS: m/z [M + H]$^+$ = 433.3 (calc. = 433.1). |

| Ex. No. | Structure | Procedure | Reactants | Analytical data |
|---|---|---|---|---|
| SC-248S | 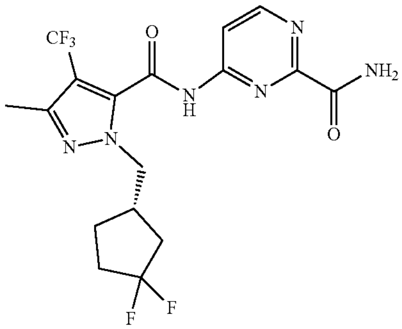 [SMILES: Cc1nn(C[C@H]2CCC(F)(F)C2)c(C(=O)Nc2ccnc(C(N)=O)n2)c1C(F)(F)F] | in analogy to SC-21 | Int-B77S, methyl 4-aminopyrimidine-2-carboxylate | $^1$H NMR (400 MHz, DMSO-d6): δ (ppm) = 12.38 (s, 1H), 8.89-8.88 (m, 1H), 8.22-8.21 (m, 1H), 8.08 (s, 1H), 7.80-7.79 (m, 1H), 4.12-4.10 (m, 2H), 2.66-2.61 (m, 1H), 2.28 (s, 3H), 2.16-2.09 (m, 2H), 2.04-1.95 (m, 2H), 1.82-1.79 (m, 1H), 1.54-1.48 (m, 1H). LCMS: m/z [M + H]$^+$ = 433.3 (calc. = 433.1). |
| SC-249 | 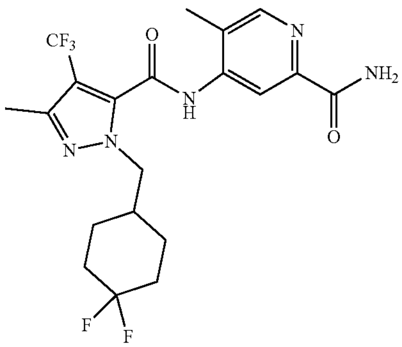 [SMILES: Cc1cnc(C(N)=O)cc1NC(=O)c1c(C(F)(F)F)c(C)nn1CC1CCC(F)(F)CC1] | in analogy to SC-21 | Int-B46, methyl 4-amino-5-methylpyridine-2-carboxylate | $^1$H NMR (400 MHz, DMSO-d6): δ (ppm) = 10.79 (s, 1H), 8.50 (s, 1H), 8.39-8.37 (d, 1H), 8.09 (s, 1H), 7.65 (s, 1H), 4.06-4.04 (d, 2H), 2.31 (s, 6H), 2.00-1.98 (m, 3H), 1.84-1.72 (m, 2H), 1.68-1.64 (m, 2H), 1.30-1.21 (m, 2H). LCMS: m/z [M + H]$^+$ = 460.3 (calc. = 460.2). |
| SC-255 | 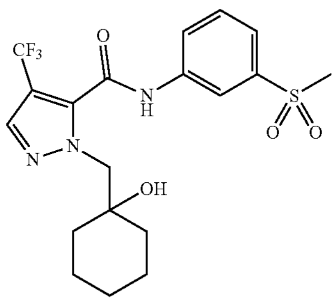 [SMILES: CS(=O)(=O)c1cccc(NC(=O)c2c(C(F)(F)F)cnn2CC2(O)CCCCC2)c1] | Step 1: in analogy to SC-01, step 2: MOM deprotection using PTSA in MeOH, rt | Int-B94, 3-(methylsulfonyl)aniline | $^1$H NMR (400 MHz, DMSO-d6): δ (ppm) = 8.33 (s, 1H), 8.00 (s, 1H), 7.88 (d, 1H), 7.71-7.64 (m, 2H), 4.26 (s, 2H), 3.23 (s, 3H), 1.53-1.49 (m, 2H), 1.47-1.44 (m, 3H), 1.41-1.39 (m, 4H), 1.23-1.21 (m, 1H). LCMS: m/z [M + H]$^+$ = 446.2 (MW calc. 446.1). |
| SC-263 | 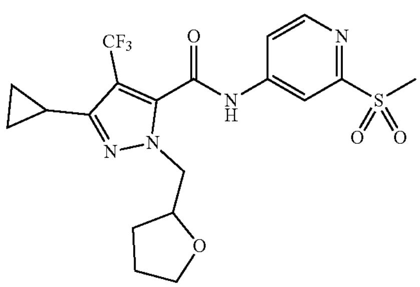 [SMILES: CS(=O)(=O)c1cc(NC(=O)c2c(C(F)(F)F)c(C3CC3)nn2CC2CCCO2)ccn1] | in analogy to SC-22 | Int-B83, 2-methanesulfonylpyridin-4-amine | $^1$H NMR (400 MHz, DMSO-d6): δ (ppm) = 11.69 (s, 1H), 8.69 (d, 1H), 8.37 (s, 1H), 7.86 (d, 1H), 4.23-4.19 (m, 1H), 4.14-4.09 (m, 2H), 3.51 (t, 2H), 1.94-1.87 (m, 2H), 1.75-1.52 (m, 3H), 0.98-0.96 (m, 2H), 0.96-0.95 (m, 2H), 0.84-0.80 (m, 2H). LC-MS: m/z [M − H]$^-$ = 457.2 (calc. = 457.1). |
| SC-264 | 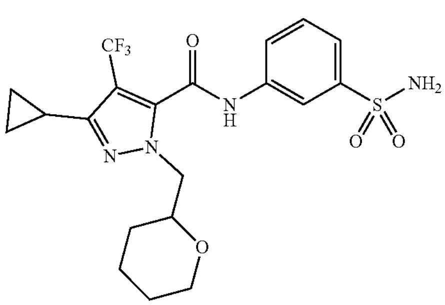 [SMILES: NS(=O)(=O)c1cccc(NC(=O)c2c(C(F)(F)F)c(C3CC3)nn2CC2CCCCO2)c1] | in analogy to SC-45 | Int-B38, 3-aminobenzenesulfonamide | $^1$H NMR (400 MHz, DMSO-d6): δ (ppm) = 11.09 (s, 1H), 8.28 (s, 1H), 7.73 (d, 1H), 7.62-7.55 (m, 2H), 7.43 (s, 2H), 4.09 (d, 2H), 3.77-3.75 (m, 1H), 3.62-3.59 (m, 1H), 3.29-3.23 (m, 1H), 1.9-1.94 (m, 1H), 1.74-1.72 (m, 1H), 1.56-1.53 (m, 1H), 1.44-1.39 (m, 3H), 1.14-1.11 (m, 1H), 0.97-0.94 (m, 2H), 0.85-0.82 (m, 2H). LCMS: m/z [M + H]$^+$ = 473.3 (calc. 473.2); |

| Ex. No. | Structure | Procedure | Reactants | Analytical data |
|---|---|---|---|---|
| SC-265 | 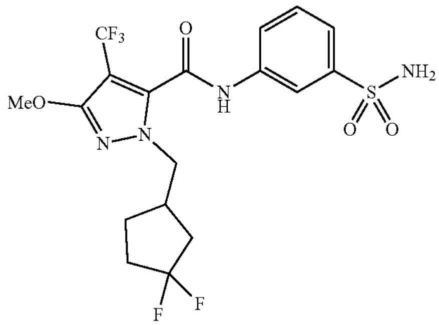 [SMILES: COc1nn(CC2CCC(F)(F)C2)c(C(=O)Nc2cccc(S(N)(=O)=O)c2)c1C(F)(F)F] | in analogy to SC-01 | Int-B41, 3-amino-benzene-sulfonamide | ¹H NMR (400 MHz, DMSO-d6): δ (ppm) = 11.30 (s, 1H), 8.24 (s, 1H), 7.77 (d, 1H), 7.64-7.57 (m, 2H), 7.44 (s, 2H), 4.06 (d, 2H), 3.93 (s, 3H), 2.67-2.64 (m, 1 H), 2.22-1.83 (m, 5H), 1.58-1.56 (m, 1H). LCMS: m/z [M + H]⁺ = 483.2 (calc. = 483.1). |
| SC-275 | 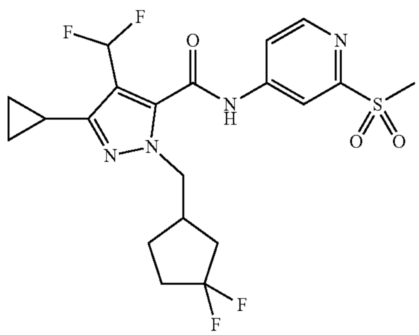 [SMILES: CS(=O)(=O)c1cc(NC(=O)c2c(C(F)F)c(C3CC3)nn2CC2CCC(F)(F)C2)ccn1] | in analogy to SC-01 | Int-B64, 2-methane-sulfonyl pyridin-4-amine | ¹H NMR (400 MHz, DMSO-d6): δ (ppm) = 11.58 (s, 1H), 8.71 (d, 1H), 8.39 (d, 1H), 7.86-7.84 (m, 1H), 7.29-7.02 (m, 1H), 4.14 (d, 2H), 3.29 (s, 3H), 2.58-2.54 (m, 1H), 2.13-2.00 (m, 4H), 1.96-1.89 (m, 1H), 1.76-174 (m, 1H), 1.50-1.45 (m, 1H), 0.96-0.91 (m, 2H), 0.84-0.80 (m, 2H). LCMS: m/z [M + H]⁺ = 475.3 (calc. = 475.1). |
| SC-297 | 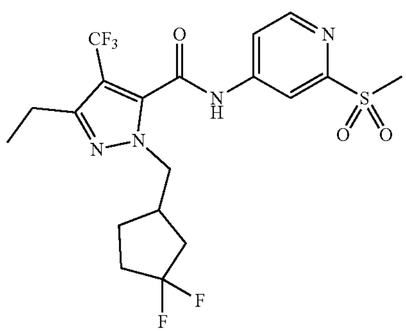 [SMILES: CCc1nn(CC2CCC(F)(F)C2)c(C(=O)Nc2ccnc(S(C)(=O)=O)c2)c1C(F)(F)F] | in analogy to SC-01 | Int-B58, 2-methane-sulfonyl pyridin-4-amine | ¹H NMR (400 MHz, DMSO-d6): δ (ppm) = 11.86 (s, 1H), 8.73 (d, 1H), 8.38 (d, 1H), 7.85-7.84 (m, 1H), 4.16 (d, 2H), 3.30 (s, 3H), 2.72-2.67 (m, 3H), 2.17-2.07 (m, 4H), 1.81-1.78 (m, 1H), 1.53-1.5 (m, 4H), 1.26 (t, 3H). LCMS: m/z [M – H]⁻ = 479.2 (calc. = 479.1). |
| SC-302 | 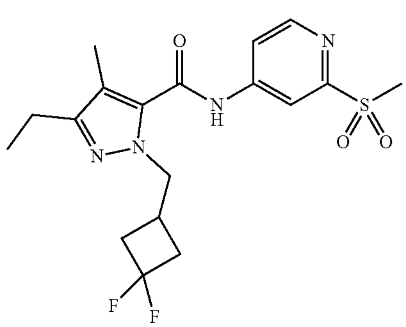 [SMILES: CCc1nn(CC2CC(F)(F)C2)c(C(=O)Nc2ccnc(S(C)(=O)=O)c2)c1C] | in analogy to SC-22 | Int-B70, 2-methane-sulfonyl pyridin-4-amine | ¹H NMR (400 MHz, DMSO-d6): δ (ppm) = 11.09 (s, 1H), 8.68 (d, 1H), 8.44 (s, 1H), 7.91-7.90 (m, 1H), 4.31-4.29 (m, 2H), 3.32-3.28 (m, 3H), 2.62-2.37 (m, 7H), 2.10 (s, 3H), 1.23-1.15 (m, 3H). LCMS: m/z [M + H]⁺ = 413.2 (calc. = 413.2). |

| Ex. No. | Structure | Procedure | Reactants | Analytical data |
|---|---|---|---|---|
| SC-322 | 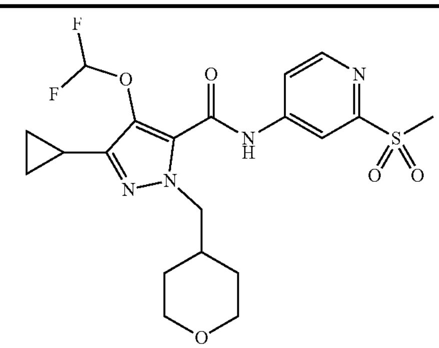 | in analogy to SC-01 | Int-104, 2-methanesulfonyl pyridin-4-amine | $^1$H NMR (400 MHz, DMSO-d6): δ (ppm) = 11.15 (s, 1H), 8.69 (d, 1H), 8.40 (d, 1H), 7.88 (d, 1H), 7.25-6.89 (m, 1H), 4.12 (d, 2H), 3.79-3.77 (m, 2H), 3.29 (s, 3H), 3.24-3.18 (m, 2H), 1.99-1.97 (m, 1H), 1.89-1.85 (m, 1H), 1.36-1.33 (m, 2H), 1.23-1.16 (m, 2H), 0.94-0.89 (m, 2H), 0.81-0.80 (m, 2H). LCMS: m/z [M + H]$^+$ = 471.3 (calc. = 471.2). |
| SC-323 | 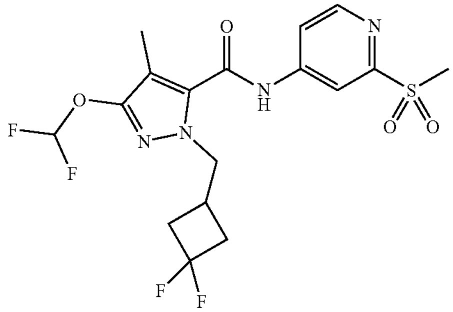 [SMILES: Cc1c(OC(F)F)nn(CC2CC(F)(F)C2)c1C(=O)Nc1ccnc(S(C)(=O)=O)c1] | in analogy to SC-01 | Int-B80, 2-methanesulfonyl pyridin-4-amine | $^1$H NMR (400 MHz, DMSO-d6): δ (ppm) = 11.23 (s, 1H), 8.71 (d, 1H), 8.43 (s, 1H), 7.90 (t, 1H), 7.46-7.09 (m, 1H), 4.31-4.29, (m, 2H), 3.31-3.28 (m, 2H), 3.26 (s, 3H), 2.70-2.60 (m, 2H), 2.50-2.38 (m, 1H), 2.05 (s, 3H). LCMS: m/z [M + H]$^+$ = 451.3 (calc. = 451.1). |
| SC-324 | 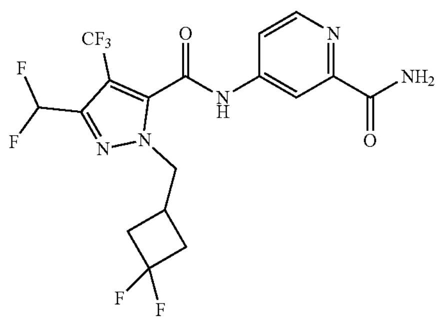 [SMILES: NC(=O)c1cc(NC(=O)c2c(C(F)(F)F)c(C(F)F)nn2CC2CC(F)(F)C2)ccn1] | in analogy to SC-21 | Int-B47, methyl 4-aminopicolinate | $^1$H NMR (400 MHz, DMSO-d6): δ (ppm) = 11.70 (s, 1H), 8.58-8.57 (m, 1H), 8.30 (s, 1H), 8.10 (s, 1H), 7.74-7.75 (m, 1H), 7.67 (s, 1H), 7.34-7.07 (m, 1H), 4.39-4.38 (m, 2H), 2.67-2.60 (m, 3H), 2.54-2.53 (m, 1H), 2.47-2.41 (m, 1H). LCMS: m/z [M + H]$^+$ = 454.3 (calc. = 454.1). |

Synthesis of 1-(cyclohexylmethyl)-N-(1-(methylsulfonyl)-1H-pyrrolo[2,3-b]pyridin-3-yl)-4-(trifluoromethyl)-1H-pyrazole-5-carboxamide (SC-53)

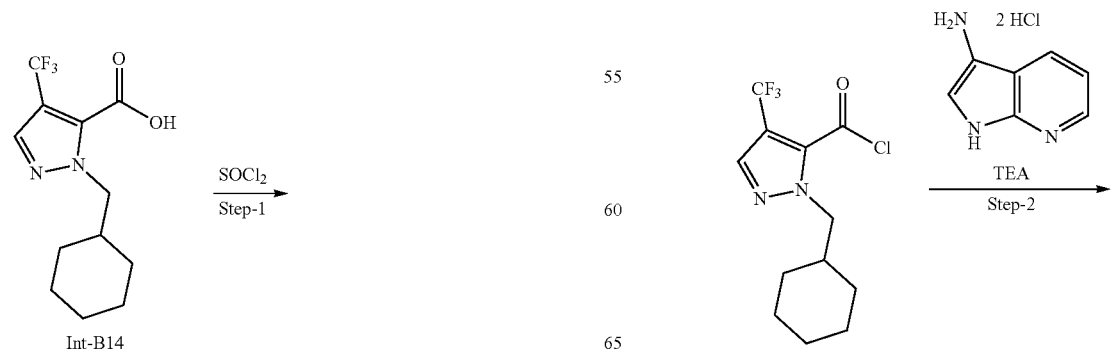

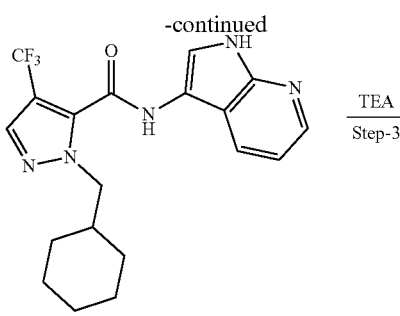

TEA
Step-3

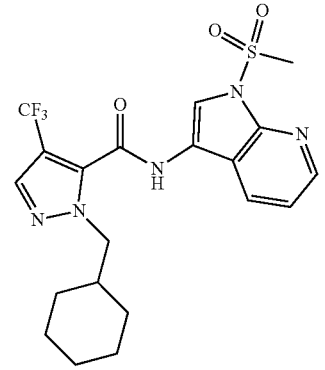

SC-53

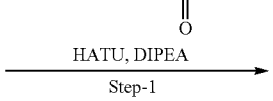

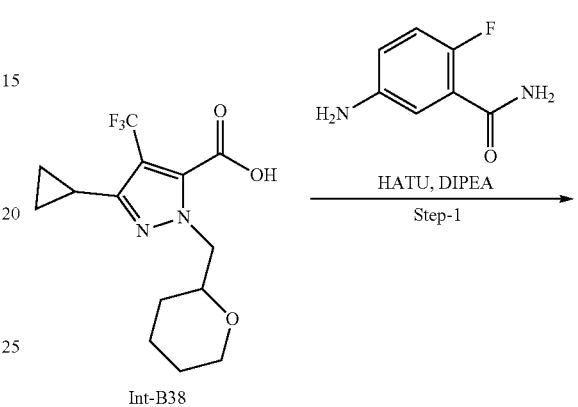

HATU, DIPEA
Step-1

Int-B38

Step-1: SOCl$_2$ (5 mL) was added to 1-(cyclohexylmethyl)-4-(trifluoromethyl)-1H-pyrazole-5-carboxylic acid (160 mg, 0.576 mmol, 1.0 eq.) at 0° C. under an argon atmosphere. The reaction mixture was then heated to 80° C. for 2 h. The reaction mixture was cooled to ambient temperature and concentrated under reduced pressure to afford 1-(cyclohexylmethyl)-4-(trifluoromethyl)-1H-pyrazole-5-carbonyl chloride (170 mg, crude).

Step-2: To a solution of 1H-pyrrolo[2,3-b]pyridin-3-amine dihydrochloride (142.4 mg, 0.691 mmol, 1.0 eq.) and Et$_3$N (0.4 mL, 2.88 mmol, 5.0 eq.) in dichloromethane (20 mL) was added 1-(cyclohexylmethyl)-4-(trifluoromethyl)-1H-pyrazole-5-carbonyl chloride (170 mg, 0.577 mmol, 0.8 eq.) at 0° C. under an argon atmosphere. The reaction mixture was slowly warmed to ambient temperature and was then stirred for 3 h. The reaction mixture was then diluted with water (30 mL) and extracted with dichloromethane (2×20 mL). The combined organic layers were dried over anhydrous Na$_2$SO$_4$ and concentrated under reduced pressure to afford 1-(cyclohexylmethyl)-N-(1H-pyrrolo[2,3-b]pyridin-3-yl)-4-(trifluoromethyl)-1H-pyrazole-5-carboxamide (190 mg, crude).

Step-3: To a solution of 1-(cyclohexylmethyl)-N-(1H-pyrrolo[2,3-b]pyridin-3-yl)-4-(trifluoromethyl)-1H-pyrazole-5-carboxamide (190 mg, 0.486 mmol, 1.0 eq) and Et$_3$N (0.24 mL, 1.701 mmol, 3.5 eq.) in dichloromethane (15 mL) was added MsCl (0.094 mL, 1.214 mmol, 2.5 eq.) at 0° C. under an argon atmosphere. The reaction mixture was then slowly warmed to ambient temperature and was stirred for 3 h. The reaction mixture was then quenched with water (30 mL) and extracted with dichloromethane (2×20 mL). The combined organic layers were dried over anhydrous Na$_2$SO$_4$ and concentrated under reduced pressure. The crude product was purified by reverse phase prep-HPLC to afford 1-(cyclohexylmethyl)-N-(1-(methylsulfonyl)-1H-pyrrolo[2,3-b]pyridin-3-yl)-4-(trifluoromethyl)-1H-pyrazole-5-carboxamide (SC-53) (20 mg, 0.043 mmol, 8%). $^1$H NMR (400 MHz, DMSO-d6): δ (ppm)=11.51 (s, 1H), 8.52 (d, 1H), 8.35 (d, 1H), 8.22 (s, 1H), 8.06 (s, 1H), 7.47-7.44 (m, 1H), 4.08 (d, 2H), 3.75 (s, 3H), 1.88-1.84 (m, 1H), 1.64-1.62 (m, 2H), 1.57-1.50 (m, 3H), 1.18-1.07 (m, 3H), 0.97-0.89 (m, 2H). LCMS: m/z [M+H]$^+$=470.1 (calc.=470.2).

Synthesis of N-(3-carbamoyl-4-fluorophenyl)-3-cyclopropyl-1-((tetrahydro-2H-pyran-2-yl)methyl)-4-(trifluoromethyl)-1H-pyrazole-5-carboxamide (SC-140)

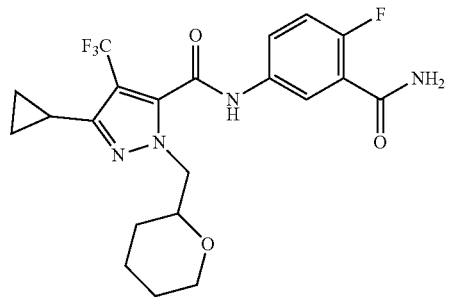

SC-140

Step-1: To a stirred solution of 3-cyclopropyl-1-(oxan-2-ylmethyl)-4-(trifluoromethyl)-1H-pyrazole-5-carboxylic acid (Int-B38, 0.15 g, 0.47 mmol, 1.0 eq.) in DMF (3 mL) were added DIPEA (0.76 mL, 4.24 mmol, 3 eq.), HATU (0.36 g, 0.94 mmol, 2 eq.) and 5-amino-2-fluorobenzamide (0.14 g, 0.94 mmol, 2 eq.) at 0° C. and the reaction mixture was stirred at ambient temperature for 16 h. The reaction mixture was quenched with crushed ice and was extracted with EtOAc (3×50 mL). The combined organic layers were washed with brine (30 mL), dried over Na$_2$SO$_4$ and concentrated under reduced pressure to get the crude material which was purified through combiflash column chromatography (silica gel; 0-80% EtOAc/hexane as eluent) to obtain N-(3-carbamoyl-4-fluorophenyl)-3-cyclopropyl-1-(oxan-2-ylmethyl)-4-(trifluoromethyl)-1H-pyrazole-5-carboxamide (SC-140). Yield: 45% (0.097 g, 0.21 mmol). NMR (400 MHz, DMSO-d6): δ (ppm)=10.93 (s, 1H), 7.96-7.94 (m, 1H), 7.74-7.68 (m, 3H), 7.32-7.27 (m, 1H), 4.08-4.07 (m, 2H), 3.77-3.74 (m, 1H), 3.62-3.57 (m, 1H), 3.27-3.21 (m, 1H), 1.94-1.91 (m, 1H), 1.74-1.72 (m, 1H), 1.55-1.52 (m, 1H), 1.43-1.34 (m, 3H), 1.16-1.10 (m, 1H), 0.98-0.97 (m, 2H), 0.87-0.85 (m, 2H). LCMS: m/z [M−H]$^-$=453.2 (calc.=453.4).

The following example was synthesized in analogy to the procedures described above using appropriate reactants and adjusted purification protocols:

| Ex. No. | Structure | Procedure | Intermediate | Analytical data |
|---|---|---|---|---|
| SC-141 | 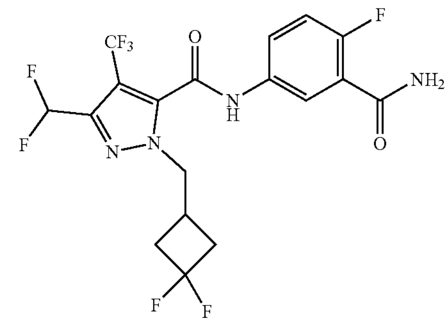 [SMILES: NC(=O)c1cc(NC(=O)c2c(C(F)(F)F)c(C(F)F)nn2CC2CC(F)(F)C2)ccc1F] | in analogy to SC-140 | Int-B47 | $^1$H NMR (400 MHz, DMSO-d6): δ (ppm) = 11.31 (s, 1H), 7.97-7.95 (m, 1H), 7.74-7.72 (m, 3H), 7.36-7.08 (m, 2H), 4.38 (d, 2H), 2.07-2.65 (m, 3H), 2.53-2.49 (m, 2H). LCMS: m/z [M − H]$^-$ = 469.3 (calc. = 469.1). |

Synthesis of 4-(3-cyclopropyl-1-((6-methyltetra-hydro-2H-pyran-2-yl)methyl)-4-(trifluoromethyl)-1H-pyrazole-5-carboxamido)picolinamide (SC-143)

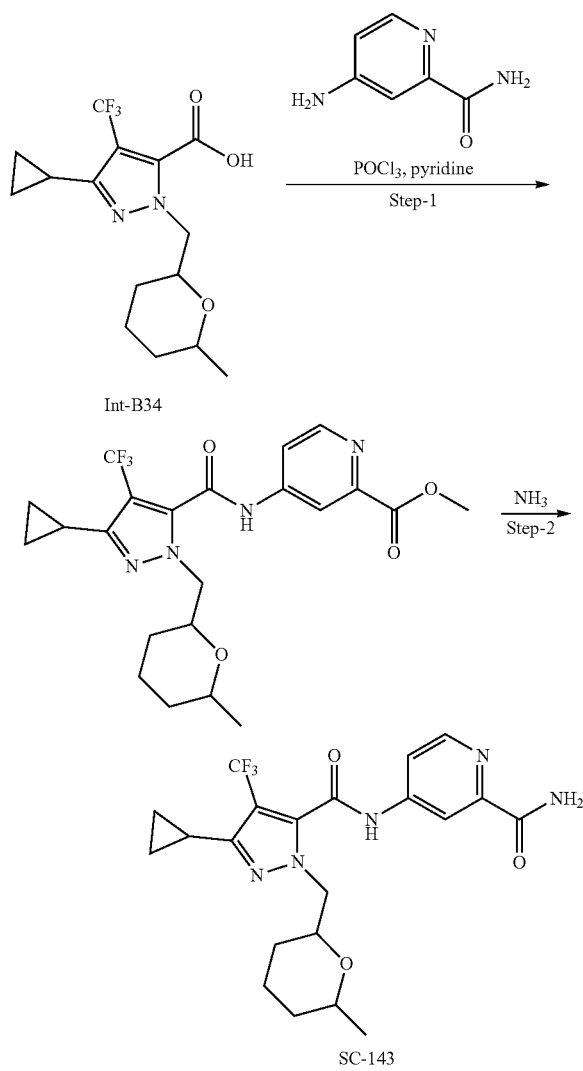

Step-1: To a solution of 3-cyclopropyl-1-[(6-methyloxan-2-yl)methyl]-4-(trifluoromethyl)-1H-pyrazole-5-carboxylic acid (Int-B34, 0.25 g, 0.75 mmol, 1.0 eq.) and methyl 4-aminopyridine-2-carboxylate (0.17 g, 1.12 mmol, 1.5 eq.) in pyridine (15 mL) was added POCl$_3$ (0.14 mL, 1.50 mmol, 2 eq.) dropwise at −10° C. The reaction mixture was the allowed to warm to ambient temperature and was stirred for 16 h. The reaction mixture was concentrated under reduced pressure and the obtained residue was taken in up water and extracted with ethyl acetate (3×50 mL). The combined organic layers were washed with brine, dried over Na$_2$SO$_4$ and concentrated under reduced pressure. The resulting crude residue was purified by combiflash (0-50% ethyl acetate in hexane) to obtain methyl 4-{3-cyclopropyl-1-[(6-methyloxan-2-yl)methyl]-4-(trifluoromethyl)-1H-pyrazole-5-amido}pyridine-2-carboxylate. Yield: 39% (0.13 g, 0.29 mmol).

Step-2: Methyl 4-{3-cyclopropyl-1-[(6-methyloxan-2-yl)methyl]-4-(trifluoromethyl)-1H-pyrazole-5-amido}pyridine-2-carboxylate (0.16 g, 0.37 mmol, 1.0 eq.) was put in a sealed tube followed by the addition of NH$_3$ solution (7 M in MeOH, 13 mL). The reaction vessel was sealed with a screw cap and was stirred at 110° C. for 24 h. The reaction mixture was concentrated under reduced pressure to get the crude product which was purified by combiflash (0-5% MeOH in DCM) and finally by washing with hexane to obtain 4-{3-cyclopropyl-1-[(6-methyloxan-2-yl)methyl]-4-(trifluoromethyl)-1H-pyrazole-5-amido}pyridine-2-carboxamide (SC-143). Yield: 53.9% (0.09 g, 0.2 mmol). NMR (400 MHz, DMSO-d6): δ (ppm)=11.26 (s, 1H), 8.55-8.54 (d, 1H), 8.33 (s, 1H), 8.09 (s, 1H), 7.79-7.77 (dd, 1H), 7.65 (s, 1H), 4.17-4.16 (d, 2H), 3.56-3.53 (m, 1H), 1.95 (m, 1H), 1.69 (m, 1H), 1.52-1.42 (m, 2H), 1.0-0.95 (m, 4H), 0.86-0.84 (m, 5H). LCMS: m/z [M+H]$^+$=452.3 (calc.=452.2).

The following examples were synthesized in analogy to the procedures described above using appropriate reactants and adjusted purification protocols:

| Ex. No. | Structure | Procedure | Intermediate | Analytical data |
|---|---|---|---|---|
| SC-135 | 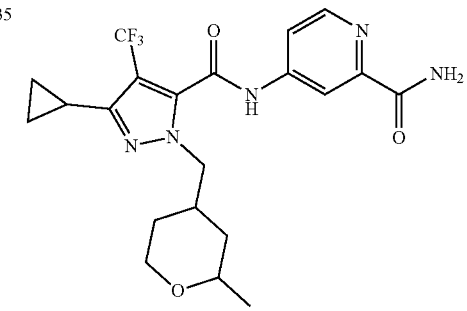 | in analogy to SC-143 | Int-B35 | $^1$H NMR (400 MHz, DMSO-d6): δ (ppm) = 11.55 (s, 1H), 8.59-8.58 (d, 1H), 8.31 (s, 1H), 8.12 (s, 1H), 7.80-7.78 (m, 1H), 7.68 (s, 1H), 4.20-4.18 (d, 2H), 3.95-3.93 (m, 1H), 3.55-3.42 (m, 3H), 2.34-2.32 (m, 1H), 1.94 (m, 1H), 1.61-1.55 (m, 1H), 1.31-1.14 (m, 4H), 1.02-0.91 (m, 5H), 0.84 (m, 3H). LCMS: m/z [M + H]$^+$ = 452.4 (calc. = 452.2). |

Synthesis of 4-(3-cyclopropyl-1-((3,3-difluorocyclobutyl)methyl)-4-(trifluoromethyl)-1H-pyrazole-5-carboxamido)picolinamide SC-144)

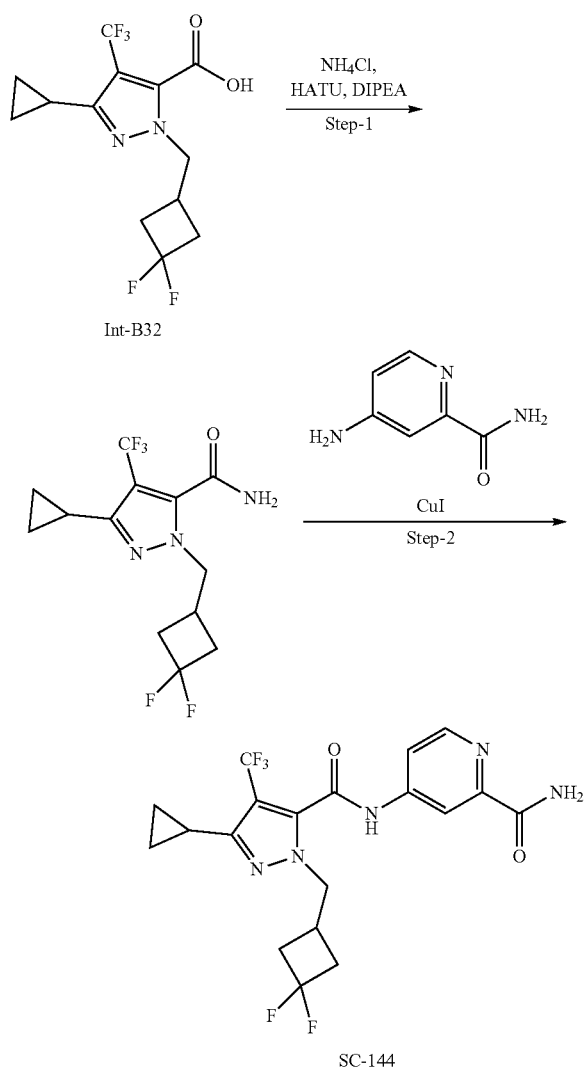

Step-1: To a solution of 3-cyclopropyl-1,3-difluorocyclobutyl)methyl)-4-(trifluoromethyl)-1H-pyrazole-5-carboxylic acid (Int-B32, 450 mg, 1.38 mmol, 1.0 eq.) in DMF (5 mL) were added HATU (1.5 g, 4.14 mmol, 3.0 eq.), DIPEA (0.7 mL, 4.14 mmol, 4.0 eq.) and NH$_4$Cl (297 mg, 5.5 mmol, 4.0 eq.) and the resulting reaction mixture was stirred at ambient temperature for 16 h. The reaction mixture was quenched with water (25 mL) and extracted with ethyl acetate (3×50 mL). The combined organic layers were washed with cold brine (50 mL) and dried over Na$_2$SO$_4$. The solvent was evaporated under reduced pressure to get the crude product which was purified by combiflash column chromatography (silica gel, 4-5% MeOH in DCM as eluent) to yield 3-cyclopropyl-1-((3,3-difluorocyclobutyl)methyl)-4-(trifluoromethyl)-1H-pyrazole-5-carboxamide (280 mg, 0.867 mmol, 62%).

Step-2: A mixture of 3-cyclopropyl-1-((3,3-difluorocyclobutyl)methyl)-4-(trifluoromethyl)-1H-pyrazole-5-carboxamide (260 mg, 0.804 mmol, 1.0 eq.), 4-bromopicolinamide (242.6 mg, 1.207 mmol, 1.5 eq.) and Cs$_2$CO$_3$ (783 mg, 2.41 mmol, 3.0 eq.) in 1,4-dioxane (20 mL) was degassed with argon for 15 minutes followed by the addition of copper iodide (61 mg, 0.32 mmol, 0.2 eq.) and trans-N,N'-dimethylcyclohexane-1,2-diamine (18 mg, 0.08 mmol, 0.1 eq.) at ambient temperature. The reaction mixture was heated to 110° C. for 16 h. The reaction mixture was then cooled to ambient temperature and was filtered through celite and the celite bed was washed with DCM (50 mL). The filtrate was concentrated under reduced pressure to get the crude product which was purified by HPLC to get 4-(3-cyclopropyl-1-((3,3-difluorocyclobutyl)methyl)-4-(trifluoromethyl)-1H-pyrazole-5-carboxamido)picolinamide (113 mg, 0.25 mmol, 31%). Yield: 31% (113 mg, 0.25 mmol). NMR (400 MHz, DMSO-d6): δ (ppm)=11.57 (s, 1H), 8.58 (d, 1H), 8.32 (s, 1H), 8.11 (s, 1H), 7.79-7.77 (m, 1H), 7.68 (s, 1H), 4.21 (d, 2H), 2.66-2.62 (m, 3H), 2.44-2.38 (m, 2H), 1.94-1.90 (m, 1H), 0.99-0.95 (m, 2H), 0.95-0.83 (m, 2H). LCMS: m/z [M+H]=444.2 (calc.=444.2).

The following examples were synthesized in analogy to the procedures described above using appropriate reactants and adjusted purification protocols:

| Ex.No. | Structure | Procedure | Intermediate | Analytical data |
|---|---|---|---|---|
| SC-172 | 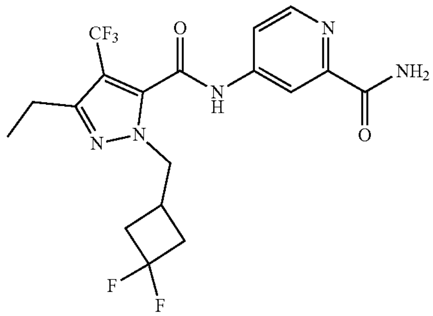 [SMILES: CCc1nn(CC2CC(F)(F)C2)c(C(=O)Nc2ccnc(C(N)=O)c2)c1C(F)(F)F] | in analogy to SC-144 | Int-B69 | ¹H NMR (400 MHz, DMSO-d6): δ (ppm) = 11.59 (s, 1H), 8.58 (d, 1H), 8.33 (s, 1H), 8.11 (s, 1H), 7.80-7.78 (m, 1H), 7.68 (s, 1H), 4.26 (d, 2H), 2.72-2.60 (m, 1H), 2.50-2.42 (m, 5H), 2.50-2.45 (m, 1H), 1.22 (t, 3H). LCMS: m/z [M + H]⁺ = 432.2 (calc. = 432.2). |
| SC-218 | 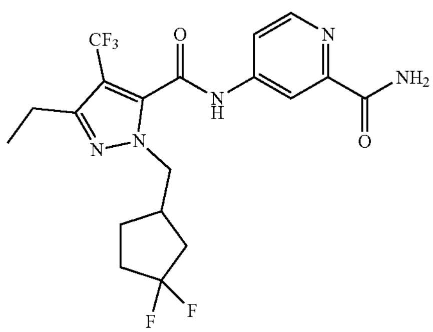 [SMILES: CCc1nn(CC2CCC(F)(F)C2)c(C(=O)Nc2ccnc(C(N)=O)c2)c1C(F)(F)F] | in analogy to SC-144 | Int-B58 | ¹H NMR (400 MHz, DMSO-d6): δ (ppm) = 11.55 (s, 1H), 8.58 (d, 1H), 8.33 (d, 1H), 8.12 (s, 1H), 7.79 (dd, 1H), 7.68 (s, 1H), 4.15 (d, 2H), 2.68 (dq, 3H), 2.22-1.77 (m, 3H), 1.55 (dt, 1H), 1.23 (t, 3H). LCMS: m/z [M + H]⁺ = 446.2 (calc. = 446.2), |
| SC-256 | 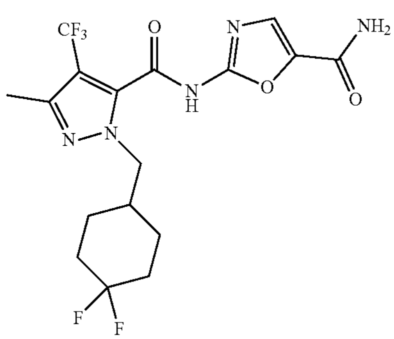 [SMILES: Cc1nn(CC2CCC(F)(F)CC2)c(C(=O)Nc2ncc(C(N)=O)o2)c1C(F)(F)F] | in analogy to SC-144 | Int-B46 | ¹H NMR (400 MHz, DMSO-d6): δ (ppm) = 12.77 (s, 1H), 7.66 (brs, 3H), 4.09 (s, 2H), 2.26 (s, 3H), 2.00-.96 (m, 3H), 1.81-1.71 (m, 2H), 1.69-1.58 (m, 2H), 1.25-1.22 (m, 2H). LCMS: m/z [M + H]⁺ = 436.3 (calc. = 436.1). |

Synthesis of 4-(3-Cyclopropyl-1-((tetrahydro-2H-pyran-3-yl)methyl)-4-(trifluoromethyl)-1H-pyrazole-5-carboxamido)picolinamide (SC-145), Synthesized in Form of Enantiomers Enantiomer 1 of 4-(3-Cyclopropyl-1-((tetrahydro-2H-pyran-3-yl)methyl)-4-(trifluoromethyl)-1H-pyrazole-5-carboxamido)picolinamide (SC-145a) and Enantiomer 2 of 4-(3-Cyclopropyl-1-((tetrahydro-2H-pyran-3-yl)methyl)-4-(trifluoromethyl)-1H-pyrazole-5-carboxamido)picolinamide (SC-145b)

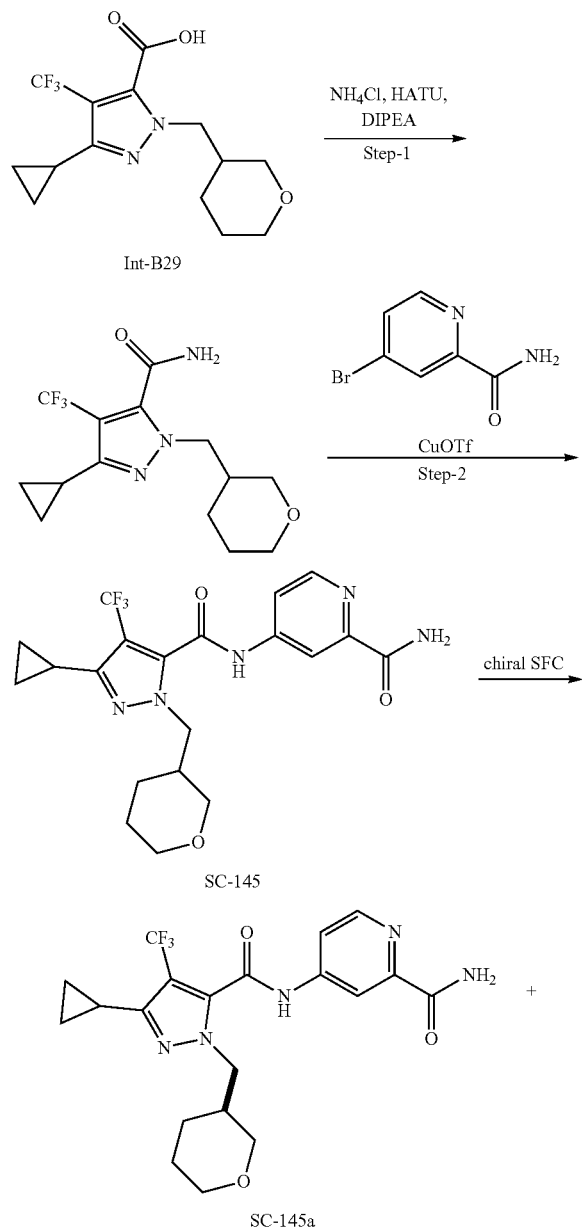
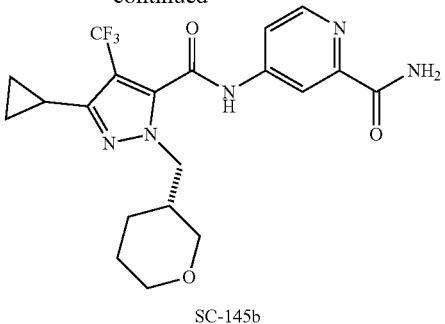

Step 1: To a solution of 3-cyclopropyl-1-((tetrahydro-2H-pyran-3-yl)methyl)-4-(trifluoromethyl)-1H-pyrazole-5-carboxylic acid (Int-B29, 0.200 g, 0.628 mmol, 1.0 eq.) and ammonium chloride (166.6 mg, 3.144 mmol, 5.0 eq.) in dry DMF (5 mL) was added DIPEA (243 mg, 1.886 mmol) followed by HATU (358.4 mg, 0.943 mmol) at ambient temperature. The resulting solution was stirred at ambient temperature for 1 h. The reaction mixture was quenched with water (30 mL) and extracted with ethyl acetate (3×30 mL). The combined organic layers were washed with water (3×30 mL), dried over anhydrous $Na_2SO_4$ and concentrated under reduced pressure to get 3-cyclopropyl-1-((tetrahydro-2H-pyran-3-yl)methyl)-4-(trifluoromethyl)-1H-pyrazole-5-carboxamide. Yield: 24% over 4 steps (100 mg).

Step 2: To a solution of 3-cyclopropyl-1-((tetrahydro-2H-pyran-2-yl)methyl)-4-(trifluoromethyl)-1H-pyrazole-5-carboxamide (100 mg, 0.315 mmol, 1.0 eq.) and 4-bromopicolinamide (75.7 mg, 0.378 mmol, 1.2 eq.) in 1,4-dioxane (6 mL) was added copper(I)trifluoromethane sulfonyl benzene complex (19.79 mg, 0.078 mmol, 0.25 eq.) followed by $Cs_2CO_3$ (205.0 g, 0.630 mmol, 2.0 eq.) at ambient temperature. The reaction mixture was purged with argon gas for 15 minutes, followed by the addition of N,N'-trans-cyclohexyl 1,2-diamine (13.43 mg, 0.094 mmol, 0.30 eq.). The resulting solution was heated to 100° C. for 16 h. The reaction mixture was quenched with water (30 mL) and extracted with ethyl acetate (2×40 mL). The combined organic layers were dried over anhydrous $Na_2SO_4$ and concentrated under reduced pressure to get the crude compound, which was purified by prep-HPLC to afford 4-(3-cyclopropyl-1-((tetrahydro-2H-pyran-3-yl)methyl)-4-(trifluoromethyl)-1H-pyrazole-5-carboxamido) picolinamide (SC-145). Yield: 22% (31 mg). $^1H$ NMR (400 MHz, DMSO-d6): δ (ppm)=11.52 (s, 1H), 8.54 (bs, 1H), 8.29 (bs, 1H), 8.09 (brs, 1H), 7.79-7.61 (m, 2H), 4.02-3.97 (m, 2H), 3.67-3.36 (m, 2H), 3.29-3.24 (m, 1H), 3.17-3.10 (m, 1H), 2.06-1.91 (m, 2H), 1.63-1.50 (m, 2H), 1.46-1.34 (m, 1H), 1.25-1.15 (m, 1H), 0.97-0.94 (2H), 0.84 (s, 2H). LCMS: m/z $[M+H]^+$=438.4 (calc.=438.2).

The above racemic compound was separated by chiral SFC (column: Lux; Cellulose-2 (250×30 mm) 5 μm, total flow: 60 g/min, 75% $CO_2$, 25% MeOH, 100 bar back pressure, 30° C.) to obtain SC-145a and SC-145b.

Analytical data for example SC-145a: chiral SFC (column: Chiracel OJ-3 (4.6×250 mm), 3 nm, total flow: 3 g/min, 90% $CO_2$, 10% MeOH, 1500 psi back pressure, 30° C., $R_t$=3.85 min.

Analytical data for example SC-145b: chiral SFC (column: Chiracel OJ-3 (4.6×250 mm), 3 nm, total flow: 3 g/min, 90% $CO_2$, 10% MeOH, 1500 psi back pressure, 30° C., $R_t$=5.21 min.

Absolute stereochemistry of SC-145a and SC145b was not determined and was assigned arbitrarily.

The following examples were synthesized in analogy to the procedures described above (with or without chiral separation at the end of the synthesis, absolute stereochemistry was not determined and was assigned arbitrarily, using appropriate reactants and adjusted purification protocols:

| Ex. No. | Structure | Procedure | Analytical data |
|---|---|---|---|
| SC-118a | 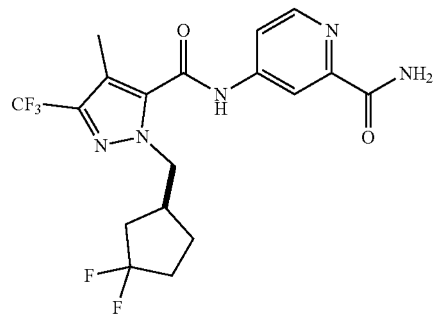 | in analogy to SC-145, using Int-B48 | $^1$H NMR (400 MHz, DMSO-d6): δ (ppm) = 11.15 (s, 1H), 8.57 (d, 1H), 8.37 (d, 1H), 8.11 (bs, 1H), 7.85 (dd, 1H), 7.67 (bs, 1H), 4.35 (d, 2H), 2.70-2.60 (m, 1H), 2.24 (s, 3H), 2.20-1.76 (m, 5H), 1.60-1.49 (m, 1H). LCMS: m/z [M + H]$^+$ = 432.2 (calc. = 432.2). chiral SFC (column: Chiracel OJ-H (4.6 × 250 mm), 5 μm, total flow: 3 mL/min, 90% CO$_2$, 10% MeOH, 100 bar back pressure, 30° C., R$_t$ = 5.79 min. |
| SC-118b | 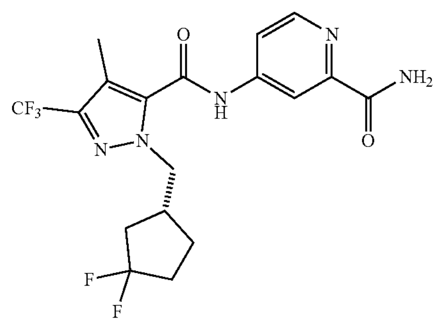 | in analogy to SC-145, using Int-B48 | $^1$H NMR (400 MHz, DMSO-d6): δ (ppm) = 11.15 (s, 1H), 8.57 (d, 1H), 8.37 (d, 1H), 8.11 (bs, 1H), 7.85 (dd, 1H), 7.67 (bs, 1H), 4.35 (d, 2H), 2.71-2.60 (m, 1H), 2.24 (s, 3H), 2.20-1.70 (m, 5H), 1.60-1.49 (m, 1H). LCMS: m/z [M + H]$^+$ = 432.2 (calc. = 432.2). chiral SFC (column: Chiracel OJ-H (4.6 × 250 mm), 5 μm, total flow: 3 mL/min, 90% CO$_2$, 10% MeOH, 100 bar back pressure, 30° C., R$_t$ = 7.08 min. |
| SC-147a | 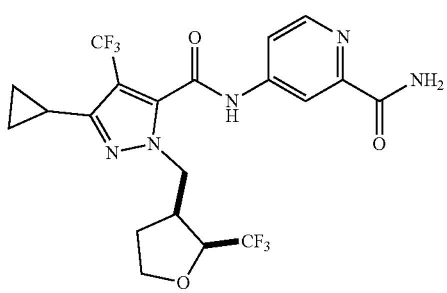 | in analogy to SC-145, using Int-B30 | $^1$H NMR (400 MHz, DMSO-d6): δ (ppm) = 11.59 (s, 1H), 8.59 (d, 1H), 8.31 (d, 1H), 8.12 (bs, 1H), 7.79 (dd, 1H), 7.68 (bs, 1H), 4.38-4.30 (m, 1H), 4.26-4.21 (m, 2H), 3.96-3.88 (m, 1H), 3.84-3.76 (m, 1H), 2.92-2.85 (m, 1H), 2.08-1.92 (m, 2H), 1.84-1.74 (m, 1H), 1.02-0.96 (m, 2H), 0.89-0.80 (m, 2H). LCMS: m/z [M + H]$^+$ = 492.2 (calc. = 492.2), Chiral HPLC (column: Chiralpak OX-H (250 × 4.6 mm) 5 μm; mobile phase: 0.2% TFA in n-Hexane/isopopanol 85:15, flow rate 1.0 mL/min), R$_t$ = 9.94 min. |
| SC-147b | 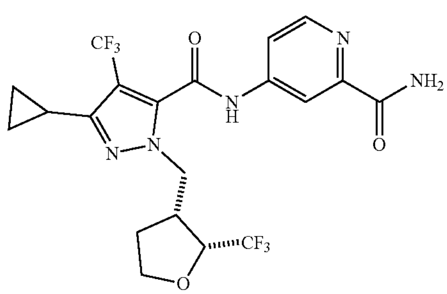 | in analogy to SC-145, using Int-B30 | $^1$H NMR (400 MHz, DMSO-d6): δ (ppm) = 11.59 (s, 1H), 8.59 (d, 1H), 8.31 (d, 1H), 8.12 (bs, 1H), 7.79 (dd, 1H), 7.68 (bs, 1H), 4.37-4.30 (m, 1H), 4.26-4.21 (m, 2H), 3.94-3.88 (m, 1H), 3.85-3.77 (m, 1H), 2.91-2.84 (m, 1H), 2.07-1.91 (m, 2H), 1.84-1.74 (m, 1H), 1.00-0.96 (m, 2H), 0.89-0.80 (m, 2H). LCMS: m/z [M + H]$^+$ = 492.2 (calc. = 492.2). Chiral HPLC (column: Chiralpak OX-H (250 × 4.6 mm) 5 μm; mobile phase: 0.2% TFA in n-Hexane/isopopanol 85:15, flow rate 1.0 mL/min), R$_t$ = 18.51 min. |

| Ex. No. | Structure | Procedure | Analytical data |
|---|---|---|---|
| SC-147c (rac) | 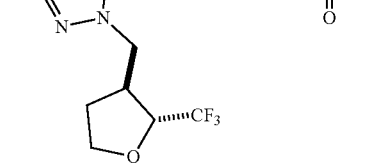 | in analogy to SC-145, using Int-B30 | $^1$H NMR (400 MHz, DMSO-d6): δ (ppm) = 11.58 (s, 1H), 8.59 (d, 1H), 8.31 (d, 1H), 8.12 (bs, 1H), 7.79 (dd, 1H), 7.68 (bs, 1H), 4.10-4.51 (m, 1H), 4.41-4.36 (m, 1H), 4.07-3.96 (m, 2H), 3.84-3.76 (m, 1H), 3.10-3.00 (m, 1H), 2.00-1.82 (m, 2H), 1.81-1.70 (m, 1H), 1.01-0.96 (m, 2H), 0.95-0.81 (m, 2H). LCMS: m/z [M + H]$^+$ = 492.2 (calc. = 492.2). |
| SC-148a | 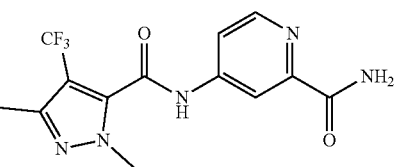 | in analogy to SC-145, using Int-B31 | $^1$H NMR (400 MHz, DMSO-d6): δ (ppm) = 11.55 (s, 1H), 8.58 (d, 1H), 8.31 (d, 1H), 8.11 (s, 1H), 7.78 (dd, 1H), 7.67 (s, 1H), 4.47-4.42 (m, 1H), 4.18-4.16 (m, 2H), 3.88 (t, 1H), 3.59 (t, 1H), 2.84-2.76 (m, 1H), 2.30-2.23 (m, 1H), 1.97-1.91 (m, 1H), 1.76-1.69 (m, 1H), 0.99-0.96 (m, 2H), 0.87-0.83 (m, 2H). LCMS: m/z [M + H]$^+$ = 492.2 (calc. = 492.2), Chiral HPLC (column: Chiracel OJ-H (250 × 4.6 mm) 5 μm; mobile phase: n-Hexane/EtOH 70:30, flow rate 1.0 mL/min), $R_t$ = 5.03 min. |
| SC-148b | 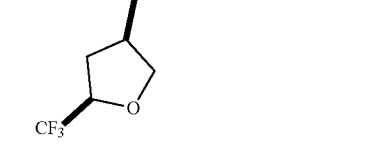 | in analogy to SC-145, using Int-B31 | $^1$H NMR (400 MHz, DMSO-d6): δ (ppm) = 11.55 (s, 1H), 8.58 (d, 1H), 8.31 (s, 1H), 8.11 (s, 1H), 7.78 (d, 1H), 7.67 (s, 1H), 4.47-4.42 (m, 1H), 4.20-4.14 (m, 2H), 3.88 (t, 1H), 3.59 (t, 1H), 2.84-2.76 (m, 1H), 2.35-2.24 (m, 1H), 1.96-1.92 (m, 1H), 1.76-1.69 (m, 1H), 0.99-0.95 (m, 2H), 0.87-0.84 (m, 2H). LCMS: m/z [M + H]$^+$ = 492.2 (calc. = 492.2), Chiral HPLC (column: Chiracel OJ-H (250 × 4.6 mm) 5 μm; mobile phase: n-Hexane/EtOH 70:30, flow rate 1.0 mL/min), $R_t$ = 9.80 min. |
| SC-149a | 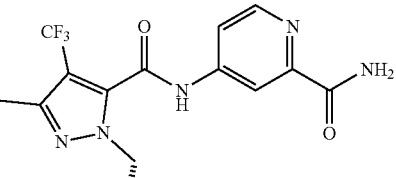 | in analogy to SC-145, using Int-B49 | $^1$H NMR (500 MHz, DMSO-d6): δ (ppm) = 11.38 (s, 1H), 8.57 (d, 1H), 8.36 (m, 1H), 8.12 (brs, 1H), 7.83 (dd, 1H), 7.68 (s, 1H), 4.33 (d, 2H), 2.70-2.58 (m, 1H), 2.22-1.75 (m, 8H), 1.60-1.49 (m, 1H). LCMS: m/z [M + H]$^+$ = 448.2 (calc. = 448.1), chiral SFC (column: Chiracel OJ-H (4.6 × 250 mm) 5 μm, total flow: 3 mL/min, 80% CO$_2$, 20% MeOH, 96 bar back pressure, 30° C., $R_t$ = 4.67 min. |
| SC-149b | 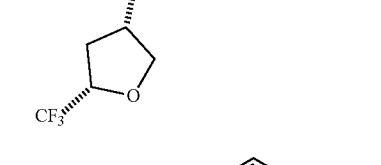 | in analogy to SC-145, using Int-B49 | $^1$H NMR (400 MHz, DMSO-d6): δ (ppm) = 11.37 (s, 1H), 8.58 (d, 1H), 8.36-8.35 (m, 1H), 8.11 (brs, 1H), 7.83 (dd, 1H), 7.67 (s, 1H), 4.33 (d, 2H), 2.70-2.59 (m, 1H), 2.25-1.75 (m, 8H), 1.60-1.49 (m, 1H). LCMS: m/z [M + H]$^+$ = 448.2 (calc. = 448.1). chiral SFC (column: Chiracel OJ-H (4.6 × 250 mm) 5 μm, total flow: 3 mL/min, 80% CO$_2$, 20% MeOH, 96 bar back pressure, 30° C., $R_t$ = 5.97 min. |

-continued

| Ex. No. | Structure | Procedure | Analytical data |
|---|---|---|---|
| SC-150a | 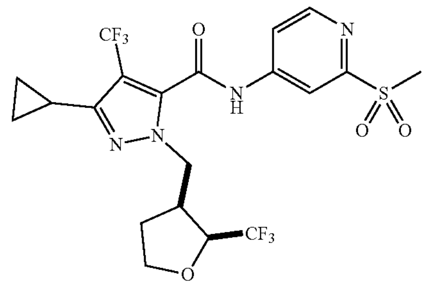 | in analogy to SC-145, using Int-B30 | ¹H NMR (400 MHz, DMSO-d6): δ (ppm) = 11.86 (s, 1H), 8.74 (s, 1H), 8.36 (s, 1H), 7.84 (s, 1H), 4.39-4.21 (m, 3H), 3.95-3.88 (m, 1H), 3.84-3.76 (m, 1H), 3.29 (s, 3H), 2.91-2.84 (m, 1H), 2.08-1.92 (m, 2H), 1.82-1.73 (m, 1H), 1.01-0.95 (m, 2H), 0.89-0.81 (m, 2H). LCMS: m/z [M − H]⁻ = 525.1 (calc. = 525.1). Chiral HPLC (column: Chiralpak IA (250 × 4.6 mm) 5 μm; mobile phase: 0.2% DEA in n-Hexane/EtOH: 95/5, flow rate 1.0 mL/min), R$_t$ = 15.17 min. |
| SC-150b | 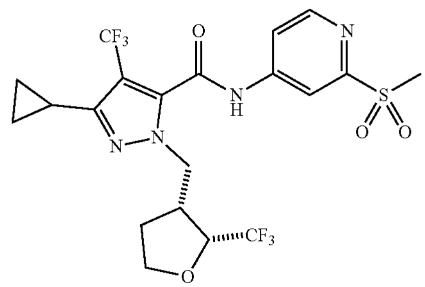 | in analogy to SC-145, using Int-B30 | ¹H NMR (400 MHz, DMSO-d6): δ (ppm) = 11.86 (s, 1H), 8.73 (s, 1H), 8.35 (s, 1H), 7.83 (s, 1H), 4.40-4.22 (m, 3H), 3.95-3.88 (m, 1H), 3.84-3.76 (m, 1H), 3.28 (s, 3H), 2.92-2.84 (m, 1H), 2.08-1.91 (m, 2H), 1.82-1.73 (m, 1H), 1.01-0.95 (m, 2H), 0.89-0.80 (m, 2H). LCMS: m/z [M − H]⁻ = 525.1 (calc. = 525.1), Chiral HPLC (column: Chiralpak IA (250 × 4.6 mm) 5 μm; mobile phase: 0.2% DEA in n-Hexane/EtOH: 95/5, flow rate 1.0 mL/min), R$_t$ = 15.93 min. |
| SC-150c (rac) | 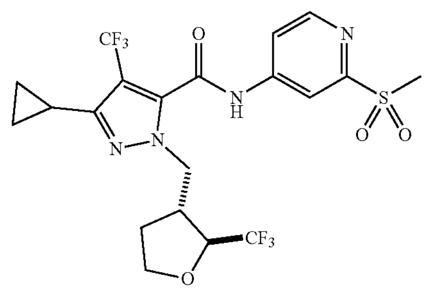 | in analogy to SC-145, using Int-B30 | ¹H NMR (400 MHz, DMSO-d6): δ (ppm) = 11.85 (s, 1H), 8.74 (d, 1H), 8.35 (s, 1H), 7.86 (d, 1H), 4.59-4.52 (m, 1H), 4.42-4.36 (m, 1H), 4.10-3.96 (m, 2H), 3.84-3.77 (m, 1H), 3.30 (s, 3H), 3.12-3.01 (m, 1H), 2.00-1.73 (m, 3H), 1.01-0.96 (m, 2H), 0.95-0.81 (m, 2H). LCMS: m/z [M − H]⁻ = 525.1 (calc. = 525.1). |
| SC-159 | 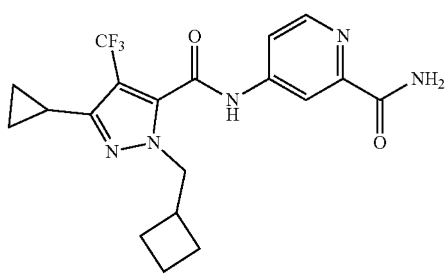 [SMILES: NC(=O)c1cc(NC(=O)c2c(C(F)(F)F)c(C3CC3)nn2CC2CCC2)ccn1] | in analogy to SC-145, using Int-B37 | ¹H NMR (400 MHz, DMSO-d6), δ (ppm) = 11.55 (s, 1H), 8.58 (d, 1H), 8.33 (d, 1H), 8.12 (s, 1H), 7.79 (dd, 1H), 7.69 (s, 1H), 4.09 (d, 2H), 2.72-2.64 (m, 1H), 1.95-1.90 (m, 3H), 1.83-1.69 (m, 4H), 1.00-0.93 (m, 2H), 0.86-0.83 (m, 2H), LCMS: m/z [M − H]⁻ = 406.2 (calc. = 406.2). |
| SC-160a | 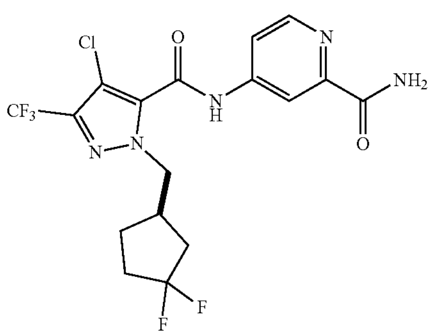 | in analogy to SC-145, using Int-B51 | ¹H NMR (400 MHz, DMSO-d6), δ (ppm) = 11.46 (s, 1H), 8.59 (d, 1H), 8.35 (brs, 1H), 8.12 (s, 1H), 7.83-7.81 (m, 1H), 7.69 (brs, 1H), 4.41 (d, 2H), 2.71-3.62 (m, 1H), 2.20-1.80 (m, 5H), 1.56-1.52 (m, 1H). LCMS: m/z [M + H]⁺ = 452.4 (calc. = 452.1), chiral SFC (column: Chiracel OJ-H (4.6 × 250 mm)), 5 μm, total flow: 3 mL/min, 90% CO$_2$, 10% MeOH, 100 bar back pressure, 30° C., R$_t$ = 5.88 min. |

| Ex. No. | Structure | Procedure | Analytical data |
|---|---|---|---|
| SC-160b | 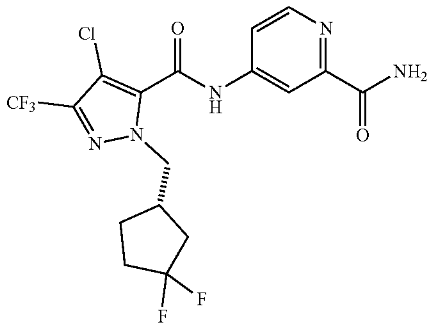 | in analogy to SC-145, using Int-B51 | $^1$H NMR (400 MHz, DMSO-d6), δ (ppm) = 11.45 (s, 1H), 8.61 (d, 1H), 8.35 (brs, 1H), 8.13 (brs, 1H), 7.85-7.83 (m, 1H), 7.69 (s, 1H), 4.40 (d, 2H), 2.69-2.66 (m, 1H), 2.17-1.81 (m, 5H), 1.56-1.52 (m, 1H). LCMS: m/z [M + H]$^+$ = 452.4 (calc. = 452.1). chiral SFC (column: Chiracel OJ-H (4.6 × 250 mm), 5 µm, total flow: 3 mL/min, 90% CO$_2$, 10% MeOH, 100 bar back pressure, 30° C., R$_t$ = 6.87 min. |
| SC-161 | 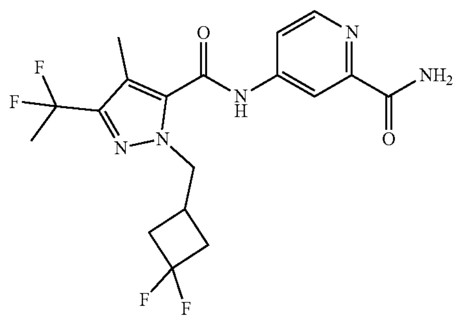 [SMILES: Cc1c(C(C)(F)F)nn(CC2CC(F)(F)C2)c1C(=O)Nc1ccnc(C(N)=O)c1] | in analogy to SC-145, using Int-B50 | $^1$H-NMR (400 MHz, DMSO-d$_6$): δ (ppm) = 11.09 (s, 1H), 8.56 (d, 1H), 8.38 (d, 1H), 8.10 (d, 1H), 7.85 (dd, 1H), 7.65 (s, 1H), 4.38 (d, 2H), 2.67-2.57 (m, 3H), 2.46-2.40 (m, 2H), 2.23 (s, 3H), 2.03 (t, 3H). LCMS: m/z [M − H]$^-$ = 412.2 (calc. = 412.1). |
| SC-180 | 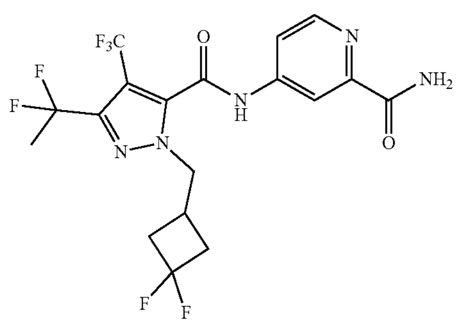 [SMILES: CC(F)(F)c1nn(CC2CC(F)(F)C2)c(C(=O)Nc2ccnc(C(N)=O)c2)c1C(F)(F)F] | in analogy to SC-145, using Int-B91 | $^1$H NMR (400 MHz, DMSO-d6): δ (ppm) = 11.75 (s, 1H), 8.59 (d, 1H), 8.31 (bs, 1H), 8.12 (bs, 1H), 7.77-7.68 (m, 2H), 4.38 (d, 2H), 2.72-2.61 (m, 4H), 2.48-2.42 (m, 1H), 2.08 (t, 3H). LCMS: m/z [M + H]$^+$ = 468.2 (calc. 468.1). |
| SC-239 | 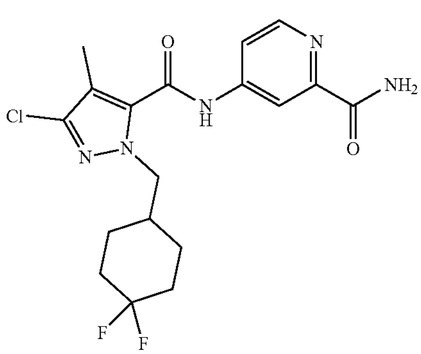 [SMILES: Cc1c(Cl)nn(CC2CCC(F)(F)CC2)c1C(=O)Nc1ccnc(C(N)=O)c1] | in analogy to SC-145, using Int-B108 | $^1$H NMR (400 MHz, DMSO-d6): δ (ppm) = 11.10 (s, 1H), 8.56 (d, 1H), 8.36-8.33 (m, 1H), 8.10 (brs, 1H), 7.84 (dd, 1H), 7.67 (brs, 1H), 4.15 (d, 2H), 2.20 (s, 3H), 2.01-1.94 (m, 3H), 1.86-1.69 (m, 2H), 1.64-1.57 (m, 2H), 1.27-1.17 (m, 2H). LCMS: m/z [M + H]$^+$ = 412.1 (calc. = 412.1). |

| Ex. No. | Structure | Procedure | Analytical data |
|---|---|---|---|
| SC-251 | 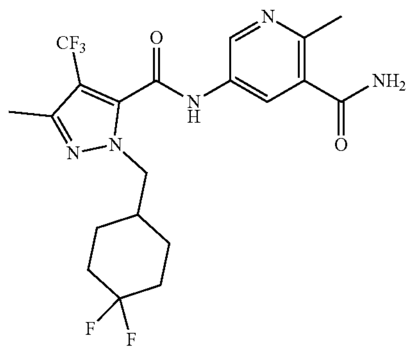 [SMILES: Cc1ncc(NC(=O)c2c(C(F)(F)F)c(C)nn2CC2CCC(F)(F)CC2)cc1C(N)=O] | in analogy to SC-145, using Int-B46 | ¹H NMR (400 MHz, DMSO-d6): δ (ppm) = 11.19 (s, 1H), 8.67 (s, 1H), 8.02 (d, 1H), 7.93 (s, 1H), 7.59 (s, 1H), 4.02 (d, 2H), 2.49 (s, 3H), 2.31 (s, 3H), 1.98-1.96 (m, 3H), 1.83-1.60 (m, 4H), 1.26-1.19 (m, 2H). LCMS: m/z [M + H]⁺ = 460.2 (calc. = 460.2). |
| SC-252 | 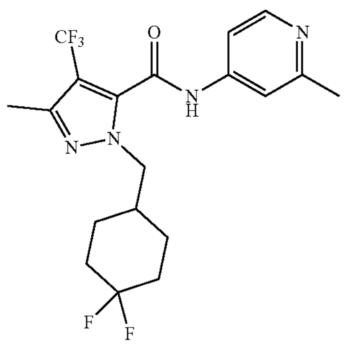 | in analogy to SC-145, using Int-B46 | ¹H NMR (400 MHz, DMSO-d6): δ (ppm) = 11.23 (s, 1H), 8.35 (d, 1H), 7.48 (s, 1H), 7.36 (d, 1H), 4.00 (d, 2H), 2.44 (s, 3H), 2.30 (s, 3H), 2.01-1.96 (m, 3H), 1.83-1.59 (m, 4H), 1.25-1.16 (m, 2H). LCMS: m/z [M + H]⁺ = 417.1 (calc. = 417.2). |
| SC-253 | 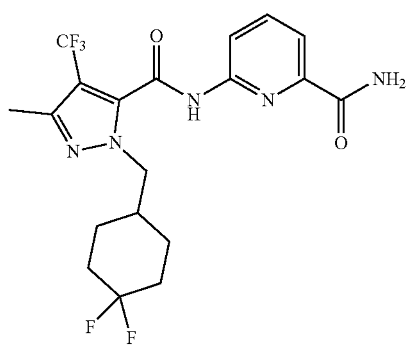 [SMILES: Cc1nn(CC2CCC(F)(F)CC2)c(C(=O)Nc2cccc(C(N)=O)n2)c1C(F)(F)F] | in analogy to SC-145, using Int-B46 | ¹H NMR (400 MHz, DMSO-d6): δ (ppm) = 11.59 (s, 1H), 8.30-8.20 (m, 1H), 8.10-8.03 (m, 1H), 7.85-7.73 (m, 2H), 7.56 (s, 1H), 4.01 (d, 2H), 2.30 (s, 3H), 2.07-1.91 (m, 3H), 1.87-1.58 (m, 4H), 1.28-1.15 (m, 2H). LCMS: m/z [M + H]⁺ = 446.1 (calc. = 446.2). |
| SC-257 | 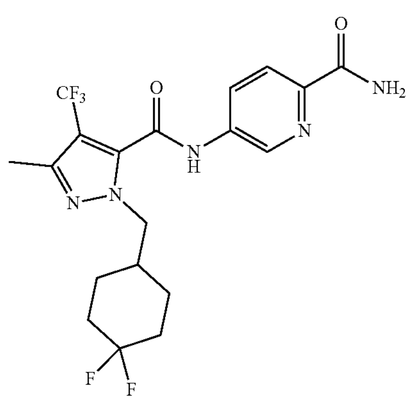 [SMILES: Cc1nn(CC2CCC(F)(F)CC2)c(C(=O)Nc2ccc(C(N)=O)nc2)c1C(F)(F)F] | in analogy to SC-145, using Int-B46 | ¹H NMR (400 MHz, DMSO-d6): δ (ppm) = 11.44 (s, 1H), 8.83 (d, 1H), 8.27-8.24 (dd, 1H), 8.09-8.04 (m, 2H), 7.59 (brs, 1H), 4.04 (d, 2H), 2.32 (s, 3H), 1.99-1.96 (m, 3H), 1.80-1.60 (m, 4H), 1.27-1.21 (m, 2H). LCMS: m/z [M + H]⁺ = 446.1 (calc. = 446.2). |

| Ex. No. | Structure | Procedure | Analytical data |
|---|---|---|---|
| SC-258a | 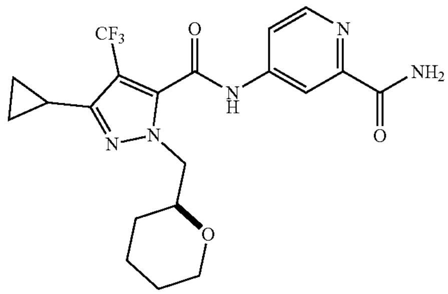 | in analogy to SC-145, using Int-B38 | $^1$H NMR (400 MHz, DMSO-d6): δ (ppm) = 11.35 (s, 1H), 8.56 (d, 1H), 8.32 (d, 1H), 8.10 (s, 1H), 7.77 (dd, 1H), 7.67 (s, 1H), 4.15-4.07 (m, 2H), 3.73-3.68 (m, 1H), 3.58-3.55 (m, 1H), 3.28-3.20 (m, 1H), 1.96-1.92 (m, 1H), 1.74-1.72 (m, 1H), 1.56-1.54 (m, 1H), 1.42-1.36 (m, 3H), 1.12-1.08 (m, 1H), 0.97-0.95 (m, 2H), 0.88-0.83 (m, 2H). LCMS: m/z [M + H]$^+$ = 438.3 (calc. 438.2). chiral SFC (column: Lux Cellulose-4 (4.6 × 150 mm) 3 μm, total flow: 3 g/min, 65% $CO_2$, 35% metanol, 1500 psi back pressure, 30° C., Rt = 1.65 min |
| SC-258b | 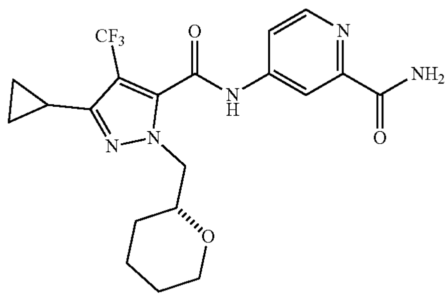 | in analogy to SC-145, using Int-B38 | $^1$H NMR (400 MHz, DMSO-d6): δ (ppm) = 11.35 (s, 1H), 8.56 (d, 1H), 8.32 (d, 1H), 8.10 (s, 1H), 7.77 (dd, 1H), 7.67 (s, 1H), 4.15-4.07 (m, 2H), 3.73-3.68 (m, 1H), 3.58-3.55 (m, 1H), 3.28-3.20 (m, 1H), 1.96-1.92 (m, 1H), 1.74-1.72 (m, 1H), 1.56-1.54 (m, 1H), 1.42-1.36 (m, 3H), 1.12-1.08 (m, 1H), 0.97-0.95 (m, 2H), 0.88-0.83 (m, 2H). LCMS: m/z [M + H]$^+$ = 438.3 (calc. 438.2). chiral SFC (column: Lux Cellulose-4 (4.6 × 150 mm) 3 μm, total flow: 3 g/min, 65% $CO_2$, 35% metanol, 1500 psi back pressure, 30° C., $R_t$ = 3.76 min. |
| SC-259a | 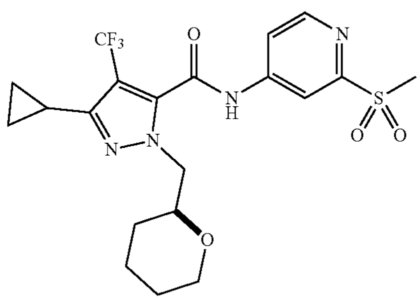 | in analogy to SC-145, using Int-B38 | $^1$H NMR (400 MHz, DMSO-d6): δ (ppm) = 11.61 (s, 1H), 8.70 (s, 1H), 8.37 (s, 1H), 7.82 (s, 1H), 4.16-4.11 (m, 2H), 3.71 (d, 1H), 3.56 (s, 1H), 3.35-3.20 (m, 4H), 1.95-1.90 (m, 1H), 1.71-1.73 (m, 1H), 1.50-1.59 (m, 1H), 1.41-1.33 (m, 3H), 1.13-1.09 (m, 1H), 0.89-0.99 (m, 2H), 0.81-0.91 (m, 2H). LCMS: m/z [M + H]$^+$ = 473.2 (calc. 473.2). chiral SFC (column: Chiralpak OJ-3 (4.6 × 150 mm) 3 μm, total flow: 3 g/min, 85% $CO_2$, 15% metanol, 1500 psi back pressure, 30° C., $R_t$ = 1.19 min. |
| SC-259b | 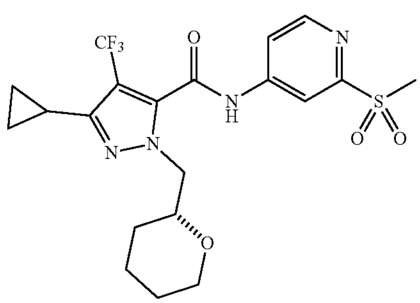 | in analogy to SC-145, using Int-B38 | $^1$H NMR (400 MHz, DMSO-d6): δ (ppm) = 11.61 (s, 1H), 8.70 (s, 1H), 8.37 (s, 1H), 7.82 (s, 1H), 4.16-4.11 (m, 2H), 3.71 (d, 1H), 3.56 (s, 1H), 3.35-3.20 (m, 4H), 1.95-1.90 (m, 1H), 1.71-1.73 (m, 1H), 1.50-1.59 (m, 1H), 1.41-1.33 (m, 3H), 1.13-1.09 (m, 1H); 0.89-0.99 (m, 2H), 0.81-0.91 (m, 2H). LCMS: m/z [M + H]$^+$ = 473.2 (calc. 473.2). chiral SFC (column: Chiralpak OJ-3 (4.6 × 150 mm) 3 μm, total flow: 3 g/min, 85% $CO_2$, 15% metanol, 1500 psi back pressure, 30° C., $R_t$ = 1.60 min. |
| SC-260 | 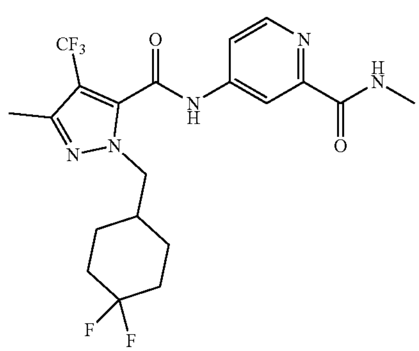 | in analogy to SC-145, using Int-B46 | $^1$H NMR (400 MHz, DMSO-d6): δ (ppm) = 11.51 (s, 1H), 8.74 (d, 1H), 8.55 (brs, 1H), 8.26 (brs, 1H), 7.80 (brs, 1H), 4.03 (d, 2H), 2.81 (d, 3H), 2.31 (s, 3H), 1.98-1.96 (m, 3H), 1.83-1.68 (m, 2H), 1.62-1.59 (m, 2H), 1.26-1.17 (m, 2H). LCMS: m/z [M + H]$^+$ = 460.3 (calc. = 460.2). |

| Ex. No. | Structure | Procedure | Analytical data |
|---|---|---|---|
| SC-261 | 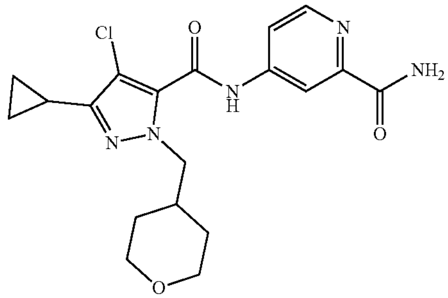 [SMILES: NC(=O)c1cc(NC(=O)c2c(Cl)c(C3CC3)nn2CC2CCOCC2)ccn1] | in analogy to SC-145, using Int-B107 | $^1$H NMR (400 MHz, DMSO-d6): δ (ppm) = 11.11 (s, 1H), 8.54 (d, 1H), 8.32 (s, 1H), 8.09 (s, 1H), 7.84-7.80 (m, 1H), 7.64 (s, 1H), 4.10 (d, 2H), 3.80-3.75 (m, 2H), 3.20 (t, 2H), 2.00-1.86 (m, 2H), 1.38-1.34 (m, 2H), 1.23-1.12 (m, 2H), 0.98-0.91 (m, 2H), 0.83-0.80 (m, 2H). LCMS: m/z [M + H]$^+$ = 404.1 (calc. = 404.2). |
| SC-266 | 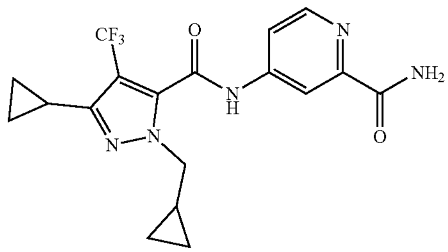 [SMILES: NC(=O)c1cc(NC(=O)c2c(C(F)(F)F)c(C3CC3)nn2CC2CC2)ccn1] | in analogy to SC-145, using Int-B68 | $^1$H NMR (400 MHz, DMSO-d6): δ (ppm) = 11.59 (s, 1H), 8.58 (d, 1H), 8.32 (s, 1H), 8.11 (s, 1H), 7.78 (d, 1H), 7.68 (s, 1H), 3.95 (d, 2H), 1.94 (s, 1H), 1.16 (m, 1H), 0.97-0.95 (m, 2H), 0.86-0.85 (m, 2H), 0.48-0.46 (m, 2H), 0.31-0.28 (m, 2H). LCMS: m/z [M + H]$^+$ = 394.2 (calc. = 394.2). |
| SC-267 | 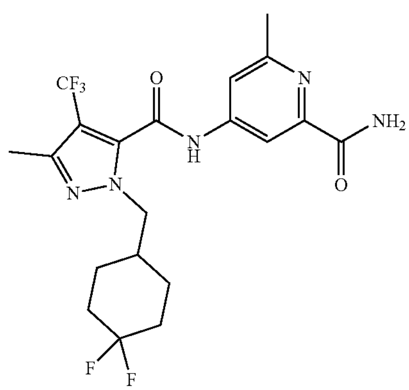 [SMILES: Cc1cc(NC(=O)c2c(C(F)(F)F)c(C)nn2CC2CCC(F)(F)CC2)cc(C(N)=O)n1] | in analogy to SC-145, using Int-B46 | $^1$H NMR (400 MHz, DMSO-d6): δ (ppm) = 11.45 (s, 1H), 8.09 (s, 1H), 7.99-7.96 (d, 1H), 7.69-7.63 (m, 2H), 4.02 (d, 2H), 2.53 (s, 3H), 2.31 (s, 3H), 2.06-1.95 (m, 3H), 1.83-1.58 (m, 4H), 1.28-1.19 (m, 2H). LCMS: m/z [M + H]$^+$ = 460.2 (calc. = 460.2). |
| SC-268 | 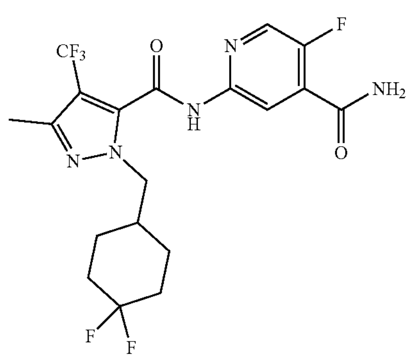 [SMILES: Cc1nn(CC2CCC(F)(F)CC2)c(C(=O)Nc2cc(C(N)=O)c(F)cn2)c1C(F)(F)F] | in analogy to SC-145, using Int-B46 | $^1$H NMR (400 MHz, DMSO-d6): δ (ppm) = 11.72 (s, 1H), 8.50 (s, 1H), 8.30 (d, 1H), 8.08 (s, 1H), 7.99 (s, 1H), 4.00 (d, 2H), 2.29 (s, 3H), 2.05-1.92 (m, 3H), 1.85-1.60 (m, 4H), 1.27-1.15 (m, 2H). LCMS: m/z [M + H]$^+$ = 464.2 (calc. = 464.2). |

| Ex. No. | Structure | Procedure | Analytical data |
|---|---|---|---|
| SC-269 | 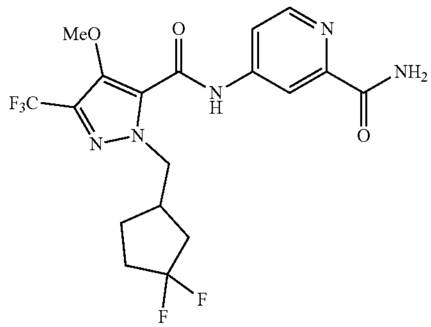 [SMILES: COc1c(C(F)(F)F)nn(CC2CCC(F)(F)C2)c1C(=O)Nc1ccnc(C(N)=O)c1] | in analogy to SC-145, using Int-B113 | $^1$H NMR (400 MHz, DMSO-d6): δ (ppm) = 10.93 (s, 1H), 8.58 (d, 1H), 8.40 (s, 1H), 8.12 (s, 1H), 7.85-7.83 (m, 1 H), 7.68 (s, 1H), 4.41 (d, 2H), 3.85 (s, 3H), 2.67-2.63 (m, 1H), 2.18-2.01 (m, 3H), 1.94-1.89 (m, 1H), 1.80-1.77 (m, 1H), 0.99-1.19 (m, 1H). LCMS: m/z [M + H]$^+$ = 448.3 (calc. 448.1). |
| SC-271a | 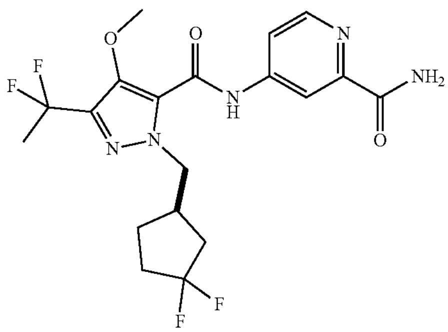 | in analogy to SC-145, using Int-B88 | $^1$H NMR (500 MHz, DMSO-d6): δ (ppm) = 10.71 (s, 1H), 8.56 (d, 1H), 8.41 (d, 1H), 8.11 (bs, 1H), 7.85 (dd, 1H), 7.67 (bs, 1H), 4.37 (d, 2H), 3.83 (s, 3H), 2.66-2.60 (m, 1H), 2.20-2.00 (m, 6H), 1.97-1.72 (m, 2H), 1.56-1.50 (m, 1H). LCMS: m/z [M − H]$^−$ = 442.2 (calc. = 442.2). chiral SFC (column: Chiralpak OJ-3 (4.6 × 150 mm) 3 μm, total flow: 3 g/min, 90% CO$_2$, 10% 0.5 % DEA metanol, 1500 psi back pressure, 30° C., R$_t$ = 2.15 min. |
| SC-271b | 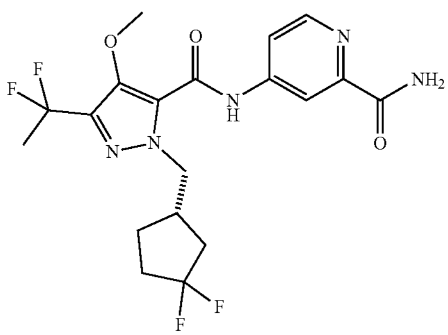 | in analogy to SC-145, using Int-B88 | $^1$H NMR (500 MHz, DMSO-d6): δ (ppm) = 10.71 (s, 1H), 8.56 (d, 1H), 8.41 (d, 1H), 8.11 (bs, 1H), 7.85 (dd, 1H), 7.67 (bs, 1H), 4.37 (d, 2H), 3.83 (s, 3H), 2.66-2.60 (m, 1H), 2.20-2.00 (m, 6H), 1.97-1.72 (m, 2H), 1.56-1.50 (m, 1H). LCMS: m/z [M − H]$^−$ = 442.2 (calc. = 442.2). chiral SFC (column: Chiralpak OJ-3 (4.6 × 150 mm) 3 μm, total flow: 3 g/min, 90% CO$_2$, 10% 0.5 % DEA metanol, 1500 psi back pressure, 30° C., R$_t$ = 2.50 min. |
| SC-273 | 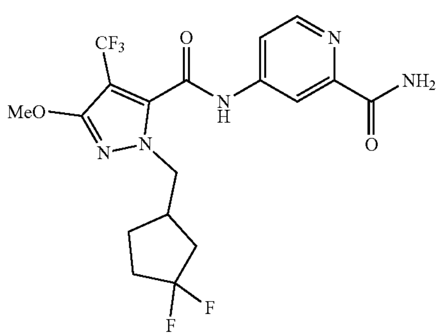 [SMILES: COc1nn(CC2CCC(F)(F)C2)c(C(=O)Nc2ccnc(C(N)=O)c2)c1C(F)(F)F] | in analogy to SC-145, using Int-B41 | $^1$H NMR (400 MHz, DMSO-d6): δ (ppm) = 11.57 (s, 1H), 8.59 (d, 1H), 8.32 (s, 1H), 8.11 (s, 1H), 7.80-7.78 (m, 1H), 7.69 (s, 1H), 4.07 (d, 2H), 3.94 (s, 3H), 2.68-2.60 (m, 1H), 2.21-1.79 (m, 5H), 1.59-1.51 (m, 1H). LCMS: m/z [M + H]$^+$ = 448.4 (calc. = 448.1). |

| Ex. No. | Structure | Procedure | Analytical data |
|---|---|---|---|
| SC-277a | 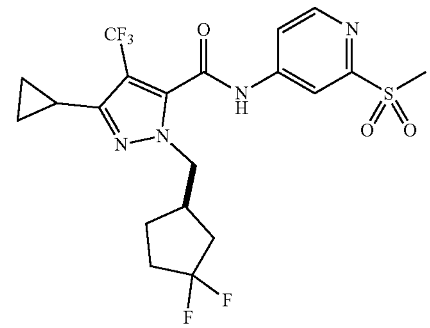 | in analogy to SC-145, using Int-B75 | ¹H NMR (400 MHz, DMSO-d6): δ (ppm) = 11.84 (s, 1H), 8.69 (s, 1H), 8.35 (bs, 1H), 7.80 (bs, 1H), 4.11 (d, 2H), 3.28 (s, 3H), 2.69-2.55 (m, 1H), 2.19-1.72 (m, 6H), 1.55-1.45 (m, 1H), 1.00-0.95 (m, 2H), 0.85-0.81 (m, 2H). LCMS: m/z [M + H]⁺ = 493.2 (calc. 493.1). chiral SFC (column: Chiralpak IC-3 (4.6 × 150 mm), 3 μm, total flow: 3 g/min, 90% CO₂, 10% (isopropylamine in isopropylalcohol), 1500 psi back pressure, 30° C., R$_t$ = 5.78 min. |
| SC-277b | 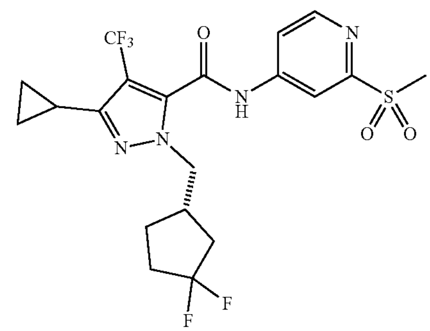 | in analogy to SC-145, using Int-B75 | ¹H NMR (400 MHz, DMSO-d6): δ (ppm) = 11.84 (s, 1H), 8.69 (s, 1H), 8.35 (bs, 1H), 7.80 (bs, 1H), 4.11 (d, 2H), 3.28 (s, 3H), 2.69-2.55 (m, 1H), 2.19-1.72 (m, 6H), 1.55-1.45 (m, 1H), 1.00-0.95 (m, 2H), 0.85-0.81 (m, 2H). LCMS: m/z [M + H]⁺ = 493.2 (calc. 493.1). chiral SFC (column: Chiralpak IC-3 (4.6 × 150 mm), 3 μm, total flow: 3 g/min, 90% CO₂, 10% (isopropylamine in isopropylalcohol), 1500 psi back pressure, 30° C., R$_t$ = 6.33 min. |
| SC-278a | 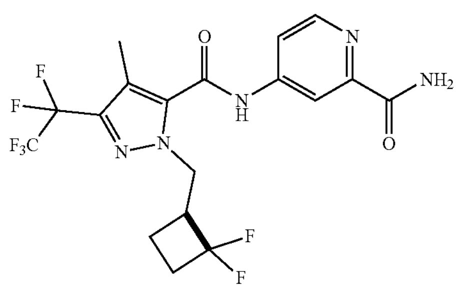 | in analogy to SC-145, using Int-B114 | ¹H NMR (400 MHz, DMSO-d6): δ (ppm) =11.16 (s, 1H), 8.56 (d, 1H), 8.38 (s, 1H), 8.11 (s, 1H), 7.86 (dd, 1H), 7.66 (s, 1H), 4.65-4.59 (m, 1H), 4.48-4.40 (m, 1H), 3.42-3.31 (m, 1H), 2.50-2.42 (m, 2H), 2.24 (s, 3H), 1.91-1.82 (m, 1H), 1.61-1.52 (m, 1H). LCMS: m/z [M + H]⁺ = 468.2 (calc. 468.1). chiral SFC (column: Chiracel OJ-H (4.6 × 250 mm), 5 μm, total flow: 3 mL/min, 90% CO₂, 10% (0.5% diethylamine in methanol), 100 bar back pressure, 30° C., R$_t$ = 2.79 min. |
| SC-278b | 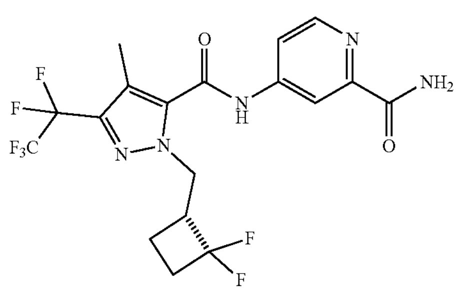 | in analogy to SC-145, using Int-B114 | ¹H NMR (400 MHz, DMSO-d6): δ (ppm) = 11.16 (s, 1H), 8.56 (d, 1H), 8.38 (s, 1H), 8.11 (s, 1H), 7.86 (dd, 1H), 7.66 (s, 1H), 4.65-4.59 (m, 1H), 4.48-4.40 (m, 1H), 3.42-3.31 (m, 1H), 2.50-2.42 (m, 2H), 2.24 (s, 3H), 1.91-1.82 (m, 1H), 1.61-1.52 (m, 1H). LCMS: m/z [M + H]⁺ = 468.2 (calc. 468.1). chiral SFC (column: Chiracel OJ-H (4.6 × 250 mm), 5 μm, total flow: 3 mL/min, 90% CO₂, 10% (0.5% diethylamine in methanol), 100 bar back pressure, 30° C., R$_t$ = 3.21 min. |
| SC-279a | 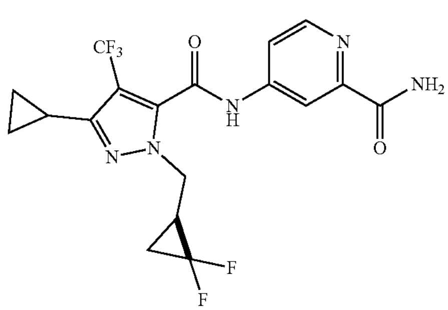 | in analogy to SC-145, using Int-B84 | ¹H NMR (400 MHz, DMSO-d6): δ (ppm) = 11.60 (s, 1H), 8.55 (d, 1H), 8.30 (s, 1H), 8.12 (s, 1H), 7.77 (m, 1H), 7.69 (s, 1H), 4.22 (d, 2H), 2.17-2.16 (m, 1H), 1.96-1.94 (s, 1H), 1.69-1.66 (s, 1H), 1.45-1.41 (s, 1H), 1.00-0.97 (m, 2H), 0.88-0.87 (m, 2H). LCMS: m/z [M + H]⁺ = 429.8 (calc. = 430.1). chiral HPLC (column: Chiralpak IG (4.6 × 250 mm), 5 μm, total flow: 1 mL/min, hexane/DCM/Isopropylalcohol/isopropylamine 40:30:30:0.1, R$_t$ = 5.04 min. |

| Ex. No. | Structure | Procedure | Analytical data |
|---|---|---|---|
| SC-279b | 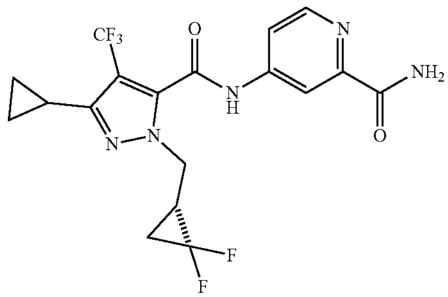 | in analogy to SC-145, using Int-B84 | ¹H NMR (400 MHz, DMSO-d6): δ (ppm) = 11.60 (s, 1H), 8.55 (d, 1H), 8.30 (s, 1H), 8.12 (s, 1H), 7.77 (m, 1H), 7.69 (s, 1H), 4.22 (d, 2H), 2.17-2.16 (m, 1H), 1.96-1.94 (s, 1H), 1.69-1.66 (s, 1H), 1.45-1.41 (s, 1H), 1.00-0.97 (m, 2H), 0.88-0.87 (m, 2H). LCMS: m/z [M + H]⁺ = 429.8 (calc. = 430.1). chiral HPLC (column: Chiralpak IG (4.6 × 250 mm), 5 μm, total flow: 1 mL/min, hexane/DCM/isopropylalcohol/isopropylamine 40:30:30:0.1, $R_t$ = 5.65 min. |
| SC-284a | 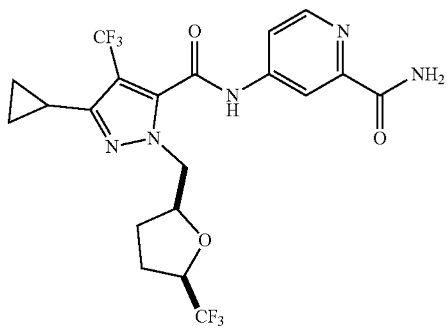 | in analogy to SC-145, using Int-B73 | ¹H NMR (500 MHz, DMSO-d6): δ (ppm) = 11.55 (s, 1H), 8.51 (s, 1H), 8.26 (s, 1H), 8.08 (s, 1H), 7.75 (s, 1H), 7.62 (s, 1H), 4.44-4.32 (m, 2H), 4.29-4.25 (m, 1H), 4.19-4.15 (m, 1H), 2.18-2.12 (m, 2H), 1.99-1.91 (m, 2H), 1.70-1.65 (m, 1H), 0.99-0.95 (m, 2H), 0.85-0.84 (m, 2H). LCMS: m/z [M + H]⁺ = 492.2 (calc. 492.2). chiral SFC (column: Chiracel OD-H (4.6 × 250 mm), 5 μm, total flow: 3 g/min, 90% CO₂, 10% methanol, 100 bar back pressure, 30° C., $R_t$ = 4.82 min. |
| SC-284b | 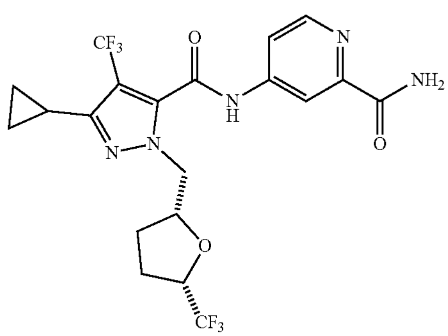 | in analogy to SC-145, using Int-B73 | ¹H NMR (500 MHz, DMSO-d6): δ (ppm) = 11.55 (s, 1H), 8.51 (s, 1H), 8.26 (s, 1H), 8.08 (s, 1H), 7.75 (s, 1H), 7.62 (s, 1H), 4.44-4.32 (m, 2H), 4.29-4.25 (m, 1H), 4.19-4.15 (m, 1H), 2.18-2.12 (m, 2H), 1.99-1.91 (m, 2H), 1.70-1.65 (m, 1H), 0.99-0.95 (m, 2H), 0.85-0.84 (m, 2H). LCMS: m/z [M + H]⁺ = 492.2 (calc. 492.2). chiral SFC (column: Chiracel OD-H (4.6 × 250 mm), 5 μm, total flow: 3 g/min, 90% CO₂, 10% methanol, 100 bar back pressure, 30° C., $R_t$ = 6.39 min. |
| SC-286a | 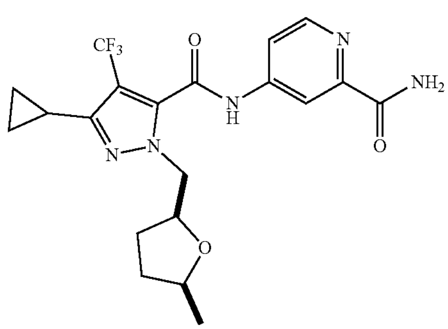 | in analogy to SC-145, using Int-B74 | ¹H NMR (500 MHz, DMSO-d6): δ (ppm) = 11.45 (s, 1H), 8.54 (s, 1H), 8.32 (s, 1H), 8.09 (s, 1H), 7.79 (s, 1H), 7.65 (s, 1H), 4.24-4.20 (m, 1H), 4.14-4.06 (m, 2H), 3.83-3.79 (m, 1H), 1.98-1.86 (m, 3H), 1.70-1.62 (m, 1H), 1.27-1.21 (m, 1H), 0.98-0.82 (m, 7H). LCMS: m/z [M + H]⁺ = 438.3 (calc. 438.2). chiral SFC (column: Cellulose-2 (4.6 × 250 mm), 5 μm, total flow: 3 g/min, 70% CO₂, 30% methanol, 99 bar back pressure, 30° C., $R_t$ = 3.04 min. |

-continued

| Ex. No. | Structure | Procedure | Analytical data |
|---|---|---|---|
| SC-286b | 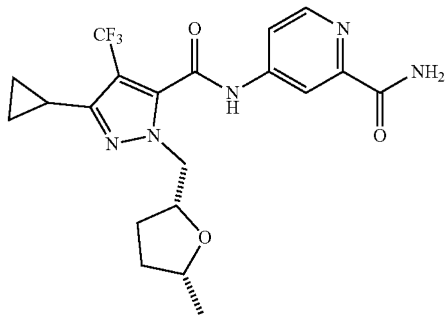 | in analogy to SC-145, using Int-B74 | ¹H NMR (500 MHz, DMSO-d6): δ (ppm) = 11.45 (s, 1H), 8.54 (s, 1H), 8.32 (s, 1H), 8.09 (s, 1H), 7.79 (s, 1H), 7.65 (s, 1H), 4.24-4.20 (m, 1H), 4.14-4.06 (m, 2H), 3.83-3.79 (m, 1H), 1.98-1.86 (m, 3H), 1.70-1.62 (m, 1H), 1.27-1.21 (m, 1H), 0.98-0.82 (m, 7H). LCMS: m/z [M + H]⁺ = 438.3 (calc. 438.2). chiral SFC (column: Cellulose-2 (4.6 × 250 mm), 5 μm, total flow: 3 g/min, 70% CO₂, 30% methanol, 99 bar back pressure, 30° C., $R_t$ = 5.51 min. |
| SC-289 | 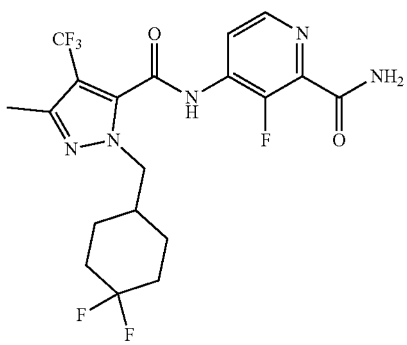 [SMILES: Cc1nn(CC2CCC(F)(F)CC2)c(C(=O)Nc2ccnc(C(N)=O)c2F)c1C(F)(F)F] | in analogy to SC-145, using Int-B46 | ¹H NMR (400 MHz, DMSO-d6): δ (ppm) = 11.42 (s, 1H), 8.40 (s, 1H), 8.20 (s, 1H), 8.04 (s, 1H), 7.68 (s, 1H), 4.03 (d, 2H), 2.30 (s, 3H), 2.06-1.93 (m, 3H), 1.85-1.61 (m, 4H), 1.28-1.18 (m, 2H). LCMS: m/z [M + H]⁺ = 464.2 (calc. = 464.2). |
| SC-290 | 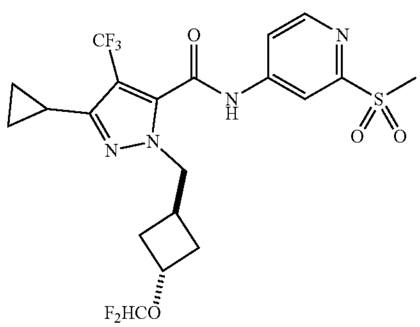 | in analogy to SC-145, using Int-B122 | ¹H NMR (500 MHz, DMSO-d6): δ (ppm) = 11.81 (s, 1H), 8.73 (d, 1H), 8.37 (s, 1H), 7.85 (d, 1H), 6.71-6.40 (t, 1H), 4.43-4.40 (m, 1H), 4.15-4.12 (d, 2H), 3.29 (s, 3H), 2.31-2.25 (m, 3H), 1.95-1.92 (m, 1H), 1.88-1.80 (m, 2H), 0.99-0.95 (m, 2H), 0.86-0.83 (m, 2H). LCMS: m/z [M + H]⁺ = 509.2 (calc. = 509.1). chiral SFC (column: Chiralpak AD-H (4.6 × 250 mm) 5 μm, total flow: 3 g/min, 90% CO₂, 10% isopropanol, 100 bar back pressure, 30° C., $R_t$ = 3.21 min. |
| SC-291a | 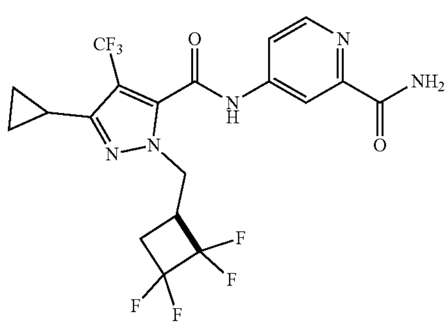 | in analogy to SC-145, using Int-B82 | ¹H NMR (400 MHz, DMSO-d6): δ (ppm) = 11.56 (s, 1H), 8.58 (d, 1H), 8.33 (d, 1H), 8.13 (d, 1H), 7.80-7.78 (m, 1H), 7.69 (d, 1H), 4.47-4.41 (m, 1H), 4.35-4.30 (m, 1H), 3.32-3.30 (m, 1H), 2.81-2.80 (m, 1H), 2.50-2.49 (m, 1H), 1.96-1.93 (m, 1H), 1.00-0.96 (m, 2H), 0.87-0.83 (m, 2H). LCMS: m/z [M + H]⁺ = 480.4 (calc. = 480.1). chiral HPLC (column: Chiralpak IG (4.6 × 250 mm), 5 μm, total flow: 1 mL/min, hexane/DCM/isso-propylalcohol 90:5:5, $R_t$ = 9.52 min. |

| Ex. No. | Structure | Procedure | Analytical data |
|---|---|---|---|
| SC-291b | 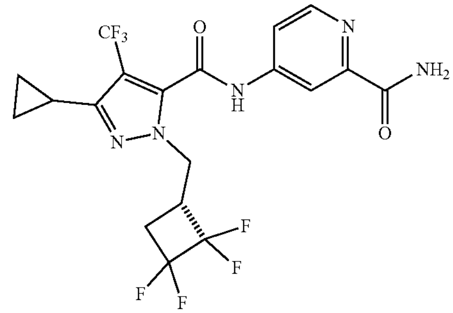 | in analogy to SC-145, using Int-B82 | ¹H NMR (400 MHz, DMSO-d6): δ (ppm) = 11.56 (s, 1H), 8.58 (d, 1H), 8.33 (d, 1H), 8.13 (d, 1H), 7.80-7.78 (m, 1H), 7.69 (d, 1H), 4.47-4.41 (m, 1H), 4.35-4.30 (m, 1H), 3.32-3.30 (m, 1H), 2.81-2.80 (m, 1H), 2.50-2.49 (m, 1H), 1.96-1.93 (m, 1H), 1.00-0.96 (m, 2H), 0.87-0.83 (m, 2H). LCMS: m/z [M + H]⁺ = 480.4 (calc. = 480.1). chiral HPLC (column: Chiralpak IG (4.6 × 250 mm), 5 μm, total flow: 1 mL/min, hexane/DCM/isso-propylalcohol 90:5:5, $R_t$ = 10.82 min. |
| SC-298 | 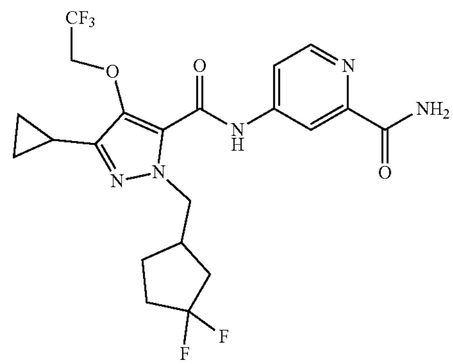 [SMILES: NC(=O)c1cc(NC(=O)c2c(OCC(F)(F)F)c(C3CC3)nn2CC2CCC(F)(F)C2)ccn1] | in analogy to SC-145, using B105 | ¹H NMR (400 MHz, DMSO-d6): δ (ppm) = 10.50 (s, 1H), 8.54 (d, 1H), 8.37 (d, 1H), 8.12 (s, 1H), 7.79-7.77 (m, 1H), 7.66 (s, 1H), 4.76-4.69 (m, 2H), 4.27-4.24 (m, 2H), 2.52-2.50 (m, 1H), 2.08-1.89 (m, 6H), 1.55-1.45 (m, 1H), 0.94-0.90 (m, 2H), 0.81-0.79 (m, 2H). UPLC-MS: m/z [M + H]⁺ = 488.2 (calc. = 488.2). |
| SC-315a | 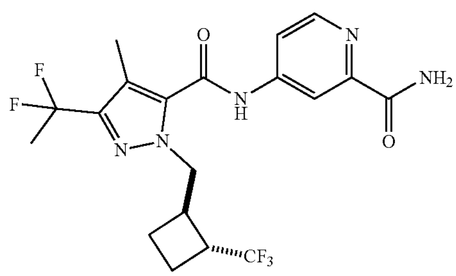 | in analogy to SC-145, using Int-B81 | ¹H NMR (400 MHz, DMSO-d6): δ (ppm) = 11.05 (s, 1H), 8.56 (d, 1H), 8.39 (d, 1H), 8.11 (d, 1H), 7.86-7.85 (m, 1H), 7.67 (d, 1H), 4.36-4.33 (m, 2H), 3.12-3.07 (m, 1H), 2.94-2.91 (m, 1H), 2.23 (s, 3H), 2.03-2.01 (m, 3H), 1.99-1.90 (m, 3H), 1.79-1.76 (m, 1H). LCMS: m/z [M + H]⁺ = 446.0 (calc. = 446.2). chiral SFC (column: Chiracel OX-H (4.6 × 250 mm), 5 μm, total flow: 4 mL/min, 70% CO₂, 30% (EtOH:MeOH:iso-proylamine 70:30:0.3), 100 bar back pressure, 35° C., $R_t$ = 1.58 min. |
| SC-315b | 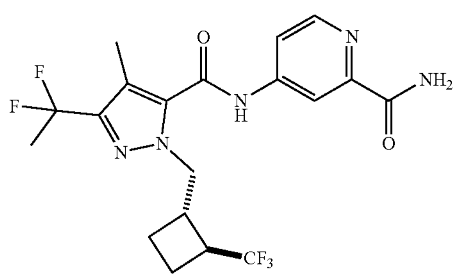 | in analogy to SC-145, using Int-B81 | ¹H NMR (400 MHz, DMSO-d6): δ (ppm) = 11.05 (s, 1H), 8.56 (d, 1H), 8.39 (d, 1H), 8.11 (d, 1H), 7.86-7.85 (m, 1H), 7.67 (d, 1H), 4.36-4.33 (m, 2H), 3.12-3.07 (m, 1H), 2.94-2.91 (m, 1H), 2.23 (s, 3H), 2.03-2.01 (m, 3H), 1.99-1.90 (m, 3H), 1.79-1.76 (m, 1H). LCMS: m/z [M + H]⁺ = 446.0 (calc. = 446.2). chiral SFC (column: Chiracel OX-H (4.6 × 250 mm), 5 μm, total flow: 4 mL/min, 70% CO₂, 30% (EtOH:MeOH:isso-proylamine 70:30:0.3), 100 bar back pressure, 35° C., $R_t$ = 2.13 min. |
| SC-321 | 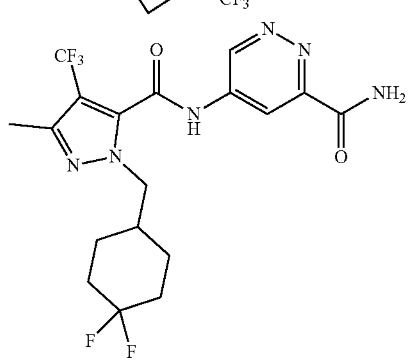 | in analogy to SC-145, using Int-B46 | ¹H NMR (400 MHz, DMSO-d6): δ (ppm) = 11.84 (s, 1H), 9.41 (s, 1H), 8.54 (s, 2H), 7.95 (s, 1H), 4.07 (d, 2H), 2.31 (s, 3H), 2.07-1.92 (m, 3H), 1.82-1.70 (m, 2H), 1.63-1.55 (m, 2H), 1.27-1.19 (m, 2H). LCMS: m/z [M − H]⁻ = 445.2 (calc. = 445.1). |

221

Synthesis of 3-cyclopropyl-1-((3,3-difluorocyclobutyl)methyl)-N-(2-(methylsulfonyl)pyridin-4-yl)-4-(trifluoromethyl)-1H-pyrazole-5-carboxamide (SC-151)

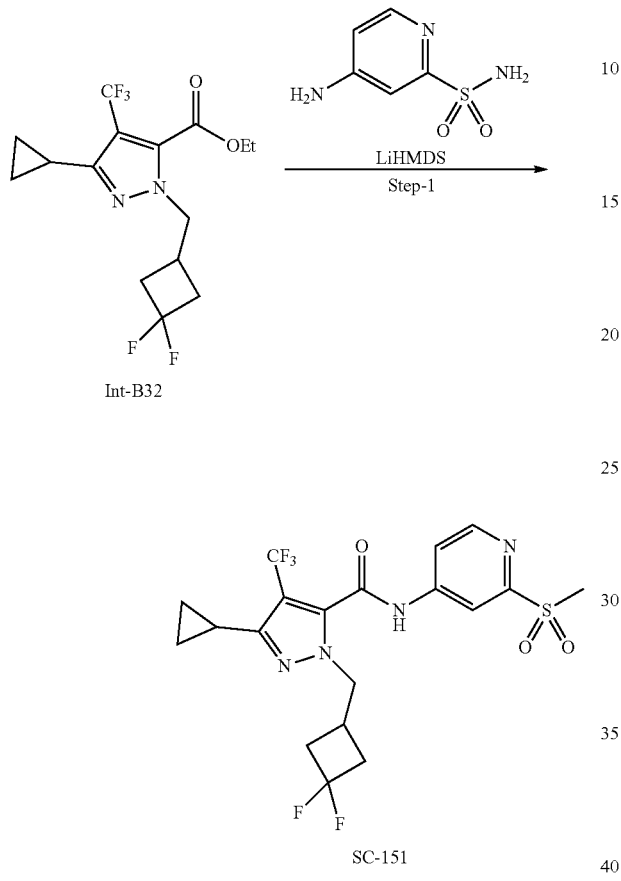

Step-1: To a mixture of ethyl 3-cyclopropyl-1-((3,3-difluorocyclobutyl)methyl)-4-(trifluoromethyl)-1H-pyrazole-5-carboxylate (Int-B32, 700 mg, 1.98 mmol, 1.0 eq.) and 2-(methylsulfonyl)pyridin-4-amine (684 mg, 3.97 mmol, 1.5 eq.) in THF (6 mL) was added a 1M solution of LiHMDS in THF (5.94 mL, 5.94 mmol, 3.0 eq.) at 0° C. and the resulting mixture was stirred at ambient temperature for 16 h. The reaction mixture was quenched with sat. NH$_4$Cl solution, diluted with cold water (30 mL) and extracted with ethyl acetate (2×50 mL). The combined organic layers were dried over Na$_2$SO$_4$ and concentrated under reduced pressure to get the crude product which was purified by reverse-phase prep HPLC purification to yield 3-cyclopropyl-1-((3,3-difluorocyclobutyl)methyl)-N-(2-(methylsulfonyl)pyridin-4-yl)-4-(trifluoromethyl)-1H-pyrazole-5-carboxamide (SC-151). Yield: 13% (130 mg, 0.0271 mmol). NMR (400 MHz, DMSO-d6): δ (ppm)=11.84 (bs, 1H), 8.70 (s, 1H), 8.73 (d, 1H), 8.38 (s, 1H), 7.83 (m, 1H), 4.23 (d, 2H), 2.66-2.61 (m, 3H), 2.45-2.38 (m, 2H), 1.72 (m, 1H), 1.95-1.92 (m, 1H), 1.00-0.95 (m, 2H), 0.95-0.84 (m, 2H). LCMS: m/z [M+H]$^+$=479.3 (calc.=479.1).

222

Synthesis of 4-(3-cyclopropyl-1-((2,2-difluorocyclobutyl)methyl)-4-(trifluoromethyl)-1H-pyrazole-5-carboxamido)picolinamide (SC-154) Synthesized in Form of Enantiomers Enantiomer 1 of 4-(3-cyclopropyl-1-((2,2-difluorocyclobutyl)methyl)-4-(trifluoromethyl)-1H-pyrazole-5-carboxamido)picolinamide (SC-154a) and Enantiomer 2 of 4-(3-cyclopropyl-1-((2,2-difluorocyclobutyl)methyl)-4-(trifluoromethyl)-1H-pyrazole-5-carboxamido)picolinamide (SC-154b)

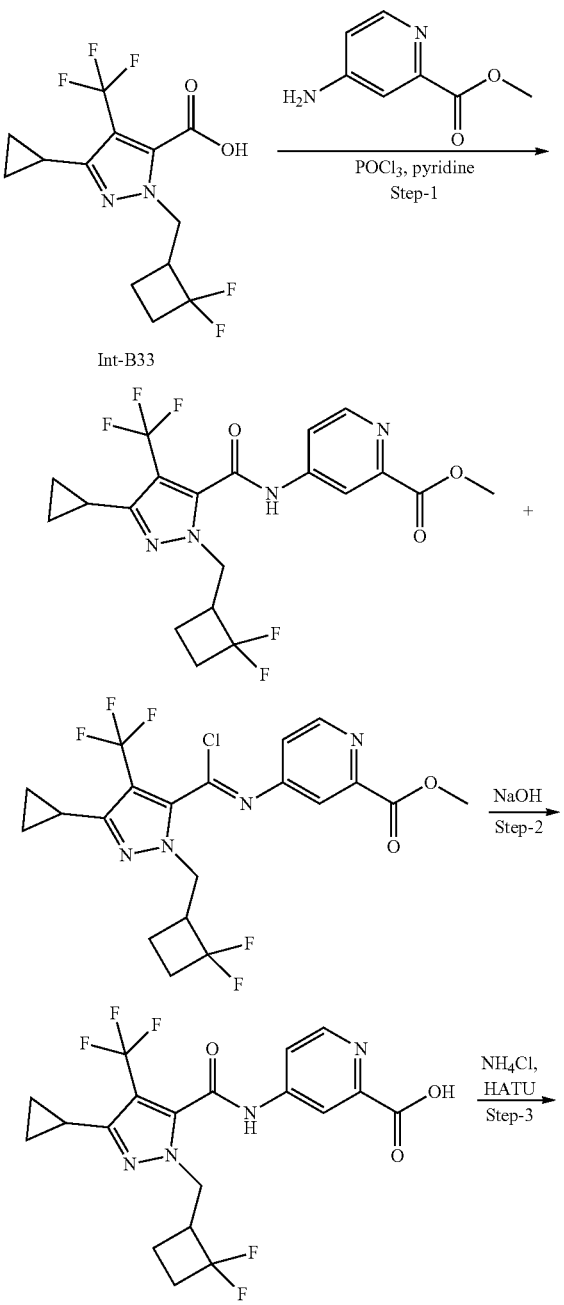

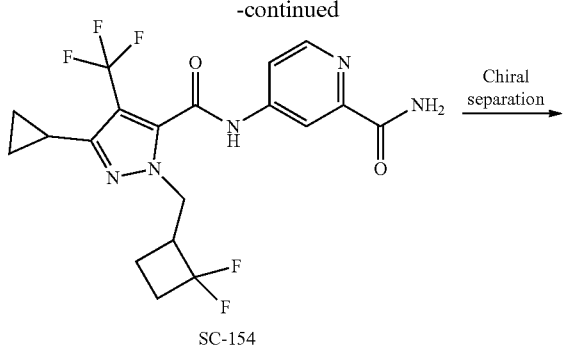

SC-154

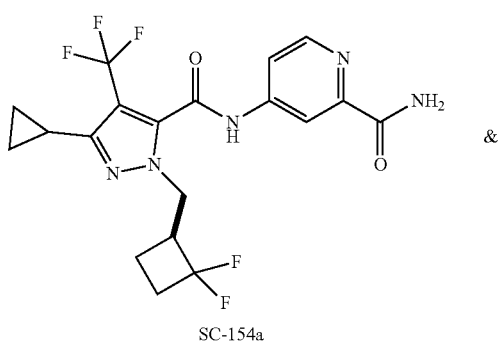

SC-154a

&

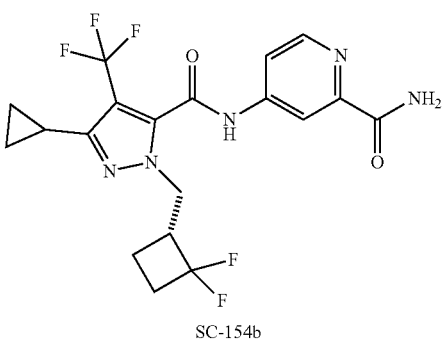

SC-154b

Step-1 and Step-2: To a solution of -3-cyclopropyl-1-((2,2-difluorocyclobutyl)methyl)-4-(trifluoromethyl)-1H-pyrazole-5-carboxylic acid (Int-B33, 580 mg, 1.54 mmol, 1.0 eq.) in pyridine (10 mL) was added POCl$_3$ (0.5 mL, 4.62 mmol, 3.0 eq.) dropwise at 0° C. followed by the addition of methyl 4-aminopyridine-2-carboxylate (281 mg, 1.85 mmol, 1.2 equiv). The reaction was then stirred at ambient temperature for 4 h. The reaction mixture was quenched with water (50 mL) and extracted with ethyl acetate (3×50 mL). The combined organic layers were washed with cold brine (60 mL), dried over Na$_2$SO$_4$ and evaporated under reduced pressure to obtain a residue. This residue was diluted with THF (20 mL), 2N NaOH solution (10 mL) was added and the reaction mixture was stirred at ambient temperature for 16 h. The reaction mixture was concentrated under reduced pressure and diluted with water (30 ml) and acidified with sat. KHSO$_4$ solution up to pH-4-5. The aqeuous layer was extracted with DCM (3×60 mL). The combined organic layers were dried over Na$_2$SO$_4$ and evaporated under reduced pressure to yield crude 4-{3-cyclopropyl-1-[(2,2-difluorocyclobutyl)methyl]-4-(trifluoromethyl)-1H-pyrazole-5-amido}pyridine-2-carboxylic acid which was used in next step without purification. Yield: 81% (550 mg, 1.24 mmol, 84% pure by LCMS). LCMS: m/z [M+H]$^+$=445.06 (calc.=445.13).

Step-3: To a solution of 4-{3-cyclopropyl-1-[(2,2-difluorocyclobutyl)methyl]-4-(trifluoromethyl)-1H-pyrazole-5-amido}pyridine-2-carboxylic acid (550 mg, 1.23 mmol, 1.0 eq.)) in DMF (10 mL) were added HATU (953 mg, 2.27 mmol, 2.0 eq.), DIPEA (0.64 mL, 3.69 mmol, 3.0 eq.) and NH$_4$Cl (664 mg, 12.3 mmol, 1.0 eq.) and the reaction mixture was stirred at ambient temperature for 16 h. The reaction mixture was quenched with water (40 mL) and extracted with ethyl acetate (3×60 mL). The combined organic layers were washed with cold brine (60 mL), dried over Na$_2$SO$_4$ and the solvent was evaporated under reduced pressure to get the crude product which was purified by combiflash column chromatography (silica gel, 0-40% EA in hexane as eluent) to yield 4-{3-cyclopropyl-1-[(2,2-difluorocyclobutyl)methyl]-4-(trifluoromethyl)-1H-pyrazole-5-amido}pyridine-2-carboxamide. Yield: 20% (300 mg, 0.189 mmol).

The resulting racemic product was separated via preparative chiral HPLC (column Chiralpak IG (250×21 mm) 5 nm; mobile phase: Hexane/IPA/DCM (90/05/05), flow rate 21 ml/min).

Analytical data for example SC154a: Chiral HPLC (column: Chiralpak IG (250×4.6 mm) 5 nm; mobile phase: hexane/DCM/isopropanol/isopropylamine: 80/10/10/0.1, flow rate 1.0 mL/min), R$_t$=5.64 min. NMR (400 MHz, DMSO-d6): δ (ppm)=11.53 (s, 1H), 8.55 (s, 1H), 8.30 (s, 1H), 8.09 (s, 1H), 7.77 (s, 1H), 7.64 (s, 1H), 4.38-4.33 (m, 1H), 4.19-4.14 (m, 1H), 2.45-2.38 (m, 2H), 1.95-1.86 (m, 2H), 1.57-1.52 (m, 2H), 0.97-0.94 (m, 2H), 0.86-0.82 (m, 2H). LCMS: m/z [M+H]$^+$=444.4 (calc.=444.2).

Analytical data for example SC154b: Chiral HPLC (column: Chiralpak IG (250×4.6 mm) 5 nm; mobile phase: hexane/DCM/isopropanol/isopropylamine: 80/10/10/0.1, flow rate 1.0 mL/min), R$_t$=6.28 min. NMR (400 MHz, DMSO-d6): δ (ppm)=11.53 (s, 1H), 8.58 (s, 1H), 8.33 (d, 1H), 8.10 (s, 1H), 7.80-7.78 (m, 1H), 7.67 (s, 1H), 4.38-4.32 (m, 1H), 4.18-4.12 (m, 1H), 330-3.28 (m, 1H, merged with DMSO water), 2.45-2.40 (m, 2H), 1.95-1.85 (m, 2H), 1.56-1.51 (m, 1H), 0.99-0.95 (m, 2H), 0.86-0.83 (m, 2H). LCMS: m/z [M+H]$^+$=444.4 (calc.=444.2).

Absolute stereochemistry of SC154a and SC154b was not determined and is assigned arbitrarily.

The following examples were synthesized in analogy to the procedures described above (with or without chiral separation at the end of the synthesis) using appropriate reactants and adjusted purification protocols:

| Ex. No. | Structure | Procedure | Intermediate | Analytical data |
|---|---|---|---|---|
| SC-163 | 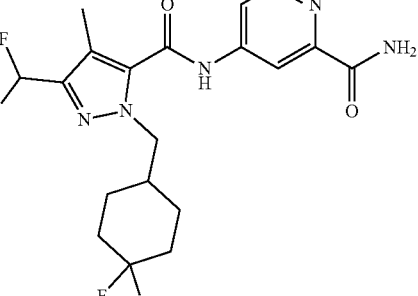 | in analogy to SC-154 | Int-B52 | $^1$H NMR (400 MHz, DMSO-d6): δ (ppm) = 11.04 (s, 1H), 8.55 (d, 1H), 8.38 (s, 1H), 8.10 (s, 1H), 7.85 (d, 1H), 7.66 (s, 1H), 7.07 (t, 1H), 4.21 (d, 2H), 2.24 (s, 3H), 2.08-1.96 (m, 2H), 1.80-1.68 (m, 2H), 1.60-1.57 (m, 2H), 1.27-1.14 (m, 3H). LCMS: m/z [M + H]$^+$ = 428.3 (calc. = 428.2). |
| SC-325 | 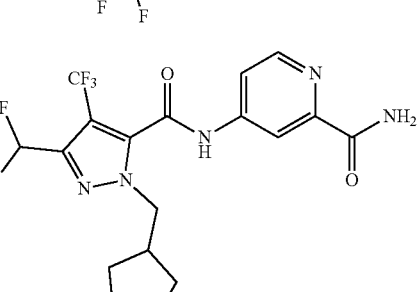 | in analogy to SC-154 | Int-B86 | $^1$H NMR (400 MHz, DMSO-d6): δ (ppm) = 11.70 (s, 1H), 8.61 (d, 1H), 8.32 (s, 1H), 8.13 (s, 1H), 7.79-7.77 (m, 1H), 7.70 (s, 1H), 7.24 (t, 1H), 4.29 (d, 2H), 2.70-2.66 (m, 1H), 2.20-1.98 (m, 4H), 1.83-1.81 (m, 1H), 1.58-1.52 (m, 1H). LCMS: m/z [M + H]$^+$ = 468.3 (calc. = 468.1). |

Synthesis of 4-(1-((3,3-difluorocyclopentyl)methyl)-3-isopropoxy-4-(trifluoromethyl)-1H-pyrazole-5-carboxamido)picolinamide (SC-155)

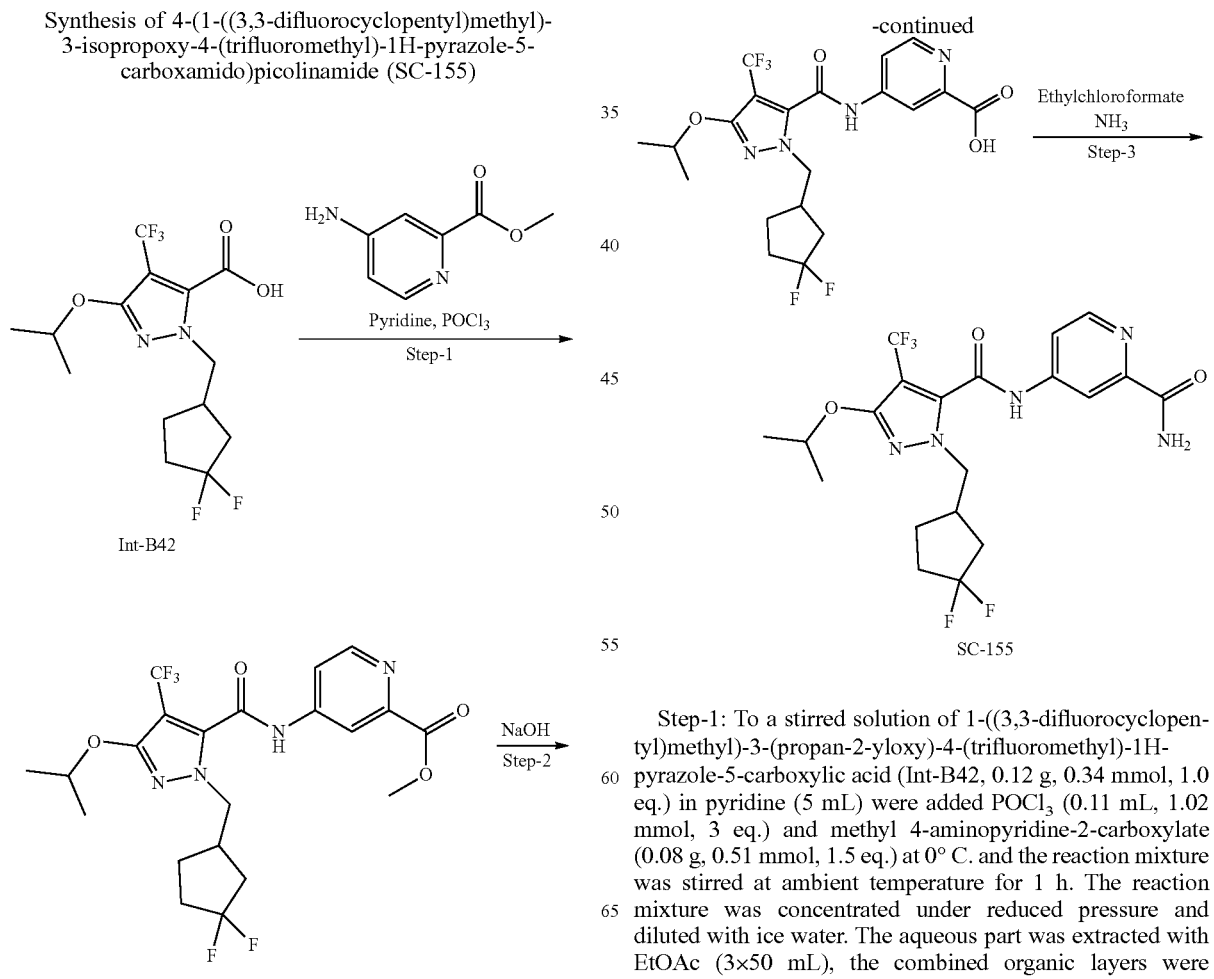

Step-1: To a stirred solution of 1-((3,3-difluorocyclopentyl)methyl)-3-(propan-2-yloxy)-4-(trifluoromethyl)-1H-pyrazole-5-carboxylic acid (Int-B42, 0.12 g, 0.34 mmol, 1.0 eq.) in pyridine (5 mL) were added POCl$_3$ (0.11 mL, 1.02 mmol, 3 eq.) and methyl 4-aminopyridine-2-carboxylate (0.08 g, 0.51 mmol, 1.5 eq.) at 0° C. and the reaction mixture was stirred at ambient temperature for 1 h. The reaction mixture was concentrated under reduced pressure and diluted with ice water. The aqueous part was extracted with EtOAc (3×50 mL), the combined organic layers were washed with brine, dried over Na₂SO₄ and concentrated under reduced pressure to yield crude methyl 4-{1-[(3,3-difluorocyclopentyl)methyl]-3-(propan-2-yloxy)-4-(trifluoromethyl)-1H-pyrazole-5-amido}pyridine-2-carboxylate. The crude was directly used in the next step without further purification. Yield: 0.16 g, crude.

Step-2: To a stirred mixture of methyl 4-{1-[(3,3-difluorocyclopentyl)methyl]-3-(propan-2-yloxy)-4-(trifluoromethyl)-1H-pyrazole-5-amido}pyridine-2-carboxylate (0.16 g, crude, 1.0 eq.) in THF (6 mL) was added 2M NaOH (3 mL) at ambient temperature and the reaction mixture was stirred at the same temperature for 16 h. The reaction mixture was concentrated under reduced pressure and was then diluted with ice water. The aqueous part was acidified with saturated NaHSO₄ to pH-2 and extracted with ethyl acetate (3×60 mL). The combined organic layers were washed with brine, dried over Na₂SO₄ and concentrated under reduced pressure to yield crude 4-{1-[(3,3-difluorocyclopentyl)methyl]-3-(propan-2-yloxy)-4-(trifluoromethyl)-1H-pyrazole-5-amido}pyridine-2-carboxylic acid. Yield: 0.20 g, crude.

Step-3: To a stirred solution of 4-{1-[(3,3-difluorocyclopentyl)methyl]-3-(propan-2-yloxy)-4-(trifluoromethyl)-1H-pyrazole-5-amido}pyridine-2-carboxylic acid (0.20 g, crude, 1 eq.) in THF (12 mL) were added TEA (0.18 mL, 1.26 mmol, 3 eq.) and ethylchloroformate (0.06 mL, 0.63 mmol, 1.5 eq.) at −10° C. and the mixture was stirred at the same temperature for 2 h. Then NH₃ solution (25% in water, 9 mL) was added to the reaction mixture at 0° C. and the reaction mixture stirred at ambient temperature for 16 h. The reaction mixture was diluted with ice water and was extracted with EtOAc (3×50 mL). The combined organic layer was washed with brine (30 mL), dried over Na₂SO₄ and concentrated under reduced pressure to get the crude material which was purified by reverse phase preparative HPLC to obtain 4-(1-((3,3-difluorocyclopentyl)methyl)-3-isopropoxy-4-(trifluoromethyl)-1H-pyrazole-5-carboxamido)picolinamide (SC-155). Yield: 18% over 3 steps (30 mg, 0.06 mmol). NMR (400 MHz, DMSO-d6): δ (ppm)=11.55 (s, 1H), 8.59 (d, 1H), 8.32 (s, 1H), 8.12 (s, 1H), 7.79 (d, 1H), 7.69 (s, 1H), 4.91-4.88 (m, 1H), 4.06 (d, 2H), 2.67-2.61 (m, 1H), 2.18-1.97 (m, 4H), 1.84-1.82 (m, 1H), 1.56-1.51 (m, 1H), 1.34-1.32 (m, 6H). UPLC-MS: m/z [M+H]⁺=476.3 (calc.=476.2).

The following examples were synthesized in analogy to the procedures described above (with or without chiral separation at the end of the synthesis) using appropriate reactants and adjusted purification protocols:

| Ex. No. | Structure | Procedure | Intermediate | Analytical data |
| --- | --- | --- | --- | --- |
| SC-156 | 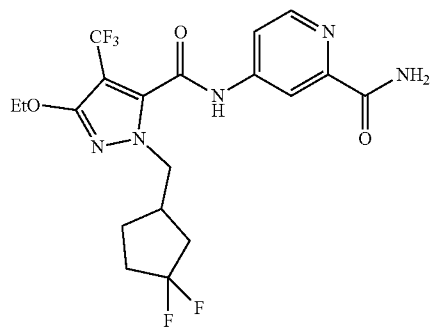 [SMILES: CCOc1nn(CC2CCC(F)(F)C2)c(C(=O)Nc2ccnc(C(N)=O)c2)c1C(F)(F)F] | in analogy to SC-155 | Int-B43 | ¹H NMR (400 MHz, DMSO-d6): δ (ppm) = 11.56 (s, 1H), 8.59 (d, 1H), 8.31 (s, 1H), 8.12 (s, 1H), 7.79 (s, 1H), 7.69 (s, 1H), 4.33-4.31 (m, 2H), 4.29-4.04 (m, 2H), 2.68-2.61 (m, 1H), 2.18-1.80 (m, 5H), 1.65-1.45 (m, 1H), 1.45-1.20 (m, 3H). UPLC-MS: m/z [M + H]⁺ = 462.3 (calc. = 462.2). |
| SC-157 | 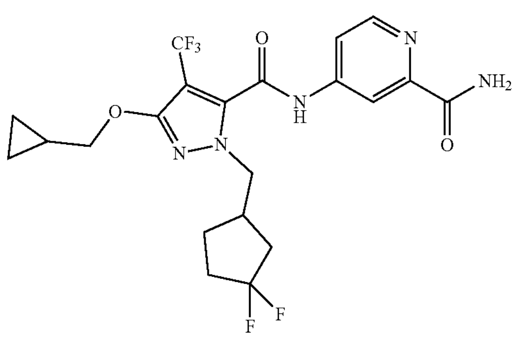 [SMILES: NC(=O)c1cc(NC(=O)c2c(C(F)(F)F)c(OCC3CC3)nn2CC2CCC(F)(F)C2)ccn1] | in analogy to SC-155 | Int-B44 | ¹H NMR (400 MHz, DMSO-d6): δ (ppm) = 11.55 (s, 1H), 8.59 (d, 1H), 8.31 (s, 1H), 8.11 (s, 1H), 7.80-7.77 (m, 1H), 7.68 (s, 1H), 4.10-4.08 (m, 2H), 4.05-4.03 (m, 2H), 2.69-2.63 (m, 1H), 2.19-1.80 (m, 5H), 1.55-1.50 (m, 1H), 1.45-1.19 (m, 1H), 0.69-0.49 (m, 2H), 0.49-0.25 (m, 2H). UPLC-MS: m/z [M + H]⁺ = 488.2 (calc. = 488.2). |
| SC-158 R | 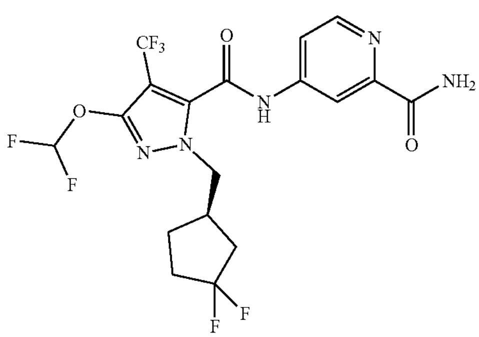 [SMILES: NC(=O)c1cc(NC(=O)c2c(C(F)(F)F)c(OC(F)F)nn2C[C@@H]2CCC(F)(F)C2)ccn1] | in analogy to SC-155 | Int-B45a | ¹H NMR (400 MHz, DMSO-d6): δ (ppm) = 11.68 (s, 1H), 8.61 (d, 1H), 8.32 (s, 1H), 8.12 (s, 1H), 7.79-7.78 (m, 1H), 7.69-7.31 (m, 2H), 4.17 (d, 2H), 2.67-2.59 (m, 1H), 2.32-1.82 (m, 5H), 1.59-1.49 (m, 1H). UPLC-MS: m/z [M + H]⁺ = 484.3 (calc. = 484.1). |

| Ex. No. | Structure | Procedure | Intermediate | Analytical data |
|---|---|---|---|---|
| SC-158 S | 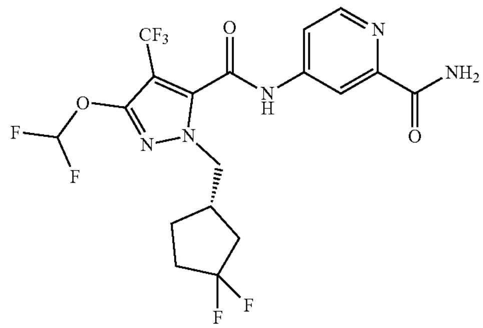 [SMILES: NC(=O)c1cc(NC(=O)c2c(C(F)(F)F)c(OC(F)F)nn2C[C@H]2CCC(F)(F)C2)ccn1] | in analogy to SC-155 | Int-B45b | $^1$H NMR (400 MHz, DMSO-d6): δ (ppm) = 11.67 (s, 1H), 8.60-8.59 (m, 1H), 8.31 (s, 1H), 8.12 (s, 1H), 7.79-7.77 (m, 1H), 7.69-7.31 (m, 2H), 4.17-4.15 (m, 2H), 2.67-2.59 (m, 1H), 2.26-2.00 (m, 4H), 1.96-1.82 (m, 1H), 1.55-1.53 (m, 1H). UPLC-MS: m/z [M + H]$^+$ = 484.3 (calc. = 484.1). |
| SC-216 | 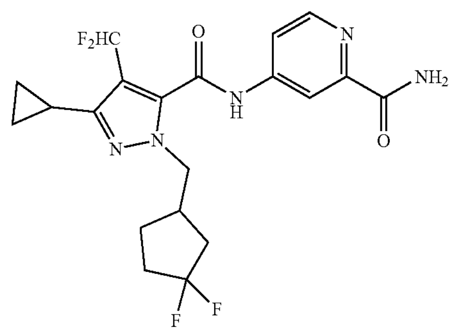 [SMILES: NC(=O)c1cc(NC(=O)c2c(C(F)F)c(C3CC3)nn2CC2CCC(F)(F)C2)ccn1] | in analogy to SC-155 | Int-B64 | $^1$H NMR (400 MHz, DMSO-d6): δ (ppm) = 11.32 (s, 1H), 8.57 (d, 1H), 8.34 (d, 1H), 8.11 (d, 1H) 7.81-7.79 (m, 1H), 7.67 (d, 1H), 7.27-7.00 (m, 1H), 7.63 (s, 1H), 4.13 (d, 2H), 2.57-2.49 (m, 1H), 2.13-2.06 (m, 4H), 2.04-2.00 (m, 1H), 1.99-1.75 (m, 1H), 1.50-1.45 (m, 1H), 0.95-0.94 (m, 2H), 0.93-0.92 (m, 2H). LC-MS: m/z [M + H]$^+$ = 440.2 (calc. = 440.2); |
| SC-309 | 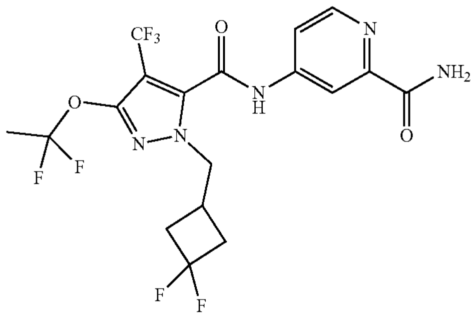 | in analogy to SC-155 | Int-B111 | $^1$H NMR (400 MHz, DMSO-d6): δ (ppm) = 8.55 (d, 1H), 8.36 (s, 1H), 8.09 (s, 1H), 7.86 (d, 1H), 7.65 (s, 1H), 4.32 (d, 2H), 2.66-2.58 (m, 3H), 2.44-2.21 (m, 2H), 2.05-1.89 (m, 6H). LCMS: m/z [M + H]$^+$ = 430.3 (calc. 430.2). |

Synthesis of 4-(1-((3,3-difluorocyclopentyl)methyl)-3-(1,1-difluoroethyl)-4-methyl-1H-pyrazole-5-carboxamido)picolinamide (SC-167)

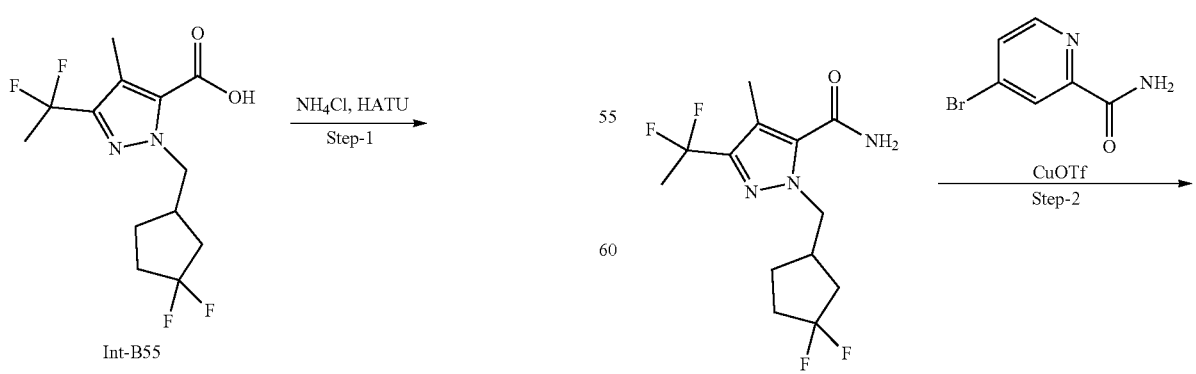

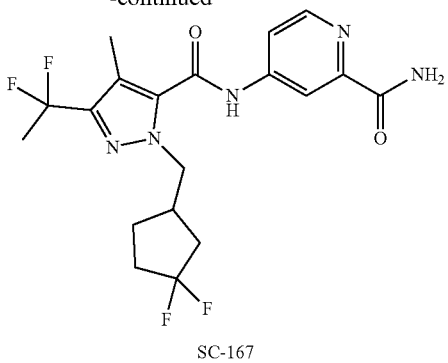

SC-167

Step-1: To a solution of 1 #3,3-difluorocyclopentyl) methyl)-3-(1,1-difluoroethyl)-4-methyl-1H-pyrazole-5-carboxylic acid (350 mg, max. 1.14 mmol, 1.0 eq.) in dry DMF (5 mL) were added DIPEA (438 mg, 3.39 mmol, 3.0 eq.), HATU (645 mg, 1.70 mmol, 1.5 eq.) and NH₄Cl (300 mg, 5.66 mmol, 5.0 eq.). The resulting reaction mixture was stirred at ambient temperature for 2 h. The reaction mixture was diluted with water (25 mL) and extracted with EtOAc (2×30 mL). The combined organic layers were washed with water (2×30 mL) and then brine (30 mL), dried over anhyd. Na₂SO₄ and concentrated under reduced pressure to get the crude product, which was purified by column chromatography (silica gel 100-200 mesh, 25% EtOAc in pet-ether as an eluent) to afford 1-((3,3-difluorocyclopentyl)methyl)-3-(1,1-difluoroethyl)-4-methyl-1H-pyrazole-5-carboxamide (180 mg, 0.59 mol, 33% over three steps).

Step-2: In a sealed tube a solution of 1-((3,3-difluorocyclopentyl)methyl)-3-(1,1-difluoroethyl)-4-methyl-1H-pyrazole-5-carboxamide (180 mg, 0.59 mmol, 1.0 eq.), 4-bromopicolinamide (180 mg, 0.90 mmol, 1.5 eq.) and Cs₂CO₃ (381 mg, 1.17 mmol, 2.0 eq.) in 1,4-dioxane (5 mL) was degassed with argon for 15 min. To the reaction mixture was then added copper(I) trifluoromethanesulfonate benzene complex (44 mg, 0.18 mmol, 0.3 eq.) followed by trans-N, N'-dimethyl-cyclohexane-1,2-diamine (24 mg, 0.17 mmol, 0.3 eq.) at ambient temperature. The resulting solution was then heated to 100° C. for 16 h. The reaction mixture was cooled to ambient temperature, filtered through a celite bed and the filtrate was concentrated under reduced pressure to get the crude product, which was purified by prep-HPLC to afford 4-(1-((3,3-difluorocyclopentyl)methyl)-3-(1,1-difluoroethyl)-4-methyl-1H-pyrazole-5-carboxamido)picolinamide (SC-167, 100 mg, 0.23 mmol, 39%). NMR (400 MHz, DMSO-d6): δ (ppm)=11.08 (s, 1H), 8.56 (d, 1H), 8.38 (d, 1H), 8.10 (bs, 1H), 7.85 (dd, 1H), 7.66 (bs, 1H), 4.28 (d, 2H), 2.69-2.55 (m, 1H), 2.23 (s, 3H) 2.19-1.75 (m, 8H), 1.57-1.48 (m, 1H); LC-MS: m/z [M+H]⁺=428.2 (calc.=428.2).

Synthesis of 4-(1-((3,3-difluoro-1-methylcyclobutyl) methyl)-3-(1,1-difluoroethyl)-4-methyl-1H-pyrazole-5-carboxamido)picolinamide (SC-208)

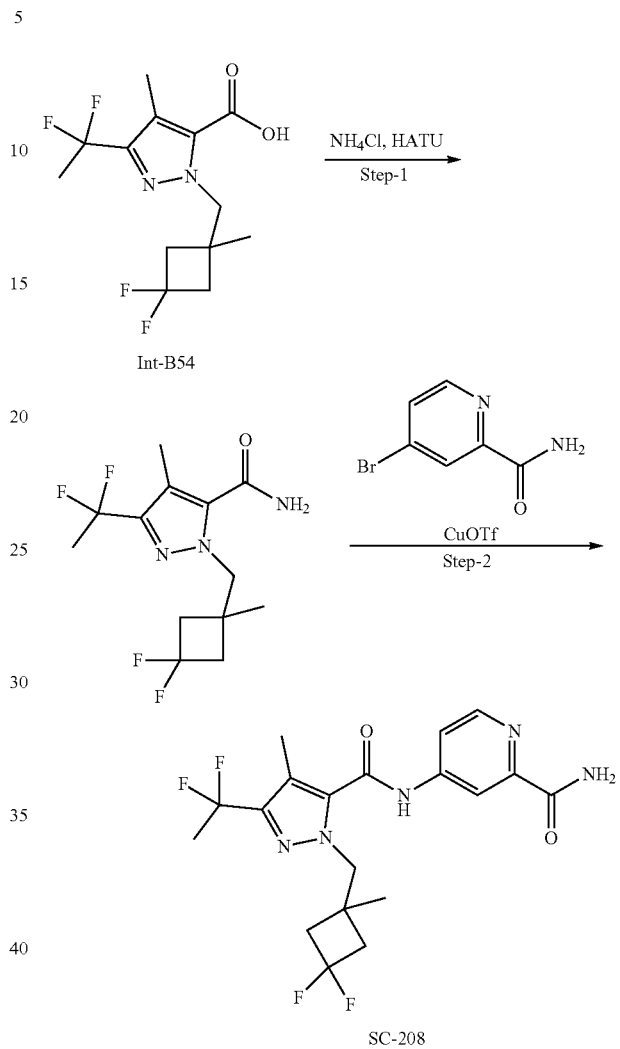

SC-208

Step-1: To a solution of crude 1-((3,3-difluoro-1-methylcyclobutyl)methyl)-3-(1,1-difluoroethyl)-4-methyl-1H-pyrazole-5-carboxylic acid (Int-B54, 700 mg, max. 2.27 mmol, 1.0 eq.) in DMF (5.0 mL) were added HATU (1.29 g, 3.41 mmol, 1.5 eq.), DIPEA (1.2 mL, 6.81 mmol, 3.0 eq.) and ammonium chloride (602 mg, 11.36 mmol, 5.0 eq.) at ambient temperature. The resulting reaction mixture was then stirred for 4 hours. The reaction mixture was then diluted with water (20 mL) and was stirred for 20 minutes at ambient temperature causing precipitation. The precipitate was filtered off, was washed with water (10 mL) and dried under reduced pressure to afford 1-((3,3-difluoro-1-methylcyclobutyl)methyl)-3-(1,1-difluoroethyl)-4-methyl-1H-pyrazole-5-carboxamide (350 mg, 1.14 mmol, 55% over 2 steps from ester).

Step-2: To a solution of 1-((3,3-difluoro-1-methylcyclobutyl)methyl)-3-(1,1-difluoroethyl)-4-methyl-1H-pyrazole-5-carboxamide (100 mg, 0.33 mmol, 1.0 eq.) in 1,4-dioxane (5.0 mL) in a sealed tube were added 4-bromopicolinamide (97.4 mg, 0.49 mmol, 1.5 eq.) and Cs₂CO₃ (264 mg, 0.81 mmol, 2.5 eq.) at ambient temperature, and the reaction mixture was degassed with argon for 10 minutes. To the reaction mixture were then added trans-N,N'-dimethyl-cyclohexane-1,2-diamine (14 mg, 0.10 mmol, 0.3 eq.) and copper (I) trifluoromethane sulfonate benzene complex (41 mg, 0.081 mmol, 0.25 eq.) at ambient temperature. The reaction mixture was then heated to 100° C. and stirred for 16 h. The reaction mixture was cooled to ambient temperature, filtered through a celite bed the and the celite bed was washed with ethyl acetate (20 mL). The filtrate was concentrated under reduced pressure to get the crude product, which was purified by flash column chromatography (0.1% formic acid in water and acetonitrile as an eluent) to afford 4-(1-((3,3-difluoro-1-methylcyclobutyl)methyl)-3-(1,1-difluoroethyl)-4-methyl-1H-pyrazole-5-carboxamido)picolinamide (SC-208, 40 mg, 0.094 mmol, 29%). $^1$H NMR (400 MHz, DMSO-d6): δ (ppm)=11.11 (s, 1H), 8.56 (d, 1H), 8.37 (d, 1H), 8.10 (s, 1H), 7.85-7.83 (m, 1H), 7.66 (s, 1H), 4.37 (s, 2H), 2.73-2.66 (m, 2H), 2.35-2.25 (m, 2H), 2.25 (s, 3H), 2.04 (t, 3H), 1.07 (s, 3H), LC-MS: m/z [M+H]$^+$=428.2 (calc.=428.2).

The following examples were synthesized in analogy to the procedures described above using appropriate reactants and adjusted purification protocols:

| Ex. No. | Structure | Procedure | Intermediate | Analytical data |
|---|---|---|---|---|
| SC-210 | 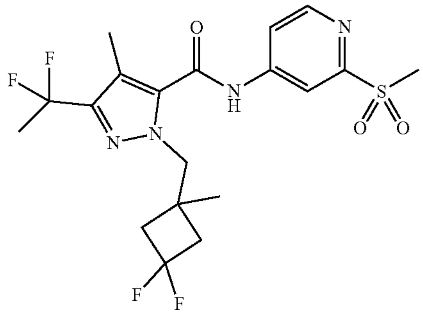 [SMILES: Cc1c(C(C)(F)F)nn(CC2(C)CC(F)(F)C2)c1C(=O)Nc1ccnc(S(C)(=O)=O)c1] | in analogy to SC-208 | Int-B54 | $^1$H NMR (400 MHz, DMSO-d6): δ (ppm) = 11.35 (s, 1H), 8.71 (d, 1H), 8.42 (s, 1H), 7.91-7.89 (dd, 1H), 4.36 (s, 2H), 3.28 (s, 3H), 2.73-2.66 (m, 2H), 2.35-2.25 (m, 2H), 2.24 (s, 3H), 2.03 (t, 3H), 1.07 (s, 3H), LC-MS: m/z [M + H]$^+$ = 463.2 (calc. = 463.1). |
| SC-213 | 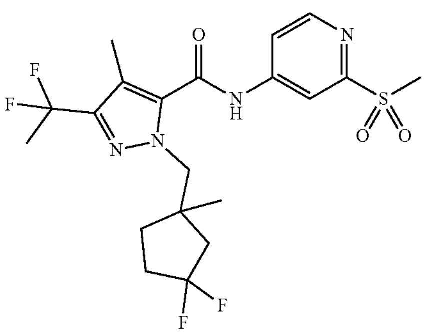 [SMILES: Cc1c(C(C)(F)F)nn(CC2(C)CCC(F)(F)C2)c1C(=O)Nc1ccnc(S(C)(=O)=O)c1] | in analogy to SC-208 | IntB-56 | $^1$H NMR (400 MHz, DMSO-d6): δ (ppm) = 11.36 (s, 1H), 8.69 (s, 1H), 8.40 (s, 1H), 7.88 (s, 1H), 4.30 (s, 2H), 3.28 (s, 3H), 2.31 (d, 1H), 2.26 (s, 4H), 2.21-2.10 (m, 1H), 2.03 (t, 4H), 1.94-1.77 (m, 1H), 1.51 (dt, 1H), 0.95 (s, 3H). LC-MS: m/z [M + H]$^+$ = 477.2 (calc. = 477.2). |
| SC-214a | 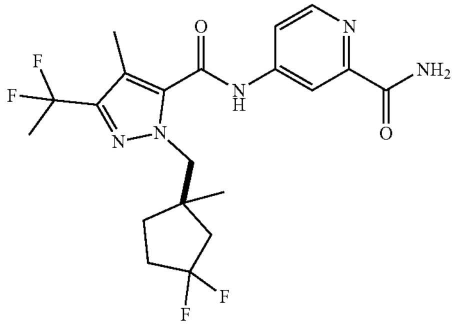 | in analogy to SC-208 | IntB-56 | NMR (500 MHz, DMSO-d6): δ (ppm) = 11.11 (s, 1H), 8.56 (d, 1H), 8.37 (d, 1H), 8.11 (d, 1H), 7.84 (dd, 1H), 7.66 (d, 1H), 4.28 (s, 2H), 2.36-2.28 (m, 4H), 2.19-1.99 (m, 5H), 1.91-1.79 (m, 2H), 1.54-1.48 (m, 1H), 0.97 (s, 3H). LC-MS: m/z [M + H]$^+$ = 442.2 (calc. = 442.2). Chiral HPLC (column: Chiralpak IG (250 × 4.6 mm) 5 μm; mobile phase: 0.2% TFA in n-Hexane/isopropanol 95:05, flow rate 1.0 mL/min), R$_t$ = 25.10 min. |
| SC-214b | 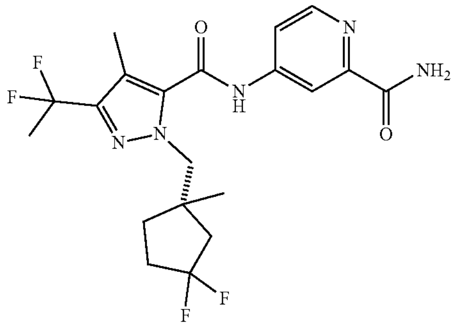 | in analogy to SC-208 | IntB-56 | NMR (500 MHz, DMSO-d6): δ (ppm) = 11.11 (s, 1H), 8.56 (d, 1H), 8.37 (d, 1H), 8.11 (d, 1H), 7.84 (dd, 1H), 7.66 (d, 1H), 4.28 (s, 2H), 2.36-2.28 (m, 4H), 2.19-1.99 (m, 5H), 1.91-1.79 (m, 2H), 1.54-1.48 (m, 1H), 0.97 (s, 3H). LC-MS: m/z [M + H]$^+$ = 442.2 (calc. = 442.2). Chiral HPLC (column: Chiralpak IG (250 × 4.6 mm) 5 μm; mobile phase: 0.2% TFA in n-Hexane/isopropanol 95:05, flow rate 1.0 mL/min), R$_t$ = 28.75 min. |

| Ex. No. | Structure | Procedure | Intermediate | Analytical data |
|---|---|---|---|---|
| SC-220 | 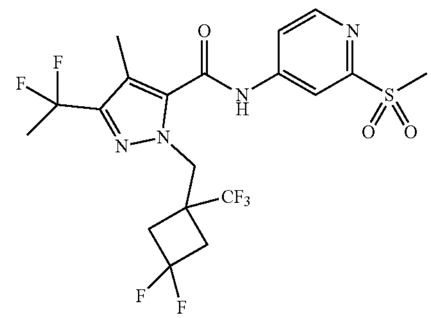 [SMILES: Cc1c(C(C)(F)F)nn(CC2(C(F)(F)F)CC(F)(F)C2)c1C(=O)Nc1ccnc(S(C)(=O)=O)c1] | in analogy to SC-208 | Int-B59 | ¹H NMR (400 MHz, DMSO-d6): δ (ppm) = 11.30 (s, 1H), 8.71 (d, 1H), 8.42 (s, 1H), 7.94-7.92 (m, 1H), 4.76 (s, 2H), 3.29 (s, 3H), 3.13-2.97 (m, 4H), 2.28 (s, 3H), 2.04 (t, 3H), LC-MS: m/z [M + H]⁺ = 517.1 (calc. = 517.1). |
| SC-223 | 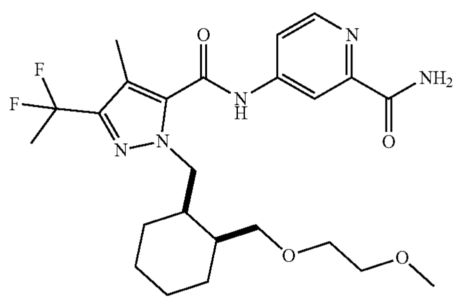 | in analogy to SC-208 | Int-B62 | ¹H NMR (400 MHz, DMSO-d6, 90° C.): δ (ppm) = 10.62 (s, 1H), 8.41 (brs, 1H), 8.24 (brs, 1H), 7.75 (brs, 2H), 7.17 (brs, 1H), 4.32 (d, 2H), 3.46-3.33 (m, 6H), 3.20 (s, 3H), 2.23-2.18 (m, 4H), 2.03-1.95 (m, 3H), 1.87-1.81 (m, 1H), 1.79-1.38 (m, 4H), 1.32-1.23 (m, 4H); LC-MS: m/z [M + H]⁺ = 494.3 (calc. = 494.3). |
| SC-299 | 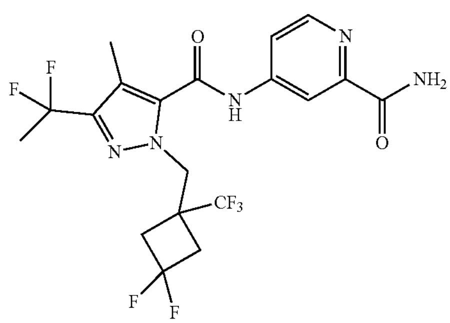 [SMILES: Cc1c(C(C)(F)F)nn(CC2(C(F)(F)F)CC(F)(F)C2)c1C(=O)Nc1ccnc(C(N)=O)c1] | in analogy to SC-208 | Int-B59 | ¹H NMR 1H NMR (400 MHz, DMSO-d6): δ (ppm) = 11.06 (s, 1H), 8.56 (d, 1H), 8.38 (s, 1H), 8.11 (s, 1H), 7.86-7.84 (m, 1H), 7.66 (s, 1H), 4.75 (s, 2H), 3.12-2.97 (m, 4H), 2.27 (s, 3H), 2.04 (t, 3H). LC-MS: m/z [M + H]⁺ = 482.2 (calc. 482.1). |
| SC-206 | 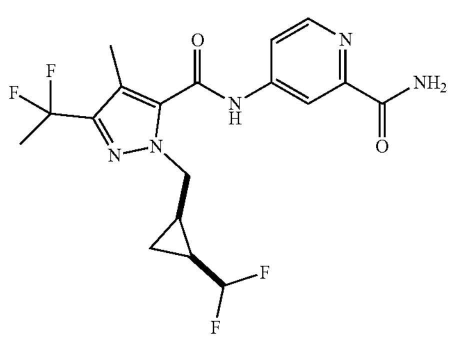 | in analogy to SC-208 | Int-B119 | ¹H NMR (400 MHz, DMSO-d6): δ (ppm) = 11.08 (s, 1H), 8.56 (d, 1H), 8.38 (d, 1H) 8.10 (s, 1H), 7.88-7.86 (s, 1H), 7.66 (s, 1H), 6.20-5.91 (m, 1H), 4.42-4.34 (m, 2H), 2.25 (s, 3H), 2.08-2.03 (m, 3H), 1.59-1.15 (m, 2H), 0.94-0.92 (m, 1H), 0.80-0.78 (m, 1H). LCMS: m/z [M + H]⁺ = 414.2 (calc. 414.2). |

-continued

| Ex. No. | Structure | Procedure | Intermediate | Analytical data |
|---|---|---|---|---|
| SC-301 | 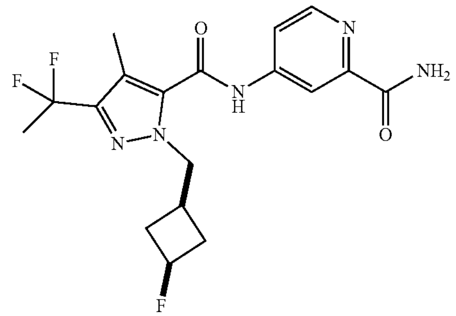 | in analogy to SC-208 | Int-B118 | $^1$H NMR (400 MHz, DMSO-d6): δ (ppm) = 11.08 (s, 1H), 8.55 (d, 1H), 8.37 (s, 1H), 8.11 (s, 1H), 7.84 (d, 1H), 7.66 (s, 1H), 4.96-4.92 (m, 1H), 4.34 (d, 2H), 2.38-2.33 (m, 2H), 2.24 (s, 3H), 2.18-1.91 (m, 6H). LCMS: m/z [M + H]$^+$ = 396.2 (calc. = 396.2). |

Synthesis of 1-((3,3-difluoro-1-methylcyclobutyl)methyl)-3-(1,1-difluoroethyl)-4-methyl-N-(2-sulfamoylpyridin-4-yl)-1H-pyrazole-5-carboxamide (SC-209)

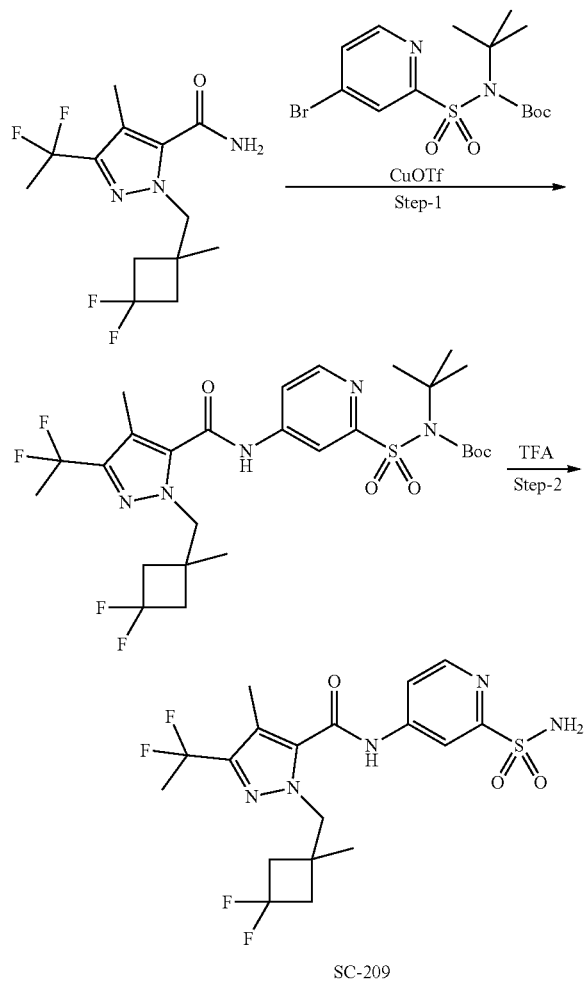

SC-209

Step-1: To a solution of 1-((3,3-difluoro-1-methylcyclobutyl)methyl)-3-(1,1-difluoroethyl)-4-methyl-1H-pyrazole-5-carboxamide (150 mg, 0.488 mmol, 1.0 eq.) in 1,4-dioxane (5 mL) in a sealed tube were added tert-butyl ((4-bromopyridin-2-yl)sulfonyl)(tert-butyl)carbamate (230 mg, 0.585 mmol, 1.2 eq.) and Cs$_2$CO$_3$ (317 mg, 0.973 mmol, 2.0 eq.) at ambient temperature and the reaction mixture was purged with argon for 10 minutes. To the reaction mixture were then added trans-N,N'-dimethyl-cyclohexane-1,2-diamine (21 mg, 0.146 mmol, 0.3 eq.) and copper (I) trifluoromethanesulfonate benzene complex (74 mg, 0.147 mmol, 0.3 eq.) at ambient temperature. The reaction mixture was then heated to 100° C. for 16 h. The reaction mixture was then cooled to ambient temperature, filtered through a celite bed and the celite bed was washed with ethyl acetate (20 mL). The combined organic layers were washed with water (2×50 mL), dried over anhydrous Na$_2$SO$_4$ and concentrated under reduced pressure to afford tert-butyl tert-butyl((4-(1-((3,3-difluoro-1-methylcyclobutyl)methyl)-3-(1,1-difluoroethyl)-4-methyl-1H-pyrazole-5-carboxamido)pyridin-2-yl) sulfonyl) carbamate (250 mg, crude).

Step-2: To a stirred solution of tert-butyl tert-butyl((4-(1-((3,3-difluoro-1-methylcyclobutyl)methyl)-3-(1,1-difluoroethyl)-4-methyl-1H-pyrazole-5-carboxamido)pyridin-2-yl) sulfonyl)carbamate (250 mg, max. 0.403 mmol, 1.0 eq.) in dichloromethane was added TFA (115 mg, 1.009 mmol, 2.5 eq.) at 0° C. The reaction mixture was allowed to warm to ambient temperature and was stirred for 2 h. The reaction mixture was quenched with sat. NaHCO$_3$ solution (10 mL) and extracted with ethyl acetate (15 mL). The combined organic layers were washed with water (10 mL) and then brine (10 mL), dried over anhydrous Na$_2$SO$_4$ and concentrated under reduced pressure to get the crude product, which was purified by column chromatography (1% formic acid in water and acetonitrile as eluent) to afford 1-((3,3-difluoro-1-methylcyclobutyl)methyl)-3-(1,1-difluoroethyl)-4-methyl-N-(2-sulfamoylpyridin-4-yl)-1H-pyrazole-5-carboxamide (SC-209, 60 mg, 0.129 mol, 26% over two steps). $^1$H NMR (500 MHz, DMSO-d6): δ (ppm)=11.26 (s, 1H), 8.60 (brs, 1H), 8.28 (brs, 1H), 7.80 (brs, 1H), 7.43 (brs, 2H), 4.39 (s, 2H), 2.76-2.67 (m, 2H), 2.32-2.23 (m, 5H), 2.03 (t, 3H), 1.07 (s, 3H), LC-MS: m/z [M+H]$^+$=464.2 (calc.=464.1).

The following examples were synthesized in analogy to the procedures described above using appropriate reactants and adjusted protocols if needed:

| Ex. No. | Structure | Procedure | Intermediate | Analytical data |
|---|---|---|---|---|
| SC-211 | 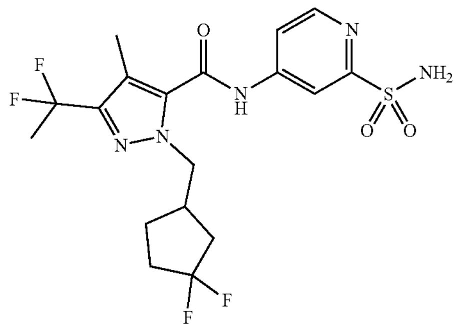 [SMILES: Cc1c(C(C)(F)F)nn(CC2CCC(F)(F)C2)c1C(=O)Nc1ccnc(S(N)(=O)=O)c1] | in analogy to SC-167 (step 1) and SC-209 | Int-B55 | ¹H NMR (400 MHz, DMSO-d6): δ (ppm) = 11.22 (s, 1H), 8.63 (d, 1H), 8.32 (s, 1H), 7.82 (d, 1H), 7.46 (bs, 2H), 4.28 (d, 2H), 2.67-2.58 (m, 1H), 2.24 (s, 3H), 2.18-1.85 (m, 7H), 1.84-1.75 (m, 1H), 1.57-1.49 (m, 1H). LC-MS: m/z [M + H]⁺ = 464.2 (calc. = 464.1). |
| SC-212a | 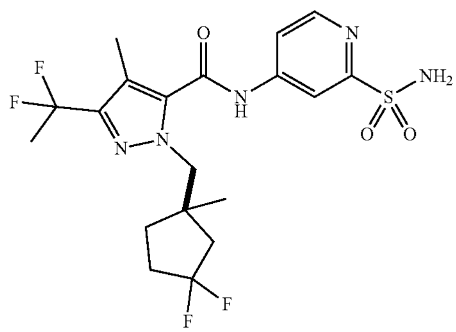 | in analogy to SC-208 (step 1) and SC-209 | Int-B56 | ¹H NMR (500 MHz, DMSO-d6): δ (ppm) = 11.26 (s, 1H), 8.63 (d, 1H), 8.31 (d, 1H), 7.84-7.83 (m, 1H), 7.47 (s, 2H), 4.28 (s, 2H), 2.28-2.23 (m, 4H), 2.19-2.00 (m, 5H), 1.89-1.79 (m, 2H), 1.53-1.48 (m, 1H), 0.97 (s, 3H). LC-MS: m/z [M + H]⁺ = 478.2 (calc. = 478.2). chiral SFC (column: Chiracel AD-H (4.6 × 250 mm), 5 μm, total flow: 3 g/min, 90% CO₂, 10% (0.5% diethylamine in hexane:ethanol (1:1)), 100 bar back pressure, 30° C., R$_t$ = 12.95 min. |
| SC-212b | 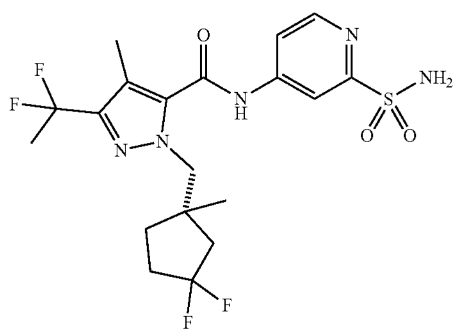 | in analogy to SC-208 (step 1) and SC-209 | Int-B56 | ¹H NMR (500 MHz, DMSO-d6): δ (ppm) = 11.26 (s, 1H), 8.63 (d, 1H), 8.31 (d, 1H), 7.84-7.83 (m, 1H), 7.47 (s, 2H), 4.28 (s, 2H), 2.28-2.23 (m, 4H), 2.19-2.00 (m, 5H), 1.89-1.79 (m, 2H), 1.53-1.48 (m, 1H), 0.97 (s, 3H). LC-MS: m/z [M + H]⁺ = 478.2 (calc. = 478.2). chiral SFC (column: Chiracel AD-H (4.6 × 250 mm), 5 μm, total flow: 3 g/min, 90% CO₂, 10% (0.5% diethylamine in hexane:ethanol (1:1)), 100 bar back pressure, 30° C., R$_t$ = 14.62 min. |
| SC-215 | 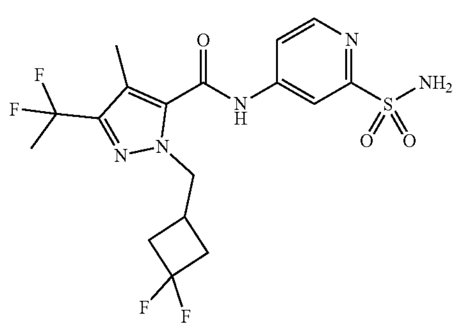 [SMILES: Cc1c(C(C)(F)F)nn(CC2CC(F)(F)C2)c1C(=O)Nc1ccnc(S(N)(=O)=O)c1] | in analogy to SC-208 (step 1) and SC-209 | Int-B50 | ¹H NMR (500 MHz, DMSO-d6): δ (ppm) = 11.23 (s, 1H), 8.64 (d, 1H), 8.33 (d, 1H), 7.82 (dd, 1H), 7.47 (s, 2H), 4.37 (d, 2H), 2.70-2.55 (m, 3H), 2.50-2.40 (m, 2H), 2.23 (s, 3H), 2.03 (t, 3H), LC-MS: m/z [M + H]⁺ = 450.1 (calc. = 450.1). |

| Ex. No. | Structure | Procedure | Intermediate | Analytical data |
|---|---|---|---|---|
| SC-242 | 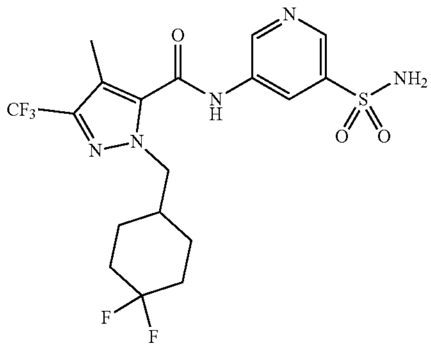 [SMILES: Cc1c(C(F)(F)F)nn(CC2CCC(F)(F)CC2)c1C(=O)Nc1cncc(S(N)(=O)=O)c1] | in analogy to SC-208 (step 1) and SC-209 | Int-B87 | $^1$H NMR (400 MHz, DMSO-d6): δ (ppm) = 11.15 (s, 1H), 8.94 (d, 1H), 8.75 (d, 1H), 8.67 (t, 1H), 7.70 (s, 2H), 4.26 (d, 2H), 2.26 (s, 3H), 2.01-1.97 (m, 3H), 1.81-1.73 (m, 2H), 1.59 (d, 2H), 1.28-1.27 (m, 2H). LCMS: m/z [M + H]$^+$ = 482.3 (calc. = 482.1). |
| SC-243 | 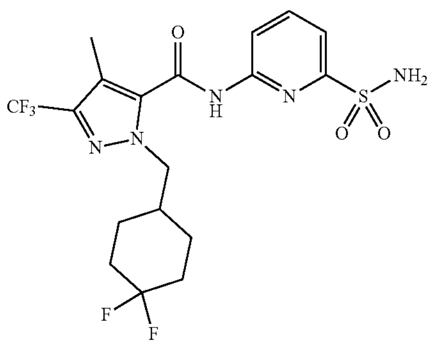 [SMILES: Cc1c(C(F)(F)F)nn(CC2CCC(F)(F)CC2)c1C(=O)Nc1cccc(S(N)(=O)=O)n1] | in analogy to SC-208 (step 1) and SC-209 | Int-B87 | $^1$H NMR (400 MHz, DMSO-d6): δ (ppm) = 11.59 (s, 1H), 8.29 (d, 1H), 8.13 (t, 1H), 7.75 (d, 1H), 7.45 (s, 2H), 4.23 (d, 2H), 2.22 (s, 3H), 1.97-1.96 (m, 3H), 1.80-1.72 (m, 2H), 1.60 (d, 2H), 1.25-1.20 (m, 2H). LCMS: m/z [M + H]$^+$ = 482.3 (calc. = 482.1). |

Synthesis of 4-(1-((4,4-difluoro-2-(trifluoromethyl)cyclopentyl)methyl)-3-(1,1-difluoroethyl)-4-methyl-1H-pyrazole-5-carboxamido)picolinamide (SC-217), synthesized as trans-racemic

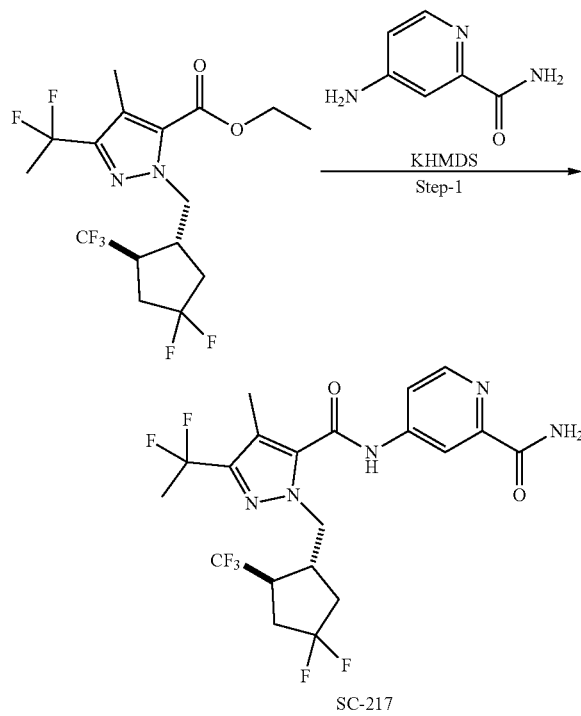

SC-217

Step-1: KHMDS in THF (1M, 0.99 mL, 0.99 mmol, 2.0 eq.) was slowly added to a stirred solution of ethyl 1-(((trans)-4,4-difluoro-2-(trifluoromethyl)cyclopentyl)methyl)-3-(1,1-difluoroethyl)-4-methyl-1H-pyrazole-5-carboxylate (200 mg, 0.496 mmol, 1.0 eq.) and 4-aminopicolinamide (67.84 mg, 0.496 mmol, 1.0 eq.) in THF (5 mL) at 0° C. The reaction mixture was then stirred for 30 minutes. The reaction mixture was quenched with saturated NH$_4$Cl (10 mL) and extracted with EtOAc (2×10 mL). The combined organic layers were dried over anhydrous Na$_2$SO$_4$ and concentrated under reduced pressure to get the crude product, which was purified by prep-HPLC to afford 4-(1-(((trans)-4,4-difluoro-2-(trifluoromethyl)cyclopentyl)methyl)-3-(1,1-difluoroethyl)-4-methyl-1H-pyrazole-5-carboxamido)picolinamide (SC-217, 30 mg, 1% over six steps). $^1$H NMR (500 MHz, DMSO-d6): δ (ppm)=11.09 (s, 1H), 8.56 (d, 1H), 8.36 (d, 1H), 8.11 (d, 1H), 7.83 (dd, 1H), 7.66 (d, 1H), 4.46-4.38 (m, 1H), 4.37-4.33 (m, 1H), 3.32-3.15 (m, 1H), 2.90-2.80 (m, 1H), 2.65-2.55 (m, 1H), 2.28-2.20 (m, 6H), 2.10-1.98 (m, 3H), LC-MS: m/z [M+H]$^+$=496.2 (calc.=496.2).

The following examples were synthesized in analogy to the procedures described above (with or without chiral separation at the end of the synthesis) using appropriate reactants and adjusted purification protocols:

| Ex. No. | Structure | Procedure | Intermediate | Analytical data |
|---|---|---|---|---|
| SC-192a | (structure shown) | in analogy to SC-217 | Int-B110 | $^1$HNMR (500 MHz, DMSO-d$_6$, 25° C.): δ = δ 10.95 (s, 1H), 8.55 (d, 1H), 8.38 (d, 1H), 8.10 (d, 1H), 7.86-7.85 (m, 1H), 7.65 (d, 1H), 6.25-6.01 (m, 1H), 4.34 (d, 2H), 3.41-3.31 (m, 1H), 2.61-2.55 (m, 3H), 2.49-2.42 (m, 2H), 2.12 (s, 3H), 1.31 (d, 3H). LCMS: m/z [M + H]$^+$ = 428.2 (calc. = 428.2). chiral SFC (column: Chiracel OX-3 (4.6 × 150 mm), 3 µm, total flow: 3 g/min, 90% CO$_2$, 10% (0.5% diethylamine in methanol), 1500 psi back pressure, 30° C., R$_t$ = 3.42 min. |
| SC-192b | (structure shown) | in analogy to SC-217 | Int-B110 | $^1$HNMR (500 MHz, DMSO-d$_6$, 25° C.): δ = δ 10.95 (s, 1H), 8.55 (d, 1H), 8.38 (d, 1H), 8.10 (d, 1H), 7.86-7.85 (m, 1H), 7.65 (d, 1H), 6.25-6.01 (m, 1H), 4.34 (d, 2H), 3.41-3.31 (m, 1H), 2.61-2.55 (m, 3H), 2.49-2.42 (m, 2H), 2.12 (s, 3H), 1.31 (d, 3H). LCMS: m/z [M + H]$^+$ = 428.2 (calc. = 428.2). chiral SFC (column: Chiracel OX-3 (4.6 × 150 mm), 3 µm, total flow: 3 g/min, 90% CO$_2$, 10% (0.5% diethylamine in methanol), 1500 psi back pressure, 30° C., R$_t$ = 4.59 min. |

Synthesis of 4-(3-cyclopropyl-1-((3-(difluoromethyl)cyclobutyl)methyl)-4-(trifluoromethyl)-1H-pyrazole-5-carboxamido)picolinamide (SC-221), Synthesized in Form of Diasteromers Diastereomer 1 of 4-(3-cyclopropyl-1-((3-(difluoromethyl)cyclobutyl)methyl)-4-(trifluoromethyl)-1H-pyrazole-5-carboxamido)picolinamide (SC-221a) and Diastereomer 2 of 4-(3-cyclopropyl-1-((3-(difluoromethyl)cyclobutyl)methyl)-4-(trifluoromethyl)-1H-pyrazole-5-carboxamido)picolinamide (SC-221b)

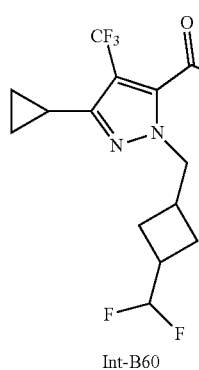

Int-B60

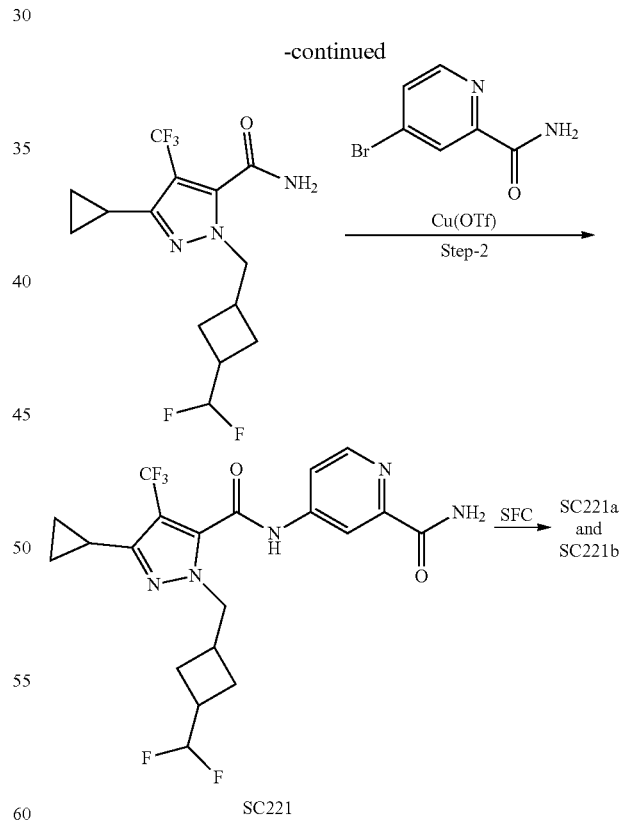

Step-1: To a solution of 3-cyclopropyl-1-((3-(difluoromethyl)cyclobutyl)methyl)-4-(trifluoromethyl)-1H-pyrazole-5-carboxylic acid (50 mg, 0.15 mmol, 1.0 eq.) in DMF (10 mL) were added HATU (56 mg, 0.15 mmol), DIPEA (39 mg, 0.30 mmol, 2.0 eq.) and ammonium chloride (16 mg, 0.30 mmol, 2.0 eq.) at ambient temperature. The resulting reaction mixture was stirred for 16 h at ambient temperature. For workup, this experiment was combined with another experiment using identical reaction conditions and 450 mg of 3-cyclopropyl-1-((3-(difluoromethyl)cyclobutyl)methyl)-4-(trifluoromethyl)-1H-pyrazole-5-carboxylic acid as starting material. The combined reaction mixtures were diluted with water (20 mL) and extracted with ethyl acetate (2×50 mL). The combined organic layers were dried over anhydrous $Na_2SO_4$ and concentrated under reduced pressure to afford 3-cyclopropyl-1-((3-(difluoromethyl)cyclobutyl)methyl)-4-(trifluoromethyl)-1H-pyrazole-5-carboxamide (400 mg, crude).

Step-2: To a solution of 3-cyclopropyl-1-((3-(difluoromethyl)cyclobutyl)methyl)-4-(trifluoromethyl)-1H-pyrazole-5-carboxamide (50 mg, 0.15 mmol, 1.0 eq.) in 1,4-dioxane (5 mL) in a sealed tube were added 4-bromopicolinamide (30 mg, 0.15 mmol, 1.0 eq.) and $Cs_2CO_3$ (121 mg, 0.38 mmol, 2.5 eq.) at ambient temperature. The reaction mixture was purged with argon gas for 10 minutes before the addition of trans-N,N'-dimethyl-cyclohexane-1,2-diamine (7 mg, 0.05 mmol, 0.30 eq.) and copper (I) trifluoromethane sulfonate benzene complex (10 mg, 0.04 mmol, 0.25 eq.) at ambient temperature. The reaction mixture was heated to 90° C. for 16 h. For workup, this experiment was combined with another experiment using identical reaction conditions and 150 mg of 3-cyclopropyl-1-((3-(difluoromethyl)cyclobutyl)methyl)-4-(trifluoromethyl)-1H-pyrazole-5-carboxamide as starting material. The reaction mixture was then cooled to ambient temperature, filtered through a celite bed and the celite bed was washed with ethyl acetate (20 mL). The filtrate was concentrated under reduced pressure to get the crude material, which was purified by flash column chromatography (0.1% aq. formic acid and acetonitrile as an eluent) to afford 4-(3-cyclopropyl-1-(difluoromethyl)cyclobutyl)methyl)-4-(trifluoromethyl)-1H-pyrazole-5-carboxamido)picolinamide (SC-221) (99 mg, 15%)

The above diasteromeric compound was separated by chiral SFC (column: Chiralpak AD-H (250×10×5 nm), total flow: 10 g/min, 90% $CO_2$, 10% (0.5% IPAmine in IPA), 100 bar back pressure, 30° C.) to obtain SC-221a and SC-221b.

Analytical data for example SC-221a (first eluting diastereomer): $^1$H NMR (400 MHz, DMSO-d6): δ (ppm)=11.54 (s, 1H), 8.57 (d, 1H), 8.31 (s, 1H), 8.11 (s, 1H), 7.79 (d, 1H), 7.68 (s, 1H), 5.92 (t, 1H), 4.07 (d, 2H), 2.68-2.57 (m, 2H), 2.01-1.93 (m, 3H), 1.79-1.74 (m, 2H), 0.98-0.94 (m, 2H), 0.88-0.83 (m, 2H), LC-MS: m/z [M+H]$^+$=458.2 (calc.=458.2), chiral SFC (column: Chiralpak AD-H (4.6× 250 mm), 5 nm, total flow: 3 mL/min, 90% $CO_2$, 10% (0.5% isopropyl amine in isopropanol), 99 bar back pressure, 30° C., $R_t$=7.38 min.

Analytical data for example SC-221b (second eluting diastereomer): NMR (400 MHz, DMSO-d6): δ (ppm)=11.54 (s, 1H), 8.57 (d, 1H), 8.31 (s, 1H), 8.11 (s, 1H), 7.79 (d, 1H), 7.68 (s, 1H), 5.92 (t, 1H), 4.07 (d, 2H), 2.68-2.57 (m, 2H), 2.01-1.93 (m, 3H), 1.79-1.74 (m, 2H), 0.98-0.94 (m, 2H), 0.88-0.83 (m, 2H). LC-MS: m/z [M+H]$^+$=458.2 (calc.=458.2), chiral SFC (column: Chiralpak AD-H (4.6× 250 mm), 5 nm, total flow: 3 mL/min, 90% $CO_2$, 10% (0.5% isopropyl amine in isopropanol), 99 bar back pressure, 30° C., $R_t$=8.10 min.

The following examples were synthesized in analogy to the procedures described above (with or without chiral separation at the end of the synthesis) using appropriate reactants and adjusted purification protocols:

| Ex. No. | Structure | Procedure | Analytical data |
| --- | --- | --- | --- |
| SC-219a | 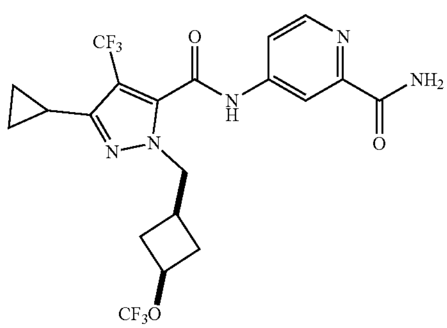 | in analogy to SC-221, using Int-B65 | $^1$H NMR (400 MHz, DMSO-d6): δ (ppm) = 11.54 (s, 1H), 8.58 (d, 1H), 8.32 (s, 1H), 8.12 (s, 1H), 7.79 (dd, 1H), 7.68 (s, 1H), 4.70-4.62 (m, 1H), 4.16 (d, 2H), 2.40-2.28 (m, 3H), 2.01-1.91 (m, 3H), 1.00-0.96 (m, 2H), 0.86-0.82 (m, 2H), LC-MS: [M − H]$^-$ = 490.1 (calc. = 490.1). HPLC (column: Acquity UPLC BEH C18(100 mm × 2.1) 1.7 μM), flow rate: 0.3 mL/min, mobile Phase A: 0.05% TFA in water, mobile phase B: 0.05% TFA in MeCN, gradient (time[min]/%B]): 0/10, 7/98, 12/98, 12.01/10, $R_t$ = 6.32 min. |
| SC-219b | 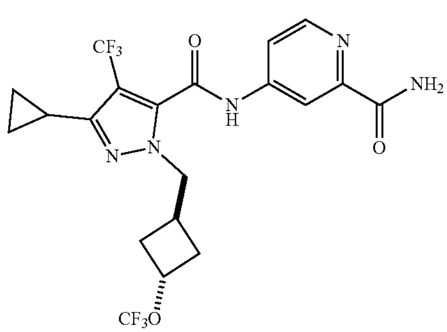 | in analogy to SC-221, using Int-B65 | $^1$H NMR (400 MHz, DMSO-d6): δ (ppm) = 11.56 (s, 1H), 8.58 (d, 1H), 8.32 (s, 1H), 8.12 (s, 1H), 7.79 (d, 1H), 7.68 (bs, 1H), 4.96-4.88 (m, 1H), 4.21 (d, 2H), 2.74-2.61 (m, 1H), 2.34-2.22 (m, 4H), 1.98-1.92 (m, 1H), 0.99-0.95 (m, 2H), 0.85-0.82 (bs, 2H), LC-MS: [M − H]$^-$ = 490.1 (calc. = 490.1). HPLC (column: Acquity UPLC BEH C18 (100 mm × 2.1) 1.7 μM), flow rate: 0.3 mL/min, mobile Phase A: 0.05% TFA in water, mobile phase B: 0.05% TFA in MeCN, gradient (time[min]/%B]): 0/10, 7/98, 12/98, 12.01/10, $R_t$ = 6.37 min. |

-continued

| Ex. No. | Structure | Procedure | Analytical data |
|---|---|---|---|
| SC-222a | 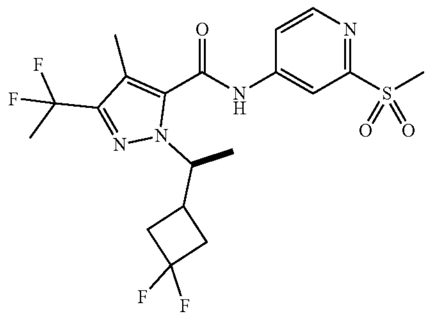 [SMILES: Cc1c(C(C)(F)F)nn([C@@H](C)C2CC(F)(F)C2)c1C(=O)Nc1ccnc(S(C)(=O)=O)c1] | in analogy to SC-221, using Int-B61 | ¹H NMR (500 MHz, DMSO-d6): δ (ppm) = 11.40 (s, 1H), 8.71 (d, 1H), 8.47 (d, 1H), 7.90 (d, 1H), 4.64 (t, 1H), 3.28 (s, 3H), 2.70-2.64 (m, 2H), 2.43-2.38 (m, 3H), 2.22 (s, 3H), 2.03 (t, 3H), 1.37 (d, 3H), LC-MS: m/z [M + H]⁺ = 463.2 (calc. = 463.1). chiral SFC (column: Chiracel OX-3 (4.6 × 150 mm) 3 μm, total flow: 3 g/min, 90% CO₂, 10% methanol), 1500 psi back pressure, 30° C., R$_t$ = 3.34 min. |
| SC-222b | 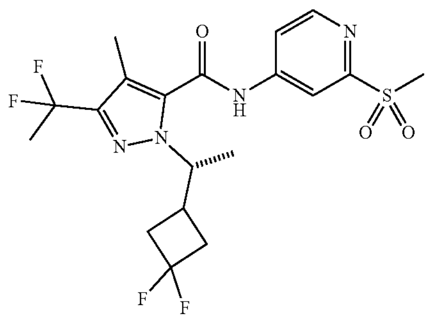 [SMILES: Cc1c(C(C)(F)F)nn([C@H](C)C2CC(F)(F)C2)c1C(=O)Nc1ccnc(S(C)(=O)=O)c1] | in analogy to SC-221, using Int-B61 | ¹H NMR (500 MHz, DMSO-d6): δ (ppm) = 11.40 (s, 1H), 8.71 (d, 1H), 8.47 (d, 1H), 7.90 (d, 1H), 4.64 (t, 1H), 3.28 (s, 3H), 2.70-2.64 (m, 2H), 2.43-2.38 (m, 3H), 2.22 (s, 3H), 2.03 (t, 3H), 1.37 (d, 3H), LC-MS: [M + H]⁺ = 463.2 (calc. = 463.1). chiral SFC (column: Chiracel OX-3 (4.6 × 150 mm) 3 μm, total flow: 3 g/min, 90% CO₂, 10% methanol), 1500 psi back pressure, 30° C., R$_t$ = 4.79 min. |
| SC-129a | 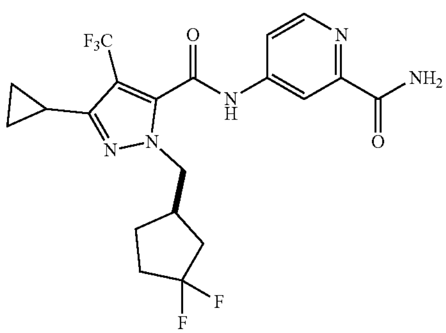 | in analogy to SC-221, using Int-B75 | ¹H NMR (400 MHz, DMSO-d6): δ (ppm) = 11.54 (s, 1H), 8.58 (d, 1H), 8.32 (bs, 1H), 8.11 (bs, 1H), 7.78 (d, 1H), 7.67 (bs, 1H), 4.10 (d, 2H), 2.65-2.55 (m, 1H), 2.19-1.72 (m, 6H), 1.55-1.45 (m, 1H), 1.00-1.95 (m, 2H), 0.87-0.81 (s, 2H). LCMS: m/z [M − H]⁻ = 456.1 (calc. = 456.2). chiral SFC (column: Chiracel OX-3 (4.6 × 150 mm) 3 μm, total flow: 3 g/min, 90% CO₂, 10% (0.5% isopropylamine in isopropylalcohol), 100 bar back pressure, 30° C., R$_t$ = 3.35 min. |
| SC-129b | 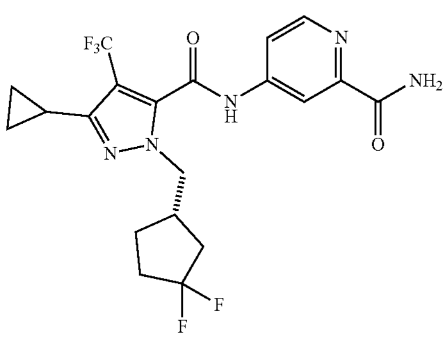 | in analogy to SC-221, using Int-B75 | ¹H NMR (400 MHz, DMSO-d6): δ (ppm) = 11.54 (s, 1H), 8.58 (d, 1H), 8.32 (bs, 1H), 8.11 (bs, 1H), 7.78 (d, 1H), 7.67 (bs, 1H), 4.10 (d, 2H), 2.65-2.55 (m, 1H), 2.19-1.72 (m, 6H), 1.55-1.45 (m, 1H), 1.00-1.95 (m, 2H), 0.87-0.81 (s, 2H). LCMS: m/z [M − H]⁻ = 456.1 (calc. = 456.2). chiral SFC (column: Chiracel OX-3 (4.6 × 150 mm) 3 μm, total flow: 3 g/min, 90% CO₂, 10% (0.5% isopropylamine in isopropylalcohol), 100 bar back pressure, 30° C., R$_t$ = 4.17 min. |

| Ex. No. | Structure | Procedure | Analytical data |
|---|---|---|---|
| SC-170 | 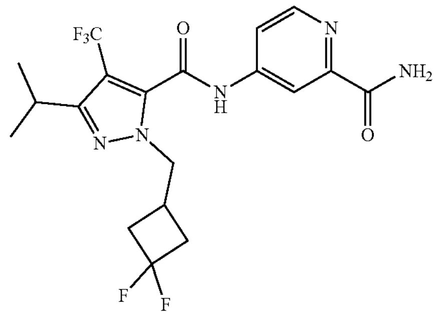 [SMILES: CC(C)c1nn(CC2CC(F)(F)C2)c(C(=O)Nc2ccnc(C(N)=O)c2)c1C(F)(F)F] | in analogy to SC-221, using Int-B71 | ¹H NMR (400 MHz, DMSO-d6): δ (ppm) = 11.59 (s, 1H), 8.58 (d, 1H), 8.33 (d, 1H), 8.11 (s, 1H), 7.79-7.78 (m, 1H), 7.68 (s, 1H), 4.27 (d, 2H), 3.10-3.04 (m, 1H), 2.66-2.61 (m, 3H), 2.50-2.42 (m, 2H), 1.26 (d, 6H). LCMS: m/z [M + H]⁺ = 446.2 (calc. = 446.2). |
| SC-188a | 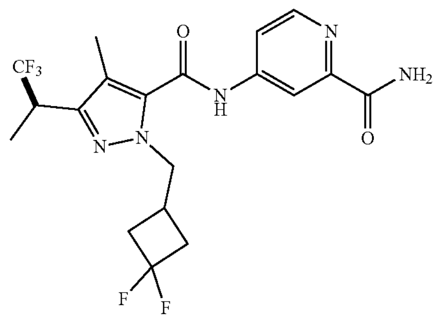 [SMILES: Cc1c([C@@H](C)C(F)(F)F)nn(CC2CC(F)(F)C2)c1C(=O)Nc1ccnc(C(N)=O)c1] | in analogy to SC-221, step 2 only, using Int-B115 | ¹H NMR (400 MHz, DMSO-d6): δ (ppm) =10.96 (s, 1H), 8.54 (d, 1H), 8.38 (d, 1H), 8.09 (d, 1H), 7.86 (dd, 1H), 7.65 (s, 1H), 4.36 (d, 2H), 3.97-3.90 (m, 1H), 2.62-2.56 (m, 3H), 2.47-2.39 (m, 2H), 2.14 (s, 3H), 1.45 (d, 3H). LCMS: m/z [M + H]⁺ = 446.2 (calc. = 446.2). chiral SFC (column: Chiralpak AD-H (4.6 × 250 mm) 5 μm, total flow: 3 g/min, 90% CO₂, 10% (0.5% isopropylamine in isopropylalcohol), 100 bar back pressure, 30° C., R_t = 3.62 min. |
| SC-188b | 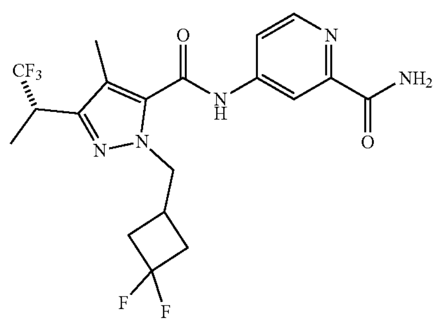 [SMILES: Cc1c([C@H](C)C(F)(F)F)nn(CC2CC(F)(F)C2)c1C(=O)Nc1ccnc(C(N)=O)c1] | in analogy to SC-221, step 2 only, using Int-B115 | ¹H NMR (400 MHz, DMSO-d6): δ (ppm) = 10.96 (s, 1H), 8.54 (d, 1H), 8.38 (d, 1H), 8.09 (d, 1H), 7.86 (dd, 1H), 7.65 (s, 1H), 4.36 (d, 2H), 3.97-3.90 (m, 1H), 2.62-2.56 (m, 3H), 2.47-2.39 (m, 2H), 2.14 (s, 3H), 1.45 (d, 3H). LCMS: m/z [M + H]⁺ = 446.2 (calc. = 446.2). chiral SFC (column: Chiralpak AD-H (4.6 × 250 mm) 5 μm, total flow: 3 g/min, 90% CO₂, 10% (0.5% isopropylamine in isopropylalcohol), 100 bar back pressure, 30° C., R_t = 9.06 min. |
| SC-281a | 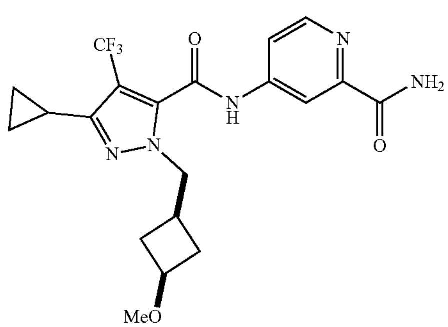 | in analogy to SC-221, using Int-B90 | ¹H NMR (400 MHz, DMSO-d6): δ (ppm) = 11.53 (s, 1H), 8.58 (d, 1H), 8.32 (d, 1H), 8.11 (s, 1H), 7.80-7.78 (m, 1H), 7.68 (d, 1H), 4.09 (d, 2H), 3.66-3.62 (m, 1H), 3.04 (s, 3H), 2.25-2.18 (m, 3H), 1.94-1.90 (m, 1H), 1.58-1.50 (m, 2H), 0.99-0.94 (m, 2H), 0.86-0.82 (m, 2H). LCMS: m/z [M + H]⁺ = 438.2 (calc. = 438.2). chiral SFC (column: Chiralpak AD-H (4.6 × 250 mm) 5 μm, totalflow: 3 mL/min, 85% CO₂, 15% (0.5% isopropylamine in isopropylalcohol), 100 bar back pressure, 30° C., R_t = 3.90 min. |

| Ex. No. | Structure | Procedure | Analytical data |
|---|---|---|---|
| SC-281b | (structure with CF3, cyclopropyl, pyrazole carboxamide, pyridine-2-carboxamide, methoxycyclobutylmethyl) | in analogy to SC-221, using Int-B90 | $^1$H NMR (400 MHz, DMSO-d6): δ (ppm) = 11.56 (s, 1H), 8.58 (d, 1H), 8.32 (s, 1H), 8.11 (s, 1H), 7.79 (d, 1H), 7.68 (s, 1H), 4.13 (d, 2H), 3.90-3.84 (m, 1H), 3.06 (s, 3H), 2.63-2.55 (m, 1H), 2.07-2.00 (m, 2H), 1.97-1.88 (m, 3H), 0.98-0.95 (m, 2H), 0.85-0.83 (m, 2H). LCMS: m/z $[M + H]^+$ = 438.2 (calc. = 438.2). chiral SFC (column: Chiralpak AD-H (4.6 × 250 mm) 5 μm, total flow: 3 mL/min, 85% $CO_2$, 15% (0.5% isopropylamine in isopropylalcohol), 100 bar back pressure, 30° C., $R_t$ = 4.72 min. |
| SC-204a | (structure with CHF2, methyl, pyrazole carboxamide, pyridine-2-carboxamide, CF3-cyclopropylmethyl) | in analogy to SC-221, using Int-B117 | $^1$H NMR (400 MHz, DMSO-d6): δ (ppm) = 11.07 (s, 1H), 8.57 (d, 1H), 8.38 (s, 1H), 8.11 (s, 1H), 7.87 (d, 1H), 7.66 (s, 1H), 4.32-4.18 (m, 2H), 2.25 (s, 3H), 2.08-1.99 (m, 4H), 1.71-1.70 (m, 1H), 0.98 (s, 2H). LCMS: $[M + H]^+$ = 432.2 (calc. = 432.2). chiral SFC (column: Chiracel OX-H (4.6 × 150 mm) 3 μm, total flow: 4 g/min, 70% $CO_2$, 30% etanol:metanol:isopropylamine 70:30:0.3), 100 bar back pressure, 35° C., $R_t$ = 1.63 min. |
| SC-204b | (structure with CHF2, methyl, pyrazole carboxamide, pyridine-2-carboxamide, CF3-cyclopropylmethyl) | in analogy to SC-221, using Int-B117 | $^1$H NMR (400 MHz, DMSO-d6): δ (ppm) = 11.07 (s, 1H), 8.57 (d, 1H), 8.38 (s, 1H), 8.11 (s, 1H), 7.87 (d, 1H), 7.66 (s, 1H), 4.32-4.18 (m, 2H), 2.25 (s, 3H), 2.08-1.99 (m, 4H), 1.71-1.70 (m, 1H), 0.98 (s, 2H). LCMS: $[M + H]^+$ = 432.2 (calc. = 432.2). chiral SFC (column: Chiracel OX-H (4.6 × 150 mm) 3 μm, total flow: 4 g/min, 70% $CO_2$, 30% etanol:metanol:isopropylamine 70:30:0.3), 100 bar back pressure, 35° C., $R_t$ = 2.07 min. |

Synthesis of 1-((3,3-difluorocyclopentyl)methyl)-3-methoxy-N-(2-(methylsulfonyl)pyridin-4-yl)-4-(trifluoromethyl)-1H-pyrazole-5-carboxamide (SC-225)

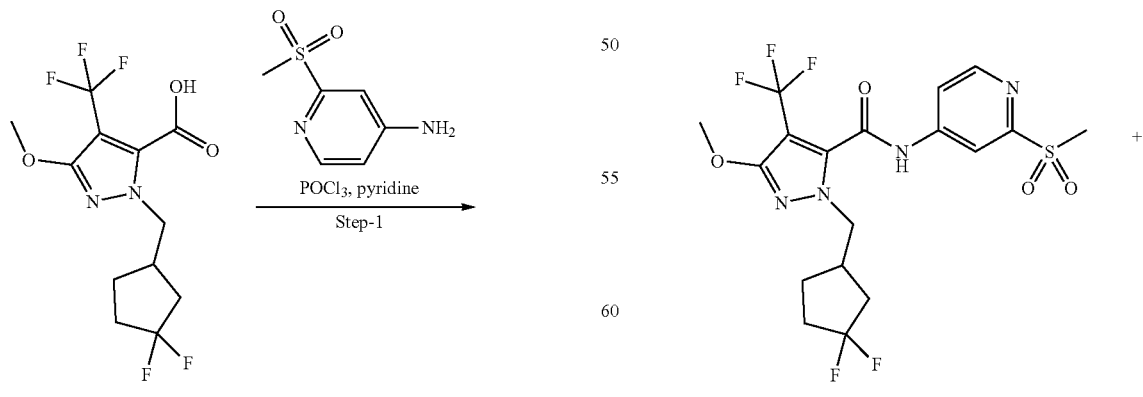

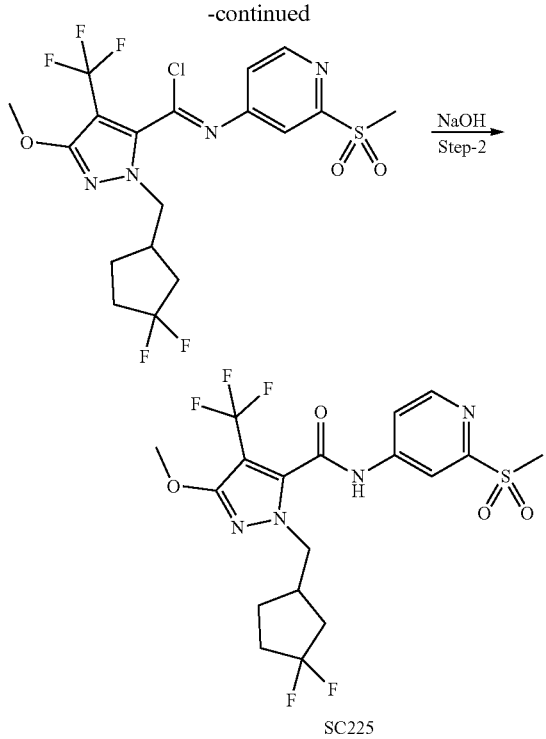

Step-1: To a solution of 1-((3,3-difluorocyclopentyl)methyl)-3-methoxy-4-(trifluoromethyl)-1H-pyrazole-5-carboxylic acid (Int-B41, 0.15 g, 0.46 mmol, 1.0 eq.) in pyridine (3 mL) were added POCl₃ (0.05 mL, 0.55 mmol, 1.2 eq.) and 2-methanesulfonylpyridin-4-amine (0.095 g, 0.55 mmol, 1.2 eq.) at 0° C. The reaction mixture was stirred at ambient temperature for 2 h. The reaction mixture was concentrated under reduced pressure, diluted with ice water and was extracted with EtOAc (3×50 mL). The combined organic layers were washed with brine, dried over Na₂SO₄ and concentrated under reduced pressure to yield a mixture of 1-((3,3-difluorocyclopentyl)methyl)-3-methoxy-N-(2-(methylsulfonyl)pyridin-4-yl)-4-(trifluoromethyl)-1H-pyrazole-5-carbimidoyl chloride and 1-((3,3-difluorocyclopentyl)methyl)-3-methoxy-N-(2-(methylsulfonyl)pyridin-4-yl)-4-(trifluoromethyl)-1H-pyrazole-5-carboxamide. This material was directly used for the next step without further purification.

Step-2: To a stirred solution of 1-((3,3-difluorocyclopentyl)methyl)-3-methoxy-N-(2-(methylsulfonyl)pyridin-4-yl)-4-(trifluoromethyl)-1H-pyrazole-5-carbimidoyl chloride and 1-((3,3-difluorocyclopentyl)methyl)-3-methoxy-N-(2-(methylsulfonyl)pyridin-4-yl)-4-(trifluoromethyl)-1H-pyrazole-5-carboxamide (0.14 g, crude, 1.0 eq.) in THF (5 mL) was added 1(M) NaOH (3 mL) at 0° C. and the reaction mixture was stirred at ambient temperature for 16 h. The reaction mixture was concentrated under reduced pressure, diluted with ice water and was extracted with EtOAc (3×60 mL). The combined organic layers were washed with brine, dried over Na₂SO₄. and concentrated under reduced pressure to yield the crude material which was purified by reverse phase preparative HPLC to yield 1-((3,3-difluorocyclopentyl)methyl)-3-methoxy-N-(2-(methylsulfonyl)pyridin-4-yl)-4-(trifluoromethyl)-1H-pyrazole-5-carboxamide (SC-225). Yield: 20% (over two steps) (45 mg, 0.093 mmol). ¹H NMR (400 MHz, DMSO-d6): δ (ppm)=11.84 (s, 1H), 8.74 (d, 1H), 8.37 (s, 1H), 7.85 (d, 1H), 4.09-4.07 (m, 2H), 3.98 (s, 3H), 2.66-2.54 (m, 1H), 2.22-1.80 (m, 5H), 1.56-1.50 (m, 1H). UPLC-MS: m/z [M+H]⁺=483.6 (calc.=483.1).

The following examples were synthesized in analogy to the procedures described above (with or without chiral separation at the end of the synthesis) using appropriate reactants and adjusted purification protocols:

| Ex. No. | Structure | Procedure | Intermediate | Analytical data |
|---|---|---|---|---|
| SC-207 | 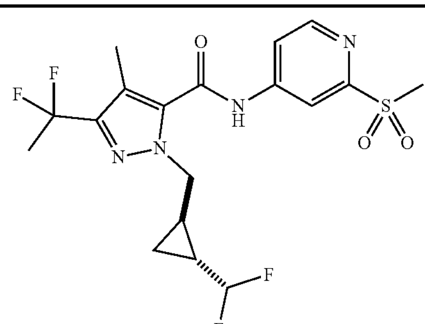 | in analogy to SC-225 | Int-B120 | ¹H NMR (400 MHz, DMSO-d₆): δ (ppm) = 11.31 (s, 1H), 8.71 (d, 1H), 8.45 (d, 1H), 7.92-7.90 (m, 1H), 5.85-5.55 (m, 1H), 4.28-4.16 (m, 2H), 3.33-3.29 (m, 3H), 2.25 (s, 3H), 2.08-1.99 (m, 3H), 1.54-1.47 (m, 2H), 0.80-0.75 (m, 2H). LCMS: m/z [M + H]⁺ = 449.2 (calc. = 449.1); |
| SC-250 | 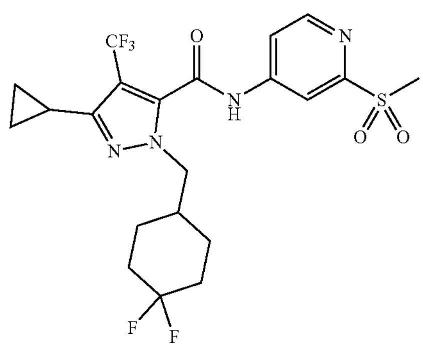 [SMILES: CS(=O)(=O)c1cc(NC(=O)c2c(C(F)(F)F)c(C3CC3)nn2CC2CCC(F)(F)CC2)ccn1] | in analogy to SC-225 | Int-B76 | ¹H NMR (400 MHz, DMSO-d₆): δ (ppm) = 11.78 (s, 1H), 8.73-8.71 (d, 1H), 8.37 (s, 1H), 7.85-7.84 (d, 1H), 4.01-4.0 (d, 2H), 3.3 (s, 3H), 1.96-1.95 (m, 4H), 1.82-1.67 (m, 2H), 1.58-1.55 (m, 2H), 1.24-1.15 (m, 2H), 1.0-0.97 (m, 2H), 0.96-0.85 (m, 2H). LCMS: m/z [M + H]⁺ = 507.3 (MW calc. = 507.2). |

-continued

| Ex. No. | Structure | Procedure | Intermediate | Analytical data |
|---|---|---|---|---|
| SC-293 | 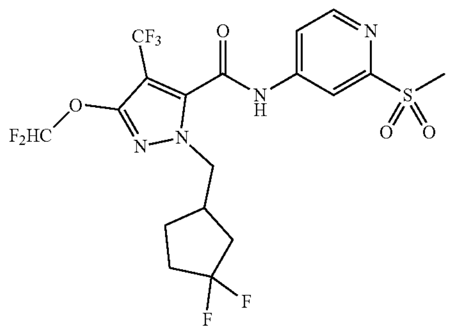 [SMILES: CS(=O)(=O)c1cc(NC(=O)c2c(C(F)(F)F)c(OC(F)F)nn2CC2CCC(F)(F)C2)ccn1] | in analogy to SC-225 | Int-B45 (rac) | $^1$H NMR (400 MHz, DMSO-$d_6$): δ (ppm) = 11.95 (s, 1H), 8.75 (d, 1H), 8.36 (d, 1H), 7.84-7.83 (m, 1H), 7.67-7.32 (m, 1H), 4.19-4.16 (m, 2H), 3.30 (s, 3H), 2.66-2.59 (m, 1H), 2.25-2.07 (m, 2H), 2.05-2.01 (m, 2H), 1.99-1.85 (m, 1H), 1.58-1.55 (m, 1H). LCMS: m/z [M + H]$^+$ = 519.2 (calc. 519.1). |
| SC-304 | 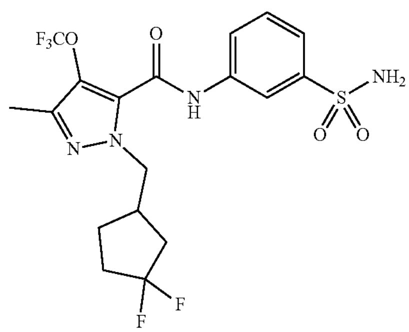 [SMILES: Cc1nn(CC2CCC(F)(F)C2)c(C(=O)Nc2cccc(S(N)(=O)=O)c2)c1OC(F)(F)F] | in analogy to SC-225 | Int-B103 | $^1$H NMR (400 MHz, DMSO-$d_6$): δ (ppm) = 10.96 (s, 1H), 8.26 (s, 1H), 7.77 (d, 1H), 7.63-7.58 (m, 2H), 7.43 (s, 2H), 4.26 (d, 2H), 2.63-2.60 (m, 1H), 2.22 (s, 3H), 2.16-1.78 (m, 5H), 1.54-1.51 (m, 1H). LCMS: m/z [M − H]$^−$ = 481.0 (calc. 481.10) |
| SC-305 | 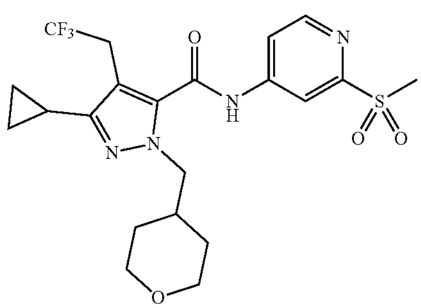 [SMILES: CS(=O)(=O)c1cc(NC(=O)c2c(CC(F)(F)F)c(C3CC3)nn2CC2CCOCC2)ccn1] | in analogy to SC-225 | Int-B105 | $^1$H NMR (400 MHz, DMSO-$d_6$): δ (ppm) = 11.41 (s, 1H), 8.69 (d, 1H), 8.39 (s, 1H), 7.87 (d, 1H), 4.06 (d, 2H), 3.77-3.67 (m, 4H), 3.29 (s, 3H), 3.18 (t, 2H), 1.98-1.93 (m, 2H), 1.31-1.28 (m, 2H), 1.18-1.12 (m, 2H), 0.91-0.86 (m, 2H), 0.76-0.74 (m, 2H). LCMS: m/z [M + H]$^+$ = 487.2 (calc. 487.2). |

Synthesis of 1-(cyclohexylmethyl)-4-(difluoromethyl)-N-(3-(methylsulfonyl)phenyl)-1H-pyrazole-5-carboxamide (SC-229)

-continued

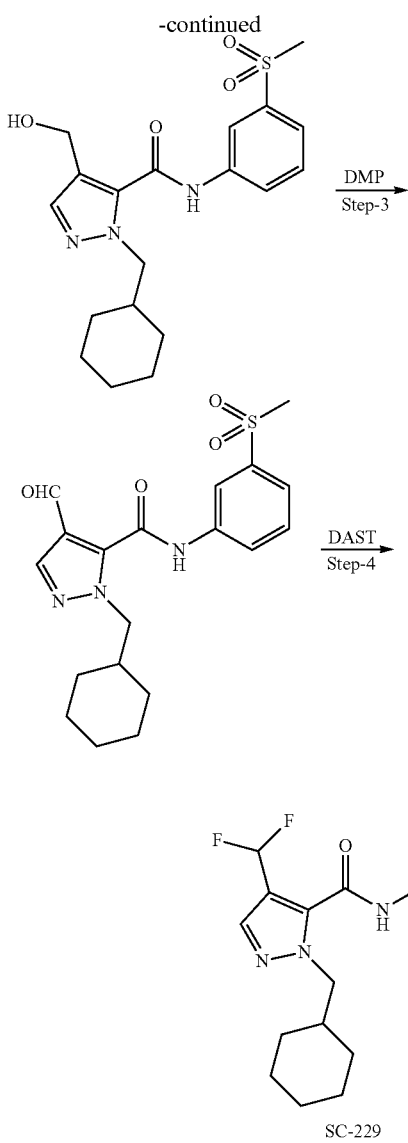

SC-229

Step-1: To a solution of 4-cyano-1-(cyclohexylmethyl)-N-(3-(methylsulfonyl)phenyl)-1H-pyrazole-5-carboxamide (SC-10, 250 mg, 0.647 mmol 1.0 eq.) was added TMSCl (8 mL) in MeOH (6 mL). The reaction mixture was stirred in a sealed tube at ambient temperature for 24 h. The solvent was removed under reduce pressure and the resulting residue was diluted with sat. NaHCO$_3$ solution (15 mL) and extracted with EtOAc (2×20 mL). The combined organic layers were dried over anhydrous Na$_2$SO$_4$ and concentrated under reduced pressure to afford the crude product which was purified by column chromatography over silica (100-200), eluting with 28% ethyl acetate in pet-ether to give methyl 1-(cyclohexylmethyl)-5-((3-(methylsulfonyl)phenyl)carbamoyl)-1H-pyrazole-4-carboxylate. Yield: 55% (150 mg, 0.357 mmol).

Step-2: To a solution of methyl 1-(cyclohexylmethyl)-5-((3-(methylsulfonyl)phenyl)carbamoyl)-1H-pyrazole-4-carboxylate (150 mg, 0.357 mmol, 1.0 eq.) in THF (10 mL) was added LiBH$_4$ (0.45 mL, 0.894 mmol, 2.5 eq.). The reaction mixture was stirred at −78° C. for 1 h. The resulting reaction mixture was diluted with ice cold water (10 mL) and extracted with EtOAc (2×20 mL). The combined organic layers were dried over anhydrous Na$_2$SO$_4$ and concentrated under reduced pressure to afford 1-(cyclohexylmethyl)-4-(hydroxymethyl)-N-(3-(methylsulfonyl)phenyl)-1H-pyrazole-5-carboxamide. Yield: 50 mg (crude).

Step-3: A solution of crude 1-(cyclohexylmethyl)-4-(hydroxymethyl)-N-(3-(methylsulfonyl)phenyl)-1H-pyrazole-5-carboxamide (50 mg, mx. 0.127 mmol, 1.0 eq.) and Dess-Martin periodinane (135 mg, 0.254 mmol, 2.0 eq.) in DCM (15 mL) was stirred at ambient temperature for 16 h. The resulting reaction mixture was diluted with sat. NaHCO$_3$ solution (15 mL) and extracted with DCM (2×20 mL). The combined organic layers were dried over anhydrous Na$_2$SO$_4$ and concentrated under reduced pressure to afford 1-(cyclohexylmethyl)-4-formyl-N-(3-(methylsulfonyl)phenyl)-1H-pyrazole-5-carboxamide. Yield: 40 mg (crude).

Step-4: A solution of crude 1-(cyclohexylmethyl)-4-formyl-N-(3-(methylsulfonyl)phenyl)-1H-pyrazole-5-carboxamide (40 mg, max. 0.102 mmol, 1.0 eq.) and DAST (0.33 mL, 0.257 mmol, 2.5 eq.) in DCM (10 mL) was stirred at ambient temperature for 16 h. The resulting reaction mixture was diluted with sat. NaHCO$_3$ solution (15 mL) and extracted with DCM (2×20 mL). The combined organic layers were dried over anhydrous Na$_2$SO$_4$ and concentrated under reduced pressure to afford a residue which upon purification by prep-HPLC gave 1-(cyclohexylmethyl)-4-(difluoromethyl)-N-(3-(methylsulfonyl)phenyl)-1H-pyrazole-5-carboxamide (SC-229). Yield: 3.5 mg. $^1$H NMR (400 MHz, DMSO-d6): δ (ppm)=11.13 (s, 1H), 8.32 (s, 1H), 7.92 (d, 1H), 7.81 (s, 1H), 7.71-7.65 (m, 2H), 7.15 (t, 1H), 4.12 (d, 2H), 3.23 (s, 3H), 1.82-1.79 (s, 1H), 1.63-1.49 (m, 5H), 1.15-1.10 (m, 3H), 0.96-0.90 (m, 2H). LCMS: m/z [M−H]$^-$=410.1 (calc.=410.1).

Synthesis of 4-(1-((4,4-difluorocyclohexyl)methyl)-3-methyl-4-(trifluoromethyl)-1H-pyrazole-5-carboxamido)picolinamide (SC-84)

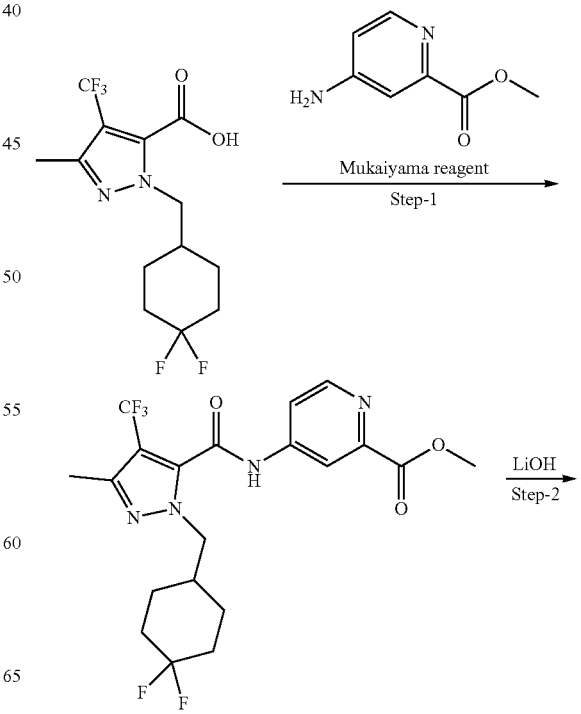

-continued

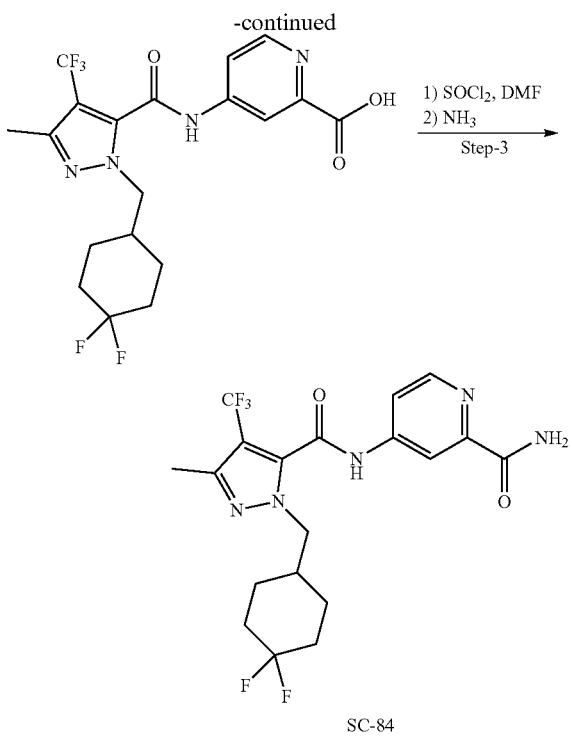

SC-84

Step-1: To a stirred solution of ethyl 2-[(4,4-difluorocyclohexyl)methyl]-5-methyl-4-(trifluoromethyl)pyrazole-3-carboxylic acid (Int-B46, 50 mg, 0.153 mmol, 1.0 eq.) in DMF (2 mL) was added Mukaiyama's reagent (50.7 mg, 0.199 mmol, 1.3 eq.) followed by methyl 4-aminopicolinate (42 mg, 0.199 mmol, 1.3 eq.) and DIPEA (50.6 mg, 0.199 mmol. 3.0 eq.) at 0° C. and the mixture was stirred at ambient temperature for 16 h. Then the reaction mixture was partitioned between water (50 mL) and EtOAc (90 mL). The organic layer was basified with sat. NaHCO₃ solution, washed with brine, dried over anhydrous Na₂SO₄ and concentrated under reduced pressure. The crude product was purified by reverse phase prep-HPLC to afford methyl 4-[[2-[(4,4-difluorocyclohexyl)methyl]-5-methyl-4-(trifluoromethyl)pyrazole-3-carbonyl]amino]pyridine-2-carboxylate. Yield: 57% (40 mg).

Step-2: To a stirred solution of methyl 4-[[2-[(4,4-difluorocyclohexyl)methyl]-5-methyl-4-(trifluoromethyl)pyrazole-3-carbonyl]amino]pyridine-2-carboxylate (200 mg, 0.565 mmol, 1.0 eq.) in THF:MeOH:H₂O (6 mL, 1:1:1) was added LiOH·H₂O (48 mg, 1.129 mmol, 2.0 eq.) at 0° C. The reaction mixture was stirred at ambient temperature for 16 h. The reaction mixture was concentrated and acidified with sat. NaHSO₄ solution until pH<7 an was extracted with EtOAc (3×50 mL). The combined organic layers were washed with brine (50 mL), dried over anhydrous Na₂SO₄ and concentrated under reduced pressure to furnish ethyl 2-[(4,4-difluorocyclohexyl)methyl]-5-methyl-4-(trifluoromethyl)pyrazole-3-carboxylic acid. Yield: 32% (80 mg).

Step-3: To a stirred solution of ethyl 2 ethyl 2-[(4,4-difluorocyclohexyl)methyl]-5-methyl-4-(trifluoromethyl) pyrazole-3-carboxylic acid (200 mg, 0.613 mmol, 1.0 eq.) in DCM (3 mL) was added SOCl₂ (0.15 ml) at 0° C. followed by the addition of a catalytic amount of DMF. The reaction mixture was then heated to 70° C. for 2 h. The reaction mixture was then concentrated under reduced pressure an the obtained residue was dissolved in THF (3 mL). To this mixture was then added NH₃ in THF (0.4 M, 3 mL). The reaction mixture was then stirred at ambient temperature for 16 h. The reaction mixture was portioned between water (60 mL) and EtOAc (150 mL). The organic layer was basified with sat. NaHCO₃ solution, washed with brine, dried over anhydrous Na₂SO₄ and concentrated under reduced pressure. The crude product was purified by prep reverse phase HPLC to afford 4-[[2-(cyclohexylmethyl)-5-methyl-4-(trifluoromethyl)pyrazole-3-carbonyl]amino]pyridine-2-carboxamide (SC-84). Yield: 37% (100 mg). ¹H NMR (400 MHz, DMSO-d6): δ (ppm)=11.51 (s, 1H), 8.59-8.57 (d, 1H), 8.32 (s, 1H), 8.17 (s, 1H), 7.80-7.78 (m, 1H), 7.38 (s, 1H), 4.04-4.02 (d, 2H), 2.31 (s, 3H), 1.97-1.17 (m, 9H). LCMS: m/z [M+H]⁺=446.3 (calc.=466.2).

Synthesis of 1-((3,3-difluorocyclopentyl)methyl)-3-(difluoromethyl)-N-(3-sulfamoylphenyl)-4-(trifluoromethyl)-1H-pyrazole-5-carboxamide (SC-262)

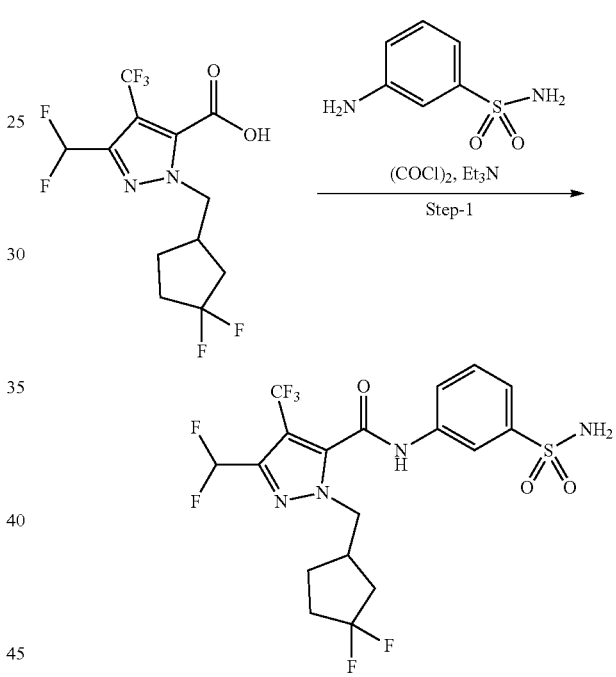

Step-1: To a solution of 1-((3,3-difluorocyclopentyl)methyl)-3-(difluoromethyl)-4-(trifluoromethyl)-1H-pyrazole-5-carboxylic acid (Int-B86, 200 mg, 0.574 mmol, 1.0 eq.) in DCM (20 mL) was added oxalyl chloride (0.15 mL, 1.72 mmol, 3.0 eq.) at 0° C. and the reaction mixture was then stirred at ambient temperature for 3 h. The reaction mixture was concentrated to dryness under reduced pressure to obtain a residue. This residue was dissolved in THF (5 mL) and was added to a solution of 3-aminobenzenesulfonamide (148 mg, 0.86 mmol, 1.5 eq.) in THF (10 mL) followed by the addition of Et₃N (0.25 mL, 1.72 mmol, 3.0 eq.). The reaction mixture was diluted with ethyl acetate (100 mL), washed with water (50 mL) and then brine (50 ml). The combined organic layers were dried over sodium sulfate and concentrated under reduced pressure to get the crude product which was purified by combiflash column chromatography (silica gel; 50% EA in hexane as eluent) to yield 1-((3,3-difluorocyclopentyl)methyl)-3-(difluoromethyl)-N-(3-sulfamoylphenyl)-4-(trifluoromethyl)-1H-pyrazole-5-carboxamide (SC-262). Yield: 16% (46 mg, 0.091 mmol). NMR (400 MHz, DMSO-d6): δ (ppm)=11.44 (s, 1H), 8.24 (s, 1H), 7.76 (d, 1H), 7.66-7.59 (m, 2H), 7.45 (s, 2H), 7.23 (d, 1H), 4.27 (d, 2H), 2.71-2.67 (m, 1H), 2.19-1.98 (m, 4H), 1.84-1.82 (m, 1H), 1.59-1.53 (m, 1H). LCMS: m/z [M−H]$^-$=501.2 (calc.=501.1).

Synthesis of 1-((4,4-difluorocyclohexyl)methyl)-3-methyl-N-(6-(methylsulfonyl)pyridazin-4-yl)-4-(trifluoromethyl)-1H-pyrazole-5-carboxamide (SC-280)

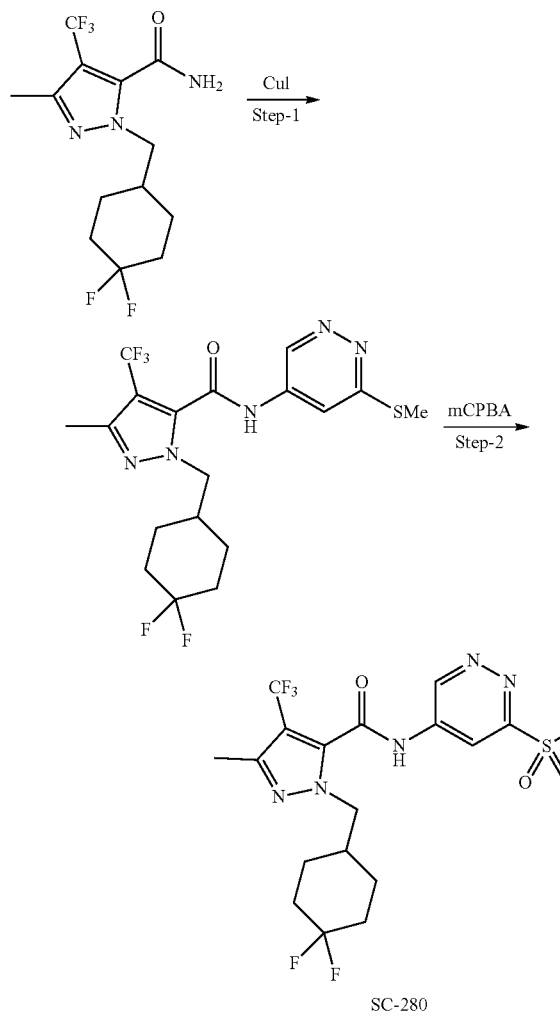

SC-280

Step-1: A solution of 1-[(4,4-difluorocyclohexyl)methyl]-3-methyl-4-(trifluoromethyl)-1H-pyrazole-5-carboxamide (0.225 g, 0.69 mmol, 1.0 eq.) and 5-bromo-3-(methylsulfanyl)pyridazine (0.22 g, 1.07 mmol, 1.5 eq.) in 1,4-dioxane (20 mL) in a sealed tube was degassed with nitrogen for 15 min. Cs$_2$CO$_3$ (0.675 g, 2.07 mmol, 3 eq.), CuI (0.026 mg, 0.14 mmol, 0.2 eq.) and trans-N,N'-dimethyl-cyclohexane-1,2-diamine (0.2 g, 0.14 mmol, 0.2 eq.) were then added, the vessel was sealed with the screw cap and the reaction mixture was heated to 110° C. for 16 h. The reaction mixture was diluted with water (50 mL) and ethyl acetate (50 mL) and filtered through celite. The organic layer was separated and the aqueous layer was extracted with ethyl acetate (25 mL). The combined organic layers were washed with brine, dried over Na$_2$SO$_4$ and concentrated under reduced pressure to get the crude material which was purified by combiflash column chromatography (silica; 0-10% MeOH in DCM) to yield 1-[(4,4-difluorocyclohexyl)methyl]-3-methyl-N-[6-(methylsulfanyl)pyridazin-4-yl]-4-(trifluoromethyl)-1H-pyrazole-5-carboxamide. Yield: 61% (0.19 g, 0.42 mmol)

Step 2: To the stirred solution of 1-[(4,4-difluorocyclohexyl)methyl]-3-methyl-N-[6-(methylsulfanyl)pyridazin-4-yl]-4-(trifluoromethyl)-1H-pyrazole-5-carboxamide (0.18 g, 0.40 mmol, 1.0 eq.) in DCM (10 mL) was added mCPBA (77% in water) (0.185 g, 0.82 mmol, 2.05 eq.) at 0° C. and the mixture was then stirred at ambient temperature for 2 h. The reaction mixture was diluted with DCM (50 mL) and quenched with a saturated aqueous solution of NaCO$_3$ until gas evolution subsided. The DCM layer was separated and the aqueous layer was extracted with DCM (25 mL). The combined organic layers were washed with brine, dried over Na$_2$SO$_4$ and concentrated under reduced pressure to get the crude material which was purified by reverse phase prep HPLC to yield 1-[(4,4-difluorocyclohexyl)methyl]-N-(6-methanesulfonylpyridazin-4-yl)-3-methyl-4-(trifluoromethyl)-1H-pyrazole-5-carboxamide (SC-280). Yield: 30% (0.057 g, 0.12 mmol). NMR (400 MHz, DMSO-d6): δ (ppm)=12.14 (s, 1H), 9.47 (s, 1H), 8.60 (s, 1H), 4.08-4.07 (d, 2H), 3.49 (s, 3H), 2.32 (s, 3H), 1.98 (m, 3H), 1.84-1.68 (m, 2H), 1.59-1.56 (m, 2H), 1.27-1.18 (m, 2H). LCMS: m/z [M+H]$^+$=482.3 (calc.=482.1).

Synthesis of 5-bromo-3-(methylthio)pyridazine

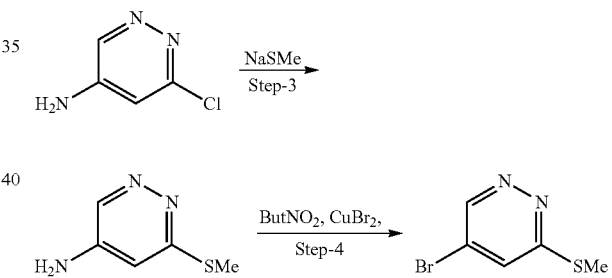

Step-3: To a stirred solution of 6-chloropyridazin-4-amine (0.5 g, 3.86 mmol, 1.0 eq.) in DMF (15 mL) in a sealed tube was added NaSMe (0.67 g, 9.65 mmol, 2.5 eq.) and the resulting reaction mixture was heated to 100° C. for 16 h. The reaction mixture was concentrated under reduced pressure to get the crude material which was purified by combiflash column chromatography (silica; 0-10% MeOH in DCM) to yield 6-(methylsulfanyl)pyridazin-4-amine. Yield: 92% (0.5 g, 3.54 mmol)

Step-4: To a stirred solution of 6-(methylsulfanyl) pyridazin-4-amine (0.5 g, 1.77 mmol, 1.0 eq.) in acetonitrile (15 mL) were added tBuNO$_2$ (0.65 mL, 2.65 mmol, 1.5 eq.) and CuBr$_2$ at 0° C. The reaction mixture was stirred for 1 h at the same temperature. The reaction mixture was diluted with water and extracted with ethyl acetate (50 mL×2). The combined organic layers were washed with brine, dried over Na$_2$SO$_4$ and concentrated under reduced pressure to get the crude material which was purified by combiflash column chromatography (silica; 0-10% MeOH in DCM) to yield 5-bromo-3-(methylsulfanyl)pyridazine Yield: 51% (0.4 g, 1.95 mmol).

Synthesis of 4-(3-(3,3-difluorocyclobutoxy)-1-((3,3-difluorocyclopentyl)methyl)-4-(trifluoromethyl)-1H-pyrazole-5-carboxamido)picolinamide (SC-283)

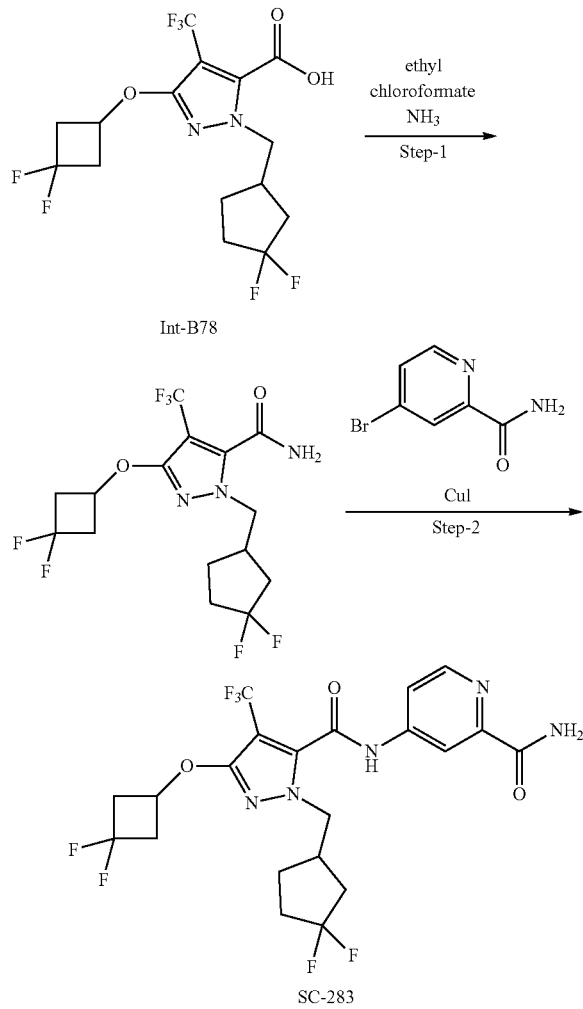

Step-1: To a solution of 3-(3,3-difluorocyclobutoxy)-1-[(3,3-difluorocyclopentyl)methyl]-4-(trifluoromethyl)-1H-pyrazole-5-carboxylic acid (Int-B78, 0.15 g, 0.371 mmol, 1.0 eq.) in THF (7 mL) were added ethyl chloroformate (0.05 mL, 0.557 mmol, 1.5 eq.) and TEA (0.16 mL, 1.11 mmol, 3.0 eq.) dropwise at 0° C. and the resulting mixture was stirred for 1 h. To this mixture was added NH$_3$ solution (25% in water, 2 mL) and the mixture was stirred for 16 h. The reaction mixture was quenched with ice-water and extracted with EtOAc (2×50 mL). The combined organic layers were washed with brine, dried over Na$_2$SO$_4$ and concentrated under reduced pressure. The resulting crude material was purified by combiflash column chromatography (silicagel; 0-30% ethyl acetate in hexane as eluent) to obtain 3-(3,3-difluorocyclobutoxy)-1-[(3,3-difluorocyclopentyl)methyl]-4-(trifluoromethyl)-1H-pyrazole-5-carboxamide. Yield: 93% (0.14 g, 0.347 mmol)

Step-2: 3-(3,3-Difluorocyclobutoxy)-1-[(3,3-difluorocyclopentyl)methyl]-4-(trifluoromethyl)-1H-pyrazole-5-carboxamide (0.15 g, 0.371 mmol, 1.0 eq.), 4-bromopyridine-2-carboxamide (0.090 g, 0.446 mmol, 1.2 eq.), Cs$_2$CO$_3$ (0.363 g, 1.11 mmol, 3.0 eq.) and 1,4-dioxane (10 mL) were taken up in a sealed tube and the mixture was degassed for 15 minutes using argon. CuI (0.014 g, 0.07 mmol, 0.2 eq.) and trans-1,2-diaminocyclohexane (0.008 g, 0.07 mmol, 0.2 eq.) were added and the reaction mixture was heated to 100° C. for 16 h. The reaction mixture was then cooled to ambient temperature, diluted with ethylacetate (50 mL) and filtered through a celite bed. The filtrate was concentrated under reduced pressure and resulting crude material was purified by combiflash column chromatography (silica gel; 0-30% acetone in hexane as eluent) and finally purified by reverse phase prep HPLC to yield 4-[3-(3,3-difluorocyclobutoxy)-1-[(3,3-difluorocyclopentyl)methyl]-4-(trifluoromethyl)-1H-pyrazole-5-amido]pyridine-2-carboxamide (SC-283). Yield: 19% (0.036 g, 0.068 mmol). NMR (400 MHz, DMSO-d6): δ (ppm)=11.58 (s, 1H), 8.56 (d, 1H), 8.31 (s, 1H), 8.30 (s, 1H), 8.10-7.78 (m, 1H), 7.77 (s, 1H), 4.98-5.00 (m, 1H), 4.06 (d, 2H), 3.21-3.10 (m, 2H), 2.79-2.64 (m, 2H), 2.62-2.58 (m, 1H), 2.21-1.96 (m, 4H), 1.95-1.80 (m, 1H), 1.57-1.53 (m, 1H). LCMS: m/z [M+H]$^+$=524.4 (calc.=524.2).

Synthesis of 4-(1-((4,4-difluorocyclohexyl)methyl)-3-methyl-4-(trifluoromethyl)-1H-pyrazole-5-carboxamido)-3-methylpicolinamide (SC-294)

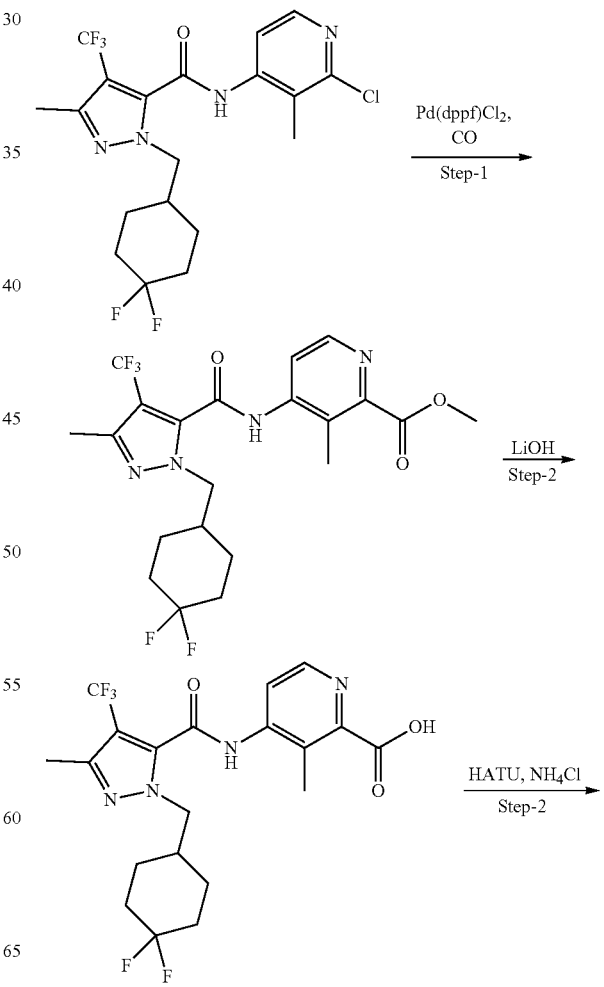

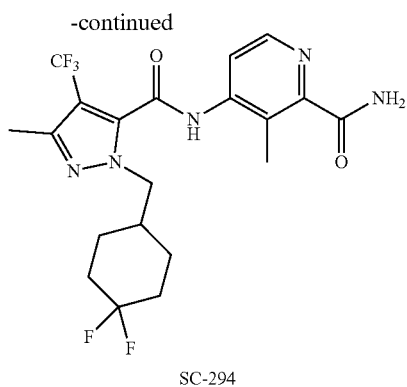

SC-294

N-(2-chloro-3-methylpyridin-4-yl)-1-((4,4-difluorocyclohexyl)methyl)-3-methyl-4-(trifluoromethyl)-1H-pyrazole-5-carboxamide was prepared from Int-B46 using the procedure described for the synthesis of SC-145 using the appropriate reagents. LCMS: m/z [M+H]⁺=451.2 (calc.=451.1).

Step-1: A steal bomb was charged with N-(2-chloro-3-methylpyridin-4-yl)-1-((4,4-difluorocyclohexyl)methyl)-3-methyl-4-(trifluoromethyl)-1H-pyrazole-5-carboxamide (100 mg, 0.222 mmol, 1.0 eq.) in methanol (30 mL). The reaction mixture was degassed with argon for 10 min, then TEA (0.064 mL, 0.444 mmol, 2.0 eq.) and Pd(dppf)Cl₂·DCM (18.1 mg, 0.022 mmol, 0.1 eq.) were added at 25° C. The reaction mixture was stirred at 80° C. under CO gas (120 psi) for 16 h. The reaction mixture was filtered through a celite bed and the celite bed was washed with methanol (25 mL). The combined organic layers were concentrated under reduced pressure to get the crude product which was purified by column chromatography (silica gel 100-200 mesh, 50% Ethyl acetate in Pet ether as an eluent) to afford methyl 4-(1-((4,4-difluorocyclohexyl)methyl)-3-methyl-4-(trifluoromethyl)-1H-pyrazole-5-carboxamido)-3-methylpicolinate. Yield: 67% (70 mg).

Step-2: To a stirred solution of methyl 4-(1-((4,4-difluorocyclohexyl)methyl)-3-methyl-4-(trifluoromethyl)-1H-pyrazole-5-carboxamido)-3-methylpicolinate (70 mg, 0.147 mmol, 1.0 eq.) in THF:MeOH:H₂O (1:0.5:0.5, 4 mL) was added LiOH·H₂O (18.5 mg, 0.441 mmol, 3.0 eq.) at ambient temperature. The reaction mixture was stirred for 4 h. The reaction mixture was then concentrated under reduced pressure, diluted with water (10 mL), acidified to pH~2 with 1N aq. HCl solution, and extracted with ethyl acetate (2×20 mL). The combined organic layers were dried over anhydrous Na₂SO₄ and concentrated under reduced pressure to afford 4-(1-((4,4-difluorocyclohexyl)methyl)-3-methyl-4-(trifluoromethyl)-1H-pyrazole-5-carboxamido)-3-methylpicolinic acid (70 mg, crude).

Step-3: To a solution of 4-(1-((4,4-difluorocyclohexyl)methyl)-3-methyl-4-(trifluoromethyl)-1H-pyrazole-5-carboxamido)-3-methylpicolinic acid (70 mg, 0.152 mmol, 1.0 eq.) in DMF (2 mL) were added HATU (86.6 mg, 0.228 mmol), DIPEA (0.079 mL, 0.456 mmol, 1.5 eq.) and ammonium chloride (40 mg, 0.760 mmol, 5.0 eq.) at ambient temperature. The resulting reaction mixture was stirred for 4 h. The reaction mixture was diluted with water (10 mL) and extracted with ethyl acetate (2×20 mL). The combined organic layers were washed with water (2×10 mL), dried over anhydrous Na₂SO₄ and concentrated under reduced pressure to afford 4-(1-((4,4-difluorocyclohexyl)methyl)-3-methyl-4-(trifluoromethyl)-1H-pyrazole-5-carboxamido)-3-methylpicolinamide (SC-294). Yield: 31% over two steps, 30 mg). ¹H NMR (400 MHz, DMSO-d6): δ (ppm)=10.79 (s, 1H), 8.42 (s, 1H), 7.93 (s, 1H), 7.70 (d, 1H), 7.54 (s, 1H), 4.05 (d, 2H), 2.35 (s, 3H), 2.31 (s, 3H), 2.10-1.92 (m, 3H), 1.85-1.62 (m, 4H), 1.32-1.18 (m, 2H). LCMS: m/z [M+H]⁺=460.2 (calc.=460.2).

Synthesis of 1-((3,3-difluorocyclobutyl)methyl)-3-(1,1-difluoroethyl)-4-methyl-N-(3-sulfamoylphenyl)-1H-pyrazole-5-carboxamide (SC-295)

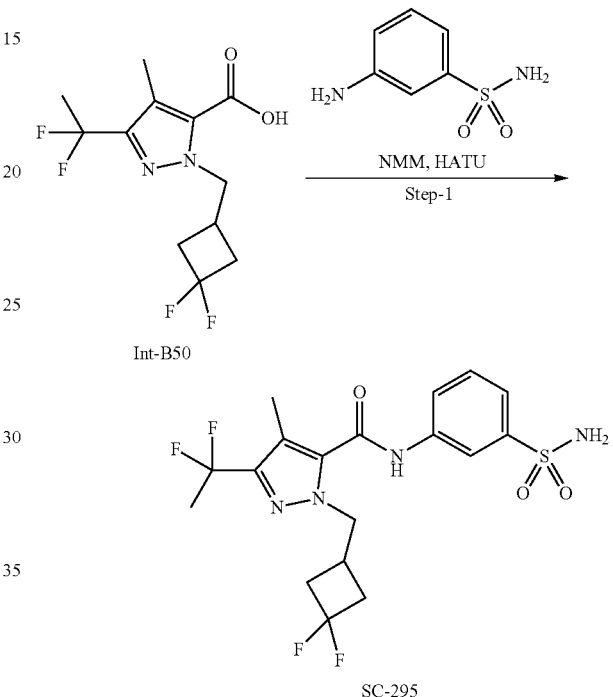

Step-1: To a stirred solution of 1-((3,3-difluorocyclobutyl)methyl)-3-(1,1-difluoroethyl)-4-methyl-1H-pyrazole-5-carboxylic acid (Int-B50, 0.20 g, 0.68 mmol, 1.0 eq.) and 3-aminobenzenesulfonamide (0.14 g, 0.81 mmol, 1.2 eq.) in DMF (10 mL) were added HATU (0.517 g, 1.36 mmol, 2.0 eq.) and N-methylmorpholine (0.137 g, 1.36 mmol, 2.0 eq.) at ambient temperature. The resulting reaction mixture was stirred for 2 h. The reaction mixture was diluted with water (20 mL) and extracted with ethyl acetate (2×20 mL). The combined organic layers were washed with water (25 mL), dried over anhydrous Na₂SO₄ and concentrated under reduced pressure to get the crude product which was purified by Grace column chromatography (0.1% formic acid in water and acetonitrile as an eluent) to afford 1-((3,3-difluorocyclobutyl)methyl)-3-(1,1-difluoroethyl)-4-methyl-N-(3-sulfamoylphenyl)-1H-pyrazole-5-carboxamide (SC-295) (100 mg, 33%). ¹H NMR (500 MHz, DMSO-d6): δ (ppm)=10.87 (bs, 1H), 8.32 (s, 1H), 7.83-7.79 (m, 1H), 7.63-7.54 (m, 2H), 7.50-7.30 (m, 2H), 4.37 (d, 2H), 2.70-2.58 (m, 3H), 2.50-2.38 (m, 2H), 2.23 (s, 3H), 2.07 (t, 3H). LCMS: m/z [M+H]⁺=449.1 (calc.=449.1).

The following examples were synthesized in analogy to the procedures described above (with or without chiral separation at the end of the synthesis) using appropriate reactants and adjusted purification protocols:

| Ex. No. | Structure | Procedure | Intermediate | Analytical data |
|---|---|---|---|---|
| SC-230 | (structure) | in analogy to SC-295 | Int-B76 | $^1$H NMR (400 MHz, DMSO-d$_6$): δ (ppm) = 11.25 (s, 1H), 8.25 (s, 1H), 7.75 (d, 1H), 7.64-7.55 (m, 2H), 7.43 (bs, 2H), 3.97 (d, 2H), 2.02-1.91 (m, 4H), 1.94-1.54 (m, 4H), 1.35-1.13 (m, 2H), 1.00-0.93 (m, 2H), 0.87-0.81 (m, 2H). LCMS: m/z [M − H]$^-$ = 505.0 (calc. = 505.1). |
| SC-235 | (structure) | in analogy to SC-295 | Int-B67 | $^1$H NMR (400 MHz, DMSO-d$_6$): δ (ppm) = 11.27 (s, 1H), 8.26 (s, 1H), 8.09 (s, 1H), 7.77 (d, 1H), 7.68-7.54 (m, 2H), 7.44 (bs, 2H), 4.47 (dd, 1H), 4.26-4.17 (m, 1H), 2.90-2.75 (m, 1H), 2.20-2.00 (m, 2H), 1.90-1.60 (m, 3H), 1.60-1.49 (m, 1H). LCMS: m/z [M − H]$^-$ = 451.0 (calc. = 451.1). |
| SC-238 | (structure) | in analogy to SC-295 | Int-B121 | $^1$H NMR (400 MHz, DMSO-d$_6$): δ (ppm) = 11.25 (s, 1H), 8.21 (dd, 1H), 7.85-7.65 (m, 3H), 7.44 (t, 1H), 3.92 (d, 2H), 2.30 (s, 3H), 1.86-1.73 (m, 1H), 1.66-1.49 (m, 5H), 1.20-1.07 (m, 3H), 0.98-0.85 (m, 2H). LCMS: m/z [M + H]$^+$ = 463.2 (calc. = 463.1). |
| SC-244 | (structure) | in analogy to SC-295 | Int-B121 | $^1$H NMR (400 MHz, DMSO-d$_6$): δ (ppm) = 11.22 (s, 1H), 8.25 (s, 1H), 7.76 (d, 1H), 7.62-7.55 (m, 2H), 7.43 (bs, 2H), 3.92 (d, 2H), 2.31 (d, 3H), 1.86-1.81 (m, 1H), 1.64-1.50 (m, 5H), 1.17-1.10 (m, 3H), 0.96-0.88 (m, 2H). LCMS: m/z [M + H]$^+$ = 445.3 (calc. = 445.2). |
| SC-274 | (structure) | in analogy to SC-295 | Int-B32 | $^1$H NMR (400 MHz, DMSO-d$_6$): δ (ppm) = 11.15 (s, 1H), 7.96 (dd, 1H), 7.77-7.67 (m, 3H), 7.31 (t, 1H), 4.18 (d, 2H), 2.70-2.52 (m, 3H), 2.45-2.35 (m, 2H), 1.98-1.89 (m, 1H), 1.00-0.92 (m, 2H), 0.87-0.81 (m, 2H). LCMS: m/z [M − H]$^-$ = 459.1 (calc. = 459.1). |

| Ex. No. | Structure | Procedure | Intermediate | Analytical data |
|---|---|---|---|---|
| SC-276 | 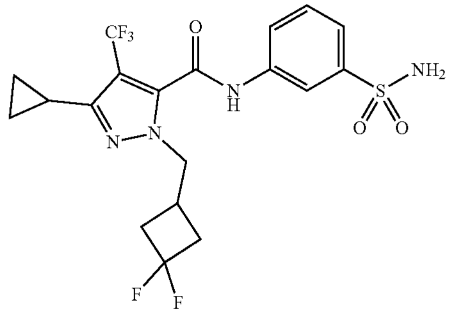 [SMILES: NS(=O)(=O)c1cccc(NC(=O)c2c(C(F)(F)F)c(C3CC3)nn2CC2CC(F)(F)C2)c1] | in analogy to SC-295 | Int-B32 | $^1$H NMR (400 MHz, DMSO-$d_6$): δ (ppm) = 11.30 (s, 1H), 8.26 (s, 1H), 7.76 (d, 1H), 7.65-7.55 (m, 2H), 7.43 (s, 2H), 4.19 (d, 2H), 2.70-2.50 (m, 3H), 2.48-2.37 (m, 2H), 1.98-1.88 (m, 1H), 1.00-0.93 (m, 2H), 0.88-0.81 (m, 2H). LCMS: m/z [M + H]$^+$ = 479.1 (calc. = 479.12). |
| SC-296 a | 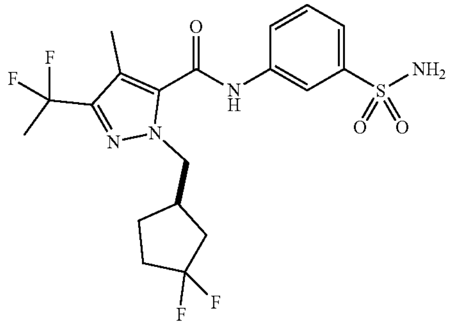 | in analogy to SC-295 | Int-B55 | $^1$H NMR (500 MHz, DMSO-$d_6$): δ (ppm) = 10.80 (bs, 1H), 8.31 (s, 1H), 7.81 (d, 1H), 7.61-7.54 (m, 2H), 7.50-7.10 (m, 2H), 4.27 (d, 2H), 2.65-2.55 (m, 1H), 2.23 (s, 3H), 2.18-2.00 (m, 6H), 1.99-1.76 (m, 2H), 1.58-1.49 (m, 1H). LCMS: m/z [M + H]$^+$ = 463.2 (calc. = 463.1). chiral SFC (column: Chiracel OJ-3 (4.6 × 150 mm) 3 μm, total flow: 3 g/min, 80% $CO_2$, 20% metanol, 1500 psi back pressure, 30° C., $R_t$ = 3.35 min. |
| SC-296 b | 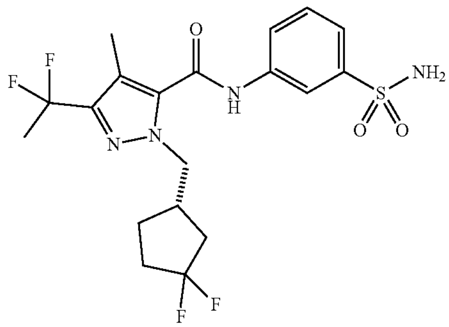 | in analogy to SC-295 | Int-B55 | $^1$H NMR (500 MHz, DMSO-$d_6$): δ (ppm) = 10.80 (bs, 1H), 8.31 (s, 1H), 7.81 (d, 1H), 7.61-7.54 (m, 2H), 7.50-7.10 (m, 2H), 4.27 (d, 2H), 2.65-2.55 (m, 1H), 2.23 (s, 3H), 2.18-2.00 (m, 6H), 1.99-1.76 (m, 2H), 1.58-1.49 (m, 1H). LCMS: m/z [M + H]$^+$ = 463.2 (calc. = 463.1). chiral SFC (column: Chiracel OJ-3 (4.6 × 150 mm) 3 μm, total flow: 3 g/min, 80% $CO_2$, 20% metanol, 1500 psi back pressure, 30° C., $R_t$ = 5.04 min. |

Synthesis of 1-((3,3-difluorocyclobutyl)methyl)-3-(1,1-difluoroethyl)-N-(2-(methylsulfinyl)pyridin-4-yl)-4-(trifluoromethyl)-1H-pyrazole-5-carboxamide (SC-303)

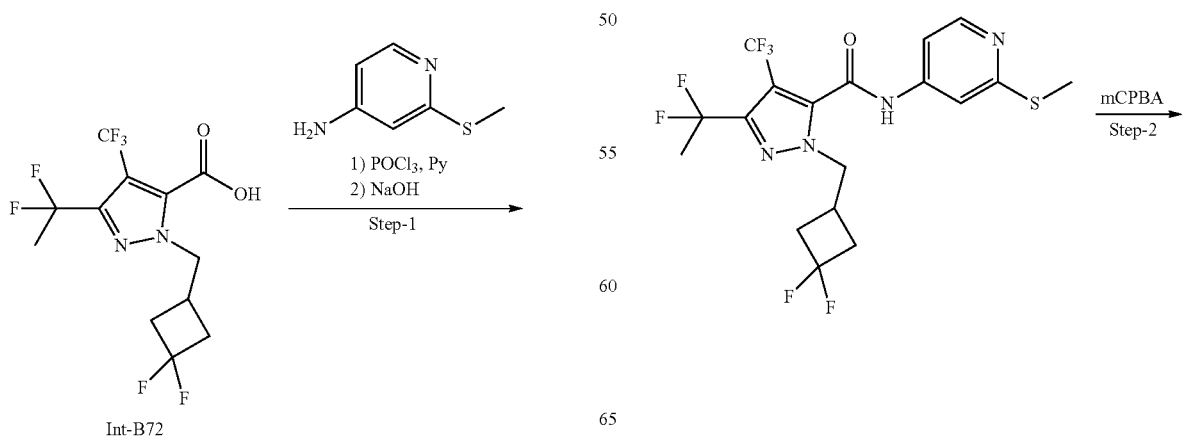

271

-continued

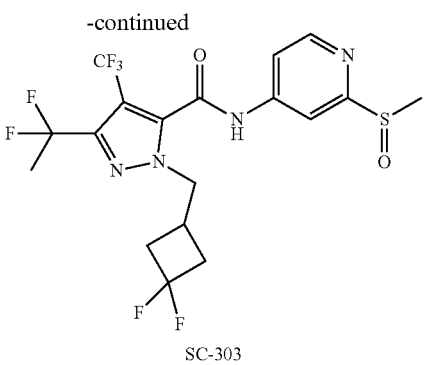

SC-303

Step-1: To a stirred solution of 1-[(3,3-difluorocyclobutyl)methyl]-3-(1,1-difluoroethyl)-4-(trifluoromethyl)-1H-pyrazole-5-carboxylic acid (Int-B72, 0.225 g, 0.644 mmol, 1.0 eq.) and 2-(methylsulfanyl)pyridin-4-amine hydrochloride (0.17 g, 0.96 mmol, 1.5 eq.) in pyridine (10 mL) was added POCl₃ (0.18 mL, 1.92 mmol, 3.0 eq.) at 0° C. and the reaction mixture was stirred at ambient temperature for 3 h. The reaction mixture was concentrated under reduced pressure and quenched with saturated NaHCO₃ solution at 0° C. The aqueous part was extracted with EtOAc (3×50 mL). The combined organic layers were washed with brine and dried over anhydrous Na₂SO₄. The organic layer was concentrated under reduced pressure to get a mixture of 1-[(3,3-difluorocyclopentyl)methyl]-3-(1,1-difluoroethyl)-4-methyl-N-[2-(methylsulfanyl)pyridin-4-yl]-1H-pyrazole-5-carboxamide and (Z)-1-[(3,3-difluorocyclobutyl)methyl]-3-(1,1-difluoroethyl)-N-[2-(methylsulfanyl)pyridin-4-yl]-4-(trifluoromethyl)-1H-pyrazole-5-carbonimidoyl chloride. The crude mixture was dissolved in THF (10 mL) and 1(M) NaOH solution (2 mL) was added at ambient temperature and was stirred for 2 h. The reaction mixture was diluted with ice water. The aqueous part was extracted with EtOAc (3×30 mL). The combined organic layers were washed with brine, dried over anhydrous Na₂SO₄ and concentrated under reduced pressure to get the crude product which was purified by combiflash column chromatography (Silica gel, 0-60% ethyl acetate in hexane as eluent.) to yield 1-[(3,3-difluorocyclopentyl)methyl]-3-(1,1-difluoroethyl)-4-methyl-N-[2-(methylsulfanyl)pyridin-4-yl]-1H-pyrazole-5-carboxamide. Yield: 46% (0.14 g, 0.298 mmol).

Step-2: To a solution of 1-[(3,3-difluorocyclopentyl)methyl]-3-(1,1-difluoroethyl)-4-methyl-N-[2-(methylsulfanyl)pyridin-4-yl]-1H-pyrazole-5-carboxamide (0.06 g, 0.127 mmol, 1.0 eq.) in DCM (6 mL) was added mCPBA (77%) (0.023 g, 0.101 mmol, 0.8 eq.) at 0° C. The reaction mixture was stirred at ambient temperature for 1 h. The reaction mixture was then quenched with a 1:1 mixture of Na₂SO₃ and NaHCO₃ solution. The aqueous part was extracted with DCM (3×25 mL). The combined organic layers were washed with water (30 mL) and then brine (30 mL), dried over Na₂SO₄, filtered and evaporated under reduced pressure to get the crude product which was purified via prep-HPLC to afford 1-((3,3-difluorocyclobutyl)methyl)-3-(1,1-difluoroethyl)-N-(2-(methylsulfinyl)pyridin-4-yl)-4-(trifluoromethyl)-1H-pyrazole-5-carboxamide (SC-303). Yield: 60% (0.037 g, 0.076 mmol). NMR (400 MHz, DMSO-d6): δ (ppm)=11.89 (s, 1H), 8.64 (d, 1H), 8.24 (s, 1H), 7.67 (d, 1H), 4.38 (d, 2H), 2.81 (s, 3H), 2.66 (brs, 4H), 2.13-2.03 (m, 3H), 1H omitted by solvent peak. LCMS: m/z [M+H]=487.2 (calc.=487.1).

272

Synthesis of 3-(1,1-difluoroethyl)-1-((1-methoxycyclopropyl)methyl)-4-methyl-N-(2-sulfamoylpyridin-4-yl)-1H-pyrazole-5-carboxamide (SC-308)

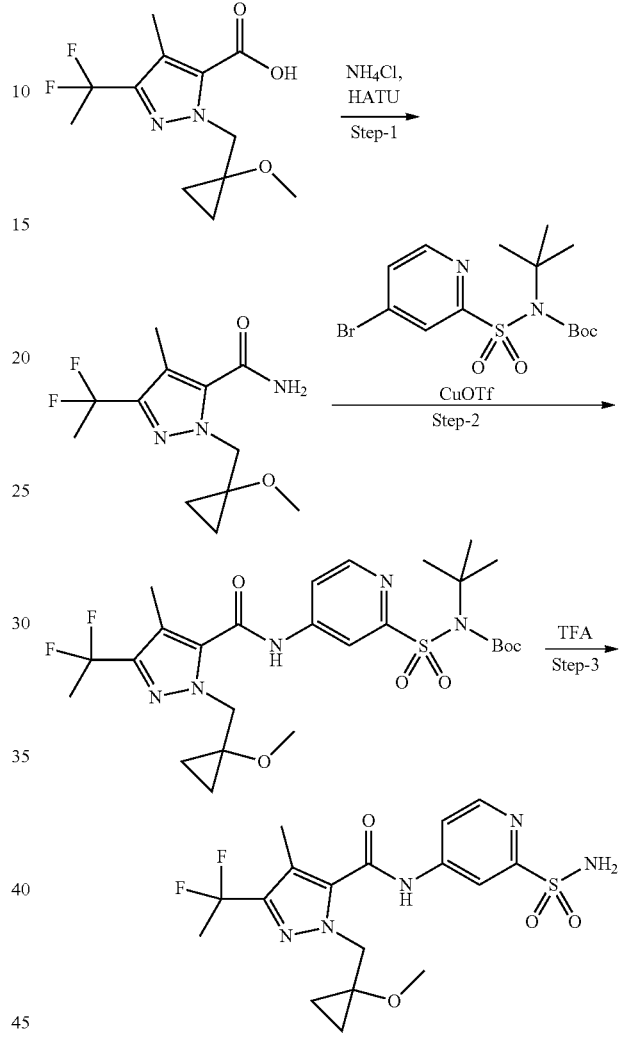

Step-1: To a solution of 3-(1,1-difluoroethyl)-1-((1-methoxycyclopropyl)methyl)-4-methyl-1H-pyrazole-5-carboxylic acid (Int-B95, 150 mg, 0.547 mmol, 1.0 eq.) in dry DMF (10 mL) were added HATU (311.7 mg, 0.821 mmol 1.5 eq.), DIPEA (0.47 mL, 2.735 mmol, 5.0 eq.) and NH₄Cl (44.3 mg, 0.821 mmol, 1.5 eq.). The resulting reaction mixture was stirred at ambient temperature for 2 h. The reaction mixture was diluted with water (20 mL) and extracted with EtOAc (2×30 mL). The combined organic layers were dried over anhyd. Na₂SO₄ and concentrated under reduced pressure to get 3-(1,1-difluoroethyl)-1-((1-methoxy cyclopropyl)methyl)-4-methyl-1H-pyrazole-5-carboxamide (150 mg, 80%).

Step 2: To a solution of 3-(1,1-difluoroethyl)-1-methoxycyclopropyl)methyl)-4-methyl-1H-pyrazole-5-carboxamide (250 mg, 0.912 mmol, 1.0 eq.) in 1,4-dioxane (10 mL) in a sealed tube were added tert-butyl ((4-bromopyridin-2-yl) sulfonyl)(tert-butyl)carbamate (430.2 mg, 1.094 mmol, 1.2 eq.) and Cs₂CO₃ (590.9 mg, 1.824 mmol 2.0 eq.) at ambient temperature and the mixture was degassed with argon for 10 min. To the reaction mixture were then added trans-N,N'-dimethyl-cyclohexane-1,2-diamine (38.7 mg, 0.273 mmol, 0.3 eq.) and copper (I) trifluoromethane sulfonate benzene complex (68.6 mg, 0.273 mmol, 0.3 eq.) at ambient temperature. The reaction mixture was heated to 80° C. for 16 h. The reaction mixture was then cooled to ambient temperature, filtered through a celite bed and the celite bed was washed with ethyl acetate (15 mL). The filtrate was concentrated under reduced pressure to afford tert-butyl tert-butyl((4-(3-(1,1-difluoroethyl)-1-((1-methoxycyclopropyl)methyl)-4-methyl-1H-pyrazole-5-carboxamido)pyridin-2-yl)sulfonyl)carbamate (320 mg, crude).

Step 3: TFA (1 mL) was added to a stirred solution of tert-butyl tert-butyl((4-(3-(1,1-difluoroethyl)-1-((1-methoxycyclopropyl)methyl)-4-methyl-1H-pyrazole-5-carboxamido)pyridin-2-yl)sulfonyl)carbamate (300 mg, 0.512 mmol, 1.0 eq.) in dichloromethane (20 mL) at 0° C. and the resulting mixture was stirred for 16 h at ambient temperature. The reaction mixture was concentrated under reduced pressure to get the crude product which was purified by Grace column chromatography (0.1% formic acid in water and acetonitrile as an eluent) to afford 3-(1,1-Difluoroethyl)-1-((1-methoxycyclopropyl)methyl)-4-methyl-N-(2-sulfamoylpyridin-4-yl)-1H-pyrazole-5-carboxamide (SC-308, 50 mg, 13% over 2 steps). $^1$H NMR (400 MHz, DMSO-d6): δ (ppm)=11.37 (s, 1H), 8.64 (d, 1H), 8.35 (d, 1H), 7.88 (dd, 1H), 7.46 (s, 2H), 4.48 (s, 2H), 3.04 (s, 3H), 2.24 (s, 3H), 2.03 (t, 3H), 0.71 (s, 4H). LCMS: m/z [M+H]$^+$=430.1 (calc.=430.1).

The following examples were synthesized in analogy to the procedures described above (with or without chiral separation at the end of the synthesis) using appropriate reactants and adjusted purification protocols:

| Ex. No. | Structure | Procedure | Intermediate | Analytical data |
|---|---|---|---|---|
| SC-282 | 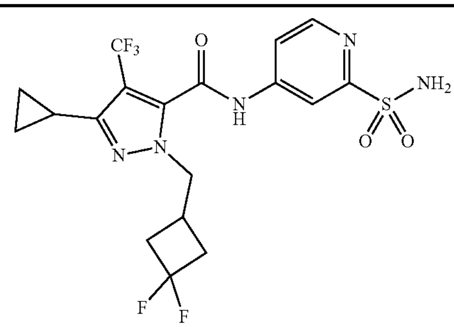 | in analogy to SC-308 | Int-B32 | $^1$H NMR (400 MHz, DMSO-d$_6$): δ (ppm) = 11.74 (s, 1H), 8.67 (d, 1H), 8.28 (d, 1H), 7.76 (dd, 1H), 7.50 (s, 2H), 4.22 (d, 2H), 2.70-2.55 (m, 3H), 2.50-2.35 (m, 2H), 1.99-1.89 (m, 1H), 1.02-0.95 (m, 2H), 0.89-0.82 (m, 2H). LCMS: m/z [M + H]$^+$ = 480.2 (calc. = 480.1). |
| SC-310 | 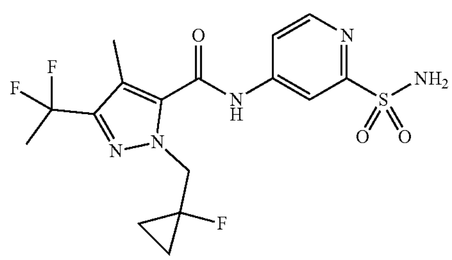 [SMILES: Cc1c(C(C)(F)F)nn(CC2(F)CC2)c1C(=O)Nc1ccnc(S(N)(=O)=O)c1] | in analogy to SC-308 | Int-B96 | $^1$H NMR (400 MHz, DMSO-d$_6$): δ (ppm) = 11.35 (d, 1H), 8.64-8.51 (m, 1H), 8.29 (s, 1H), 7.77 (s, 1H), 7.40 (bs, 2H), 4.88 (m, 2H), 2.26 (s, 3H), 2.08-1.97 (m, 3H), 1.05-0.97 (m, 2H), 0.90-0.83 (m, 2H). LCMS: m/z [M + H]$^+$ = 418.1 (calc. = 418.1). |
| SC-312 a | 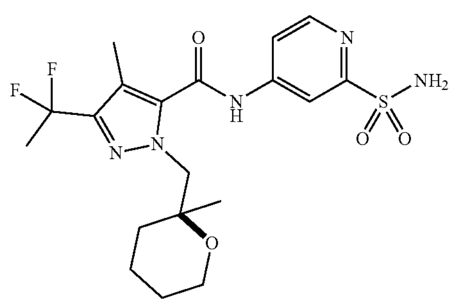 | in analogy to SC-308 | Int-B97 | $^1$H NMR (400 MHz, DMSO-d$_6$): δ (ppm) = 11.08 (s, 1H), 8.61 (d, 1H), 8.32 (s, 1H), 7.81 (d, 1H), 7.45 (bs, 2H), 4.42-4.22 (m, 2H), 3.44-3.36 (m, 2H), 2.22 (s, 3H), 2.02 (t, 3H), 1.60-1.50 (m, 2H), 1.41-1.20 (m, 4H), 0.99 (s, 3H). LCMS: m/z [M + H]$^+$ = 458.3 (calc. = 458.2). chiral SFC (column: Chiralpak AD-H (4.6 × 250 mm) 5 μm, total flow: 3 mL/min, 85% CO$_2$, 15% (0.5% isopropylamine in isopropylalcohol) 1500 psi back pressure, 30° C., R$_t$ = 8.58 min |
| SC-312 b | 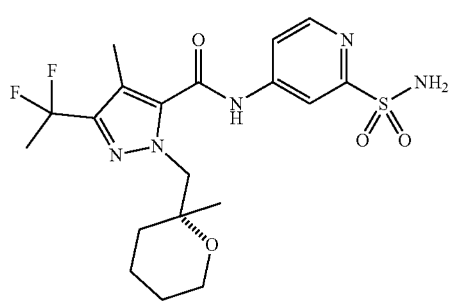 | in analogy to SC-308 | Int-B97 | $^1$H NMR (400 MHz, DMSO-d$_6$): δ (ppm) = 11.08 (s, 1H), 8.61 (d, 1H), 8.32 (s, 1H), 7.81 (d, 1H), 7.45 (bs, 2H), 4.42-4.22 (m, 2H), 3.44-3.36 (m, 2H), 2.22 (s, 3H), 2.02 (t, 3H), 1.60-1.50 (m, 2H), 1.41-1.20 (m, 4H), 0.99 (s, 3H). LCMS: m/z [M + H]$^+$ = 458.3 (calc. = 458.2). chiral SFC (column: Chiralpak AD-H (4.6 × 250 mm) 5 μm, total flow: 3 mL/min, 85% CO$_2$, 15% (0.5% isopropylamine in isopropylalcohol) 1500 psi back pressure, 30° C., R$_t$ = 9.38 min |

| Ex. No. | Structure | Procedure | Intermediate | Analytical data |
|---|---|---|---|---|
| SC-313 | 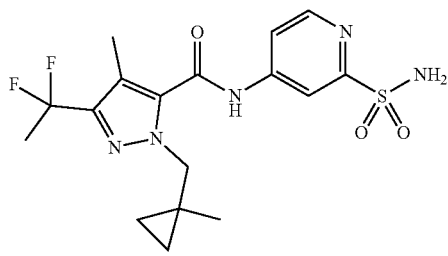 [SMILES: Cc1c(C(C)(F)F)nn(CC2(C)CC2)c1C(=O)Nc1ccnc(S(N)(=O)=O)c1] | in analogy to SC-308 | Int-B100 | $^1$H NMR (400 MHz, DMSO-d6): δ (ppm) = δ 11.30 (s, 1H), 8.64 (d, 1H), 8.32 (s, 1H), 7.83 (d, 1H), 7.47 (s, 2H), 4.23 (s, 2H), 2.23 (s, 3H), 2.10-1.97 (m, 3H), 0.91 (s, 3H), 0.50 (t, 2H), 0.29 (t, 2H). LCMS: m/z [M + H]$^+$ = 414.3 (calc. = 414.1). |
| SC-314 | 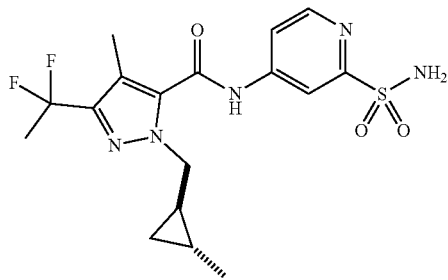 | in analogy to SC-308 | Int-B101 | $^1$H NMR (500 MHz, DMSO-d6): δ (ppm) = 11.28 (s, 1H), 8.63 (d, 1H), 8.33 (s, 1H), 7.83 (d, 1H), 7.46 (s, 2H), 4.20-4.07 (m, 2H), 2.24 (s, 3H), 2.03 (t, 3H), 0.95-0.89 (m, 4H), 0.76-0.70 (m, 1H), 0.48-0.45 (m, 1H), 0.24-0.20 (d, 1H). LCMS: m/z [M + H]$^+$ = 414.1 (calc. = 414.1). |
| SC-316 | 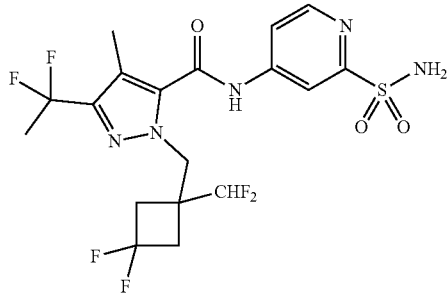 [SMILES: Cc1c(C(C)(F)F)nn(CC2(C(F)F)CC(F)(F)C2)c1C(=O)Nc1ccnc(S(N)(=O)=O)c1] | in analogy to SC-308 | Int-B116 | $^1$H NMR (500 MHz, DMSO-d6): δ (ppm) = 11.23 (s, 1H), 8.63 (d, 1H), 8.30 (s, 1H), 7.83 (s, 1H), 7.46 (s, 2H), 6.21 (t, 1H), 4.59 (s, 2H), 2.85-2.76 (m, 4H), 2.25 (s, 3H), 2.04 (t, 3H). LCMS: m/z [M + H]$^+$ = 500.1 (calc. = 500.1). |
| SC-317 | 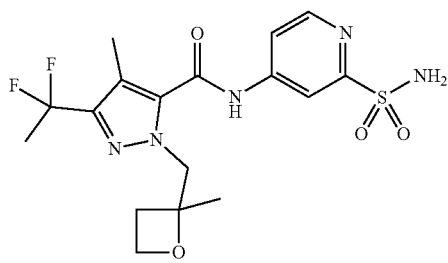 [SMILES: Cc1c(C(C)(F)F)nn(CC2(C)CCO2)c1C(=O)Nc1ccnc(S(N)(=O)=O)c1] | in analogy to SC-308 | Int-B99 | $^1$H NMR (400 MHz, DMSO-d6): δ (ppm) = 11.02 (s, 1H), 8.57 (s, 1H), 8.28 (s, 1H), 7.80 (s, 1H), 7.40 (s, 2H), 4.63-4.40 (m, 2H), 4.22-4.17 (m, 1H), 3.95-3.89 (m, 1H), 2.45-2.25 (m, 5H), 2.03 (t, 3H), 1.27 (s, 3H). LCMS: m/z [M + H]$^+$ = 430.3 (calc. = 430.1). |
| SC-319 a | 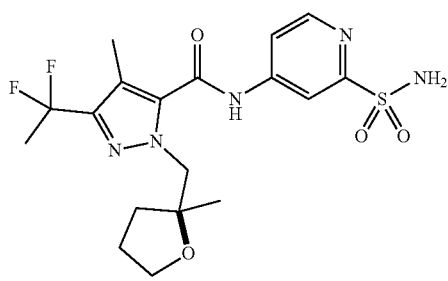 | in analogy to SC-308 | Int-B98 | $^1$H NMR (400 MHz, DMSO-d$_6$): δ (ppm) = 11.08 (s, 1H), 8.61 (d, 1H), 8.34 (s, 1H), 7.87 (d, 1H), 7.45 (bs, 2H), 4.43-4.37 (m, 1H), 4.30-4.24 (m, 1H), 3.54-3.41 (m, 2H), 2.23 (s, 3H), 2.02 (m, 3H), 1.86-1.69 (m, 2H), 1.68-1.57 (m, 1H), 1.56-1.45 (m, 1H), 1.04 (s, 3H). LCMS: m/z [M + H]$^+$ = 444.3 (calc. = 444.2). chiral SFC (column: Chiralpak OJ-H (4.6 × 250 mm) 5 μm, total flow: 3 mL/min, 80% CO$_2$, 20% methanol, 1500 psi back pressure, 30° C., R$_t$ = 2.09 min. |

| Ex. No. | Structure | Procedure | Intermediate | Analytical data |
|---|---|---|---|---|
| SC-319 b | 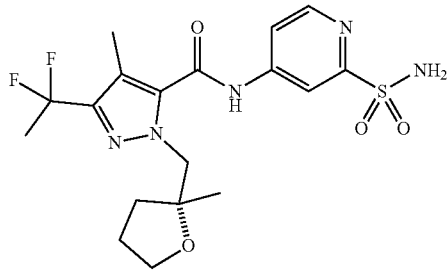 | in analogy to SC-308 | Int-B98 | $^1$H NMR (400 MHz, DMSO-$d_6$): δ (ppm) = 11.08 (s, 1H), 8.61 (d, 1H), 8.34 (s, 1H), 7.87 (d, 1H), 7.45 (bs, 2H), 4.43-4.37 (m, 1H), 4.30-4.24 (m, 1H), 3.54-3.41 (m, 2H), 2.23 (s, 3H), 2.02 (m, 3H), 1.86-1.69 (m, 2H), 1.68-1.57 (m, 1H), 1.56-1.45 (m, 1H), 1.04 (s, 3H). LCMS: m/z [M + H]$^+$ = 444.3 (calc. = 444.2). chiral SFC (column: Chiralpak OJ-H (4.6 × 250 mm) 5 μm, total flow: 3 mL/min, 80% CO$_2$, 20% methanol, 1500 psi back pressure, 30° C., R$_t$ = 3.22 min. |

Synthesis of 4-(3-(1,1-difluoroethyl)-1-((1-(difluoromethyl)-3,3-difluorocyclobutyl)methyl)-4-methyl-1H-pyrazole-5-carboxamido)picolinamide (SC-311)

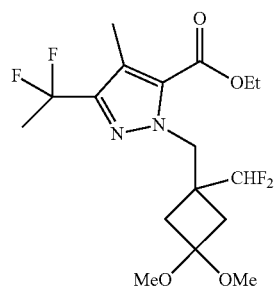

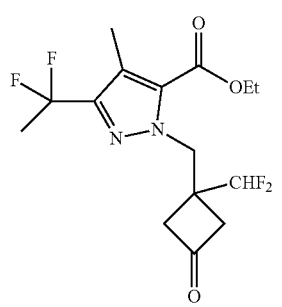

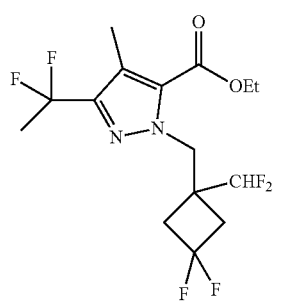

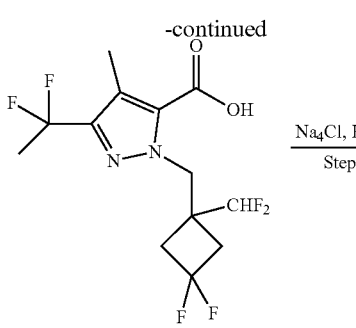

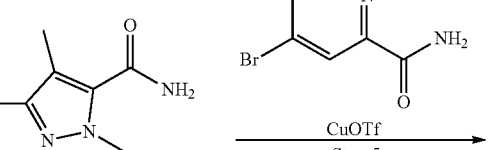

Step-1: Conc. HCl (10 mL) was slowly added to a stirred solution of ethyl 3-(1,1-difluoroethyl)-1-((1-(difluoromethyl)-3,3-dimethoxycyclobutyl)methyl)-4-methyl-1H-pyrazole-5-carboxylate (Int-B102, 1.4 g, 3.53 mmol, 1.0 eq.) in methanol (10 mL) at ambient temperature and the resulting mixture was stirred for 16 h. The reaction mixture was diluted with water (25 mL), basified with saturated NaHCO$_3$ solution and extracted with diethyl ether (3×25 mL). The combined organic layers were washed with water (50 mL), dried over anhydrous Na$_2$SO$_4$ and concentrated under reduced pressure to afford ethyl 3-(1,1-difluoroethyl)-1-((1-

(difluoromethyl)-3-oxocyclobutyl)methyl)-4-methyl-1H-pyrazole-5-carboxylate (1.1 g, crude).

Step-2: To a stirred solution of ethyl 3-(1,1-difluoroethyl)-1-(difluoromethyl)-3-oxocyclobutyl)methyl)-4-methyl-1H-pyrazole-5-carboxylate (1.1 g, 3.14 mmol, 1.0 eq.) in dichloromethane (20 mL) was added DAST (1.51 g, 9.42 mmol, 3.0 eq.) at 0° C. under argon atmosphere. The resulting reaction mixture was stirred at ambient temperature for 16 h. The reaction mixture was diluted with dichloromethane (15 mL) and the organic layer was washed with water (25 mL), NaHCO$_3$ solution (25 mL) and brine (25 mL), dried over anhydrous Na$_2$SO$_4$ and concentrated under reduced pressure to afford ethyl 3-(1,1-difluoroethyl)-1-((1-(difluoromethyl)-3,3-difluorocyclobutyl)methyl)-4-methyl-1H-pyrazole-5-carboxylate (1.0 g, crude).

Step-3: To a stirred solution of ethyl 3-(1,1-difluoroethyl)-1-((1-(difluoromethyl)-3,3-difluorocyclobutyl)methyl)-4-methyl-1H-pyrazole-5-carboxylate (1.0 g, max. 2.68 mmol, 1.0 eq.) in THF:MeOH:H$_2$O (1:1:1, 15 mL) was added LiOH·H$_2$O (338 mg, 8.06 mmol, 3.0 eq.) at 0° C. The reaction mixture was then stirred at ambient temperature for 1 h. The reaction mixture was concentrated under reduced pressure to obtain a crude residue which was diluted with water (20 mL) and acidified to pH~5 with 1N aq. HCl solution and extracted with ethylacetate (2×20 mL). The combined organic layers were washed with water (25 mL), dried over anhydrous Na$_2$SO$_4$ and concentrated under reduced pressure to afford 3-(1,1-difluoroethyl)-1-((1-(difluoromethyl)-3,3-difluorocyclobutyl)methyl)-4-methyl-1H-pyrazole-5-carboxylic acid (750 mg, crude). The crude material was directly used in the next step without further purification.

Step-4: To a solution of 3-(1,1-difluoroethyl)-1-((1-(difluoromethyl)-3,3-difluorocyclobutyl)methyl)-4-methyl-1H-pyrazole-5-carboxylic acid (750 mg, 2.18 mmol, 1.0 eq.) in DMF (15 mL) were added ammonium chloride (465 mg, 8.72 mmol, 4.0 eq.), DIPEA (1.20 mL, 6.54 mmol, 3.0 eq.) and HATU (1.65 g, 4.36 mmol, 2.0 eq.) at ambient temperature. The resulting reaction mixture was stirred for 2 h. The reaction mixture was quenched with water (25 mL) and extracted with diethylether (2×30 mL). The combined organic layers were washed with water (30 mL) and then brine (25 mL), dried over anhydrous Na$_2$SO$_4$ and concentrated under reduced pressure to afford 3-(1,1-difluoroethyl)-1-(difluoromethyl)-3,3-difluorocyclobutyl)methyl)-4-methyl-1H-pyrazole-5-carboxamide (650 mg, crude).

Step-5: To a solution of 3-(1,1-difluoroethyl)-1-((1-(difluoromethyl)-3,3-difluorocyclobutyl)methyl)-4-methyl-1H-pyrazole-5-carboxamide (200 mg, 0.58 mmol, 1.0 eq.) in 1,4-dioxane (10 mL) in a sealed tube were added 4-bromopicolinamide (128.9 mg, 0.64 mmol, 1.1 eq.) and Cs$_2$CO$_3$ (379 mg, 1.16 mmol, 2.0 eq.) at ambient temperature. The resulting mixture was degassed with argon for 10 min. To the reaction mixture were then added trans-N,N'-dimethylcyclohexane-1,2-diamine (24.8 mg, 0.17 mmol, 0.3 eq.) and copper (I) trifluoromethane sulfonate benzene complex (44 mg, 0.17 mmol, 0.3 eq.) at ambient temperature. The resulting reaction mixture was heated to 80° C. for 16 h. The reaction mixture was cooled to ambient temperature, filtered through a celite bed and the celite bed was washed with ethyl acetate (20 mL). The filtrate was concentrated under reduced pressure to get the crude product which was purified by Grace flash column chromatography (50% acetonitrile in 0.1% Formic acid as an eluent) to afford 4-(3-(1,1-difluoroethyl)-1-((1-(difluoromethyl)-3,3-difluorocyclobutyl)methyl)-4-methyl-1H-pyrazole-5-carboxamido)picolinamide (SC-311, 97 mg, 19% over 5 steps). $^1$H NMR (400 MHz, DMSO-d6): δ (ppm)=11.10 (s, 1H), 8.56 (d, 1H), 8.37 (d, 1H), 8.10 (s, 1H), 7.85 (dd, 1H), 7.65 (s, 1H), 6.22 (t, 1H), 4.57 (s, 2H), 2.90-2.70 (m, 4H), 2.25 (s, 3H), 2.04 (t, 3H). LCMS: m/z [M+H]$^+$=464.1 (calc.=464.2).

Synthesis of 4-(1-((3,3-difluorocyclobutyl)methyl)-4-methyl-3-(trifluoromethoxy)-1H-pyrazole-5-carboxamido)picolinamide (SC-318)

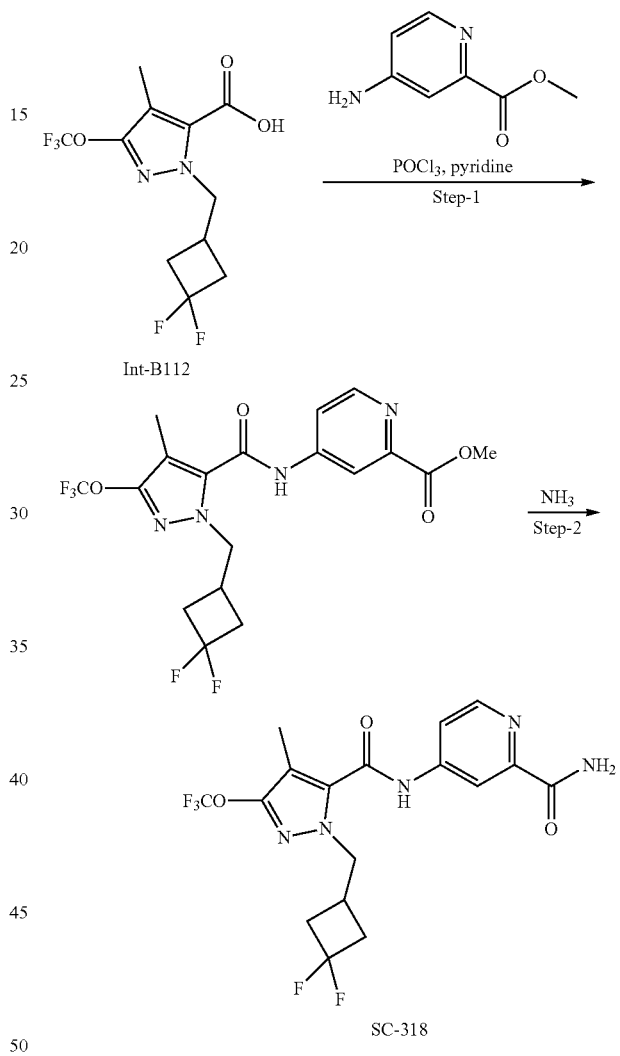

Step-1: To a stirred solution of 1-[(3,3-difluorocyclobutyl)methyl]-4-methyl-3-(trifluoromethoxy)-1H-pyrazole-5-carboxylic acid (Int-B112, 0.12 g, 0.382 mmol, 1.0 eq.) in pyridine (5 mL) were added methyl 4-aminopicolinate (0.07 g, 0.46 mmol, 1.2 eq.) and POCl$_3$ (0.06 mL, 0.573 mmol, 1.5 eq.) at 0° C. and the reaction mixture was stirred at room temperature for 2 h. The reaction mixture was then concentrated under reduced pressure. The obtained residue was diluted with ice water and extracted with EtOAc (3×50 mL). The combined organic layers were washed with brine, dried over anhy. Na$_2$SO$_4$ and concentrated under reduced pressure. The crude material was purified by combiflash column chromatography (silica gel; 0-40% EtOAc in hexane as eluent) to yield methyl 4-(1-((3,3-difluorocyclobutyl)methyl)-4-methyl-3-(trifluoromethoxy)-1H-pyrazole-5-carboxamido)picolinate. Yield: 41% (0.07 g, 0.156 mmol).

Step 2: A solution of methyl 4-(1-((3,3-difluorocyclobutyl)methyl)-4-methyl-3-(trifluoromethoxy)-1H-pyrazole-5-carboxamido) picolinate (0.07 g, 0.156 mmol, 1.0 eq.) in methanolic ammonia (7M, 7 mL) was heated to 90° C. under microwave irradiation for 2 h. The reaction mixture was then concentrated under reduced pressure and the residue was purified by prep HPLC to obtain 4-{1-[(3,3-difluorocyclobutyl)methyl]-4-methyl-3-(trifluoromethoxy)-1H-pyrazole-5-amido}pyridine-2-carboxamide (SC-318). Yield: 19% (0.013 g, 0.03 mmol). NMR (400 MHz, DMSO-d6): δ (ppm)=8.50-8.49 (m, 1H), 8.31 (s, 1H), 8.07 (brs, 1H), 7.81-7.80 (m, 1H), 7.60 (brs, 1H), 4.40 (s, 2H), 2.66-2.50 (m, 5H), 2.10 (s, 3H). LCMS: m/z [M+H]$^+$=434.2 (calc.=434.1).

Synthesis of 1-((4,4-difluorocyclohexyl)methyl)-4-methyl-N-(2-sulfamoylpyridin-4-yl)-3-(trifluoromethyl)-1H-pyrazole-5-carboxamide (SC-320)

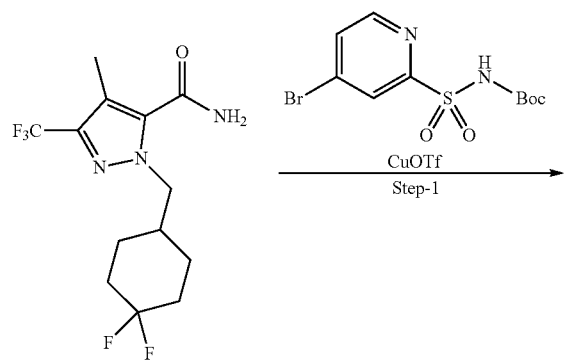

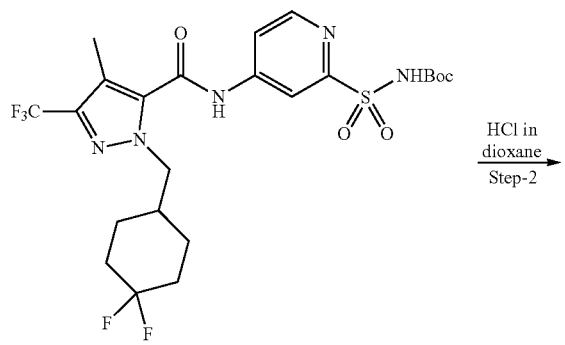

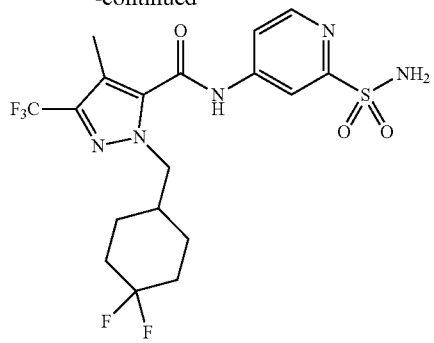

SC-320

1-((4,4-Difluorocyclohexyl)methyl)-4-methyl-3-(trifluoromethyl)-1H-pyrazole-5-carboxamide was prepared in analogy to the synthesis of SC-118 using the appropriate starting materials.

Step-1: A mixture of 1-((4,4-difluorocyclohexyl)methyl)-4-methyl-3-(trifluoromethyl)-1H-pyrazole-5-carboxamide (200 mg, 0.615 mmol, 1.0 eq.), tert-butyl ((4-bromopyridin-2-yl) sulfonyl) carbamate (397.8 mg, 0.923 mmol, 1.5 eq.), Cs$_2$CO$_3$ (500 mg, 1.538 mmol, 2.5 eq.) and copper(I) trifluoromethane sulfonate benzene complex (38.6 mg, 0.153 mmol, 0.25 eq.) in 1,4-dioxane (10 mL) in a sealed tube was degassed with argon for 10 min. To the reaction mixture was then added N,N-trans cyclohexane 1,2-diamine (26.2 mg, 0.184 mmol, 0.3 eq.) at ambient temperature. The reaction mixture was then stirred at 100° C. for 16 h. The reaction mixture was cooled to ambient temperature, diluted with water (50 mL) and extracted with ethyl acetate (2×50 mL). The combined organic layers were washed with water (50 mL) and then brine (50 mL), dried over anhydrous Na$_2$SO$_4$ and concentrated under reduced pressure to get the crude material which was purified by Grace flash chromatography using 54% of aq. formic acid (1%) in acetonitrile as an eluent to afford tert-butyl ((4-(1-((4,4-difluorocyclohexyl)methyl)-4-methyl-3-(trifluoromethyl)-1H-pyrazole-5-carboxamido)pyridin-2-yl)sulfonyl)carbamate (120 mg; 50%).

Step-2: To a stirred solution of tert-butyl 44-(1-((4,4-difluorocyclohexyl)methyl)-4-methyl-3-(trifluoromethyl)-1H-pyrazole-5-carboxamido)pyridin-2-yl)sulfonyl)carbamate (120 mg, 0.206 mmol, 1.0 eq.) in 1,4-dioxane was added HCl in dioxane (4M, 2.5 mL) at ambient temperature. The reaction mixture was heated to 70° C. for 3 h. The reaction mixture was concentrated under reduced pressure to get the crude material which was purified by prep-HPLC to afford 1-((4,4-difluorocyclohexyl)methyl)-4-methyl-N-(2-sulfamoylpyridin-4-yl)-3-(trifluoromethyl)-1H-pyrazole-5-carboxamide (SC-320, 140 mg; 93%). NMR (400 MHz, DMSO-d6): δ (ppm)=11.30 (s, 1H), 8.56-8.25 (m, 2H), 7.75-7.39 (m, 3H), 4.32 (brs, 2H), 2.25 (s, 3H), 1.98-1.96 (m, 2H), 1.82-1.70 (m, 3H), 1.59-1.56 (m, 2H), 1.26-1.19 (m, 2H). LCMS: m/z [M+H]$^+$=482.3 (calc.=482.1).

The following examples were synthesized in analogy to the procedures described above (with or without chiral separation at the end of the synthesis) using appropriate reactants and adjusted purification protocols:

| Ex. No. | Structure | Procedure | Intermediate | Analytical data |
|---|---|---|---|---|
| SC-246 | 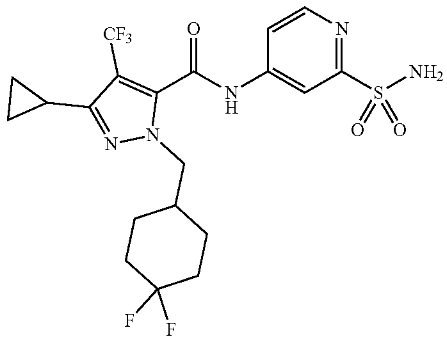 [SMILES: NS(=O)(=O)c1cc(NC(=O)c2c(C(F)(F)F)c(C3CC3)nn2CC2CCC(F)(F)CC2)ccn1] | in analogy to SC308 (step 1) and SC-320 | Int-B76 | ¹H NMR (400 MHz, DMSO-d6): δ (ppm) = 11.67 (s, 1H), 8.66 (d, 1H), 8.27 (s, 1H), 7.76 (brs, 1H), 7.48 (s, 2H), 4.00 (d, 2H), 1.95 (m, 4H), 1.79-1.70 (m, 2H), 1.59-1.56 (m, 2H), 1.23-1.18 (m, 2H), 0.97 (d, 2H), 0.84 (d, 2H). LCMS: m/z [M + H]⁺ = 508.1 (calc. = 508.1). |
| SC-254 a | 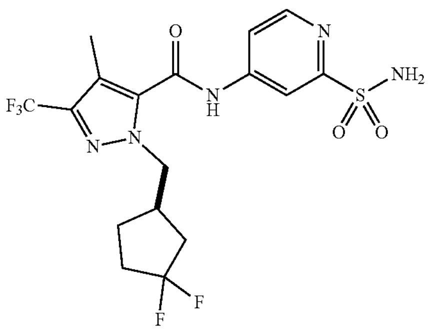 | in analogy to SC308 (step 1) and SC-320 | Int-B48 | ¹H NMR (400 MHz, DMSO-d6): δ (ppm) = 11.29 (s, 1H), 8.65 (d, 1H), 8.31 (d, 1H), 7.82 (dd, 1H), 7.48 (s, 2H), 4.35 (d, 2H), 2.68-2.64 (m, 1H), 2.24 (s, 3H), 2.17-1.76 (m, 5H), 1.55-1.50 (m, 1H). LCMS: m/z [M + H]⁺ = 468.1 (calc. = 468.1). chiral SFC (column: Chiracel OJ-3 (4.6 × 150 mm) 3 μm, total flow: 3 g/min, 90% CO₂, 10% (diethylamine in methanol), 1500 psi back pressure, 30° C., R$_t$ = 5.41 min. |
| SC-254 b | 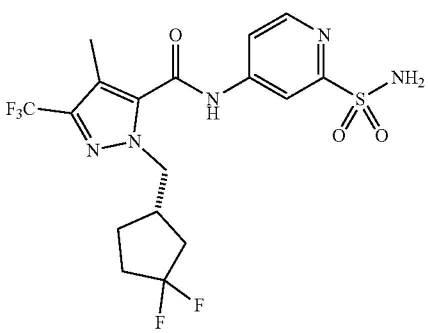 | in analogy to SC308 (step 1) and SC-320 | Int-B48 | ¹H NMR (400 MHz, DMSO-d6): δ (ppm) = 11.29 (s, 1H), 8.65 (d, 1H), 8.31 (d, 1H), 7.82 (dd, 1H), 7.48 (s, 2H), 4.35 (d, 2H), 2.68-2.64 (m, 1H), 2.24 (s, 3H), 2.17-1.76 (m, 5H), 1.55-1.50 (m, 1H). LCMS: m/z [M + H]⁺ = 468.1 (calc. = 468.1). chiral SFC (column: Chiracel OJ-3 (4.6 × 150 mm) 3 μm, total flow: 3 g/min, 90% CO₂, 10% (diethylamine in methanol), 1500 psi back pressure, 30° C., R$_t$ = 7.64 min. |

The following prophetic examples could be synthesized according to the general schemes 1-3 and/or by analogy to the synthetic procedures described above:

| Structure | Ex. No. | Chemical name |
|---|---|---|
| 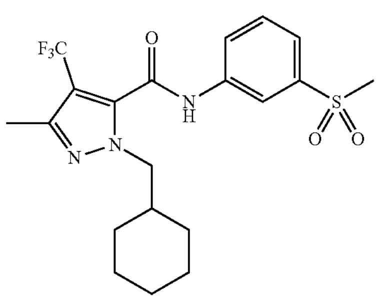 | SC-46 | 2-(cyclohexylmethyl)-5-methyl-N-(3-methylsulfonylphenyl)-4-(trifluoromethyl)pyrazole-3-carboxamide |

| Structure | Ex. No. | Chemical name |
|---|---|---|
| 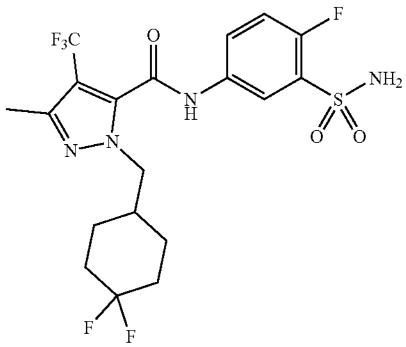 [SMILES: Cc1nn(CC2CCC(F)(F)CC2)c(C(=O)Nc2ccc(F)c(S(N)(=O)=O)c2)c1C(F)(F)F] | SC-47 | N-(3-carbamoyl-4-fluorophenyl)-2-[(4,4-difluorocyclohexyl)methyl]-5-methyl-4-(trifluoromethyl)pyrazole-3-carboxamide |
| 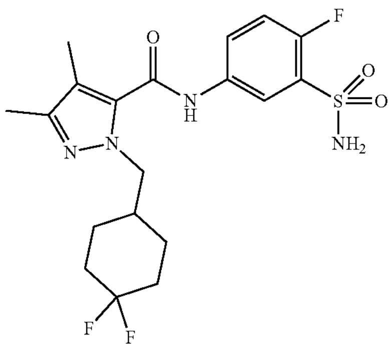 [SMILES: Cc1nn(CC2CCC(F)(F)CC2)c(C(=O)Nc2ccc(F)c(S(N)(=O)=O)c2)c1C] | SC-48 | 2-[(4,4-difluorocyclohexyl)methyl]-N-(4-fluoro-3-sulfamoylphenyl)-4,5-dimethylpyrazole-3-carboxamide |
| 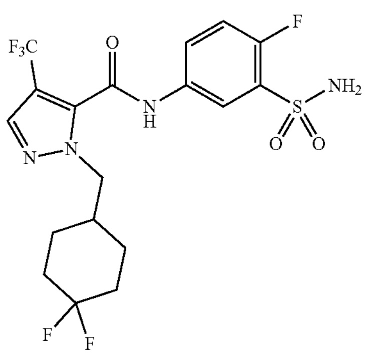 [SMILES: NS(=O)(=O)c1cc(NC(=O)c2c(C(F)(F)F)cnn2CC2CCC(F)(F)CC2)ccc1F] | SC-49 | 2-[(4,4-difluorocyclohexyl)methyl]-N-(4-fluoro-3-sulfamoylphenyl)-4-(trifluoromethyl)pyrazole-3-carboxamide |
| 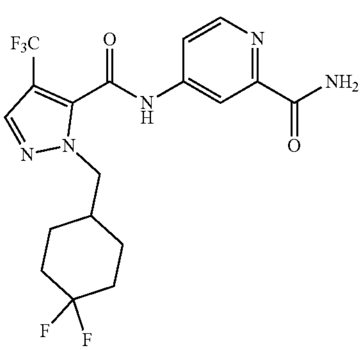 [SMILES: NC(=O)c1cc(NC(=O)c2c(C(F)(F)F)cnn2CC2CCC(F)(F)CC2)ccn1] | SC-50 | 4-[[2-[(4,4-difluorocyclohexyl)methyl]-4-(trifluoromethyl)pyrazole-3-carbonyl]amino]pyridine-2-carboxamide |

| Structure | Ex. No. | Chemical name |
|---|---|---|
| 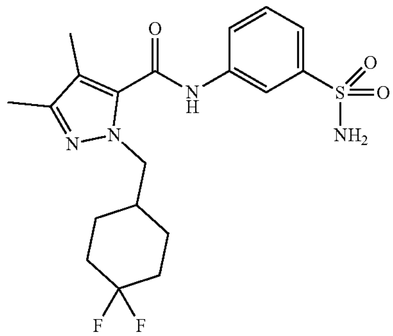 [SMILES: Cc1nn(CC2CCC(F)(F)CC2)c(C(=O)Nc2cccc(S(N)(=O)=O)c2)c1C] | SC-51 | 2-[(4,4-difluorocyclohexyl)methyl]-4,5-dimethyl-N-(3-sulfamoylphenyl)pyrazole-3-carboxamide |
| 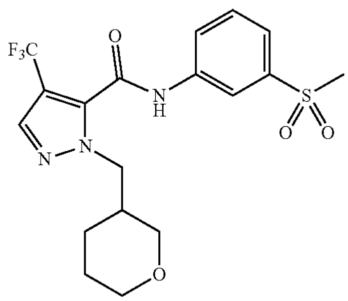 [SMILES: CS(=O)(=O)c1cccc(NC(=O)c2c(C(F)(F)F)cnn2CC2CCCOC2)c1] | SC-52 | N-(3-(methylsulfonyl)phenyl)-1-((tetrahydro-2H-pyran-3-yl)methyl)-4-(trifluoromethyl)-1H-pyrazole-5-carboxamide |
| 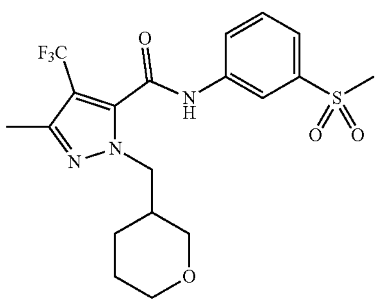 | SC-54 | 5-methyl-N-(3-methylsulfonylphenyl)-2-(oxan-3-ylmethyl)-4-(trifluoromethyl)pyrazole-3-carboxamide |
| 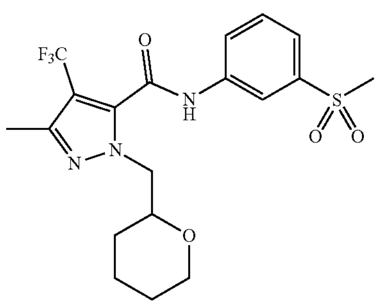 | SC-55 | 5-methyl-N-(3-methylsulfonylphenyl)-2-(oxan-2-ylmethyl)-4-(trifluoromethyl)pyrazole-3-carboxamide |
| 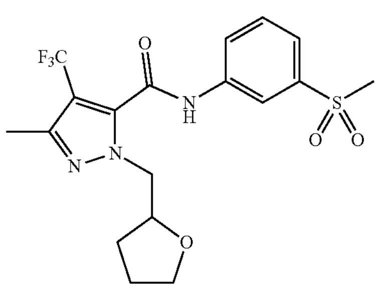 | SC-56 | 5-methyl-N-(3-methylsulfonylphenyl)-2-(oxolan-2-ylmethyl)-4-(trifluoromethyl)pyrazole-3-carboxamide |

-continued

| Structure | Ex. No. | Chemical name |
|---|---|---|
| 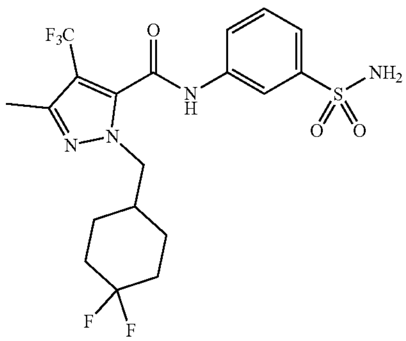 [SMILES: Cc1nn(CC2CCC(F)(F)CC2)c(C(=O)Nc2cccc(S(N)(=O)=O)c2)c1C(F)(F)F] | SC-57 | 2-[(4,4-difluorocyclohexyl)methyl]-5-methyl-N-(3-sulfamoylphenyl)-4-(trifluoromethyl)pyrazole-3-carboxamide |
| 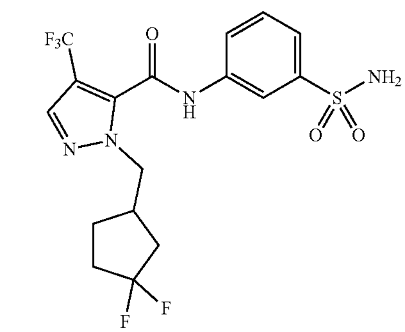 [SMILES: NS(=O)(=O)c1cccc(NC(=O)c2c(C(F)(F)F)cnn2CC2CCC(F)(F)C2)c1] | SC-60 | 2-[(3,3-difluorocyclopentyl)methyl]-N-(3-sulfamoylphenyl)-4-(trifluoromethyl)pyrazole-3-carboxamide |
| 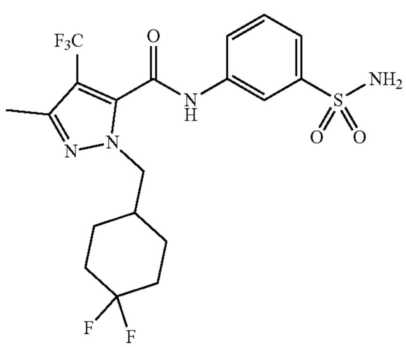 [SMILES: Cc1nn(CC2CCC(F)(F)CC2)c(C(=O)Nc2cccc(S(N)(=O)=O)c2)c1C(F)(F)F] | SC-61 | N-(3-carbamoylphenyl)-2-[(4,4-difluorocyclohexyl)methyl]-5-methyl-4-(trifluoromethyl)pyrazole-3-carboxamide |
| 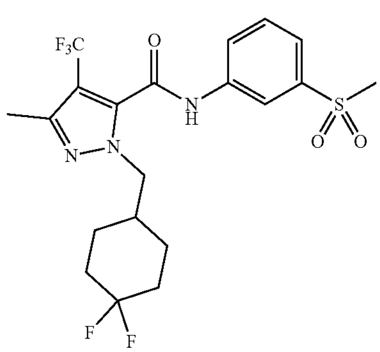 | SC-62 | 2-[(4,4-difluorocyclohexyl)methyl]-5-methyl-N-(3-methylsulfonylphenyl)-4-(trifluoromethyl)pyrazole-3-carboxamide |

| Structure | Ex. No. | Chemical name |
|---|---|---|
| 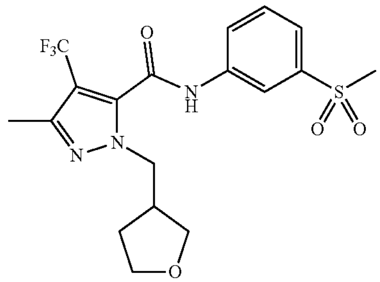 | SC-63 | 3-methyl-N-(3-(methylsulfonyl)phenyl)-1-((tetrahydrofuran-3-yl)methyl)-4-(trifluoromethyl)-1H-pyrazole-5-carboxamide |
| 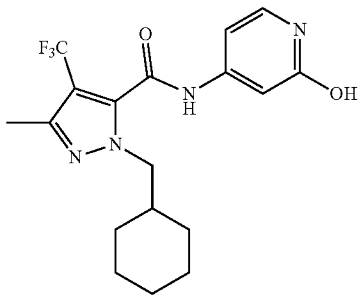 [SMILES: Cc1nn(CC2CCCCC2)c(C(=O)Nc2ccnc(O)c2)c1C(F)(F)F] | SC-64 | 2-(cyclohexylmethyl)-N-(2-hydroxypyridin-4-yl)-5-methyl-4-(trifluoromethyl)pyrazole-3-carboxamide |
| 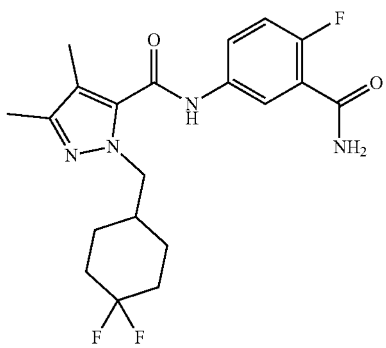 [SMILES: Cc1nn(CC2CCC(F)(F)CC2)c(C(=O)Nc2ccc(F)c(C(N)=O)c2)c1C] | SC-65 | N-(3-carbamoyl-4-fluorophenyl)-2-[(4,4-difluorocyclohexyl)methyl]-4,5-dimethylpyrazole-3-carboxamide |
| 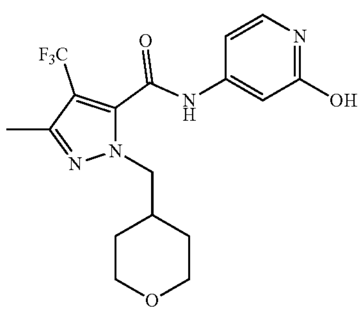 [SMILES: Cc1nn(CC2CCOCC2)c(C(=O)Nc2ccnc(O)c2)c1C(F)(F)F] | SC-66 | N-(2-hydroxypyridin-4-yl)-5-methyl-2-(oxan-4-ylmethyl)-4-(trifluoromethyl)pyrazole-3-carboxamide |
| 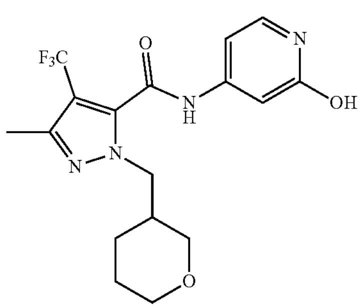 [SMILES: Cc1nn(CC2CCCOC2)c(C(=O)Nc2ccnc(O)c2)c1C(F)(F)F] | SC-67 | N-(2-hydroxypyridin-4-yl)-3-methyl-1-((tetrahydro-2H-pyran-3-yl)methyl)-4-(trifluoromethyl)-1H-pyrazole-5-carboxamide |

-continued

| Structure | Ex. No. | Chemical name |
|---|---|---|
| 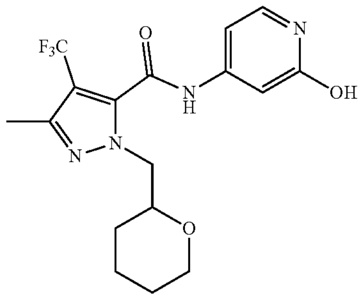 [SMILES: Cc1nn(CC2CCCCO2)c(C(=O)Nc2ccnc(O)c2)c1C(F)(F)F] | SC-68 | N-(2-hydroxypyridin-4-yl)-3-methyl-1-((tetrahydro-2H-pyran-2-yl)methyl)-4-(trifluoromethyl)-1H-pyrazole-5-carboxamide |
| 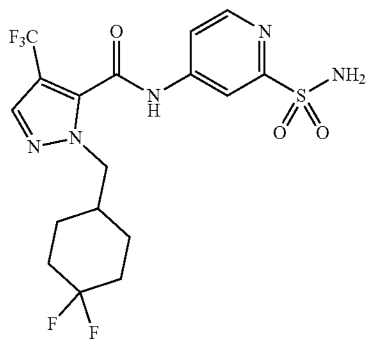 [SMILES: NS(=O)(=O)c1cc(NC(=O)c2c(C(F)(F)F)cnn2CC2CCC(F)(F)CC2)ccn1] | SC-69 | 2-[(4,4-difluorocyclohexyl)methyl]-N-(2-sulfamoylpyridin-4-yl)-4-(trifluoromethyl)pyrazole-3-carboxamide |
| 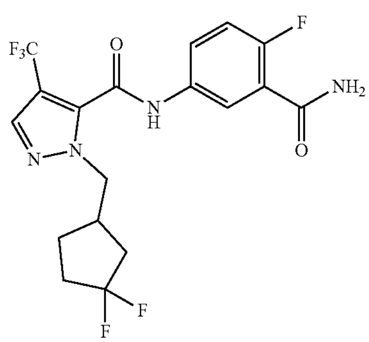 [SMILES: NC(=O)c1cc(NC(=O)c2c(C(F)(F)F)cnn2CC2CCC(F)(F)C2)ccc1F] | SC-73 | N-(3-carbamoyl-4-fluorophenyl)-2-[(3,3-difluorocyclopentyl)methyl]-4-(trifluoromethyl)pyrazole-3-carboxamide |
| 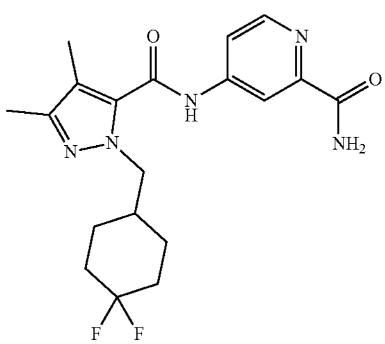 [SMILES: Cc1nn(CC2CCC(F)(F)CC2)c(C(=O)Nc2ccnc(C(N)=O)c2)c1C] | SC-77 | 4-[[2-[(4,4-difluorocyclohexyl)methyl]-4,5-dimethylpyrazole-3-carbonyl]amino]pyridine-2-carboxamide |

-continued

| Structure | Ex. No. | Chemical name |
|---|---|---|
| 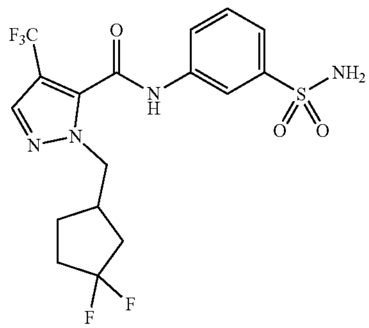 [SMILES: NS(=O)(=O)c1cccc(NC(=O)c2c(C(F)(F)F)cnn2CC2CCC(F)(F)C2)c1] | SC-78 | 1-((3,3-difluorocyclopentyl)methyl)-N-(3-sulfamoylphenyl)-4-(trifluoromethyl)-1H-pyrazole-5-carboxamide |
| 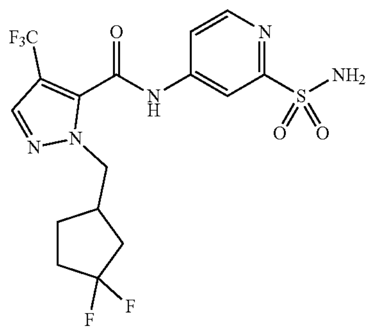 [SMILES: NS(=O)(=O)c1cc(NC(=O)c2c(C(F)(F)F)cnn2CC2CCC(F)(F)C2)ccn1] | SC-80 | 1-((3,3-difluorocyclopentyl)methyl)-N-(2-sulfamoylpyridin-4-yl)-4-(trifluoromethyl)-1H-pyrazole-5-carboxamide |
| 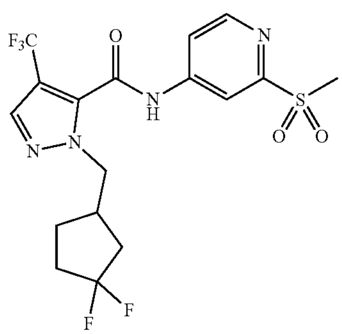 [SMILES: CS(=O)(=O)c1cc(NC(=O)c2c(C(F)(F)F)cnn2CC2CCC(F)(F)C2)ccn1] | SC-82 | 1-((3,3-difluorocyclopentyl)methyl)-N-(2-(methylsulfonyl)pyridin-4-yl)-4-(trifluoromethyl)-1H-pyrazole-5-carboxamide |
| 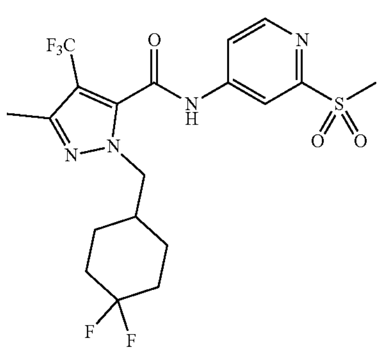 | SC-85 | 1-((4,4-difluorocyclohexyl)methyl)-3-methyl-N-(2-(methylsulfonyl)pyridin-4-yl)-4-(trifluoromethyl)-1H-pyrazole-5-carboxamide |

| Structure | Ex. No. | Chemical name |
|---|---|---|
| 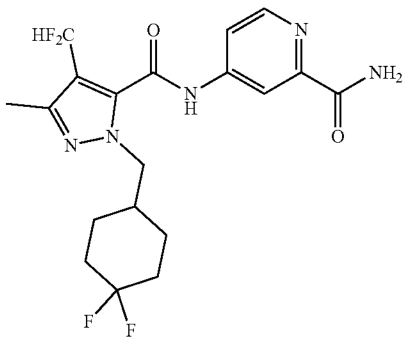 | SC-86 | 4-(1-((4,4-difluorocyclohexyl)methyl)-4-(difluoromethyl)-3-methyl-1H-pyrazole-5-carboxamido)picolinamide |
| 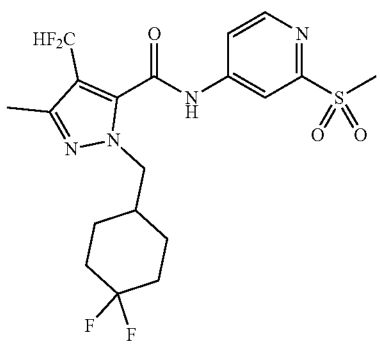 | SC-87 | 1-((4,4-difluorocyclohexyl)methyl)-4-(difluoromethyl)-3-methyl-N-(2-(methylsulfonyl)pyridin-4-yl)-1H-pyrazole-5-carboxamide |
| 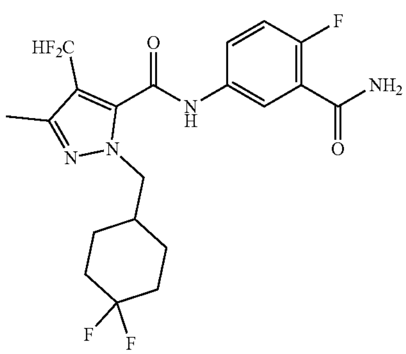 | SC-88 | N-(3-carbamoyl-4-fluorophenyl)-1-((4,4-difluorocyclohexyl)methyl)-4-(difluoromethyl)-3-methyl-1H-pyrazole-5-carboxamide |
| 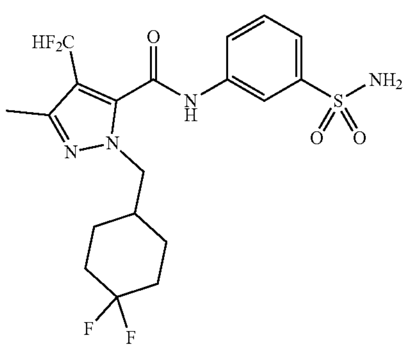 | SC-89 | 1-((4,4-difluorocyclohexyl)methyl)-4-(difluoromethyl)-3-methyl-N-(3-sulfamoylphenyl)-1H-pyrazole-5-carboxamide |

-continued

| Structure | Ex. No. | Chemical name |
|---|---|---|
| 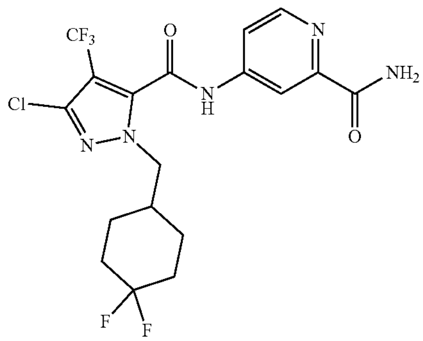 [SMILES: NC(=O)c1cc(NC(=O)c2c(C(F)(F)F)c(Cl)nn2CC2CCC(F)(F)CC2)ccn1] | SC-90 | 4-(3-chloro-1-((4,4-difluorocyclohexyl)methyl)-4-(trifluoromethyl)-1H-pyrazole-5-carboxamido)picolinamide |
| 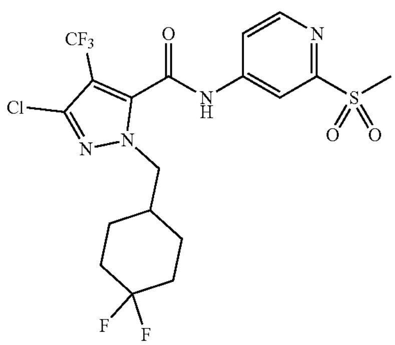 [SMILES: CS(=O)(=O)c1cc(NC(=O)c2c(C(F)(F)F)c(Cl)nn2CC2CCC(F)(F)CC2)ccn1] | SC-91 | 3-chloro-1-((4,4-difluorocyclohexyl)methyl)-N-(2-(methylsulfonyl)pyridin-4-yl)-4-(trifluoromethyl)-1H-pyrazole-5-carboxamide |
| 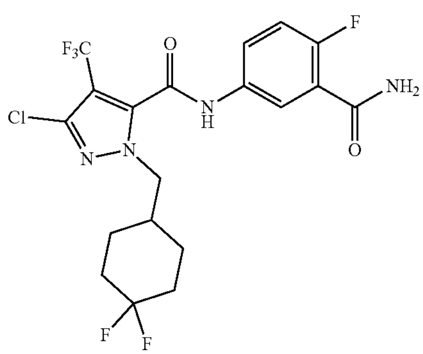 [SMILES: NC(=O)c1cc(NC(=O)c2c(C(F)(F)F)c(Cl)nn2CC2CCC(F)(F)CC2)ccc1F] | SC-92 | N-(3-carbamoyl-4-fluorophenyl)-3-chloro-1-((4,4-difluorocyclohexyl)methyl)-4-(trifluoromethyl)-1H-pyrazole-5-carboxamide |
| 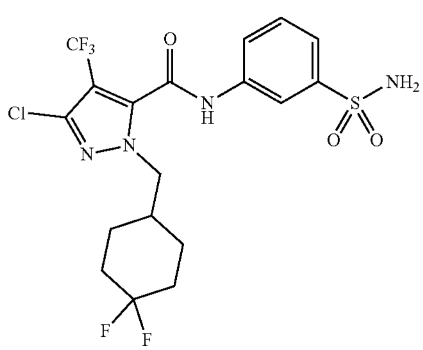 [SMILES: NS(=O)(=O)c1cccc(NC(=O)c2c(C(F)(F)F)c(Cl)nn2CC2CCC(F)(F)CC2)c1] | SC-93 | 3-chloro-1-((4,4-difluorocyclohexyl)methyl)-N-(3-sulfamoylphenyl)-4-(trifluoromethyl)-1H-pyrazole-5-carboxamide |

-continued

| Structure | Ex. No. | Chemical name |
|---|---|---|
| 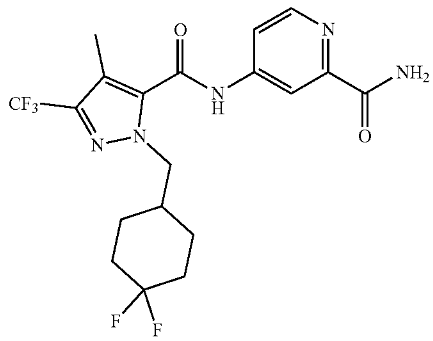 [SMILES: Cc1c(C(F)(F)F)nn(CC2CCC(F)(F)CC2)c1C(=O)Nc1ccnc(C(N)=O)c1] | SC-94 | 4-(1-((4,4-difluorocyclohexyl)methyl)-4-methyl-3-(trifluoromethyl)-1H-pyrazole-5-carboxamido)picolinamide |
| 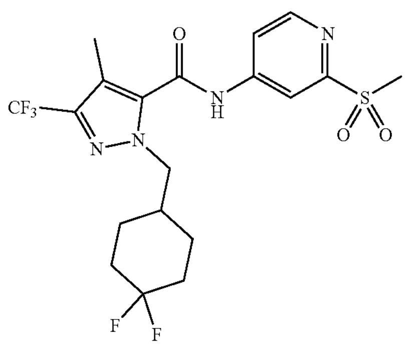 [SMILES: Cc1c(C(F)(F)F)nn(CC2CCC(F)(F)CC2)c1C(=O)Nc1ccnc(S(C)(=O)=O)c1] | SC-95 | 1-((4,4-difluorocyclohexyl)methyl)-4-methyl-N-(2-(methylsulfonyl)pyridin-4-yl)-3-(trifluoromethyl)-1H-pyrazole-5-carboxamide |
| 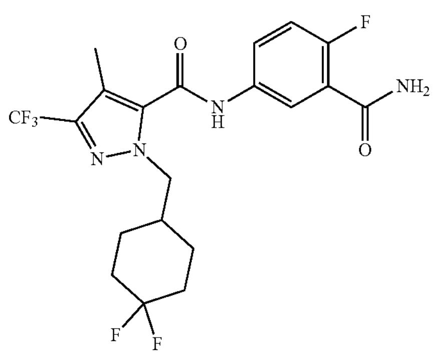 [SMILES: Cc1c(C(F)(F)F)nn(CC2CCC(F)(F)CC2)c1C(=O)Nc1ccc(F)c(C(N)=O)c1] | SC-96 | N-(3-carbamoyl-4-fluorophenyl)-1-((4,4-difluorocyclohexyl)methyl)-4-methyl-3-(trifluoromethyl)-1H-pyrazole-5-carboxamide |
| 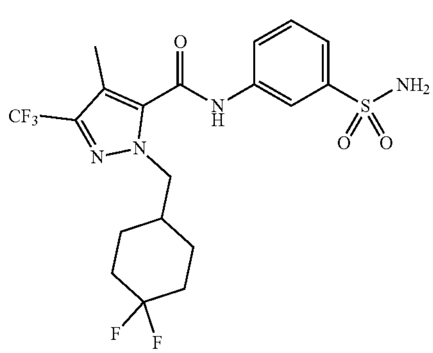 [SMILES: Cc1c(C(F)(F)F)nn(CC2CCC(F)(F)CC2)c1C(=O)Nc1cccc(S(N)(=O)=O)c1] | SC-97 | 1-((4,4-difluorocyclohexyl)methyl)-4-methyl-N-(3-sulfamoylphenyl)-3-(trifluoromethyl)-1H-pyrazole-5-carboxamide |

-continued

| Structure | Ex. No. | Chemical name |
|---|---|---|
| 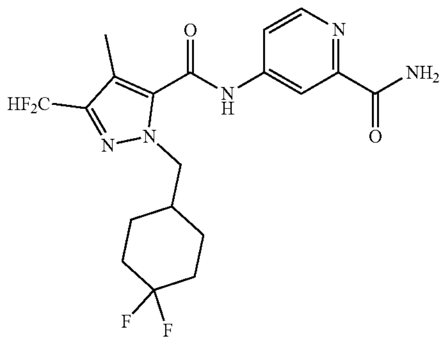 | SC-98 | 4-(1-((4,4-difluorocyclohexyl)methyl)-3-(difluoromethyl)-4-methyl-1H-pyrazole-5-carboxamido)picolinamide |
| 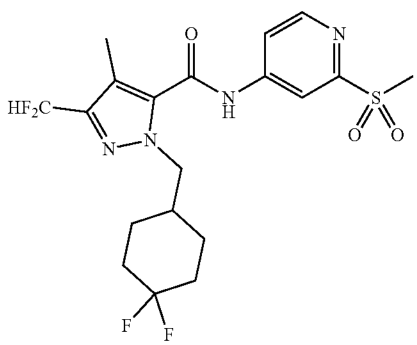 | SC-99 | 1-((4,4-difluorocyclohexyl)methyl)-3-(difluoromethyl)-4-methyl-N-(2-(methylsulfonyl)pyridin-4-yl)-1H-pyrazole-5-carboxamide |
| 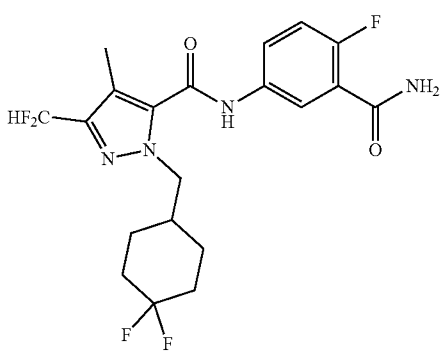 | SC-100 | N-(3-carbamoyl-4-fluorophenyl)-1-((4,4-difluorocyclohexyl)methyl)-3-(difluoromethyl)-4-methyl-1H-pyrazole-5-carboxamide |
| 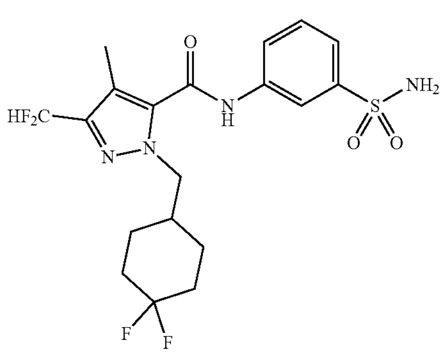 | SC-101 | 1-((4,4-difluorocyclohexyl)methyl)-3-(difluoromethyl)-4-methyl-N-(3-sulfamoylphenyl)-1H-pyrazole-5-carboxamide |

-continued

| Structure | Ex. No. | Chemical name |
|---|---|---|
| 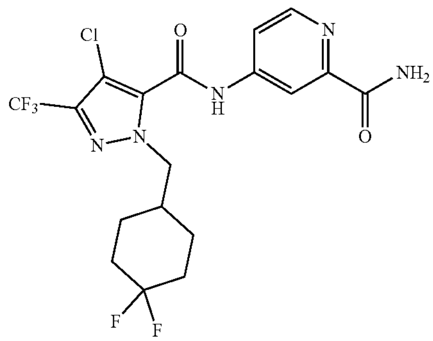 [SMILES: NC(=O)c1cc(NC(=O)c2c(Cl)c(C(F)(F)F)nn2CC2CCC(F)(F)CC2)ccn1] | SC-102 | 4-(4-chloro-1-((4,4-difluorocyclohexyl)methyl)-3-(trifluoromethyl)-1H-pyrazole-5-carboxamido)picolinamide |
| 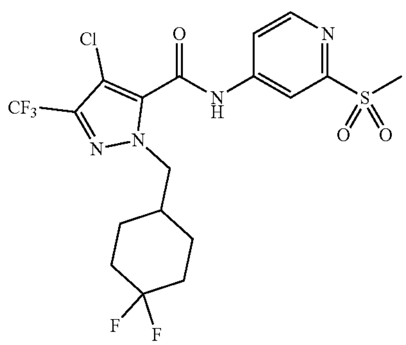 [SMILES: CS(=O)(=O)c1cc(NC(=O)c2c(Cl)c(C(F)(F)F)nn2CC2CCC(F)(F)CC2)ccn1] | SC-103 | 4-chloro-1-((4,4-difluorocyclohexyl)methyl)-N-(2-(methylsulfonyl)pyridin-4-yl)-3-(trifluoromethyl)-1H-pyrazole-5-carboxamide |
| 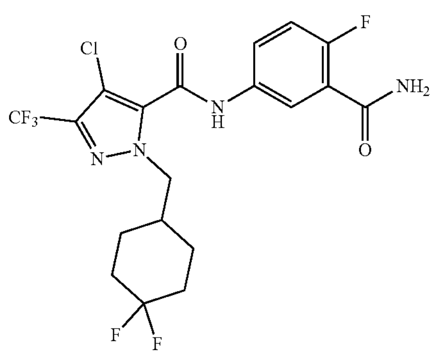 [SMILES: NC(=O)c1cc(NC(=O)c2c(Cl)c(C(F)(F)F)nn2CC2CCC(F)(F)CC2)ccc1F] | SC-104 | N-(3-carbamoyl-4-fluorophenyl)-4-chloro-1-((4,4-difluorocyclohexyl)methyl)-3-(trifluoromethyl)-1H-pyrazole-5-carboxamide |
| 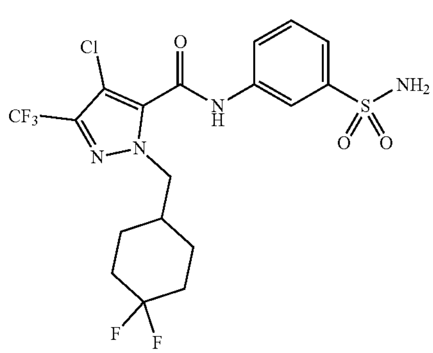 [SMILES: NS(=O)(=O)c1cccc(NC(=O)c2c(Cl)c(C(F)(F)F)nn2CC2CCC(F)(F)CC2)c1] | SC-105 | 4-chloro-1-((4,4-difluorocyclohexyl)methyl)-N-(3-sulfamoylphenyl)-3-(trifluoromethyl)-1H-pyrazole-5-carboxamide |

-continued

| Structure | Ex. No. | Chemical name |
|---|---|---|
| 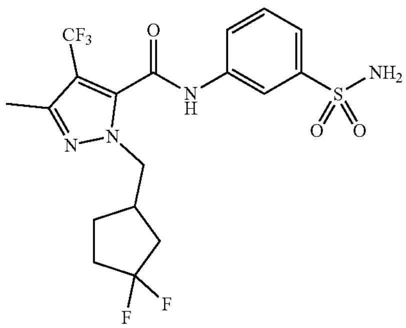 [SMILES: Cc1nn(CC2CCC(F)(F)C2)c(C(=O)Nc2cccc(S(N)(=O)=O)c2)c1C(F)(F)F] | SC-106 | 1-((3,3-difluorocyclopentyl)methyl)-3-methyl-N-(3-sulfamoylphenyl)-4-(trifluoromethyl)-1H-pyrazole-5-carboxamide |
| 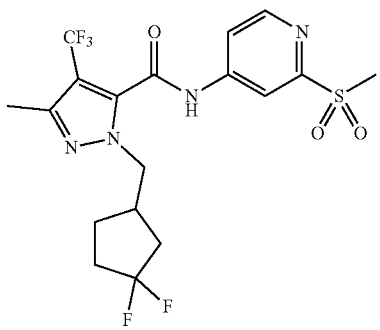 | SC-108 | 1-((3,3-difluorocyclopentyl)methyl)-3-methyl-N-(2-(methylsulfonyl)pyridin-4-yl)-4-(trifluoromethyl)-1H-pyrazole-5-carboxamide |
| 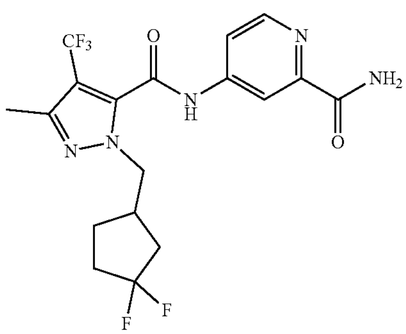 [SMILES: Cc1nn(CC2CCC(F)(F)C2)c(C(=O)Nc2ccnc(C(N)=O)c2)c1C(F)(F)F] | SC-110 | 4-(1-((3,3-difluorocyclopentyl)methyl)-3-methyl-4-(trifluoromethyl)-1H-pyrazole-5-carboxamido)picolinamide |
| 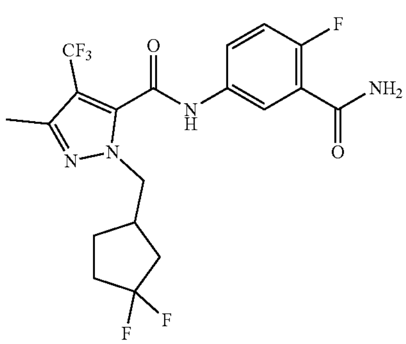 [SMILES: Cc1nn(CC2CCC(F)(F)C2)c(C(=O)Nc2ccc(F)c(C(N)=O)c2)c1C(F)(F)F] | SC-112 | N-(3-carbamoyl-4-fluorophenyl)-1-((3,3-difluorocyclopentyl)methyl)-3-methyl-4-(trifluoromethyl)-1H-pyrazole-5-carboxamide |

| Structure | Ex. No. | Chemical name |
|---|---|---|
| 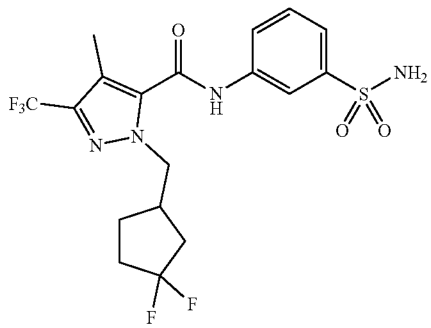 [SMILES: Cc1c(C(F)(F)F)nn(CC2CCC(F)(F)C2)c1C(=O)Nc1cccc(S(N)(=O)=O)c1] | SC-114 | 1-((3,3-difluorocyclopentyl)methyl)-4-methyl-N-(3-sulfamoylphenyl)-3-(trifluoromethyl)-1H-pyrazole-5-carboxamide |
| 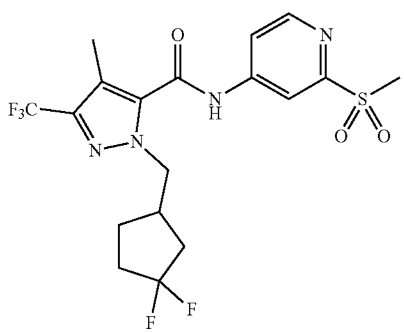 [SMILES: Cc1c(C(F)(F)F)nn(CC2CCC(F)(F)C2)c1C(=O)Nc1ccnc(S(C)(=O)=O)c1] | SC-116 | 1-((3,3-difluorocyclopentyl)methyl)-4-methyl-N-(2-(methylsulfonyl)pyridin-4-yl)-3-(trifluoromethyl)-1H-pyrazole-5-carboxamide |
| 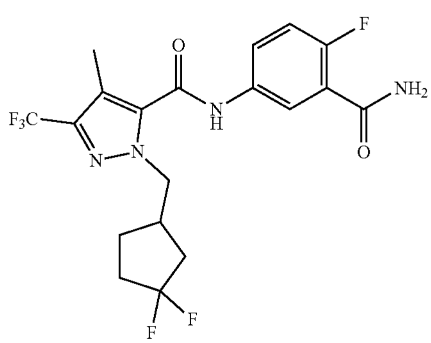 [SMILES: Cc1c(C(F)(F)F)nn(CC2CCC(F)(F)C2)c1C(=O)Nc1ccc(F)c(C(N)=O)c1] | SC-120 | N-(3-carbamoyl-4-fluorophenyl)-1-((3,3-difluorocyclopentyl)methyl)-4-methyl-3-(trifluoromethyl)-1H-pyrazole-5-carboxamide |
| 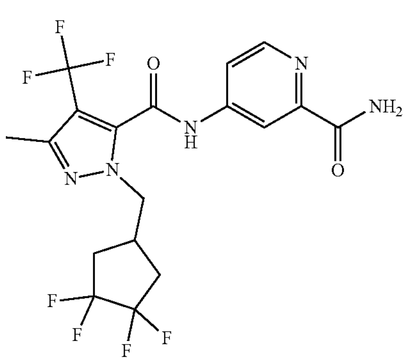 [SMILES: Cc1nn(CC2CC(F)(F)C(F)(F)C2)c(C(=O)Nc2ccnc(C(N)=O)c2)c1C(F)(F)F] | SC-122 | 4-(3-methyl-1-((3,3,4,4-tetrafluorocyclopentyl)methyl)-4-(trifluoromethyl)-1H-pyrazole-5-carboxamido)picolinamide |

-continued

| Structure | Ex. No. | Chemical name |
|---|---|---|
| 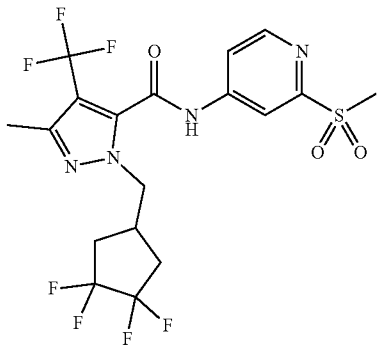 | SC-123 | 3-methyl-N-(2-(methylsulfonyl)pyridin-4-yl)-1-((3,3,4,4-tetrafluorocyclopentyl)methyl)-4-(trifluoromethyl)-1H-pyrazole-5-carboxamide |
| 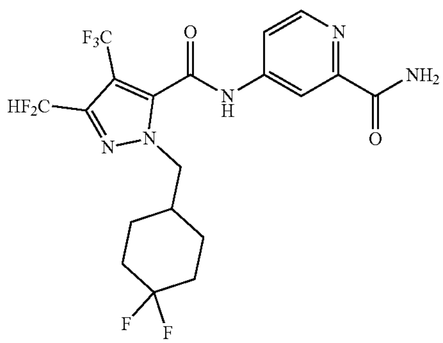 | SC-124 | 4-(1-((4,4-difluorocyclohexyl)methyl)-3-(difluoromethyl)-4-(trifluoromethyl)-1H-pyrazole-5-carboxamido)picolinamide |
| 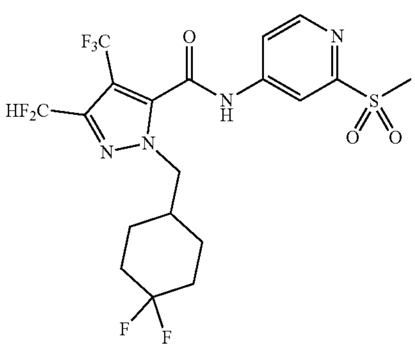 | SC-125 | 1-((4,4-difluorocyclohexyl)methyl)-3-(difluoromethyl)-N-(2-(methylsulfonyl)pyridin-4-yl)-4-(trifluoromethyl)-1H-pyrazole-5-carboxamide |
| 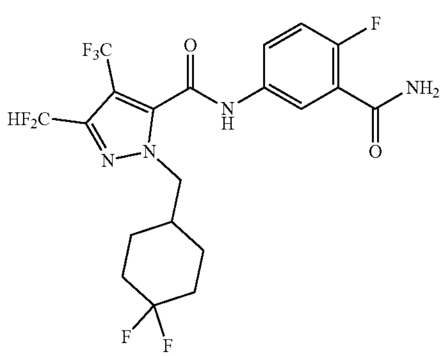 | SC-126 | N-(3-carbamoyl-4-fluorophenyl)-1-((4,4-difluorocyclohexyl)methyl)-3-(difluoromethyl)-4-(trifluoromethyl)-1H-pyrazole-5-carboxamide |

-continued

| Structure | Ex. No. | Chemical name |
|---|---|---|
| 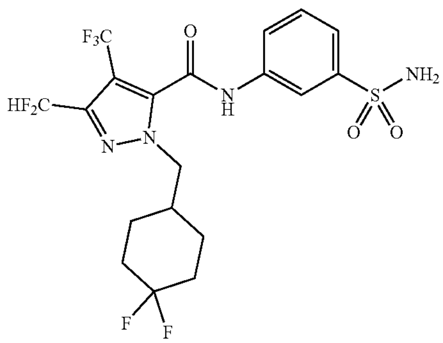 | SC-127 | 1-((4,4-difluorocyclohexyl)methyl)-3-(difluoromethyl)-N-(3-sulfamoylphenyl)-4-(trifluoromethyl)-1H-pyrazole-5-carboxamide |
| 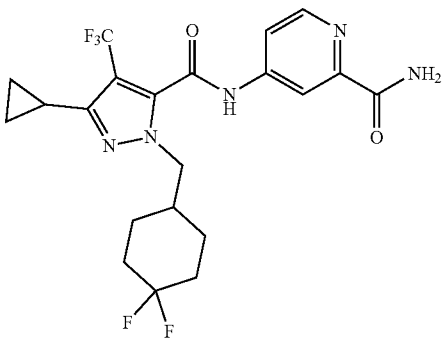 [SMILES: NC(=O)c1cc(NC(=O)c2c(C(F)(F)F)c(C3CC3)nn2CC2CCC(F)(F)CC2)ccn1] | SC-128 | 4-(3-cyclopropyl-1-((4,4-difluorocyclohexyl)methyl)-4-(trifluoromethyl)-1H-pyrazole-5-carboxamido)picolinamide |
| 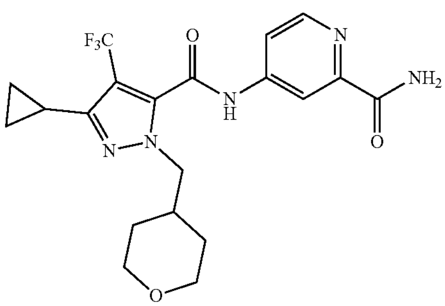 [SMILES: NC(=O)c1cc(NC(=O)c2c(C(F)(F)F)c(C3CC3)nn2CC2CCOCC2)ccn1] | SC-131 | 4-(3-cyclopropyl-1-((tetrahydro-2H-pyran-4-yl)methyl)-4-(trifluoromethyl)-1H-pyrazole-5-carboxamido)picolinamide |
| 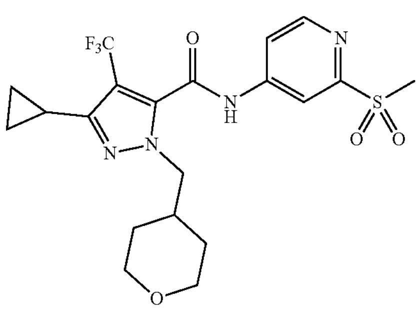 [SMILES: CS(=O)(=O)c1cc(NC(=O)c2c(C(F)(F)F)c(C3CC3)nn2CC2CCOCC2)ccn1] | SC-132 | 3-cyclopropyl-N-(2-(methylsulfonyl)pyridin-4-yl)-1-((tetrahydro-2H-pyran-4-yl)methyl)-4-(trifluoromethyl)-1H-pyrazole-5-carboxamide |
| 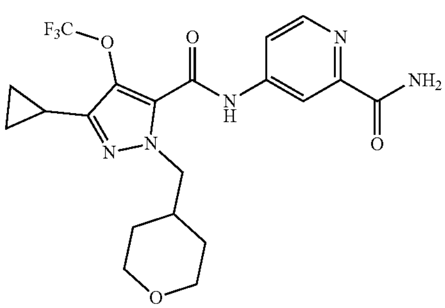 [SMILES: NC(=O)c1cc(NC(=O)c2c(OC(F)(F)F)c(C3CC3)nn2CC2CCOCC2)ccn1] | SC-133 | 4-(3-cyclopropyl-1-((tetrahydro-2H-pyran-4-yl)methyl)-4-(trifluoromethoxy)-1H-pyrazole-5-carboxamido)picolinamide |

-continued

| Structure | Ex. No. | Chemical name |
|---|---|---|
| 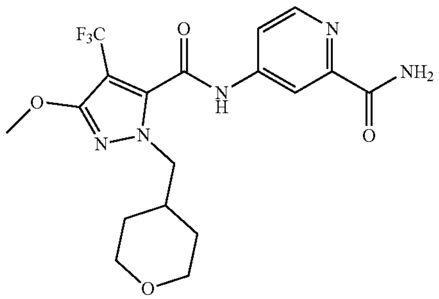 [SMILES: COc1nn(CC2CCOCC2)c(C(=O)Nc2ccnc(C(N)=O)c2)c1C(F)(F)F] | SC-134 | 4-(3-methoxy-1-((tetrahydro-2H-pyran-4-yl)methyl)-4-(trifluoromethyl)-1H-pyrazole-5-carboxamido)picolinamide |
| 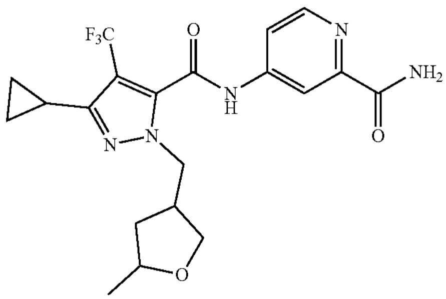 [SMILES: CC1CC(Cn2nc(C3CC3)c(C(F)(F)F)c2C(=O)Nc2ccnc(C(N)=O)c2)CO1] | SC-138 | 4-(3-cyclopropyl-1-((5-methyltetrahydrofuran-3-yl)methyl)-4-(trifluoromethyl)-1H-pyrazole-5-carboxamido)picolinamide |
| 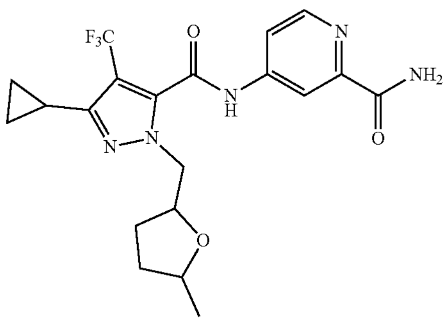 [SMILES: CC1CCC(Cn2nc(C3CC3)c(C(F)(F)F)c2C(=O)Nc2ccnc(C(N)=O)c2)O1] | SC-139 | 4-(3-cyclopropyl-1-((5-methyltetrahydrofuran-2-yl)methyl)-4-(trifluoromethl)-1H-pyrazole-5-carboxamido)picolinamide |
| 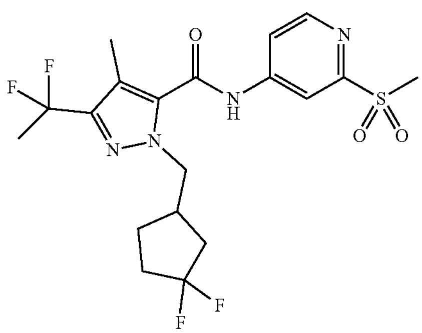 [SMILES: Cc1c(C(C)(F)F)nn(CC2CCC(F)(F)C2)c1C(=O)Nc1ccnc(S(C)(=O)=O)c1] | SC-165 | 1-((3,3-difluorocyclopentyl)methyl)-3-(1,1-difluoroethyl)-4-methyl-N-(2-(methylsulfonyl)pyridin-4-yl)-1H-pyrazole-5-carboxamide |
| 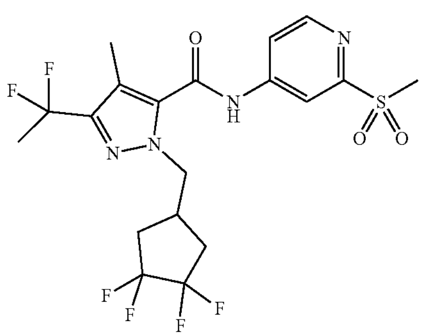 [SMILES: Cc1c(C(C)(F)F)nn(CC2CC(F)(F)C(F)(F)C2)c1C(=O)Nc1ccnc(S(C)(=O)=O)c1] | SC-166 | 3-(1,1-difluoroethyl)-4-methyl-N-(2-(methylsulfonyl)pyridin-4-yl)-1-((3,3,4,4-tetrafluorocyclopentyl)methyl)-1H-pyrazole-5-carboxamide |

| Structure | Ex. No. | Chemical name |
|---|---|---|
| 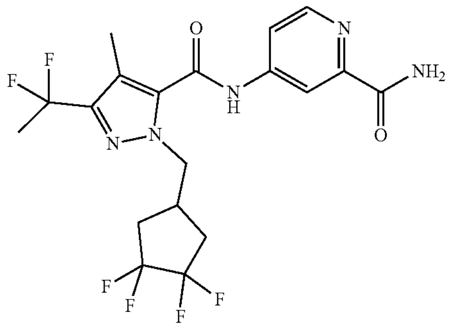 [SMILES: Cc1c(C(C)(F)F)nn(CC2CC(F)(F)C(F)(F)C2)c1C(=O)Nc1ccnc(C(N)=O)c1] | SC-168 | 4-(3-(1,1-difluoroethyl)-4-methyl-1-((3,3,4,4-tetrafluorocyclopentyl)methyl)-1H-pyrazole-5-carboxamido)picolinamide |
| 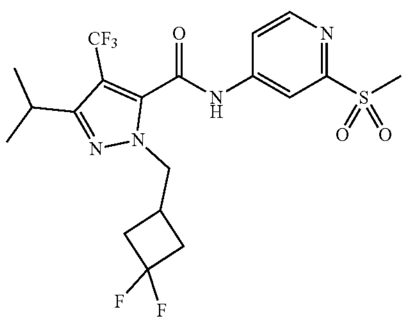 [SMILES: CC(C)c1nn(CC2CC(F)(F)C2)c(C(=O)Nc2ccnc(S(C)(=O)=O)c2)c1C(F)(F)F] | SC-169 | 1-((3,3-difluorocyclobutyl)methyl)-3-isopropyl-N-(2-(methylsulfonyl)pyridin-4-yl)-4-(trifluoromethyl)-1H-pyrazole-5-carboxamide |
| 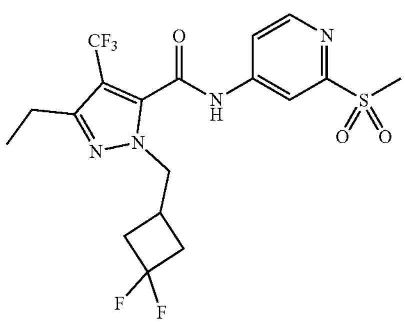 [SMILES: CCc1nn(CC2CC(F)(F)C2)c(C(=O)Nc2ccnc(S(C)(=O)=O)c2)c1C(F)(F)F] | SC-171 | 1-((3,3-difluorocyclobutyl)methyl)-3-ethyl-N-(2-(methylsulfonyl)pyridin-4-yl)-4-(trifluoromethyl)-1H-pyrazole-5-carboxamide |
| 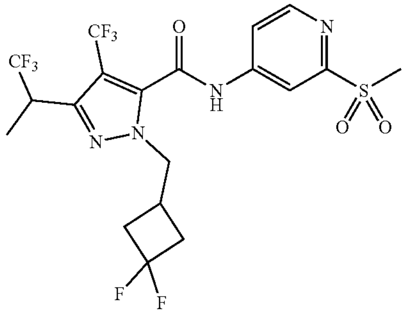 [SMILES: CC(c1nn(CC2CC(F)(F)C2)c(C(=O)Nc2ccnc(S(C)(=O)=O)c2)c1C(F)(F)F)C(F)(F)F] | SC-173 | 1-((3,3-difluorocyclobutyl)methyl)-N-(2-(methylsulfonyl)pyridin-4-yl)-4-(trifluoromethyl)-3-(1,1,1-trifluoropropan-2-yl)-1H-pyrazole-5-carboxamide |

-continued

| Structure | Ex. No. | Chemical name |
|---|---|---|
| 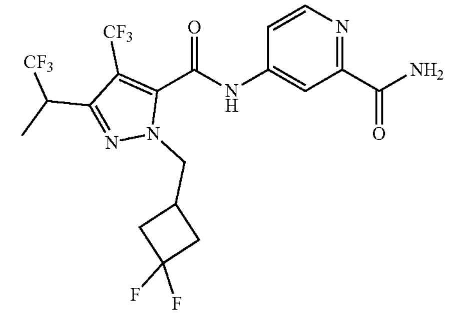 [SMILES: CC(c1nn(CC2CC(F)(F)C2)c(C(=O)Nc2ccnc(C(N)=O)c2)c1C(F)(F)F)C(F)(F)F] | SC-174 | 4-(1-((3,3-difluorocyclobutyl)methyl)-4-(trifluoromethyl)-3-(1,1,1-trifluoropropan-2-yl)-1H-pyrazole-5-carboxamido)picolinamide |
| 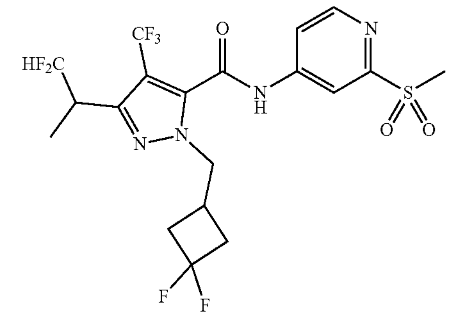 | SC-175 | 1-((3,3-difluorocyclobutyl)methyl)-3-(1,1-difluoropropan-2-yl)-N-(2-(methylsulfonyl)pyridin-4-yl)-4-(trifluoromethyl)-1H-pyrazole-5-carboxamide |
| 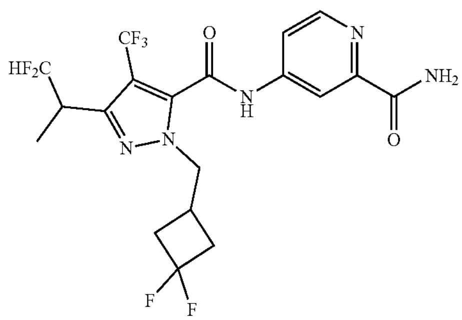 | SC-176 | 4-(1-((3,3-difluorocyclobutyl)methyl)-3-(1,1-difluoropropan-2-yl)-4-(trifluoromethyl)-1H-pyrazole-5-carboxamido)picolinamide |
| 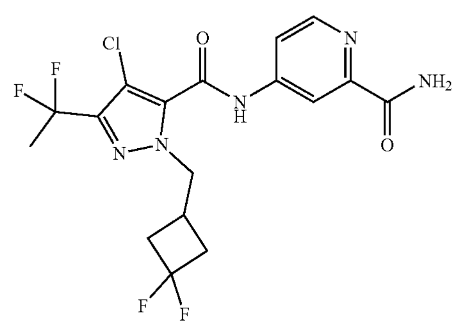 [SMILES: CC(F)(F)c1nn(CC2CC(F)(F)C2)c(C(=O)Nc2ccnc(C(N)=O)c2)c1Cl] | SC-177 | 4-(4-chloro-1-((3,3-difluorocyclobutyl)methyl)-3-(1,1-difluoroethyl)-1H-pyrazole-5-carboxamido)picolinamide |
| 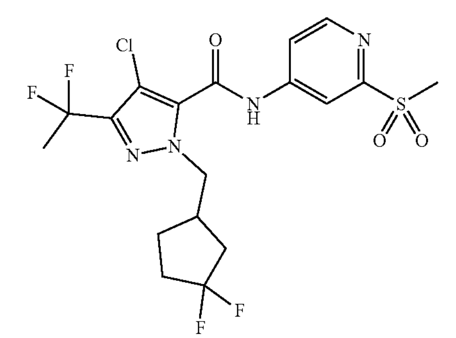 [SMILES: CC(F)(F)c1nn(CC2CCC(F)(F)C2)c(C(=O)Nc2ccnc(S(C)(=O)=O)c2)c1Cl] | SC-178 | 4-chloro-1-((3,3-difluorocyclopentyl)methyl)-3-(1,1-difluoroethyl)-N-(2-(methylsulfonyl)pyridin-4-yl)-1H-pyrazole-5-carboxamide |

-continued

| Structure | Ex. No. | Chemical name |
|---|---|---|
| 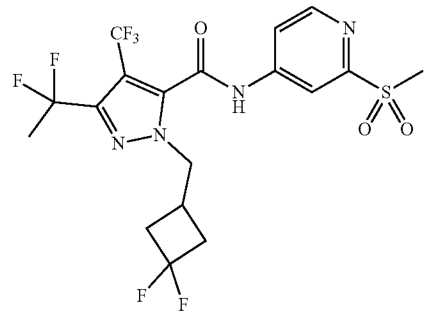 [SMILES: CC(F)(F)c1nn(CC2CC(F)(F)C2)c(C(=O)Nc2ccnc(S(C)(=O)=O)c2)c1C(F)(F)F] | SC-179 | 1-((3,3-difluorocyclobutyl)methyl)-3-(1,1-difluorethyl)-N-(2-(methylsulfonyl)pyridin-4-yl)-4-(trifluoromethyl)-1H-pyrazole-5-carboxamide |
| 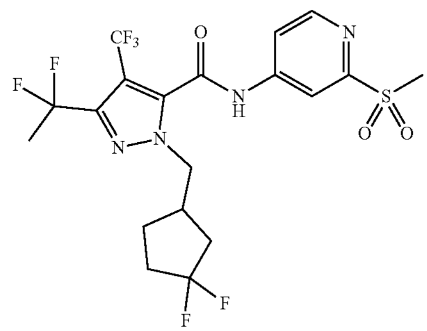 [SMILES: CC(F)(F)c1nn(CC2CCC(F)(F)C2)c(C(=O)Nc2ccnc(S(C)(=O)=O)c2)c1C(F)(F)F] | SC-181 | 1-((3,3-difluorocyclopentyl)methyl)-3-(1,1-difluorethyl)-N-(2-(methylsulfonyl)pyridin-4-yl)-4-(trifluoromethyl)-1H-pyrazole-5-carboxamide |
| 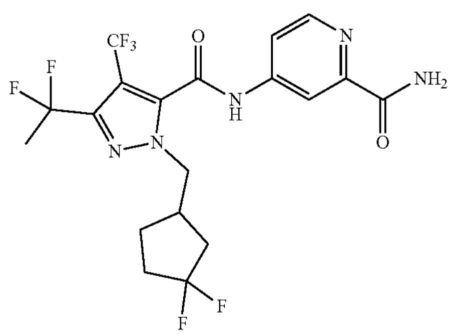 [SMILES: CC(F)(F)c1nn(CC2CCC(F)(F)C2)c(C(=O)Nc2ccnc(C(N)=O)c2)c1C(F)(F)F] | SC-182 | 4-(1-((3,3-difluorocyclopentyl)methyl)-3-(1,1-difluoroethyl)-4-(trifluoromethyl)-1H-pyrazole-5-carboxamido)picolinamide |
| 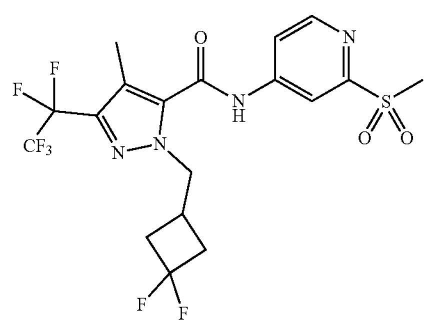 [SMILES: Cc1c(C(F)(F)C(F)(F)F)nn(CC2CC(F)(F)C2)c1C(=O)Nc1ccnc(S(C)(=O)=O)c1] | SC-183 | 1-((3,3-difluorocyclobutyl)methyl)-4-methyl-N-(2-(methylsulfonyl)pyridin-4-yl)-3-(perfluoroethyl)-1H-pyrazole-5-carboxamide |

| Structure | Ex. No. | Chemical name |
|---|---|---|
| 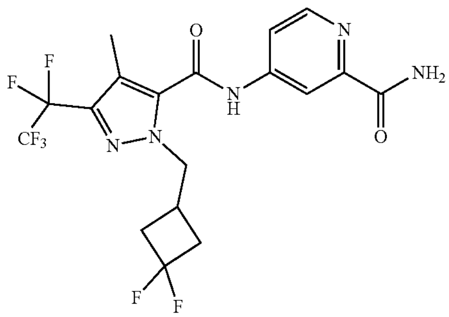 [SMILES: Cc1c(C(F)(F)C(F)(F)F)nn(CC2CC(F)(F)C2)c1C(=O)Nc1ccnc(C(N)=O)c1] | SC-184 | 4-(1-((3,3-difluorocyclobutyl)methyl)-4-methyl-3-(perfluoroethyl)-1H-pyrazole-5-carboxamido)picolinamide |
| 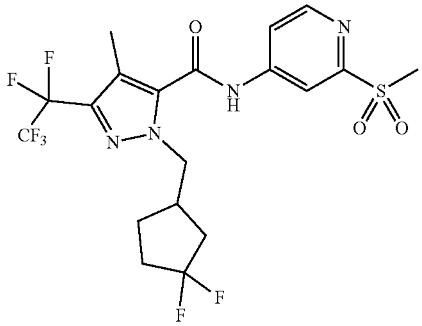 [SMILES: Cc1c(C(F)(F)C(F)(F)F)nn(CC2CCC(F)(F)C2)c1C(=O)Nc1ccnc(S(C)(=O)=O)c1] | SC-185 | 1-((3,3-difluorocyclopentyl)methyl)-4-methyl-N-(2-(methylsulfonyl)pyridin-4-yl)-3-(perfluoroethyl)-1H-pyrazole-5-carboxamide |
| 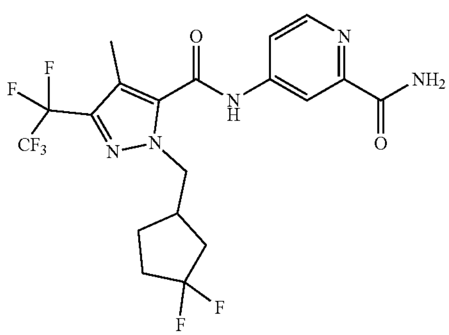 [SMILES: Cc1c(C(F)(F)C(F)(F)F)nn(CC2CCC(F)(F)C2)c1C(=O)Nc1ccnc(C(N)=O)c1] | SC-186 | 4-(1-((3,3-difluorocyclopentyl)methyl)-4-methyl-3-(perfluoroethyl)-1H-pyrazole-5-carboxamido)picolinamide |
| 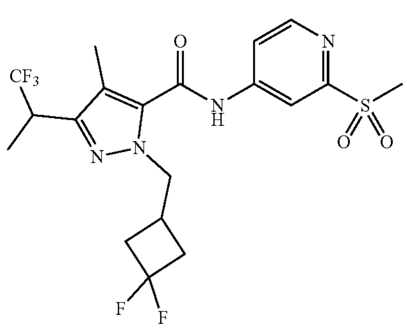 [SMILES: Cc1c(C(C)C(F)(F)F)nn(CC2CC(F)(F)C2)c1C(=O)Nc1ccnc(S(C)(=O)=O)c1] | SC-187 | 1-((3,3-difluorocyclobutyl)methyl)-4-methyl-N-(2-(methylsulfonyl)pyridin-4-yl)-3-(1,1,1-trifluoropropan-2-yl)-1H-pyrazole-5-carboxamide |

-continued

| Structure | Ex. No. | Chemical name |
|---|---|---|
| 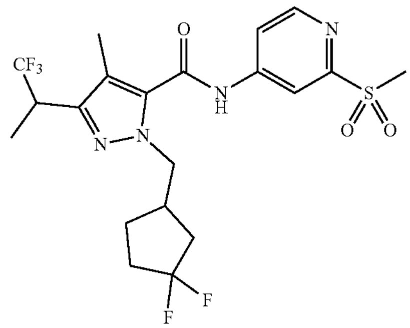 [SMILES: Cc1c(C(C)C(F)(F)F)nn(CC2CCC(F)(F)C2)c1C(=O)Nc1ccnc(S(C)(=O)=O)c1] | SC-189 | 1-((3,3-difluorocyclopentyl)methyl)-4-methyl-N-(2-(methylsulfonyl)pyridin-4-yl)-3-(1,1,1-trifluoropropan-2-yl)-1H-pyrazole-5-carboxamide |
| 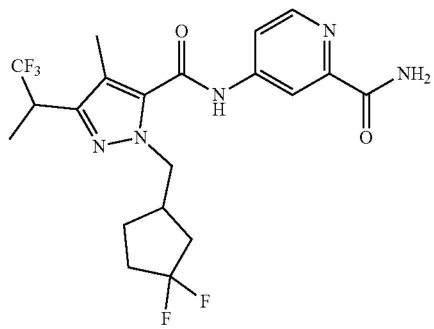 [SMILES: Cc1c(C(C)C(F)(F)F)nn(CC2CCC(F)(F)C2)c1C(=O)Nc1ccnc(C(N)=O)c1] | SC-190 | 4-(1-((3,3-difluorocyclopentyl)methyl)-4-methyl-3-(1,1,1-trifluoropropan-2-yl)-1H-pyrazole-5-carboxamido)picolinamide |
| 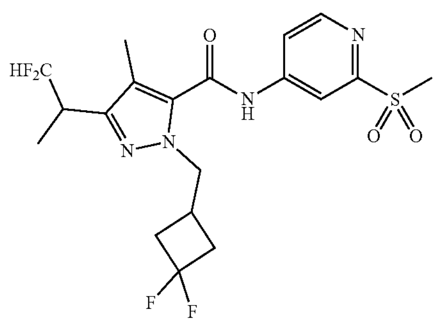 | SC-191 | 1-((3,3-difluorocyclobutyl)methyl)-3-(1,1-difluoropropan-2-yl)-4-methyl-N-(2-(methylsulfonyl)pyridin-4-yl)-1H-pyrazole-5-carboxamide |
| 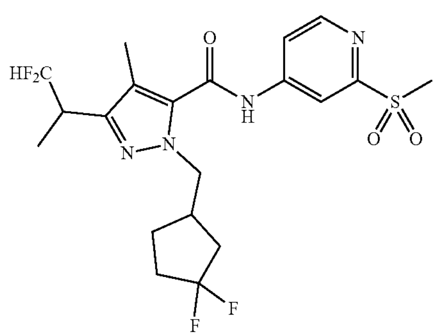 | SC-193 | 1-((3,3-difluorocyclopentyl)methyl)-3-(1,1-difluoropropan-2-yl)-4-methyl-N-(2-(methylsulfonyl)pyridin-4-yl)-1H-pyrazole-5-carboxamide |

-continued

| Structure | Ex. No. | Chemical name |
|---|---|---|
| 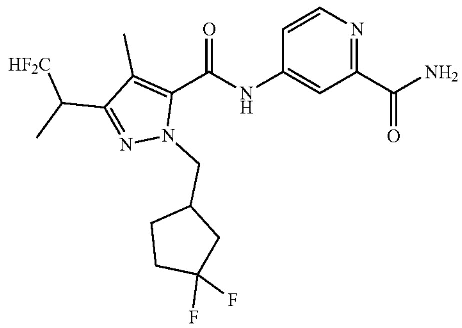 | SC-194 | 4-(1-((3,3-difluorocyclopentyl)methyl)-3-(1,1-difluoropropan-2-yl)-4-methyl-1H-pyrazole-5-carboxamido)picolinamide |
| 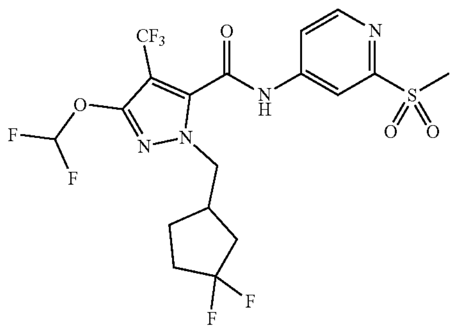 [SMILES: CS(=O)(=O)c1cc(NC(=O)c2c(C(F)(F)F)c(OC(F)F)nn2CC2CCC(F)(F)C2)ccn1] | SC-195 | 1-((3,3-difluorocyclopentyl)methyl)-3-(difluoromethoxy)-N-(2-(methylsulfonyl)pyridin-4-yl)-4-(trifluoromethyl)-1H-pyrazole-5-carboxamide |
| 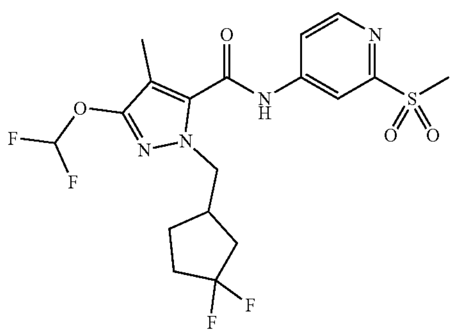 [SMILES: Cc1c(OC(F)F)nn(CC2CCC(F)(F)C2)c1C(=O)Nc1ccnc(S(C)(=O)=O)c1] | SC-197 | 1-((3,3-difluorocyclopentyl)methyl)-3-(difluoromethoxy)-4-methyl-N-(2-(methylsulfonyl)pyridin-4-yl)-1H-pyrazole-5-carboxamide |
| 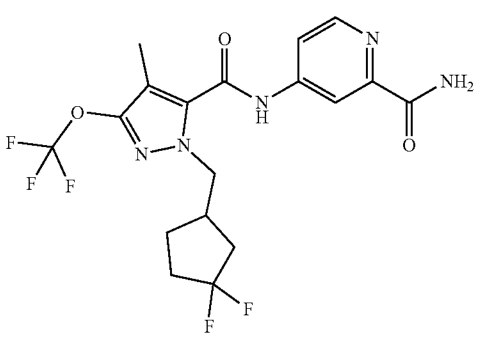 [SMILES: Cc1c(OC(F)(F)F)nn(CC2CCC(F)(F)C2)c1C(=O)Nc1ccnc(C(N)=O)c1] | SC-198 | 4-(1-((3,3-difluorocyclopentyl)methyl)-4-methyl-3-(trifluoromethoxy)-1H-pyrazole-5-carboxamido)picolinamide |

-continued

| Structure | Ex. No. | Chemical name |
|---|---|---|
| 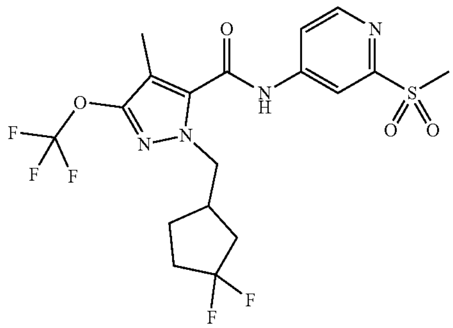 [SMILES: Cc1c(OC(F)(F)F)nn(CC2CCC(F)(F)C2)c1C(=O)Nc1ccnc(S(C)(=O)=O)c1] | SC-199 | 1-((3,3-difluorocyclopentyl)methyl)-4-methyl-N-(2-(methylsulfonyl)pyridin-4-yl)-3-(trifluoromethoxy)-1H-pyrazole-5-carboxamide |
| 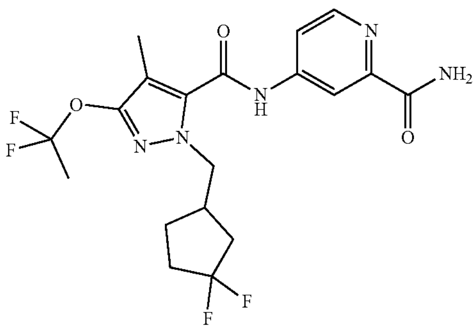 [SMILES: Cc1c(OC(C)(F)F)nn(CC2CCC(F)(F)C2)c1C(=O)Nc1ccnc(C(N)=O)c1] | SC-200 | 4-(1-((3,3-difluorocyclopentyl)methyl)-3-(1,1-difluoroethoxy)-4-methyl-1H-pyrazole-5-carboxamido)picolinamide |
| 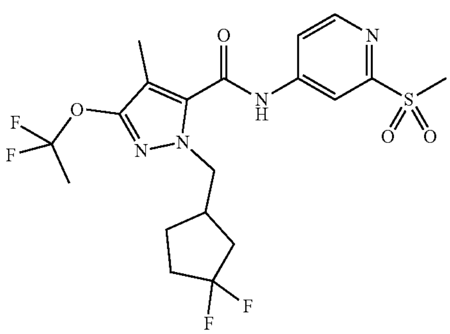 [SMILES: Cc1c(OC(C)(F)F)nn(CC2CCC(F)(F)C2)c1C(=O)Nc1ccnc(S(C)(=O)=O)c1] | SC-201 | 1-((3,3-difluorocyclopentyl)methyl)-3-(1,1-difluoroethoxy)-4-methyl-N-(2-(methylsulfonyl)pyridin-4-yl)-1H-pyrazole-5-carboxamide |
| 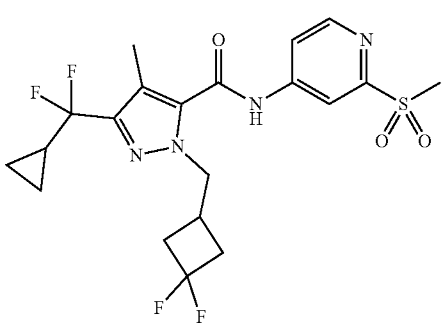 [SMILES: Cc1c(C(F)(F)C2CC2)nn(CC2CC(F)(F)C2)c1C(=O)Nc1ccnc(S(C)(=O)=O)c1] | SC-202 | 3-(cyclopropyldifluoromethyl)-1-((3,3-difluorocyclobutyl)methyl)-4-methyl-N-(2-(methylsulfonyl)pyridin-4-yl)-1H-pyrazole-5-carboxamide |

-continued

| Structure | Ex. No. | Chemical name |
|---|---|---|
| 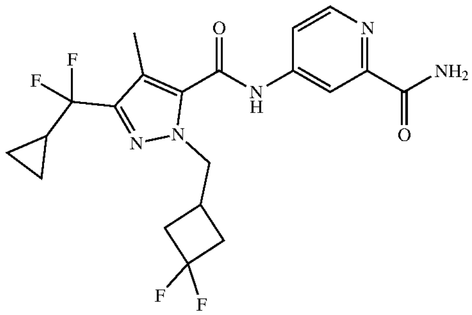 [SMILES: Cc1c(C(F)(F)C2CC2)nn(CC2CC(F)(F)C2)c1C(=O)Nc1ccnc(C(N)=O)c1] | SC-203 | 4-(3-(cyclopropyldifluoromethyl)-1-((3,3-difluorocyclobutyl)methyl)-4-methyl-1H-pyrazole-5-carboxamido)picolinamide |
| 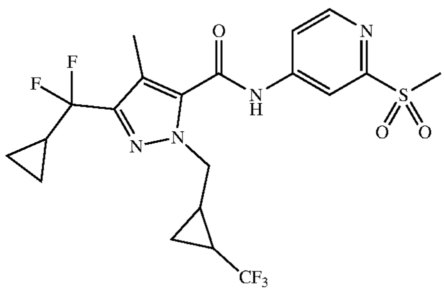 [SMILES: Cc1c(C(F)(F)C2CC2)nn(CC2CC2C(F)(F)F)c1C(=O)Nc1ccnc(S(C)(=O)=O)c1] | SC-205 | 3-(1,1-difluoroethyl)-4-methyl-N-(2-(methylsulfonyl)pyridin-4-yl)-1-((2-(trifluoromethyl)cyclopropyl)methyl)-1H-pyrazole-5-carboxamide |

Electrophysiology: Voltage-Clamp Recordings

The following $Na_V1.8$ recombinant cell line was used for recordings: HEK-$Na_V$1.8 (NM 006514.1) with in (NM 018400.3).

Sodium currents were measured using the patch clamp technique in the whole-cell configuration using the Qube384 (Sophion A/S, Copenhagen, Denmark) automated voltage clamp platform. "Multi hole" plates were used for the cell line expressing $Na_V$1.8 while "single hole" plates were used for the recombinant cell lines expressing the other subtypes. Appropriate filters (for minimum seal resistance and minimum current size) and series resistance compensation (for high quality sodium channel recordings) were applied. Data was collected at ambient room temperature.

The recording extracellular solution contained (in mM): NaCl 145 mM, KCl 4 mM, $CaCl_2$ 2 mM, $MgCl_2$ 1 mM, HEPES 10 mM, Glucose 10 mM, pH 7.4 (NaOH). The intracellular recording solution contained (in mM): CsF 120 mM, CsCl 20 mM, NaCl 10 mM, EGTA 10 mM, HEPES 10 mM, pH 7.2 (CsOH). Currents were recorded at 25 kHz sampling frequency and filtered at 5 kHz. Series resistance compensation was applied at 65%.

Vehicle (VEH) is the control condition where cells are exposed to 0.3% DMSO without compound. All runs include VEH controls being exposed to the same voltage protocols to assess non-compound related phenomena such as run down and then used to isolate compound dependent effects on currents.

To check for state-dependence inhibition, the following voltage-sequence was applied every 20 seconds:

From a resting membrane potential of −120 mV, the first test pulse (P1; 20 ms to −10 mV) was applied to check for channels in the Resting State followed by a brief recovery (20 ms to −120 mV), then holding the membrane voltage to V112 (4 seconds at voltage to obtain half the channel at Rest and half Inactivated) with a subsequent second test pulse (P2; 20 ms to −10 mV) to check for channels in the Inactivated State, followed by another brief recovery (20 ms to −120 mV) and a final third test pulse (P3; 20 ms to −10 mV) to check for recovered channels.

To check for frequency-dependent inhibition, a 10 Hz protocol and a 20 Hz protocol were applied; namely, From a resting membrane potential of −120 mV, 40-pulses (10 ms to −10 mV) was applied at 10 Hz (at 100 ms between pulses) and then at 20 Hz (at 50 ms between pulses).

Each parameter was recorded (P1, P2, P3, P40 from 10 Hz and P40 from 20 Hz) during a control period (lasting 5 minutes) when establishing the baseline and during compound period (lasting ~12 minutes) when test compound (or vehicle) was applied. For each parameter, the value at the end of the compound period was normalized to the vehicle baseline; as follows $$\text{Normalized Inhibition (Norm}_{CPD}) = \frac{CPD \text{ Value}_{end\ CPD\ period}}{VEH \text{ Value}_{end\ Control\ Period}}$$

To adjust for any variance in the $Na^+$ current signal during the compound period (owing to cumulative inactivation independent of compound or shifts in biophysics over time), a dedicated segment of the recording wells in each 384 plate were dedicated to having only vehicle exposure. These vehicle-only recordings were used to correct for any apparent "run-up" or "run-down" in the experiment.

$$\text{Normalized Inhibition (Norm}_{VEH}) = \frac{VEH \text{ Value}_{end\ CPD\ period}}{VEH \text{ Value}_{end\ Control\ Period}}$$

The adjusted inhibition was calculated as follows:

$$\% \text{ Inhibition}_{corrected} = 100 \times \frac{\text{Norm}_{CPD} - \text{Norm}_{VEH}}{100 - \text{Norm}_{VEH}}$$

Percent inhibition was determined and $IC_{50}$ values were calculated using a 4 parameter logistic model within XLFit Software (IDBS, Boston MA):

$$\% \text{ Inhibition}_{corrected} = A + \frac{(B-A)}{\left(1 + \left(\frac{x}{C}\right)^D\right)}$$

where A and B are the maximal and minimum inhibition respectively, C is the $IC_{50}$ concentration and D is the (Hill) slope.

The potency data of the example compounds are summarized in the table below (category A: human NaV1.8 $IC_{50} \leq 0.1$ µM; category B: 0.1 µM < human NaV1.8 $IC_{50} \leq 1$ µM; category C: 1 µM < human NaV1.8 $IC_{50} \leq 10$ µM; "n.d.": not determined). The potency data was either taken from inactivated or resting state.

| Example number | Potency category |
|---|---|
| SC-01 | B |
| SC-02 | B |
| SC-03 | B |
| SC-04 | C |
| SC-05 | B |
| SC-06 | B |
| SC-07 | C |
| SC-08 | C |
| SC-09 | B |
| SC-10 | B |
| SC-11 | C |
| SC-12 | B |
| SC-13 | B |
| SC-14 | C |
| SC-15 | C |
| SC-16 | C |
| SC-17 | B |
| SC-18 | C |
| SC-19 | B |
| SC-21 | C |
| SC-22 | C |
| SC-23 | B |
| SC-24 | B |
| SC-25 | B |
| SC-26 | A |
| SC-27 | A |
| SC-28 | C |
| SC-29 | B |
| SC-30 | B |
| SC-31 | B |
| SC-32 | C |
| SC-33 | A |
| SC-35 | A |
| SC-36 | B |
| SC-37 | C |
| SC-38 | B |
| SC-39 | B |
| SC-41 | B |
| SC-42 | C |
| SC-43 | B |
| SC-44 | B |
| SC-45 | C |
| SC-53 | A |
| SC-84 | A |
| SC-129a | A |
| SC-129b | A |
| SC-135 | A |
| SC-140 | A |
| SC-141 | A |
| SC-143 | A |
| SC-144 | A |
| SC-145a | A |
| SC-145b | A |
| SC-147a | A |
| SC-147b | A |
| SC-147c | A |
| SC-148a | A |
| SC-148b | A |
| SC-149a | A |
| SC-149b | A |
| SC-150a | A |
| SC-150b | A |
| SC-150c | A |
| SC-151 | A |
| SC-153 | A |
| SC-154a | A |
| SC-154b | A |
| SC-155 | A |
| SC-156 | A |
| SC-157 | A |
| SC-158R | A |
| SC-158S | A |
| SC-159 | A |
| SC-160a | A |
| SC-160b | A |
| SC-161 | A |
| SC-163 | A |
| SC-167 | A |
| SC-170 | A |
| SC-172 | A |
| SC-180 | A |
| SC-188a | B |
| SC-188b | B |
| SC-192a | B |
| SC-192b | B |
| SC-196 | A |
| SC-204a | A |
| SC-204b | A |
| SC-206 | B |
| SC-207 | B |
| SC-208 | A |
| SC-209 | A |
| SC-210 | A |
| SC-211 | A |
| SC-212a | A |
| SC-212b | A |
| SC-213 | A |
| SC-214a | A |
| SC-214b | A |
| SC-215 | A |
| SC-216 | A |
| SC-217 | A |
| SC-218 | A |
| SC-219a | A |
| SC-219b | A |
| SC-220 | A |
| SC-221a | A |
| SC-221b | A |
| SC-222a | B |
| SC-222b | C |
| SC-223 | A |
| SC-224 | B |
| SC-225 | A |
| SC-226 | C |
| SC-229 | A |
| SC-230 | A |
| SC-231 | C |
| SC-232 | A |
| SC-233 | B |
| SC-234 | C |
| SC-235 | A |
| SC-236 | A |

| Example number | Potency category |
|---|---|
| SC-237 | C |
| SC-238 | A |
| SC-239 | B |
| SC-241 | B |
| SC-242 | B |
| SC-243 | B |
| SC-244 | A |
| SC-246 | A |
| SC-247R | C |
| SC-247S | B |
| SC-248R | C |
| SC-248S | C |
| SC-249 | B |
| SC-250 | A |
| SC-251 | C |
| SC-252 | B |
| SC-253 | C |
| SC-254a | A |
| SC-254b | A |
| SC-255 | C |
| SC-256 | C |
| SC-257 | B |
| SC-258a | A |
| SC-258b | A |
| SC-259a | A |
| SC-259b | A |
| SC-260 | B |
| SC-261 | B |
| SC-262 | A |
| SC-263 | B |
| SC-264 | A |
| SC-265 | A |
| SC-266 | A |
| SC-267 | B |
| SC-268 | C |
| SC-269 | B |
| SC-271a | B |
| SC-271b | B |
| SC-273 | A |
| SC-274 | A |
| SC-275 | A |
| SC-276 | A |
| SC-277a | A |
| SC-277b | A |
| SC-278a | A |
| SC-278b | A |
| SC-279a | B |
| SC-279b | B |
| SC-280 | B |
| SC-281a | B |
| SC-281b | B |
| SC-282 | A |
| SC-283 | A |
| SC-284a | A |
| SC-284b | A |
| SC-286a | B |
| SC-286b | B |
| SC-289 | C |
| SC-290 | B |
| SC-291a | A |
| SC-291b | A |
| SC-293 | A |
| SC-294 | C |
| SC-295 | A |
| SC-296a | A |
| SC-296b | A |
| SC-297 | A |
| SC-298 | C |
| SC-299 | A |
| SC-301 | B |
| SC-302 | B |
| SC-303 | A |
| SC-304 | B |
| SC-305 | C |
| SC-308 | C |
| SC-309 | C |
| SC-310 | B |
| SC-311 | A |
| SC-312a | B |
| SC-312b | B |
| SC-313 | A |
| SC-314 | A |
| SC-315a | A |
| SC-315b | A |
| SC-316 | A |
| SC-317 | C |
| SC-318 | B |
| SC-319a | B |
| SC-319b | C |
| SC-320 | A |
| SC-321 | B |
| SC-322 | C |
| SC-323 | B |
| SC-324 | A |
| SC-325 | A |
| SC-118a | A |
| SC-118b | A |

The invention claimed is:

1. A compound according to general formula (I)

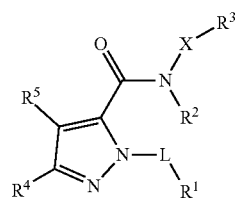

wherein

L represents $CH_2$, $CH(CH_3)$ or $CH(CH_2CH_3)$;

$R^1$ represents $C_{3-10}$-cycloalkyl, or 4 to 10-membered heterocycloalkyl, $R^2$ represents H or $C_{1-6}$-alkyl;

X represents phenyl, or 5 to 10-membered heteroaryl;

$R^3$ represents $S(O)_2$—$C_{1-6}$-alkyl, $S(O)_2$—$(C_{3-6}$-cycloalkyl), $S(O)_2$-(4 to 6-membered heterocycloalkyl), $S(O)_2$-phenyl, $S(O)_2$-(5 or 6-membered heteroaryl), $S(O)$—$NH_2$, $S(O)$—$N(H)(C_{1-6}$-alkyl), $S(O)$—$N(C_{1-6}$-alkyl)$_2$, $S(O)_2$—$NH_2$, $S(O)_2$—$N(H)(C_{1-6}$-alkyl), $S(O)_2$—$N(H)(C_{3-6}$-cycloalkyl), $S(O)_2$—$N(C_{1-6}$-alkyl)$_2$, $C(O)$—$NH_2$, $C(O)$—$N(H)(C_{1-6}$-alkyl), $C(O)$—$N(H)(C_{3-6}$-cycloalkyl), $C(O)$—$N(C_{1-6}$-alkyl)$_2$, $C(O)$—$N(C_{1-6}$-alkyl)($C_{3-6}$-cycloalkyl), $OCF_3$, $OCF_2H$, CN, OH, O—$C_{3-6}$-cycloalkyl, O-(4 to 6-membered heterocycloalkyl), $S(O)$—$C_{1-6}$-alkyl, $S(O)$—($C_{3-6}$-cycloalkyl), $S(O)$-(4 to 6-membered heterocycloalkyl), $S(O)$-phenyl, or $S(O)$-(5 or 6-membered heteroaryl);

$R^4$ and $R^5$ independently from one another represent H, F, Cl, Br, CN, $CHF_2$, $CH_2F$, $CF_3$, $C_{1-6}$-alkyl, $C_{3-10}$-cycloalkyl, $C_{1-6}$-alkylene-$C_{3-10}$-cycloalkyl, 4 to 10-membered heterocycloalkyl, $C_{1-6}$-alkylene-(4 to 10-membered heterocycloalkyl), $NH_2$, $N(H)(C_{1-6}$-alkyl), $N(C_{1-6}$-alkyl)$_2$, O—$C_{1-6}$-alkyl, O—$C_{3-10}$-cycloalkyl, O—$C_{1-6}$-alkylene-$C_{3-10}$-cycloalkyl, O-(4 to 6-membered heterocycloalkyl), or O—$C_{1-6}$-alkylene-(4 to 6-membered heterocycloalkyl), provided that at least one of $R^4$ and $R^5$ does not represent H;

wherein $C_{1-6}$-alkyl and $C_{1-6}$-alkylene in each case independently from one another is linear or branched;

wherein $C_{1-6}$-alkyl, $C_{1-6}$-alkylene, $C_{3-10}$-cycloalkyl, $C_{3-6}$-cycloalkyl, 4 to 10-membered heterocycloalkyl and 4 to 6-membered heterocycloalkyl in each case independently from one another are unsubstituted or mono- or polysubstituted with F; and/or are unsubstituted or monosubstituted with one substituent selected from the group consisting of Cl, CN, $C_{1-6}$-alkyl, $C_{1-6}$-alkylene-OH, $C_{1-6}$-alkylene-OCH$_3$, CF$_3$, CF$_2$H, CFH$_2$, C(O)—$C_{1-6}$-alkyl, OH, =O, OCF$_3$, OCF$_2$H, OCFH$_2$, O—$C_{1-6}$-alkyl, $C_{1-4}$-alkylene-O—$C_{1-4}$-alkylene-O—CH$_3$, and $C_{0-4}$-alkylene-O—(C$_{1-4}$-alkylene-O)$_{1-4}$—CH$_3$;

wherein phenyl, 5 to 10-membered heteroaryl and 5 or 6-membered heteroaryl in each case independently from one another are unsubstituted or mono- or polysubstituted with one or more substituents selected from the group consisting of F, Cl, Br, CN, $C_{1-6}$-alkyl, $C_{3-6}$-cycloalkyl, CF$_3$, CF$_2$H, CFH$_2$, $C_{1-6}$-alkylene-CF$_3$, $C_{1-6}$-alkylene-CF$_2$H, $C_{1-6}$-alkylene-CFH$_2$, $C_{1-6}$-alkylene-OH, $C_{1-6}$-alkylene-OCH$_3$, C(O)—$C_{1-6}$-alkyl, OCF$_3$, OCF$_2$H, OCFH$_2$, and O—$C_{1-6}$-alkyl;

in the form of the free compound or a physiologically acceptable salt thereof.

2. The compound according to claim 1, wherein $R^3$ represents S(O)$_2$—$C_{1-6}$-alkyl, S(O)$_2$—(C$_{3-6}$-cycloalkyl), S(O)$_2$-(4 to 6-membered heterocycloalkyl), S(O)$_2$-phenyl, S(O)$_2$-(5 or 6-membered heteroaryl), S(O)—NH$_2$, S(O)—N(H)(C$_{1-6}$-alkyl), S(O)—N(C$_{1-6}$-alkyl)$_2$, C(O)—NH$_2$, C(O)—N(H)(C$_{1-6}$-alkyl), C(O)—N(H)(C$_{3-6}$-cycloalkyl), C(O)—N(C$_{1-6}$-alkyl)$_2$, C(O)—N(C$_{1-6}$-alkyl)(C$_{3-6}$-cycloalkyl), OCF$_3$, OCF$_2$H, CN, OH, O—$C_{3-6}$-cycloalkyl, O-(4 to 6-membered heterocycloalkyl), S(O)—$C_{1-6}$-alkyl, S(O)—(C$_{3-6}$-cycloalkyl), S(O)-(4 to 6-membered heterocycloalkyl), S(O)-phenyl, or S(O)-(5 or 6-membered heteroaryl).

3. The compound according claim 1, wherein $R^4$ and $R^5$ independently from one another represent H, F, Cl, Br, CN, CHF$_2$, CH$_2$F, CF$_3$, $C_{1-6}$-alkyl, $C_{1-6}$-alkylene-$C_{3-10}$-cycloalkyl, $C_{1-6}$-alkylene-(4 to 10-membered heterocycloalkyl), NH$_2$, N(H)(C$_{1-6}$-alkyl), N(C$_{1-6}$-alkyl)$_2$, O—$C_{1-6}$-alkyl, O—$C_{3-10}$-cycloalkyl, O—$C_{1-6}$-alkylene-$C_{3-10}$-cycloalkyl, O-(4 to 6-membered heterocycloalkyl), or O—$C_{1-6}$-alkylene-(4 to 6-membered heterocycloalkyl).

4. The compound according to claim 1, wherein $R^2$ represents H.

5. The compound according to claim 1, wherein $R^4$ and $R^5$ independently from one another represent H, F, Cl, CN, CHF$_2$, CH$_2$F, CF$_3$, CH$_2$CHF$_2$, CH$_2$CH$_2$F, CH$_2$CF$_3$, CF$_2$CH$_3$, CHFCH$_3$, CF$_2$CF$_3$, CHFCF$_3$, CH(CHF$_2$)(CH$_3$), CH(CH$_2$F)(CH$_3$), CH(CF$_3$)(CH$_3$), CH$_3$, CH$_2$CH$_3$, CH(CH$_3$)$_2$, cyclopropyl, CH$_2$-cyclopropyl, CF$_2$-cyclopropyl, O—CHF$_2$, O—CH$_2$F, O—CF$_3$, O—CH$_2$CHF$_2$, O—CH$_2$CH$_2$F, O—CH$_2$CF$_3$, O—CF$_2$CH$_3$, O—CHFCH$_3$, O—CF$_2$CF$_3$, O—CHFCF$_3$, O—CH$_3$, O—CH$_2$CH$_3$, O—CH(CH$_3$)$_2$, O-cyclopropyl, or O—CH$_2$-cyclopropyl, provided that at least one of $R^4$ and $R^5$ does not represent H.

6. The compound according to claim 1, wherein $R^1$ represents $C_{3-10}$-cycloalkyl selected from the group consisting of cyclopropyl, cyclobutyl, cyclopentyl, cyclohexyl, cycloheptyl, and cyclooctyl;

wherein the $C_{3-10}$-cycloalkyl is unsubstituted or mono- or polysubstituted with F; and/or is unsubstituted or monosubstituted with one substituent selected from the group consisting of Cl, CN, CH$_3$, CF$_3$, CHF$_2$, CH$_2$FOH, OCH$_3$, OCF$_3$, OCF$_2$H, OCFH$_2$, and CH$_2$—O—CH$_2$CH$_2$—O—CH$_3$; or 4 to 10-membered heterocycloalkyl selected from the group consisting of oxetanyl, tetrahydrofuranyl, tetrahydropyranyl, morpholinyl, thiomorpholinyl, tetrahydrothiopyranyl, tetrahydrothiopyranyl 1,1-dioxide, oxepanyl, piperidinyl, piperidinonyl, azetidinyl, pyrrolidinyl, pyrrolidinonyl, 4-methylpiperazinyl, morpholinonyl, dioxanyl, piperazinyl, and tetrahydropyrrolyl;

wherein the 4 to 10-membered heterocycloalkyl is unsubstituted or mono- or polysubstituted with F; and/or is unsubstituted or monosubstituted with one substituent selected from the group consisting of Cl, CN, CH$_3$, CF$_3$, CHF$_2$, CH$_2$F, OH, OCH$_3$, OCF$_3$, OCF$_2$H, and OCFH$_2$.

7. The compound according to claim 6, wherein $R^1$ represents cyclopropyl, cyclobutyl, cyclopentyl, cyclohexyl, cycloheptyl, tetrahydrofuranyl, or tetrahydropyranyl;

wherein said cyclopropyl, cyclobutyl, cyclopentyl, cyclohexyl, cycloheptyl, tetrahydrofuranyl, or tetrahydropyranyl is unsubstituted or mono- or polysubstituted with F; and/or is unsubstituted or monosubstituted with CH$_3$ or CF$_3$.

8. The compound according to claim 1, wherein X represents phenyl, wherein phenyl is unsubstituted or mono- or polysubstituted with one or more substituents selected from the group consisting of F, Cl, Br, CN, CH$_3$, CF$_3$, CHF$_2$, CH$_2$F, OH, OCH$_3$, OCF$_3$, OCF$_2$H, and OCFH$_2$; or 5 to 10-membered heteroaryl selected from the group consisting of pyridyl, pyrazolyl, pyrrolo[2,3-b]pyridyl, pyridonyl, thienyl, thiazolyl, 2,3-dihydrobenzo[d]isothiazolyl 1,1-dioxide, isoindolinonyl, pyrimidinyl, pyrazinyl, pyridazinyl, isoxazolyl, triazolyl, oxazolyl, oxadiazolyl, indazolyl, pyrazolopyridyl, pyrrolyl, imidazolyl, isothiazolyl, furanyl, and thiadiazolyl;

wherein said 5 to 10-membered heteroaryl is unsubstituted or mono- or polysubstituted with one or more substituents selected from the group consisting of F, Cl, Br, CN, CH$_3$, CF$_3$, CHF$_2$, CH$_2$F, OH, OCH$_3$, OCF$_3$, OCF$_2$H, and OCFH$_2$.

9. The compound according to claim 8, wherein X represents phenyl, pyridyl, pyrazolyl, or pyrrolo[2,3-b]pyridyl;

wherein said phenyl, pyridyl, pyrazolyl, or pyrrolo[2,3-b]pyridyl is unsubstituted or mono- or polysubstituted with F.

10. The compound according to claim 1, wherein $R^3$ represents S(O)$_2$—NH$_2$, S(O)$_2$—CH$_3$, S(O)$_2$-(cyclopropyl), S(O)$_2$-(oxetanyl), S(O)$_2$-phenyl, S(O)$_2$-(pyridyl), S(O)—NH$_2$, S(O)—N(H)(CH$_3$), S(O)—N(CH$_3$)$_2$, C(O)—NH$_2$, C(O)—N(H)(CH$_3$), C(O)—N(H)(cyclopropyl), C(O)—N(CH$_3$)$_2$, C(O)—N(CH$_3$)(cyclopropyl), OCF$_3$, OCF$_2$H, CN, OH, O-cyclopropyl, O-(oxetanyl), S(O)—CH$_3$, S(O)-(cyclopropyl), S(O)-(oxetanyl), S(O)-phenyl, or S(O)-(pyridyl).

11. The compound according to claim 10, wherein $R^3$ represents S(O)$_2$—CH$_3$, C(O)NH$_2$, OH, S(O)—CH$_3$, or S(O)$_2$—NH$_2$.

12. A compound selected from the group consisting of:

| | |
|---|---|
| SC-01 | 2-(cyclohexylmethyl)-N-(3-methylsulfonylphenyl)-5-(trifluoromethyl)pyrazole-3-carboxamide |
| SC-02 | 2-[ (4,4-difluorocyclohexyl)methyl] -N-(3-methylsulfonylphenyl)-5-(trifluoromethyl)pyrazole-3-carboxamide; |
| SC-03 | 2-(cyclopentylmethyl)-N-(3-methylsulfonylphenyl)-5-(trifluoromethyl)pyrazole-3-carboxamide; |
| SC-04 | N-(3-methylsulfonylphenyl)-2-(oxan-4-ylmethyl)-5-(trifluoromethyl)pyrazole-3-carboxamide; |
| SC-05 | 2-[ (4,4-difluorocyclohexyl)methyl] -N-(3-methylsulfonylphenyl)-4-(trifluoromethyl)pyrazole-3-carboxamide; |
| SC-06 | 2-(cyclohexylmethyl)-4,5-dimethyl-N-(3-methylsulfonylphenyl)pyrazole-3-carboxamide; |
| SC-07 | 1-(cyclohexylmethyl)-3,4-dimethyl-N-(2-oxo-1,2-dihydropyridin-4-yl)-1H-pyrazole-5-carboxamide; |
| SC-08 | 2-(cyclohexylmethyl)-4-fluoro-N-(3-methylsulfonylphenyl)pyrazole-3-carboxamide; |
| SC-09 | 1-(cyclohexylmethyl)-3-(difluoromethyl)-N-(3-(methylsulfonyl)phenyl)-1H-pyrazole-5-carboxamide; |
| SC-10 | 4-cyano-2-(cyclohexylmethyl)-N-(3-methylsulfonylphenyl)pyrazole-3-carboxamide; |
| SC-11 | 2-(cyclohexylmethyl)-5-methyl-N-(3-methylsulfonylphenyl)pyrazole-3-carboxamide; |
| SC-12 | 2-(cyclohexylmethyl)-5-cyclopropyl-N-(3-methylsulfonylphenyl)pyrazole-3-carboxamide; |
| SC-13 | 2-[ (4,4-difluorocyclohexyl)methyl] -N-(4-fluoro-3-methylsulfonylphenyl)-4-(trifluoromethyl)pyrazole-3-carboxamide; |
| SC-14 | 2-[ (4,4-difluorocyclohexyl)methyl] -N-(2-methylsulfonylpyridin-4-yl)-4-(trifluoromethyl)pyrazole-3-carboxamide; |
| SC-15 | 2-[ (4,4-difluorocyclohexyl)methyl] -N-(5-methylsulfonylpyridin-3-yl)-4-(trifluoromethyl)pyrazole-3-carboxamide; |
| SC-16 | 2-[ (4,4-difluorocyclohexyl)methyl] -N-(2-fluoro-3-methylsulfonylphenyl)-4-(trifluoromethyl)pyrazole-3-carboxamide; |
| SC-17 | 2-(cyclohexylmethyl)-5-methoxy-N-(3-methylsulfonylphenyl)pyrazole-3-carboxamide; |
| SC-18 | 2-(cyclohexylmethyl)-N-(3-methylsulfonylphenyl)-4-propan-2-ylpyrazole-3-carboxamide; |
| SC-19 | 2-(cyclohexylmethyl)-4-cyclopropyl-N-(3-methylsulfonylphenyl)pyrazole-3-carboxamide; |
| SC-21 | N-(4-carbamoyl-3-fluorophenyl)-1-[ (4,4-difluorocyclohexyl)methyl] -4-(trifluoromethyl)-1H-pyrazole-5-carboxamide; |
| SC-22 | 2-[ (4,4-difluorocyclohexyl)methyl] -N-(2-fluoro-5-methylsulfonylphenyl)-4-(trifluoromethyl)pyrazole-3-carboxamide; |
| SC-23 | 2-[ (3,3-difluorocyclohexyl)methyl] -N-(3-methylsulfonylphenyl)-4-(trifluoromethyl)pyrazole-3-carboxamide; |
| SC-24 | 2-(cyclobutylmethyl)-N-(3-methylsulfonylphenyl)-4-(trifluoromethyl)pyrazole-3-carboxamide; |
| SC-25 | 2-(cyclopentylmethyl)-N-(3-methylsulfonylphenyl)-4-(trifluoromethyl)pyrazole-3-carboxamide; |
| SC-26 | 2-(cyclohexylmethyl)-N-(3-methylsulfonylphenyl)-4-(trifluoromethyl)pyrazole-3-carboxamide; |
| SC-27 | 2-(cycloheptylmethyl)-N-(3-methylsulfonylphenyl)-4-(trifluoromethyl)pyrazole-3-carboxamide; |
| SC-28 | N-(3-methylsulfonylphenyl)-2-(oxan-4-ylmethyl)-4-(trifluoromethyl)pyrazole-3-carboxamide; |
| SC-29 | 2-(1-cyclohexylethyl)-N-(3-methylsulfonylphenyl)-4-(trifluoromethyl)pyrazole-3-carboxamide; |
| SC-30 | 1-(cyclohexylmethyl)-N-(2-oxo-1,2-dihydropyridin-4-yl)-4-(trifluoromethyl)-1H-pyrazole-5-carboxamide; |
| SC-31 | 2-(cycloheptylmethyl)-N-(2-hydroxypyridin-4-yl)-4-(trifluoromethyl)pyrazole-3-carboxamide; |
| SC-32 | 2-(1-cyclohexylethyl)-N-(2-hydroxypyridin-4-yl)-4-(trifluoromethyl)pyrazole-3-carboxamide; |
| SC-33 | 2-(cyclohexylmethyl)-N-(3-sulfamoylphenyl)-4-(trifluoromethyl)pyrazole-3-carboxamide; |
| SC-35 | N-(3-carbamoyl-4-fluorophenyl)-1-(cyclohexylmethyl)-4-(trifluoromethyl)-1H-pyrazole-5-carboxamide; |
| SC-36 | 2-(cyclohexylmethyl)-N-(1-methylsulfonylpyrazol-4-yl)-4-(trifluoromethyl)pyrazole-3-carboxamide; |
| SC-37 | 2-(cyclohexylmethyl)-4-methyl-N-(3-methylsulfonylphenyl)pyrazole-3-carboxamide; |
| SC-38 | 5-cyano-2-(cyclohexylmethyl)-N-(3-methylsulfonylphenyl)pyrazole-3-carboxamide; |
| SC-39 | N-(3-carbamoyl-4-fluorophenyl)-2-[ (4,4-difluorocyclohexyl)methyl] -4-(trifluoromethyl)pyrazole-3-carboxamide; |
| SC-41 | N-(3-carbamoylphenyl)-2-[ (4,4-difluorocyclohexyl)methyl] -4-(trifluoromethyl)pyrazole-3-carboxamide; |
| SC-42 | 2-[ (4,4-difluorocyclohexyl)methyl] -N-(3-fluoro-5-methylsulfonylphenyl)-4-(trifluoromethyl)pyrazole-3-carboxamide; |
| SC-43 | 2-[ (4,4-difluorocyclohexyl)methyl] -N-(3-sulfamoylphenyl)-4-(trifluoromethyl)pyrazole-3-carboxamide; |
| SC-44 | 2-[ (4,4-difluorocyclohexyl)methyl] -4,5-dimethyl-N-(3-methylsulfonylphenyl)pyrazole-3-carboxamide; |
| SC-45 | 3,4-dimethyl-N-(3-sulfamoylphenyl)-1-((tetrahydro-2H-pyran-4-yl)methyl)-1H-pyrazole-5-carboxamide; |
| SC-46 | 2-(cyclohexylmethyl)-5-methyl-N-(3-methylsulfonylphenyl)-4-(trifluoromethyl)pyrazole-3-carboxamide; |
| SC-47 | N-(3-carbamoyl-4-fluorophenyl)-2-[ (4,4-difluorocyclohexyl)methyl] -5-methyl-4-(trifluoromethyl)pyrazole-3-carboxamide; |
| SC-48 | 2-[ (4,4-difluorocyclohexyl)methyl] -N-(4-fluoro-3-sulfamoylphenyl)-4,5-dimethylpyrazole-3-carboxamide; |
| SC-49 | 2-[ (4,4-difluorocyclohexyl)methyl] -N-(4-fluoro-3-sulfamoylphenyl)-4-(trifluoromethyl)pyrazole-3-carboxamide; |

| | -continued |
|---|---|
| SC-50 | 4-[ [ 2-[ (4,4-difluorocyclohexyl)methyl] -4-(trifluoromethyl)pyrazole-3-carbonyl] amino] pyridine-2-carboxamide; |
| SC-51 | 2-[ (4,4-difluorocyclohexyl)methyl] -4,5-dimethyl-N-(3-sulfamoylphenyl)pyrazole-3-carboxamide; |
| SC-52 | N-(3-(methylsulfonyl)phenyl)-1-((tetrahydro-2H-pyran-3-yl)methyl)-4-(trifluoromethyl)-1H-pyrazole-5-carboxamide; |
| SC-53 | 2-(cyclohexylmethyl)-N-(1-methylsulfonylpyrrolo[ 2,3-b] pyridin-3-yl)-4-(trifluoromethyl)pyrazole-3-carboxamide; |
| SC-54 | 5-methyl-N-(3-methylsulfonylphenyl)-2-(oxan-3-ylmethyl)-4-(trifluoromethyl)pyrazole-3-carboxamide; |
| SC-55 | 5-methyl-N-(3-methylsulfonylphenyl)-2-(oxan-2-ylmethyl)-4-(trifluoromethyl)pyrazole-3-carboxamide; |
| SC-56 | 5-methyl-N-(3-methylsulfonylphenyl)-2-(oxolan-2-ylmethyl)-4-(trifluoromethyl)pyrazole-3-carboxamide; |
| SC-57 | 2-[ (4,4-difluorocyclohexyl)methyl] -5-methyl-N-(3-sulfamoylphenyl)-4-(trifluoromethyl)pyrazole-3-carboxamide; |
| SC-60 | 2-[ (3,3-difluorocyclopentyl)methyl] -N-(3-sulfamoylphenyl)-4-(trifluoromethyl)pyrazole-3-carboxamide; |
| SC-61 | N-(3-carbamoylphenyl)-2-[ (4,4-difluorocyclohexyl)methyl] -5-methyl-4-(trifluoromethyl)pyrazole-3-carboxamide; |
| SC-62 | 2-[ (4,4-difluorocyclohexyl)methyl] -5-methyl-N-(3-methylsulfonylphenyl)-4-(trifluoromethyl)pyrazole-3-carboxamide; |
| SC-63 | 3-methyl-N-(3-(methylsulfonyl)phenyl)-1-((tetrahydrofuran-3-yl)methyl)-4-(trifluoromethyl)-1H-pyrazole-5-carboxamide; |
| SC-64 | 2-(cyclohexylmethyl)-N-(2-hydroxypyridin-4-yl)-5-methyl-4-(trifluoromethyl)pyrazole-3-carboxamide; |
| SC-65 | N-(3-carbamoyl-4-fluorophenyl)-2-[ (4,4-difluorocyclohexyl)methyl] -4,5-dimethylpyrazole-3-carboxamide; |
| SC-66 | N-(2-hydroxypyridin-4-yl)-5-methyl-2-(oxan-4-ylmethyl)-4-(trifluoromethyl)pyrazole-3-carboxamide; |
| SC-67 | N-(2-hydroxypyridin-4-yl)-3-methyl-1-((tetrahydro-2H-pyran-3-yl)methyl)-4-(trifluoromethyl)-1H-pyrazole-5-carboxamide; |
| SC-68 | N-(2-hydroxypyridin-4-yl)-3-methyl-1-((tetrahydro-2H-pyran-2-yl)methyl)-4-(trifluoromethyl)-1H-pyrazole-5-carboxamide; |
| SC-69 | 2-[ (4,4-difluorocyclohexyl)methyl] -N-(2-sulfamoylpyridin-4-yl)-4-(trifluoromethyl)pyrazole-3-carboxamide; |
| SC-73 | N-(3-carbamoyl-4-fluorophenyl)-2-[ (3,3-difluorocyclopentyl)methyl] -4-(trifluoromethyl)pyrazole-3-carboxamide; |
| SC-77 | 4-[ [ 2-[ (4,4-difluorocyclohexyl)methyl] -4,5-dimethylpyrazole-3-carbonyl] amino] pyridine-2-carboxamide; |
| SC-78 | (1-((3,3-difluorocyclopentyl)methyl)-N-(3-sulfamoylphenyl)-4-(trifluoromethyl)-1H-pyrazole-5-carboxamide; |
| SC-80 | 1-((3,3-difluorocyclopentyl)methyl)-N-(2-sulfamoylpyridin-4-yl)-4-(trifluoromethyl)-1H-pyrazole-5-carboxamide; |
| SC-82 | 1-((3,3-difluorocyclopentyl)methyl)-N-(2-(methylsulfonyl)pyridin-4-yl)-4-(trifluoromethyl)-1H-pyrazole-5-carboxamide; |
| SC-84 | 4-(1-((4,4-difluorocyclohexyl)methyl)-3-methyl-4-(trifluoromethyl)-1H-pyrazole-5-carboxamido)picolinamide; |
| SC-85 | 1-((4,4-difluorocyclohexyl)methyl)-3-methyl-N-(2-(methylsulfonyl)pyridin-4-yl)-4-(trifluoromethyl)-1H-pyrazole-5-carboxamide; |
| SC-86 | 4-(1-((4,4-difluorocyclohexyl)methyl)-4-(difluoromethyl)-3-methyl-1H-pyrazole-5-carboxamido)picolinamide; |
| SC-87 | 1-((4,4-difluorocyclohexyl)methyl)-4-(difluoromethyl)-3-methyl-N-(2-(methylsulfonyl)pyridin-4-yl)-1H-pyrazole-5-carboxamide; |
| SC-88 | N-(3-carbamoyl-4-fluorophenyl)-1-((4,4-difluorocyclohexyl)methyl)-4-(difluoromethyl)-3-methyl-1H-pyrazole-5-carboxamide; |
| SC-89 | 1-((4,4-difluorocyclohexyl)methyl)-4-(difluoromethyl)-3-methyl-N-(3-sulfamoylphenyl)-1H-pyrazole-5-carboxamide; |
| SC-90 | 4-(3-chloro-1-((4,4-difluorocyclohexyl)methyl)-4-(trifluoromethyl)-1H-pyrazole-5-carboxamido)picolinamide; |
| SC-91 | 3-chloro-1-((4,4-difluorocyclohexyl)methyl)-N-(2-(methylsulfonyl)pyridin-4-yl)-4-(trifluoromethyl)-1H-pyrazole-5-carboxamide; |
| SC-92 | N-(3-carbamoyl-4-fluorophenyl)-3-chloro-1-((4,4-difluorocyclohexyl)methyl)-4-(trifluoromethyl)-1H-pyrazole-5-carboxamide; |
| SC-93 | 3-chloro-1-((4,4-difluorocyclohexyl)methyl)-N-(3-sulfamoylphenyl)-4-(trifluoromethyl)-1H-pyrazole-5-carboxamide; |
| SC-94 | 4-(1-((4,4-difluorocyclohexyl)methyl)-4-methyl-3-(trifluoromethyl)-1H-pyrazole-5-carboxamido)picolinamide; |
| SC-95 | 1-((4,4-difluorocyclohexyl)methyl)-4-methyl-N-(2-(methylsulfonyl)pyridin-4-yl)-3-(trifluoromethyl)-1H-pyrazole-5-carboxamide; |
| SC-96 | N-(3-carbamoyl-4-fluorophenyl)-1-((4,4-difluorocyclohexyl)methyl)-4-methyl-3-(trifluoromethyl)-1H-pyrazole-5-carboxamide; |
| SC-97 | 1-((4,4-difluorocyclohexyl)methyl)-4-methyl-N-(3-sulfamoylphenyl)-3-(trifluoromethyl)-1H-pyrazole-5-carboxamide; |
| SC-98 | 4-(1-((4,4-difluorocyclohexyl)methyl)-3-(difluoromethyl)-4-methyl-1H-pyrazole-5-carboxamido)picolinamide; |
| SC-99 | 1-((4,4-difluorocyclohexyl)methyl)-3-(difluoromethyl)-4-methyl-N-(2-(methylsulfonyl)pyridin-4-yl)-1H-pyrazole-5-carboxamide; |

| | |
|---|---|
| SC-100 | N-(3-carbamoyl-4-fluorophenyl)-1-((4,4-difluorocyclohexyl)methyl)-3-(difluoromethyl)-4-methyl-1H-pyrazole-5-carboxamide; |
| SC-101 | 1-((4,4-difluorocyclohexyl)methyl)-3-(difluoromethyl)-4-methyl-N-(3-sulfamoylphenyl)-1H-pyrazole-5-carboxamide; |
| SC-102 | 4-(4-chloro-1-((4,4-difluorocyclohexyl)methyl)-3-(trifluoromethyl)-1H-pyrazole-5-carboxamido)picolinamide; |
| SC-103 | 4-chloro-1-((4,4-difluorocyclohexyl)methyl)-N-(2-(methylsulfonyl)pyridin-4-yl)-3-(trifluoromethyl)-1H-pyrazole-5-carboxamide; |
| SC-104 | N-(3-carbamoyl-4-fluorophenyl)-4-chloro-1-((4,4-difluorocyclohexyl)methyl)-3-(trifluoromethyl)-1H-pyrazole-5-carboxamide; |
| SC-105 | 4-chloro-1-((4,4-difluorocyclohexyl)methyl)-N-(3-sulfamoylphenyl)-3-(trifluoromethyl)-1H-pyrazole-5-carboxamide; |
| SC-106 | 1-((3,3-difluorocyclopentyl)methyl)-3-methyl-N-(3-sulfamoylphenyl)-4-(trifluoromethyl)-1H-pyrazole-5-carboxamide; |
| SC-108 | 1-((3,3-difluorocyclopentyl)methyl)-3-methyl-N-(2-(methylsulfonyl)pyridin-4-yl)-4-(trifluoromethyl)-1H-pyrazole-5-carboxamide; |
| SC-110 | 4-(1-((3,3-difluorocyclopentyl)methyl)-3-methyl-4-(trifluoromethyl)-1H-pyrazole-5-carboxamido)picolinamide; |
| SC-112 | N-(3-carbamoyl-4-fluorophenyl)-1-((3,3-difluorocyclopentyl)methyl)-3-methyl-4-(trifluoromethyl)-1H-pyrazole-5-carboxamide; |
| SC-114 | 1-((3,3-difluorocyclopentyl)methyl)-4-methyl-N-(3-sulfamoylphenyl)-3-(trifluoromethyl)-1H-pyrazole-5-carboxamide; |
| SC-116 | 1-((3,3-difluorocyclopentyl)methyl)-4-methyl-N-(2-(methylsulfonyl)pyridin-4-yl)-3-(trifluoromethyl)-1H-pyrazole-5-carboxamide; |
| SC-118 | 4-(1-((3,3-difluorocyclopentyl)methyl)-4-methyl-3-(trifluoromethyl)-1H-pyrazole-5-carboxamido)picolinamide; |
| SC-120 | N-(3-carbamoyl-4-fluorophenyl)-1-((3,3-difluorocyclopentyl)methyl)-4-methyl-3-(trifluoromethyl)-1H-pyrazole-5-carboxamide; |
| SC-122 | 4-(3-methyl-1-((3,3,4,4-tetrafluorocyclopentyl)methyl)-4-(trifluoromethyl)-1H-pyrazole-5-carboxamido)picolinamide; |
| SC-123 | 3-methyl-N-(2-(methylsulfonyl)pyridin-4-yl)-1-((3,3,4,4-tetrafluorocyclopentyl)methyl)-4-(trifluoromethyl)-1H-pyrazole-5-carboxamide; |
| SC-124 | 4-(1-((4,4-difluorocyclohexyl)methyl)-3-(difluoromethyl)-4-(trifluoromethyl)-1H-pyrazole-5-carboxamido)picolinamide; |
| SC-125 | 1-((4,4-difluorocyclohexyl)methyl)-3-(difluoromethyl)-N-(2-(methylsulfonyl)pyridin-4-yl)-4-(trifluoromethyl)-1H-pyrazole-5-carboxamide; |
| SC-126 | N-(3-carbamoyl-4-fluorophenyl)-1-((4,4-difluorocyclohexyl)methyl)-3-(difluoromethyl)-4-(trifluoromethyl)-1H-pyrazole-5-carboxamide; |
| SC-127 | 1-((4,4-difluorocyclohexyl)methyl)-3-(difluoromethyl)-N-(3-sulfamoylphenyl)-4-(trifluoromethyl)-1H-pyrazole-5-carboxamide; |
| SC-128 | 4-(3-cyclopropyl-1-((4,4-difluorocyclohexyl)methyl)-4-(trifluoromethyl)-1H-pyrazole-5-carboxamido)picolinamide; |
| SC-129 | 4-(3-cyclopropyl-1-((3,3-difluorocyclopentyl)methyl)-4-(trifluoromethyl)-1H-pyrazole-5-carboxamido)picolinamide; |
| SC-131 | 4-(3-cyclopropyl-1-((tetrahydro-2H-pyran-4-yl)methyl)-4-(trifluoromethyl)-1H-pyrazole-5-carboxamido)picolinamide; |
| SC-132 | 3-cyclopropyl-N-(2-(methylsulfonyl)pyridin-4-yl)-1-((tetrahydro-2H-pyran-4-yl)methyl)-4-(trifluoromethyl)-1H-pyrazole-5-carboxamide; |
| SC-133 | 4-(3-cyclopropyl-1-((tetrahydro-2H-pyran-4-yl)methyl)-4-(trifluoromethoxy)-1H-pyrazole-5-carboxamido)picolinamide; |
| SC-134 | 4-(3-methoxy-1-((tetrahydro-2H-pyran-4-yl)methyl)-4-(trifluoromethyl)-1H-pyrazole-5-carboxamido)picolinamide; |
| SC-135 | 4-(3-cyclopropyl-1-((2-methyltetrahydro-2H-pyran-4-yl)methyl)-4-(trifluoromethyl)-1H-pyrazole-5-carboxamido)picolinamide; |
| SC-138 | 4-(3-cyclopropyl-1-((5-methyltetrahydrofuran-3-yl)methyl)-4-(trifluoromethyl)-1H-pyrazole-5-carboxamido)picolinamide; |
| SC-139 | 4-(3-cyclopropyl-1-((5-methyltetrahydrofuran-2-yl)methyl)-4-(trifluoromethyl)-1H-pyrazole-5-carboxamido)picolinamide; |
| SC-140 | N-(3-carbamoyl-4-fluorophenyl)-3-cyclopropyl-1-((tetrahydro-2H-pyran-2-yl)methyl)-4-(trifluoromethyl)-1H-pyrazole-5-carboxamide; |
| SC-141 | N-(3-carbamoyl-4-fluorophenyl)-1-((3,3-difluorocyclobutyl)methyl)-3-(difluoromethyl)-4-(trifluoromethyl)-1H-pyrazole-5-carboxamide; |
| SC-143 | 4-(3-cyclopropyl-1-((6-methyltetrahydro-2H-pyran-2-yl)methyl)-4-(trifluoromethyl)-1H-pyrazole-5-carboxamido)picolinamide; |
| SC-144 | 4-(3-cyclopropyl-1-((3,3-difluorocyclobutyl)methyl)-4-(trifluoromethyl)-1H-pyrazole-5-carboxamido)picolinamide; |
| SC-145 | 4-(3-cyclopropyl-1-((tetrahydro-2H-pyran-3-yl)methyl)-4-(trifluoromethyl)-1H-pyrazole-5-carboxamido)picolinamide; |
| SC-147 | 4-(3-cyclopropyl-4-(trifluoromethyl)-1-((2-(trifluoromethyl)tetrahydrofuran-3-yl)methyl)-1H-pyrazole-5-carboxamido)picolinamide; |
| SC-148 | 4-(3-cyclopropyl-4-(trifluoromethyl)-1-((5-(trifluoromethyl)tetrahydrofuran-3-yl)methyl)-1H-pyrazole-5-carboxamido)picolinamide; |
| SC-149 | 4-(4-chloro-1-((3,3-difluorocyclopentyl)methyl)-3-(1,1-difluoroethyl)-1H-pyrazole-5-carboxamido)picolinamide; |
| SC-150 | 3-cyclopropyl-N-(2-(methylsulfonyl)pyridin-4-yl)-4-(trifluoromethyl)-1-((2-(trifluoromethyl)tetrahydrofuran-3-yl)methyl)-1H-pyrazole-5-carboxamide; |
| SC-151 | 3-cyclopropyl-1-((3,3-difluorocyclobutyl)methyl)-N-(2-(methylsulfonyl)pyridin-4-yl)-4-(trifluoromethyl)-1H-pyrazole-5-carboxamide; |

| | |
|---|---|
| SC-153 | 3-cyclopropyl-4-(difluoromethyl)-N-(2-(methylsulfonyl)pyridin-4-yl)-1-((tetrahydro-2H-pyran-4-yl)methyl)-1H-pyrazole-5-carboxamide; |
| SC-154 | 4-(3-cyclopropyl-1-((2,2-difluorocyclobutyl)methyl)-4-(trifluoromethyl)-1H-pyrazole-5-carboxamido)picolinamide; |
| SC-155 | 4-(1-((3,3-difluorocyclopentyl)methyl)-3-isopropoxy-4-(trifluoromethyl)-1H-pyrazole-5-carboxamido)picolinamide; |
| SC-156 | 4-(1-((3,3-difluorocyclopentyl)methyl)-3-ethoxy-4-(trifluoromethyl)-1H-pyrazole-5-carboxamido)picolinamide; |
| SC-157 | 4-(3-(cyclopropylmethoxy)-1-((3,3-difluorocyclopentyl)methyl)-4-(trifluoromethyl)-1H-pyrazole-5-carboxamido)picolinamide; |
| SC-158 | 4-(1-((3,3-difluorocyclopentyl)methyl)-3-(difluoromethoxy)-4-(trifluoromethyl)-1H-pyrazole-5-carboxamido)picolinamide; |
| SC-159 | 4-(1-(cyclobutylmethyl)-3-cyclopropyl-4-(trifluoromethyl)-1H-pyrazole-5-carboxamido)picolinamide; |
| SC-160 | 4-(4-chloro-1-((3,3-difluorocyclopentyl)methyl)-3-(trifluoromethyl)-1H-pyrazole-5-carboxamido)picolinamide; |
| SC-161 | 4-(1-((3,3-difluorocyclobutyl)methyl)-3-(1,1-difluoroethyl)-4-methyl-1H-pyrazole-5-carboxamido)picolinamide; |
| SC-163 | 4-(1-((4,4-difluorocyclohexyl)methyl)-3-(difluoromethyl)-4-methyl-1H-pyrazole-5-carboxamido)picolinamide; |
| SC-165 | 1-((3,3-difluorocyclopentyl)methyl)-3-(1,1-difluoroethyl)-4-methyl-N-(2-(methylsulfonyl)pyridin-4-yl)-1H-pyrazole-5-carboxamide; |
| SC-166 | 3-(1,1-difluoroethyl)-4-methyl-N-(2-(methylsulfonyl)pyridin-4-yl)-1-((3,3,4,4-tetrafluorocyclopentyl)methyl)-1H-pyrazole-5-carboxamide; |
| SC-167 | 4-(1-((3,3-difluorocyclopentyl)methyl)-3-(1,1-difluoroethyl)-4-methyl-1H-pyrazole-5-carboxamido)picolinamide; |
| SC-168 | 4-(3-(1,1-difluoroethyl)-4-methyl-1-((3,3,4,4-tetrafluorocyclopentyl)methyl)-1H-pyrazole-5-carboxamido)picolinamide; |
| SC-169 | 1-((3,3-difluorocyclobutyl)methyl)-3-isopropyl-N-(2-(methylsulfonyl)pyridin-4-yl)-4-(trifluoromethyl)-1H-pyrazole-5-carboxamide; |
| SC-170 | 4-(1-((3,3-difluorocyclobutyl)methyl)-3-isopropyl-4-(trifluoromethyl)-1H-pyrazole-5-carboxamido)picolinamide; |
| SC-171 | 1-((3,3-difluorocyclobutyl)methyl)-3-ethyl-N-(2-(methylsulfonyl)pyridin-4-yl)-4-(trifluoromethyl)-1H-pyrazole-5-carboxamide; |
| SC-172 | 4-(1-((3,3-difluorocyclobutyl)methyl)-3-ethyl-4-(trifluoromethyl)-1H-pyrazole-5-carboxamido)picolinamide; |
| SC-173 | 1-((3,3-difluorocyclobutyl)methyl)-N-(2-(methylsulfonyl)pyridin-4-yl)-4-(trifluoromethyl)-3-(1,1,1-trifluoropropan-2-yl)-1H-pyrazole-5-carboxamide; |
| SC-174 | 4-(1-((3,3-difluorocyclobutyl)methyl)-4-(trifluoromethyl)-3-(1,1,1-trifluoropropan-2-yl)-1H-pyrazole-5-carboxamido)picolinamide; |
| SC-175 | 1-((3,3-difluorocyclobutyl)methyl)-3-(1,1-difluoropropan-2-yl)-N-(2-(methylsulfonyl)pyridin-4-yl)-4-(trifluoromethyl)-1H-pyrazole-5-carboxamide; |
| SC-176 | 4-(1-((3,3-difluorocyclobutyl)methyl)-3-(1,1-difluoropropan-2-yl)-4-(trifluoromethyl)-1H-pyrazole-5-carboxamido)picolinamide; |
| SC-177 | 4-(4-chloro-1-((3,3-difluorocyclobutyl)methyl)-3-(1,1-difluoroethyl)-1H-pyrazole-5-carboxamido)picolinamide; |
| SC-178 | 4-chloro-1-((3,3-difluorocyclopentyl)methyl)-3-(1,1-difluoroethyl)-N-(2-(methylsulfonyl)pyridin-4-yl)-1H-pyrazole-5-carboxamide; |
| SC-179 | 1-((3,3-difluorocyclobutyl)methyl)-3-(1,1-difluoroethyl)-N-(2-(methylsulfonyl)pyridin-4-yl)-4-(trifluoromethyl)-1H-pyrazole-5-carboxamide; |
| SC-180 | 4-(1-((3,3-difluorocyclobutyl)methyl)-3-(1,1-difluoroethyl)-4-(trifluoromethyl)-1H-pyrazole-5-carboxamido)picolinamide; |
| SC-181 | 1-((3,3-difluorocyclopentyl)methyl)-3-(1,1-difluoroethyl)-N-(2-(methylsulfonyl)pyridin-4-yl)-4-(trifluoromethyl)-1H-pyrazole-5-carboxamide; |
| SC-182 | 4-(1-((3,3-difluorocyclopentyl)methyl)-3-(1,1-difluoroethyl)-4-(trifluoromethyl)-1H-pyrazole-5-carboxamido)picolinamide; |
| SC-183 | 1-((3,3-difluorocyclobutyl)methyl)-4-methyl-N-(2-(methylsulfonyl)pyridin-4-yl)-3-(perfluoroethyl)-1H-pyrazole-5-carboxamide; |
| SC-184 | 4-(1-((3,3-difluorocyclobutyl)methyl)-4-methyl-3-(perfluoroethyl)-1H-pyrazole-5-carboxamido)picolinamide; |
| SC-185 | 1-((3,3-difluorocyclopentyl)methyl)-4-methyl-N-(2-(methylsulfonyl)pyridin-4-yl)-3-(perfluoroethyl)-1H-pyrazole-5-carboxamide; |
| SC-186 | 4-(1-((3,3-difluorocyclopentyl)methyl)-4-methyl-3-(perfluoroethyl)-1H-pyrazole-5-carboxamido)picolinamide; |
| SC-187 | 1-((3,3-difluorocyclobutyl)methyl)-4-methyl-N-(2-(methylsulfonyl)pyridin-4-yl)-3-(1,1,1-trifluoropropan-2-yl)-1H-pyrazole-5-carboxamide; |
| SC-188 | 4-(1-((3,3-difluorocyclobutyl)methyl)-4-methyl-3-(1,1,1-trifluoropropan-2-yl)-1H-pyrazole-5-carboxamido)picolinamide; |
| SC-189 | 1-((3,3-difluorocyclopentyl)methyl)-4-methyl-N-(2-(methylsulfonyl)pyridin-4-yl)-3-(1,1,1-trifluoropropan-2-yl)-1H-pyrazole-5-carboxamide; |
| SC-190 | 4-(1-((3,3-difluorocyclopentyl)methyl)-4-methyl-3-(1,1,1-trifluoropropan-2-yl)-1H-pyrazole-5-carboxamido)picolinamide; |
| SC-191 | 1-((3,3-difluorocyclobutyl)methyl)-3-(1,1-difluoropropan-2-yl)-4-methyl-N-(2-(methylsulfonyl)pyridin-4-yl)-1H-pyrazole-5-carboxamide; |
| SC-192 | 4-(1-((3,3-difluorocyclobutyl)methyl)-3-(1,1-difluoropropan-2-yl)-4-methyl-1H-pyrazole-5-carboxamido)picolinamide; |
| SC-193 | 1-((3,3-difluorocyclopentyl)methyl)-3-(1,1-difluoropropan-2-yl)-4-methyl-N-(2-(methylsulfonyl)pyridin-4-yl)-1H-pyrazole-5-carboxamide; |

| | |
|---|---|
| SC-194 | 4-(1-((3,3-difluorocyclopentyl)methyl)-3-(1,1-difluoropropan-2-yl)-4-methyl-1H-pyrazole-5-carboxamido)picolinamide; |
| SC-195 | 1-((3,3-difluorocyclopentyl)methyl)-3-(difluoromethoxy)-N-(2-(methylsulfonyl)pyridin-4-yl)-4-(trifluoromethyl)-1H-pyrazole-5-carboxamide; |
| SC-196 | 4-(1-((3,3-difluorocyclopentyl)methyl)-3-(difluoromethoxy)-4-methyl-1H-pyrazole-5-carboxamido)picolinamide; |
| SC-197 | 1-((3,3-difluorocyclopentyl)methyl)-3-(difluoromethoxy)-4-methyl-N-(2-(methylsulfonyl)pyridin-4-yl)-1H-pyrazole-5-carboxamide; |
| SC-198 | 4-(1-((3,3-difluorocyclopentyl)methyl)-4-methyl-3-(trifluoromethoxy)-1H-pyrazole-5-carboxamido)picolinamide; |
| SC-199 | 1-((3,3-difluorocyclopentyl)methyl)-4-methyl-N-(2-(methylsulfonyl)pyridin-4-yl)-3-(trifluoromethoxy)-1H-pyrazole-5-carboxamide; |
| SC-200 | 4-(1-((3,3-difluorocyclopentyl)methyl)-3-(1,1-difluoroethoxy)-4-methyl-1H-pyrazole-5-carboxamido)picolinamide; |
| SC-201 | 1-((3,3-difluorocyclopentyl)methyl)-3-(1,1-difluoroethoxy)-4-methyl-N-(2-(methylsulfonyl)pyridin-4-yl)-1H-pyrazole-5-carboxamide; |
| SC-202 | 3-(cyclopropyldifluoromethyl)-1-((3,3-difluorocyclobutyl)methyl)-4-methyl-N-(2-(methylsulfonyl)pyridin-4-yl)-1H-pyrazole-5-carboxamide; |
| SC-203 | 4-(3-(cyclopropyldifluoromethyl)-1-((3,3-difluorocyclobutyl)methyl)-4-methyl-1H-pyrazole-5-carboxamido)picolinamide; |
| SC-204 | 4-(3-(1,1-difluoroethyl)-4-methyl-1-((2-(trifluoromethyl)cyclopropyl)methyl)-1H-pyrazole-5-carboxamido)picolinamide; |
| SC-205 | 3-(1,1-difluoroethyl)-4-methyl-N-(2-(methylsulfonyl)pyridin-4-yl)-1-((2-(trifluoromethyl)cyclopropyl)methyl)-1H-pyrazole-5-carboxamide; |
| SC-206 | 4-(3-(1,1-difluoroethyl)-1-((2-(difluoromethyl)cyclopropyl)methyl)-4-methyl-1H-pyrazole-5-carboxamido)picolinamide; |
| SC-207 | 3-(1,1-difluoroethyl)-1-((2-(difluoromethyl)cyclopropyl)methyl)-4-methyl-N-(2-(methylsulfonyl)pyridin-4-yl)-1H-pyrazole-5-carboxamide; |
| SC-208 | 4-(1-((3,3-difluoro-1-methyleyclobutyl)methyl)-3-(1,1-difluoroethyl)-4-methyl-1H-pyrazole-5-carboxamido)picolinamide; |
| SC-209 | 1-((3,3-difluoro-1-methyleyclobutyl)methyl)-3-(1,1-difluoroethyl)-4-methyl-N-(2-sulfamoylpyridin-4-yl)-1H-pyrazole-5-caiboxamide; |
| SC-210 | 1-((3,3-difluoro-1-methyleyclobutyl)methyl)-3-(1,1-difluoroethyl)-4-methyl-N-(2-(methylsulfonyl)pyridin-4-yl)-1H-pyrazole-5-carboxamide; |
| SC-211 | 1-((3,3-difluorocyclopentyl)methyl)-3-(1,1-difluoroethyl)-4-methyl-N-(2-sulfamoylpyridin-4-yl)-1H-pyrazole-5-ca±oxamide; |
| SC-212 | 1-((3,3-difluoro-1-methylcyclopentyl)methyl)-3-(1,1-difluoroethyl)-4-methyl-N-(2-sulfamoylpyridin-4-yl)-1H-pyrazole-5-caiboxamide; |
| SC-213 | 1-((3,3-difluoro-1-methylcyclopentyl)methyl)-3-(1,1-difluoroethyl)-4-methyl-N-(2-(methylsulfonyl)pyridin-4-yl)-1H-pyrazole-5-carboxamide; |
| SC-214 | 4-(1-((3,3-difluoro-1-methyleyclopentyl)methyl)-3-(1,1-difluoroethyl)-4-methyl-1H-pyrazole-5-carboxamido)picolinamide; |
| SC-215 | 1-((3,3-difluorocyclobutyl)methyl)-3-(l,1-difluoroethyl)-4-methyl-N-(2-sulfamoylpyridin-4-yl)-1H-pyrazole-5-ca±oxamide; |
| SC-216 | 4-(3-cyclopropyl-1-((3,3-difluorocyclopentyl)methyl)-4-(difluoromethyl)-1H-pyrazole-5-carboxamido)picolinamide; |
| SC-217 | 4-(1-((4,4-difluoro-2-(trifluoromethyl)cyclopentyl)methyl)-3-(1,1-difluoroethyl)-4-methyl-lH-pyrazole-5-carboxamido)picolinamide; |
| SC-218 | 4-(1-((3,3-difluorocyclopentyl)methyl)-3-ethyl-4-(trifluoromethyl)-1H-pyrazole-5-carboxamido)picolinamide; |
| SC-219 | 4-(3-cyclopropyl-1-((3-(trifluoromethoxy)cyclobutyl)methyl)-4-(trifluoromethyl)-1H-pyrazole-5-carboxamido)picolinamide; |
| SC-220 | 1-((3,3-difluoro-1-(trifluoromethyl)cyclobutyl)methyl)-3-(l,l-difluoroethyl)-4-methyl-N-(2-(methylsulfonyl)pyridin-4-yl)-1H-pyrazole-5-carboxamide; |
| SC-221 | 4-(3-cyclopropyl-1-((3-(difluoromethyl)cyclobutyl)methyl)-4-(trifluoromethyl)-1H-pyrazole-5-carboxamido)picolinamide; |
| SC-222 | 1-(1-(3,3-difluorocyclobutyl)ethyl)-3-(1,1-difluoroethyl)-4-methyl-N-(2-(methylsulfonyl)pyridin-4-yl)-1H-pyrazole-5-carboxamide; |
| SC-223 | 4-(3-(1,1-difluoroethyl)-1-((2-((2-methoxyethoxy)methyl)cyclohexyl)methyl)-4-methyl-1H-pyrazole-5-carboxamido)picolinamide; |
| SC-224 | 1-((3,4-difluorocyclopentyl)methyl)-3-(1,1-difluoroethyl)-4-methyl-N-(2-(methylsulfonyl)pyridin-4-yl)-1H-pyrazole-5-carboxamide; |
| SC-225 | 1-((3,3-difluorocyclopentyl)methyl)-3-methoxy-N-(2-(methylsulfonyl)pyridin-4-yl)-4-(trifluoromethyl)-1H-pyrazole-5-carboxamide; |
| SC-226 | 1-(cyclohexylmethyl)-N-(3-(methylsulfonyl)phenyl)-1H-pyrazole-5-carboxamide; |
| SC-229 | 1-(cyclohexylmethyl)-4-(difluoromethyl)-N-(3-(methylsulfonyl)phenyl)-1H-pyrazole-5-carboxamide; |
| SC-230 | 3-cyclopropyl-1-((4,4-difluorocyclohexyl)methyl)-N-(3-sulfamoylphenyl)-4-(trifluoromethyl)-1H-pyrazole-5-carboxamide; |
| SC-231 | N-(2-cyanopyridin-4-yl)-1-((4,4-difluorocyclohexyl)methyl)-3,4-dimethyl-1H-pyrazole-5-carboxamide; |
| SC-232 | 1-((1-methylcyclohexyl)methyl)-N-(3-(methylsulfonyl)phenyl)-4-(trifluoromethyl)-1H-pyrazole-5-carboxamide; |
| SC-233 | 1-((1-fluorocyclohexyl)methyl)-N-(3-(methylsulfonyl)phenyl)-4-(trifluoromethyl)-1H-pyrazole-5-carboxamide; |
| SC-234 | 3-methyl-N-(3-(methylsulfonyl)phenyl)-1-(oxetan-3-yimethyl)-4-(trifluoromethyl)-1H-pyrazole-5-carboxamide; |
| SC-235 | 1-((2,2-difluorocyclopentyl)methyl)-N-(3-sulfamoylphenyl)-4-(trifluoromethyl)-1H-pyrazole-5-carboxamide; |

| | |
|---|---|
| SC-236 | 4-chloro-1-((4,4-difluorocyclohexyl)methyl)-3-methyl-N-(3-sulfamoylphenyl)-1H-pyrazole-5-carboxamide; |
| SC-237 | 3-methyl-N-(3-(methylsulfonyl)phenyl)-1-(oxetan-2-ylmethyl)-4-(trifluoromethyl)-1H-pyrazole-5-carboxamide; |
| SC-238 | 1-(cyclohexylmethyl)-N-(4-fluoro-3-sulfamoyiphenyl)-3-methyl-4-(trifluoromethyl)-1H-pyrazole-5-carboxamide; |
| SC-239 | 4-(3-chloro-1-((4,4-difluorocyclohexyl)methyl)-4-methyl-1H-pyrazole-5-carboxamido)picolinamide; |
| SC-241 | 1-((4,4-difluorocyclohexyl)methyl)-3-methyl-N-(5-(methylsulfonyl)pyridin-3-yl)-4-(trifluoromethyl)-1H-pyrazole-5-carboxamide; |
| SC-242 | 1-((4,4-difluorocyclohexyl)methyl)-4-methyl-N-(5-sulfamoylpyridin-3-yl)-3-(trifluoromethyl)-1H-pyrazole-5-carboxamide; |
| SC-243 | 1-((4,4-difluorocyclohexyl)methyl)-4-methyl-N-(6-sulfamoylpyridin-2-yl)-3-(trifluoromethyl)-1H-pyrazole-5-carboxamide; |
| SC-244 | 1-(cyclohexylmethyl)-3-methyl-N-(3-sulfamoylphenyl)-4-(trifluoromethyl)-1H-pyrazole-5-carboxamide; |
| SC-246 | 3-cyclopropyl-1-((4,4-difluorocyclohexyl)methyl)-N-(2-sulfamoylpyridin-4-yl)-4-(trifluoromethyl)-1H-pyrazole-5-carboxamide; |
| SC-247 | 5-(1-((3,3-difluorocyclopentyl)methyl)-3-methyl-4-(trifluoromethyl)-1H-pyrazole-5-carboxamido)nicotinamide; |
| SC-248 | 4-(1-((3,3-difluorocyclopentyl)methyl)-3-methyl-4-(trifluoromethyl)-1H-pyrazole-5-carboxamido)pyrimidine-2-carboxamide; |
| SC-249 | 4-(1-((4,4-difluorocyclohexyl)methyl)-3-methyl-4-(trifluoromethyl)-1H-pyrazole-5-carboxamido)-5-methylpicolinamide; |
| SC-250 | 3-cyclopropyl-1-((4,4-difluorocyclohexyl)methyl)-N-(2-(methylsulfonyl)pyridin-4-yl)-4-(trifluoromethyl)-1H-pyrazole-5-carboxamide; |
| SC-251 | 5-(1-((4,4-difluorocyclohexyl)methyl)-3-methyl-4-(trifluoromethyl)-1H-pyrazole-5-carboxamido)-2-methylnicotinamide; |
| SC-252 | 1-((4,4-difluorocyclohexyl)methyl)-3-methyl-N-(2-methylpyridin-4-yl)-4-(trifluoromethyl)-1H-pyrazole-5-carboxamide; |
| SC-253 | 6-(1-((4,4-difluorocyclohexyl)methyl)-3-methyl-4-(trifluoromethyl)-1H-pyrazole-5-carboxamido)picolinamide; |
| SC-254 | 1-((3,3-difluorocyclopentyl)methyl)-4-methyl-N-(2-sulfamoylpyridin-4-yl)-3-(trifluoromethyl)-1H-pyrazole-5-carboxamide; |
| SC-255 | 1-((1-hydroxycyclohexyl)methyl)-N-(3-(methylsulfonyl)phenyl)-4-(trifluoromethyl)-1H-pyrazole-5-carboxamide; |
| SC-256 | 2-(1-((4,4-difluorocyclohexyl)methyl)-3-methyl-4-(trifluoromethyl)-1H-pyrazole-5-carboxamido)oxazole-5-carboxamide; |
| SC-257 | 5-(1-((4,4-difluorocyclohexyl)methyl)-3-methyl-4-(trifluoromethyl)-1H-pyrazole-5-carboxamido)picolinamide; |
| SC-258 | 4-(3-cyclopropyl-1-((tetrahydro-2H-pyran-2-yl)methyl)-4-(trifluoromethyl)-1H-pyrazole-5-carboxamido)picolinamide; |
| SC-259 | 3-cyclopropyl-N-(2-(methylsulfonyl)pyridin-4-yl)-1-((tetrahydro-2H-pyran-2-yl)methyl)-4-(trifluoromethyl)-1H-pyrazole-5-carboxamide; |
| SC-260 | 4-(1-((4,4-difluorocyclohexyl)methyl)-3-methyl-4-(trifluoromethyl)-1H-pyrazole-5-carboxamido)-N-methylpicolinamide; |
| SC-261 | 4-(4-chloro-3-cyclopropyl-1-((tetrahydro-2H-pyran-4-yl)methyl)-1H-pyrazole-5-carboxamido)picolinamide; |
| SC-262 | 1-((3,3-difluorocyclopentyl)methyl)-3-(difluoromethyl)-N-(3-sulfamoylphenyl)-4-(trifluoromethyl)-1H-pyrazole-5-carboxamide; |
| SC-263 | 3-cyclopropyl-N-(2-(methylsulfonyl)pyridin-4-yl)-1-((tetrahydrofuran-2-yl)methyl)-4-(trifluoromethyl)-1H-pyrazole-5-carboxamide; |
| SC-264 | 3-cyclopropyl-N-(3-sulfamoylphenyl)-1-((tetrahydro-2H-pyran-2-yl)methyl)-4-(trifluoromethyl)-1H-pyrazole-5-carboxamide; |
| SC-265 | 1-((3,3-difluorocyclopentyl)methyl)-3-methoxy-N-(3-sulfamoylphenyl)-4-(trifluoromethyl)-1H-pyrazole-5-carboxamide; |
| SC-266 | 4-(3-cyclopropyl-1-(cyclopropylmethyl)-4-(trifluoromethyl)-1H-pyrazole-5-carboxamido)picolinamide; |
| SC-267 | 4-(1-((4,4-difluorocyclohexyl)methyl)-3-methyl-4-(trifluoromethyl)-1H-pyrazole-5-carboxamido)-6-methylpicolinamide; |
| SC-268 | 2-(1-((4,4-difluorocyclohexyl)methyl)-3-methyl-4-(trifluoromethyl)-1H-pyrazole-5-carboxamido)-5-fluoroisonicotinamide; |
| SC-269 | 4-(1-((3,3-difluorocyclopentyl)methyl)-4-methoxy-3-(trifluoromethyl)-1H-pyrazole-5-carboxamido)picolinamide; |
| SC-271 | 4-(1-((3,3-difluorocyclopentyl)methyl)-3-(1,1-difluoroethyl)-4-methoxy-1H-pyrazole-5-carboxamido)picolinamide; |
| SC-273 | 4-(1-((3,3-difluorocyclopentyl)methyl)-3-methoxy-4-(trifluoromethyl)-1H-pyrazole-5-carboxamido)picolinamide; |
| SC-274 | N-(3-carbamoyl-4-fluorophenyl)-3-cyclopropyl-1-((3,3-difluorocyclobutyl)methyl)-4-(trifluoromethyl)-1H-pyrazole-5-carboxamide; |
| SC-275 | 3-cyclopropyl-1-((3,3-difluorocyclopentyl)methyl)-4-(difluoromethyl)-N-(2-(methylsulfonyl)pyridin-4-yl)-1H-pyrazole-5-carboxamide; |
| SC-276 | 3-cyclopropyl-1-((3,3-difluorocyclobutyl)methyl)-N-(3-sulfamoylphenyl)-4-(trifluoromethyl)-1H-pyrazole-5-carboxamide; |
| SC-277 | 3-cyclopropyl-1-((3,3-difluorocyclopentyl)methyl)-N-(2-(methylsulfonyl)pyridin-4-yl)-4-(trifluoromethyl)-1H-pyrazole-5-carboxamide; |
| SC-278 | 4-(1-((2,2-difluorocyclobutyl)methyl)-4-methyl-3-(perfluoroethyl)-1H-pyrazole-5-carboxamido)picolinamide; |

| | -continued |
|---|---|
| SC-279 | 4-(3-cyclopropyl-1-((2,2-difluorocyclopropyl)methyl)-4-(trifluoromethyl)-1H-pyrazole-5-carboxamido)picolinamide; |
| SC-280 | 1-((4,4-difluorocyclohexyl)methyl)-3-methyl-N-(6-(methylsulfonyl)pyridazin-4-yl)-4-(trifluoromethyl)-1H-pyrazole-5-carboxamide; |
| SC-281 | 4-(3-cyclopropyl-1-((3-methoxycyclobutyl)methyl)-4-(trifluoromethyl)-1H-pyrazole-5-carboxamido)picolinamide; |
| SC-282 | 3-cyclopropyl-1-((3,3-difluorocyclobutyl)methyl)-N-(2-sulfamoylpyridin-4-yl)-4-(trifluoromethyl)-1H-pyrazole-5-carboxamide; |
| SC-283 | 4-(3-(3,3-difluorocyclobutoxy)-1-((3,3-difluorocyclopentyl)methyl)-4-(trifluoromethyl)-1H-pyrazole-5-carboxamido)picolinamide; |
| SC-284 | 4-(3-cyclopropyl-4-(trifluoromethyl)-1-((5-(trifluoromethyl)tetrahydrofuran-2-yl)methyl)-1H-pyrazole-5-carboxamido)picolinamide; |
| SC-286 | 3-cyclopropyl-N-(2-(methylsulfonyl)pyridin-4-yl)-1-((5-methyltetrahydrofuran-2-yl)methyl)-4-(trifluoromethyl)-1H-pyrazole-5-carboxamide; |
| SC-289 | 4-(1-((4,4-difluorocyclohexyl)methyl)-3-methyl-4-(trifluoromethyl)-1H-pyrazole-5-carboxamido)-3-fluoropicolinamide; |
| SC-290 | 3-cyclopropyl-1-((3-(difluoromethoxy)cyclobutyl)methyl)-N-(2-(methylsulfonyl)pyridin-4-yl)-4-(trifluoromethyl)-1H-pyrazole-5-carboxamide; |
| SC-291 | 4-(3-cyclopropyl-1-((2,2,3,3-tetrafluorocyclobutyl)methyl)-4-(trifluoromethyl)-1H-pyrazole-5-carboxamido)picolinamide; |
| SC-293 | 1-((3,3-difluorocyclopentyl)methyl)-3-(difluoromethoxy)-N-(2-(methylsulfonyl)pyridin-4-yl)-4-(trifluoromethyl)-1H-pyrazole-5-carboxamide; |
| SC-294 | 4-(1-((4,4-difluorocyclohexyl)methyl)-3-methyl-4-(trifluoromethyl)-1H-pyrazole-5-carboxamido)-3-methylpicolinamide; |
| SC-295 | 1-((3,3-difluorocyclobutyl)methyl)-3-(1,1-difluoroethyl)-4-methyl-N-(3-sulfamoylphenyl)-1H-pyrazole-5-carboxamide; |
| SC-296 | 1-((3,3-difluorocyclopentyl)methyl)-3-(1,1-difluoroethyl)-4-methyl-N-(3-sulfamoylphenyl)-1H-pyrazole-5-carboxamide; |
| SC-297 | 1-((3,3-difluorocyclopentyl)methyl)-3-ethyl-N-(2-(methylsulfonyl)pyridin-4-yl)-4-(trifluoromethyl)-1H-pyrazole-5-carboxamide; |
| SC-298 | 4-(3-cyclopropyl-1-((3,3-difluorocyclopentyl)methyl)-4-(2,2,2-trifluoroethoxy)-1H-pyrazole-5-carboxamido)picolinamide; |
| SC-299 | 4-(1-((3,3-difluoro-1-(trifluoromethyl)cyclobutyl)methyl)-3-(1,1-difluoroethyl)-4-methyl-1H-pyrazole-5-carboxamido)picolinamide; |
| SC-301 | 4-(3-(1,1-difluoroethyl)-1-((3-fluorocyclobutyl)methyl)-4-methyl-1H-pyrazole-5-carboxamido)picolinamide; |
| SC-302 | 1-((3,3-difluorocyclobutyl)methyl)-3-ethyl-4-methyl-N-(2-(methylsulfonyl)pyridin-4-yl)-1H-pyrazole-5-carboxamide; |
| SC-303 | 1-((3,3-difluorocyclobutyl)methyl)-3-(1,1-difluoroethyl)-N-(2-(methylsulfinyl)pyridin-4-yl)-4-(trifluoromethyl)-1H-pyrazole-5-carboxamide; |
| SC-304 | 1-((3,3-difluorocyclopentyl)methyl)-3-methyl-N-(3-sulfamoylphenyl)-4-(trifluoromethoxy)-1H-pyrazole-5-carboxamide; |
| SC-305 | 3-cyclopropyl-N-(2-(methylsulfonyl)pyridin-4-yl)-1-((tetrahydro-2H-pyran-4-yl)methyl)-4-(2,2,2-trifluoroethyl)-1H-pyrazole-5-carboxamide; |
| SC-308 | 3-(1,1-difluoroethyl)-1-((1-methoxycyclopropyl)methyl)-4-methyl-N-(2-sulfamoylpyridin-4-yl)-1H-pyrazole-5-carboxamide; |
| SC-309 | 4-(1-((3,3-difluorocyclobutyl)methyl)-3-(1,1-difluoroethoxy)-4-methyl-1H-pyrazole-5-carboxamido)picolinamide; |
| SC-310 | 3-(1,1-difluoroethyl)-1-((1-fluorocyclopropyl)methyl)-4-methyl-N-(2-sulfamoylpyridin-4-yl)-1H-pyrazole-5-carboxamide; |
| SC-311 | 4-(3-(1,1-difluoroethyl)-1-((1-(difluoromethyl)-3,3-difluorocyclobutyl)methyl)-4-methyl-1H-pyrazole-5-carboxamido)picolinamide; |
| SC-312 | 3-(1,1-difluoroethyl)-4-methyl-1-((2-methyltetrahydro-2H-pyran-2-yl)methyl)-N-(2-sulfamoylpyridin-4-yl)-1H-pyrazole-5-caiboxamide; |
| SC-313 | 3-(1,1-difluoroethyl)-4-methyl-1-((1-methylcyclopropyl)methyl)-N-(2-sulfamoylpyridin-4-yl)-1H-pyrazole-5-carboxamide; |
| SC-314 | 3-(1,1-difluoroethyl)-4-methyl-1-((2-methylcyclopropyl)methyl)-N-(2-sulfamoylpyridin-4-yl)-1H-pyrazole-5-carboxamide; |
| SC-315 | 4-(3-(1,1-difluoroethyl)-4-methyl-1-((2-(trifluoromethyl)cyclobutyl)methyl)-1H-pyrazole-5-carboxamido)picolinamide; |
| SC-316 | 3-(1,1-difluoroethyl)-1-((1-(difluoromethyl)-3,3-difluorocyclobutyl)methyl)-4-methyl-N-(2-sulfamoylpyridin-4-yl)-1H-pyrazole-5-carboxamide; |
| SC-317 | 3-(1,1-difluoroethyl)-4-methyl-1-((2-methyloxetan-2-yl)methyl)-N-(2-sulfamoylpyridin-4-yl)-1H-pyrazole-5-carboxamide; |
| SC-318 | 4-(1-((3,3-difluorocyclobutyl)methyl)-4-methyl-3-(trifluoromethoxy)-1H-pyrazole-5-carboxamido)picolinamide; |
| SC-319 | 3-(1,1-difluoroethyl)-4-methyl-1-((2-methyltetrahydrofuran-2-yl)methyl)-N-(2-sulfamoylpyridin-4-yl)-1H-pyrazole-5-caiboxamide; |
| SC-320 | 1-((4,4-difluorocyclohexyl)methyl)-4-methyl-N-(2-sulfamoylpyridin-4-yl)-3-(trifluoromethyl)-1H-pyrazole-5-carboxamide; |
| SC-321 | 5-(1-((4,4-difluorocyclohexyl)methyl)-3-methyl-4-(trifluoromethyl)-1H-pyrazole-5-carboxamido)pyridazine-3-carboxamide; |
| SC-322 | 3-cyclopropyl-4-(difluoromethoxy)-N-(2-(methylsulfonyl)pyridin-4-yl)-1-((tetrahydro-2H-pyran-4-yl)methyl)-1H-pyrazole-5-carboxamide; |

-continued

| | |
|---|---|
| SC-323 | 1-((3,3-difluorocyclobutyl)methyl)-3-(difluoromethoxy)-4-methyl-N-(2-(methylsulfonyl)pyridin-4-yl)-1H-pyrazole-5-carboxamide; |
| SC-324 | 4-(1-((3,3-difluorocyclobutyl)methyl)-3-(difluoromethyl)-4-(trifluoromethyl)-1H-pyrazole-5-carboxamido)picolinamide; |
| SC-325 | 4-(1-((3,3-difluorocyclopentyl)methyl)-3-(difluoromethyl)-4-(trifluoromethyl)-1H-pyrazole-5-carboxamido)picolinamide; | in the form of the free compound or a physiologically acceptable salt thereof.

13. A pharmaceutical dosage form comprising a compound according to claim 1.

14. A pharmaceutical dosage form comprising a compound according to claim 12.

15. A method of treating pain comprising administering to a subject in need thereof an effective amount therefor of a compound according to claim 1.

16. A method of treating pain comprising administering to a subject in need thereof an effective amount therefor of a compound according to claim 12.

* * * * *